US012799096B2

(12) United States Patent
Abbineni et al.

(10) Patent No.: US 12,799,096 B2
(45) Date of Patent: Nov. 17, 2026

(54) HETEROCYCLIC COMPOUNDS AS CBP/EP300 BROMODOMAIN INHIBITORS

(71) Applicant: AURIGENE ONCOLOGY LIMITED, Bangalore (IN)

(72) Inventors: Chandrasekhar Abbineni, Hyderabad (IN); Susanta Samajdar, Bangalore (IN); Ramesh S. Senaiar, Mumbai (IN); Girish Aggunda Renukappa, Bangalore (IN); Subhendu Mukherjee, Hooghly (IN); Suraj Tatyasaheb Gore, Maharashtra (IN); Gerd Wohlfahrt, Helsinki (FI); Mikko Myllymaki, Espoo (FI)

(73) Assignee: AURIGENE ONCOLOGY LIMITED, Bangalore (IN)

( * ) Notice: Subject to any disclaimer, the term of this patent is extended or adjusted under 35 U.S.C. 154(b) by 663 days.

(21) Appl. No.: 18/044,329

(22) PCT Filed: Sep. 9, 2021

(86) PCT No.: PCT/IB2021/058201
§ 371 (c)(1),
(2) Date: Mar. 7, 2023

(87) PCT Pub. No.: WO2022/053967
PCT Pub. Date: Mar. 17, 2022

(65) Prior Publication Data

US 2023/0322724 A1 Oct. 12, 2023

(30) Foreign Application Priority Data

Sep. 9, 2020 (IN) ............................ 202041038913

(51) Int. Cl.

| | |
|---|---|
| ***C07D 401/14*** | (2006.01) |
| ***C07D 401/10*** | (2006.01) |
| ***C07D 405/14*** | (2006.01) |
| ***C07D 413/14*** | (2006.01) |
| ***C07D 471/04*** | (2006.01) |
| ***C07D 498/04*** | (2006.01) |
| ***C07D 513/04*** | (2006.01) |
| ***C07D 519/00*** | (2006.01) |

(52) U.S. Cl.
CPC ......... *C07D 401/14* (2013.01); *C07D 401/10* (2013.01); *C07D 405/14* (2013.01); *C07D 413/14* (2013.01); *C07D 471/04* (2013.01); *C07D 498/04* (2013.01); *C07D 513/04* (2013.01); *C07D 519/00* (2013.01)

(58) Field of Classification Search
CPC .. C07D 401/14; C07D 401/10; C07D 405/14; C07D 413/14; C07D 471/04; C07D 498/04; C07D 513/04; C07D 519/00; C07D 401/04
See application file for complete search history.

(56) References Cited

U.S. PATENT DOCUMENTS

| | | | | |
|---|---|---|---|---|
| 5,688,810 | A | 11/1997 | Jones et al. | |
| 11,078,188 | B2 | 8/2021 | Xiong et al. | |
| 2019/0152949 | A1 * | 5/2019 | Cyr ..................... | A61K 31/519 |

FOREIGN PATENT DOCUMENTS

| | | | |
|---|---|---|---|
| WO | 2011027289 | A1 | 3/2011 |
| WO | 2014159837 | A1 | 10/2014 |
| WO | 2015015318 | A2 | 2/2015 |
| WO | 2015054642 | A1 | 4/2015 |
| WO | 2016055028 | A1 | 4/2016 |
| WO | 2016077656 | A1 | 5/2016 |
| WO | 2016086200 | A1 | 6/2016 |
| WO | 2017001733 | A1 | 1/2017 |
| WO | 2017205536 | A2 | 11/2017 |
| WO | 2018161876 | A1 | 9/2018 |

OTHER PUBLICATIONS

Hay et al., "Discovery and optimization of small-molecule ligands for the CBP/p300 bromodomains," Journal of the American Chemical Society, 136(26):9308-19 (2014).
Jones et al., "The epigenomics of cancer," Cell, 128(4):683-92 (2007).
Nicolaou et al., "Calicheamicin 0: A Rationally Designed Molecule with Extremely Potent and Selective DNA Cleaving Properties and Apoptosis Inducing Activity," Angewandte Chemie International Edition, 33(2):183-186 (1994).
Chen et al., "Design, synthesis, and biological evaluation of tetrahydroquinoline derivatives as potent inhibitors of CBP bromodomain," Bioorganic Chemistry, 101:103991 (2020).
Romero et al., "GNE-781, A Highly Advanced Potent and Selective Bromodomain Inhibitor of Cyclic Adenosine Monophosphate Response Element Binding Protein, Binding Protein (CBP)," Journal of Medicinal Chemistry, 60(22):9162-9183 (2017).
Zhang et al., "Discovery of Chemical Inhibitors of Human Bromodomains," Chemical Reviews, 115(21):11625-68 (2015).
Chaikuad, et al., "Structure-Based Identification of Inhibitory Fragments Targeting the p300/CBP-Associated Factor Bromodomain," *Journal of Medicinal Chemistry* 59: 1648-1653 (2016).

(Continued)

*Primary Examiner* — Susanna Moore

(74) *Attorney, Agent, or Firm* — MEDLER FERRO WOODHOUSE & MILLS PLLC

(57) ABSTRACT

The present invention provides heterocyclic compounds of formula (I), which are therapeutically useful as CBP/EP300 inhibitors. These compounds are useful in the treatment and/or prevention of diseases or disorders mediated by CBP and/or EP300 in an individual. The present invention also provides preparation of the compounds and pharmaceutical compositions comprising at least one of the compounds of formula (I) or a pharmaceutically acceptable salt, or a stereoisomer or a tautomer, an N-oxide or an ester thereof.

19 Claims, No Drawings

(56) References Cited

OTHER PUBLICATIONS

Popp, et al., "Development of Selective CBP/P300 Benzoxazepine Bromodomain Inhibitors" *Journal of Medicinal Chemistry* 59: 8889-8912 (2016).

SID 407279066, National Library of Medicine, https://pubchem.ncbi.nlm.nih.gov/, available date Aug. 12, 2020.

* cited by examiner

HETEROCYCLIC COMPOUNDS AS CBP/EP300 BROMODOMAIN INHIBITORS

RELATED APPLICATIONS

This application claims a benefit of Indian provisional application number 202041038913, filed on Sep. 9, 2020; the specification of which is hereby incorporated by reference in their entirety.

FIELD OF THE INVENTION

The present invention relates to a compound of formula (I) as inhibitors of CBP and/or EP300 bromodomain. The invention also relates to pharmaceutical compositions comprising said compound of formula (I), a pharmaceutically acceptable salt, a stereoisomer, a tautomer, an N-oxide or an ester thereof. The present invention further relates to methods of treatment of CBP and/or EP300-mediated diseases or disorders using the compounds of present invention and pharmaceutical compositions comprising said compounds or a pharmaceutically acceptable salt, a stereoisomer, a tautomer, an N-oxide or an ester thereof.

BACKGROUND OF THE INVENTION

Genetic and epigenetic modifications are critical to all stages of cancer disease progression and epigenetic silencing has been shown to be important in the mis-regulation of genes involved in all of the hallmarks of cancer (Jones, P. A. et al., Cell, 2007, Vol. 128, pp. 683-692). The underlying epigenetic modifications that mediate regulation include DNA methylation and post translational histone modification. The latter includes methylation, acetylation and ubiquitination. DNA-demethylating agents and histone deacetylase inhibitors have shown anti-tumour activity and a number of agents have been approved for use in the treatment of haematological malignancies. The enzymes mediating histone modification, including histone acetyltransferases (HATs) which acetylate histone and non-histone proteins, represent a wave of second-generation targets for small molecule drug intervention.

The CREB (cyclic-AMP response element binding protein) binding protein (CBP, also known as KAT3A) and p300 (EP300, also known as KAT3B) are lysine acetyltransferases (KAT) acting as a transcriptional co-activator in human cells that catalyze the attachment of an acetyl group to a lysine side chain of histones and other protein substrates. p300 is a protein with multiple domains that bind to diverse proteins including many DNA binding transcription factors. Both CBP and p300 possess a single bromodomain (BRD) and a KAT, which are involved in the post-translational modification and recruitment of histones and non-histone proteins. There is high sequence similarity between CBP and p300 in the conserved functional domains (Duncan A. Hay et al, JACS 2014, 135, 9308-9319). CBP/p300-catalyzed acetylation of histones and other proteins is pivotal to gene activation. Heightened p300 expression and activities have been observed in advanced human cancers such as prostate and in human primary breast cancer specimens.

Modulation of CBP activity therefore provides a promising route to the treatment of certain cancers. Accordingly, compounds that can modulate, e.g. inhibit, the activity of p300 and/or CBP are of interest in cancer therapy.

SUMMARY OF THE INVENTION

Provided herein heterocyclic compounds and pharmaceutical compositions thereof used for the treatment of diseases or disorders mediated by CBP and/or EP300.

In one aspect, the present invention provides compounds of formula (I):

(I)

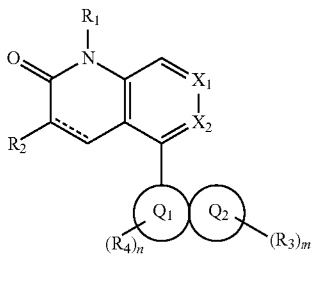

or a pharmaceutical acceptable salt, a stereoisomer, a tautomer, an N-oxide or an ester thereof; wherein

- - - - - - represents single bond or double bond;

$X_1$—$X_2$ represents $CR_{X1}$—$CR_{X2}$, N—$CR_{X2}$ or $CR_{X1}$—N;

$R_{X1}$ and $R_{X2}$ independently represents hydrogen, —$OR_a$, alkyl, alkynyl-OH, —$N(alkyl)_2$, cycloalkyl, heterocycloalkyl or heteroaryl; wherein the cycloalkyl, heterocycloalkyl and heteroaryl are optionally substituted with 1 to 3 substituent(s) selected from alkyl, acyl, halogen, —CN, oxo, —$NH_2$, —OH, —NHCO-alkyl, —$SO_2NH_2$ and —CONH-alkyl;

$R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted with 1 to 3 substituent(s) independently selected from —OH, —COOH, —COO-alkyl, alkoxy, —$NH(alkyl)_2$, —CONH—O-alkyl and heterocycloalkyl; and wherein the heterocycloalkyl and heteroaryl are optionally substituted with 1 to 3 substituent(s) independently selected from alkyl, oxo and acyl;

$Q_1$ represents 5- to 7-membered heterocycloalkyl ring;

$Q_2$ represents fused 5- to 6-membered heteroaryl ring or fused benzo ring;

$R_1$ represents hydrogen, alkyl or haloalkyl;

$R_2$ represents hydrogen, alkyl or —$NH_2$;

$R_3$, at each occurrence, independently, represents hydrogen, halogen, —CN, alkyl, alkoxy, haloalkyl, —CHO, acyl, —CONH-alkyl, —COO-alkyl, —COOH, —OH, —$SO_2NH_2$, —$SO_2NH$-alkyl, —$SO_2N(alkyl)_2$, —$SO_2NH$-aryl, —SO-alkyl, —$SO_2$-alkyl, —$SO_2NHCO$-alkyl, —$SO_2NHCO$-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$;

$R_{3A}$, at each occurrence, independently, is alkoxy, —OH, —CONHOH or —NHCO-alkyl;

$R_{3B}$, at each occurrence, independently, is alkyl, alkoxy, —OH, —COOH, oxo, —COO— alkyl, —CONH-alkyl or —CONH—OH;

$R_{3C}$, at each occurrence, independently, is alkyl, —CN, —OH, —$NH_2$, —$N(alkyl)_2$, acyl, oxo, —CONH-alkyl, —NHCO-alkyl or —CONH-alkyl-OH;

$R_4$, at each occurrence, independently, represents hydrogen, alkyl, haloalkyl, acyl, —CONH-alkyl, oxo, —$SO_2$-alkyl, aralkyl, heteroaryl, heterocycloalkyl or cycloalkyl; wherein the alkyl, aryl, heteroaryl and heterocycloalkyl are optionally substituted with 1 to 3 occurrence(s) of $R_{4A}$;

$R_{4A}$, at each occurrence, independently, is alkoxy, —$COOCH_2CH_3$, —COOH or —CONH— alkyl;

m is 1, 2, 3 or 4; and n is 1, 2, 3 or 4.

In yet another aspect, the present invention provides a pharmaceutical composition comprising a compound of formula (I), a pharmaceutically acceptable salt, a stereoisomer, a tautomer, an N-oxide or an ester thereof and at least one pharmaceutically acceptable excipient (such as a pharmaceutically acceptable carrier or diluent).

In another aspect, the present invention provides a pharmaceutical composition for the treatment of diseases or conditions that are dependent upon inhibiting the activity of CBP and/or EP300.

In yet another aspect, the present invention relates to preparation of compounds of formula (I).

Another aspect of the present invention provides methods of treating CBP and/or EP300-mediated diseases or disorders by administering a therapeutically effective amount of a compound of formula (I) a pharmaceutically acceptable salt, a stereoisomer, a tautomer, an N-oxide or an ester thereof to an individual, e.g., a human, in need thereof.

Yet another aspect of the present invention provides methods of treating CBP and/or EP300-mediated diseases or disorders wherein the CBP and/or EP300-mediated diseases or disorders is cancer, by administering a therapeutically effective amount of a compound of formula (I) a pharmaceutically acceptable salt, a stereoisomer, a tautomer, an N-oxide or an ester thereof to an individual, e.g., a human, in need thereof.

DETAILED DESCRIPTION OF THE INVENTION

The present invention relates to heterocyclic compounds acting as inhibitors of CBP and/or EP300 and pharmaceutical compositions comprising said compounds. The present invention also relates to an use of said compounds and composition comprising said compounds for the treatment and/or prevention of diverse array of CBP and/or EP300-mediated diseases or disorders.

In one embodiment, the present invention provides compounds of formula (I), (I)

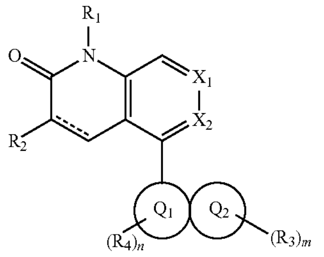

or a pharmaceutical acceptable salt, a stereoisomer, a tautomer, an N-oxide or an ester thereof; wherein ------ represents single bond or double bond;

$X_1$—$X_2$ represents $CR_{X1}$—$CR_{X2}$, N—$CR_{X2}$ or $CR_{X1}$—N;

$R_{X1}$ and $R_{X2}$ independently represents hydrogen, —$OR_a$, alkyl, alkynyl-OH, —N(alkyl)$_2$, cycloalkyl, heterocycloalkyl or heteroaryl; wherein the cycloalkyl, heterocycloalkyl and heteroaryl are optionally substituted with 1 to 3 substituent(s) selected from alkyl, acyl, halogen, —CN, oxo, —$NH_2$, —OH, NHCO alkyl, —$SO_2NH_2$ and —CONH-alkyl;

$R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted with 1 to 3 substituent(s) independently selected from —OH, —COOH, —COO-alkyl, alkoxy, —NH(alkyl)$_2$, —CONH—O-alkyl and heterocycloalkyl; and wherein the heterocycloalkyl and heteroaryl are optionally substituted with 1 to 3 substituent(s) independently selected from alkyl, oxo and acyl;

$Q_1$ represents 5- to 7-membered heterocycloalkyl ring;

$Q_2$ represents fused 5- to 6-membered heteroaryl ring or fused benzo ring;

$R_1$ represents hydrogen, alkyl or haloalkyl;

$R_2$ represents hydrogen, alkyl or —$NH_2$;

$R_3$, at each occurrence, independently, represents hydrogen, halogen, —CN, alkyl, alkoxy, haloalkyl, —CHO, acyl, —CONH-alkyl, —COO-alkyl, —COOH, —OH, —$SO_2NH_2$, —$SO_2$NH-alkyl, —$SO_2$N(alkyl)$_2$, —$SO_2$NH-aryl, —SO-alkyl, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$;

$R_{3A}$, at each occurrence, independently, is alkoxy, —OH, —CONHOH or —NHCO-alkyl;

$R_{3B}$, at each occurrence, independently, is alkyl, alkoxy, —OH, —COOH, oxo, —COO— alkyl, —CONH-alkyl or —CONH—OH;

$R_{3C}$, at each occurrence, independently, is alkyl, —CN, —OH, —$NH_2$, —N(alkyl)$_2$, acyl, oxo, —CONH-alkyl, —NHCO-alkyl or —CONH-alkyl-OH;

$R_4$, at each occurrence, independently, represents hydrogen, alkyl, haloalkyl, acyl, —CONH-alkyl, oxo, —$SO_2$-alkyl, aralkyl, heteroaryl, heterocycloalkyl or cycloalkyl, wherein the alkyl, aryl, heteroaryl and heterocycloalkyl are optionally substituted with 1 to 3 occurrence(s) of $R_{4A}$;

$R_{4A}$, at each occurrence, independently, is alkoxy, —$COOCH_2CH_3$, —COOH or —CONH— alkyl;

m is 1, 2, 3 or 4; and n is 1, 2, 3 or 4.

In one embodiment, the compounds of the present invention can exist as N-oxides, which are defined in that at least one nitrogen of the compounds of the present invention is oxidised. The present invention includes all such possible N-oxides.

In one embodiment, $X_1$—$X_2$ represents $CR_{X1}$—$CR_{X2}$. In one embodiment, $X_1$—$X_2$ represents N—$CR_{X2}$. In one embodiment, $X_1$—$X_2$ represents $CR_{X1}$—N. In one embodiment, $X_1$—$X_2$ represents $CR_{X1}$—CH. In one embodiment, $X_1$ and $X_2$ are selected from (i), (ii) and (iii)

i) $X_1$ is $CR_{X1}$; and $X_2$ is $CR_{X2}$, ii) $X_1$ is N; and $X_2$ is $CR_{X2}$; or iii) $X_1$ is $CR_{X1}$; and $X_2$ is N.

In one embodiment, ------ represents optional bond. In one embodiment, ------ represents single bond. In one embodiment, ------ represents double bond.

In one embodiment, $R_1$ represents hydrogen or alkyl. In one embodiment, $R_1$ represents hydrogen or —$CH_3$. In one embodiment, $R_2$ represents hydrogen or alkyl. In one embodiment, both $R_1$ and $R_2$ represent alkyl. In one embodiment, both $R_1$ and $R_2$ represent —$CH_3$. In one embodiment, both $R_1$ and $R_2$ represent hydrogen. In one embodiment, $R_1$ represents alkyl or haloalkyl; and $R_2$ represents alkyl or amino.

In one embodiment, $R_{X1}$ represents hydrogen, —$OR_a$, —$N(alkyl)_2$, cycloalkyl, heterocycloalkyl or heteroaryl; wherein the heterocycloalkyl and heteroaryl are optionally substituted with 1 to 3 substituent(s) selected from alkyl, acyl, halogen, —CN, oxo, —$NH_2$, —OH, —NHCO-alkyl, —$SO_2NH_2$ and —CONH-alkyl.

In one embodiment, $R_{X1}$ represents hydrogen, —$OR_a$, —$CH_3$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl, wherein each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$.

In one embodiment, $R_{X1}$ represents hydrogen or —$OR_a$. In one embodiment, $R_a$ represents alkyl, haloalkyl, alkoxy, (heterocycloalkyl)alkyl-, heterocycloalkyl, heteroaryl or (heteroaryl)alkyl-; wherein the alkyl, at each occurrence, is optionally substituted by 1 to 3 substituent(s) selected from heterocycloalkyl, —COOH, alkoxy, —$NH(alkyl)_2$ and —CONH—O-alkyl; and wherein the heterocycloalkyl and heteroaryl are optionally substituted by 1 to 3 substituent(s) selected from alkyl and acyl.

In one embodiment, $R_a$ represents alkyl, (heterocycloalkyl)alkyl- or (heteroaryl)alkyl-; wherein the alkyl, at each occurrence, is optionally substituted by 1 to 3 substituent(s) selected from heterocycloalkyl, —COOH, alkoxy, —$NH(alkyl)_2$ and —CONH—O-alkyl.

In one embodiment, $R_a$ represents (heterocycloalkyl)alkyl-, heterocycloalkyl, heteroaryl or (heteroaryl)alkyl-; wherein the heterocycloalkyl and heteroaryl are optionally substituted by 1 to 3 substituent(s) selected from alkyl and acyl.

In one embodiment, $R_{X1}$ represents —$OR_a$; wherein $R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted by 1 to 3 substituent(s) selected from heterocycloalkyl, —COOH, —COO-alkyl, alkoxy, —$NH(alkyl)_2$ and —CONH—O-alkyl; and wherein the heterocycloalkyl and heteroaryl are optionally substituted by 1 to 3 substituent(s) selected from alkyl and acyl.

In one embodiment, $R_{X1}$ represents $OR_a$; wherein $R_a$ represents alkyl, (heterocycloalkyl)alkyl-, heterocycloalkyl, heteroaryl or (heteroaryl)alkyl-; wherein the alkyl, at each occurrence, is optionally substituted by 1 to 3 substituent(s) selected from heterocycloalkyl, —COOH and alkoxy; and wherein the heterocycloalkyl and heteroaryl are optionally substituted by 1 to 3 substituent(s) selected from alkyl and acyl.

In one embodiment, $R_{X1}$ represents —$OR_a$; wherein $R_a$ represents alkyl optionally substituted by heterocycloalkyl.

In one embodiment, $R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—$CONH(OCH_3)$, —$CHF_2$ or —$CH_2$—$CHF_2$.

In certain embodiment, $R_{X2}$ represents hydrogen or alkyl.

In one embodiment, $Q_1$ represents 5- to 7-membered heterocycloalkyl ring. In one embodiment, $Q_1$ represents 5- to 6-membered heterocycloalkyl ring. In one embodiment, $Q_1$ represents 6-membered heterocycloalkyl ring.

In one embodiment, $Q_1$ represents

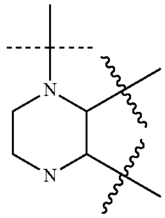 , 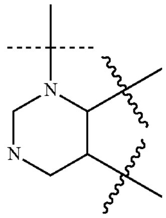 ,

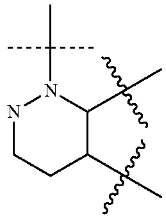 , 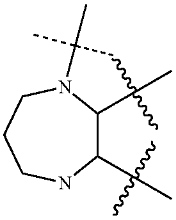 ,

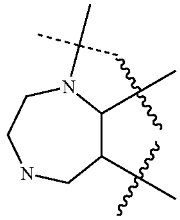 , 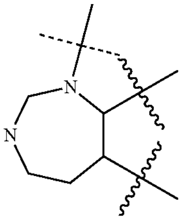 ,

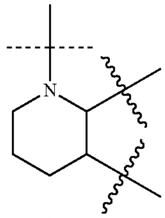 , 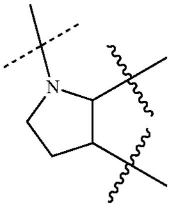 ,

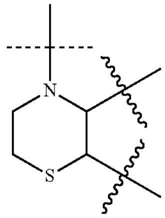 , 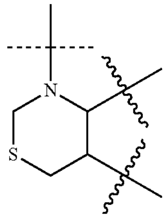 ,

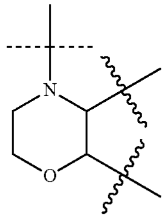 or 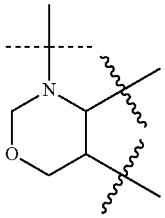 ;

wherein ------ represents point of attachment to the ring containing $X_1$ and $X_2$; and ∿∿∿ represents the points of fusion with $Q_2$.

In one embodiment, $Q_2$ represents fused 5- to 6-membered heteroaryl ring. In one embodiment, $Q_2$ represents fused 6-membered heteroaryl ring. In one embodiment, $Q_2$ represents fused benzo ring.
In one embodiment, $Q_2$ represents
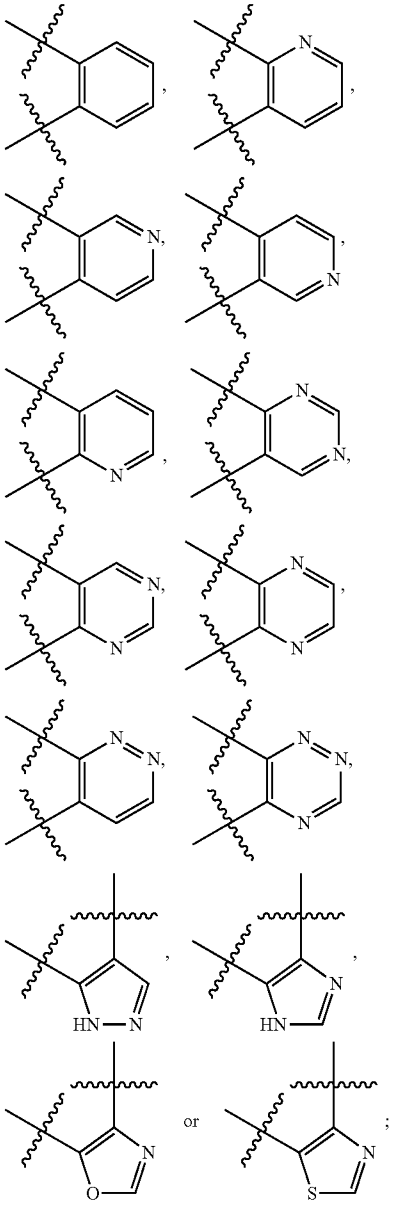
wherein  represents the points of fusion with $Q_1$.
In one embodiment, represents
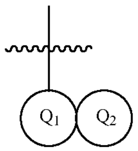
represents
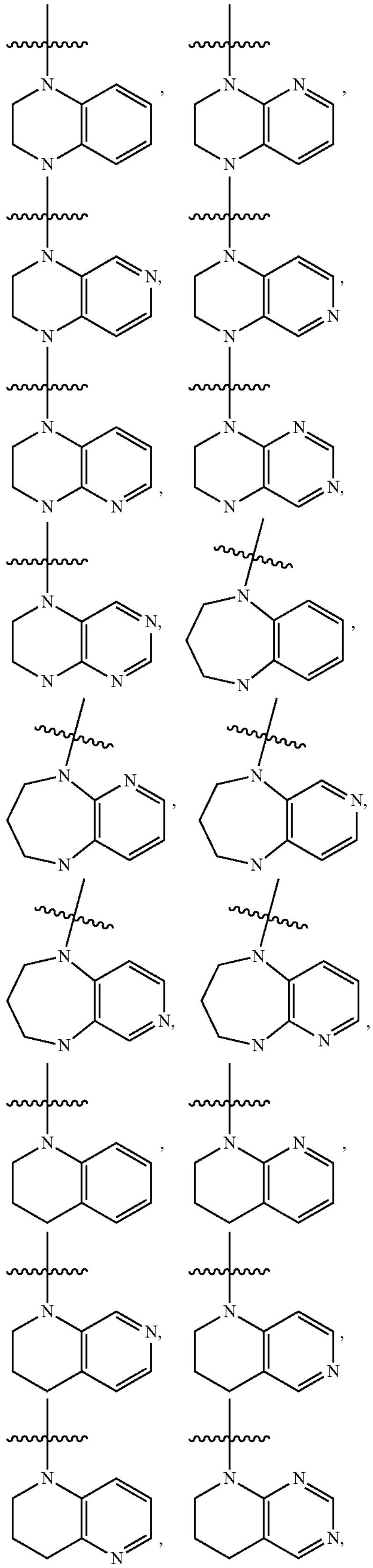

-continued
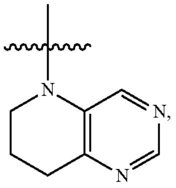 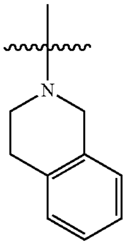 , 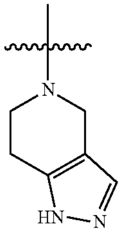 ,
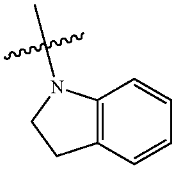 , 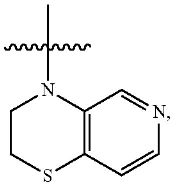
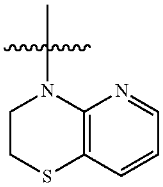 , 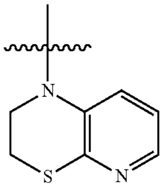 ,
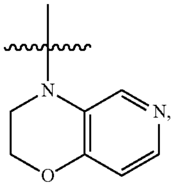 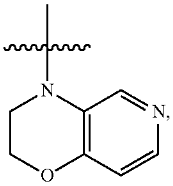 or
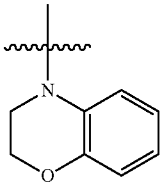 ;
wherein  represents the point of attachment to the ring containing $X_1$ and $X_2$.
In one embodiment,
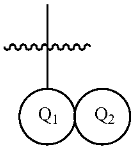
represents
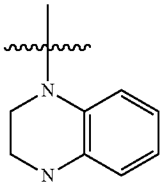 , 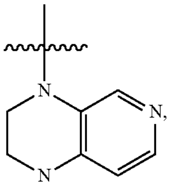
-continued
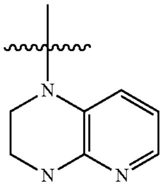 , 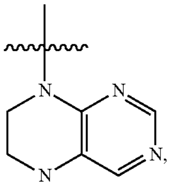
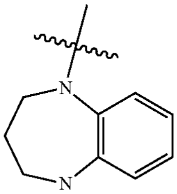 , 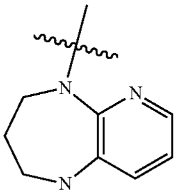 ,
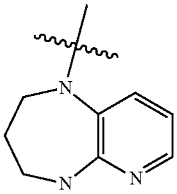 , 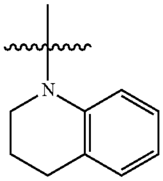 ,
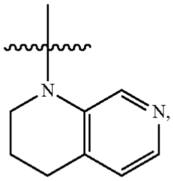 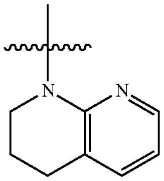 ,
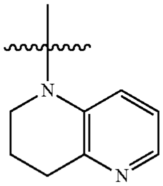 , 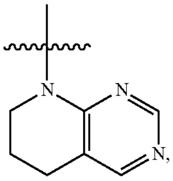
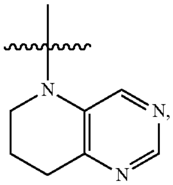 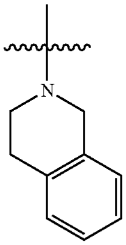 , 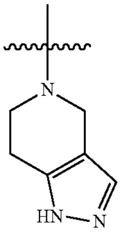 ,
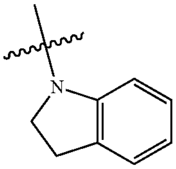 , 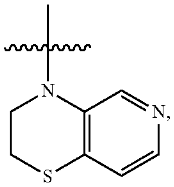
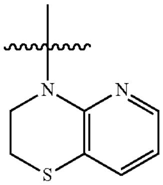 or 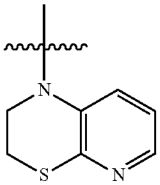 ;
wherein  represents the point of attachment to the ring containing $X_1$ and $X_2$.

In one embodiment,

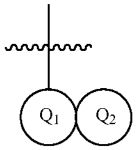

represents

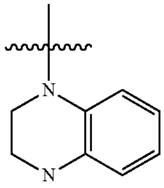
,
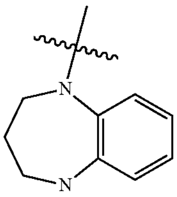
,
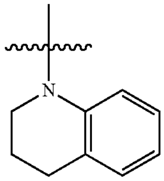
,
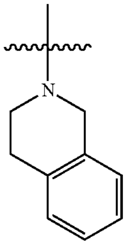
,
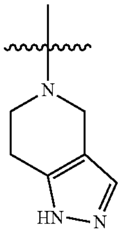
,
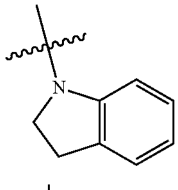
,
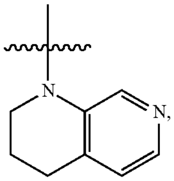
,
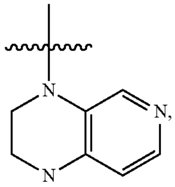
,
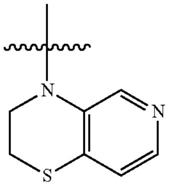
or
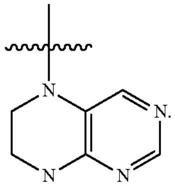
.

In one embodiment,

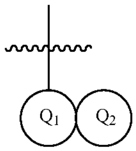

represents

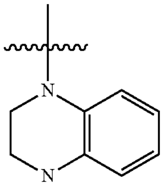
,
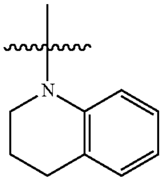
,
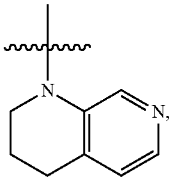
,
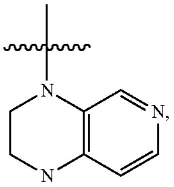
,
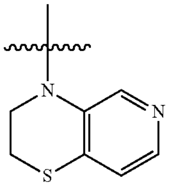
or
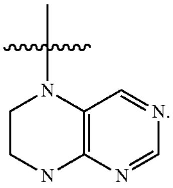
.

In one embodiment,

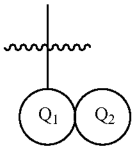

represents

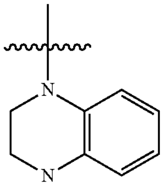
,
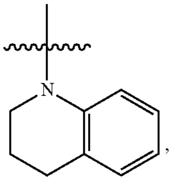
,
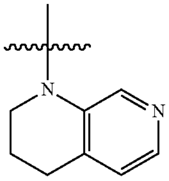
or
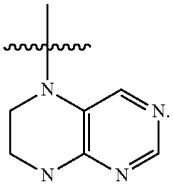
.

In one embodiment, $R_3$, at each occurrence, independently, represents hydrogen, halogen, —CN, alkyl, alkoxy, haloalkyl, —CHO, acyl, —CONH-alkyl, —COO-alkyl, —COOH, oxo, —OH, —$SO_2NH_2$, —$SO_2$NH-alkyl, —$SO_2$N(alkyl)$_2$, —$SO_2$NH-aryl, —SO-alkyl, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl and aryl, at each occurrence, are optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment, $R_3$, at each occurrence, independently, represents hydrogen, —CN, alkyl, alkoxy, haloalkyl, —CHO, —CONH-alkyl, —COO-alkyl, —COOH, —$SO_2NH_2$, —$SO_2$NH-alkyl, —$SO_2N$(alkyl)$_2$, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment, $R_3$, at each occurrence, independently, represents hydrogen, —CN, alkyl, alkoxy, haloalkyl, —CHO, —CONH-alkyl, —COO-alkyl, —COOH, —$SO_2NH_2$, —$SO_2$NH-alkyl, —$SO_2N$(alkyl)$_2$, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, heteroaryl or heterocycloalkyl, wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment, $R_3$, at each occurrence, independently, represents hydrogen, alkyl, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2$NHCOCF3, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl, thienyl, 2H-pyridyl, dihydropyridyl, dihydrooxazolyl, tetrahydrofuranyl, morpholinyl, piperazinyl, pyrrolidinyl, piperidinyl, azetidinyl, cyclopentenyl or cyclopropyl, wherein the alkyl is optionally substituted with 1 to 3 occurrence(s) of $R_{3A}$; the pyrazolyl, pyridyl, tetrazolyl and thienyl are optionally substituted with 1 to 3 occurrence(s) of $R_{3B}$; and the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 occurrence(s) of $R_{3C}$.

In one embodiment, $R_3$, at each occurrence, independently, represents hydrogen, alkyl, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2$NHCOCF3, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the alkyl is optionally substituted with 1 to 3 occurrence(s) of $R_{3A}$; and the pyrazolyl, pyridyl, tetrazolyl and thienyl are optionally substituted with 1 to 3 occurrence(s) of $R_{3B}$.

In one embodiment, $R_{3A}$, at each occurrence, independently, is alkoxy, —OH, —CONHOH or —NHCO—$CH_3$. In one embodiment, $R_{3A}$, at each occurrence, independently, is —OH, —CONHOH or —NHCO—$CH_3$.

In one embodiment, $R_{3B}$, at each occurrence, independently, is alkyl, alkoxy, —OH, —COOH, oxo, —COO-alkyl, —CONH-alkyl or —CONH—OH. In one embodiment, $R_{3B}$, at each occurrence, independently, is alkyl, —OH, oxo, —CONH-alkyl or —CONH—OH. In one embodiment, $R_{3B}$, at each occurrence, independently, is —$CH_3$, —OH, —$CONHCH_3$ or oxo.

In one embodiment, $R_3$, at each occurrence, independently, represents hydrogen, —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) selected from alkyl, alkoxy, —OH, —COOH, oxo, —COO-alkyl, —CONH-alkyl and —CONH—OH.

In one embodiment, $R_3$, at each occurrence, independently, represents hydrogen, —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2$NHCOCF3, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) selected from —$CH_3$, —OH, —$CONHCH_3$ and oxo.

In one embodiment, $R_3$, at each occurrence, independently, represents 2H-pyridyl, dihydropyridyl, dihydrooxazolyl, tetrahydrofuranyl, morpholinyl, piperazinyl, pyrrolidinyl, piperidinyl or azetidinyl; wherein the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 substituent(s) of $R_{3C}$.

In one embodiment, $R_{3C}$, at each occurrence, independently, is alkyl, —CN, —OH, —$NH_2$, —N(alkyl)$_2$, acyl, oxo, —CONH-alkyl, —NHCO-alkyl or —CONH-alkyl-OH. In one embodiment, $R_{3C}$, at each occurrence, independently, is —$CH_3$, —CN, —OH, —$NH_2$, —$N(CH_3)_2$, —$COCH_3$, oxo, —$CONHCH_3$, —$NHCOCH_3$ or —$CONHCH_2CH_2OH$. In one embodiment, $R_{3C}$, at each occurrence, independently, is —$CH_3$, —CN, —OH, —$NH_2$, —$COCH_3$, —$CONHCH_3$ or —$NHCOCH_3$.

In one embodiment, $R_3$, at each occurrence, independently, represents dihydropyridyl, dihydrooxazolyl, tetrahydrofuranyl, morpholinyl, piperazinyl, pyrrolidinyl, piperidinyl or azetidinyl; wherein the dihydropyridyl, dihydrooxazolyl, tetrahydrofuranyl, morpholinyl, piperazinyl, pyrrolidinyl, piperidinyl and azetidinyl are optionally substituted with 1 to 3 substituent(s) selected from —$CH_3$, —CN, —OH, —$NH_2$, —$N(CH_3)_2$, —$COCH_3$, oxo, —$CONHCH_3$, —$NHCOCH_3$ and —$CONHCH_2CH_2OH$.

In one embodiment, $R_4$, at each occurrence, independently, represents hydrogen, alkyl, haloalkyl, acyl, —CONH-alkyl, oxo, —$SO_2$-alkyl, aralkyl, heteroaryl, heterocycloalkyl or cycloalkyl, wherein the alkyl, aryl, heteroaryl and heterocycloalkyl are optionally substituted with 1 to 3 occurrence(s) of $R_{4A}$.

In one embodiment, $R_{4A}$, at each occurrence, independently, is alkoxy, —$COOCH_2CH_3$, —COOH or —CONH-alkyl. In one embodiment, $R_{4A}$, at each occurrence, independently, is —$OCH_3$, —$COOCH_2CH_3$, —COOH or —$CONHCH_3$.

In further embodiments, $R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein morpholinyl, pyranyl and cyclopropyl are optionally substituted with 1 to 3 substituent(s) selected from —$OCH_3$, —$COOCH_2CH_3$, —COOH and —$CONHCH_3$.

In one embodiment, m is 1, 2 or 3. In one embodiment, m is 1 or 2.

In one embodiment, n is 1, 2 or 3. In one embodiment, n is 1 or 2.

In one embodiment, the present invention provides a compound of formula (I): or a pharmaceutical acceptable salt, stereoisomer, a tautomer, an N-oxide or an ester thereof; wherein

- ------ represents single bond or double bond;
- $X_1$—$X_2$ represents $CR_{X1}$—$CR_{X2}$, N—$CR_{X2}$ or $CR_{X1}$—N;
- $R_{X1}$ represents hydrogen, —$OR_a$, —$CH_3$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; wherein each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$.
- $R_{X2}$ represents hydrogen or —$CH_3$;
- $R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—$CONH(OCH_3)$, —$CHF_2$ or —$CH_2$—$CHF_2$,

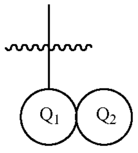

represents

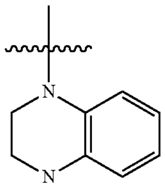,
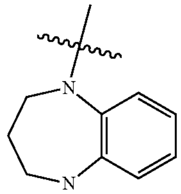,
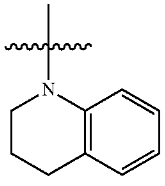,
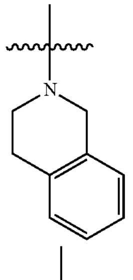,
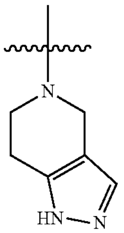,
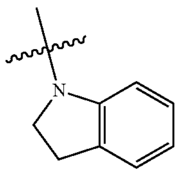,
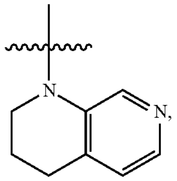

-continued

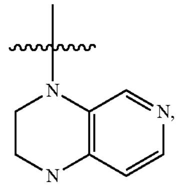
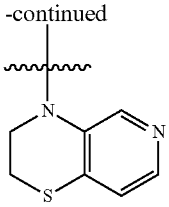
or
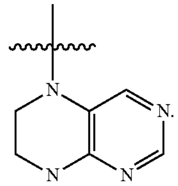

- $R_3$, at each occurrence, independently, represents hydrogen, —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2NH$(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl, thienyl, 2H-pyridyl, dihydropyridyl, dihydrooxazolyl, tetrahydrofuranyl, morpholinyl, piperazinyl, pyrrolidinyl, piperidinyl or azetidinyl; wherein the pyrazolyl, pyridyl, tetrazolyl and thienyl are optionally substituted with 1 to 3 substituent(s) selected from methyl, ethyl, methoxy, —OH, —COOH, oxo, —COO-alkyl, —CONH-alkyl or —CONH—OH; and the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 substituent(s) selected from —$CH_3$, —CN, —OH, —$NH_2$, —$N(CH_3)_2$, —$COCH_3$, oxo, —$CONHCH_3$, —$NHCOCH_3$ and —$CONHCH_2CH_2OH$;
- $R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl.

In one embodiment, the present invention provides a compound of formula (IA):

(IA)

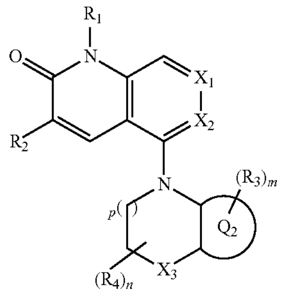

or a pharmaceutical acceptable salt, a stereoisomer, a tautomer, an N-oxide or an ester thereof;

wherein $X_3$ represents N, O, S or C; p is 0, 1 or 2; and $Q_2$, $R_1$, $X_1$, $X_2$, $R_3$, $R_4$, m and n are as defined in compound of formula (I).

In one embodiment of compound of formula (IA), $X_3$ represents N, S or C. In one embodiment, $X_3$ represents N or C.

In one embodiment of compound of formula (IA), p is 1.

In one embodiment of compound of formula (IA), $R_1$ and $R_2$ independently represents hydrogen or alkyl. In one embodiment, $R_1$ and $R_2$ independently represents hydrogen or —$CH_3$.

In one embodiment of compound of formula (IA), $X_1$—$X_2$ represents $CR_{X1}$—CH. In one embodiment of compound of formula (IA), $X_1$—$X_2$ represents $CR_{X1}$—N.

In one embodiment of compound of formula (IA), $Q_2$ represents fused 5- to 6-membered heteroaryl ring or fused benzo ring.

In one embodiment of compound of formula (IA), the formula

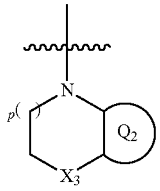

represents

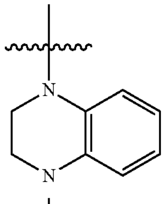,
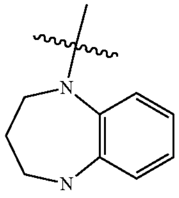,
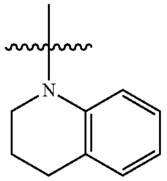,
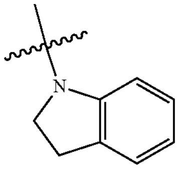,
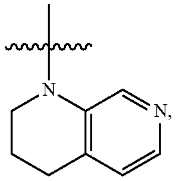
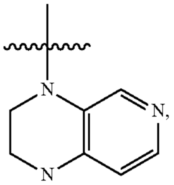
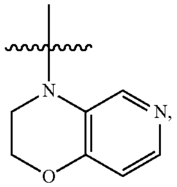
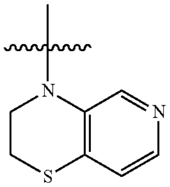
or -continued

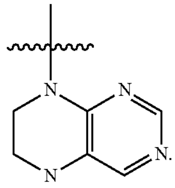

In one embodiment compound of formula (IA), $R_3$, at each occurrence, independently, represents hydrogen, alkyl, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2NH$(phenyl), —$SOCH_3$, —$SO_2CH_3$, —$SO_2CH(CH_3)_2$, —$SO_2NHCOCH_3$, —$SO_2NHCOCF_3$, —$S(O)(NH)CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl, thienyl, 2H-pyridyl, dihydropyridyl, dihydrooxazolyl, tetrahydrofuranyl, morpholinyl, piperazinyl, pyrrolidinyl, piperidinyl, azetidinyl, cyclopentenyl or cyclopropyl, wherein the alkyl is optionally substituted with 1 to 3 occurrence(s) of $R_{3A}$; the pyrazolyl, pyridyl, tetrazolyl and thienyl are optionally substituted with 1 to 3 occurrence(s) of $R_{3B}$; and the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 occurrence(s) of $R_{3C}$.

In one embodiment compound of formula (IA), $R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein morpholinyl, pyranyl and cyclopropyl are optionally substituted with 1 to 3 substituent(s) selected from —$OCH_3$, —$COOCH_2CH_3$, —COOH and —$CONHCH_3$.

In one embodiment, the present invention provides a compound of formula (IA): or a pharmaceutical acceptable salt, a stereoisomer, a tautomer, an N-oxide or an ester thereof; wherein $R_1$ and $R_2$ independently represents hydrogen or —$CH_3$;

$X_1$—$X_2$ represents $CR_{X1}$—CH or $CR_{X1}$—N;

$R_{X1}$ represents hydrogen, —$OR_a$, —$CH_3$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl, wherein each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$;

$R_{X2}$ represents hydrogen or alkyl;

$R_a$ represents alkyl, haloalkyl, alkoxy, (heterocycloalkyl)alkyl-, heterocycloalkyl, heteroaryl or (heteroaryl)alkyl-; wherein the alkyl, at each occurrence, is optionally substituted by 1 to 3 substituent(s) independently selected from heterocycloalkyl, —COOH, alkoxy, —$NH(alkyl)_2$ and —CONH—O-alkyl; and wherein the heterocycloalkyl and heteroaryl are optionally substituted by 1 to 3 substituent(s) independently selected from alkyl and acyl;

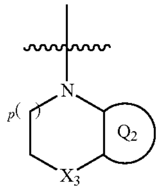

represents

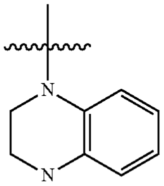,
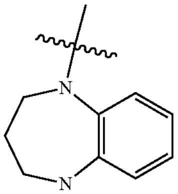,
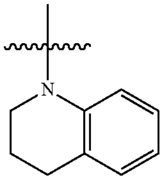,
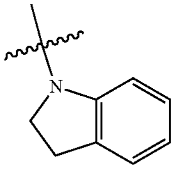,
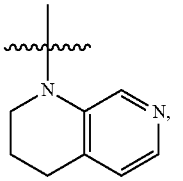,
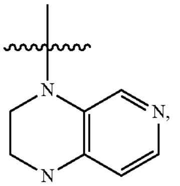,
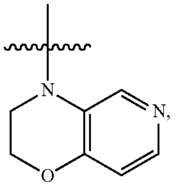,
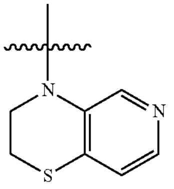 or
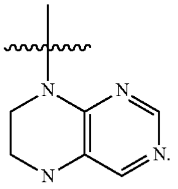.

$R_3$, at each occurrence, independently, represents hydrogen, —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2NH$(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl, thienyl, 2H-pyridyl, dihydropyridyl, dihydrooxazolyl, tetrahydrofuranyl, morpholinyl, piperazinyl, pyrrolidinyl, piperidinyl or azetidinyl; wherein the pyrazolyl, pyridyl, tetrazolyl and thienyl are optionally substituted with 1 to 3 substituent(s) independently selected from alkyl, alkoxy, —OH, —COOH, oxo, —COO-alkyl, —CONH-alkyl and —CONH—OH; and the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 substituent(s) independently selected from —$CH_3$, —CN, —OH, —$NH_2$, —$N(CH_3)_2$, —$COCH_3$, oxo, —$CONHCH_3$, —$NHCOCH_3$ and —$CONHCH_2CH_2OH$;

$R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; and n is 1, 2 or 3.

In one embodiment, the present invention provides a compound of formula (IA): or a pharmaceutical acceptable salt, a stereoisomer, a tautomer, an N-oxide or an ester thereof; wherein $X_1$—$X_2$ represents $CR_{X1}$—CH or $CR_{X1}$—N;

$R_{X1}$ represents hydrogen, —$OR_a$, —$CH_3$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; wherein each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$.

$R_{X2}$ represents hydrogen or alkyl;

$R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—$CONH(OCH_3)$, —$CHF_2$ or —$CH_2$—$CHF_2$;

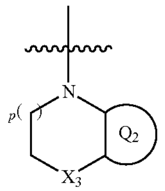

represents

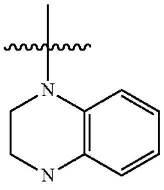,
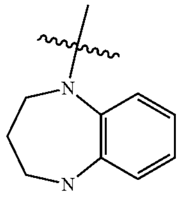,
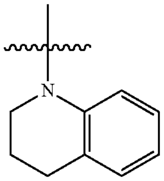,
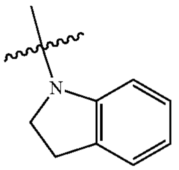,

-continued

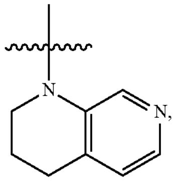 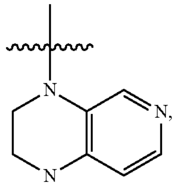

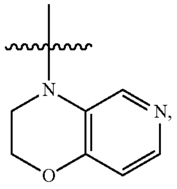 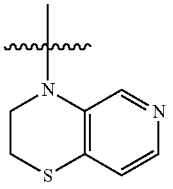 or

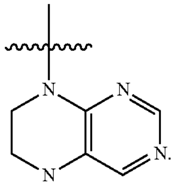

$R_3$, at each occurrence, independently, represents hydrogen, —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2NH$(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl, thienyl, 2H-pyridyl, dihydropyridyl, dihydrooxazolyl, tetrahydrofuranyl, morpholinyl, piperazinyl, pyrrolidinyl, piperidinyl or azetidinyl; wherein the pyrazolyl, pyridyl, tetrazolyl and thienyl are optionally substituted with 1 to 3 substituent(s) independently selected from alkyl, alkoxy, —OH, —COOH, oxo, COO alkyl, —CONH-alkyl and —CONH—OH; and the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 substituent(s) independently selected from —$CH_3$, —CN, —OH, —$NH_2$, —$N(CH_3)_2$, —$COCH_3$, oxo, —$CONHCH_3$, —$NHCOCH_3$ and —$CONHCH_2CH_2OH$;

$R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; and n is 1, 2 or 3.

In one embodiment, the present invention provides a compound of formula (IB):

(IB)

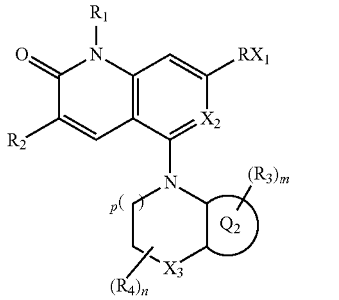

or a pharmaceutical acceptable salt, a stereoisomer, a tautomer, an N-oxide or an ester thereof; wherein $X_2$, $X_3$, $Q_2$, $R_{X1}$, $R_1$, $R_2$, $R_3$, $R_4$, m, n, and p are as defined in compound of formula (IA).

In one embodiment of compound of formula (IB), $X_2$ represents CH or N.

In one embodiment of compound of formula (IB), $R_{X1}$ represents hydrogen, —$OR_a$, —$CH_3$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; wherein each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$.

In one embodiment of compound of formula (IB), $R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted by 1 to 3 substituent(s) selected from heterocycloalkyl, —OH, —COOH, —COO-alkyl, alkoxy, —NH(alkyl)$_2$ and —CONH—O-alkyl; and wherein the heterocycloalkyl and heteroaryl are optionally substituted by 1 to 3 substituent(s) selected from alkyl and acyl.

In one embodiment of compound of formula (IB), $R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—CONH($OCH_3$), —$CHF_2$ or —$CH_2$—$CHF_2$.

In one embodiment of compound of formula (IB), $Q_2$ represents fused 5- to 6-membered heteroaryl ring. In one embodiment of compound of formula (IB), $Q_2$ represents fused benzo ring.

In one embodiment of compound of formula (IB), $Q_2$ represents

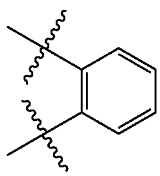, 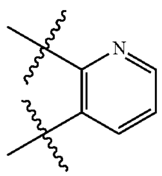,

-continued

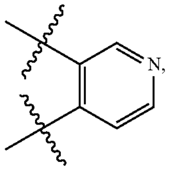 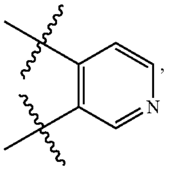,

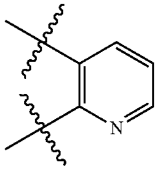, 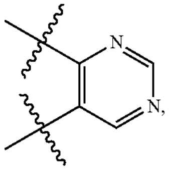

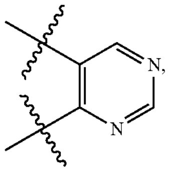 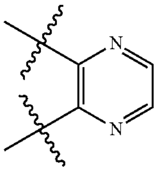,

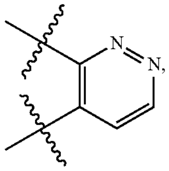 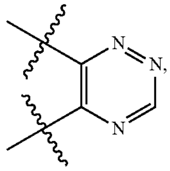

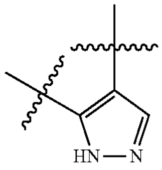, 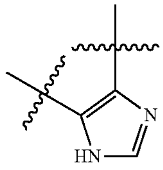,

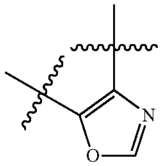 or 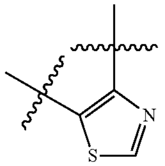;

wherein ~~~ represents the points of fusion with $Q_1$.

In one embodiment of compound of formula (IB), $Q_2$ represents $X_3$ represents N, O, S or C.

In one embodiment of compound of formula (IB), the formula

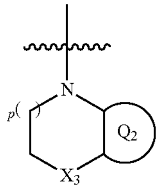

represents

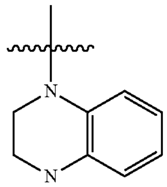, 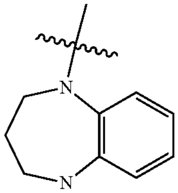,

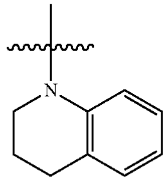, 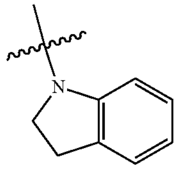,

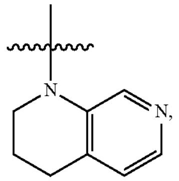 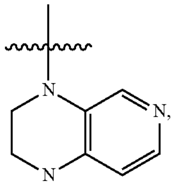

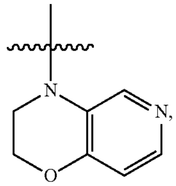 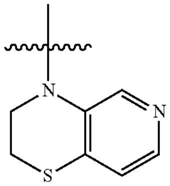 or

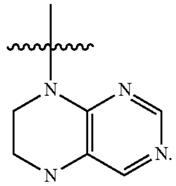.

In one embodiment of compound of formula (IB), $R_3$, at each occurrence, independently, represents hydrogen, halogen, —CN, alkyl, alkoxy, haloalkyl, —CHO, acyl, —CONH-alkyl, —COO-alkyl, —COOH, oxo, —OH, —$SO_2NH_2$, —$SO_2$NH-alkyl, —$SO_2$N(alkyl)$_2$, —$SO_2$NH-aryl, —SO-alkyl, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IB), $R_3$, at each occurrence, independently, represents hydrogen, —$CH_3$, —$CH_2OH$, —$CH_2$CONHOH, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) independently selected from alkyl, alkoxy, —OH, —COOH, oxo, —COO-alkyl, —CONH-alkyl and —CONH—OH.

In one embodiment of compound of formula (IB), $R_4$, at each occurrence, independently, represents hydrogen, $—CH_3$, $—CH_2CH_3$, $—CH_2COOH$, $—CH_2$(p-($OCH_3$)phenyl), $—CHF_2$, $—COCH_3$, $—CH_2COOCH_2CH_3$, $—CH_2CONHCH_3$, $—CONHCH_3$, oxo, $—SO_2CH_2CH_3$, morpholinyl, pyranyl or cyclopropyl; wherein morpholinyl, pyranyl and cyclopropyl are optionally substituted with 1 to 3 substituent(s) selected from $—OCH_3$, $—COOCH_2CH_3$, —COOH and $—CONHCH_3$.

In one embodiment of compound of formula (IB), m is 1, 2 or 3. In one embodiment of compound of formula (IB), m is 1 or 2.

In one embodiment of compound of formula (IB), n is 1, 2 or 3. In one embodiment of compound of formula (IB), n is 1 or 2.

In one embodiment, the present invention provides a compound of formula (IB): a pharmaceutical acceptable salt, a stereoisomer, a tautomer, an N-oxide or an ester thereof; wherein $X_2$ represents CH or N.

$R_{X1}$ represents hydrogen, $—OR_a$, $—CH_3$, $—C{\equiv}CCH_2OH$, $—N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl, each is optionally substituted with 1 to 3 substituent(s) selected from $—CH_3$, $—COCH_3$, —F, —CN, oxo, $—NH_2$, —OH, $—NHCOCH_3$, $—SO_2NH_2$ and $—CONHCH_3$;

$R_a$ represents $—CH_3$, $—CH(CH_3)_2$, $—CH_2—COOC(CH_3)_3$, $—CH_2$-piperidinyl($CH_3$), $—CH_2—CH_2$-morpholine, $—CH_2—CH_2—OCH_3$, $—CH_2—CH_2—N(CH_3)_2$, azetidinyl, $—CH_2$-oxazole, $—CH_2—CH_2—OH$, $—CH_2—CH_2$-piperizinyl($COCH_3$), $—CH_2—COOH$, $—CH_2—CONH(OCH_3)$, $—CHF_2$ or $—CH_2—CHF_2$;

$Q_2$ represents

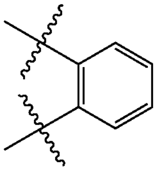, 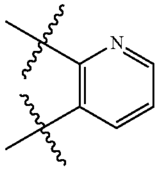,

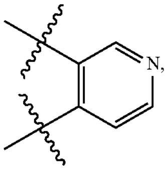 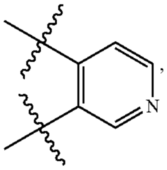,

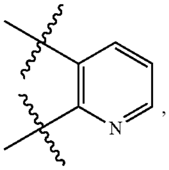, 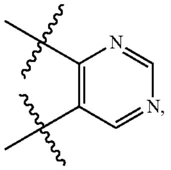

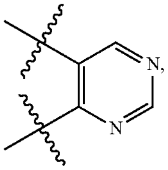 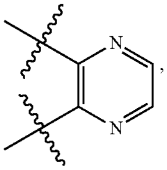,

-continued

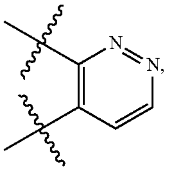 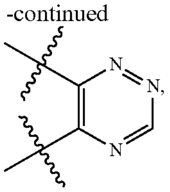

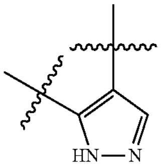, 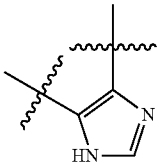,

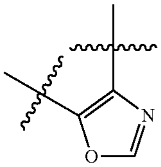 or 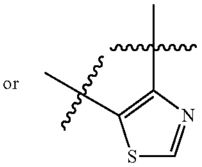;

$R_3$, at each occurrence, independently, represents hydrogen, $—CH_3$, $—CH_2OH$, $—CH_2CONHOH$, —F, —CN, $—OCH_3$, $—CHF_2$, $—CF_3$, —CHO, acyl, $—CONHCH_3$, $—COOCH_3$, —COOH, oxo, —OH, $—SO_2NH_2$, $—SO_2NHCH_3$, $—SO_2N(CH_3)_2$, $—SO_2NH$(phenyl), $—SOCH_3$, $—SO_2CH_3$, $—SO_2CH(CH_3)_2$, $—SO_2NHCOCH_3$, $—SO_2NHCOCF_3$, —S(O)(NH)$CH_3$, $—NHSO_2CH_3$, $—NHSO_2CH_2CH_3$, $—NHSO_2CH(CH_3)_3$, $—NHCOCH_3$, $—N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) selected from alkyl, alkoxy, —OH, —COOH, oxo, —COO— alkyl, —CONH-alkyl and —CONH—OH;

$R_4$, at each occurrence, independently, represents hydrogen, $—CH_3$, $—CH_2CH_3$, $—CH_2COOH$, $—CH_2$(p-($OCH_3$)phenyl), $—CHF_2$, $—COCH_3$, $—CH_2COOCH_2CH_3$, $—CH_2CONHCH_3$, $—CONHCH_3$, oxo, $—SO_2CH_2CH_3$, morpholinyl, pyranyl or cyclopropyl; wherein morpholinyl, pyranyl and cyclopropyl are optionally substituted with 1 to 3 substituent(s) independently selected from $—OCH_3$, $—COOCH_2CH_3$, —COOH and $—CONHCH_3$;

$X_3$ represents N, O, S or C;

p is 0, 1 or 2; and n is 1, 2 or 3.

In one embodiment, the present invention provides a compound of formula (IC):

(IC)

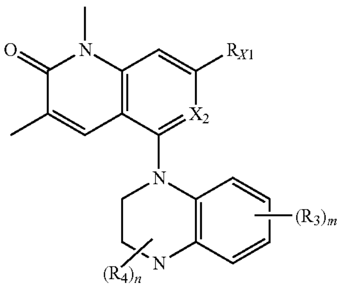

or a pharmaceutical acceptable salt, a stereoisomer, a tautomer, an N-oxide or an ester thereof; wherein $X_2$, $R_{X1}$, $R_3$, $R_4$, m and n are as defined in compound of formula (I).

In one embodiment of compound of formula (IC), $R_{X1}$ represents hydrogen, —$OR_a$, —$CH_3$, —$C\equiv CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl, each is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$.

In one embodiment of compound of formula (IC), $R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted by 1 to 3 substituent(s) selected from heterocycloalkyl, —OH, —COOH, —COO-alkyl, alkoxy, —NH(alkyl)$_2$ and —CONH—O-alkyl; and wherein the heterocycloalkyl or heteroaryl is optionally substituted by 1 to 3 substituent(s) selected from alkyl and acyl.

In one embodiment of compound of formula (IC), $R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—CONH($OCH_3$), —$CHF_2$ or —$CH_2$—$CHF_2$.

In one embodiment of compound of formula (IC), $R_3$, at each occurrence, independently, represents halo, —CN, alkyl, alkoxy, haloalkyl, —CHO, acyl, —CONH-alkyl, —COO-alkyl, —COOH, oxo, —OH, —$SO_2NH_2$, —$SO_2$NH-alkyl, —$SO_2$N(alkyl)$_2$, —$SO_2$NH-aryl, —SO—alkyl, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IC), $R_3$, at each occurrence, independently, represents —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl or thienyl is optionally substituted with 1 to 3 substituent(s) selected from alkyl, alkoxy, —OH, —COOH, oxo, —COO-alkyl, —CONH-alkyl and —CONH—OH.

In one embodiment of compound of formula (IC), $R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein morpholinyl, pyranyl and cyclopropyl are optionally substituted with 1 to 3 substituent(s) selected from —$OCH_3$, —$COOCH_2CH_3$, —COOH and —$CONHCH_3$.

In one embodiment of compound of formula (IC), m is 1, 2 or 3. In one embodiment of compound of formula (IB), m is 1 or 2.

In one embodiment, the present invention provides a compound of formula (IC): a pharmaceutical acceptable salt, a stereoisomer, a tautomer, an N-oxide or an ester thereof; wherein $X_2$ represents CH or N;

$R_{X1}$ represents hydrogen, —$OR_a$, —$CH_3$, —$C\equiv CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; wherein, each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$;

$R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—CONH($OCH_3$), —$CHF_2$ or —$CH_2$—$CHF_2$;

$R_3$, at each occurrence, independently, represents —$CH_3$, —$CH_2OH$, —$CH_2CONHOH$, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl or thienyl is optionally substituted with 1 to 3 substituent(s) independently selected from alkyl, alkoxy, —OH, —COOH, oxo, —COO-alkyl, —CONH-alkyl and —CONH—OH;

$R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein morpholinyl, pyranyl and cyclopropyl are optionally substituted with 1 to 3 substituent(s) independently selected from —$OCH_3$, —$COOCH_2CH_3$, —COOH and —$CONHCH_3$;

m is 1, 2 or 3;

n is 1, 2 or 3.

In one embodiment, the present invention provides a compound of formula (ID):

(ID)

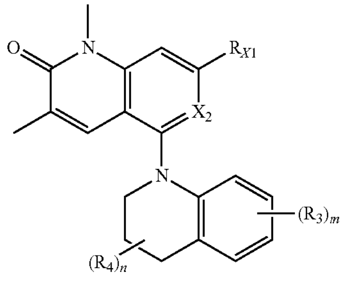

or a pharmaceutical acceptable salt, a stereoisomer, a tautomer, an N-oxide or an ester thereof; wherein $X_2$, $R_{X1}$, $R_3$, $R_4$, m and n are as defined in compound of formula (I).

In one embodiment of compound of formula (ID), $X_2$ represents CH or N.

In one embodiment of compound of formula (ID), $R_{X1}$ represents hydrogen, —$OR_a$, —$CH_3$, azetidinyl, furanyl, pyrrolidinyl, piperazinyl, piperidinyl, morpholinyl, pyranyl, dihydropyranyl, 8-oxa-3-azabicyclo[3.2.1]octanyl, 2-oxa-6-azaspiro[3.3]heptanyl, 3-oxa-6-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; wherein each cyclic group is optionally substituted with 1 to 3 substituent(s) selected from —$CH_3$, —$COCH_3$, —$NH_2$, —OH, —$SO_2NH_2$ and —$CONHCH_3$.

In one embodiment of compound of formula (ID), $R_3$, at each occurrence, independently, represents hydrogen, halogen, —CN, alkyl, alkoxy, haloalkyl, —OH, heteroaryl or heterocycloalkyl, wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (ID), $R_3$, at each occurrence, independently, represents hydrogen, alkoxy, haloalkyl, —OH, heteroaryl or heterocycloalkyl, wherein the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (ID), $R_{3A}$, at each occurrence, independently, is alkoxy, —OH, —CONHOH or —NHCO-alkyl.

In one embodiment of compound of formula (ID), $R_{3B}$, at each occurrence, independently, is alkyl, alkoxy, —OH, —COOH, oxo, —COO-alkyl, —CONH-alkyl or —CONH—OH.

In one embodiment of compound of formula (ID), $R_{3C}$, at each occurrence, independently, is alkyl, —CN, —OH, —$NH_2$, —$N(alkyl)_2$, acyl, oxo, —CONH-alkyl, —NHCO-alkyl or —CONH-alkyl-OH.

In one embodiment of compound of formula (ID), $R_{3C}$, at each occurrence, independently, is —$CH_3$, —$N(alkyl)_2$, acyl, —CONH-alkyl or —NHCO-alkyl.

In one embodiment of compound of formula (ID), $R_{3C}$, at each occurrence, independently, is —$CH_3$, acyl, —CONH-alkyl or —NHCO-alkyl.

In one embodiment of compound of formula (ID), $R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo or —$SO_2CH_2CH_3$.

In one embodiment of compound of formula (ID), $R_4$, at each occurrence, independently, represents hydrogen, —$CH_3$, —$CH_2CH_3$, —$CH_2COOH$, —$CH_2$(p-($OCH_3$)phenyl), —$CHF_2$ or —$COCH_3$.

In one embodiment of compound of formula (ID), $R_4$, at each occurrence, independently, represents hydrogen, —$CH_3$, —$CH_2CH_3$ or —$CH_2COOH$.

In one embodiment of compound of formula (ID), m is 1, 2 or 3.

In one embodiment of compound of formula (ID), n is 1 or 2.

In one embodiment, the present invention provides a compound of formula (ID): or a pharmaceutical acceptable salt, a stereoisomer, a tautomer, an N-oxide or an ester thereof; wherein $X_2$ represents CH or N;

$R_{X1}$ represents hydrogen, —$OR_a$, —$CH_3$, azetidinyl, furanyl, pyrrolidinyl, piperazinyl, piperidinyl, morpholinyl, pyranyl, dihydropyranyl, 8-oxa-3-azabicyclo[3.2.1]octanyl, 2-oxa-6-azaspiro[3.3]heptanyl, 3-oxa-6-azabicyclo[3.2.1]octanyl, 2-oxa-6-azaspiro[3.4]octanyl or 2-oxa-5-azabicyclo[2.2.1]heptanyl, wherein each is optionally substituted with 1 to 3 substituent(s) selected from —$CH_3$, —$COCH_3$, —$NH_2$, —OH, —$SO_2NH_2$ and —$CONHCH_3$;

$R_a$ represents hydrogen, —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$—$CH_2$—OH, —$CH_2$—$CH_2$-piperizinyl($COCH_3$) or —$CH_2$—COOH;

$R_3$, at each occurrence, independently, represents alkyl, haloalkyl, acyl, oxo, —OH, heteroaryl, heterocycloalkyl or cycloalkyl, wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$;

$R_{3A}$, at each occurrence, independently, is alkoxy, —OH, —CONHOH or —NHCO-alkyl;

$R_{3B}$, at each occurrence, independently, is alkyl, alkoxy, —OH, —COOH, oxo, —COO— alkyl, —CONH-alkyl or —CONH—OH;

$R_{3C}$, at each occurrence, independently, is alkyl, —CN, —OH, —$NH_2$, —$N(alkyl)_2$, acyl, oxo, —CONH-alkyl, —NHCO-alkyl or —CONH-alkyl-OH;

$R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2CONHCH_3$, —$CONHCH_3$;

m is 1, 2 or 3;

n is 1, 2 or 3.

In one embodiment, the present invention provides a compound of formula (IE):

(IE)

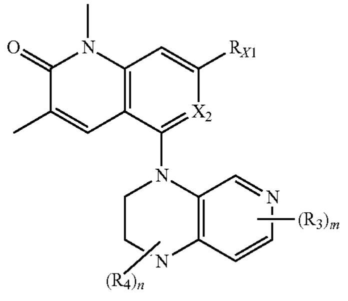

or a pharmaceutical acceptable salt, a stereoisomer, a tautomer, an N-oxide or an ester thereof; wherein $R_{X1}$, $R_3$, m and n are as defined in compound of formula (I).

In one embodiment of compound of formula (IE), $X_2$ represents CH or N.

In one embodiment of compound of formula (IE), $R_{X1}$ represents hydrogen, —$OR_a$, —$CH_3$, —$CH(CH_3)_2$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; each cyclic group is optionally substituted with 1 to 3 substituent(s) independently selected from —$CH_3$, —$COCH_3$, —F, —CN, oxo, —$NH_2$, —OH, —$NHCOCH_3$, —$SO_2NH_2$ and —$CONHCH_3$.

In one embodiment of compound of formula (IE), $R_{X1}$ represents hydrogen, —$OR_a$, —$CH_3$, —$CH(CH_3)_2$, —C≡$CCH_2OH$, pyrrolidinyl, piperazinyl, piperidinyl, morpholinyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; wherein each cyclic group is optionally substituted with 1 to 3 substituent(s) independently selected from —$CH_3$, —$COCH_3$, —F, —CN, —$NH_2$, —OH, —$NHCOCH_3$ and —$CONHCH_3$.

In one embodiment of compound of formula (IE), $R_{X1}$ represents hydrogen, —$OR_a$, —$CH_3$, —$CH(CH_3)_2$, —C≡$CCH_2OH$, piperidinyl, morpholinyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isoxazolyl; each cyclic group is optionally substituted with 1 to 3 substituent(s) independently selected from —$CH_3$, —CN, —$NH_2$ and —OH.

In one embodiment of compound of formula (IE), $R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted by 1 to 3 substituent(s) selected from heterocycloalkyl, —OH, —COOH, —COO-alkyl, alkoxy, —NH(alkyl)$_2$ and —CONH—O-alkyl; and wherein the heterocycloalkyl and heteroaryl are optionally substituted by 1 to 3 substituent(s) selected from alkyl and acyl.

In one embodiment of compound of formula (IE), $R_a$ represents hydrogen, alkyl, haloalkyl, (heterocycloalkyl) alkyl- or heterocycloalkyl; wherein the alkyl, at each occurrence, is optionally substituted by 1 to 3 substituent(s) selected from heterocycloalkyl, —OH, —COOH, —COO-alkyl, alkoxy and —NH(alkyl)$_2$; and wherein the heterocycloalkyl and heteroaryl are optionally substituted by 1 to 3 substituent(s) selected from alkyl and acyl.

In one embodiment of compound of formula (IE), $R_a$ represents hydrogen, —$CH_3$, —$CH(CH_3)_2$, —$CH_2$—COOC$(CH_3)_3$, —$CH_2$-piperidinyl($CH_3$), —$CH_2$—$CH_2$-morpholine, —$CH_2$—$CH_2$—$OCH_3$, —$CH_2$—$CH_2$—N$(CH_3)_2$, azetidinyl, —$CH_2$—$CH_2$—OH, —$CH_2$—$CH_2$-piperizinyl($COCH_3$) or $CH_2$—COOH.

In one embodiment of compound of formula (IE), $R_3$, at each occurrence, independently, represents hydrogen, halogen, —CN, alkyl, alkoxy, haloalkyl, —CHO, acyl, —CONH-alkyl, —COO-alkyl, —COOH, oxo, —OH, —$SO_2NH_2$, —$SO_2$NH-alkyl, —$SO_2$N(alkyl)$_2$, —$SO_2$NH-aryl, —SO-alkyl, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IE), $R_3$, at each occurrence, independently, represents hydrogen, alkyl, haloalkyl, acyl, oxo, —OH, heteroaryl, heterocycloalkyl or cycloalkyl, wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IE), $R_{3A}$, at each occurrence, independently, is alkoxy, —OH, —CONHOH or —NHCO-alkyl.

In one embodiment of compound of formula (IE), $R_{3B}$, at each occurrence, independently, is alkyl, alkoxy, —OH, —COOH, oxo, —COO-alkyl, —CONH-alkyl or —CONH—OH.

In one embodiment of compound of formula (IE), $R_{3C}$, at each occurrence, independently, is alkyl, —CN, —OH, —$NH_2$, —N(alkyl)$_2$, acyl, oxo, —CONH-alkyl, —NHCO-alkyl or —CONH-alkyl-OH.

In one embodiment of compound of formula (IE), $R_3$, at each occurrence, independently, represents hydrogen, —$CH_3$, —$CH_2OH$, —$CH_2$CONHOH, —$CHF_2$, —$CF_3$, acyl, oxo, —OH, —$SO_2NH_2$, pyrazolyl, pyridyl, tetrazolyl, thienyl, pyrrolidinyl, piperazinyl, piperidinyl or morpholinyl; wherein the pyrazolyl, pyridyl, tetrazolyl, thienyl, pyrrolidinyl, piperazinyl, piperidinyl and morpholinyl is optionally substituted with 1 to 3 substituent(s) selected from alkyl, alkoxy, —OH, —COOH, oxo, —COO-alkyl, —CONH-alkyl and —CONH—OH.

In one embodiment of compound of formula (IE), $R_4$, at each occurrence, independently, represents hydrogen, —$CH_3$, —$CH_2CH_3$, —$CH_2$COOH, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein morpholinyl, pyranyl and cyclopropyl are optionally substituted with 1 to 3 substituent(s) selected from —$OCH_3$, —$COOCH_2CH_3$, —COOH and —$CONHCH_3$.

In one embodiment of compound of formula (IE), $R_4$, at each occurrence, independently, represents hydrogen, —$CH_3$, —$CH_2CH_3$, —$CH_2$COOH, —$CH_2$(p-($OCH_3$)phenyl), —$CHF_2$, —$COCH_3$, —$CH_2CONHCH_3$, —$CONHCH_3$.

In one embodiment of compound of formula (IE), m is 1, 2 or 3. In one embodiment of compound of formula (IE), m is 1 or 2.

In one embodiment of compound of formula (IE), n is 1 or 2.

In one embodiment, the present invention provides a compound of formula (IE): a pharmaceutical acceptable salt, a stereoisomer, a tautomer, an N-oxide or an ester thereof; wherein $X_2$ represents CH or N;

$R_{X1}$ represents hydrogen, —$OR_a$, —$CH_3$, —$CH(CH_3)_2$, —C≡$CCH_2OH$, piperidinyl, morpholinyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl, each is optionally substituted with 1 to 3 substituent(s) independently selected from —$CH_3$, —CN, —$NH_2$ and —OH;

$R_a$ represents hydrogen, —$CH_3$, —$CH(CH_3)_2$, —$CH_2$—COOC$(CH_3)_3$, —$CH_2$-piperidinyl($CH_3$), —$CH_2$—$CH_2$-morpholine, —$CH_2$—$CH_2$—$OCH_3$, —$CH_2$—$CH_2$—N$(CH_3)_2$, azetidinyl, —$CH_2$—$CH_2$—OH, —$CH_2$—$CH_2$-piperizinyl($COCH_3$) or —$CH_2$—COOH; $R_3$, at each occurrence, independently, represents hydrogen, alkyl, haloalkyl, acyl, oxo, —OH, heteroaryl, heterocycloalkyl or cycloalkyl, wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$;

$R_{3A}$, at each occurrence, independently, is alkoxy, —OH, —CONHOH or —NHCO-alkyl;

$R_{3B}$, at each occurrence, independently, is alkyl, alkoxy, —OH, —COOH, oxo, —COO— alkyl, —CONH-alkyl or —CONH—OH;

$R_{3C}$, at each occurrence, independently, is alkyl, —CN, —OH, —$NH_2$, —N(alkyl)$_2$, acyl, oxo, —CONH-alkyl, —NHCO-alkyl or —CONH-alkyl-OH;

$R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2CONHCH_3$, —$CONHCH_3$.

m is 1, 2 or 3;

n is 1 or 2.

In one embodiment, the present invention provides a compound of formula (IF):

(IF)

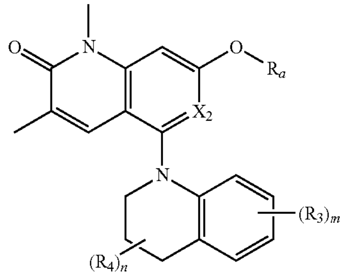

or a pharmaceutical acceptable salt, a stereoisomer, a tautomer, an N-oxide or an ester thereof; wherein $R_a$, $R_3$, $R_4$, m and n are as defined in compound of formula (I).

In one embodiment of compound of formula (IF), $X_2$ represents CH or N.

In one embodiment of compound of formula (IF), $R_3$, at each occurrence, independently, represents hydrogen, halogen, —CN, alkyl, alkoxy, haloalkyl, —OH, heteroaryl or heterocycloalkyl, wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IF), $R_3$, at each occurrence, independently, represents hydrogen, alkoxy, haloalkyl, —OH, heteroaryl or heterocycloalkyl, wherein the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IF), $R_{3A}$ is alkoxy, —OH, —CONHOH or —NHCO-alkyl.

In one embodiment of compound of formula (IF), $R_{3B}$ is alkyl, alkoxy, —OH, —COOH, oxo, —COO-alkyl, —CONH-alkyl or —CONH—OH.

In one embodiment of compound of formula (IF), $R_{3C}$, at each occurrence, independently, is alkyl, —CN, —OH, —$NH_2$, —N(alkyl)$_2$, acyl, oxo, —CONH-alkyl, —NHCO-alkyl or —CONH-alkyl-OH.

In one embodiment of compound of formula (IF), $R_{3C}$, at each occurrence, independently, is —$CH_3$, —N(alkyl)$_2$, acyl, —CONH-alkyl or —NHCO-alkyl.

In one embodiment of compound of formula (IF), $R_{3C}$, at each occurrence, independently, is —$CH_3$, acyl, —CONH-alkyl or —NHCO-alkyl.

In one embodiment of compound of formula (IF), $R_4$, at each occurrence, independently, represents hydrogen, —$CH_3$, —$CH_2CH_3$, —$CH_2COOH$, —$CH_2$(p-($OCH_3$)phenyl), —$CHF_2$, —$COCH_3$, —$CH_2COOCH_2CH_3$, —$CH_2CONHCH_3$, —$CONHCH_3$, oxo or —$SO_2CH_2CH_3$.

In one embodiment of compound of formula (IF), $R_4$, at each occurrence, independently, represents hydrogen, —$CH_3$, —$CH_2CH_3$, —$CH_2COOH$, —$CH_2$(p-($OCH_3$)phenyl), —$CHF_2$ or —$COCH_3$.

In one embodiment of compound of formula (IF), $R_4$, at each occurrence, independently, represents hydrogen, —$CH_3$, —$CH_2CH_3$ or —$CH_2COOH$.

In one embodiment of compound of formula (IF), m is 1, 2 or 3.

In one embodiment of compound of formula (IF), n is 1 or 2.

In one embodiment, the present invention provides a compound of formula (IF): or a pharmaceutical acceptable salt, a stereoisomer, a tautomer, an N-oxide or an ester thereof; wherein $X_2$ represents CH or N;

$R_a$ represents hydrogen, —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$—$CH_2$—OH, —$CH_2$—$CH_2$-piperizinyl($COCH_3$) or —$CH_2$—COOH;

$R_3$, at each occurrence, independently, represents alkoxy, haloalkyl, —OH, heteroaryl or heterocycloalkyl, wherein the heteroaryl is optionally substituted with 1 to 3 occurrence(s) of $R_{3B}$; and heterocycloalkyl is optionally substituted with 1 to 3 occurrence(s) of $R_{3C}$;

$R_{3B}$, at each occurrence, independently, is alkyl, alkoxy, —OH, —COOH, oxo, —COO— alkyl, —CONH-alkyl or —CONH—OH.

$R_{3C}$, at each occurrence, independently, is —$CH_3$, acyl, —CONH-alkyl or —NHCO-alkyl;

$R_4$, at each occurrence, independently, represents hydrogen, —$CH_3$, —$CH_2CH_3$ or —$CH_2COOH$.

m is 1, 2 or 3;

n is 1 or 2.

In one embodiment, the present invention provides a compound of formula (IG):

(IG)

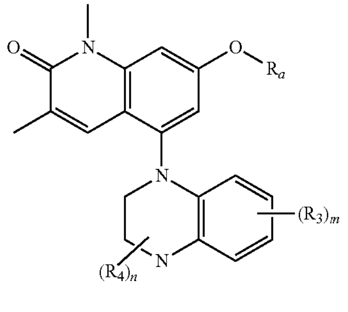

or a pharmaceutical acceptable salt, a stereoisomer, a tautomer, an N-oxide or an ester thereof; wherein $R_a$, $R_3$, $R_4$, m and n are as defined in compound of formula (I).

In one embodiment of compound of formula (IG), $R_a$ represents hydrogen, alkyl, haloalkyl, alkoxy, (heterocycloalkyl)alkyl-, heterocycloalkyl, heteroaryl, (heteroaryl)alkyl-; wherein the alkyl, at each occurrence, is optionally substituted by 1 to 3 substituent(s) independently selected from heterocycloalkyl, —OH, —COOH, —COO-alkyl, alkoxy, —NH(alkyl)$_2$ and —CONH—O-alkyl; and wherein the heterocycloalkyl and heteroaryl are optionally substituted by 1 to 3 substituent(s) selected from alkyl and acyl.

In one embodiment of compound of formula (IG), $R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—CONH($OCH_3$), —$CHF_2$ or —$CH_2$—$CHF_2$.

In one embodiment of compound of formula (IG), $R_3$, at each occurrence, independently, represents halo, —CN, alkyl, alkoxy, haloalkyl, —CHO, acyl, —CONH-alkyl, —COO-alkyl, —COOH, oxo, —OH, —$SO_2NH_2$, —$SO_2$NH-alkyl, —$SO_2$N(alkyl)$_2$, —$SO_2$NH-aryl, —SO—alkyl, —$SO_2$-alkyl, —$SO_2$NHCO-alkyl, —$SO_2$NHCO-haloalkyl, —S(O)(NH)-alkyl, —$NHSO_2$-alkyl, —NHCO-alkyl, —N(alkyl)CO-alkyl, heteroaryl, heterocycloalkyl, carbocyclyl or cycloalkyl; wherein the alkyl, at each occurrence, is optionally substituted with 1 to 3 occurrence(s) of $R_{3A}$; the heteroaryl is optionally substituted with 1 to 3 occurrence(s) of $R_{3B}$; and heterocycloalkyl is optionally substituted with 1 to 3 occurrence(s) of $R_{3C}$.

In one embodiment of compound of formula (IG), $R_3$, at each occurrence, independently, represents —$CH_3$, —$CH_2$OH, —$CH_2$CONHOH, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) independently selected from alkyl, alkoxy, —OH, —COOH, oxo, —COO-alkyl, —CONH-alkyl and —CONH—OH.

In one embodiment of compound of formula (IG), $R_4$, at each occurrence, independently, represents hydrogen, —$CH_3$, —$CH_2CH_3$, —$CH_2$COOH, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein the morpholinyl, pyranyl and cyclopropyl are optionally substituted with 1 to 3 substituent(s) independently selected from —$OCH_3$, —$COOCH_2CH_3$, —COOH and —$CONHCH_3$.

In one embodiment of compound of formula (IG), m is 1, 2 or 3. In one embodiment of compound of formula (IG), m is 1 or 2.

In one embodiment, the present invention provides a compound of formula (IG): a pharmaceutical acceptable salt, a stereoisomer, a tautomer, an N-oxide or an ester thereof; wherein

- $R_a$ represents —$CH_3$, —$CH(CH_3)_2$, —$CH_2$—$COOC(CH_3)_3$, —$CH_2$-piperidinyl($CH_3$), —$CH_2$—$CH_2$-morpholine, —$CH_2$—$CH_2$—$OCH_3$, —$CH_2$—$CH_2$—$N(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—CONH($OCH_3$), —$CHF_2$ or —$CH_2$—$CHF_2$;
- $R_3$, at each occurrence, independently, represents —$CH_3$, —$CH_2$OH, —$CH_2$CONHOH, —F, —CN, —$OCH_3$, —$CHF_2$, —$CF_3$, —CHO, acyl, —$CONHCH_3$, —$COOCH_3$, —COOH, oxo, —OH, —$SO_2NH_2$, —$SO_2NHCH_3$, —$SO_2N(CH_3)_2$, —$SO_2$NH(phenyl), —$SOCH_3$, —$SO_2CH_3$, —$SO_2CH(CH_3)_2$, —$SO_2NHCOCH_3$, —$SO_2NHCOCF_3$, —S(O)(NH)$CH_3$, —$NHSO_2CH_3$, —$NHSO_2CH_2CH_3$, —$NHSO_2CH(CH_3)_3$, —$NHCOCH_3$, —$N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) selected from alkyl, alkoxy, —OH, —COOH, oxo, —COO-alkyl, —CONH-alkyl and —CONH—OH;
- $R_4$, at each occurrence, independently, represents hydrogen, —$CH_3$, —$CH_2CH_3$, —$CH_2$COOH, —$CH_2$(p-($OCH_3$)phenyl), —$CHF_2$, —$COCH_3$, —$CH_2COOCH_2CH_3$, —$CH_2CONHCH_3$, —$CONHCH_3$, oxo, —$SO_2CH_2CH_3$, morpholinyl, pyranyl or cyclopropyl; wherein morpholinyl, pyranyl and cyclopropyl are optionally substituted with 1 to 3 substituent(s) selected from —$OCH_3$, —$COOCH_2CH_3$, —COOH and —$CONHCH_3$;
- m is 1, 2 or 3;
- n is 1 or 2.

Method of Treatment

In one embodiment, CBP/EP300 bromodomain inhibitor of the present invention binds to the CBP and/or EP300 primarily (e.g., solely) through contacts and/or interactions with the CBP bromodomain and/or EP300 bromodomain. In one embodiment, CBP/EP300 bromodomain inhibitor of the present invention binds to the CBP and/or EP300 through contacts and/or interactions with the CBP bromodomain and/or EP300 bromodomain as well as additional CBP and/or EP300 residues and/or domains. In one embodiment, CBP/EP300 bromodomain inhibitor of the present invention substantially or completely inhibits the biological activity of the CBP and/or EP300. In one embodiment, the biological activity is binding of the bromodomain of CBP and/or EP300 to chromatin (e.g., histones associated with DNA) and/or another acetylated protein. In one embodiment, the CBP/EP300 bromodomain inhibitor of the present invention blocks CBP/EP300 activity so as to restore a functional response by T-cells (e.g., proliferation, cytokine production, target cell killing) from a dysfunctional state to antigen stimulation. In one embodiment, the CBP/EP300 bromodomain inhibitor of the present invention binds to and/or inhibits CBP bromodomain. In one embodiment, CBP/EP300 bromodomain inhibitor of the present invention binds to and/or inhibits EP300 bromodomain.

In one embodiment, the present invention provides a compound of formula (I) or a pharmaceutically acceptable salt thereof; for the treatment of diseases or disorders mediated by CBP/EP300 bromodomain in an individual.

In one embodiment, the present invention provides the use of a compound of formula (I), (IA), (IB), (IC), (ID), (IE), (IF) and (IG) or a pharmaceutical acceptable salt, a stereoisomer, a tautomer, an N-oxide or an ester thereof for the inhibition of a CBP/EP300 bromodomain (in vitro or in vivo) (e.g., in vitro or in vivo inhibition of the bromodomain of CBP/EP300).

In one embodiment, the present invention provides a method of increasing efficacy of a cancer treatment comprising administering to the individual a therapeutically effective amount of a compound of formula (I) or a pharmaceutical acceptable salt, a stereoisomer, a tautomer, an N-oxide or an ester thereof.

A "CBP and/or EP300-mediated disease or disorder" is characterized by the participation of the bromodomains of CBP and/or EP300 in the inception, manifestation of one or more symptoms or disease markers, severity, or progression of a disease or disorder.

In one embodiment, the methods provided herein are useful in treating a CBP and/or EP300-mediated disease or disorder involving fibrosis. In one embodiment, the CBP and/or EP300-mediated disease or disorder is a fibrotic disease. In one embodiment, fibrotic diseases include pulmonary fibrosis, silicosis, cystic fibrosis, renal fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, systemic sclerosis or arthro fibrosis.

In one embodiment, the present invention provides a method of treating CBP and/or EP300-mediated disease or disorder in an comprising administering the subject in need thereof a therapeutically effective amount of compound of formula (I), (IA), (IB), (IC), (ID), (IE), (IF) and (IG) or a pharmaceutical acceptable salt, a stereoisomer, a tautomer, an N-oxide or an ester thereof.

In one embodiment, the present invention provides a compound of formula (I), (IA), (IB), (IC), (ID), (IE), (IF) and (IG) or a pharmaceutical acceptable salt, a stereoisomer, a tautomer, an N-oxide or an ester thereof for use in the treatment of CBP and/or EP300-mediated disease or disorder in an individual.

In one embodiment, the present invention provides a use of compound of formula (I), (IA), (IB), (IC), (ID), (IE), (IF) and (IG) or a pharmaceutical acceptable salt, a stereoisomer, a tautomer, an N-oxide or an ester thereof in the manufacture of a medicament for the treatment of CBP and/or EP300-mediated disease or disorder in an individual.

In one embodiment, CBP and/or EP300 bromodomain-mediated disease or disorder is selected from cancer, fibrosis, inflammation, or an inflammatory disease and disorder.

In one embodiment, CBP and/or EP300 bromodomain-mediated disease or disorder is a fibrotic lung disease selected from pulmonary fibrosis, idiopathic pulmonary fibrosis, fibrotic interstitial lung disease, renal fibrosis, interstitial pneumonia, fibrotic variant of non-specific interstitial pneumonia, cystic fibrosis, lung fibrosis, chronic obstructive pulmonary lung disease (COPD), lung cirrhosis and pulmonary arterial hypertension. In one embodiment, CBP and/or EP300 bromodomain-mediated disease or disorder is fibrotic interstitial lung disease. In one embodiment, CBP and/or EP300 bromodomain-mediated disease or disorder is interstitial pneumonia. In one embodiment, CBP and/or EP300 bromodomain-mediated disease or disorder fibrotic variant of non-specific interstitial pneumonia. In one embodiment, CBP and/or EP300 bromodomain-mediated disease or disorder is cystic fibrosis. In one embodiment, CBP and/or EP300 bromodomain-mediated disease or disorder is lung fibrosis. In one embodiment, CBP and/or EP300 bromodomain-mediated disease or disorder is chronic obstructive pulmonary lung disease (COPD). In one embodiment, CBP and/or EP300 bromodomain-mediated disease or disorder or pulmonary arterial hypertension.

In one embodiment, CBP and/or EP300 bromodomain-mediated disease or disorder is cancer. In one embodiment, CBP and/or EP300 bromodomain-mediated disease or disorder is cancer selected from acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, Burkitt's lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, NPM1c mutant leukemia, liposarcoma, lung cancer, lymphagioendotheliosarcoma, lymphangiosarcoma, lymphoblastic leukemia, lymphoma (Hodgkin's and non-Hodgkin's), Merkel cell carcinoma, malignancies and hyperproliferative diseases or disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In one embodiment, the cancer is lung cancer, breast cancer, pancreatic cancer, colorectal cancer, and/or melanoma. In one embodiment, the cancer is lung cancer. In one embodiment, the lung cancer is NSCLC i.e., non-small cell lung cancer. In one embodiment, the cancer is breast cancer. In one embodiment, the caner is melanoma.

In one embodiment, the present invention provides a method of treating lymphoma, leukemia, or prostate cancer in an individual comprising administering the individual an effective amount of compound of formula (I) or a pharmaceutical acceptable salt, a stereoisomer, a tautomer, an N-oxide or an ester thereof.

In one embodiment, CBP and/or EP300-mediated diseases or disorders also include inflammatory diseases, inflammatory conditions, and autoimmune diseases selected from Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

In one embodiment, CBP and/or EP300-mediated disease or disorder is a) a fibrotic lung disease selected from idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD) and pulmonary arterial hypertension; or b) a cancer selected from acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cancer of male and female reproductive system, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastro-intestinal tumors including GIST, germ cell testicular cancer, glioma, glioblastoma, gliosarcoma, head and neck squamous cell carcinoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

an inflammatory diseases, an inflammatory conditions, and an autoimmune diseases, selected from Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis or Wegener's granulomatosis. In one embodiment, CBP and/or EP300-mediated diseases or disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

Co-Administration of Compounds of Present Invention with Other Agents

In one embodiment, compounds of formula (I) or a pharmaceutical acceptable salt, a stereoisomer, a tautomer, an N-oxide or an ester thereof, may be employed alone or in combination with other agents for treatment.

In one embodiment, potential combination agents include but not restricted with biologic agents, targeted agents, check point modulators, epigenetic modulators, gene-based therapies, oncolytic viruses, and chemotherapeutic agents such as cytotoxic agents.

In one embodiment, chemotherapeutic agent are chemical compounds useful in the treatment of cancer. In one embodiment, compounds of the present invention, or a pharmaceutically acceptable composition thereof, are administered in combination with chemotherapeutic agent which includes erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5a-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancrati statin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γîî and calicheamicin coll (Angew Chem. Intl. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, 111), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

In one embodiment, biologics agents include antibodies such as alemtuzumab (Campath), bevacizumab (A VASTEST®, Genentech); cetuximab (ERBITUX®, Imclone); panitumumab (VECTIBIX®, Amgen), rituximab (RTTUXAN®, Genentech/Biogen Idee), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgGi λ antibody genetically modified to recognize interleukin-12 p40 protein.

Defintions

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur and that the description includes instances where the event or circumstance occurs as well as instances in which it does not. For example, "optionally substituted alkyl" refers to the alkyl that may be substituted as well as the event or circumstance where the alkyl is not substituted. As another instance, "optionally substituted" refers to a substituent that may be present as well as the event or circumstance where the substituent is not present.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl or an acyl), a thiocarbonyl (such as a thioester, a thioacetate or a thioformate), an alkoxyl, an oxo, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heteroaryl a heterocycloalkyl, an aralkyl or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. In one embodiment, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

As used herein, the term "acyl" refers to —CO—R wherein R is alkyl group as defined. In one embodiment, acyl contains ($C_1$-$C_6$)alkyl and preferably ($C_1$-$C_4$)alkyl. Exemplary acyl groups include, but not limited to, acetyl, propanoyl, 2-methylpropanoyl, t-butylacetyl and butanoyl.

As used herein, the term "ester' refers to ROCO—, wherein R is alkyl group as defined above. In one embodiment, an ester contains ($C_1$-$C_6$)alkyl and preferably ($C_1$-$C_4$) alkyl. Exemplary ester groups include, but not limited to, methoxycarbonyl, ethoxycarbonyl, propoxycarbonyl, butoxycarbonyl, tert-butoxy carbonyl and pentoxycarbonyl.

As used herein, the term "alkenylene" refers to a carbon chain which contains at least one carbon-carbon double bond and which may be linear or branched or combinations thereof. In one embodiment, "alkenylene" refers to ($C_2$-$C_6$) alkenylene. Examples of "alkenyl" include, but not limited to, vinyl, allyl, isopropenyl, pentenyl, hexenyl, heptenyl, 1-propenyl, 2-butenyl and 2-methyl-2-butenyl.

As used herein, the term "alkylene" means divalent, straight or branched chain hydrocarbon moieties containing one or more than one carbon-carbon single bonds. Examples of "alkylene" include, but not limited to, $—CH_2—$, $—CH_2—CH_2—$ and $—CH(CH_3)—CH_2—$.

As used herein, the term "alkynylene" means divalent, straight or branched chain hydrocarbon moieties containing at least one carbon-carbon triple bonds. In one embodiment, "alkynylene" refers to ($C_2$-$C_6$) alkynylene. Examples of "alkynylene" include, but not limited to, ethynylene, propynylene, butynylene, pentynylene and hexynylene.

As used herein, the term "halo" or "halogen" alone or in combination with other term(s) means fluorine, chlorine, bromine or iodine.

As used herein, the term "haloalkyl" means alkyl substituted with one or more halogen atoms, wherein the halo and alkyl groups are as defined above. The term "halo" is used herein interchangeably with the term "halogen" means F, Cl, Br or I. In one embodiment, haloalkyl contains ($C_1$-$C_6$)alkyl and preferably ($C_1$-$C_4$)alkyl. Examples of "haloalkyl" include, but not limited to, fluoromethyl, difluoromethyl, chloromethyl, trifluoromethyl and 2,2,2-trifluoroethyl.

As used herein, the term "hydroxy" or "hydroxyl" alone or in combination with other term(s) means —OH.

As used herein, the term "oxo" refers to =O group.

As used herein, "amino" refers to an $—NH_2$ group. As used herein, "amido" refers to an $—CONH_2$ group.

As used herein, the term "cycloalkyl" alone or in combination with other term(s) means ($C_3$-$C_{10}$) saturated cyclic hydrocarbon ring. A cycloalkyl may be a single ring, which typically contains from 3 to 7 carbon ring atoms. Examples of single ring cycloalkyls include but are not limited to cyclopropyl, cyclobutyl, cyclopentyl, cyclohexyl and cycloheptyl. A cycloalkyl may alternatively be polycyclic or contain more than one ring. Examples of polycyclic cycloalkyls include bridged, fused and spirocyclic carbocyclyls. In one embodiment, cycloalkyl refers to ($C_3$-$C_7$)cycloalkyl.

As used herein the term, "carbocycle" or "carbocyclyl" used alone or as part of a larger moiety, refer to a radical of a saturated or partially unsaturated cyclic aliphatic monocyclic or bicyclic ring system, as described herein, having the specified number of carbons. Exemplary carbocyclyls have from 3 to 18 carbon atoms, for example 3 to 12 carbon atoms, wherein the aliphatic ring system is optionally substituted as defined and described herein. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5, 6] or [6, 6] system, or as bridged systems such as bicyclo[2.2.1]heptane, bicyclo[2.2.2]octane and bicyclo [3.2.2]nonane. The aliphatic ring system is optionally substituted as defined and described herein. Examples of monocyclic carbocycles include, but are not limited to, cycloalkyls and cycloalkenyls, such as cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The terms "carbocyclyl" or "carbocycle," also includes aliphatic rings that are fused to one or more aromatic or nonaromatic rings, such as decahydronaphthyl, tetrahydronaphthyl, decalin, or bicyclo [2.2.2]octane.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula (I), an additional therapeutic agent, and a pharmaceutically acceptable carrier, adjuvant, or vehicle.

As used herein, the term 'heterocycloalkyl' refers to a non-aromatic, saturated or partially saturated, monocyclic or polycyclic ring system of 3 to 15 membered (unless the ring size is specifically mentioned) having at least one heteroatom selected from O, N and S, with the remaining ring atoms being independently selected from the group consisting of carbon, oxygen, nitrogen and sulfur. The term "heterocycloalkyl" also refers to the bridged bicyclic ring system, unless the ring size is specifically mentioned, having at least one heteroatom selected from O, N, and S. Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 10-membered ring. In one embodiment, "heterocycloalkyl" refers to 5- to 6-membered ring selected from the group consisting of imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocycloalkyl" includes azetidinyl, pyrrolidinyl, morpholinyl and piperidinyl. All heterocycloalkyl are optionally substituted by one or more aforesaid groups.

As used herein, the term "heteroaryl" refers to an aromatic heterocyclic ring system containing, unless the ring size is specifically mentioned, 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, pyrazolopyrimidyl, furopyridinyl, purinyl, benzothiadiazolyl, benzooxadiazolyl, benzotriazolyl, benzotriadiazolyl, carbazolyl, dibenzothienyl, acridinyl and the like. Preferably "heteroaryl" refers to 5- to 6-membered ring selected from the group consisting of furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more aforesaid groups.

In one embodiment, heteroaryl (for e.g., pyridine or pyridyl) can be optionally substituted by oxo to form a respective pyridine-N-oxide or pyridyl-N-oxide.

As used herein, the term 'heteroaryl-alkyl' refers to a group wherein the 'alkyl' group is substituted with one or more 'heteroaryl' groups and the groups 'alkyl' and 'heteroaryl' are as defined above. In one embodiment, heteroaryl-alkyl contains ($C_1$-$C_6$)alkyl and preferably ($C_1$-$C_4$) alkyl.

As used herein, the term "aryl" is optionally substituted monocyclic, bicyclic or polycyclic aromatic hydrocarbon ring system of about 6 to 14 carbon atoms. In one embodiment, "aryl" refers to $C_6$-$C_{10}$ aryl group. Examples of a $C_6$-$C_{14}$ aryl group include, but are not limited to, phenyl, naphthyl, biphenyl, anthryl, fluorenyl, indanyl, biphenylenyl and acenaphthyl. Aryl group can be unsubstituted or substituted with one or more suitable groups.

As used herein, the term 'arylalkyl' refers to a group wherein the 'alkyl' group is substituted with one or more 'aryl' groups.

The term "heteroatom" as used herein designates a sulfur, nitrogen or oxygen atom.

As used herein, the term 'compound(s)' comprises the compounds disclosed in the present invention.

As used herein, the term "comprise" or "comprising" is generally used in the sense of include, that is to say permitting the presence of one or more features or components.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts.

As used herein, the term "pharmaceutical composition" refers to a composition(s) containing a therapeutically effective amount of at least one compound of formula (I) or (IA) or (IB), a pharmaceutically acceptable salt, a stereoisomer, a tautomer, an N-oxide or an ester thereof; and a pharmaceutically acceptable carrier.

The pharmaceutical composition(s) usually contain(s) about 1% to 99%, for example, about 5% to 75% or from about 25% to about 50% or from about 10% to about 30% by weight of the compound of formula (I) or pharmaceutically acceptable salt, a stereoisomer, a tautomer, an N-oxide or an ester thereof. The amount of the compound of formula (I) or pharmaceutically acceptable salt thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

The term "tautomer" refers to compounds in which hydrogen atoms are transposed to other parts of the molecules and the chemical bonds between the atoms of the molecules are consequently rearranged. Compounds of the present invention, free form and salts thereof, may exist in multiple tautomeric forms. It is understood that all tautomeric forms, insofar as they may exist, are included within the invention. For example, pyridine or pyridyl can be optionally substituted by oxo to form a respective pyridone or pyridon-yl and may include its tautomeric form such as a respective hydroxy-pyridine or hydroxy-pyridyl, provided said tautomeric form may be obtainable.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease.

As used herein, the term "subject" refers to an animal, preferably a mammal and most preferably a human.

As used herein, the term, "therapeutically effective amount" refers to an amount of a compound of formula (I), a pharmaceutically acceptable salt, a stereoisomer, a tautomer, an N-oxide or an ester thereof; or a composition comprising the compound of formula (I) or a pharmaceutically acceptable salt, a stereoisomer, a tautomer, an N-oxide or an ester thereof, effective in producing the desired therapeutic or pharmacological response in a particular subject suffering from a disease or disorder mediated by CBP/EP300 bromodomain. Particularly, the term "therapeutically effective amount" includes the amount of the compound of formula (I), a pharmaceutically acceptable salt, a stereoisomer, a tautomer, an N-oxide or an ester thereof, when administered, that elicits a positive modification or alteration in the disease or disorder to be treated or is sufficient to effectively prevent development of or alleviate to some extent, one or more of the symptoms associated with the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied depending upon factors such as the condition of the subject being treated, the severity of the condition being treated or prevented, the duration of the treatment, the nature of concurrent therapy, the age and physical condition of the end user, the specific compound or composition employed the particular pharmaceutically acceptable carrier utilized.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

"Pharmaceutically acceptable salt" refers to a product obtained by reaction of the compound of the present invention with a suitable acid or a base. Pharmaceutically acceptable salt of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compound of formula (I)) can form pharmaceutically acceptable salt with various organic bases such as lysine, arginine, guanidine, diethanolamine or metformin. Suitable base salts include, but are not limited to, aluminum, calcium, lithium, magnesium, potassium, sodium or zinc salts.

As used herein, "CBP/EP300 bromodomain inhibitor" or "CBP and/or EP300 bromodomain inhibitor" refers to a compound that binds to CBP bromodomain and/or EP300 bromodomain and inhibits and/or reduces a pharmacological activity of CBP and/or EP300.

The present invention also provides methods for formulating the disclosed compounds as for pharmaceutical administration.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

In one embodiment, present invention provides a pharmaceutical composition comprising the compound of formula (I) and a pharmaceutically acceptable salt thereof.

Pharmaceutical Composition and Use Thereof

The compounds of the present invention may be used as single drug or as a pharmaceutical composition in which the compound is mixed with various pharmacologically acceptable materials.

The compounds of the invention are typically administered in the form of a pharmaceutical composition. Such compositions can be prepared using procedures well known in the pharmaceutical art and comprise at least one compound of this invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents and solvents.

The pharmaceutical composition can be administered by oral, parenteral or inhalation routes. Examples of the parenteral administration include administration by injection, percutaneous, transmucosal, trans-nasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions and sterile injectable liquids, such as suspensions or solutions.

Topical dosage forms of the compounds include ointments, pastes, creams, lotions, powders, solutions, eye or ear drops, impregnated dressings and may contain appropriate conventional additives such as preservatives, solvents to assist drug penetration.

The pharmaceutical compositions of the present patent application may be prepared by conventional techniques known in literature.

In one embodiment, the present invention provides a composition comprising a compound of the disclosure and an excipient and/or pharmaceutically acceptable carrier for treating diseases or conditions or disorders that are dependent upon CBP/EP300 signalling pathway.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms and suitable pharmaceutical excipients can also be well used and adjusted by those skilled in the art. All changes and modifications are envisioned within the scope of the present patent application.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$ $^{14}C$ $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the schemes and/or in the examples herein below, by substituting an isotopically labeled reagent for a non-isotopically labeled reagent.

The following abbreviations refer respectively to the definitions herein:

LDA (Lithium diisopropylamide); $K_2CO_3$ (Potassium carbonate); EtOH (Ethanol); rt (Retention time); RT (Room temperature); DMF (Dimethylformamide); h, hr (hour); NaOH (Sodium hydroxide); THE (tetrahydrofuran); LC-MS (Liquid chromatography mass spectroscopy); HCl (Hydrochloric acid); DCM, $CH_2C_{12}$ (Dichloromethane); TFA (Trifluoroacetic acid); TLC (Thin layer chromatography); DIPEA (Diisopropyl Ethyl amine); $Na_2SO_4$ (Sodium sulphate); $Pd(DPPF)Cl_2$ (1,1'-Bis(diphenylphosphino)ferrocene]dichloropalladium(II)); Me OH (Methanol); DMSO-$d_6$ (Dimethyl sulfoxide-D); $Boc_2O$ (Ditert-butyl dicarbonate); HPLC (High pressure liquid chromatography); $NaHCO_3$ (Sodium bicarbonate); MHz (mega hertz); s (singlet); m (multiplet); brs (Broad singlet) and d (doublet); NBS (N-bromosuccinimide); BuLi (Butyllithium); $NH_4OH$ Ammonium hydroxide); NaOH (Sodium hydroxide); McOH (Methanol); $KOBu^t$ (potassium tert butoxide); NaI (Sodium iodide); DMAP (4-Dimethylaminopyridine); EtOAc (Ethyl acetate); $NaHCO_3$(Sodium bicarbonate); RT (Room temperature); $LiAlH_4$ (Lithium aluminium hydride); MeI (Methyl iodide); $Cs_2CO_3$ (Caesium carbonate); SOCl2 (Thionyl chloride); EDC.HCl (1-Ethyl-3-(3-dimethylaminopropyl)carbodiimide. Hydrochloride); $Pd(Amphos)Cl_2$ (Bis (di-tert-butyl(4-dimethylaminophenyl)phosphine)dichloropalladium(II)); $Pd_2(dba)_3$ (Tris(dibenzylideneacetone) dipalladium(0)); HOBT (1-Hydroxybenzotriazole); Pd—C (Palladium on carbon); TLC (Thin layer chromatography); mCPBA (3-Chloroperbenzoic acid); Xantphos (4,5-Bis(diphenylphosphino)-9,9-dimethylxanthene); Rac-BINAP ((±)-2,2'-Bis(diphenylphosphino)-1,1'-binaphthalene, (±)-BINAP, [1,1'-Binaphthalene]-2,2'-diylbis[diphenylphosphine]); $Pd(OAc)_2$ (Palladium(II) acetate); Dave-Phos (2-Dicyclohexylphosphino-2'-(N,N-dimethylamino)biphenyl); WT/VOL (Weight/Volume).

EXPERIMENTAL

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Synthesis of North Part Intermediates

Intermediate-N1: 5-bromo-3-methylquinolin-2(1H)-one

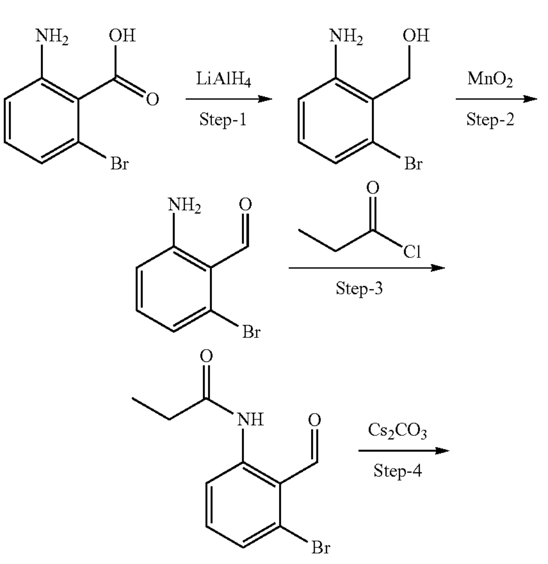

-continued

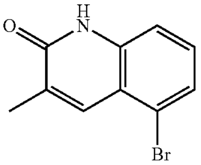

N1

Step-1: Synthesis of (2-amino-6-bromophenyl)methanol (IN5316-055)

To a solution of 2-amino-6-bromobenzoic acid (10 g, 46 mmol) in THE (100 mL) was added 1.0M $LiAlH_4$ solution (41 mL, 41 mmol) at 0° C. The reaction mixture was gradually warmed to room temperature in 12 h. After the completion of reaction, the reaction mixture was quenched with ice water and extracted with DCM. The organic layer was washed with brine, dried over sodium sulphate and concentrated to get pure title compound (7 g, 76%). LC-MS: 204.2 [M+2H]+

Step-2: Synthesis of 2-amino-6-bromobenzaldehyde

To a solution of (2-amino-6-bromophenyl)methanol (7 g, 34.8 mmol) in DCM (70 mL) was added $MnO_2$ (15.2 g, 174 mmol) at room temperature. The reaction mixture was stirred at room temperature for 2 h. After the completion of reaction, the reaction mixture was passing through the Celite® bed and washed with DCM. The organic layer was washed with brine, dried over sodium sulphate and concentrated to get pure title compound (6.5 g, 69.6%), LC-MS: 202.1 [M+214]+

Step-3: Synthesis of N-(3-bromo-2-formylphenyl)propionamide

To a solution of 2-amino-6-bromobenzaldehyde (6.5 g, 32.5 mmol) in DCM (60 mL) were added pyridine (5.15 g, 65 mmol) and followed by propionyl chloride (3.6 g, 39 mmol) at 0° C. The reaction mixture was gradually warmed to room temperature in 2 h. After the completion of reaction, the reaction mixture was quenched with ice water and extracted with DCM. The organic layer was washed with brine, dried over sodium sulphate and concentrated to get the title compound (8 g, 96.3%). LC-MS: 258.1 $[M+2H]^+$

Step-4: Synthesis of 5-bromo-3-methylquinolin-2(1H)-one (N1)

To a solution of N-(3-bromo-2-formylphenyl)propionamide (6.5 g, 32.5 mmol) in DMF (80 mL) was added $Cs_2CO_3$ (5.15 g, 65 mmol) to the reaction mixture at room temperature. The reaction mixture was stirred at 50° C. for 12 h. After the completion of reaction, the reaction mixture was poured into ice water to get the precipitate which was filtered and washed with water to obtain the title compound (6.3 g, 81.8%). LC-MS: 239.8 $[M+2H]^+$

Intermediate-N2: 5-bromo-3,6-dimethylquinolin-2(1H)-one

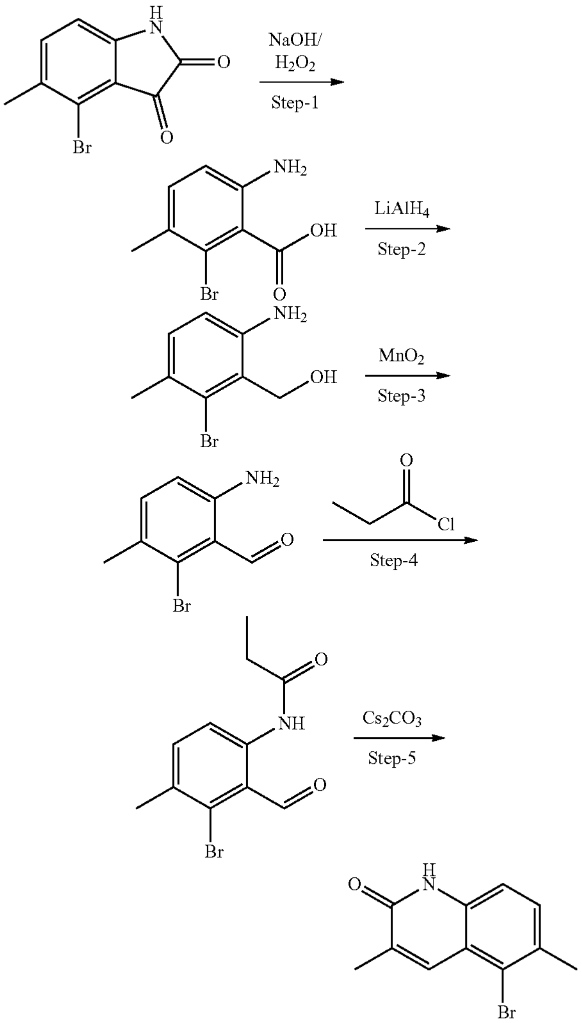

N2

Step-1: Synthesis of 6-amino-2-bromo-3-methylbenzoic acid

To a suspension of 4-bromo-5-methylindoline-2,3-dione (1 g, 4.18 mmol) in 1N NaOH solution (5 mL) was added 30% $H_2O_2$ (0.72 mL) solution at 70° C. for 5 min. The reaction mixture was stirred at 100° C. for 4 h. After the completion of reaction, the reaction mixture was cooled to room temperature, adjusted to pH-5 using saturated citric acid solution and extracted with 10% McOH in DCM. The organic layer was washed with brine, dried over sodium sulphate and concentrated to get the title compound (700 mg, 72.8%). LC-MS: 230.2 $[M+]^+$

Step-2: Synthesis of 6-amino-2-bromo-3-methylphenyl)methanol

To a solution of 6-amino-2-bromo-3-methylbenzoic acid (0.7 g, 3.0 mmol) in THE (5 mL) was added 2.0M $LiAlH_4$ solution (1.36 mL, 2.7 mmol) at 0° C. The reaction mixture was gradually warmed to room temperature in 12 h. After the completion of reaction, the reaction mixture was quenched with ice, 10% NaOH solution and extracted with DCM. The organic layer was washed with brine, dried over sodium sulphate and concentrated to get title compound (500 mg, 77.1%). LC-MS: 216.0 $[M+]^+$.

Step-3: Synthesis of 6-amino-2-bromo-3-methylbenzaldehyde

To a solution of (6-amino-2-bromo-3-methylphenyl) methanol (0.5 g, 2.3 mmol) in DCM (10 mL) was added $MnO_2$ (1 g, 11.6 mmol) to the reaction mixture at room temperature. The reaction mixture was stirred at room temperature for 4 h. After the completion of reaction, the reaction mixture was passing through the Celite® bed and washed with DCM. The organic layer was washed with brine, dried over sodium sulphate and concentrated to get pure title compound (350 mg, 71.8%). 1H-NMR (CDCl3, 300 MHz) δ: 8.54 (d, J=5.6 Hz, 1H), 7.17 (d, J=5.6 Hz, 1H), 1.60-1.54 (m, 6H), 1.37-1.28 (m, 6H), 1.21-1.17 (m, 6H), 0.88 (t, J=7.6 Hz, 9H).

Step-4: Synthesis of N-(3-bromo-2-formyl-4-methylphenyl)propionamide

To a solution of 6-amino-2-bromo-3-methylbenzaldehyde (0.35 g, 1.63 mmol) in DCM (10 mL) were added pyridine (0.26 g, 3.3 mmol) and propionyl chloride (0.15 g, 1.9 mmol) to the reaction mixture at 0° C. The reaction mixture was gradually warmed to room temperature in 1 h. After the completion of reaction, the reaction mixture was quenched with ice water and extracted with DCM. The organic layer was washed with brine, dried over sodium sulphate and concentrated to get the title compound (400 mg, 90.9%). LC-MS: 272.2 $[M+2H]^+$ Step-5: Synthesis of 5-bromo-3,6-dimethylquinolin-2(1H)-one To a solution of N-(3-bromo-2-formyl-4-methylphenyl) propionamide (0.4 g, 1.48 mmol) in DMF (10 mL) was added $Cs_2CO_3$ (2.4 g, 7.4 mmol) at room temperature. The reaction mixture was stirred at 50° C. for 12 h. After the completion of reaction, the reaction mixture was poured into ice water to get the precipitate which was filtered and washed with water to obtain the title compound (250 mg, 67.0%). LC-MS: 254.1 $[M+2H]^+$ Intermediate-N3: 5-bromo-1,3-dimethylquinolin-2(1H)-one

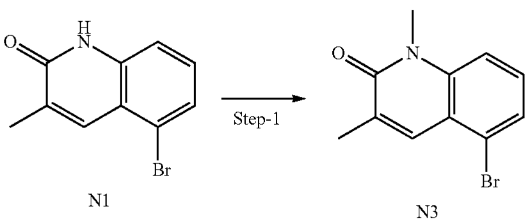

N1 N3

Step-1: Synthesis of 5-bromo-1,3-dimethylquinolin-2(1H)-one

To a solution of 5-bromo-3-methylquinolin-2(1H)-one (2 g, 8.4 mmol) in DMF (10 mL) were added $Cs_2CO_3$ (5.46 g, 16.8 mmol), MeI (1.92 g, 8.4 mmol) to the reaction mixture at room temperature. The reaction mixture was stirred at RT for 2 h. After the completion of reaction, the reaction mixture was poured into ice water to get the precipitate which was filtered and washed with water to obtain the title compound (1.1 g, 52.3%). LC-MS: 253.8 $[M+2H]^+$ Intermediate-N4: 5-bromo-1-ethyl-3-methylquinolin-2(1H)-one

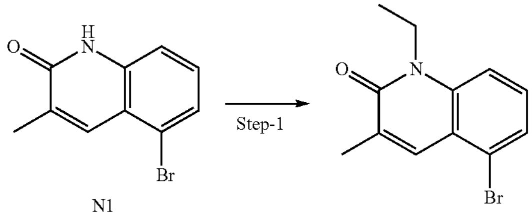

N1 N4

Step-1: Synthesis of 5-bromo-1-ethyl-3-methylquinolin-2(1H)-one: (N4)

To a solution of 5-bromo-3-methylquinolin-2(1H)-one (0.25 g, 1.05 mmol) in DMF (3 mL) were added NaH (0.051 g, 1.26 mmol) at 0° C. for 10 min. After 10 min, bromoethane (0.21 g, 1.36 mmol) was added to the reaction mixture at 0° C. and stirred for room temperature for 2 h. After completion of reaction, the reaction mixture was quenched with ice water and extracted with ethyl acetate. The organic layer was washed with brine, dried over sodium sulphate and concentrated to get the title compound (180 mg, 64.7%) LC-MS: 268.3$[M+2H]^+$ Intermediate-N5: 5-bromo-3-ethylquinolin-2(1H)-one (N5)

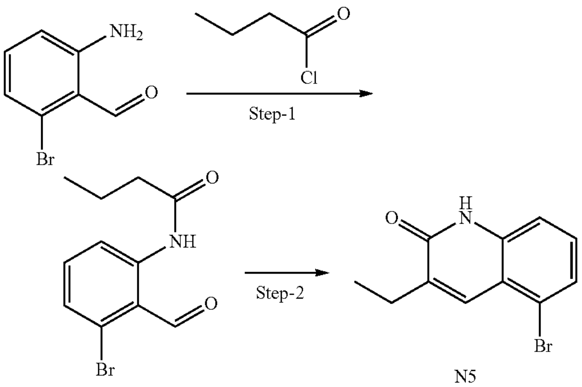

N5

Step-1: Synthesis of N-(3-bromo-2-formylphenyl)butyramide

To a solution of 2-amino-6-bromobenzaldehyde (0.5 g, 2.5 mmol) in DCM (5 mL) were added pyridine (0.49 g, 6.25 mmol) and butyryl chloride (0.4 g, 3.75 mmol) to the reaction mixture at 0° C. The reaction mixture was gradually warmed to room temperature for 12 h. After the completion of reaction, the reaction mixture was quenched with ice water and extracted with DCM. The organic layer was washed with brine, dried over sodium sulphate and concentrated to get the title compound quantitatively yield. LC-MS: 269.9 $[M+]^+$.

Step-2: Synthesis of 5-bromo-3-ethylquinolin-2(1H)-one

To a solution of N-(3-bromo-2-formylphenyl)butyramide (0.55 g, 2.03 mmol) in DMF (6 mL) was added $Cs_2CO_3$ (1.52 g, 4.68 mmol) to the reaction mixture at room temperature. The reaction mixture was stirred at 60° C. for 2 h. After the completion of reaction, the reaction mixture was poured into ice water to get the precipitate which was filtered and washed with water to obtain the title compound (350 mg. 68.4%). 1H NMR (400 MHz, $CDCl_3$) δ 11.56 (brs, 1H), 7.96 (s, 1H), 7.50-7.43 (m, 1H), 7.28-7.11 (m, 2H), 2.75-2.69 (q, 2H, J=9 Hz), 1.43-1.29 (m, 3H).

Intermediates-N6 & N7: 5-bromoquinolin-2(1H)-one & 5-bromo-1-methylquinolin-2(1H)-one

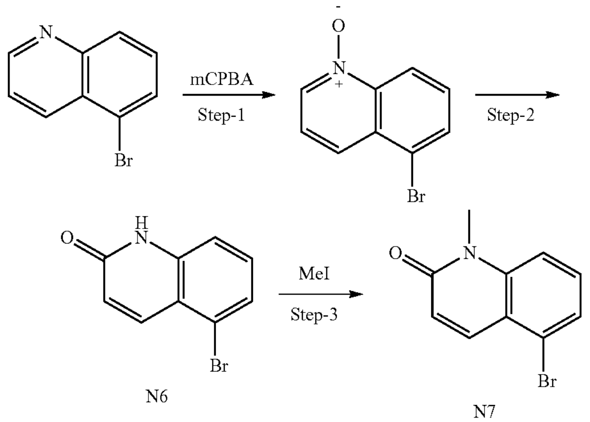

N6 N7

Step-1: Synthesis of 5-bromoquinoline 1-oxide

To a solution of 5-bromoquinoline (2 g, 9.6 mmol) in chloroform (25 mL) was added mCPBA (4.4 g, 19.2 mmol) to the reaction mixture at 0° C. for 5 min. The reaction mixture was stirred at room temperature for 12 h. After the completion of reaction, the reaction mixture was quenched with $K_2CO_3$ solution and extracted with DCM. The organic layer was washed with brine, dried over sodium sulphate and concentrated to get the title compound (2 g, 93%). LC-MS: 224.1 $[M+]^+$

Step-2: Synthesis of 5-bromoquinolin-2(1H)-one

To a solution of 5-bromoquinoline 1-oxide (2 g, 8.92 mmol) in DMF (20 mL) was added trifluoacetic anhydride (4 g, 17.8 mmol) to the reaction mixture at 0° C. for 5 min. The reaction mixture was stirred at room temperature for 5 h. After the completion of reaction, the reaction mixture was quenched with ice water and extracted with DCM. The organic layer was washed with brine, dried over sodium sulphate and concentrated to get the title compound (1.1 g, 55.2%). LC-MS: 226.1 $[M+2H]^+$

Step-3: Synthesis of 5-bromo-1-methylquinolin-2(1H)-one

To a solution of 5-bromoquinolin-2(1H)-one (1 g, 4.76 mmol) in DMF (15 mL) was added NaH (0.137 mg, 5.71 mmol) at 0° C. for 10 min. After 10 min added MeI (0.81 g, 5.71 mmol) to the reaction mixture at 0° C. and stirred for room temperature for 12 h. After completion of reaction, the reaction mixture was quenched with ice water and extracted with ethyl acetate. The organic layer was washed with brine, dried over sodium sulphate and concentrated to get the title compound (800 mg, 70.8%). LC-MS: 240.1 $[M+2H]^+$

Intermediate-N8: 5-bromo-1,3-dimethyl-1,7-naphthyridin-2(1H)-one

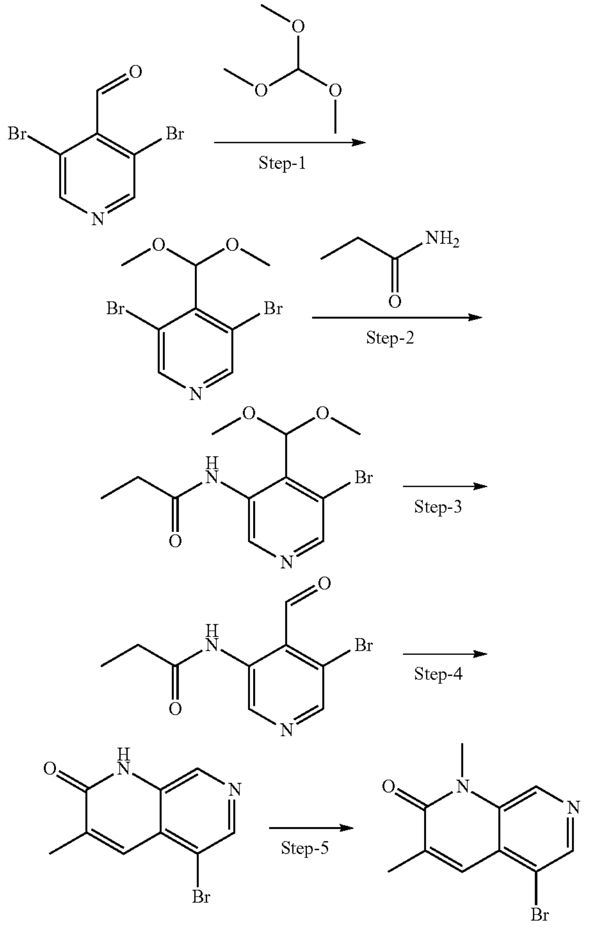

N8

Step-1: Synthesis of 3,5-dibromo-4-(dimethoxymethyl)pyridine

To a solution of 3,5-dibromoisonicotinaldehyde (10 g, 37.7 mmol), trimethoxymethane (5.67 g, 75.4 mmol) in McOH (30 mL) was added catalytic amount of $H_2SO_4$ (0.1 mL, 1.88 mmol) to the reaction mixture at room temperature. The reaction mixture was stirred at 70° C. for 2 h. After completion of reaction, the reaction mixture was quenched with ice water and extracted with ethyl acetate. The organic layer was washed with saturated $NaHCO_3$, brine, dried over sodium sulphate and concentrated to get the title compound (11 g, 94.8%). 1H NMR (400 MHz, $CDCl_3$) δ 8.65 (s, 2H), 5.72 (s, 1H), 3.49 (s, 6H).

Step-2: Synthesis of N-(5-bromo-4-(dimethoxymethyl)pyridin-3-yl)propionamide A degassed solution of 3,5-dibromo-4-(dimethoxymethyl) pyridine (1 g, 3.22 mmol) and propionamide (0.23 g, 3.22 mmol) in 1,4-Dioxane (4 mL) was added $Pd_2(dba)_3$ (295 mg, 0.32 mmol), Xantphos (186 mg, 0.322 mmol) and Caesium carbonate (3.15 g, 9.6 mmol). The mixture was stirred at 100° C. for 12 h. The reaction mixture was cooled, water was added and extracted with ethyl acetate. The organic extracts were washed with brine, dried over Sodium sulphate and concentrated to get the residue. The residue was purified by column chromatography (60-120 mesh) using ethyl acetate in hexane to afford title pure compound (700 mg, 71.7%). LC-MS: 305.2 [M+2H]+

Step-3: Synthesis of N-(5-bromo-4-formylpyridin-3-yl)propionamide

To a solution of N-(5-bromo-4-(dimethoxymethyl)pyridin-3-yl)propionamide (3 g, 9.9 mmol) in McOH/Water (20 mL/20 mL) (1:1) was added 48% fluoroboric acid solution (0.2 mL, 0.23 mmol) at 0° C. for 5 min. The reaction mixture was stirred at 50° C. for 5 h. After the completion of reaction, the reaction mixture was quenched with ice and extracted with ethyl acetate. The organic layer was washed with saturated $NaHCO_3$, brine solution and dried over sodium sulphate and concentrated to get the residue. The residue was purified by Combiflash® column chromatography using 15% ethyl acetate in hexane to afford title pure compound (650 mg, 25.6%). LC-MS: 256.8 $[M+]^+$

Step-4: Synthesis of 5-bromo-3-methyl-1,7-naphthyridin-2(1H)-one

To a solution of N-(5-bromo-4-formylpyridin-3-yl)propionamide (0.65 g, 2.15 mmol) in DMF (10 mL) was added $Cs_2CO_3$ (1.4 g, 4.3 mmol) to the reaction mixture at room temperature. The reaction mixture was stirred at 60° C. for 12 h. After the completion of reaction, the reaction mixture was poured into ice water to get the precipitate. This was filtered and washed with water to obtain the title compound (370 mg, 72.6%). LC-MS: 238.8 $[M+]^+$

Step-5: Synthesis of 5-bromo-1,3-dimethyl-1,7-naphthyridin-2(1H)-one

To a solution of 5-bromo-3-methyl-1,7-naphthyridin-2 (1H)-one (300 mg, 1.1 mmol) in DMF (10 mL) were added $Cs_2CO_3$ (725 mg, 2.2 mmol), MeI (0.14 mL, 2.2 mmol) to the reaction mixture at room temperature. The reaction mixture was stirred at 40° C. for 12 h. After the completion of reaction, the reaction mixture was poured into ice water to get the precipitate which was filtered and washed with water to obtain the title compound (250 mg, 89.9%. LC-MS: 254.7 $[M+2H]^+$

Intermediate-N9: 5-chloro-3-methyl-1,6-naphthyridin-2(1H)-one

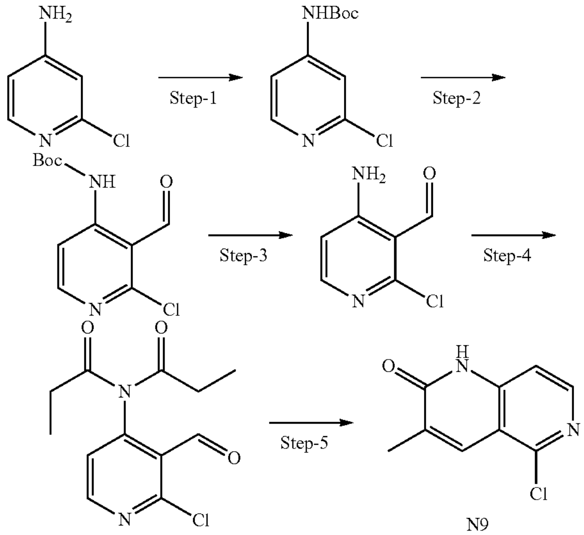

N9

Step-1: Synthesis of tert-butyl (2-chloropyridin-4-yl)carbamate

To a solution of 2-chloropyridin-4-amine (1H)-one (3 g, 23.4 mmol) in DCM (50 mL) was added $Et_3N$ (4.7 g, 46.8 mmol), DMAP (0.57 g, 4.6 mmol) and followed by $(Boc)_2O$ (10.2 g, 46.8 mmol) at 0° C. to the reaction mixture. The reaction mixture was stirred for room temperature for 2 h. After completion of reaction, the reaction mixture was quenched with ice water and extracted with DCM. The organic layer was washed with brine, dried over sodium sulphate and concentrated to get the title compound (3.6 g, 67.9%). LC-MS: 173.2 $[M-Bu^t]^+$

Step-2: Synthesis of tert-butyl (2-chloro-3-formylpyridin-4-yl)carbamate

To a solution of tert-butyl (2-chloropyridin-4-yl)carbamate (1H)-one (1 g, 4.37 mmol) in dry THE (20 mL) was added t-BuLi (11.8 mL, 11.8 mmol) at −78° C. The reaction mixture was stirred at same temperature for 30 min. DMF (1.06 mL, 13.5 mmol) was added to the reaction mixture at −78° C., and the reaction mixture was stirred at same temperature for 2 h. After completion of reaction, the reaction mixture was quenched with ammonium chloride solution and extracted with ethyl acetate. The organic layer was washed with brine, dried over sodium sulphate and concentrated to get the title compound (400 mg, 40%). LC-MS: 257.2 $[M+H]^+$

Step-3: Synthesis of 4-amino-2-chloronicotinaldehyde

To a solution of tert-butyl (2-chloro-3-formylpyridin-4-yl)carbamate (400 mg, 1.56 mmol) in DCM/TFA (10 mL, (1:1)) to the reaction mixture at the room temperature. The reaction mixture was stirred at same temperature for 6 h. After completion of reaction, the reaction mixture, the reaction mixture was evaporated completely to get the residue which was washed with diethyl ether to get the pure title compound in quantitatively yield LC-MS: 156.8 $[M+]^+$ Step-4: Synthesis of N-(2-chloro-3-formylpyridin-4-yl)-N-propionylpropionamide To a solution of 4-amino-2-chloronicotinaldehyde (300 mg, 1.92 mmol) in dioxane (10 mL) were added $Et_3N$ (387 mg, 3.8 mmol) and followed by propionyl chloride (212 mg, 2.3 mmol) to the reaction mixture at 0° C. The reaction mixture was gradually warmed to room temperature in 2 h. After the completion of reaction, the reaction mixture was quenched with ice water and extracted with DCM. The organic layer was washed with brine, dried over sodium sulphate and concentrated to get the residue. The residue was purified by Combiflash® column chromatography using 20% ethyl acetate in hexane to afford title pure compound (280 mg, 55.1%). LC-MS: 270.8 [M+2H]+

Step-5: Synthesis of 5-chloro-3-methyl-1,6-naphthyridin-2(1H)-one

To a solution of N-(2-chloro-3-formylpyridin-4-yl)-N-propionylpropionamide (280 mg, 1.04 mmol) in DMF (10 mL) was added $Cs_2CO_3$ (679 mg, 2.0 mmol) to the reaction mixture at room temperature. The reaction mixture was stirred at 90° C. for 12 h. After the completion of reaction, the reaction mixture was poured into ice water to get the precipitate. This was filtered and washed with water to obtain the title compound (140 mg, 69.6%). LC-MS: 195.2 $[M+H]^+$ Intermediates-N10: 5-bromo-7-methoxy-3-methylquinolin-2(1H)-one Intermediate-N10a: 7-bromo-5-methoxy-3-methylquinolin-2(1H)-one Intermediate-N11: 5-bromo-7-methoxy-1,3-dimethylquinolin-2(1H)-one Intermediate-N12: 7-bromo-5-methoxy-1,3-dimethylquinolin-2(1H)-one

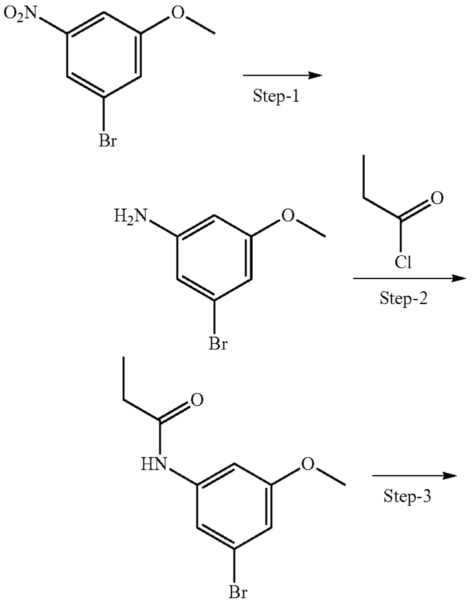

-continued

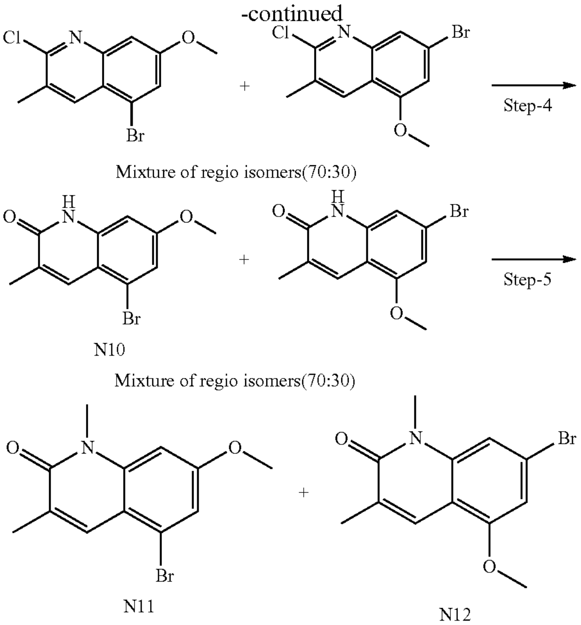

Mixture of regio isomers(70:30)

N10

Mixture of regio isomers(70:30)

N11

N12

Seperated regio isomers

Step-1: Synthesis of 3-bromo-5-methoxyaniline

To a solution of 1-bromo-3-methoxy-5-nitrobenzene (38 g, 232 mmol in THE (380 mL) was added saturated solution of $NH_4C_1$ (70 g, 1310 mmol) and followed by Zinc powder (85.7 g, 1310 mmol) to the reaction mixture at room temperature. The reaction mixture was stirred at same temperature for 30 min. After completion of reaction, the reaction mixture was diluted with ethyl acetate and passed through the Celite® bed and washed with ethyl acetate. The organic layer extracted with ethyl acetate and washed with saturated $NaHCO_3$, brine, dried over sodium sulphate and concentrated to get the title compound in quantitatively yield (33.92 g). LC-MS: 204.1 $[M+2H]^+$ Step-2: Synthesis of N-(3-bromo-5-methoxyphenyl)propionamide To a solution of 3-bromo-5-methoxyaniline (33 g, 163 mmol) in DCM were added pyridine (32.3 g, 408.3 mmol) and followed by propionyl chloride (19.64 g, 212.3 mmol) to the reaction mixture at 0° C. The reaction mixture was gradually warmed to room temperature in 3 h. After the completion of reaction, the reaction mixture was quenched with ice water and extracted with DCM. The organic layer was washed with brine, dried over sodium sulphate and concentrated to get the title compound quantitatively yield. LC-MS: 260.1 [M+2H]+

Step-3: Synthesis of 5-bromo-2-chloro-7-methoxy-3-methylquinoline (IN6514-016) & 7-bromo-2-chloro-5-methoxy-3-methylquinoline (mixture of regioisomers 70:30)

DMF (970 mL) was taken in RB flask, cooled to 0° C. added $POCl_3$ (137.2 g, 894.9 mmol) dropwise to the reaction mixture. After 1 h white solid formation in that mass N-(3-bromo-5-methoxyphenyl)propionamide (42 g, 258.1 mmol) was added at 0° C. The entire reaction mixture was heated at 100° C. for 4 h. After the completion of reaction, the reaction mixture was poured into ice water to get the precipitate which was filtered and washed with water to obtain the title mixture of regio isomers (25 g, 58.1%). LC-MS: 288.1 [M+2H]$^+$.

Step-4: Synthesis of 5-bromo-7-methoxy-3-methylquinolin-2(1H)-one & 7-bromo-5-methoxy-3-methylquinolin-2(1H)-one To a solution of 5-bromo-2-chloro-7-methoxy-3-methylquinoline & 7-bromo-2-chloro-5-methoxy-3-methylquinoline (25 g, 286.5 mmol in acetic acid (220 mL), water (75 mL) was added to the reaction mixture at room temperature. The reaction mixture was stirred 100° C. for 12 h. After the completion of reaction, the reaction mixture was poured into ice water to get the precipitate which was filtered and washed with water to obtain the title mixture of regio isomers (22 g, 94.4%). LC-MS: 267.9 [M+]$^+$ Step-5: Synthesis of 5-bromo-7-methoxy-1,3-dimethylquinolin-2(1H)-one & 7-bromo-5-methoxy-1,3-dimethylquinolin-2(1H)-one To a solution of 5-bromo-7-methoxy-3-methylquinolin-2(1H)-one & 7-bromo-5-methoxy-3-methylquinolin-2(1H)-one (22 g, 268.1 mmol) in DMF (220 mL) were added $Cs_2CO_3$ (80.2 g, 325.8 mmol), MeI (17.47 g, 141.9 mmol) to the reaction mixture at room temperature. The reaction mixture was stirred at RT for 30 min. After the completion of reaction, the reaction mixture was poured into ice water to get the precipitate. This mixture of regio isomers were separated by silica gel (100-200 mesh) column chromatography using 20-30% Ethyl acetate in hexane. This afforded 5-bromo-7-methoxy-1,3-dimethylquinolin-2(1H)-one (N11) (13 g). 1H NMR (300 MHz, $CDCl_3$) δ 7.87 (s, 1H), 7.09 (d, J=2.1 Hz, 1H), 6.74 (d, J=1.8 Hz, 1H), 3.84 (s, 3H), 3.69 (s, 3H), 2.25 (s, 3H). LC-MS: 284.1 [M+2H]+ and 7-bromo-5-methoxy-1,3-dimethylquinolin-2(1H)-one (N12) (6 g). 1HNMR (300 MHz, $CDCl_3$) δ 7.91 (s, 1H), 7.11 (s, 1H), 6.80 (s, 1H), 3.93 (s, 3H), 3.68 (s, 3H), 2.22 (s, 3H). LC-MS: 284.2 [M+2H]+

Intermediate-N13: 5-bromo-7-hydroxy-1,3-dimethylquinolin-2(1H)-one

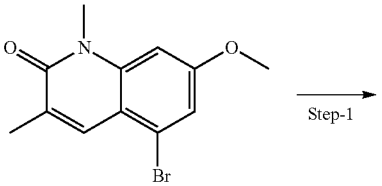

N11

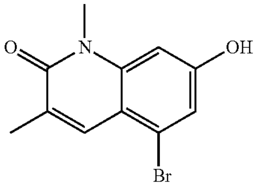

N13

Step-1: Synthesis of 5-bromo-7-hydroxy-1,3-dimethylquinolin-2(1H)-one (IN5498-022)

To a solution of 5-bromo-7-methoxy-1,3-dimethylquinolin-2(1H)-one (250 mg, 0.88 mmol) in 50% aq HBr in water solution (10 mL) to the reaction mixture at room temperature. The reaction mixture was stirred to 100° C. for 12 h. After the completion of reaction, the reaction mixture was poured into ice water to get the precipitate which was filtered and washed with water to obtain the title compound (190 mg, 80.1%). LC-MS: 270.1 [M+2H]$^+$ Intermediate-N14: Synthesis of 5-bromo-1,3-dimethyl-7-((1-methylpiperidin-3-yl)methoxy)quinolin-2(1H)-one

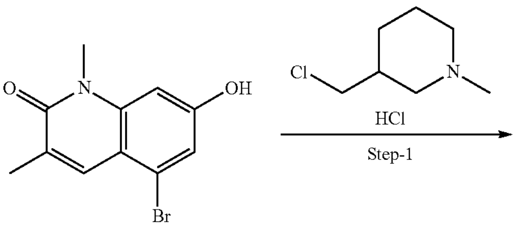

N13

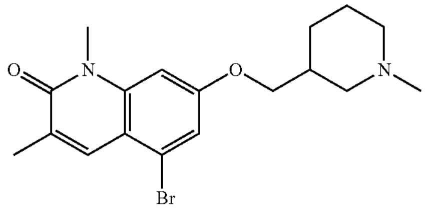

N14

Step-1: Synthesis of 5-bromo-1,3-dimethyl-7-(2-morpholinoethoxy)quinolin-2(1H)-one To a solution of 5-bromo-7-hydroxy-1,3-dimethylquinolin-2(1H)-one (100 mg, 0.37 mmol), in DMF (5 mL) was added $Cs_2CO_3$ (361 mg, 1.1 mmol), 3-(chloromethyl)-1-methylpiperidine hydro chloride (82 mg, 0.44 mmol) to the reaction mixture at room temperature. The reaction mixture was stirred at 80° C. for 12 h. After the completion of reaction, the reaction mixture was poured into ice water to get the precipitate which was filtered and washed with water to obtain the title compound (75 mg, 53.2%). LC-MS: 381.2 [M+2H]$^+$ Intermediate-N15: 5-bromo-1,3-dimethyl-7-(2-morpholinoethoxy)quinolin-2(1H)-one

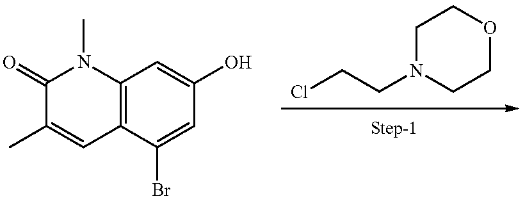

N13

-continued

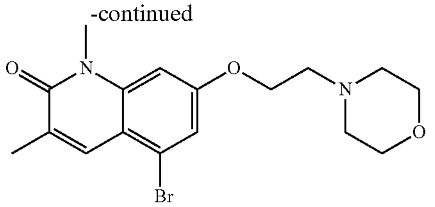

N15

Step-1: Synthesis of 5-bromo-1,3-dimethyl-7-(2-morpholinoethoxy)quinolin-2(1H)-one To a solution of 5-bromo-7-hydroxy-1,3-dimethylquinolin-2(1H)-one (150 mg, 0.55 mmol), in DMF (5 mL) was added $Cs_2CO_3$ (536 mg, 1.6 mmol), 4-(2-chloroethyl)morpholine (155 mg, 0.83 mmol) to the reaction mixture at room temperature. The reaction mixture was stirred at 80° C. for 12 h. After the completion of reaction, the reaction mixture was poured into ice water to get the precipitate which was filtered and washed with water to obtain the title compound (120 mg, 57.4%). LC-MS: 383.2 $[M+2H]^+$ The below intermediates (N16-N23) were prepared according to the protocols described in the synthesis of N15 with appropriate coupling methods, variations in reactants, quantities of reagents, solvents.

| Intermediate | Structure | Reagent | Analytical data |
|---|---|---|---|
| N16 | 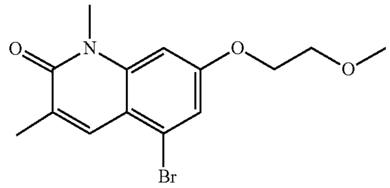 [SMILES: COCCOc1cc(Br)c2cc(C)c(=O)n(C)c2c1] | 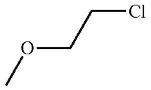 | LC-MS: 326.2 $[M + 2H]^+$ |
| N17 | 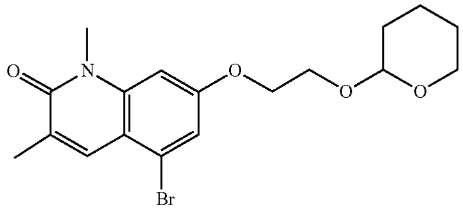 [SMILES: Cc1cc2c(Br)cc(OCCOC3CCCCO3)cc2n(C)c1=O] | 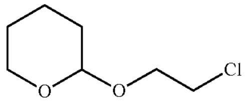 | LC-MS: 396.2 $[M+]^+$ |
| N18 | 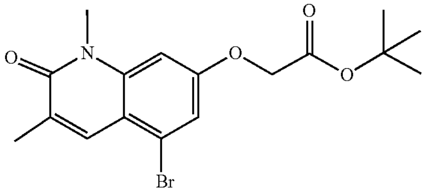 [SMILES: Cc1cc2c(Br)cc(OCC(=O)OC(C)(C)C)cc2n(C)c1=O] | 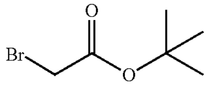 | LC-MS: 382.2 $[M+]^+$ |
| N19 | 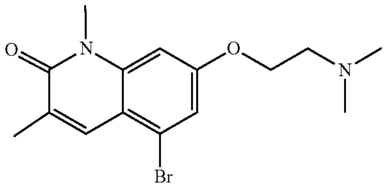 [SMILES: Cc1cc2c(Br)cc(OCCN(C)C)cc2n(C)c1=O] | 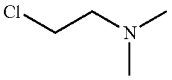 | LC-MS: 341.2 $[M + 2H]^+$ |
| N20 | 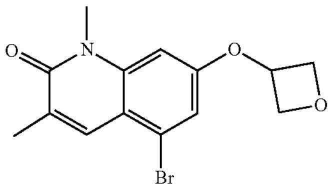 [SMILES: Cc1cc2c(Br)cc(OC3COC3)cc2n(C)c1=O] | 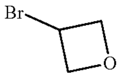 | LC-MS: 326.1 $[M + 2H]^+$ |

-continued

| Inter-mediate | Structure | Reagent | Analytical data |
|---|---|---|---|
| N21 | 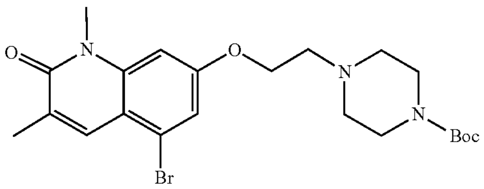 [SMILES: Cc1cc2c(Br)cc(OCCN3CCN(C(=O)OC(C)(C)C)CC3)cc2n(C)c1=O] | 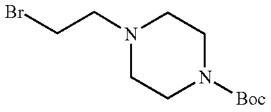 [SMILES: CC(C)(C)OC(=O)N1CCN(CCBr)CC1] | LC-MS: 480.0 $[M+]^+$ |
| N22 | 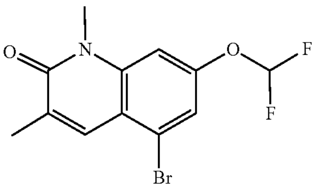 [SMILES: Cc1cc2c(Br)cc(OC(F)F)cc2n(C)c1=O] | 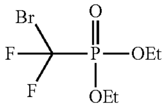 | LC-MS: 319.8 $[M + 2H]^+$ |
| N23 | 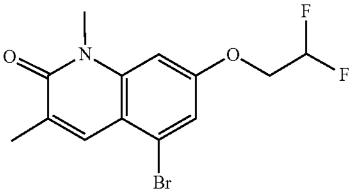 [SMILES: Cc1cc2c(Br)cc(OCC(F)F)cc2n(C)c1=O] | 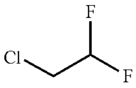 | LC-MS: 332.0 $[M+]^+$ |
| N24 | 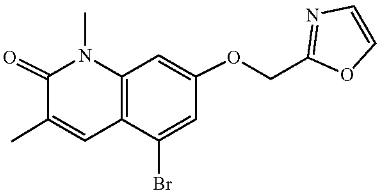 [SMILES: Cc1cc2c(Br)cc(OCc3ncco3)cc2n(C)c1=O] | 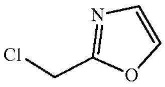 | LC-MS: 349.2 $[M + H]^+$ |

Intermediate-N25: 1,3-dimethyl-7-morphohno-2-oxo-1,2-dihydroquinolin-5-yl trifluoromethane-sulfonate

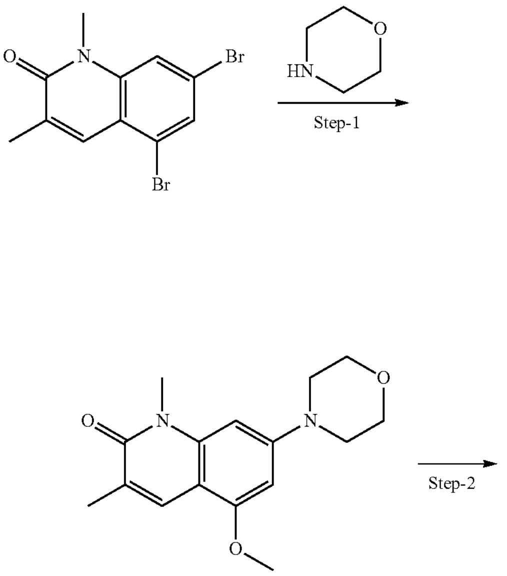

-continued

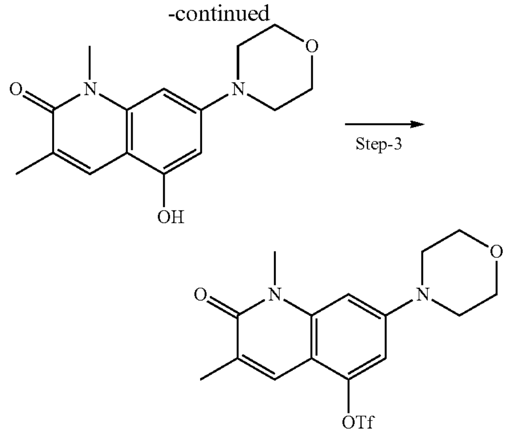

Step-1: Synthesis of 5-methoxy-1,3-dimethyl-7-morpholinoquinolin-2(1H)-one

A degassed solution of 7-bromo-5-methoxy-1,3-dimethylquinolin-2(1H)-one (600 mg, 2.13 mmol) and morpholine (190 mg, 2.13 mmol) in dioxane (10 mL) was added $Pd_2(dba)_3$ (100 mg, 0.11 mmol), rac BINAP (270 mg, 0.43 mmol) and Caesium carbonate (1.73 g, 5.3 mmol). The mixture was stirred at 100° C. for 12 h. The reaction mixture was cooled, water was added and extracted with ethyl acetate. The organic extracts were washed with brine, dried over Sodium sulphate and concentrated to get the residue. The residue was purified by Combiflash® column chromatography using 80% ethyl acetate in hexane to afford title pure compound (550 mg, 89.5%). LC-MS: 290.0 $[M+2H]^+$ Step-2: Synthesis of 5-hydroxy-1,3-dimethyl-7-morpholinoquinolin-2(1H)-one To a solution of 5-methoxy-1,3-dimethyl-7-morpholinoquinolin-2(1H)-one (450 mg, 0.56 mmol), in DMF (20 mL) was added sodium ethanethiolate (1.3 g, 15.6 mmol to the reaction mixture at room temperature. The reaction mixture was stirred at 100° C. for 12 h. After the completion of reaction, the reaction mixture was quenched with ice water and extracted with ethyl acetate. The organic layer was washed with brine, dried over sodium sulphate and concentrated to get the title compound (350 mg, 81.9%). LC-MS: 275.3 $[M+H]^+$ Step-3: Synthesis of 1,3-dimethyl-7-morpholino-2-oxo-1,2-dihydroquinolin-5-yl trifluoromethanesulfonate To a solution of 5-hydroxy-1,3-dimethyl-7-morpholinoquinolin-2(1H)-one (300 mg, 1.09 mmol) in DCM (20 mL) were added pyridine (260 mg, 3.27 mmol) and followed by trifluoro methanesulfinic anhydride (620 mg, 2.18 mmol) to the reaction mixture at 0° C. The reaction mixture was gradually warmed to room temperature in 3 h. After the completion of reaction, the reaction mixture was quenched with ice water and extracted with DCM. The organic layer was washed with brine, dried over sodium sulphate and concentrated to get the title compound (350 mg, 79.1%). LC-MS: 407.3 $[114+H]^+$ The below intermediates (N25-N29) were prepared according to the protocols described in the synthesis of N24 with appropriate coupling methods, variations in reactants, quantities of reagents, solvents.

| Intermediate | Structure | Reagent | Analytical data |
|---|---|---|---|
| N26 | 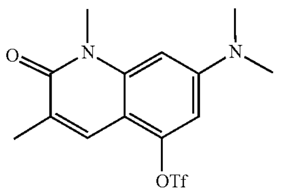 [SMILES: Cc1cc2c(OS(=O)(=O)C(F)(F)F)cc(N(C)C)cc2n(C)c1=O] | 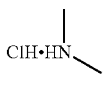 | LC-MS: 365.15 $[M + H]^+$ |
| N27 | 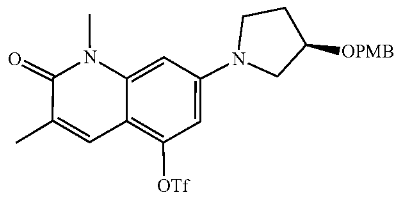 | 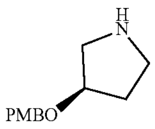 | LC-MS: 365.15 $[M + H]^+$ |
| N28 | 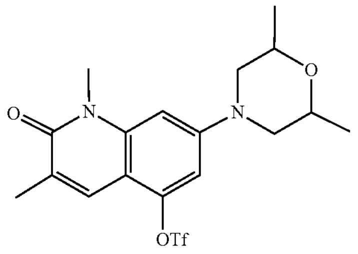 [SMILES: Cc1cc2c(OS(=O)(=O)C(F)(F)F)cc(N3CC(C)OC(C)C3)cc2n(C)c1=O] | 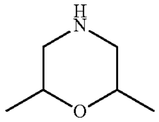 | LC-MS: 435.2 $[M + H]^+$ |
| N29 | 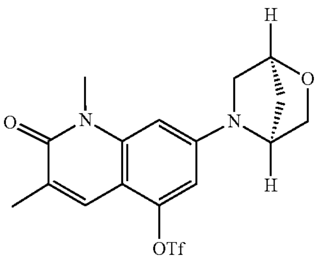 | 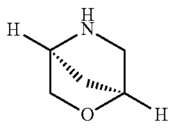 | LC-MS: 407.4 $[M + H]^+$ |

-continued

| Intermediate | Structure | Reagent | Analytical data |
|---|---|---|---|
| N30 | 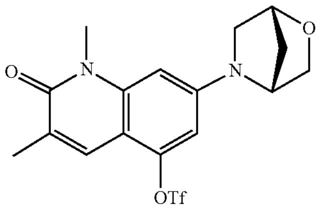 [SMILES: Cc1cc2c(OS(=O)(=O)C(F)(F)F)cc(N3C[C@H]4C[C@@H]3CO4)cc2n(C)c1=O] | 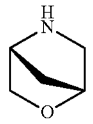 | LC-MS: 419.2 [M + H]$^+$ |

Intermediate-N31: 1,3-dimethyl-2-oxo-7-(tetrahydro-2H-pyran-4-yl)-1,2-dihydroquinolin-5-yl trifluoromethanesulfonate

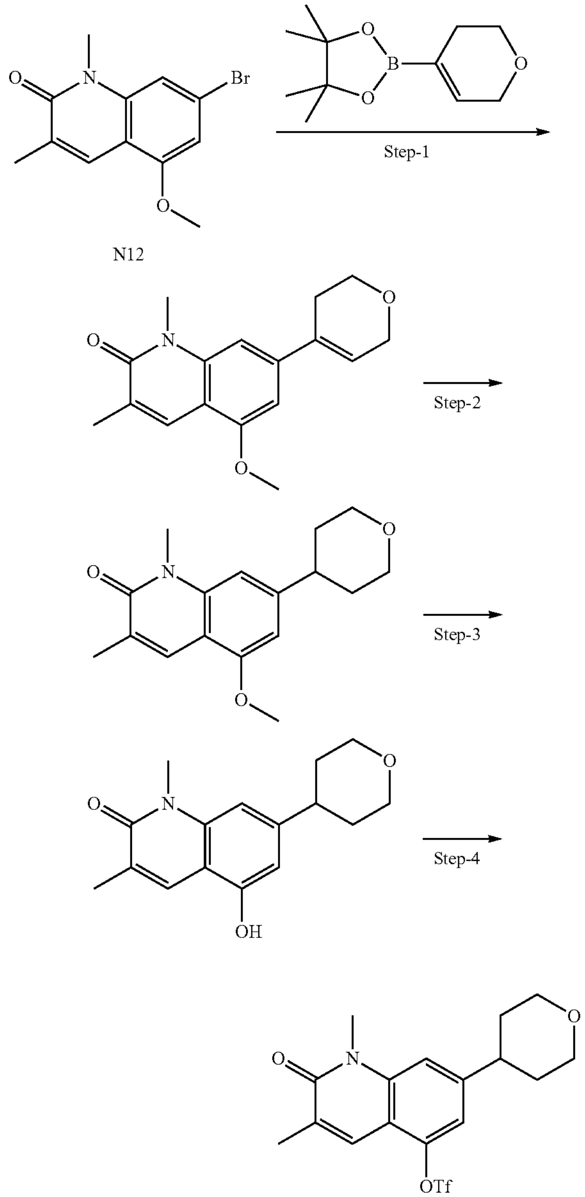

Step-1: Synthesis of 7-(3,6-dihydro-2H-pyran-4-yl)-5-methoxy-1,3-dimethylquinolin-2(1H)-one A degassed solution of 7-bromo-5-methoxy-1,3-dimethylquinolin-2(1H)-one (250 mg, 0.89 mmol) and 2-(3,6-dihydro-2H-pyran-4-yl)-4,4,5,5-tetramethyl-1,3,2-dioxaborolane (220 mg, 1.07 mmol) in dioxane (12 mL) and water (3 mL). The mixture was then added Pd(Amphos)$Cl_2$ (30 mg, 0.04 mmol) and potassium carbonate (370 mg, 2.67 mmol). The mixture was stirred at 100° C. for 12 h. The reaction mixture was then cooled to room temperature, water was added and the mixture was extracted with ethyl acetate. The organic extracts were washed with water, brine dried over sodium sulphate and concentrated to get the crude compound. The crude compound was passed through flash column using Combiflash® chromatography using 30% ethyl acetate in hexane as eluent to yield (150 mg, 59.2%). LC-MS: 286.2 [M+H]$^+$ Step-2: Synthesis of 5-methoxy-1,3-dimethyl-7-(tetrahydro-2H-pyran-4-yl)quinolin-2(1H)-one A degassed solution of 7-(3,6-dihydro-2H-pyran-4-yl)-5-methoxy-1,3-dimethylquinolin-2(1H)-one (220 mg, 0.77 mmol), in ethanol (10 mL) was added Pd/C (80 mg, 0.77 mmol to the reaction mixture at room temperature. The reaction mixture was hydrogenated with hydrogen bladder and stirred at room temperature for 8 h. After the completion of reaction, the reaction mixture passed through Celite® bed and washed with ethanol. The organic layer dried over sodium sulphate and concentrated to get the title compound quantitatively yield LC-MS: 288.3 [M+H]$^+$ Step-3: Synthesis of 5-hydroxy-1,3-dimethyl-7-(tetrahydro-2H-pyran-4-yl)quinolin-2(1H)-one To a solution of 5-methoxy-1,3-dimethyl-7-(tetrahydro-2H-pyran-4-yl)quinolin-2(1H)-one (200 mg, 0.7 mmol), in DMF (5 mL) was added sodium ethane thiolate (590 mg, 7.0 mmol to the reaction mixture at room temperature. The reaction mixture was stirred at 110° C. for 2 h. After the completion of reaction, the reaction mixture was quenched with ice water, saturated $NH_4Cl$ and extracted with ethyl acetate. The organic layer was washed with brine, dried over sodium sulphate and concentrated to get the crude compound which was washed with diethyl ether to obtain the pure title compound (150 mg, 78.4%). LC-MS: 274.4 [M+H]$^+$.

Step-4: Synthesis of 1,3-dimethyl-2-oxo-7-(tetrahydro-2H-pyran-4-yl)-1,2-dihydroquinolin-5-yl trifluoromethanesulfonate To a solution of 5-hydroxy-1,3-dimethyl-7-(tetrahydro-2H-pyran-4-yl)quinolin-2(1H)-one (150 mg, 0.55 mmol) in DCM (8 mL) were added pyridine (220 mg, 2.75 mmol) and followed by trifluoro methanesulfinic anhydride (310 mg, 1.1 mmol) to the reaction mixture at 0° C. The reaction mixture was gradually warmed to room temperature in 3 h. After the completion of reaction, the reaction mixture was quenched with ice water and extracted with DCM. The organic layer was washed with brine, dried over sodium sulphate and concentrated to get the title compound (160 mg, 71.7%). LC-MS: 406.3 $[M+H]^+$ The below intermediates (N31-N32) were prepared according to the protocols described in the synthesis of N30 with appropriate coupling methods, variations in reactants, quantities of reagents, solvents.

| Intermediate | Structure | Reagent | Analytical data |
|---|---|---|---|
| N32 | 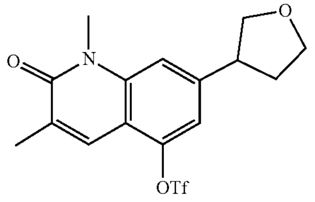 [SMILES: Cc1cc2c(OS(=O)(=O)C(F)(F)F)cc(C3CCOC3)cc2n(C)c1=O] | 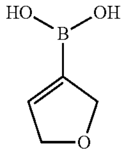 | LC-MS: 392.3 $[M + H]^+$ |
| N33 | 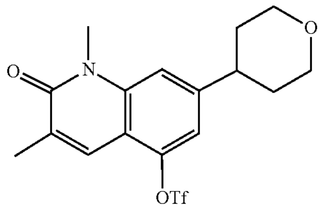 [SMILES: Cc1cc2c(OS(=O)(=O)C(F)(F)F)cc(C3CCOCC3)cc2n(C)c1=O] | 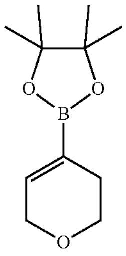 | LC-MS: 406.3 $[M + H]^+$ |

Intermediate Structure Reagent Analytical Data

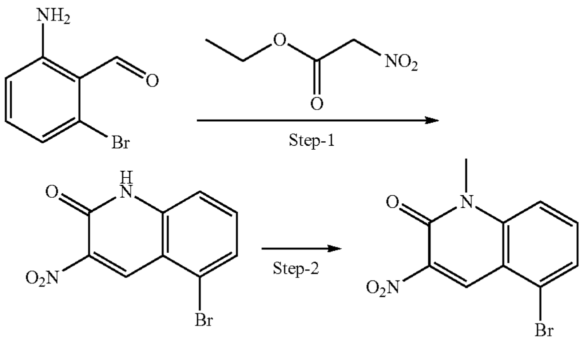

N34

Intermediate-N34: 5-bromo-1-methyl-3-nitroquinolin-2(1H)-one

Step-1: Synthesis of 5-bromo-3-nitroquinolin-2(1H)-one

In a seal tube to a solution of 2-amino-6-bromobenzaldehyde (300 mg, 1.5 mmol), ethyl 2-nitroacetate (239 mg, 1.8 mmol) in toluene (3 mL) were added piperadine (25 mg, 0.3 mmol) to the reaction mixture at RT. The reaction mixture was heated to 150° C. in microwave for 30 min. After the completion of reaction, the reaction mixture was evaporated completely to get the crude compound which was washed with pentane to obtain the pure title compound (270 mg, 67.5%). LC-MS: 271.2 $[M+2H]^+$

Step-2: Synthesis of 5-bromo-1-methyl-3-nitroquinolin-2(1H)-one

To a solution of 5-bromo-3-nitroquinolin-2(1H)-one (300 mg, 1.1 mmol) in DMF (4 mL) was added NaH (66 mg, 1.67 mmol) at 0° C. for 10 min. After 10 min added MeI (189 mg, 1.33 mmol) to the reaction mixture at 0° C. and stirred for room temperature for 2 h. After completion of reaction, the reaction mixture was poured into ice water to get the precipitate which was filtered and washed with water to obtain the title compound (235 mg, 74.8%). 1H NMR (400 MHz, $CDCl_3$) δ 8.91 (s, 1H), 7.36-7.59 (m, 1H), 7.41-7.39 (m, 1H), 3.81 (s, 3H).

Intermediate-N35: 5-iodo-7-methoxy-1,3-dimethylquinolin-2(1H)-one

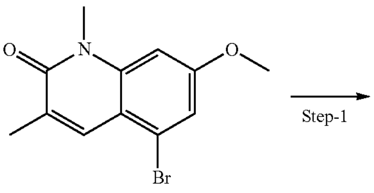

N11

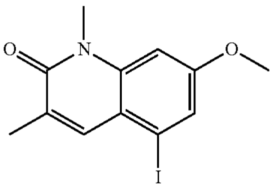

N35

Step-1: Synthesis of 5-iodo-7-methoxy-1,3-dimethylquinolin-2(1H)-one

To a solution of 5-bromo-7-methoxy-1,3-dimethylquinolin-2(1H)-one (1 g, 3.54 mmol) in dioxane (20 mL) was added CuI (70 mg, 0.35 mmol), NaI (1.06 g, 7.09 mmol), trans-N,N'-Dimethylcyclohexane-1,2-diamine (500 mg, 3.54 mmol) at room temperature. The reaction mixture heated to 120° C. for 24 h. After the completion of reaction, the reaction mixture was quenched with ice water and extracted with ethyl acetate. The organic layer was washed with brine, dried over sodium sulphate and concentrated to get the title compound (1 g, 86.2%). LC-MS: 330.1 $[M+H]^+$ Intermediate-N36: 5,7-dichloro-1,3-dimethyl-1,6-naphthyridin-2(1H)-one

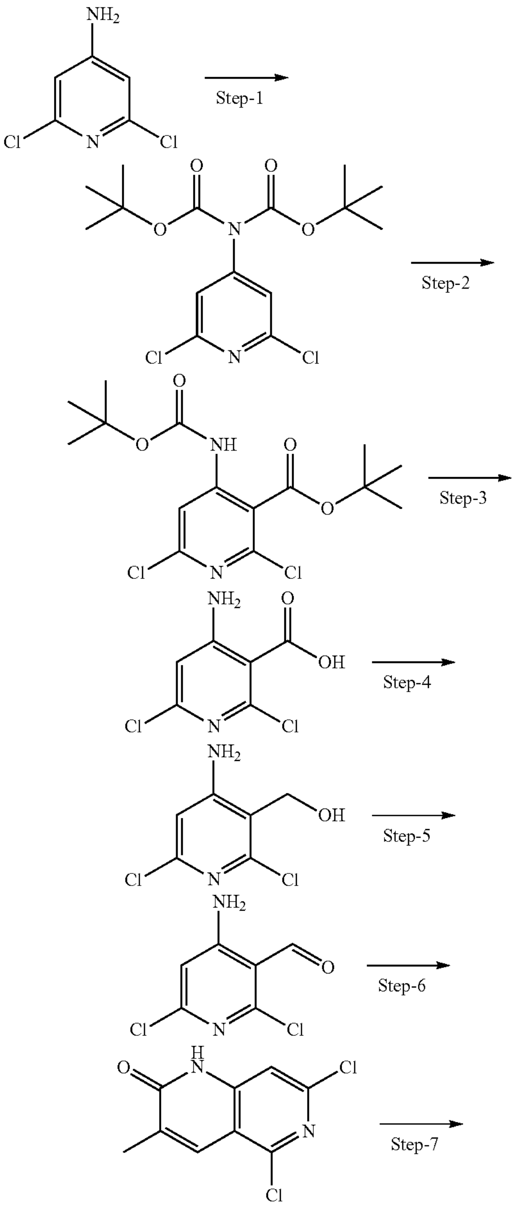

-continued

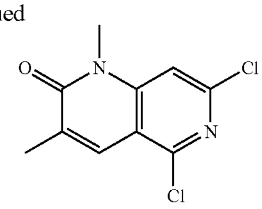

N36

Step-1: Synthesis of tert-butyl (tert-butoxycarbonyl)(2,6-dichloropyridin-4-yl)carbamate To a solution of 2,6-dichloropyridin-4-amine (300 g, 1840 mmol) in DCM (5000 mL) was added $(Boc)_2O$ (803.37 g, 3680 mmol) and followed by DMAP (68 g, 552.14 mmol) at 0° C. for 10 min. The reaction mixture was stirred for room temperature for 12 h. After the completion of reaction, the reaction mixture was quenched with ice water and extracted with DCM. The organic layer was washed with brine, dried over sodium sulphate and concentrated to get the crude compound which was recrystallized using 10% DCM in hexane to get the precipitate, filtered and washed with cold hexane (530 g, 79.28%). LC-MS: 363.1$[M+H]^+$ Step-2: Synthesis of tert-butyl 4-((tert-butoxycarbonyl)amino)-2,6-dichloronicotinate To a solution of tert-butyl (tert-butoxycarbonyl)(2,6-dichloropyridin-4-yl)carbamate (200 g, 550.6 mmol) in THF (2000 mL) was added LDA (635 mL, 1927.1 mmol) to the reaction mixture at −78° C. and stirred at the same temperature for 45 min. After the completion of reaction, the reaction mixture was quenched with $NH_4C_1$ solution and extracted with ethyl acetate. The organic layer was washed with brine, dried over sodium sulphate and concentrated to get the crude compound which was recrystallized using n-pentane to get the precipitate, which was filtered and washed with cold pentane (155 g, 77.5%). LC-MS: 363.2 $[M+H]^+$ Step-3: Synthesis of 4-amino-2,6-dichloronicotinic acid To a solution of tert-butyl tert-butyl 4-((tert-butoxycarbonyl)amino)-2,6-dichloronicotinate (145 g, 399.18 mmol) in DCM (400 mL), TFA (100 mL) and then stirred at room temperature for 12 h. After the completion of reaction, the reaction mixture was evaporated completely to get the crude compound which was washed with diethyl ether to obtain the title pure compound. (80 g, 96.8%). LC-MS: 206.8 [M+]+

Step-4: Synthesis of (4-amino-2,6-dichloropyridin-3-yl)methanol

To a solution of tert-butyl 4-amino-2,6-dichloronicotinic acid (60 g, 289.8 mmol) in THF (1200 mL) was added $LiAlH_4$ (2.0M) (363 mL, 1014.4 mmol) to the reaction mixture at 0° C. and stirred at the room temperature for 4 h. After the completion of reaction, the reaction mixture was quenched with sodium sulphate solution at 0° C. and extracted with ethyl acetate. The organic layer was washed with brine, dried over sodium sulphate and concentrated to get the crude compound which was recrystallized using 20% diethyl ether in pentane to obtain the precipitate was filtered and washed with pentane to offered the pure title compound (51 g, 91.6%). LC-MS: 193.0[M+]+

Step-5: Synthesis of 4-amino-2,6-dichloronicotinaldehyde

To a solution of tert-butyl (4-amino-2,6-dichloropyridin-3-yl)methanol (40 g, 207.2 mmol) in THF (400 mL) was added $MnO_2$ (144.12 g, 1657.7 mmol) to the reaction mixture at 0° C. and stirred at the room temperature for 12 h. After the completion of reaction, the reaction mixture passed through Celite® bed and washed with THF. The organic layer dried over sodium sulphate and concentrated to get the title pure compound (37 g, 93.48%). LC-MS: 191.0 $[M+]^+$ Step-6: Synthesis of 5,7-dichloro-3-methyl-1,6-naphthyridin-2(1H)-one To a solution of 4-amino-2,6-dichloronicotinaldehyde (38 g, 198.8 mmol) in THF (400 mL) were added $Et_3N$ (20.1 g, 198.9 mmol), DMAP (24.5 g, 198.9 mmol) and followed by propionyl chloride (27.6 g, 298.4 mmol) to the reaction mixture at 0° C. The reaction mixture was heated to 90° C. for 12 h. After the completion of reaction, the reaction mixture was quenched with ice water to get the precipitate was filtered and washed with water, dried under vacuum to obtain the title pure compound. (30 g, 65.8%). LC-MS: 229.2 $[M+]^+$ Step-7: Synthesis of 5,7-dichloro-1,3-dimethyl-1,6-naphthyridin-2(1H)-one To a solution of 5,7-dichloro-3-methyl-1,6-naphthyridin-2(1H)-one (30 g, 130.9 mmol) in DMF (450 mL) were added $Cs_2CO_3$ (85.3 g, 261.94 mmol), MeI (37.2 g, 261.94 mmol)

to the reaction mixture at room temperature. The reaction mixture was stirred at room temperature for 12 h. After the completion of reaction, the reaction mixture was poured into ice water to get the precipitate which was filtered and washed with water to obtain the title compound (28 mg, 87.95%). LC-MS: 243.1 $[M+]^+$ Synthesis of South Part Intermediates General Scheme:-1

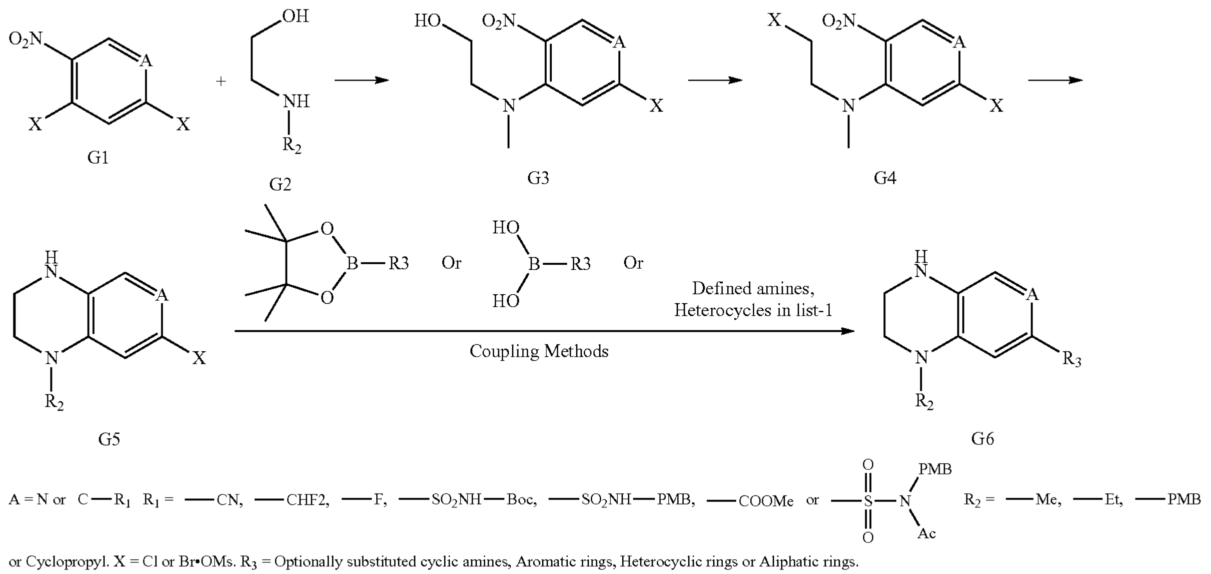

Intermediate-S1 & S2: 7-bromo-1-methyl-1,2,3,4-tetrahydroquinoxaline-6-carbonitrile & tert-butyl 6-bromo-7-cyano-4-methyl-3,4-dihydroquinoxaline-1(2H)-carboxylate

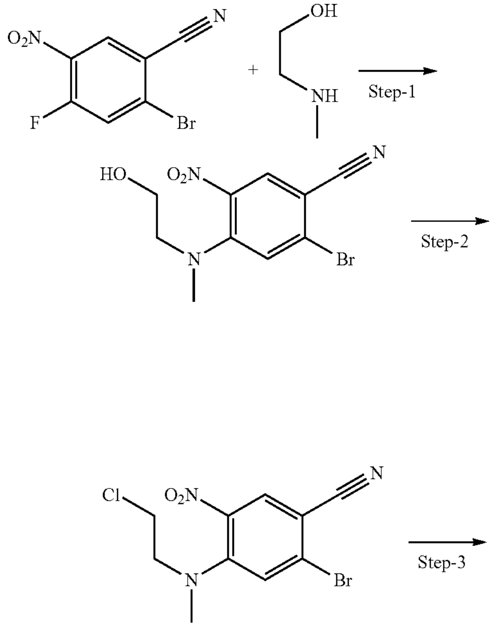

-continued

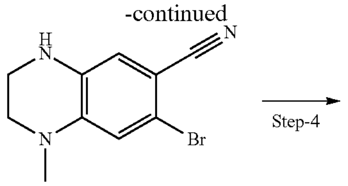

S1

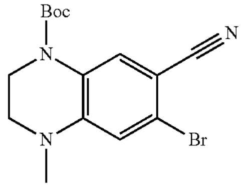

S2

Step-1: Synthesis of 2-bromo-4-((2-hydroxyethyl)(methyl)amino)-5-nitrobenzonitrile To a solution of 2-bromo-4-fluoro-5-nitrobenzonitrile (44 g, 180 mmol) in DMF (200 mL) were added DIPEA (62 mL, 36 mmol) and followed by 2-(methylamino)ethan-1-ol (16.2 g, 261.0 mmol) to the reaction mixture at 0° C. The reaction mixture stirred at 80° C. for 12 h. After completion of reaction, the reaction mixture was poured into ice water and extracted with ethyl acetate. The organic layer washed with brine and dried over sodium sulphate and concentrated to get the crude compound which was recrystallized using methanol to obtain the solid was filtered and washed with methanol. (35 g, 65.2%). LC-MS: 302.1 $[M+2H]^+$

Step-2: Synthesis of 2-bromo-4-((2-chloroethyl)(methyl)amino)-5-nitrobenzonitrile To a solution of 2-bromo-4-((2-hydroxyethyl)(methyl)amino)-5-nitrobenzonitrile (31.5 g, 105 mmol) in DCM (320 mL) were added pyridine (8.3 g, 105 mmol) and $SOCl_2$ (39.7 g, 210.0 mmol) to the reaction mixture at 0° C. The reaction mixture stirred at room temperature for 12 h. After completion of reaction, the reaction mixture was poured into ice water and extracted with DCM. The organic layer washed with saturated NaHCO3 solution, brine and dried over sodium sulphate and concentrated to get the title pure compound quantitatively yield (35 g). 1H NMR (300 MHz, $CDCl_3$) δ 8.03 (s, 1H), 7.34 (s, 1H), 3.74-3.70 (m, 2H), 3.60-3.56 (m, 2H), 3.0 (s, 3H).

Step-3: Synthesis of 7-bromo-1-methyl-1,2,3,4-tetrahydroquinoxaline-6-carbonitrile To a solution of 2-bromo-4-((2-chloroethyl)(methyl)amino)-5-nitrobenzonitrile (10 g, 30 mmol) in ethanol (90 mL), water (15 mL) were added Fe powder (16.9 g, 300 mmol) and followed by catalytic amount of conc. HCl (0.2 mL) to the reaction mixture at room temperature. The reaction mixture stirred at 90° C. for 2 h. After completion of reaction, the reaction mixture was diluted with ethyl acetate and passed through the Celite® bed and washed with ethyl acetate. The organic layer washed with brine solution and dried over sodium sulphate and concentrated to get the title pure compound (3.1 g, 41.1%). LC-MS: 252.2 $[M+2H]^+$

Step-4: Synthesis of tert-butyl 6-bromo-7-cyano-4-methyl-3,4-dihydroquinoxaline-1(2H)-carboxylate To a solution of 7-bromo-1-methyl-1,2,3,4-tetrahydroquinoxaline-6-carbonitrile (3 g, 11.8 mmol) in DCM (30 mL) were added DIPEA (4.2 mL, 23.6 mmol), DMAP (144 mg, 1.14 mmol) and followed by $(Boc)_2O$ (5.1 g, 23.6 mmol) to the reaction mixture at 0° C. The reaction mixture stirred at room temperature for 12 h. After completion of reaction, the reaction mixture was poured into ice water and extracted with DCM The organic layer washed with brine and dried over sodium sulphate and concentrated to get the crude compound. Crude compound was purified by Combiflash® column chromatography using solvent eluent (20-30%) ethyl acetate in hexane to obtain the pure title compound. (2.5 g, 60.2%). LC-MS: 298.0 $[M+Bu^t]^+$ The below intermediates were prepared by the similar procedure described in Ex. 95 of WO2017205536, pages 152-153 or Ex. 262 of WO2016086200 pages 389-391 with appropriate variations in reactants, quantities of reagents, solvents and reaction conditions. The characterization data of the intermediates are summarized herein below table.

| Intermediate | Structure | Reactant | Coupling reagent | LC-MS data |
|---|---|---|---|---|
| S3 | 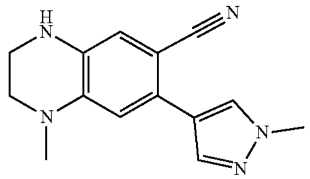 [SMILES: CN1CCNc2cc(C#N)c(-c3cnn(C)c3)cc21] | 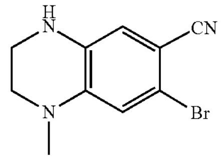 | 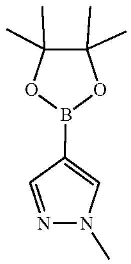 | 254.3 [M + H]+ |

-continued
| Intermediate | Structure | Reactant | Coupling reagent | LC-MS data |
| --- | --- | --- | --- | --- |
| S4 | 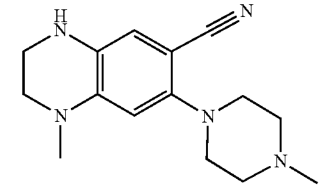 [SMILES: CN1CCN(c2cc3c(cc2C#N)NCCN3C)CC1] | 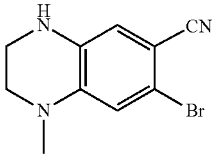 | 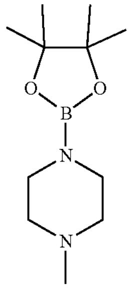 | 272.3 [M + H]+ |
| S5 | 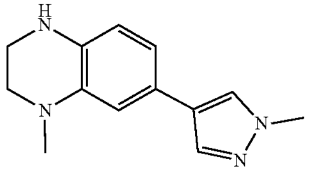 [SMILES: CN1CCNc2ccc(-c3cnn(C)c3)cc21] | 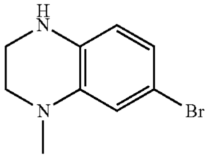 | 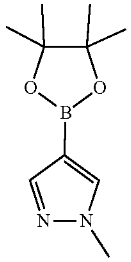 | 229.3 $[M + H]^+$ |
| S6 | 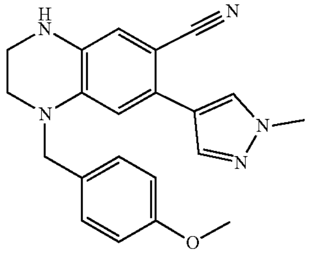 [SMILES: COc1ccc(CN2CCNc3cc(C#N)c(-c4cnn(C)c4)cc32)cc1] | 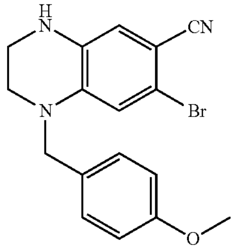 [SMILES: COc1ccc(CN2CCNc3cc(C#N)c(Br)cc32)cc1] | 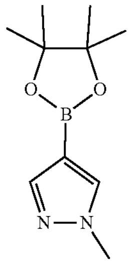 | 360.3 $[M + H]^+$ |
| S7 | 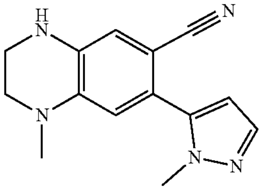 [SMILES: CN1CCNc2cc(C#N)c(-c3ccnn3C)cc21] | 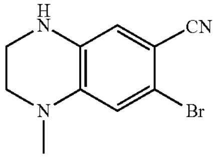 | 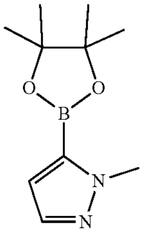 | 254.3 $[M + H]^+$ |
| S8 | 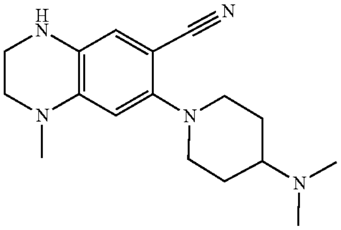 [SMILES: CN1CCNc2cc(C#N)c(N3CCC(N(C)C)CC3)cc21] | 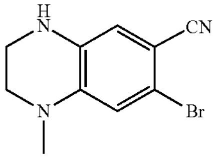 | 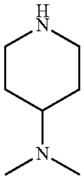 | 300.0 $[M + H]^+$ |
| S9 | 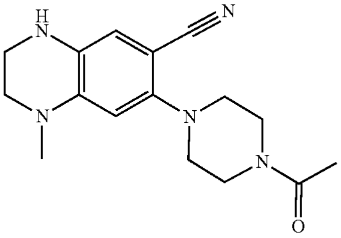 [SMILES: CC(=O)N1CCN(c2cc3c(cc2C#N)NCCN3C)CC1] | 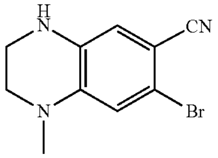 | 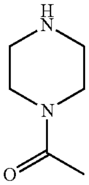 | 300.0 $[M + H]^+$ |

-continued
| Intermediate | Structure | Reactant | Coupling reagent | LC-MS data |
|---|---|---|---|---|
| S10 | 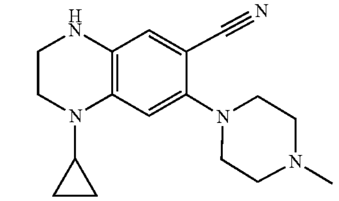 [SMILES: CN1CCN(c2cc3c(cc2C#N)NCCN3C2CC2)CC1] | 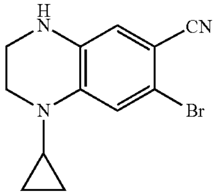 [SMILES: N#Cc1cc2c(cc1Br)N(C1CC1)CCN2] | 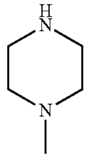 | 300.0 [M + H]$^+$ |
| S11 | 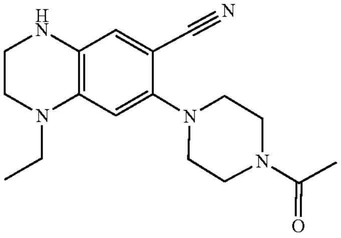 | 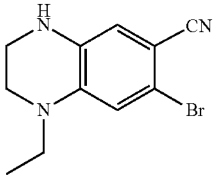 | 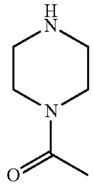 | 298.1 [M + H]$^+$ |
| S12 | 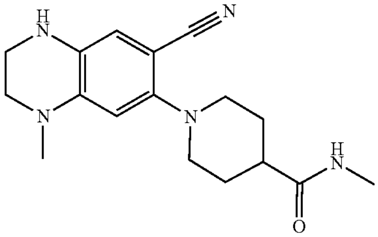 [SMILES: CNC(=O)C1CCN(c2cc3c(cc2C#N)NCCN3C)CC1] | 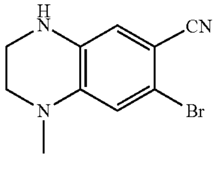 | 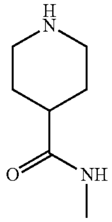 | 314.55 [M + H]$^+$ |
| S13 | 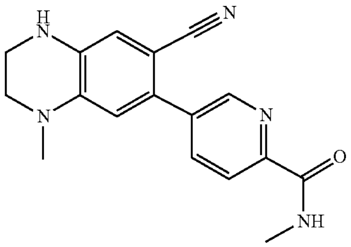 [SMILES: CNC(=O)c1ccc(-c2cc3c(cc2C#N)NCCN3C)cn1] | 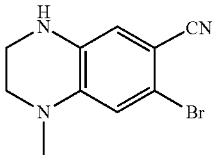 | 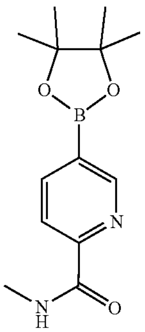 | 308.3 [M + H]$^+$ |
| S14 | 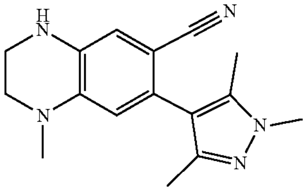 [SMILES: Cc1nn(C)c(C)c1-c1cc2c(cc1C#N)NCCN2C] | 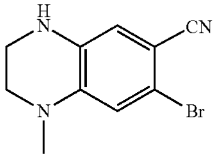 | 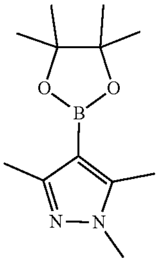 | 282.3 [M + H]$^+$ |
| S15 | 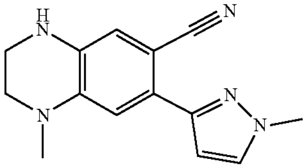 [SMILES: CN1CCNc2cc(C#N)c(-c3ccn(C)n3)cc21] | 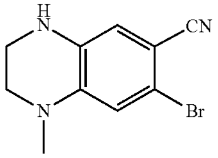 | 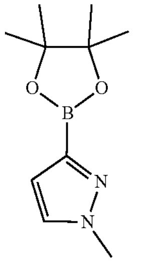 | 254.3 [M + H]$^+$ |

-continued
| Intermediate | Structure | Reactant | Coupling reagent | LC-MS data |
|---|---|---|---|---|
| S16 | 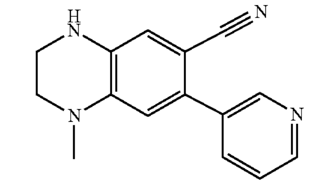 [SMILES: CN1CCNc2cc(C#N)c(-c3cccnc3)cc21] | 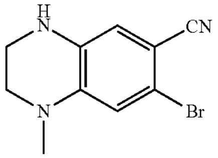 | 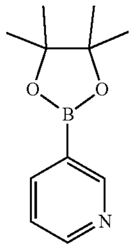 | 251.1 [M + H]+ |
| S17 | 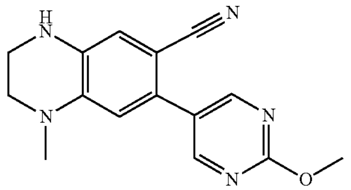 [SMILES: COc1ncc(-c2cc3c(cc2C#N)NCCN3C)cn1] | 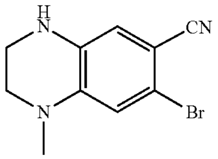 | 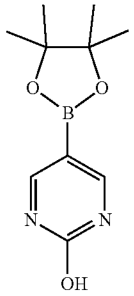 | 282.3 [M + H]+ |
| S18 | 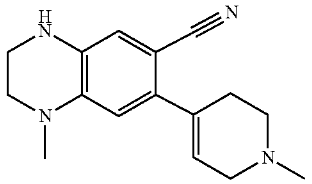 [SMILES: CN1CC=C(c2cc3c(cc2C#N)NCCN3C)CC1] | 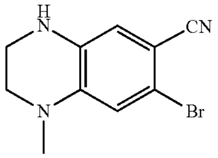 | 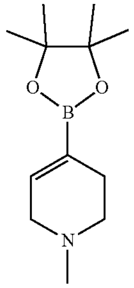 | 269.0 [M + H]+ |
| S19 | 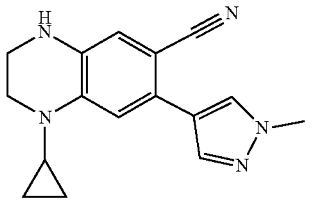 [SMILES: Cn1cc(-c2cc3c(cc2C#N)NCCN3C2CC2)cn1] | 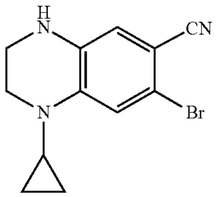 [SMILES: N#Cc1cc2c(cc1Br)N(C1CC1)CCN2] | 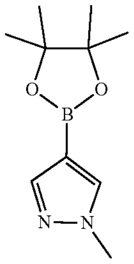 | 280.0 [M + H]+ |
| S20 | 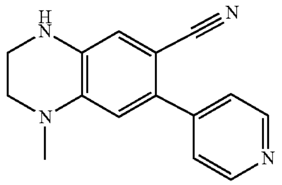 [SMILES: CN1CCNc2cc(C#N)c(-c3ccncc3)cc21] | 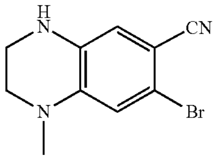 | 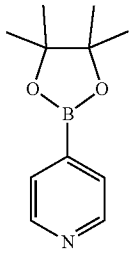 | 251.3 [M + H]+ |

-continued
| Intermediate | Structure | Reactant | Coupling reagent | LC-MS data |
|---|---|---|---|---|
| S21 | 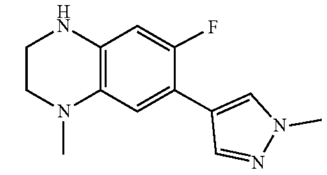 [SMILES: CN1CCNc2cc(F)c(-c3cnn(C)c3)cc21] | 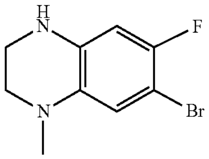 | 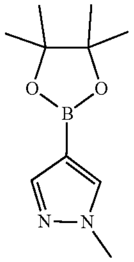 | 247.2 [M + H]$^+$ |
| S22 | 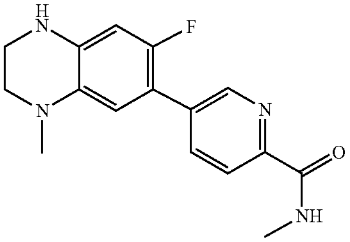 [SMILES: CNC(=O)c1ccc(-c2cc3c(cc2F)NCCN3C)cn1] | 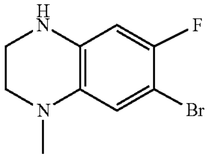 | 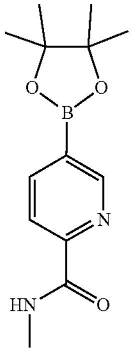 | 301.0 [M + H]$^+$ |
| S23 | 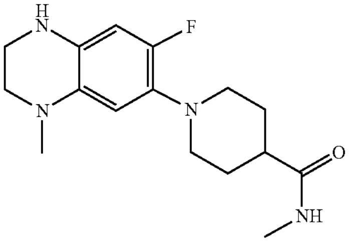 [SMILES: CNC(=O)C1CCN(c2cc3c(cc2F)NCCN3C)CC1] | 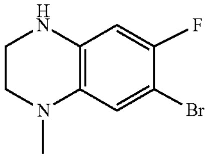 | 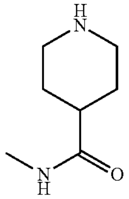 | 307.2 [M + H]$^+$ |
| S24 | 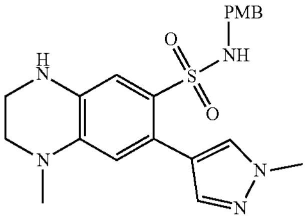 | 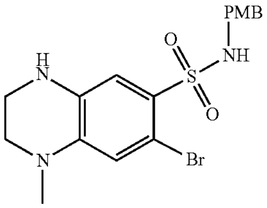 | 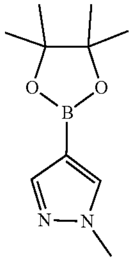 | 428.0 [M + H]$^+$ |
| S25 | 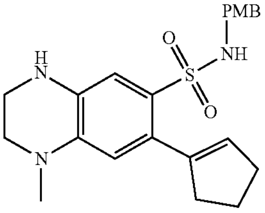 | 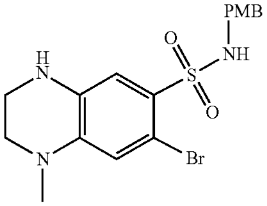 | 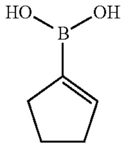 | 414.3 [M + H]$^+$ |
| S26 | 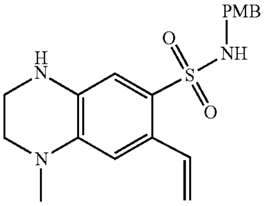 | 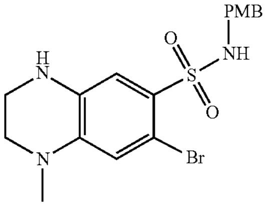 | 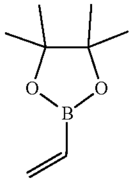 | 414.3 [M + H]$^+$ |

-continued
| Intermediate | Structure | Reactant | Coupling reagent | LC-MS data |
|---|---|---|---|---|
| S27 | 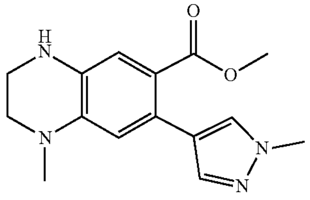 | 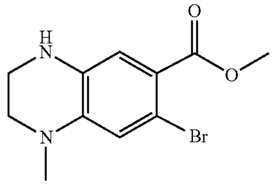 | 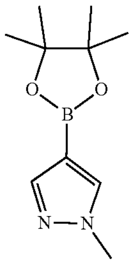 | 374.0 [M + H]+ |
| S28 | 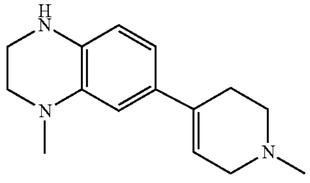 | 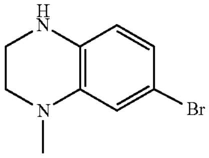 | 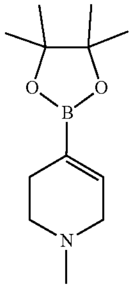 | 269.0 [M + H]+ |
| S29 | 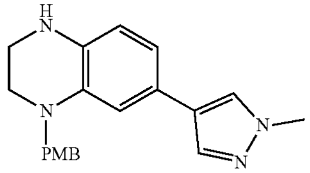 | 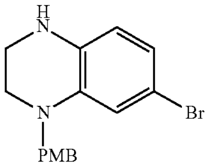 | 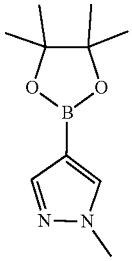 | 335.2 [M + H]+ |
| S30 | 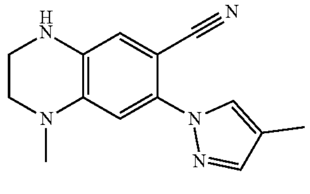 [SMILES: Cc1cnn(-c2cc3c(cc2C#N)NCCN3C)c1] | 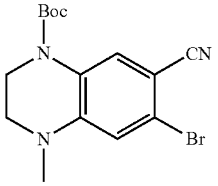 | 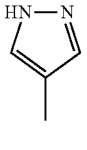 | 254.0 [M + H]+ |
| S31 | 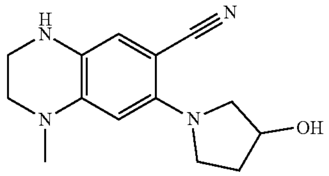 [SMILES: CN1CCNc2cc(C#N)c(N3CCC(O)C3)cc21] | 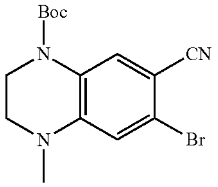 [SMILES: CN1CCN(C(=O)OC(C)(C)C)c2cc(C#N)c(Br)cc21] | 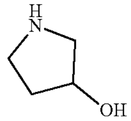 | NA |
| S32 | 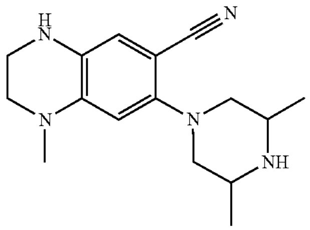 [SMILES: CC1CN(c2cc3c(cc2C#N)NCCN3C)CC(C)N1] | 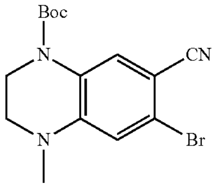 | 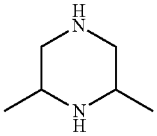 | 286.1 [M + H]+ |

-continued
| Intermediate | Structure | Reactant | Coupling reagent | LC-MS data |
| --- | --- | --- | --- | --- |
| S33 | 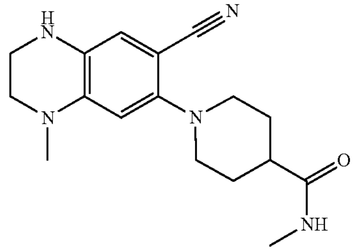 [SMILES: CNC(=O)C1CCN(c2cc3c(cc2C#N)NCCN3C)CC1] | 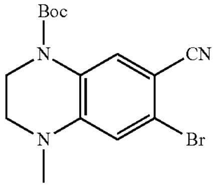 | 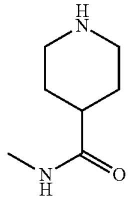 | 314.5 [M + H]$^+$ |
| S34 | 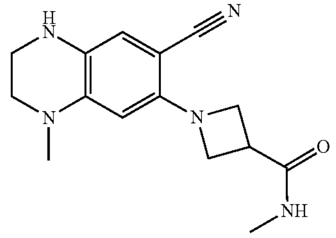 [SMILES: CNC(=O)C1CN(c2cc3c(cc2C#N)NCCN3C)C1] | 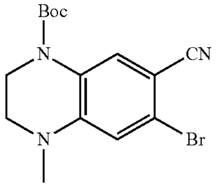 | 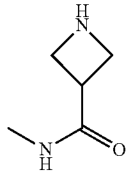 | 286.0 [M + H]$^+$ |
| S35 | 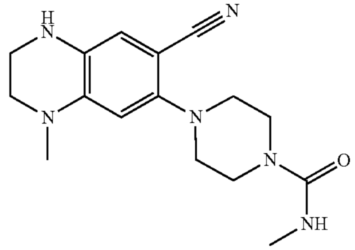 | 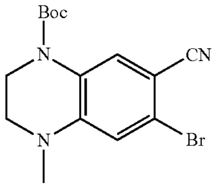 | 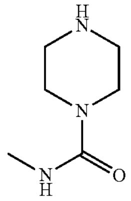 | 286.0 [M + H]$^+$ |
| S36 | 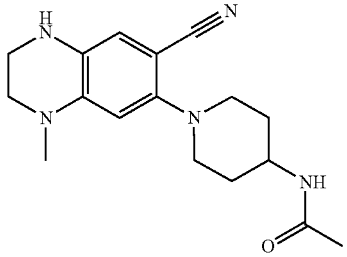 [SMILES: CC(=O)NC1CCN(c2cc3c(cc2C#N)NCCN3C)CC1] | 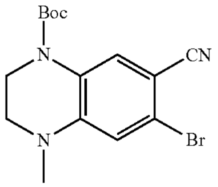 | 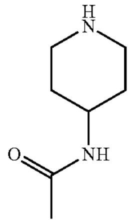 | 314.4 [M + H]$^+$ |
| S37 | 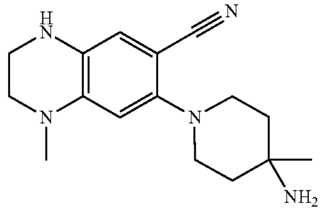 [SMILES: CN1CCNc2cc(C#N)c(N3CCC(C)(N)CC3)cc21] | 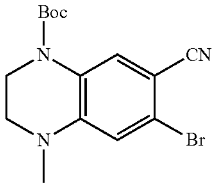 | 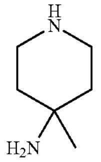 | 286.1 [M + H]$^+$ |
| S38 | 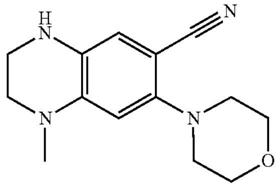 | 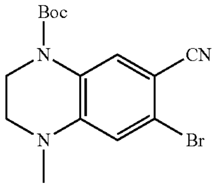 | 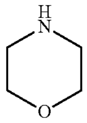 | 307.2 [M + H]$^+$ |

-continued
| Intermediate | Structure | Reactant | Coupling reagent | LC-MS data |
|---|---|---|---|---|
| S39 | 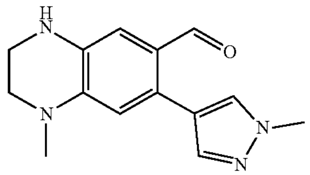 [SMILES: CN1CCNc2cc(C=O)c(-c3cnn(C)c3)cc21] | 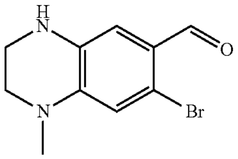 | 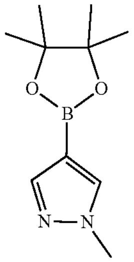 | 257.0 [M + H]+ |
General Scheme-2
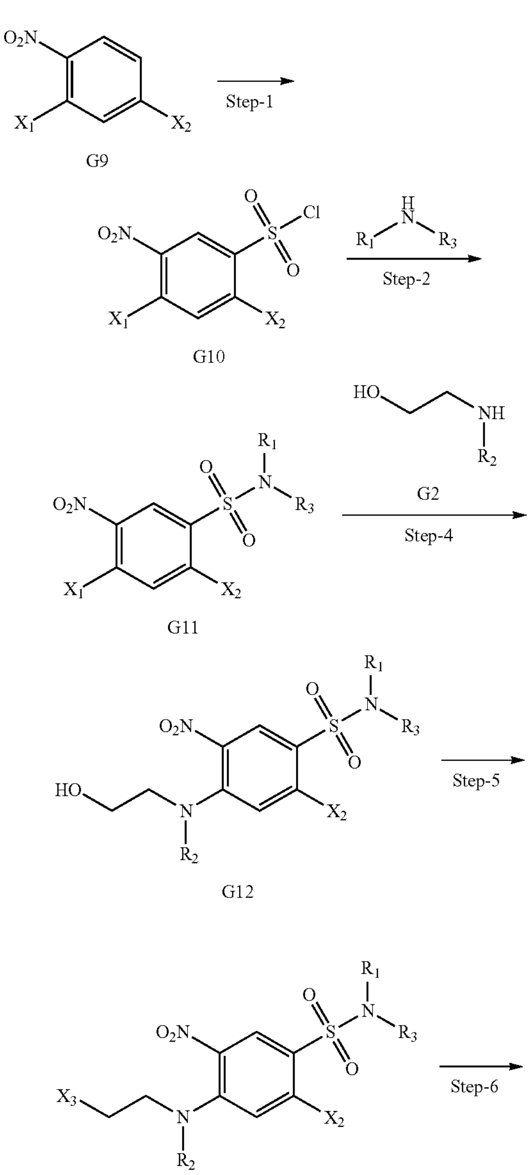
G9
G10
G11
G12
G13
-continued
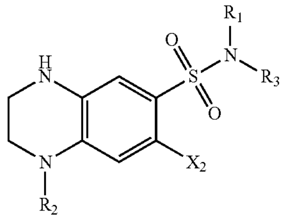
G14
$R_1$ = —H, —Me $R_2$ = —Me, —Et, —PMB, -Cyclopropyl.
$R_3$ = —H, —PMB, —Me $X_1$ = —F, or —Cl. $X_2$ = —H, —F
$X_3$ = —Br or —Cl
Intermediate-S40: N-(4-methoxybenzyl)-1-methyl-1,2,3,4-tetrahydroquinoxaline-6-sulfonamide
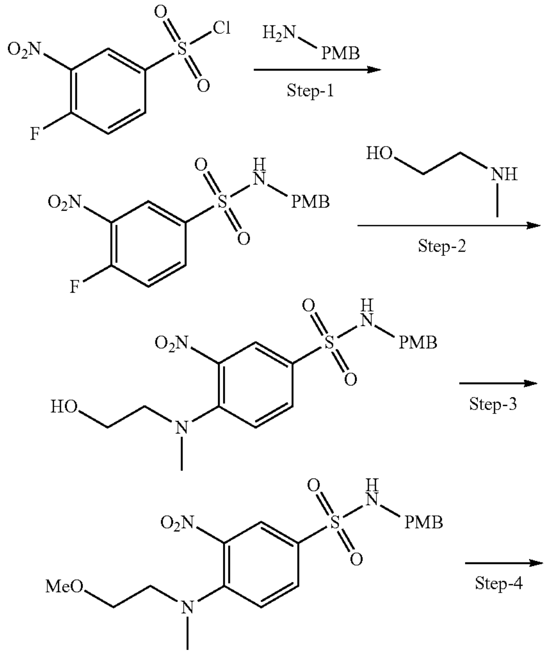

-continued

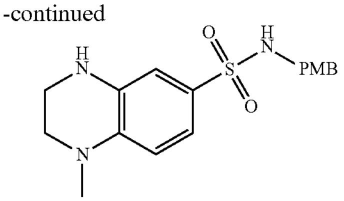

S40

Step-1: Synthesis of 4-fluoro-N-(4-methoxybenzyl)-3-nitrobenzenesulfonamide

To a solution of 4-fluoro-3-nitrobenzenesulfonyl chloride (5 g, 21 mmol) in DMF (50 mL) were added (4-methoxyphenyl)methanamine (3.45 g, 5.04 mmol) to the reaction mixture at 0° C. The reaction mixture was stirred at room temperature for 2 h. After completion of reaction, the reaction mixture was poured into ice water and extracted with ethyl acetate. The organic layer was washed with brine, dried over sodium sulphate and concentrated to get the pure title compound. (3.5 g, 49.2%). LC-MS: 339.05 $[M-H]^+$ Step-2: Synthesis of 4-((2-hydroxyethyl)(methyl)amino)-N-(4-methoxybenzyl)-3-nitrobenzenesulfonamide To a solution of 4-fluoro-N-(4-methoxybenzyl)-3-nitrobenzenesulfonamide (2 g, 5.88 mmol) in DMF (20 mL) were added DIPEA (1.51 g, 11.7 mmol) and 2-(methylamino)ethan-1-ol (485 mg, 6.47 mmol) to the reaction mixture at 0° C. The reaction mixture was stirred at room temperature for 2 h. After completion of reaction, the reaction mixture was poured into ice water and extracted with ethyl acetate. The organic layer was washed with brine, dried over sodium sulphate and concentrated to get the pure title compound. (2.2 g, 94.8%). LC-MS: 396.2 $[M+H]^+$ Step-3: Synthesis of 4-((2-chloroethyl)(methyl)amino)-N-(4-methoxybenzyl)-3-nitrobenzenesulfonamide To a solution of 4-((2-hydroxyethyl)(methyl)amino)-N-(4-methoxybenzyl)-3-nitrobenzenesulfonamide (2.2 g, 5.5 mmol) in DCM (20 mL) were added $Et_3N$ (1.68 g, 16.6 mmol) and followed by MsCl (761 mg, 6.68 mmol) to the reaction mixture at 0° C. The reaction mixture was stirred at room temperature for 5 h. After completion of reaction, the reaction mixture was poured into ice water and extracted with DCM. The organic layer was washed with brine solution and dried over sodium sulphate and concentrated to get the title pure compound (2.3 g, 88.4%). LC-MS: 474.4 [M+H]+

Step-4: Synthesis of N-(4-methoxybenzyl)-1-methyl-1,2,3,4-tetrahydroquinoxaline-6-sulfonamide To a solution of 2-((4-(N-(4-methoxybenzyl)sulfamoyl)-2-nitrophenyl)(methyl)amino)ethyl methanesulfonate (2.3 g, 4.81 mmol) in Ethanol (17 mL), water (3 mL) were added Iron powder (2.7 g, 48.1 mmol) and followed by catalytic amount of conc. HCl (0.5 mL) to the reaction mixture at room temperature. The reaction mixture was stirred at 90° C. for 5 h. After completion of reaction, the reaction mixture was diluted with ethyl acetate and passed through the Celite® bed and washed with ethyl acetate. The organic layer was washed with brine solution and dried over sodium sulphate and concentrated to get the title pure compound (500 mg, 30.1%). LC-MS: 348.15 $[M+H]^+$ The intermediate S41 was prepared according to the procedure described in the synthesis of S40 with appropriate variations in coupling methods, reactants, quantities of reagents, and solvents.

| Intermediate | Structure | Reactant | LCMS data |
|---|---|---|---|
| S41 | 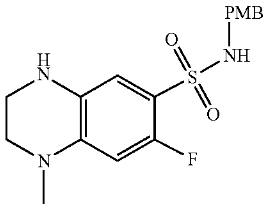 | 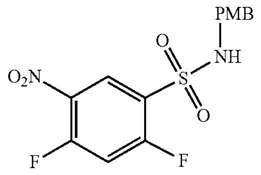 | 366.1 $[M + H]^+$ |
| S42 | 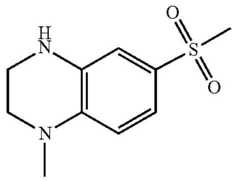 | 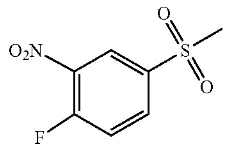 | 227.0 $[M + H]^+$ |
| S43 | 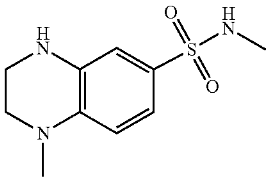 [SMILES: CNS(=O)(=O)c1ccc2c(c1)NCCN2C] | 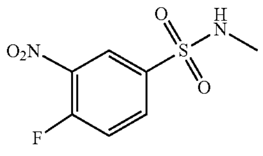 | 242.0 $[M + H]^+$ |

-continued
| Intermediate | Structure | Reactant | LCMS data |
|---|---|---|---|
| S44 | 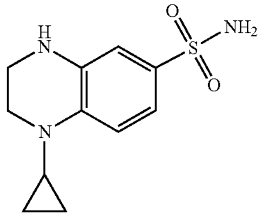 [SMILES: NS(=O)(=O)c1ccc2c(c1)NCCN2C1CC1] | 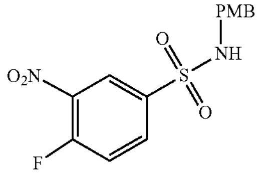 | 254.1 [M + H]+ |
| S45 | 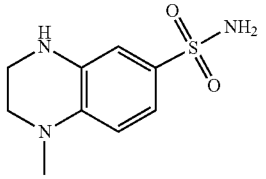 | 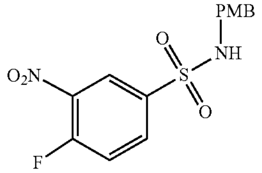 | 228.1 [M + H]+ |
| S46 | 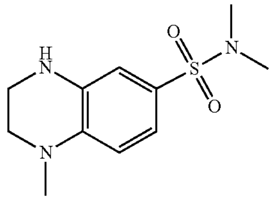 [SMILES: CN1CCNc2cc(S(=O)(=O)N(C)C)ccc21] | 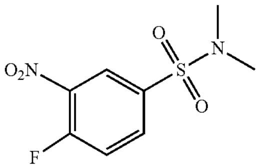 | 256.2 [M + H]+ |
| S47 | 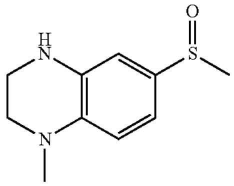 | 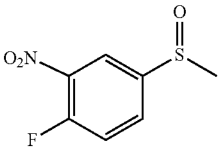 | 211.3 [M + H]+ |
| S48 | 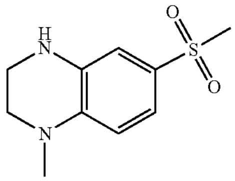 | 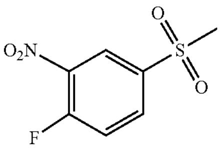 | 227.0 [M + H]+ |
| S49 | 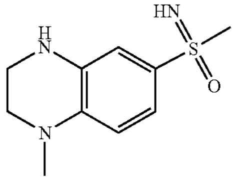 | 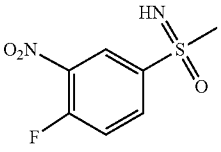 | 226.0 [M + H]+ |
| S50 | 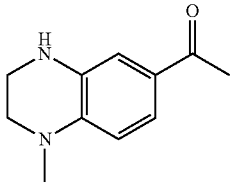 | 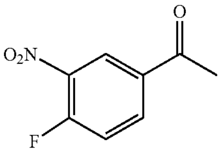 | 191.1 [M + H]+ |
| S51 | 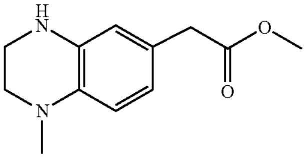 [SMILES: COC(=O)Cc1ccc2c(c1)NCCN2C] | 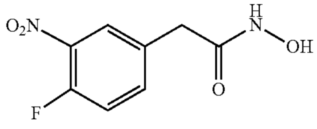 [SMILES: O=C(Cc1ccc(F)c([N+](=O)[O-])c1)NO] | 221.2 [M + H]+ |

-continued

| Intermediate | Structure | Reactant | LCMS data |
|---|---|---|---|
| S52 | 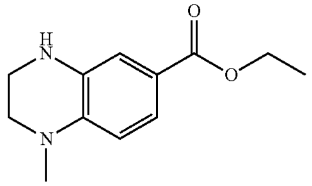 [SMILES: CCOC(=O)c1ccc2c(c1)NCCN2C] | 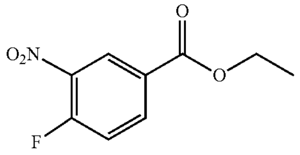 | 220.8 [M + H]$^+$ |
| S53 | 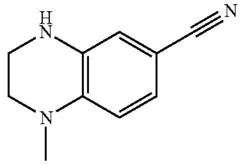 | 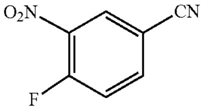 [SMILES: N#Cc1ccc(F)c([N+](=O)[O-])c1] | 173.8 [M + H]$^+$ |
| S54 | 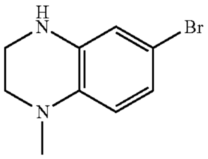 | 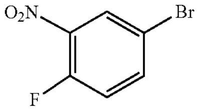 | 227.0 [M + H]$^+$ |
| S55 | 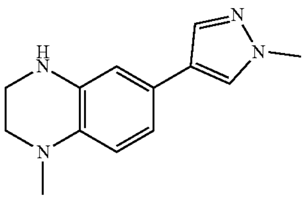 [SMILES: CN1CCNc2cc(-c3cnn(C)c3)ccc21] | 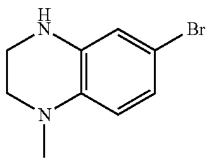 | 229.3 [M + H]$^+$ |

Intermediate-S56: N,1-dimethyl-1,2,3,4-tetrahydroquinoxaline-6-carboxamide

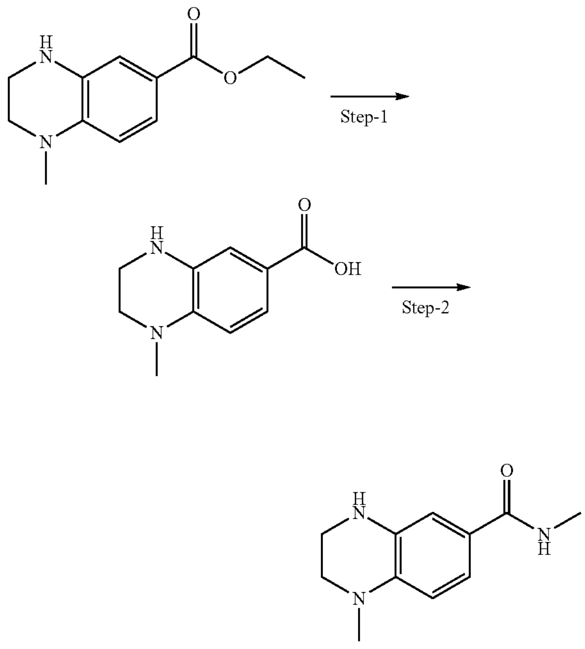

S56

Step-1: Synthesis of 1-methyl-1,2,3,4-tetrahydroquinoxaline-6-carboxylic acid

To a solution of ethyl 1-methyl-1,2,3,4-tetrahydroquinoxaline-6-carboxylate (300 mg, 1.26 mmol) in THE (2 mL), Methanol (2 mL), water (1 mL) was added Iron LiOH·$H_2O$ (302 mg, 7.21 mmol) to the reaction mixture at room temperature. The reaction mixture was stirred at 70° C. for 3 h. After completion of reaction, the reaction mixture was cooled 0° C. and adjusted pH-5 using citric acid solution and ethyl acetate. The organic layer was washed with brine solution and dried over sodium sulphate and concentrated to get the title pure compound. (111 mg, 45.8%). LC-MS: 193.0 [M+H]$^+$ Step-2: Synthesis of N,1-dimethyl-1,2,3,4-tetrahydroquinoxaline-6-carboxamide To a solution of 1-methyl-1,2,3,4-tetrahydroquinoxaline-6-carboxylic acid (110 mg, 0.57 mmol) in DMF (5 mL) was DIPEA (369.8 mg, 2.86 mmol), EDC.HCl (163.9, 0.86 mmol), HOBT (94.5 mg, 0.68 mmol) and followed by methylamine hydrochloride (191.5 mg, 2.86 mmol) to the reaction mixture at 0° C. The reaction mixture was stirred at room temperature for 12 h. After completion of reaction, the reaction mixture was extracted with ethyl acetate. The organic layer was washed with brine solution and dried over sodium sulphate and concentrated to get the crude compound which was purified by Combiflash® column chromatography to eluent (60-70%) ethyl acetate in hexane to obtained pure title compound. (57 mg, 49.1%). LC-MS: 206.0 [M+H]$^+$.

Intermediate Coupling Method-IC

Intermediate-S57: 1-methyl-7-(1-methyl-1H-pyrazol-4-yl)-1,2,3,4-tetrahydropyrido[3,4-b]pyrazine

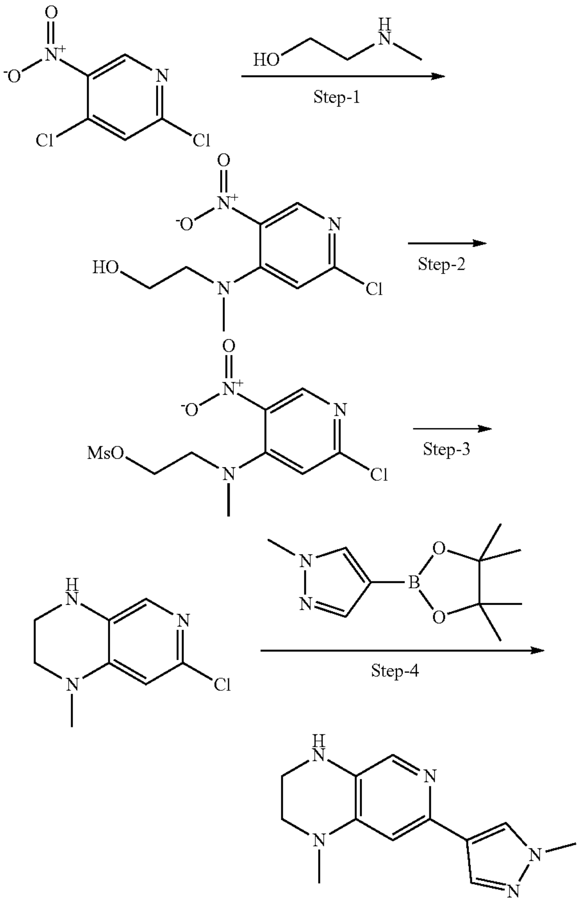

S57

Step-1: Synthesis of 2-((2-chloro-5-nitropyridin-4-yl)(methyl)amino)ethan-1-ol

To a solution of 2,4-dichloro-5-nitropyridine (25 g, 129.54 mmol) in THE (200 mL) were added DIPEA (33.4 g, 259.08 mmol) and 2-(methylamino)ethan-1-ol (10.7 g, 142.5 mmol) to the reaction mixture at 0° C. The reaction mixture stirred at room temperature for 3 h. After completion of reaction, the reaction mixture was poured into ice water and extracted with ethyl acetate. The organic layer washed with brine and dried over sodium sulphate and concentrated to get the pure title compound. (29.5, 98.3%). LC-MS: 232.1 $[M+H]^+$ Step-2: Synthesis of 2-((2-chloro-5-nitropyridin-4-yl)(methyl)amino)ethyl methanesulfonate To a solution of 2-((2-chloro-5-nitropyridin-4-yl)(methyl)amino)ethan-1-ol (29 g, 125.1 mmol) in DCM (300 mL) were added $Et_3N$ (25.3 g, 250.38 mmol) and MsCl (15.8 g, 137.7 mmol) to the reaction mixture at 0° C. The reaction mixture stirred at room temperature for 2 h. After completion of reaction, the reaction mixture was poured into ice water and extracted with DCM. The organic layer washed with brine solution and dried over sodium sulphate and concentrated to get the title compound (37 g, 95.4%). LC-MS: $310[M+H]^+$.

Step-3: Synthesis of 7-chloro-1-methyl-1,2,3,4-tetrahydropyrido[3,4-b]pyrazine

To a solution of 2-((2-chloro-5-nitropyridin-4-yl)(methyl)amino)ethyl methanesulfonate (37 g, 119.4 mmol) in ethanol (360 mL), water (40 mL) were added Iron powder (65.9 g, 1194.6 mmol) and catalytic amount of conc. HCl (3 mL) to the reaction mixture at room temperature. The reaction mixture stirred at 90° C. for 2 h. After completion of reaction, the reaction mixture was diluted with ethyl acetate and passed through the Celite® bed and washed with ethyl acetate. The organic layer washed with brine solution and dried over sodium sulphate and concentrated to get the crude compound. The crude compound was purified by (100-200 mesh) silica gel column chromatography as eluent 50-60% ethyl acetate in hexane to obtain the title compound quantitatively yield (22 g). LC-MS: 184.4 $[M+H]^+$ Step-4: Synthesis of 1-methyl-7-(1-methyl-1H-pyrazol-4-yl)-1,2,3,4-tetrahydropyrido[3,4-b]pyrazine A degassed solution of 7-chloro-1-methyl-1,2,3,4-tetrahydropyrido[3,4-b]pyrazine (2.5 g, 13.6 mmol) and 1-methyl-4-(4,4,5,5-tetramethyl-1,3,2-dioxaborolan-2-yl)-1H-pyrazole (5.6 g, 27.22 mmol) in 1,2-dimethoxy ethane (40 mL) and water (10 mL). The mixture was then added $Pd(Amphos)Cl_2$ (480 mg, 0.68 mmol) and potassium carbonate (5.63, 40.8 mmol). The mixture was stirred at 100° C. for 12 h. The reaction mixture was then cooled to room temperature, water was added and the mixture was extracted with ethyl acetate. Organic extracts were washed with water, brine dried over Sodium sulphate and concentrated to get the title crude compound. (2.3 g). LC-MS: 230.2 $[M+H]^+$. By using the same procedure as described above the following intermediates were prepared.

Intermediate Coupling Method-ID

Intermediate-S58: 1-methyl-7-(piperidin-1-yl)-1,2,3,4-tetrahydropyrido[3,4-b]pyrazine

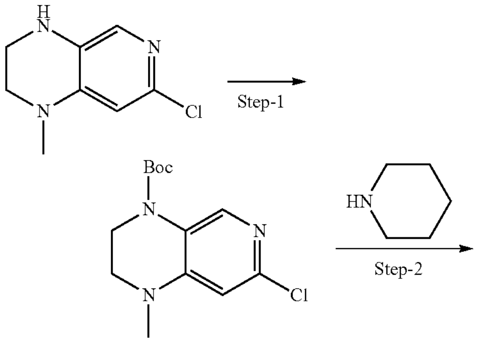

-continued

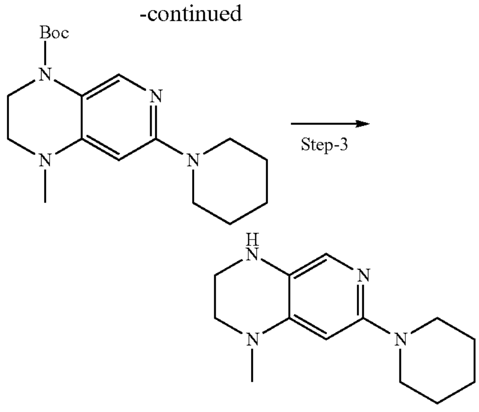

S58

Step-1: Synthesis of tert-butyl 7-chloro-1-methyl-2,3-dihydropyrido[3,4-b]pyrazine-4(1H)-carboxylate To a solution of tert-butyl 7-chloro-1-methyl-2,3-dihydropyrido[3,4-b]pyrazine-4(1H)-carboxylate (1 g, 5.45 mmol) in DCM (20 mL) were added $Et_3N$ (1.1 g, 10.8 mmol), DMAP (330 mg, 27.3 mmol) and followed by $(Boc)_2O$ (1.43 g, 6.5 mmol) to the reaction mixture at 0° C. The reaction mixture was stirred at room temperature for 12 h. After completion of reaction, the reaction mixture was poured into ice water and extracted with DCM. The organic layer was washed with brine, dried over sodium sulphate and concentrated to get the crude compound. Crude compound was purified by Combiflash® column chromatography using solvent eluent (10-20%) ethyl acetate in hexane to obtain the pure title compound. (1.2 g, 77.6%). LC-MS: 284.1 $[M+H]^+$ Step-2: Synthesis of tert-butyl 1-methyl-7-(piperidin-1-yl)-2,3-dihydropyrido[3,4-b]pyrazine-4(1H)-carboxylate A degassed solution of tert-butyl 7-chloro-1-methyl-2,3-dihydropyrido[3,4-b]pyrazine-4(1H)-carboxylate (500 mg, 1.76 mmol), piperidine (450 mg, 5.28 mmol) in dioxane (10 mL) was added $Pd_2(dba)_3$ (160 mg, 0.18 mmol), BINAP (220 mg, 0.35 mmol) and sodium tert butoxide (510 mg, 5.28 mmol). The mixture was stirred at 100° C. for 14 h. The reaction mixture was then cooled to room temperature and diluted with 10% methanol in DCM and passed through the Celite® bed. The organic layer sodium sulphate and concentrated to get the crude compound. The crude compound was purified by Combiflash® column chromatography using 4% methanol in DCM as eluent to yield (400 mg, 68.3%). LC-MS: 333.2 $[M+H]^+$ Step-3: Synthesis of 1-methyl-7-(piperidin-1-yl)-1,2,3,4-tetrahydropyrido[3,4-b]pyrazine To a solution of tert-butyl 1-methyl-7-(piperidin-1-yl)-2,3-dihydropyrido[3,4-b]pyrazine-4(1H)-carboxylate (400 mg, 1.2 mmol) in dioxane. HCl and then the reaction mixture was stirred at room temperature for 8 h. After completion of reaction, the reaction mixture evaporated the solvent completely to get the residue. The residue was extracted with ethyl acetate and washed with saturated $NaHCO_3$ solution, dried over $Na_2SO_4$, concentrated to obtain pure title compound (200 mg, 71.7%). LC-MS: 233.2 $[M+H]^+$ The below intermediates (S59-S73) were prepared according to the procedure described in the synthesis of Intermediate-S58 with appropriate variations in coupling methods, reactants, quantities of reagents, and solvents.

| Intermediate | Structure | Reactant | Coupling reagent | LCMS data |
|---|---|---|---|---|
| S59 | 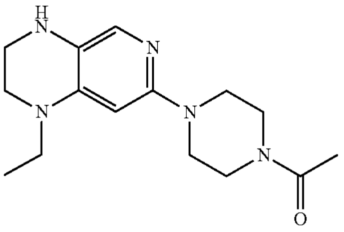 [SMILES: CCN1CCNc2cnc(N3CCN(C(C)=O)CC3)cc21] | 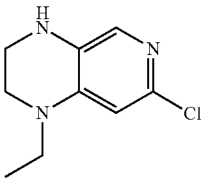 | 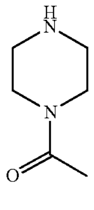 | 290.0 $[M + H]^+$ |
| S60 | 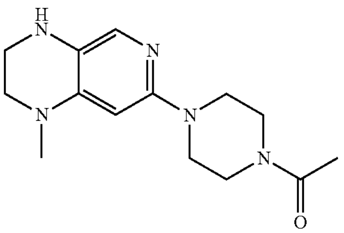 [SMILES: CC(=O)N1CCN(c2cc3c(cn2)NCCN3C)CC1] | 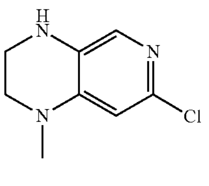 | 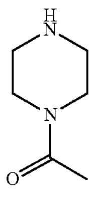 | 276.0 $[M + H]^+$ |

-continued
| Inter-mediate | Structure | Reactant | Coupling reagent | LCMS data |
|---|---|---|---|---|
| S61 | 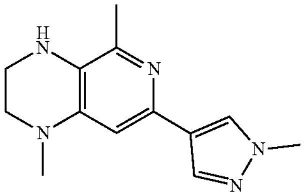 [SMILES: Cc1nc(-c2cnn(C)c2)cc2c1NCCN2C] | 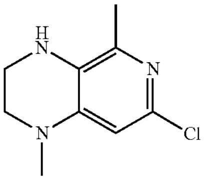 | 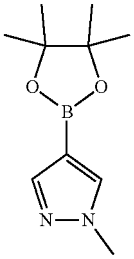 | 244.4 [M + H]$^+$ |
| S62 | 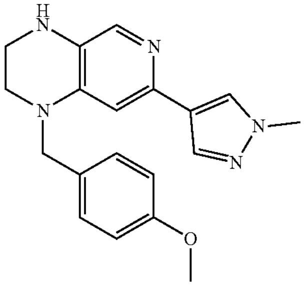 [SMILES: COc1ccc(CN2CCNc3cnc(-c4cnn(C)c4)cc32)cc1] | 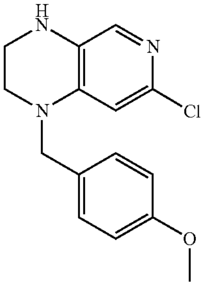 | 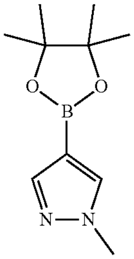 | 336.1 [M + H]$^+$ |
| S63 | 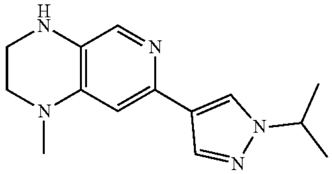 [SMILES: CC(C)n1cc(-c2cc3c(cn2)NCCN3C)cn1] | 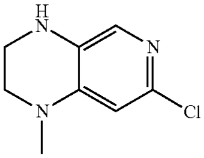 | 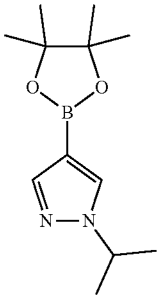 [SMILES: CC(C)n1cc(B2OC(C)(C)C(C)(C)O2)cn1] | 258.5 [M + H]$^+$ |
| S64 | 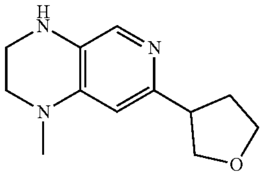 [SMILES: CN1CCNc2cnc(C3CCOC3)cc21] | 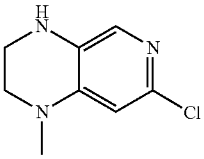 | 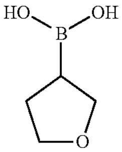 | 220.2 [M + H]$^+$ |
| S65 | 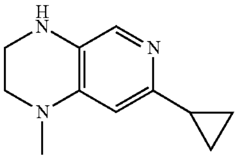 | 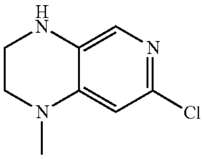 | 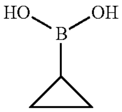 | 190.0 [M + H]$^+$ |
| S66 | 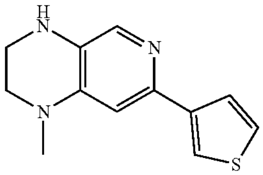 [SMILES: CN1CCNc2cnc(-c3ccsc3)cc21] | 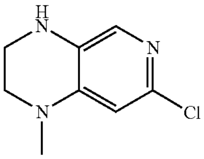 | 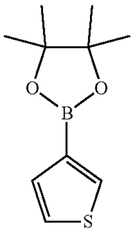 | 232.0 [M + H]$^+$ |

-continued
| Intermediate | Structure | Reactant | Coupling reagent | LCMS data |
|---|---|---|---|---|
| S67 | 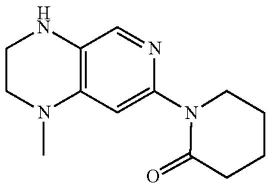 [SMILES: CN1CCNc2cnc(N3CCCCC3=O)cc21] | 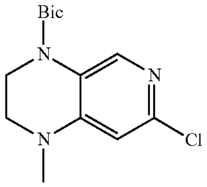 | 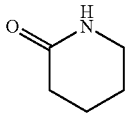 | 247.6 [M + H]+ |
| S68 | 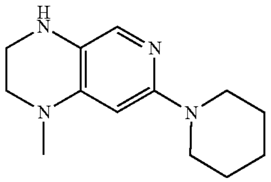 [SMILES: CN1CCNc2cnc(N3CCCCC3)cc21] | 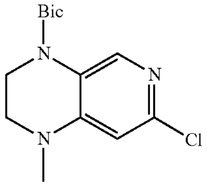 | 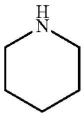 | 233.2 [M + H]+ |
| S69 | 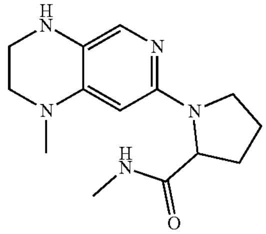 [SMILES: CNC(=O)C1CCCN1c1cc2c(cn1)NCCN2C] | 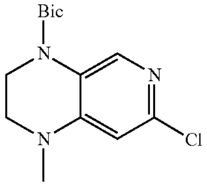 | 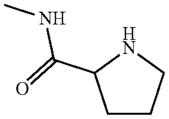 | 6033-027-P 276.0 [M + H]+ |
| S70 | 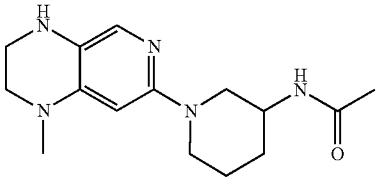 [SMILES: CC(=O)NC1CCCN(c2cc3c(cn2)NCCN3C)C1] | 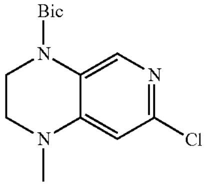 | 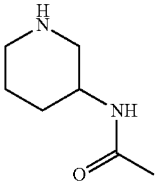 | 6033-033-P 290.0 [M + H]+ |
| S71 | 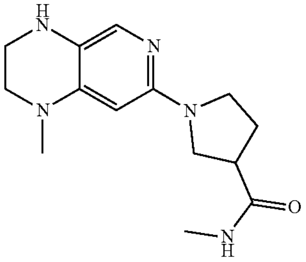 [SMILES: CNC(=O)C1CCN(c2cc3c(cn2)NCCN3C)C1] | 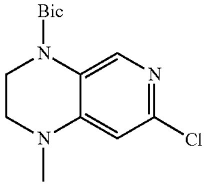 | 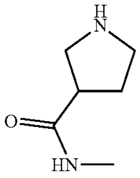 | 5951-084-P 276.1 [M + H]+ |
| S72 | 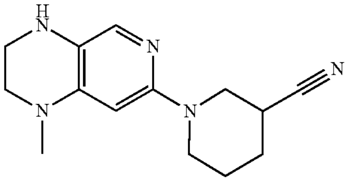 [SMILES: CN1CCNc2cnc(N3CCCC(C#N)C3)cc21] | 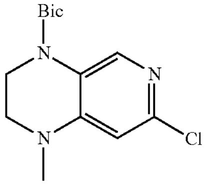 | 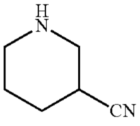 | 6003-029-P1 257.8 [M + H]+ |
| S73 | 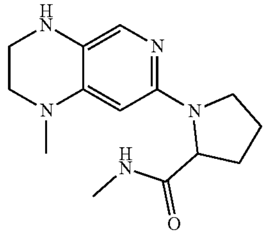 [SMILES: CNC(=O)C1CCCN1c1cc2c(cn1)NCCN2C] | 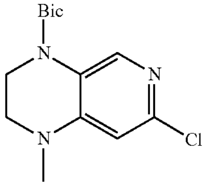 | 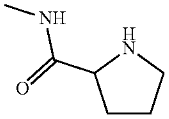 | 6033-027-P 276.0 [M + H]+ |

The below intermediates were prepared by the similar procedure described in pages 69-71 of WO2017205536 with appropriate variations in reactants, quantities of reagents, solvents and reaction conditions. The characterization data of the intermediates are summarized herein below table.

| Intermediates | Structure | Reagent | Coupling reagent | Analytical data |
|---|---|---|---|---|
| S74 | 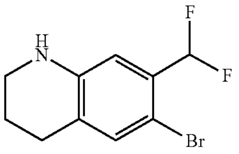 [SMILES: FC(F)c1cc2c(cc1Br)CCCN2] | 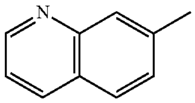 | — | $^1$H NMR (400 MHz, $CDCl_3$) δ 7.09 (s, 2H), 4.53 (brs, 1H), 3.39-3.35 (m, 2H), 2.74-2.71 (m, 2H), 1.91-1.85 (m, 2H). |
| S75 | 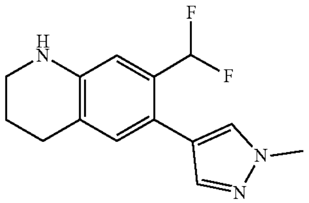 [SMILES: Cn1cc(-c2cc3c(cc2C(F)F)NCCC3)cn1] | 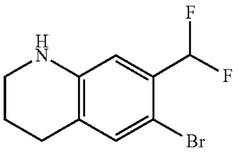 [SMILES: FC(F)c1cc2c(cc1Br)CCCN2] | 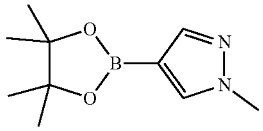 | 264.3 $[M + H]^+$ |
| S76 | 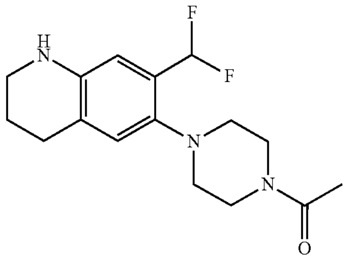 | 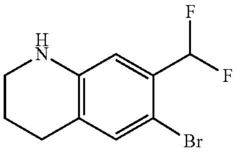 [SMILES: FC(F)c1cc2c(cc1Br)CCCN2] | 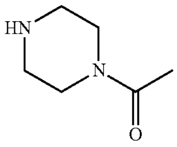 | 285.1 $[M + H]^+$ |
| S77 | 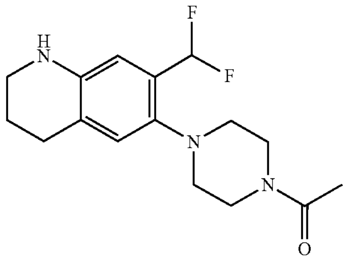 [SMILES: CC(=O)N1CCN(c2cc3c(cc2C(F)F)NCCC3)CC1] | 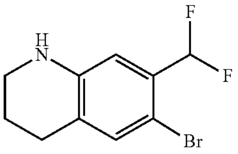 [SMILES: FC(F)c1cc2c(cc1Br)CCCN2] | 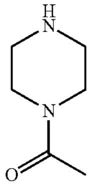 | 310.2 $[M + H]^+$ |
| S78 | 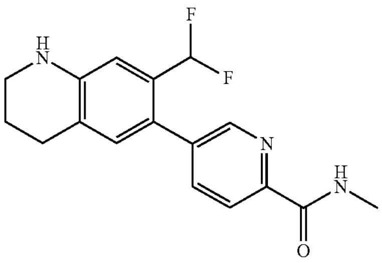 [SMILES: CNC(=O)c1ccc(-c2cc3c(cc2C(F)F)NCCC3)cn1] | 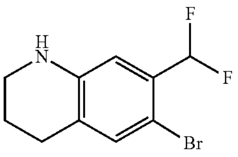 [SMILES: FC(F)c1cc2c(cc1Br)CCCN2] | 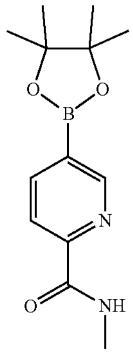 | 318.2 $[M + H]^+$ |

-continued
| Inter-mediates | Structure | Reagent | Coupling reagent | Analytical data |
|---|---|---|---|---|
| S79 | 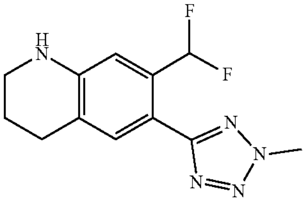 [SMILES: Cn1nnc(-c2cc3c(cc2C(F)F)NCCC3)n1] | 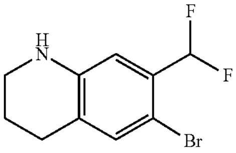 [SMILES: FC(F)c1cc2c(cc1Br)CCCN2] | 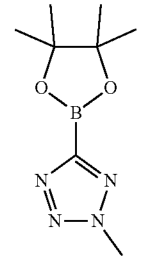 | 266.0 [M + H]+ |
| S80 | 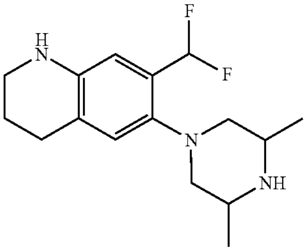 [SMILES: CC1CN(c2cc3c(cc2C(F)F)NCCC3)CC(C)N1] | 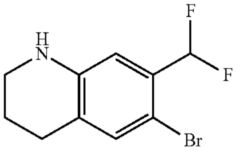 [SMILES: FC(F)c1cc2c(cc1Br)CCCN2] | 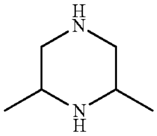 | 296.2 [M + H]+ |
| S81 | 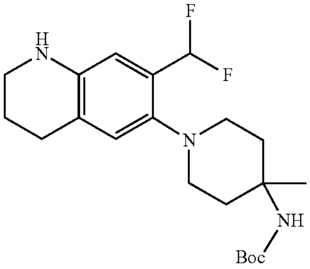 [SMILES: CC1(NC(=O)OC(C)(C)C)CCN(c2cc3c(cc2C(F)F)NCCC3)CC1] | 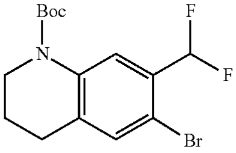 [SMILES: CC(C)(C)OC(=O)N1CCCc2cc(Br)c(C(F)F)cc21] | 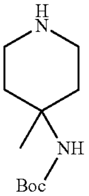 | 396.2 [M + H]+ |
| S82 | 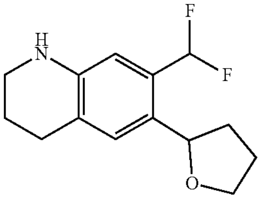 [SMILES: FC(F)c1cc2c(cc1C1CCCO1)CCCN2] | 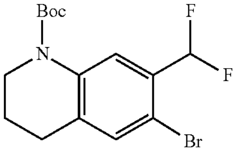 [SMILES: CC(C)(C)OC(=O)N1CCCc2cc(Br)c(C(F)F)cc21] | 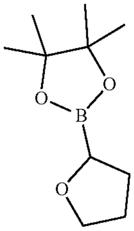 | 254.3 [M + H]+ |
| S83 | 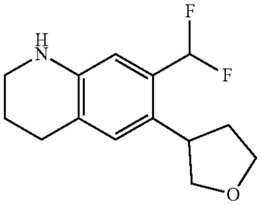 [SMILES: FC(F)c1cc2c(cc1C1CCOC1)CCCN2] | 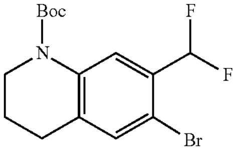 [SMILES: CC(C)(C)OC(=O)N1CCCc2cc(Br)c(C(F)F)cc21] | 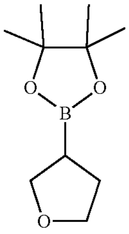 | 254.3 [M + H]+ |
| S84 | 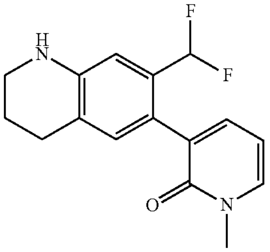 [SMILES: Cn1cccc(-c2cc3c(cc2C(F)F)NCCC3)c1=O] | 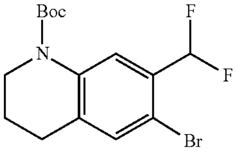 [SMILES: CC(C)(C)OC(=O)N1CCCc2cc(Br)c(C(F)F)cc21] | 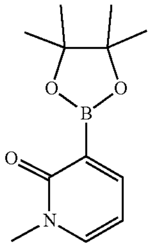 | 291.2 [M + H]+ |

Intermediate-S85: N-(7-(difluoromethyl)-1,2,3,4-tetrahydroquinolin-6-yl)-N-methylacetamide

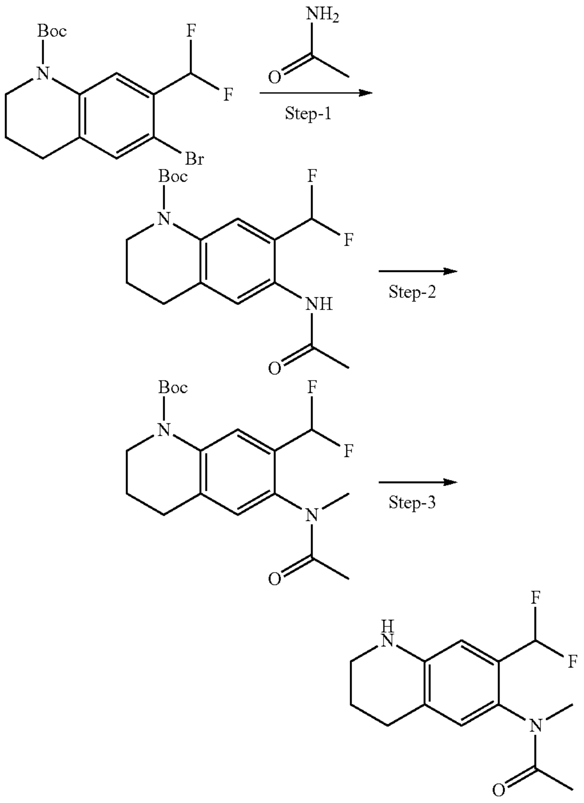

S85

Step-1: Synthesis of tert-butyl 6-acetamido-7-(difluoromethyl)-3,4-dihydroquinoline-1(2H)-carboxylate A degassed solution of tert-butyl 6-bromo-7-(difluoromethyl)-3,4-dihydroquinoline-1(2H)-carboxylate (350 mg, 0.97 mmol), acetamide (70 mg, 1.15 mmol) in dioxane (12 mL) was added $Pd_2(dba)_3$ (90 mg, 0.1 mmol), BINAP (119 mg, 0.18 mmol) and $Cs_2CO_3$ (950 mg, 2.91 mmol). The mixture was stirred at 100° C. for 12 h. The reaction mixture was then cooled to room temperature and diluted with 10% methanol in DCM and passed through the Celite® bed. The organic layer sodium sulphate and concentrated to get the crude compound. The crude compound was purified by Combiflash® column chromatography using 50% ethyl acetate in hexane as eluent title pure compound quantitively yield (350 mg). LC-MS: 285.0 $[M\text{-}Bu^tH]^+$ Step-2: Synthesis of tert-butyl 7-(difluoromethyl)-6-(N-methylacetamido)-3,4-dihydroquinoline-1(2H)-carboxylate To a solution of tert-butyl 6-acetamido-7-(difluoromethyl)-3,4-dihydroquinoline-1(2H)-carboxylate (200 mg, 0.59 mmol) in DMF (5 mL) was added NaH (60 mg, 2.65 mmol) to the reaction mixture at 0° C. and then the reaction mixture was stirred at room temperature for 1 h. After completion of reaction, the reaction mixture evaporated the solvent completely to get the pure title compound (160 mg, 76.5%). LCMS: 355.0 $[M+H]^+$ Step-3: Synthesis of N-(7-(difluoromethyl)-1,2,3,4-tetrahydroquinolin-6-yl)-N-methylacetamide To a solution of tert-butyl tert-butyl 7-(difluoromethyl)-6-(N-methylacetamido)-3,4-dihydroquinoline-1(2H)-carboxylate (160 mg, 0.45 mmol) in DCM (3 mL) was added TFA (510 mg, 4.50 mmol) to the reaction mixture and then the reaction mixture was stirred at room temperature for 12 h. After completion of reaction, the reaction mixture evaporated the solvent completely to get the crude compound which was washed with diethyl ether to obtain the pure title compound (100 mg, 87.4%). LC-MS: 255.2 $[M+H]^+$.

Intermediate-S86: 7-methoxy-6-(1-methyl-1H-pyrazol-4-yl)-1,2,3,4-tetrahydroquinoline

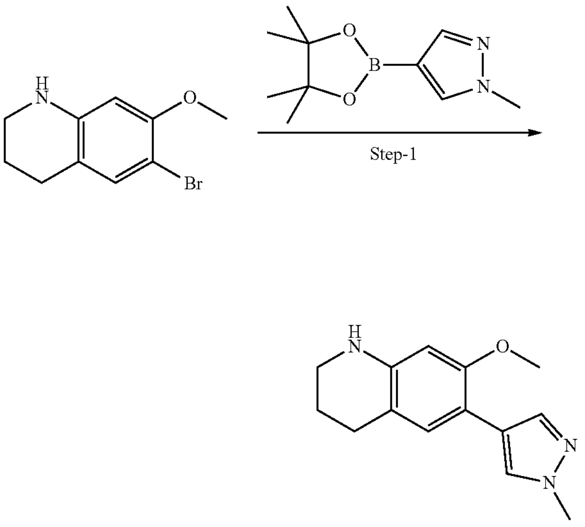

S86

Step-1: Synthesis of 7-methoxy-6-(1-methyl-1H-pyrazol-4-yl)-1,2,3,4-tetrahydroquinoline A degassed solution of 6-bromo-7-methoxy-1,2,3,4-tetrahydroquinoline (prepared as per the procedure described in WO2016155573, page-32, line-20) (0.78 g, 3.76 mmol) and 1-methyl-4-(4,4,5,5-tetramethyl-1,3,2-dioxaborolan-2-yl)-1H-pyrazole (0.7 g, 2.89 mmol) in dioxane (16 mL) and water (4 mL). The reaction mixture was then added Pd(Amphos)$Cl_2$ (100 mg, 0.14 mmol) and potassium carbonate (1.2 g, 8.67 mmol). The mixture was stirred at 100° C. for 12 h. The reaction mixture was then cooled to room temperature, water was added and the mixture was extracted with ethyl acetate. Organic extracts were washed with water, brine dried over Sodium sulphate and concentrated to get the crude compound. The crude compound was purified by Combiflash® column chromatography using 30-40% ethyl acetate in hexane as eluent to yield (5 g, 72%). LC-MS: 244.3 $[M+H]^+$ Intermediate-S87: 1-(4-(1,2,3,4-tetrahydroquinolin-6-yl)piperazin-1-yl)ethan-1-one

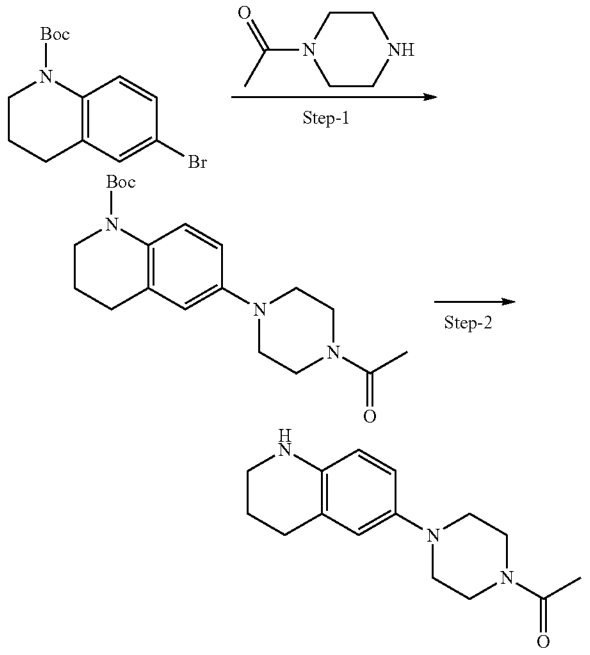

S87

Step-1: Synthesis of tert-butyl 6-(4-acetylpiperazin-1-yl)-3,4-dihydroquinoline-1(2H)-carboxylate A degassed solution of tert-butyl 6-bromo-3,4-dihydroquinoline-1(2H)-carboxylate (prepared as per the procedure described in WO2016/086200, page-331, Example-175) (200 mg, 0.64 mmol), 1-(piperazin-1-yl)ethan-1-one (244 mg, 1.92 mmol) in dioxane (6 mL) was added $Pd_2(dba)_3$ (58 mg, 0.064 mmol), Dave-Phos (24 mg, 0.064 mmol) and sodium tert butoxide (184.5 mg, 1.82 mmol). The mixture was stirred at 100° C. for 12 h. The reaction mixture was then cooled to room temperature, water was added and the mixture was extracted with ethyl acetate. Organic extracts were washed with water, brine dried over sodium sulphate and concentrated to get the crude compound. The crude compound was purified by Combiflash® column chromatography using 60-70% ethyl acetate in hexane as eluent to yield (160 mg, 69.5%). LC-MS: 260.1 $[M-Boc]^+$ Step-2: Synthesis of 1-(4-(1,2,3,4-tetrahydroquinolin-6-yl)piperazin-1-yl)ethan-1-one To a solution of tert-butyl 6-(4-acetylpiperazin-1-yl)-3,4-dihydroquinoline-1(2H)-carboxylate (160 mg, 0.61 mmol) in DCM (4 mL), TFA (4 mL) and then the reaction mixture stirred at room temperature for 2 h. After completion of reaction, the reaction mixture evaporated the solvent completely to get the crude compound was extracted with 5% McOH in DCM. The organic layer washed with aq. $NH_4OH$ solution and brine dried over sodium sulphate and concentrated to get the pure compound quantitatively yield (150 mg). LC-MS: 260.15 $[M+H]^+$ Intermediate-S88: 5-(7-cyano-1,2,3,4-tetrahydroquinolin-6-yl)-N-methylpicolinamide

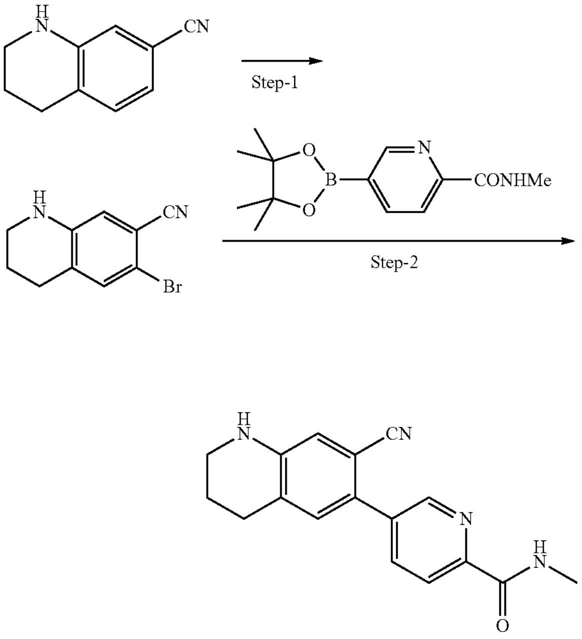

S88

Step-1: 6-bromo-1,2,3,4-tetrahydroquinoline-7-carbonitrile

To a solution of 1,2,3,4-tetrahydroquinoline-7-carbonitrile (350 mg, 2.21 mmol) in DCM (5 mL) was added NBS (390 mg, 2.21 mmol) to the reaction mixture at 0° C. The reaction mixture stirred at room temperature for 1 h. After completion of reaction, the reaction mixture was extracted with DCM. The organic layer washed with brine dried over sodium sulphate and concentrated to get the crude compound. The crude compound was purified by Combiflash® column chromatography using 7% ethyl acetate in hexane as eluent to yield (800 g, 51.7%). LC-MS:237.1 $[M+]^+$ Step-2: Synthesis of N-methyl-5-(1,2,3,4-tetrahydroquinolin-6-yl)picolinamide A degassed solution of 6-bromo-1,2,3,4-tetrahydroquinoline-7-carbonitrile (300 mg, 1.18 mmol) and N-methyl-5-(4,4,5,5-tetramethyl-1,3,2-dioxaborolan-2-yl)picolinamide (438 mg, 1.42 mmol) in dioxane (12 mL) and water (3 mL). The mixture was then added $Pd(Amphos)Cl_2$ (42 mg, 0.06 mmol) and potassium carbonate (485.5 mg, 3.54 mmol). The mixture was stirred at 100° C. for 12 h. The reaction mixture was then cooled to room temperature, water was added and the mixture was extracted with ethyl acetate. The organic extracts were washed with water, brine dried over sodium sulphate and concentrated to get the crude compound. The crude compound was purified by Combiflash® column chromatography using 70-80% ethyl acetate in hexane as eluent to yield (150 mg, 43.6%). LC-MS:308.3 $[M+H]^+$ Intermediate-S89: 7-(1-(4-methoxybenzyl)-1H-pyrazol-4-yl)-1,2,3,4-tetrahydroquinoline

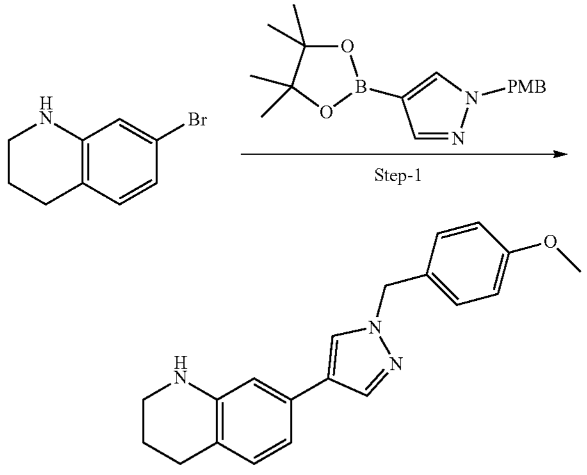

S89

Step-1: Synthesis of 7-(1-(4-methoxybenzyl)-1H-pyrazol-4-yl)-1,2,3,4-tetrahydroquinoline A degassed solution of 7-bromo-1,2,3,4-tetrahydroquinoline (200 mg, 0.94 mmol) and 1-(4-methoxybenzyl)-4-(4,4,5,5-tetramethyl-1,3,2-dioxaborolan-2-yl)-1H-pyrazole (300 mg, 1.04 mmol) in DME (5 mL) and water (0.5 mL). The mixture was then added Pd(Amphos)$Cl_2$ (70 mg, 0.09 mmol) and potassium carbonate (330 mg, 2.36 mmol). The mixture was stirred at 90° C. for 6 h. The reaction mixture was then cooled to room temperature, diluted with 5% McOH in DCM and passed through the Celite® bed. Evaporated the solvent completely to get the crude compound. The crude compound was purified by Combiflash® column chromatography using 20% ethyl acetate in hexane as eluent to yield (150 mg, 55.14%). LC-MS: 290.3 $[M+H]^+$ Intermediate-S90: 7-methoxy-4-methyl-6-(1-methyl-1H-pyrazol-4-yl)-1,2,3,4-tetrahydroquinoline

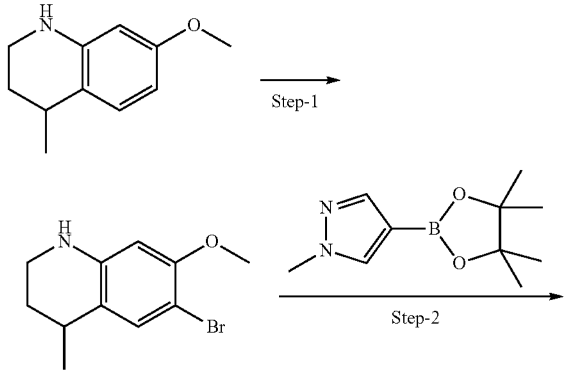

-continued

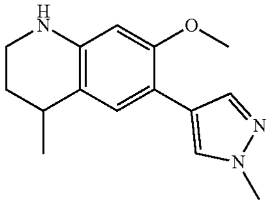

S90

Step-1: Synthesis of 6-bromo-7-methoxy-4-methyl-1,2,3,4-tetrahydroquinoline (IN6624-094)

To a solution of 7-methoxy-4-methyl-1,2,3,4-tetrahydroquinoline (Synthesized as described in U.S. Pat. No. 5,688,810, 18 Nov. 1997) (500 mg, 2.82 mmol) in DCM (5 mL) was added N-bromosuccinimie (550 mg, 3.1 mmol) to the reaction mixture at 0° C. The reaction mixture stirred at room temperature for 2 h. After completion of reaction, the reaction mixture was extracted with DCM. The organic layer washed with brine and dried over sodium sulphate and concentrated to get the crude compound. Crude compound was purified by Combiflash® column chromatography and eluted at (10%) ethyl acetate in hexane to obtain the pure title compound (500 mg, 69.2%). LC-MS: 256.0 $[M+]^+$ Step-2: Synthesis of 7-methoxy-4-methyl-6-(1-methyl-1H-pyrazol-4-yl)-1,2,3,4-tetrahydroquinoline A degassed solution of 6-bromo-7-methoxy-4-methyl-1,2,3,4-tetrahydroquinoline (500 mg, 1.95 mmol) and 1-methyl-4-(4,4,5,5-tetramethyl-1,3,2-dioxaborolan-2-yl)-1H-pyrazole (810 mg, 3.9 mmol) in DME (9 mL) and water (1 mL). The mixture was then added Pd(Amphos)$Cl_2$ (70 mg, 0.1 mmol) and potassium carbonate (810 mg, 5.85 mmol). The mixture was stirred at 90° C. for 6 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography using 40% ehyl acetate in hexane as eluent to yield (500 mg, 99.5%). LC-MS:258.4 $[M+H]^+$ Intermediate-S91: 7-methoxy-4,4-dimethyl-6-(1-methyl-1H-pyrazol-4-yl)-1,2,3,4-tetrahydroquinoline

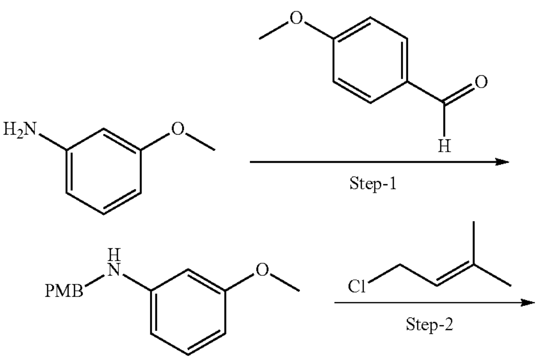

-continued

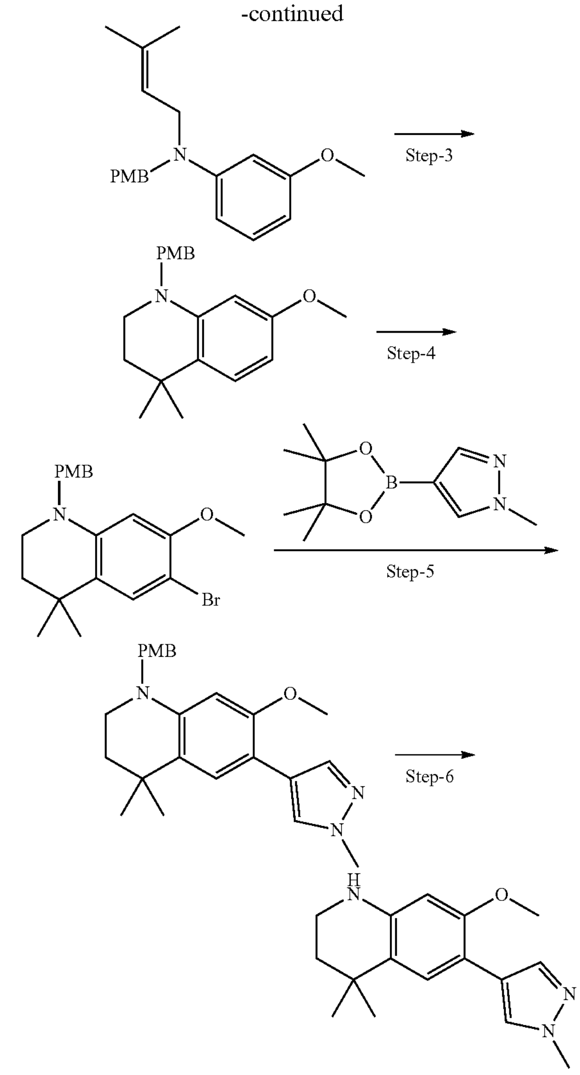

S91

Step-1: Synthesis of 3-methoxy-N-(4-methoxybenzyl)aniline

To a solution of 3-methoxyaniline (1 g, 8.12 mmol) in ethanol (10 mL) was added 4-methoxybenzaldehyde (1.1 g, 8.12 mmol) to the reaction at room temperature and then stirred same temperature for 2 h. $NaBH_4$ (0.55 g, 16.24 mmol) was added to the reaction mixture at 0° C. The combined reaction mixture stirred at room temperature for 12 h. After completion of reaction, the reaction mixture was evaporated the solvent and extracted with ethyl acetate. The organic layer washed with brine and dried over sodium sulphate and concentrated to get the crude compound. The crude compound was purified by Combiflash® column chromatography using 5% ethyl acetate in hexane as eluent to yield (1.5 g, 75.93%). LC-MS: 244.1 $[M+H]^+$ Step-2: Synthesis of 3-methoxy-N-(4-methoxybenzyl)-N-(3-methylbut-2-en-1-yl)aniline To a solution of 3-methoxy-N-(4-methoxybenzyl)aniline (1.5 g, 6.17 mmol) in acetonitrile (15 mL) were added $K_2CO_3$ (2.56 g, 18.51 mmol) and followed by 1-chloro-3-methylbut-2-ene (0.77 g, 7.4 mmol) to the reaction mixture at room temperature. The reaction mixture stirred at 75° C. for 12 h. After completion of reaction, the reaction mixture was poured into ice water and extracted with ethyl acetate. The organic layer washed with brine and dried over sodium sulphate and concentrated to get the crude compound. The crude compound was purified by Combiflash® column chromatography using 3.5% ethyl acetate in hexane as eluent to yield (1.4 g, 72.8%). LC-MS: 312.4 $[M+H]^+$ Step-3: Synthesis of 7-methoxy-1-(4-methoxybenzyl)-4,4-dimethyl-1,2,3,4-tetrahydroquinoline To a suspension of 3-methoxy-N-(4-methoxybenzyl)-N-(3-methylbut-2-en-1-yl)aniline (1.4 g, 4.5 mmol) in methane sulfonic acid (1.5 mL) and then heated to 95° C. for 2 h. After completion of reaction, the reaction mixture was poured into ice water and adjusted pH-7. Extracted with ethyl acetate, the organic layer washed with brine and dried over sodium sulphate and concentrated to get the crude compound. The crude compound was purified by Combiflash® column chromatography using 2% ethyl acetate in hexane as eluent to yield (0.5 g, 35.6%). LC-MS: 312.2 $[M+H]^+$ Step-4: Synthesis of 6-bromo-7-methoxy-1-(4-methoxybenzyl)-4,4-dimethyl-1,2,3,4-tetrahydroquinoline To a solution of 7-methoxy-1-(4-methoxybenzyl)-4,4-dimethyl-1,2,3,4-tetrahydroquinoline (0.46 g, 1.48 mmol) in DCM (10 mL) was added N-bromosuccinimie (0.26 g, 1.48 mmol) to the reaction mixture at 0° C. The reaction mixture stirred at room temperature for 2 h. After completion of reaction, the reaction mixture was extracted with DCM. The organic layer washed with brine and dried over sodium sulphate and concentrated to get the crude compound. Crude compound was purified by Combiflash® column chromatography and eluted at (2-2.5%) ethyl acetate in hexane to obtain the pure title compound (450 mg, 77.9%). LC-MS: 392.2 $[M+2H]^+$ Step-5: Synthesis of 7-methoxy-1-(4-methoxybenzyl)-4,4-dimethyl-6-(1-methyl-1H-pyrazol-4-yl)-1,2,3,4-tetrahydroquinoline A degassed solution of 6-bromo-7-methoxy-1-(4-methoxybenzyl)-4,4-dimethyl-1,2,3,4-tetrahydroquinoline (450 g, 1.15 mmol) and 1-methyl-4-(4,4,5,5-tetramethyl-1,3,2-dioxaborolan-2-yl)-1H-pyrazole (450 mg, 2.3 mmol) in DME (9 mL) and water (1 mL). The mixture was then added Pd(Amphos)$Cl_2$ (80 mg, 0.11 mmol) and potassium carbonate (480 mg, 3.45 mmol). The mixture was stirred at 90° C. for 4 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography using 15% ehyl acetate in hexane as eluent to yield (450 mg, 99.9%). LC-MS:392.4 $[M+H]^+$ Step-6: Synthesis of 7-methoxy-4,4-dimethyl-6-(1-methyl-1H-pyrazol-4-yl)-1,2,3,4-tetrahydroquinoline To a solution of 7-methoxy-1-(4-methoxybenzyl)-4,4-dimethyl-6-(1-methyl-1H-pyrazol-4-yl)-1,2,3,4-tetrahydroquinoline (0.45 g, 1.15 mmol) in TFA (10 mL) and then heated 100° C. for 12 h. After completion of reaction, the reaction mixture was evaporated completely and quenched with aq ammonium hydroxide solution. Extracted with ethyl acetate. The organic layer washed with brine and dried over sodium sulphate and concentrated to get the crude compound. Crude compound was purified by Combiflash® column chromatography and eluted at (25%) ethyl acetate in hexane to obtain the pure title compound (300 mg, 96.4%). LC-MS: 272.2 $[M+2H]^+$ Intermediate-S92: 8-(1-methyl-1H-pyrazol-4-yl)-1,2,3,4-tetrahydroisoquinoline

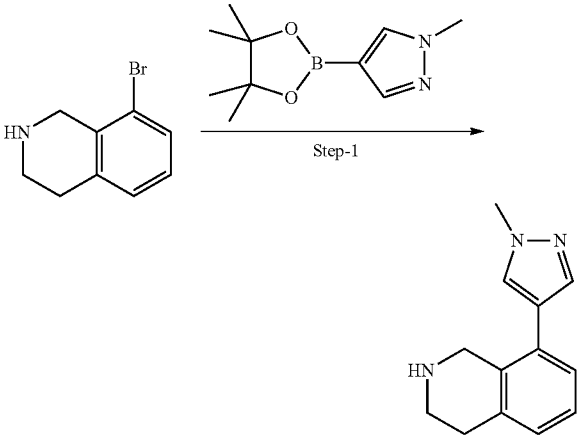

S92

Step-1: Synthesis of 8-(1-methyl-1H-pyrazol-4-yl)-1,2,3,4-tetrahydroisoquinoline A degassed solution of 8-bromo-1,2,3,4-tetrahydroisoquinoline (400 mg, 1.8 mmol) and 1-methyl-4-(4,4,5,5-tetramethyl-1,3,2-dioxaborolan-2-yl)-1H-pyrazole (470 mg, 2.2 mmol) in dioxane (4 mL) and water (1 mL). The mixture was then added Pd(Amphos)$Cl_2$ (66 mg, 0.094 mmol) and potassium carbonate (651 mg, 4.7 mmol). The mixture was stirred at 100° C. for 12 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography using 40-50% ehyl acetate in hexane as eluent to yield (450 mg, 91.3%). LC-MS: 214.0 $[M+H]^+$ Intermediate-S93: 1-methyl-3-(1-methyl-1H-pyrazol-4-yl)-4,5,6,7-tetrahydro-1H-pyrazolo[4,3-c]pyridine

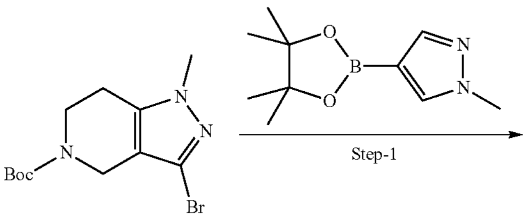

-continued

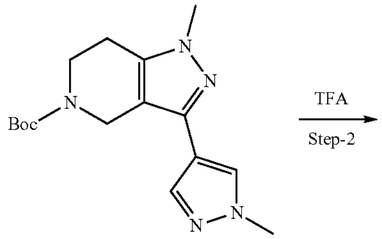

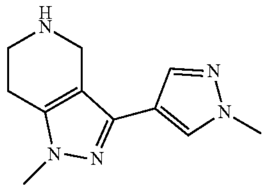

S93

Step-1: Synthesis of tert-butyl 1-methyl-3-(1-methyl-1H-pyrazol-4-yl)-1,4,6,7-tetrahydro-5H-pyrazolo[4,3-c]pyridine-5-carboxylate A degassed solution of tert-butyl 3-bromo-1-methyl-1,4,6,7-tetrahydro-5H-pyrazolo[4,3-c]pyridine-5-carboxylate (prepared as per the procedure described in the patent WO2016/086200, page-141, line-15) (360 mg, 1.13 mmol) and 1-methyl-4-(4,4,5,5-tetramethyl-1,3,2-dioxaborolan-2-yl)-1H-pyrazole (260 mg, 1.25 mmol) in dioxane (10 mL) and water (5 mL). The mixture was then added Pd(Amphos)$Cl_2$ (40 mg, 0.056 mmol) and potassium carbonate (305 mg, 2.26 mmol). The mixture was stirred at 100° C. for 12 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography using 20% ethyl acetate in hexane as eluent to get the pure compound (quantitative yield). LC-MS: 318.3 $[M+H]^+$ Step-2: Synthesis of 1-methyl-3-(1-methyl-1H-pyrazol-4-yl)-4,5,6,7-tetrahydro-1H-pyrazolo[4,3-c]pyridine To a solution of tert-butyl 1-methyl-3-(1-methyl-1H-pyrazol-4-yl)-1,4,6,7-tetrahydro-5H-pyrazolo[4,3-c]pyridine-5-carboxylate (400 mg, 1.26 mmol) in dioxane (10 mL), dioxane. HCl (10 mL) and then the reaction mixture stirred at room temperature for 1 h. After completion of reaction, the reaction mixture evaporated the solvent completely to get the crude compound was washed with diethyl ether to obtained the compound was used next step without any purification (360 mg, 90.9%)LC-MS: 218.0 $[M+H]^+$ Intermediate-S94: 6-(difluoromethyl)-5-(1-methyl-1H-pyrazol-4-yl)indoline

S94

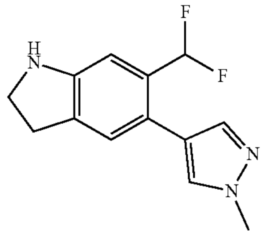

The intermediate-S94 was prepared as per the procedure described in WO2016/086200, page-350, line-15 with appropriate variations in reactants, quantities of reagents, solvents and reaction conditions (Yield:80.7%). LC-MS: 150.3 $[M+H]^+$ Intermediate-S95: 1-(4-(1,2,3,4-tetrahydro-1,7-naphthyridin-6-yl)piperazin-1-yl)ethan-1-one

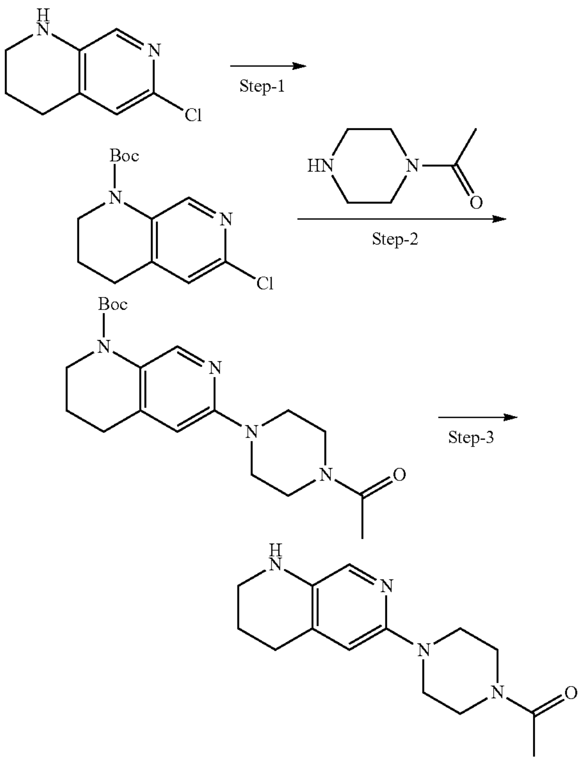

S95

Step-1: Synthesis of tert-butyl 6-chloro-3,4-dihydro-1,7-naphthyridine-1(2H)-carboxylate To a solution of 6-bromo-7-(difluoromethyl)-1,2,3,4-tetrahydroquinoline (571 mg, 3.3 mmol) in THE (15 mL) were added DMAP (1.1 g, 10.19 mmol), and followed by $(Boc)_2O$ (1.6 mL, 6.7 mmol) to the reaction mixture at 0° C. The reaction mixture stirred at room temperature for 12 h. After completion of reaction, the reaction mixture was poured into ice water and extracted with ethyl acetate. The organic layer washed with brine and dried over sodium sulphate and concentrated to get the crude compound. Crude compound was purified by Combiflash® column chromatography using solvent eluent (20-25%) ethyl acetate in hexane to obtain the pure title compound (617 mg, 70%). 1H NMR (600 MHz, $CDCl_3$) δ 8.69 (brs, 1H), 7.26 (s, 1H), 7.04 (s, 1H), 3.73-3.71 (m, 2H), 2.76-2.74 (m, 2H), 1.94-1.92 (m, 2H), 1.52 (s, 9H).

Step-2: Synthesis of tert-butyl 6-(4-acetylpiperazin-1-yl)-3,4-dihydro-1,7-naphthyridine-1(2H)-carboxylate A degassed solution of tert-butyl 6-chloro-3,4-dihydro-1,7-naphthyridine-1(2H)-carboxylate (200 mg, 0.74 mmol), 1-(piperazin-1-yl)ethan-1-one (287 mg, 2.23 mmol) in dioxane (5 mL) was added $Pd_2(dba)_3$ (68 mg, 0.074 mmol), Dave-phos (30 mg, 0.074 mmol) and sodium tert butoxide (215 mg, 2.23 mmol). The mixture was stirred at 100° C. for 12 h. The reaction mixture was then cooled to room temperature and diluted with 10% methanol in DCM and passed through the Celite® bed. The organic layer sodium sulphate and concentrated to get the crude compound. The crude compound was purified by Combiflash® column chromatography and eluted at 80-100% ethyl acetate in hexane to obtain the pure title compound (160 mg, 60.1%). LC-MS: 361.4 $[M+H]^+$ Step-3: Synthesis of 1-(4-(1,2,3,4-tetrahydro-1,7-naphthyridin-6-yl)piperazin-1-yl)ethan-1-one To a solution of tert-butyl 6-(4-acetylpiperazin-1-yl)-3,4-dihydro-1,7-naphthyridine-1(2H)-carboxylate (160 mg, 0.44 mmol) in DCM (3 mL) was added TFA (2 mL) to the reaction at 0° C. and then the reaction mixture stirred at room temperature for 2 h. After completion of reaction, the reaction mixture evaporated the solvent completely to get the residue. The residue was quenched with ammonium hydroxide solution and extracted with ethyl acetate. The organic layer dried over $Na_2SO_4$, concentrated to get the pure title compound (100 mg, 87.7%). LC-MS: 261.3 $[M+H]^+$ Intermediate-S96: 4-methyl-1,2,3,4-tetrahydroquinoxaline-6-sulfonamide

S96

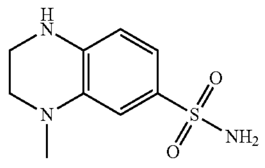

The intermediate-S96 was prepared as per the procedure described in preparation of intermediate S1, with appropriate variations in reactants, quantities of reagents, solvents and reaction conditions. Yield: 67.1%) LC-MS: 228.0 $[M+H]^+$ Intermediate-S97: 6-(1-methyl-1H-pyrazol-4-yl)-1,2,3,4-tetrahydro-1,7-naphthyridine

S97

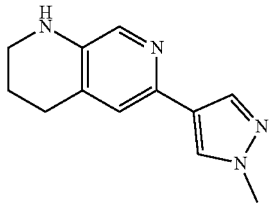

The intermediate-S97 was prepared as per the procedure described in WO2016/086200, page-365, line-10, with appropriate variations in reactants, quantities of reagents, solvents and reaction conditions (Yield: 70.5%). LC-MS: 215.0 $[M+H]^+$ Intermediate-S98: 7-(1-methyl-1H-pyrazol-4-yl)-3,4-dihydro-2H-pyrido[4,3-b][1,4]

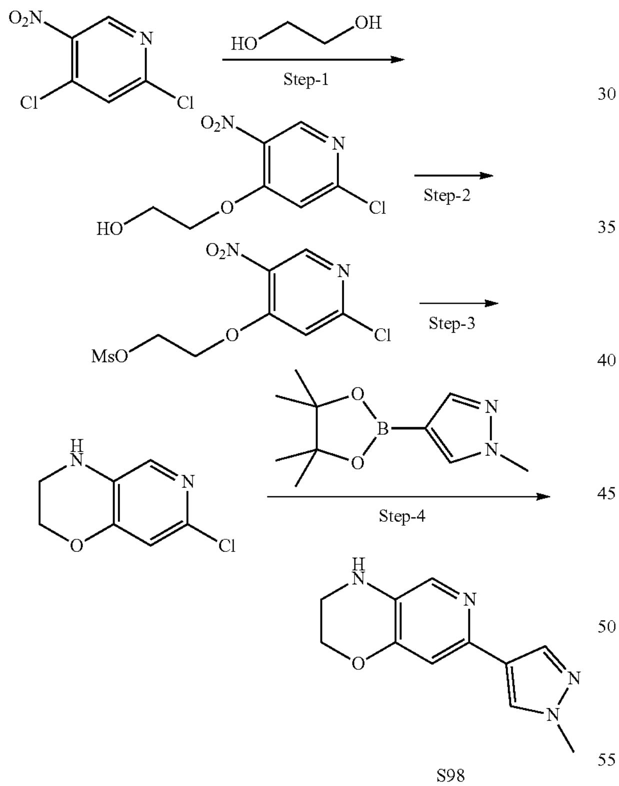

S98

Step-1: Synthesis of 2-((2-chloro-5-nitropyridin-4-yl)oxy)ethan-1-ol

To a solution of 2,4-dichloro-5-nitropyridine (3 g, 15.54 mmol) in DMF (15 mL) were added DIPEA (4.0 g, 31 mmol) and ethane-1,2-diol (1.4 g, 18.6 mmol) to the reaction mixture at 0° C. The reaction mixture stirred at room temperature for 1 h. After completion of reaction, the reaction mixture was poured into ice water and extracted with ethyl acetate. The organic layer washed with brine and dried over sodium sulphate and concentrated to get the title compound. LC-MS: 232.1$[M+H]^+$ Step-2: Synthesis of 2-((2-chloro-5-nitropyridin-4-yl)oxy)ethyl methanesulfonate To a solution of 2-((2-chloro-5-nitropyridin-4-yl)oxy)ethan-1-ol (300 mg, 1.37 mmol) in DCM (5 mL) were added $Et_3N$ (419 mg, 4.11 mmol) and MsCl (118 mg, 1.65 mmol) to the reaction mixture at 0° C. The reaction mixture stirred at room temperature for 2 h. After completion of reaction, the reaction mixture was poured into ice water and extracted with DCM. The organic layer washed with saturated $NaHCO_3$, brine solution and dried over sodium sulphate and concentrated to get the title compound (381 mg, 94%). 1H NMR (400 MHz, $CDCl_3$) δ 8.89 (s, 1H), 7.07 (s, 1H), 4.65-3.4.63 (m, 2H), 4.49-4.67 (m, 2H), 3.13 (s, 3H).

Step-3: Synthesis of 7-chloro-3,4-dihydro-2H-pyrido[4,3-b][1,4]oxazine

To a solution of 2-((2-chloro-5-nitropyridin-4-yl)oxy) ethyl methanesulfonate (300 mg, 1.01 mmol) in Ethanol (5 mL), water (2 mL) were added Iron powder (559 mg, 10.16 mmol) and $NH_4C_1$ (555 mg, 10.16 mmol) to the reaction mixture at room temperature. The reaction mixture stirred at 80° C. for 3 h. After completion of reaction, the reaction mixture was diluted with ethyl acetate and passed through the Celite® bed and washed with ethyl acetate. The organic layer washed with brine solution and dried over sodium sulphate and concentrated to get the crude compound. The crude compound was purified by prep TLC as eluent 30% ethyl acetate in hexane to obtain the title compound. (120 mg, 70.1%). LC-MS: 171.0 $[M+H]^+$ Step-4: Synthesis of 7-(1-methyl-1H-pyrazol-4-yl)-3,4-dihydro-2H-pyrido[4,3-b][1,4]oxazine A degassed solution of 7-chloro-3,4-dihydro-2H-pyrido[4,3-b][1,4]oxazine (100 mg, 0.58 mmol) and 1-methyl-4-(4,4,5,5-tetramethyl-1,3,2-dioxaborolan-2-yl)-1H-pyrazole (367 mg, 1.76 mmol) in dioxane (3 mL) and ethanol (1 mL), water (3 mL). The mixture was then added $Pd(Amphos)Cl_2$ (20 mg, 0.029 mmol) and potassium carbonate (202 mg, 1.47 mmol). The mixture was stirred at 90° C. for 6 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by prep TLC as eluent 5% McOH in DCM to obtain the title compound. (85 mg, 68%). LC-MS: 217.2 $[114+H]^+$ Intermediate-S99: 6-fluoro-7-(1-methyl-1H-pyrazol-4-yl)-3,4-dihydroquinoxalin-2(1H)-one

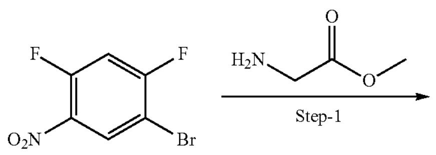

-continued

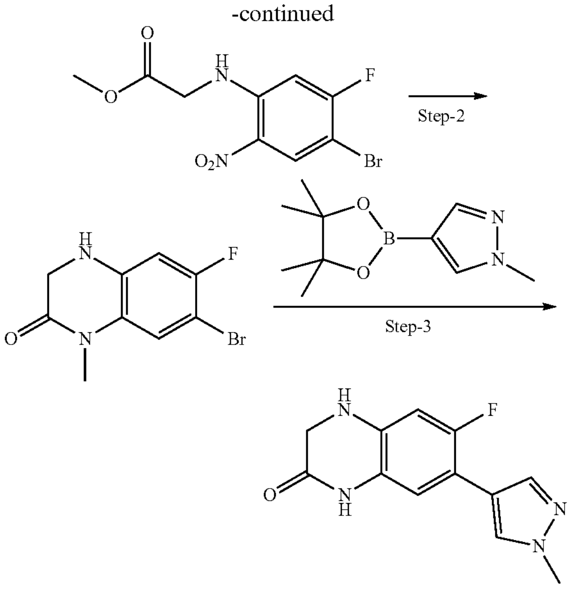

S99

Step-1: Synthesis of methyl (4-bromo-5-fluoro-2-nitrophenyl)glycinate

To a solution of 1-bromo-2,4-difluoro-5-nitrobenzene (2 g, 8.4 mmol) in THE (10 mL) were added DIPEA (3.26 mL, 25.2 mmol) and methyl glycinate (1.12 g, 12.6 mmol) to the reaction mixture at 0° C. The reaction mixture stirred at room temperature for 3 h. After completion of reaction, the reaction mixture was poured into ice water and extracted with ethyl acetate. The organic layer washed with brine and dried over sodium sulphate and concentrated to get the pure title compound (2.5 g, 96.9%). LC-MS: 309.0 $[M+2H]^+$ Step-2: Synthesis of 7-bromo-6-fluoro-1-methyl-3,4-dihydroquinoxalin-2(1H)-one To a solution of methyl (4-bromo-5-fluoro-2-nitrophenyl) glycinate (0.5 g, 1.63 mmol) in Ethanol (8 mL), water (2 mL) were added Iron powder (0.9 g, 16.2 mmol) and followed by catalytic amount of conc. HCl (0.02 mL) to the reaction mixture at room temperature. The reaction mixture stirred at 80° C. for 13 h. After completion of reaction, the reaction mixture was diluted with ethyl acetate and extracted. The organic layer washed with brine solution and dried over sodium sulphate and concentrated to get the crude compound. The crude compound was purified by Combiflash® column chromatography and eluted at 50% ethyl acetate in hexane to obtain the pure title compound (101 mg, 25.3%). 1H NMR (300 MHz, DMSO-$d_6$) δ 10.34 (brs, 1H), 6.87 (d, J=6.9 Hz, 1H), 6.61 (d, J=10.2 Hz, 1H), 6.40 (s, 1H), 3.77 (s, 3H).

Step-3: Synthesis of 6-fluoro-7-(1-methyl-1H-pyrazol-4-yl)-3,4-dihydroquinoxalin-2(1H)-one A degassed solution of 7-bromo-6-fluoro-1-methyl-3,4-dihydroquinoxalin-2(1H)-one (100 mg, 0.41 mmol) and 1-methyl-4-(4,4,5,5-tetramethyl-1,3,2-dioxaborolan-2-yl)-1H-pyrazole (170 mg, 0.82 mmol) in dioxane (2 mL) and ethanol (1 mL), water (2 mL). The mixture was then added Pd(Amphos)$Cl_2$ (30 mg, 0.04 mmol) and potassium carbonate (170 mg, 1.12 mmol). The mixture was stirred at 100° C. for 12 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography and eluted at 5% McOH in DCM to obtain the pure title compound (20 mg, 19.81%). LC-MS: 247.2 $[M+H]^+$ Intermediate-S100: 7-(1-methyl-1H-pyrazol-4-yl)-1,2,3,4-tetrahydroisoquinoline

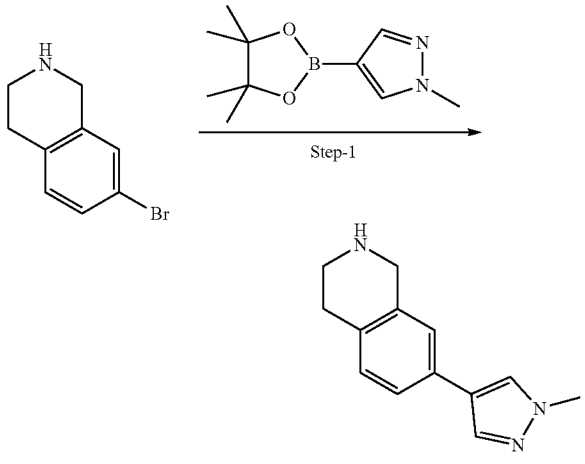

S100

Step-1: Synthesis of 7-(1-methyl-1H-pyrazol-4-yl)-1,2,3,4-tetrahydroisoquinoline A degassed solution of 7-bromo-1,2,3,4-tetrahydroisoquinoline (1 g, 4.7 mmol) and 1-methyl-4-(4,4,5,5-tetramethyl-1,3,2-dioxaborolan-2-yl)-1H-pyrazole (1.17 g, 5.66 mmol) in dioxane (10 mL) water (2 mL). The mixture was then added Pd(Amphos)$Cl_2$ (166 mg, 0.23 mmol) and potassium carbonate (1.62 g, 11.79 mmol). The mixture was stirred at 100° C. for 12 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography and eluted at 3-5% McOH in DCM to obtain the pure title compound (900 mg, 90%). LC-MS: 214.3 $[M+H]^+$ Intermediate-S101: 1,2-dimethyl-7-(1-methyl-1H-pyrazol-4-yl)-1,2,3,4-tetrahydropyrido[3,4-b]pyrazine

S101

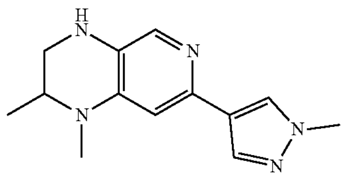

The intermediate-S101 was prepared as per the procedure described in preparation of intermediate S1, with appropriate variations in reactants, quantities of reagents, solvents and reaction conditions. LC-MS: 244.2 $[M+H]^+$ Intermediate-S102: 7-(1-methyl-1H-pyrazol-4-yl)-3,4-dihydro-2H-pyrido[4,3-b][1,4]thiazine

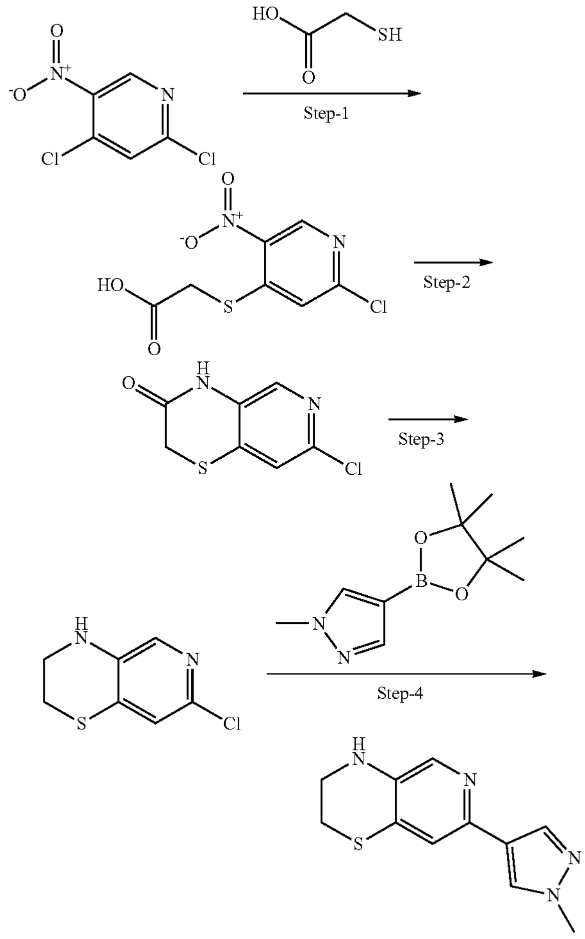

S102

Step-1: Synthesis of 2-((2-chloro-5-nitropyridin-4-yl)thio)acetic acid

To a solution of 2,4-dichloro-5-nitropyridine (1.5 g, 7.77 mmol) in THF (30 mL) were added DIPEA (2 g, 15.54 mmol) and 2-mercaptoacetic acid (0.79 g, 8.55 mmol) to the reaction mixture at room temperature. The reaction mixture stirred at room temperature for 2 h. After completion of reaction, the reaction mixture was concentrated completely to get the pure title compound (1.9, 98.3%). LC-MS: 249.1 $[M+H]^+$ Step-2: Synthesis of 7-chloro-2H-pyrido[4,3-b][1,4]thiazin-3(4H)-one To a solution of 2-((2-chloro-5-nitropyridin-4-yl)thio)acetic acid (1.9 g, 7.64 mmol) in acetic acid (30 mL) was added Iron powder (4.26 g, 76.4 mmol) to the reaction mixture at room temperature. The reaction mixture stirred at 90° C. for 4 h. After completion of reaction, the reaction mixture was diluted with ethyl acetate and quenched with NaHCO3 solution and extracted with ethyl acetate. The organic layer washed with brine solution and dried over sodium sulphate and concentrated to get the pure title compound (1.2 g, 78.2%). LC-MS: 201.0 $[M+H]^+$ Step-3: Synthesis of 7-chloro-3,4-dihydro-2H-pyrido[4,3-b][1,4]thiazine To a solution of 7-chloro-2H-pyrido[4,3-b][1,4]thiazin-3(4H)-one (1 g, 4.98 mmol) in THF (15 mL) was added $LiAlH_4$ (230 mg, 5.98 mmol) to the reaction mixture at 0° C. The reaction mixture stirred at room temperature for 2 h. After completion of reaction, the reaction mixture quenched with saturated sodium sulphate solution diluted with ethyl acetate and extracted with ethyl acetate. The organic layer washed with brine solution and dried over sodium sulphate and concentrated to get the title compound (0.7 g, 75.5%). LC-MS: 187.0 $[M+]^+$ Step-4: Synthesis of 7-(1-methyl-1H-pyrazol-4-yl)-3,4-dihydro-2H-pyrido[4,3-b][1,4]thiazine A degassed solution of 7-chloro-3,4-dihydro-2H-pyrido[4,3-b][1,4]thiazine (0.5 g, 2.68 mmol) and 1-methyl-4-(4,4,5,5-tetramethyl-1,3,2-dioxaborolan-2-yl)-1H-pyrazole (1.12 g, 5.36 mmol) in DME (20 mL) water (5 mL). In the mixture, $Pd(Amphos)Cl_2$ (190 mg, 0.27 mmol) and potassium carbonate (1.11 g, 8.04 mmol) was then added. The mixture was stirred at 90° C. for 12 h. The reaction mixture was then cooled to room temperature, diluted with ethyl acetate and extracted with ethyl acetate. The organic extracts were washed with water, brine dried over sodium sulphate and concentrated to get the crude compound. The crude compound was purified by Combiflash® column chromatography and eluted at 5-7% McOH in DCM to obtain the pure title compound (300 mg, 48.19%). LC-MS: 233.1 $[M+H]^+$ Intermediate-S103: 8-methyl-2-(1-methyl-1H-pyrazol-4-yl)-5,6,7,8-tetrahydropteridine

S103

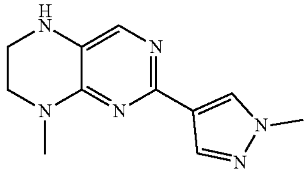

The intermediate-S103 was prepared as per the procedure described in preparation of intermediate S1, with appropriate variations in reactants, quantities of reagents, solvents and reaction conditions (Yield: 19.1%). LC-MS: 233.1 $[M+H]^+$ Intermediate-S104: 1-methyl-8-(1-methyl-1H-pyrazol-4-yl)-2,3,4,5-tetrahydro-1H-benzo[b][1,4]diazepine-7-carbonitrile

S104

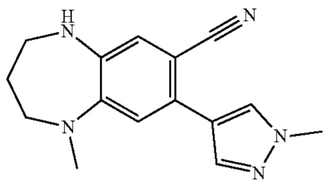

The intermediate S104 was prepared by the similar procedure described in Ex. 95 of WO2017205536, page 152-153 or Ex. 262 of WO2016086200 page 389-391 with appropriate variations in reactants, quantities of reagents, solvents and reaction conditions (Yield:73.3%). LC-MS: 268.3 $[M+H]^+$.

Intermediate-S105: 1,2-dimethyl-7-(1-methyl-1H-pyrazol-4-yl)-1,2,3,4-tetrahydroquinoxaline-6-carbonitrile

S105

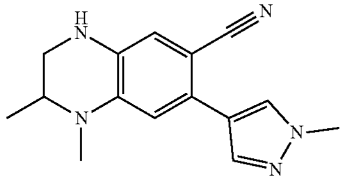

The intermediate-S105 was prepared by the similar procedure described in Ex. 95 of WO2017205536, page 152-153 or Ex. 262 of WO2016086200 page 389-391 with appropriate variations in reactants, quantities of reagents, solvents and reaction conditions. LC-MS: 268.3 $[M+H]^+$.

Intermediate-S106: methyl 7-cyano-4-methyl-1,2,3,4-tetrahydroquinoxaline-6-carboxylate

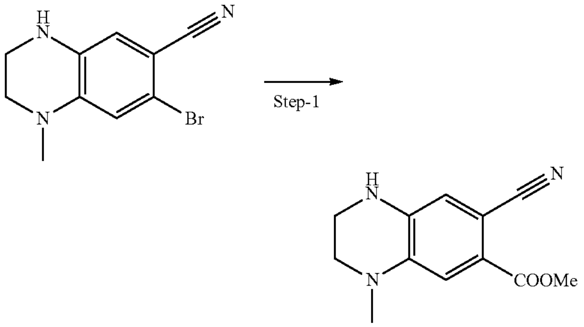

S106

Step-1: methyl 7-cyano-4-methyl-1,2,3,4-tetrahydroquinoxaline-6-carboxylate

A degassed solution of 7-bromo-1-methyl-1,2,3,4-tetrahydroquinoxaline-6-carbonitrile (2.5 g, 9.96 mmol) in McOH (250 mL) was added $Et_3N$ (1.5 g, 14.9 mmol) and $Pd(dppf)Cl_2$ (406 mg, 0.49 mmol) to the reaction mixture at room temperature. The mixture was stirred at 80° C. for 12 h under carbon monoxide bladder. The reaction mixture was then cooled to room temperature, water was added, and the mixture was extracted with ethyl acetate. Organic extracts were washed with water, brine dried over Sodium sulphate and concentrated to get the crude compound. The crude compound was purified by Combiflash® column chromatography using 50-60% ethyl acetate in hexane as eluent to yield (800 mg, 36.3%). LC-MS: 232.3 $[M+H]^+$ Intermediate-S107: N-(4-methoxybenzyl)-1-methyl-2-oxo-1,2,3,4-tetrahydroquinoxaline-6-sulfonamide

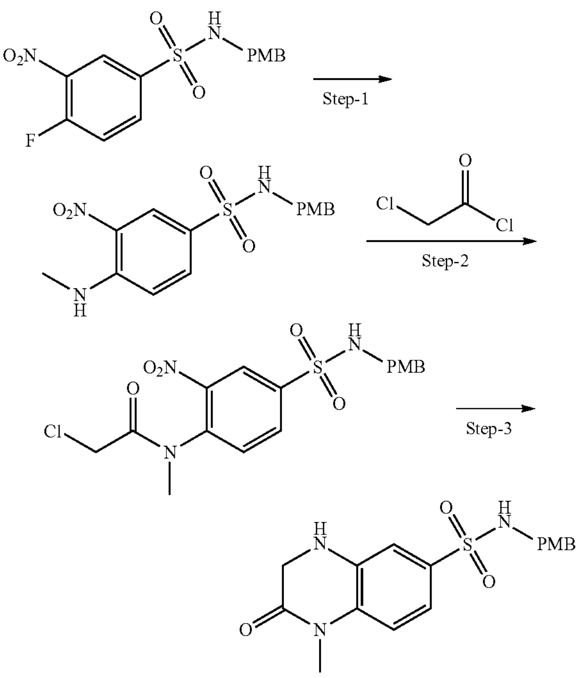

S107

Step-1: Synthesis of N-(4-methoxybenzyl)-4-(methylamino)-3-nitrobenzenesulfonamide In seal tube to a solution of 4-fluoro-N-(4-methoxybenzyl)-3-nitrobenzenesulfonamide (3 g, 8.8 mmol) in THE (10 mL), was added Methylamine solution in EtOH dropwise slowly to the reaction mixture at 0° C. and stirred for 2 h at same temperature. After completion of reaction, the reaction mixture evaporated to get the crude compound was washed with diethyl ether to obtain title compound (3 g, 99%). 1H NMR (400 MHz, DMSO-$d_6$) δ 8.56 (d, J=5.2 Hz, 1H), 8.26 (d, J=2.4 Hz, 1H), 7.73-7.71 (m, 1H), 7.08-7.04 (m, 3H), 6.76-6.72 (m, 2H), 3.89 (s, 3H), 3.66 (s, 3H), 2.98 (s, 3H).

Step-2: Synthesis of 2-chloro-N-(4-(N-(4-methoxybenzyl)sulfamoyl)-2-nitrophenyl)-N-methylacetamide To a solution of N-(4-methoxybenzyl)-4-(methylamino)-3-nitrobenzenesulfonamide (3 g, 8.54 mmol) in DCM (40 mL) were added DIPEA (2.75 g 21.36 mmol) and 2-chloroacetyl chloride (1.12 g, 10.25 mmol) to the reaction mixture at 0° C. for 1 h. After completion of reaction, the reaction mixture was poured into ice water and extracted with DCM. The organic layer washed with brine and dried over sodium sulphate and concentrated to get the pure compound. (3 g, 82.4%). 1H NMR (400 MHz, DMSO-$d_6$) δ 8.72 (d, J=4.8 Hz, 1H), 8.36 (d, J=2.4 Hz, 1H), 7.91-7.88 (m, 1H), 7.19-7.17 (m, 2H), 7.09 (d, J=9.6 Hz, 1H), 6.90-6.88 (m, 2H), 4.95 (s, 2H), 4.64 (s, 2H), 3.72 (s, 3H), 3.00 (s, 3H).

Step-3: Synthesis of N-(4-methoxybenzyl)-1-methyl-2-oxo-1,2,3,4-tetrahydroquinoxaline-6-sulfonamide To a solution of 2-chloro-N-(4-(N-(4-methoxybenzyl)sulfamoyl)-2-nitrophenyl)-N-methylacetamide (1 g, 2.3 mmol) in Ethanol (20 mL), water (4 mL) were added Iron powder (1.1 g, 18.7 mmol) and the reaction mixture heated to 90° C. for 2 h. After completion of reaction, the reaction mixture was diluted with ethyl acetate and extracted with ethyl acetate. The organic layer washed with saturated $NaHCO_3$ solution, brine solution and dried over sodium sulphate and concentrated to get the title pure compound (0.5 g, 60.2%). LC-MS: 362.1 $[M+H]^+$.

EXAMPLES

Coupling Method-A:

Example-1: 4-(7-Methoxy-1,3-dimethyl-2-oxo-1,2-dihydroquinolin-5-yl)-1-methyl-7-(1-methyl-1H-pyrazol-4-yl)-1,2,3,4-tetrahydroquinoxaline-6-carbonitrile

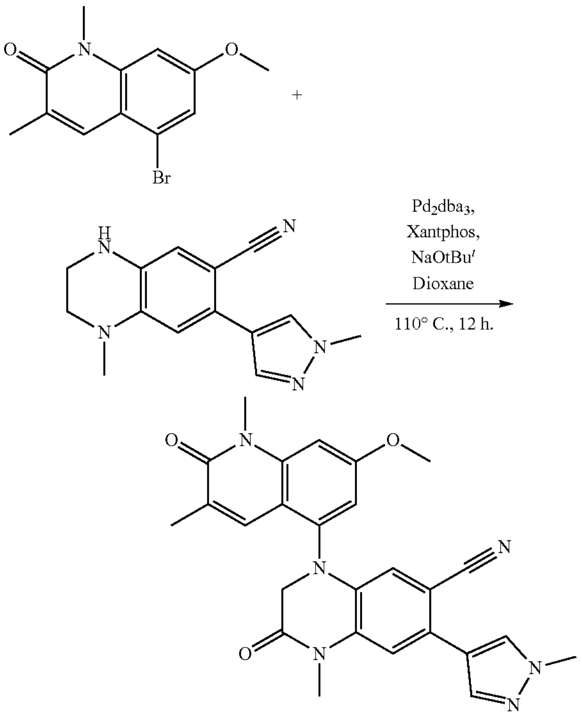

Example-1

A solution of 1-methyl-7-(1-methyl-1H-pyrazol-4-yl)-1,2,3,4-tetrahydroquinoxaline-6-carbonitrile (100 mg, 0.393 mmol) and 5-bromo-7-methoxy-1,3-dimethylquinolin-2(1H)-one (109 mg, 0.393 mmol) in 1,4-Dioxane (5 mL) was added $Pd_2(dba)_3$ (36 mg, 0.039 mmol), Xantphos (23 mg, 0.039 mmol) and Sodium tert-butoxide (85 mg, 0.26 mmol). The mixture was stirred at 100° C. for overnight. The mixture was cooled to RT, added water, extracted with ethyl acetate. Organic extracts were washed with brine, dried over Sodium sulphate and concentrated to get the residue. The residue was purified by preparative HPLC to afford pure compound (30 mg, 17%). LC-MS: 455.4 $[M+H]^+$; 1H-NMR (400 MHz, DMSO-D6) δ 8.07 (d, J=0.9 Hz, 1H), 7.81 (d, J=0.9 Hz, 1H), 7.61-7.57 (m, 1H), 6.94 (d, J=2.2 Hz, 1H), 6.87 (d, J=2.2 Hz, 1H), 6.71 (s, 1H), 5.91 (s, 1H), 3.89 (d, J=14.4 Hz, 6H), 3.78 (d, J=9.6 Hz, 4H), 3.68 (s, 3H), 3.08 (s, 3H), 2.05 (d, J=1.2 Hz, 3H).

Coupling Method-B:

Example-2: 1-methyl-7-(1-methyl-1H-pyrazol-4-yl)-4-(3-methyl-2-oxo-1,2-dihydroquinolin-5-yl)-1,2,3,4-tetrahydroquinoxaline-6-carbonitrile

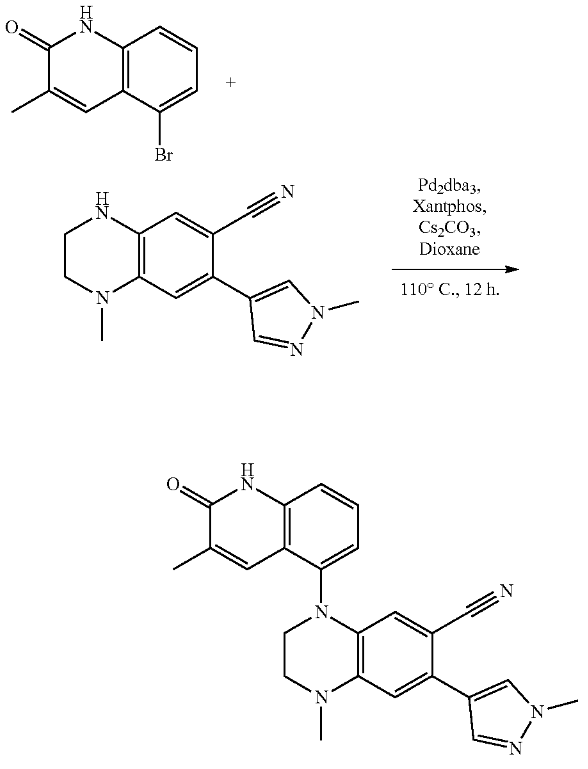

Example-2

A degassed solution of 1-methyl-7-(1-methyl-1H-pyrazol-4-yl)-1,2,3,4-tetrahydroquinoxaline-6-carbonitrile (50 mg, 0.196 mmol) and 5-bromo-3-methylquinolin-2(1H)-one (62 mg, 0.26 mmol) in 1,4-dioxane (2 mL) was added $Pd_2(dba)_3$ (5.9 mg, 0.006 mmol), Xantphos (4.5 mg, 0.007 mmol) and Caesium carbonate (85 mg, 0.26 mmol). The mixture was stirred at 110° C. for 12 h. Water was added and the mixture was extracted with ethyl acetate. The organic extracts were washed with brine, dried over Sodium sulphate and concentrated to get the residue. The residue was purified by column chromatography (60-120 mesh) using 10-60% of ethyl acetate in hexane to afford pure compound (20 mg, 25%). LC-MS: 411.4[M+H]$^+$; 1H-NMR (400 MHz, Chloroform-D) δ 11.21 (s, 1H), 7.87 (s, 1H), 7.76 (s, 1H), 7.70 (d, J=1.3 Hz, 1H), 7.51 (t, J=8.0, 8.0 Hz, 1H), 7.29 (d, J=8.2 Hz, 1H), 7.04 (dd, J=7.8, 1.0 Hz, 1H), 6.64 (s, 1H), 6.21 (s, 1H), 3.94 (s, 3H), 3.80 (q, J=10.1, 9.2, 9.2 Hz, 2H), 3.61 (d, J=6.3 Hz, 1H), 3.53-3.45 (m, 1H), 3.11 (s, 3H), 2.26 (d, J=1.2 Hz, 3H).

Coupling Method-C:

Example-3: Tert-butyl 2-((5-(7-cyano-4-methyl-6-(1-methyl-1H-pyrazol-4-yl)-3,4-dihydroquinoxalin-1(2H)-yl)-1,3-dimethyl-2-oxo-1,2-dihydroquinolin-7-yl)oxy)acetate

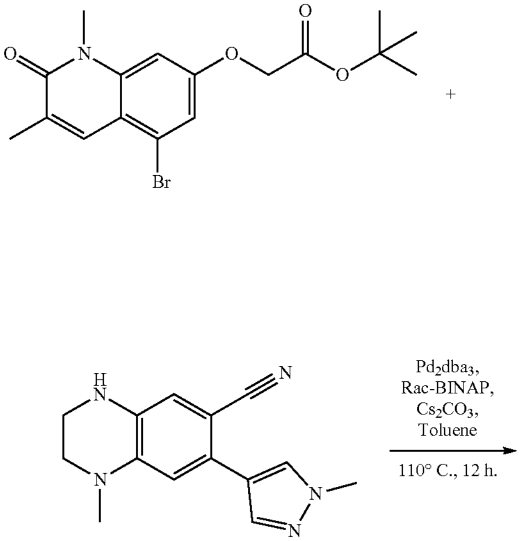

-continued

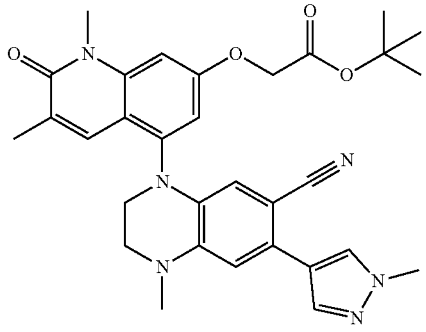

Example-3

A solution of 1-methyl-7-(1-methyl-1H-pyrazol-4-yl)-1,2,3,4-tetrahydroquinoxaline-6-carbonitrile (150 mg, 0.59 mmol) and tert-butyl 2-((5-bromo-1,3-dimethyl-2-oxo-1,2-dihydroquinolin-7-yl)oxy)acetate (248 mg, 0.649 mmol) in Toluene (10 mL) was added $Pd_2(dba)_3$ (54 mg, 0.059 mmol), Rac-BINAP (48 mg, 0.059 mmol), and Sodium tert-butoxide (575 mg, 1.77 mmol). The mixture was stirred at 100° C. for overnight. The mixture was cooled to RT, added water, extracted with ethyl acetate. Organic extracts were washed with brine, dried over Sodium sulphate and concentrated to get the residue. The residue was purified by preparative HPLC to afford pure compound (40 mg, 12%). LC-MS: 411.4[M+H]$^+$; 555.4; $^1$H-NMR (600 MHz, Chloroform-D) δ 7.85 (d, J=2.3 Hz, 1H), 7.74 (d, J=2.3 Hz, 1H), 7.54 (s, 1H), 6.74 (d, J=2.4 Hz, 1H), 6.66-6.62 (m, 2H), 6.19 (d, J=2.5 Hz, 1H), 4.59 (d, J=2.4 Hz, 2H), 3.92 (s, 3H), 3.76 (d, J=8.3 Hz, 2H), 3.73 (d, J=2.4 Hz, 3H), 3.55 (d, J=9.3 Hz, 1H), 3.48-3.44 (m, 1H), 3.09 (s, 3H), 2.17 (s, 3H), 1.48 (d, J=2.4 Hz, 9H). The Examples (4-56) were prepared according to the protocols described in the synthesis of Example-1 or Example-2 or Example-3 with appropriate coupling methods, variations in reactants, quantities of reagents, solvents and reaction conditions.

| Example | Structure | Coupling Method | Analytical data |
|---|---|---|---|
| 4 | 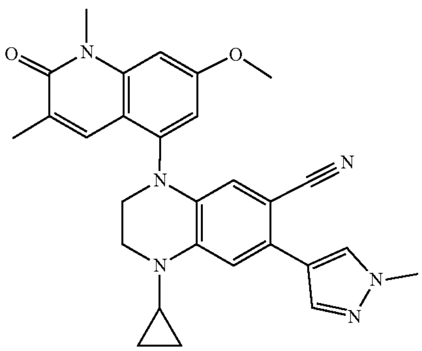 [SMILES: COc1cc(N2CCN(C3CC3)c3cc(-c4cnn(C)c4)c(C#N)cc32)c2cc(C)c(=O)n(C)c2c1] | B | LC-MS: 481 [M + H]$^+$; $^1$H NMR (600 MHz, DMSO-D6) δ 8.05 (s, 1H), 7.76 (s, 1H), 7.59 (s, 1H), 7.20 (s, 1H), 6.96 (s, 1H), 6.88 (s, 1H), 5.96 (s, 1H), 3.90 (d, J = 8.3 Hz, 7H), 3.73 (t, J = 10.9, 10.9 Hz, 2H), 3.69 (s, 3H), 3.52 (d, J = 9.4 Hz, 3H), 2.08 (d, J = 10.8 Hz, 4H), 0.98 (d, J = 43.3 Hz, 2H). |

-continued

| Example | Structure | Coupling Method | Analytical data |
|---|---|---|---|
| 5 | 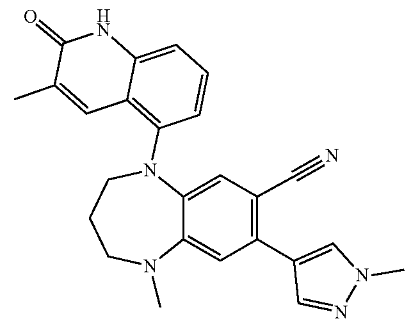 | B | LC-MS: 425 [M + H]$^+$: 1H-NMR (400 MHz, $CD_3OD$) δ 8.04 (s, 1H), 7.87 (s, 1H), 7.53-7.47 (m, 2H), 7.18-7.16 (d, 1H), 7.10-7.08 (d, 1H), 6.97 (s, 1H), 6.51 (s, 1H), 3.92 (s, 3H), 3.70-3.65 (m, 5H), 3.15 (s, 3H), 2.06-2.03-(m, 2H), 1.98 (s, 3H). |
| 6 | 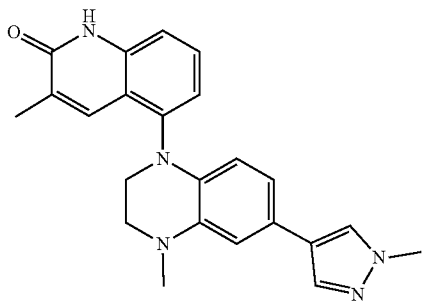 [SMILES: Cc1cc2c(N3CCN(C)c4cc(-c5cnn(C)c5)ccc43)cccc2[nH]c1=O] | A | LC-MS: 386.3 [M + H]$^+$; $^1$H NMR (400 MHz, Chloroform-D) δ 10.41 (s, 1H), 7.80 (s, J = 1.5 Hz, 1H), 7.66 (s, J = 0.8 Hz, 1H), 7.51-7.44 (m, 2H), 7.14 (d, J = 8.2 Hz, 1H), 7.09-7.06 (d, 1H), 6.76 (s, J = 1.9 Hz, 1H), 6.59 (dd, J = 8.1, 1.9 Hz, 1H), 6.11 (d, J = 8.2 Hz, 1H), 3.92 (s, 3H), 3.59 (s, 4H), 3.04 (s, 3H), 2.23 (s, J = 1.3 Hz, 3H). |
| 7 | 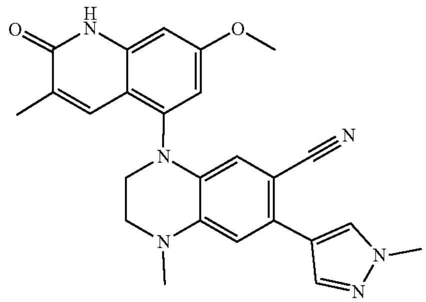 [SMILES: COc1cc(N2CCN(C)c3cc(-c4cnn(C)c4)c(C#N)cc32)c2cc(C)c(=O)[nH]c2c1] | A | LC-MS: 441.4 [M + H]$^+$; $^1$H-NMR (400 MHz, DMSO-D6) δ 11.81 (brs, 1H), 8.07 (s, 1H), 7.81 (d, J = 0.8 Hz, 1H), 7.52-7.50 (m, 1H), 6.79 (d, J = 2.4 Hz, 1H), 6.73-6.70 (m, 2H), 5.95 (s, 1H), 3.87 (s, 3H), 3.81 (s, 3H), 3.76 (s, 1H), 3.66-3.63 (m, 1H), 3.55-3.48 (m, 2H), 3.07 (s, 3H), 2.00 (d, J = 1.2 Hz, 3H). |
| 8 | 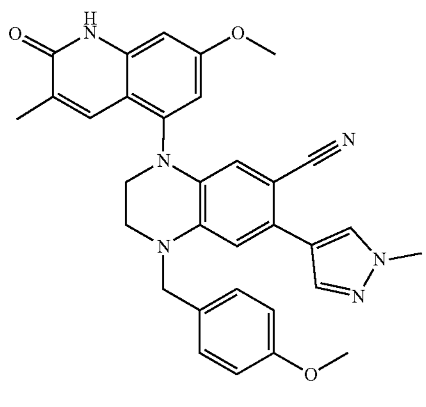 | A | LC-MS: 561.4 [M + H]$^+$ $^1$H-NMR (400 MHz, DMSO-D6) δ 8.08 (d, J = 0.8 Hz, 1H), 7.81 (d, J = 0.8 Hz, 1H), 7.54-7.50 (m, 1H), 6.79 (d, J = 2.4 Hz, 1H), 6.73-6.70 (m, 2H), 5.95 (s, 1H), 3.87 (s, 3H), 3.81 (s, 3H), 3.76 (s, 1H), 3.07 (s, 3H), 2.00 (d, J = 1.2 Hz, 3H), 11.85-11.74 (m, 1H). |

-continued

| Example | Structure | Coupling Method | Analytical data |
|---|---|---|---|
| 9 | 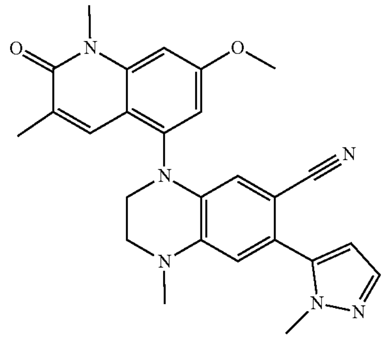 [SMILES: COc1cc(N2CCN(C)c3cc(-c4ccnn4C)c(C#N)cc32)c2cc(C)c(=O)n(C)c2c1] | A | LC-MS: 455.4 [M + H]+ $^1$H-NMR (400 MHz, Chloroform-D) δ 7.53 (d, J = 1.8 Hz, 2H), 6.79 (d, J = 2.3 Hz, 1H), 6.71 (d, J = 2.2 Hz, 1H), 6.50 (s, 1H), 6.35 (d, J = 1.9 Hz, 1H), 6.26 (s, 1H), 3.93 (s, 3H), 3.84 (d, J = 3.5 Hz, 4H), 3.78 (s, 3H), 3.70-3.58 (m, 2H), 3.54-3.41 (m, 1H), 3.07 (s, 3H), 2.20 (s, J = 1.1 Hz, 3H). |
| 10 | 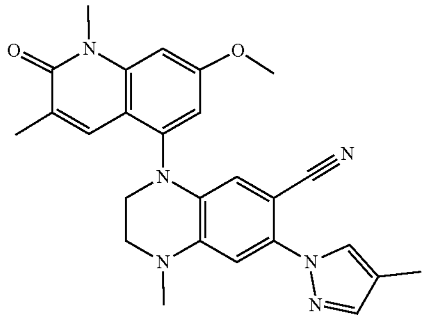 [SMILES: COc1cc(N2CCN(C)c3cc(-n4cc(C)cn4)c(C#N)cc32)c2cc(C)c(=O)n(C)c2c1] | A | LC-MS: 455.4 [M + H]+ $^1$H-NMR (400 MHz, Chloroform-D) δ 7.78 (p, J = 0.9, 0.9, 0.9, 0.9 Hz, 1H), 7.53-7.49 (m, 2H), 6.85 (s, 1H), 6.75 (d, J = 2.2 Hz, 1H), 6.67 (d, J = 2.2 Hz, 1H), 6.17 (s, 1H), 3.92 (s, 3H), 3.80 (d, J = 7.8 Hz, 2H), 3.76 (s, 3H), 3.59 (s, 1H), 3.53-3.45 (m, 1H), 3.10 (s, 3H), 2.18 (s, J = 1.2 Hz, 3H), 2.13 (s, J = 0.7, 0.7 Hz, 3H) |
| 11 | 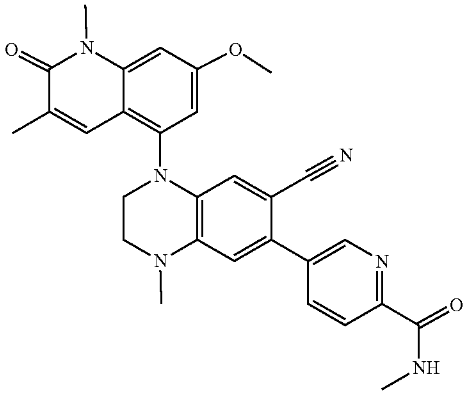 [SMILES: CNC(=O)c1ccc(-c2cc3c(cc2C#N)N(c2cc(OC)cc4c2cc(C)c(=O)n4C)CCN3C)cn1] | A | LC-MS: [M + H]+ 509.4; 1H-NMR (400 MHz, Chloroform-D) δ 8.70 (dd, J = 2.3, 0.8 Hz, 1H), 8.24 (d, J = 0.8 Hz, 1H), 8.01-7.96 (m, 2H), 7.53-7.51 (m, 1H), 6.79 (s, 1H), 6.70 (d, J = 2.2 Hz, 1H), 6.58 (s, 1H), 6.29 (s, 1H), 3.93 (s, 3H), 3.86-3.82 (m, 2H), 3.78 (s, 3H), 3.64 (dd, J = 7.3, 3.3 Hz, 1H), 3.52-3.49 (m, 1H), 3.12 (s, 3H), 3.05 (s, J = 5.1 Hz, 3H), 2.19 (s, J = 1.3 Hz, 3H). |
| 12 | 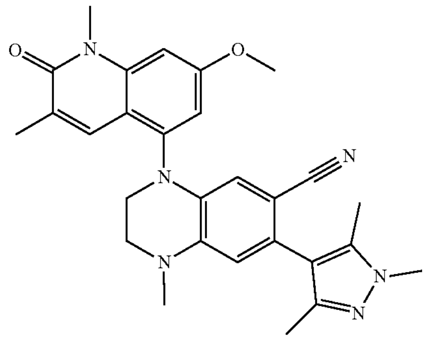 [SMILES: COc1cc(N2CCN(C)c3cc(-c4c(C)nn(C)c4C)c(C#N)cc32)c2cc(C)c(=O)n(C)c2c1] | A | LC-MS: 483.4 [M + H]+; 1H-NMR (400 MHz, Chloroform-D) δ 7.59 (s, 1H), 6.76 (d, J = 2.3 Hz, 1H), 6.72 (s, 1H), 6.40 (s, 1H), 6.26 (s, 1H), 3.92 (s, 3H), 3.81 (s, 1H), 3.77 (s, 3H), 3.76 (s, 3H), 3.60 (d, J = 5.9 Hz, 1H), 3.50-3.48 (m, 1H), 3.04 (s, 3H), 2.20-2.18 (m, 8H), 1.25 (d, J = 7.3 Hz, 2H). |

-continued

| Example | Structure | Coupling Method | Analytical data |
|---|---|---|---|
| 13 | 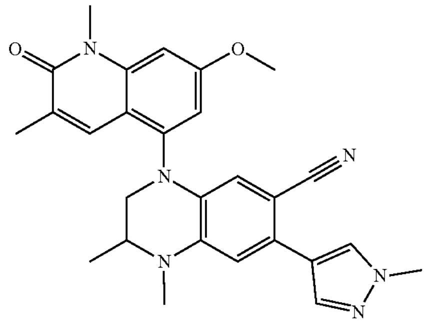 [SMILES: COc1cc(N2CC(C)N(C)c3cc(-c4cnn(C)c4)c(C#N)cc32)c2cc(C)c(=O)n(C)c2c1] | A | LC-MS: 469 [M + H]+; 1H-NMR (400 MHz, Chloroform-D) δ 7.86 (d, J = 0.7 Hz, 1H), 7.75 (d, J = 0.8 Hz, 1H), 7.59 (t, J = 1.0, 1.0 Hz, 1H), 6.75 (s, 1H), 6.67 (d, J = 2.3 Hz, 1H), 6.58 (s, 1H), 6.17 (s, 1H), 3.93 (s, 6H), 3.83 (d, J = 7.7 Hz, 1H), 3.77 (s, J = 3.8 Hz, 3H), 3.25 (d, J = 9.0 Hz, 1H), 3.09 (s, 3H), 2.18-2.15 (m, 3H), 1.45 (s, J = 6.4 Hz, 3H), 1.30 (s, 1H). |
| 14 | 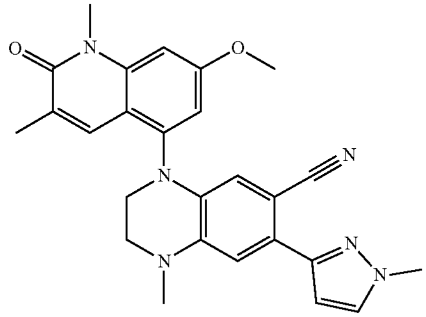 [SMILES: COc1cc(N2CCN(C)c3cc(-c4ccn(C)n4)c(C#N)cc32)c2cc(C)c(=O)n(C)c2c1] | A | LC-MS: 455.33 [M + H]+; 1H-NMR (600 MHz, Chloroform-D) δ 7.53 (s, 1H), 7.38 (d, J = 2.3 Hz, 1H), 7.08 (s, 1H), 6.80 (d, J = 2.3 Hz, 1H), 6.75 (d, J = 2.3 Hz, 1H), 6.68 (s, 1H), 6.24 (s, 1H), 3.95 (s, 3H), 3.91 (s, 3H), 3.81-3.78 (m, 1H), 3.76 (s, 3H), 3.60 (m, J = 10.9, 3.6, 3.6 Hz, 1H), 3.49-3.44 (m, 1H), 3.13 (s, 3H), 2.17 (s, J = 1.3 Hz, 3H). |
| 15 | 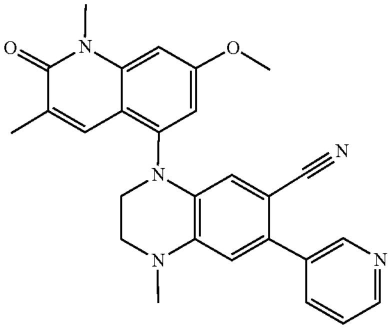 [SMILES: COc1cc(N2CCN(C)c3cc(-c4cccnc4)c(C#N)cc32)c2cc(C)c(=O)n(C)c2c1] | A | LC-MS: 452.4 [M + H]+; 1H-NMR (600 MHz, Chloroform-D) δ 8.74 (s, 1H), 8.61 (dd, J = 4.8, 1.7 Hz, 1H), 7.90 (d, J = 8.0, 1.9, 1.9 Hz, 1H), 7.54 (s, 1H), 7.38-7.33 (m, 1H), 6.78 (d, J = 2.2 Hz, 1H), 6.71 (t, J = 1.8, 1.8 Hz, 1H), 6.59 (s, 1H), 6.29 (d, J = 1.3 Hz, 1H), 3.93 (s, 3H), 3.85-3.81 (m, 2H), 3.78 (s, 3H), 3.64-3.60 (m, 1H), 3.51 (d, J = 5.8 Hz, 1H), 3.11 (d, J = 1.4 Hz, 3H), 2.20 (s, 3H). |
| 16 | 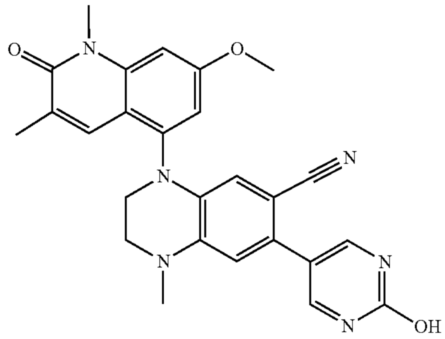 [SMILES: COc1cc(N2CCN(C)c3cc(-c4cnc(O)nc4)c(C#N)cc32)c2cc(C)c(=O)n(C)c2c1] | A | LC-MS: 469.4 [M + H]+; 1H-NMR (600 MHz, DMSO-D6) δ 8.38 (s, 2H), 7.57 (s, 1H), 6.93 (d, J = 2.0 Hz, 1H), 6.85 (t, J = 2.0, 2.0 Hz, 1H), 6.66 (d, J = 1.7 Hz, 1H), 5.92 (d, J = 1.8 Hz, 1H), 3.88 (d, J = 1.7 Hz, 3H), 3.78 (dd, J = 12.0, 3.4 Hz, 2H), 3.65 (d, J = 1.7 Hz, 3H), 3.50-3.46 (m, 2H), 3.05 (s, 3H), 2.03 (s, 3H). |

-continued

| Example | Structure | Coupling Method | Analytical data |
|---|---|---|---|
| 17 | 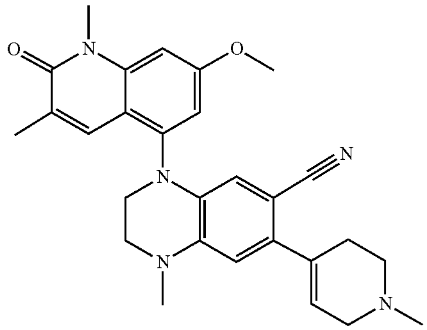 [SMILES: COc1cc(N2CCN(C)c3cc(C4=CCN(C)CC4)c(C#N)cc32)c2cc(C)c(=O)n(C)c2c1] | A | LC-MS: 470.4 [M + H]$^+$; 1H-NMR (600 MHz, Chloroform-D) δ 7.51 (s, 1H), 6.75 (d, J = 2.1 Hz, 1H), 6.66 (t, J = 1.8, 1.8 Hz, 1H), 6.42 (d, J = 1.3 Hz, 1H), 6.15 (d, J = 1.3 Hz, 1H), 5.82 (brs, 1H), 3.91 (s, 3H), 3.79-3.76 (m, 6H), 3.7-3.55 (m, 1H), 3.68-3.62 (m, 2H), 3.48-3.46 (m, 1H), 3.24-3.18 (m, 2H), 3.06 (s, 3H), 2.78 (brs, 4H), 2.18 (s, 3H). |
| 18 | 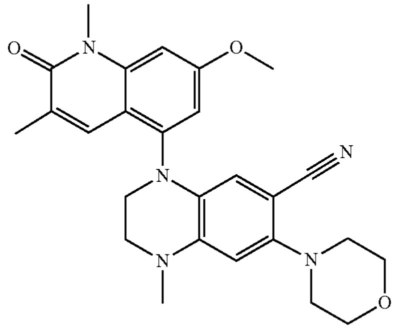 [SMILES: COc1cc(N2CCN(C)c3cc(N4CCOCC4)c(C#N)cc32)c2cc(C)c(=O)n(C)c2c1] | A | LC-MS: 460.4 [M + H]$^+$; 1H-NMR (400 MHz, Chloroform-D) δ 7.57 (s, 1H), 6.70 (d, J = 2.2 Hz, 1H), 6.60 (s, 1H), 6.18 (s, 2H), 3.90 (s, 3H), 3.86 (t, J = 1.5, 1.5 Hz, 4H), 3.76 (s, 3H), 3.72 (d, J = 8.8 Hz, 2H), 3.50 (d, J = 26.3 Hz, 2H), 3.11-3.10 (m, 3H), 3.08 (s, 4H), 2.17 (d, J = 1.2 Hz, 3H). |
| 19 | 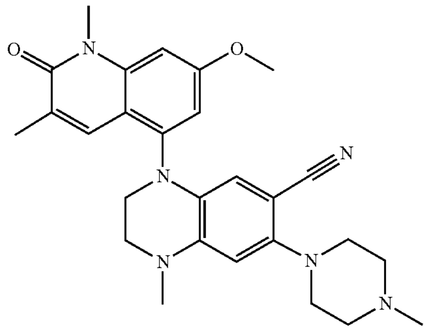 [SMILES: COc1cc(N2CCN(C)c3cc(N4CCN(C)CC4)c(C#N)cc32)c2cc(C)c(=O)n(C)c2c1] | A | LC-MS: 473.5 [M + H]$^+$; 1H-NMR (400 MHz, Chloroform-D) δ 7.59-7.57 (m, 1H), 6.70 (d, J = 2.2 Hz, 1H), 6.59 (d, J = 2.3 Hz, 1H), 6.19 (d, J = 9.8 Hz, 2H), 3.89 (s, 3H), 3.75 (s, 3H), 3.72 (s, 2H), 3.52 (s, 1H), 3.45 (s, 1H), 3.13 (t, J = 4.8, 4.8 Hz, 4H), 3.07 (s, 3H), 2.60 (t, J = 4.7, 4.7 Hz, 4H), 2.34 (s, 3H), 2.17 (d, J = 1.2 Hz, 3H). |
| 20 | 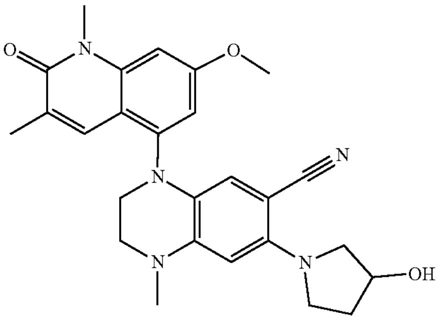 [SMILES: COc1cc(N2CCN(C)c3cc(N4CCC(O)C4)c(C#N)cc32)c2cc(C)c(=O)n(C)c2c1] | A | LC-MS: [M + H]+; 1H-NMR (400 MHz, DMSO-D6) δ 7.63 (s, 1H), 6.84 (d, J = 2.2 Hz, 1H), 6.66 (d, J = 2.2 Hz, 1H), 5.79 (d, J = 9.0 Hz, 2H), 4.96 (d, J = 3.4 Hz, 1H), 4.33 (s, 1H), 3.88 (s, 3H), 3.68-3.61 (m, 5H), 3.56-3.48 (m, 3H), 3.22 (d, J = 10.2 Hz, 1H), 3.02 (s, 3H), 2.05 (s, 3H), 1.95 (t, J = 6.6, 6.6 Hz, 2H), 1.84 (s, 1H). |

-continued

| Example | Structure | Coupling Method | Analytical data |
| --- | --- | --- | --- |
| 21 | 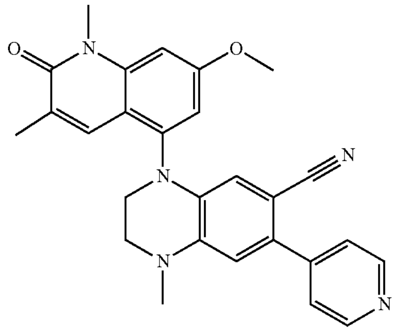 [SMILES: COc1cc(N2CCN(C)c3cc(-c4ccncc4)c(C#N)cc32)c2cc(C)c(=O)n(C)c2c1] | A | LC-MS: 451.8 [M + H]+; 1H-NMR (400 MHz, Chloroform-D) δ 8.69-8.63 (m, 2H), 7.52 (d, J = 1.4 Hz, 1H), 7.47-7.45 (m, 1H), 6.79 (d, J = 2.3 Hz, 1H), 6.70 (d, J = 2.3 Hz, 1H), 6.60 (s, 1H), 6.29 (s, 1H), 3.93 (s, 3H), 3.88-3.79 (m, 2H), 3.78 (s, 3H), 3.67-3.60 (m, 1H), 3.55-3.48 (m, 2H), 3.12 (s, 3H), 2.20 (d, J = 1.3 Hz, 3H). |
| 22 | 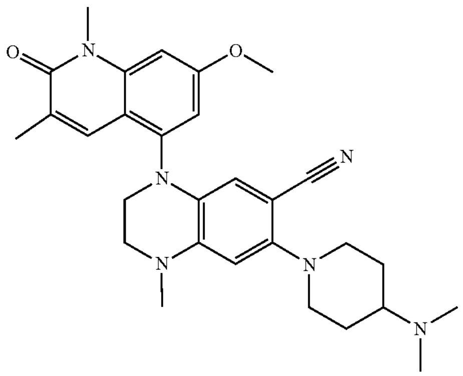 [SMILES: COc1cc(N2CCN(C)c3cc(N4CCC(N(C)C)CC4)c(C#N)cc32)c2cc(C)c(=O)n(C)c2c1] | A | LC-MS: 501 [M + H]+; 1H-NMR (400 MHz, Chloroform-D) δ 7.59 (d, J = 1.4 Hz, 1H), 6.69 (d, J = 2.3 Hz, 1H), 6.59 (d, J = 2.4 Hz, 1H), 6.18 (d, J = 0.5 Hz, 2H), 3.89 (d, J = 0.5 Hz, 3H), 3.76 (s, 3H), 3.72 (s, 2H), 3.52 (s, 3H), 3.47 (s, 2H), 3.06 (s, 3H), 2.72 (d, J = 11.6 Hz, 3H), 2.31 (s, 5H), 2.17 (d, J = 0.7 Hz, 2H), 1.90-1.75 (m, 5H). |
| 23 | 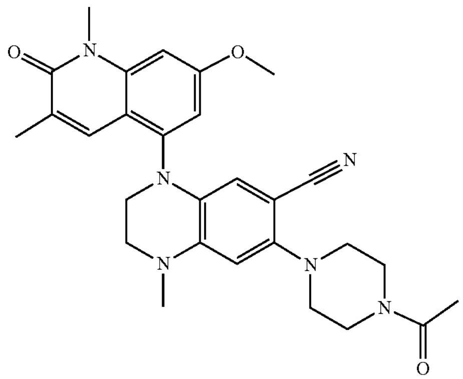 [SMILES: COc1cc(N2CCN(C)c3cc(N4CCN(C(C)=O)CC4)c(C#N)cc32)c2cc(C)c(=O)n(C)c2c1] | A | LC-MS: 501.1 [M + H]+; 1H-NMR (600 MHz, Chloroform-D) δ 7.56 (s, 1H), 6.71 (d, J = 2.5 Hz, 1H), 6.60 (d, J = 2.5 Hz, 1H), 6.17 (d, J = 8.5 Hz, 2H), 3.90 (s, 3H), 3.77 (d, J = 13.8 Hz, 7H), 3.63 (t, J = 4.7, 4.7 Hz, 2H), 3.54-3.44 (m, 2H), 3.09-3.03 (m, 7H), 2.15 (d, J = 27.6 Hz, 6H). |
| 24 | 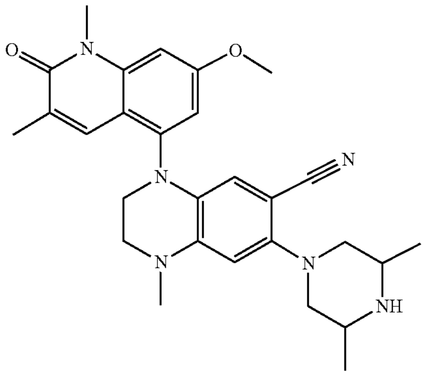 [SMILES: COc1cc(N2CCN(C)c3cc(N4CC(C)NC(C)C4)c(C#N)cc32)c2cc(C)c(=O)n(C)c2c1] | A | LC-MS: 487.2 [M + H]+; 1H-NMR (400 MHz, Chloroform-D) δ 8.56 (s, 1H), 7.56-7.55 (m, 1H), 6.71 (s, 1H), 6.59 (s, 1H), 6.22 (s, 1H), 6.16 (s, 1H), 3.90 (s, 3H), 3.76 (s, 5H), 3.54 (s, 1H), 3.49 (s, 1H), 3.39-3.35 (m, 4H), 3.09 (s, 3H), 2.85 (s, 2H), 2.18 (s, 3H), 1.33-1.31 (m, 5H). |

-continued

| Example | Structure | Coupling Method | Analytical data |
|---|---|---|---|
| 25 | 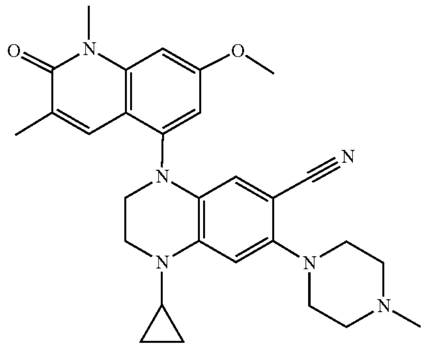 | A | LC-MS: 449.1 [M + H]+; 1H-NMR (400 MHz, Chloroform-D) δ 7.54 (s, 1H), 6.85 (s, 1H), 6.70 (s, 1H), 6.60 (s, 1H), 6.18 (s, 1H), 3.88 (s, 3H), 3.75 (s, 3H), 3.65-3.63 (t, 2H), 3.49 (brs, 2H), 3.16 (s, 4H), 2.68 (brs, 3H), 2.51 (s, 1H), 2.40 (s, 3H), 2.17 (s, 3H), 1.25 (brs, 1H), 0.95 (s, 2H), 0.74-0.68 (m, 2H). |
| 26 | 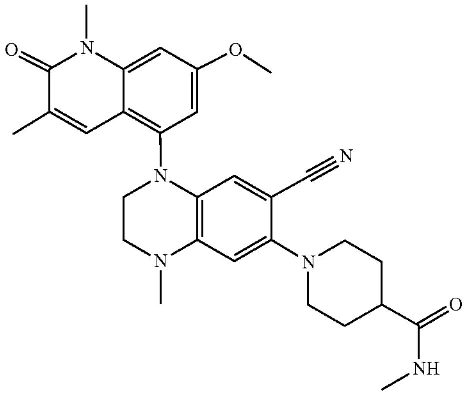 [SMILES: CNC(=O)C1CCN(c2cc3c(cc2C#N)N(c2cc(OC)cc4c2cc(C)c(=O)n4C)CCN3C)CC1] | A | LC-MS: 515.1 [M + H]+; 1H-NMR (600 MHz, Chloroform-D) δ 7.56 (s, 1H), 6.68 (s, 1H), 6.58 (d, J = 1.8 Hz, 1H), 6.17 (d, J = 6 Hz, 1H), 5.54 (brs, 1H), 3.88 (s, 3H), 3.74 (s, 3H), 3.73-3.70 (m, 2H), 3.48-3.46 (m, 5H), 3.05 (s, 3H), 2.81-2.76 (m, 5H), 2.25 (brs, 1H), 2.16 (s, 3H), 1.99-1.97 (m, 2H), 1.88-1.86 (m, 2H). |
| 27 | 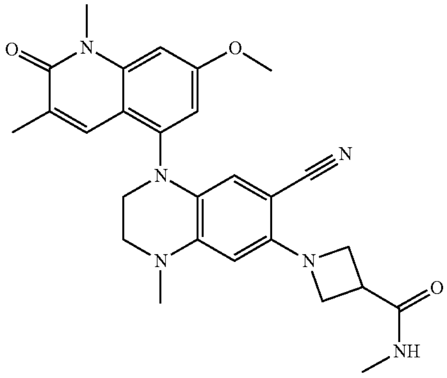 [SMILES: CNC(=O)C1CN(c2cc3c(cc2C#N)N(c2cc(OC)cc4c2cc(C)c(=O)n4C)CCN3C)C1] | A | LC-MS: 487.15 [M + H]+; 1H-NMR (600 MHz, Chloroform-D) δ 7.6 (s, 1H), 6.65 (s, 1H), 6.53 (s, 1H), 6.05 (s, 1H), 5.7 (s, 1H), 5.60 (s, 1H), 4.1-4.3 (m, 3H), 3.87 (s, 3H), 3.73 (s, 3H), 3.71-3.3 (m, 4H), 3.02 (brs, 2H), 2.84 (d, J = 4.8 Hz, 3H), 2.17 (s, 3H), 1.23 (s, 3H). |
| 28 | 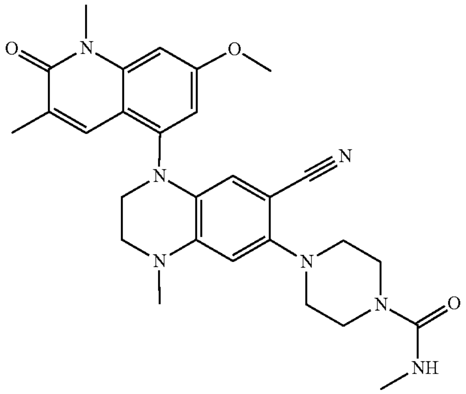 [SMILES: CNC(=O)N1CCN(c2cc3c(cc2C#N)N(c2cc(OC)cc4c2cc(C)c(=O)n4C)CCN3C)CC1] | A | LC-MS: 516.3 [M + H]+; 1H-NMR (600 MHz, Chloroform-D) δ 7.57 (s, 1H), 6.70 (s, 1H), 6.59 (d, J = 2.7 Hz, 1H), 6.17 (s, 2H), 4.47 (s, 1H), 3.90 (s, 3H), 3.75 (d, J = 3.2 Hz, 5H), 3.55-3.52 (m, 5H), 3.45 (d, J = 10.9 Hz, 1H), 3.07 (s, 7H), 2.83 (d, J = 4.5 Hz, 3H), 2.17 (s, 3H). |

-continued

| Example | Structure | Coupling Method | Analytical data |
|---|---|---|---|
| 29 | 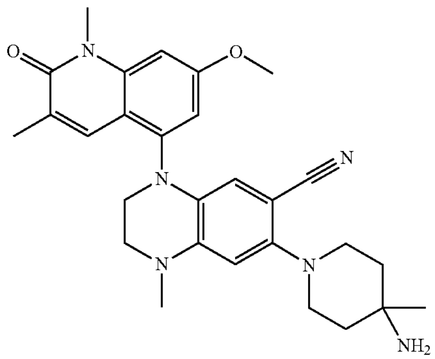 [SMILES: COc1cc(N2CCN(C)c3cc(N4CCC(C)(N)CC4)c(C#N)cc32)c2cc(C)c(=O)n(C)c2c1] | A | LC-MS: 487.3 [M + H]+; 1H-NMR (400 MHz, DMSO-D6) δ 7.562 (s, 1H), 6.83 (d, J = 2.4 Hz, 1H), 6.65 (d, J = 2 Hz, 1H), 6.22 (s, 1H), 5.77 (s, 1H), 3.8 (s, 3H), 3.6 (s, 5H), 3.39-3.31 (m, 2H), 2.95 (s, 5H), 2.88 (d, J = 9.2 Hz, 2H), 1.9 (d, J = 1.2 Hz, 3H), 1.48 (s, 4H), 1.02-0.99 (m, 3H). |
| 30 | 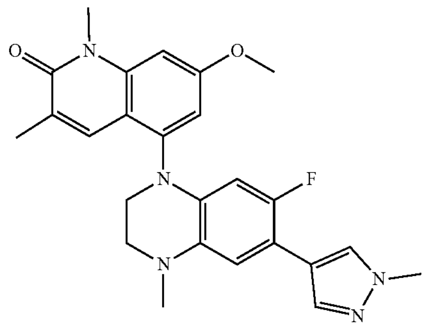 [SMILES: COc1cc(N2CCN(C)c3cc(-c4cnn(C)c4)c(F)cc32)c2cc(C)c(=O)n(C)c2c1] | A | LC-MS: 448.2 [M + H]+; 1H-NMR (300 MHz, Chloroform-D) δ 3.75 (d, J = 0.7 Hz, 3H), 2.18 (d, J = 0.9 Hz, 3H), 3.67-3.65 (m, 1H), 3.51 (m, 1H), 3.34 (m, 1H), 3.00 (s, 3H), 3.83-3.81 (m, 1H), 7.73 (s, 1H), 7.61 (d, J = 2.5 Hz, 1H), 7.57-7.56 (s, 1H), 6.74 (s, 2H), 6.69 (s, 1H), 5.87 (d, J = 0.7 Hz, 1H), 3.92-3.89 (m, 6H). |
| 31 | 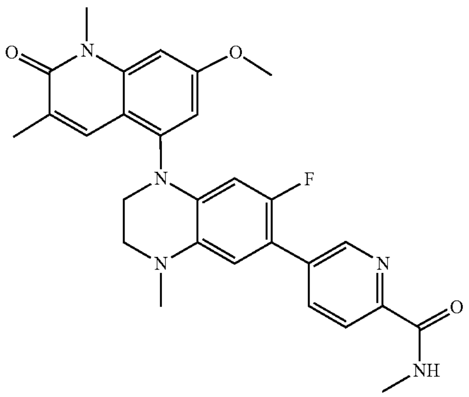 [SMILES: CNC(=O)c1ccc(-c2cc3c(cc2F)N(c2cc(OC)cc4c2cc(C)c(=O)n4C)CCN3C)cn1] | A | LC-MS: 502 [M + H]+; 1H-NMR (600 MHz, Chloroform-D) δ 8.68 (s, 1H), 8.20 (s, 1H), 8.00 (d, J = 5.7 Hz, 1H), 7.95 (s, 1H), 7.53 (s, 1H), 6.77 (dd, J = 11.4, 2.5 Hz, 2H), 6.63 (d, J = 7.2 Hz, 1H), 5.86 (d, J = 2.9 Hz, 1H), 3.91 (s, 3H), 3.87 (d, J = 3.2 Hz, 1H), 3.76 (d, J = 3.0 Hz, 3H), 3.70 (q, J = 3.6, 3.6, 3.4 Hz, 1H), 3.54 (dd, J = 7.8, 3.3 Hz, 1H), 3.36 (dd, J = 7.5, 3.7 Hz, 1H), 3.03 (d, J = 16.3 Hz, 6H), 2.19 (d, J = 2.7 Hz, 3H). |
| 32 | 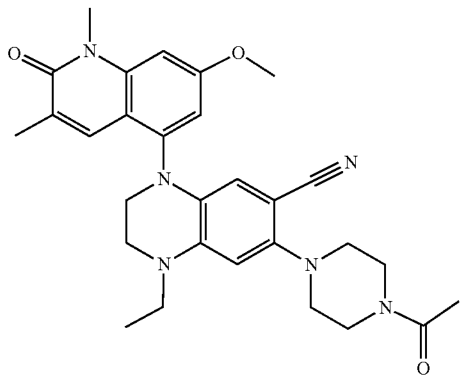 [SMILES: CCN1CCN(c2cc(OC)cc3c2cc(C)c(=O)n3C)c2cc(C#N)c(N3CCN(C(C)=O)CC3)cc21] | A | LC-MS: 515.4 [M + H]+; 1H-NMR (600 MHz, Chloroform-D) δ 7.59 (s, 1H), 6.70 (d, J = 2.7 Hz, 1H), 6.58 (d, J = 2.6 Hz, 1H), 6.21 (s, 2H), 3.90 (d, J = 2.8 Hz, 3H), 3.80-3.79 (m, 1H), 3.76 (d, J = 2.9 Hz, 3H), 3.68 (d, J = 10.5 Hz, 1H), 3.65-3.62 (m, 4H), 3.48 (dt, J = 25.8, 9.6, 9.6 Hz, 4H), 3.10-3.01 (m, 4H), 2.18 (s, 3H), 2.13 (d, J = 2.8 Hz, 3H), 1.27 (t, J = 7.1, 7.1 Hz, 3H). |

-continued

| Example | Structure | Coupling Method | Analytical data |
|---|---|---|---|
| 33 | 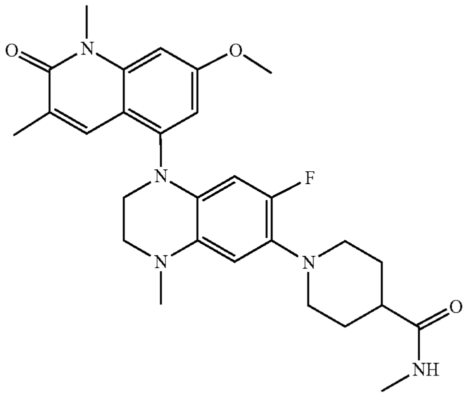 [SMILES: CNC(=O)C1CCN(c2cc3c(cc2F)N(c2cc(OC)cc4c2cc(C)c(=O)n4C)CCN3C)CC1] | A | LC-MS: 508.25 [M + H]+; 1H-NMR (400 MHz, Chloroform-D) δ 7.59 (s, 1H), 6.66 (dd, J = 2 Hz, 2H), 6.32 (d, J = 8 Hz, 1H), 5.90 (s, 1H), 5.5 (brs, 1H), 3.84 (s, 3H), 3.72 (s, 4H), 3.6 (s, 2H), 3.45 (s, 1H), 3.32 (s, 2H), 2.93 (s, 3H), 2.82 (d, J = 4.4 Hz, 3H), 2.68 (s, 2H), 2.2 (s, 1H), 2.16 (d, J = 1.2 Hz, 3H), 1.91 (s, 4H). |
| 34 | 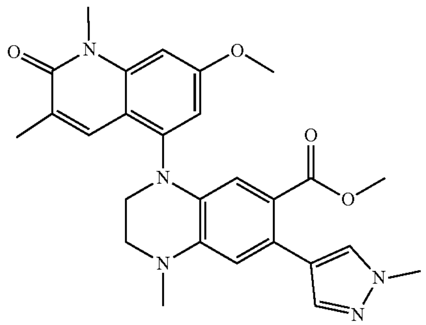 [SMILES: COC(=O)c1cc2c(cc1-c1cnn(C)c1)N(C)CCN2c1cc(OC)cc2c1cc(C)c(=O)n2C] | A | LC-MS: 488.4 [M + H]+; 1H-NMR (600 MHz, Chloroform-D) δ 7.64 (s, 1H), 7.50 (s, 1H), 7.47 (s, 1H), 6.71 (s, 1H), 6.68 (s, 1H), 6.67 (s, 1H), 6.53 (s, 1H), 3.92 (s, 3H), 3.88 (s, 3H), 3.75 (s, 3H), 3.72 (s, 1H), 3.65-3.61 (m, 2H), 3.56 (s, 3H), 3.42 (brs, 1H), 3.04 (s, 3H), 2.18 (s, 3H). |
| 35 | 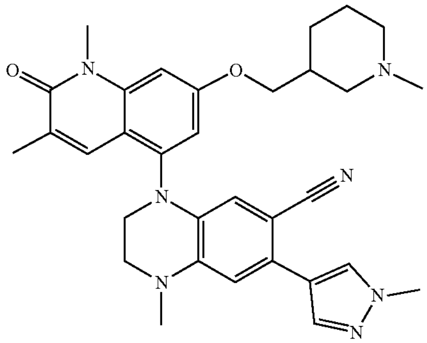 [SMILES: Cc1cc2c(N3CCN(C)c4cc(-c5cnn(C)c5)c(C#N)cc43)cc(OCC3CCCN(C)C3)cc2n(C)c1=O] | A | LC-MS: 552.5 [M + H]+; 1H-NMR (400 MHz, DMSO-D6) δ 8.08 (s, 1H), 7.81 (d, J = 0.9 Hz, 1H), 7.60 (s, 1H), 6.93 (s, 1H), 6.87 (d, J = 2.2 Hz, 1H), 1.79-1.46 (m, 5H), 6.71 (s, 1H), 4.01 (s, 2H), 3.19-3.13 (m, 1H), 5.91 (s, 1H), 3.87 (s, 2H), 3.79 (s, 2H), 3.67 (s, 2H), 1.17-1.05 (m, 2H), 3.51 (s, 2H), 3.08 (s, 3H), 2.19 (s, 2H), 2.05 (d, J = 1.3 Hz, 3H), 1.24 (s, 1H). |
| 36 | 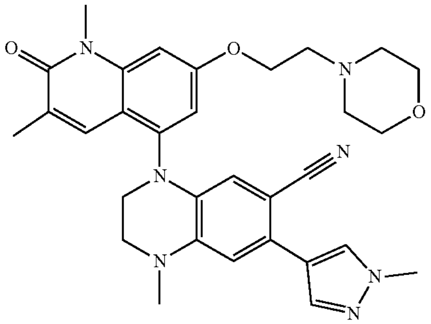 [SMILES: Cc1cc2c(N3CCN(C)c4cc(-c5cnn(C)c5)c(C#N)cc43)cc(OCCN3CCOCC3)cc2n(C)c1=O] | A | 1H-NMR (400 MHz, DMSO-D6) δ 8.07 (s, 1H), 7.81 (s, 1H), 7.60 (s, 1H), 6.95 (d, J = 2.2 Hz, 1H), 6.87 (d, J = 2.1 Hz, 1H), 6.71 (s, 1H), 5.91 (s, 1H), 4.24 (t, J = 5.8, 5.8 Hz, 4H), 3.87 (s, 3H), 3.79 (s, 4H), 3.69-3.65 (s, 3H), 3.57 (t, J = 4.6, 4.6 Hz, 4H), 3.52-3.49 (m, 1H), 3.08 (s, 3H), 2.72 (t, J = 5.7, 5.7 Hz, 4H), 2.07-2.01 (s, 3H). |

-continued

| Example | Structure | Coupling Method | Analytical data |
|---|---|---|---|
| 37 | 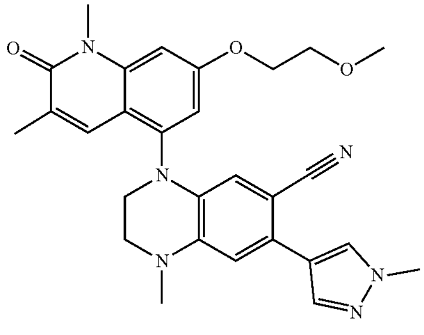 [SMILES: COCCOc1cc(N2CCN(C)c3cc(-c4cnn(C)c4)c(C#N)cc32)c2cc(C)c(=O)n(C)c2c1] | A | LC-MS: 499.4 [M + H]+; 1H-NMR (400 MHz, Chloroform-D) δ 7.86 (s, 1H), 7.75 (s, 1H), 7.55 (d, 1H), 6.80 (d, J = 2.3 Hz, 1H), 6.71 (d, J = 2.3 Hz, 1H), 6.63 (s, 1H), 6.22 (s, 1H), 4.23-4.18 (m, 2H), 3.94 (s, 3H), 3.82-3.73 (m, 7H), 3.47 (s, 4H), 3.10 (s, 3H), 2.18 (d, J = 1.3 Hz, 3H). |
| 38 | 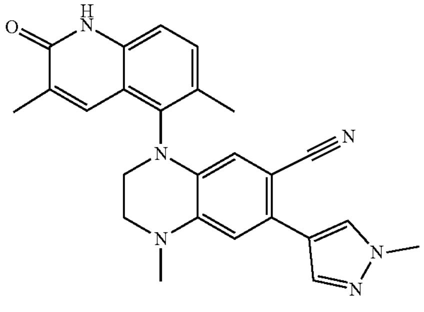 [SMILES: Cc1ccc2[nH]c(=O)c(C)cc2c1N1CCN(C)c2cc(-c3cnn(C)c3)c(C#N)cc21] | A | LC-MS: 425.4 [M + H]+; 1H-NMR (400 MHz, Chloroform-D) δ 9.87 (s, 1H), 7.84 (s, 1H), 7.75 (d, J = 1.0 Hz, 1H), 7.51 (s, 1H), 7.41 (d, J = 8.4 Hz, 1H), 7.18-7.15 (m, 1H), 6.67 (s, 1H), 5.98 (d, J = 1.2 Hz, 1H), 3.93 (d, J = 1.2 Hz, 3H), 3.73-3.51 (m, 4H), 3.09 (d, J = 1.2 Hz, 3H), 2.27-2.13 (m, 6H). |
| 39 | 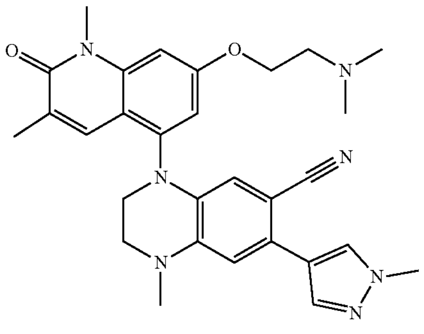 [SMILES: Cc1cc2c(N3CCN(C)c4cc(-c5cnn(C)c5)c(C#N)cc43)cc(OCCN(C)C)cc2n(C)c1=O] | A | LC-MS: 512.3 [M + H]+; 1H-NMR (600 MHz, Chloroform-D) δ 7.86 (s, 1H), 7.75 (s, 1H), 6.79 (s, 1H), 6.70 (s, 1H), 6.21 (s, 1H), 4.15 (d, J = 5.6 Hz, 2H), 6.63-6.60 (m, 1H), 3.94 (s, 3H), 3.75 (s, 5H), 3.57 (s, 2H), 3.10 (s, 3H), 2.78 (s, 2H), 2.37 (s, 6H), 2.18 (s, 3H), 7.54-7.51 (m, 1H). |
| 40 | 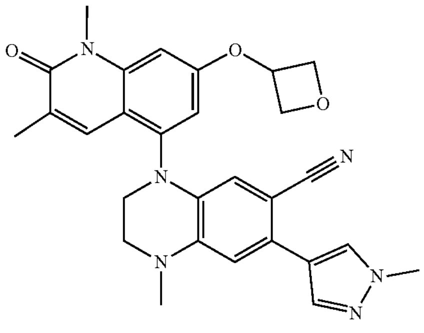 [SMILES: Cc1cc2c(N3CCN(C)c4cc(-c5cnn(C)c5)c(C#N)cc43)cc(OC3COC3)cc2n(C)c1=O] | A | LC-MS: 497.4 [M + H]+; 1H-NMR (600 MHz, Chloroform-D) δ 7.87 (s, 1H), 7.76 (s, 1H), 6.65 (s, 1H), 6.50 (s, 2H), 6.20 (s, 1H), 5.33-5.30 (m, 1H), 5.01 (d, J = 7.2 Hz, 2H), 4.83-4.78 (m, 2H), 3.94 (s, 3H), 3.80-3.76 (m, 2H), 3.73 (s, 3H), 3.58 (s, 1H), 3.50 (s, 1H), 3.11 (s, 3H), 2.18 (s, 3H), 7.54-7.52 (m, 1H). |

-continued

| Example | Structure | Coupling Method | Analytical data |
|---|---|---|---|
| 41 | 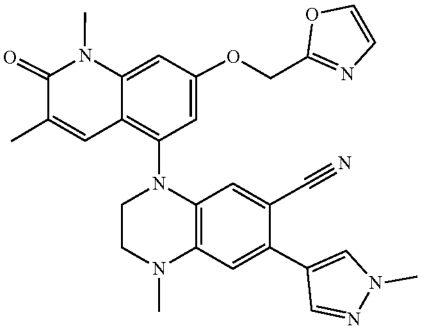 [SMILES: Cc1cc2c(N3CCN(C)c4cc(-c5cnn(C)c5)c(C#N)cc43)cc(OCc3ncco3)cc2n(C)c1=O] | A | LC-MS: 522.4 [M + H]+; 1H-NMR (600 MHz, Chloroform-D) δ 7.87 (s, 1H), 7.74 (d, J = 18.2 Hz, 2H), 7.55 (s, 1H), 7.19 (s, 1H), 6.96 (s, 1H), 6.78 (s, 1H), 6.64 (s, 1H), 6.20 (s, 1H), 5.28 (s, 2H), 3.94 (s, 3H), 3.77 (d, J = 13.4 Hz, 5H), 3.58-3.48 (m, 2H), 3.11 (s, 3H), 2.18 (s, 3H). |
| 42 | 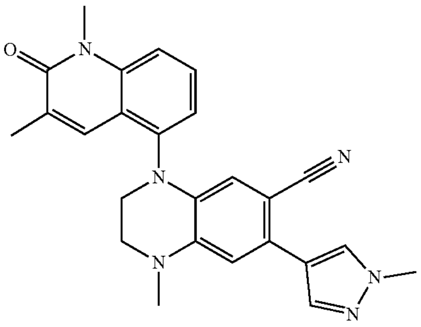 [SMILES: Cc1cc2c(N3CCN(C)c4cc(-c5cnn(C)c5)c(C#N)cc43)cccc2n(C)c1=O] | A | LC-MS: 425.3 [M + H]+; 1H-NMR (400 MHz, Chloroform-D) δ 7.86 (s, 1H), 7.75 (s, 1H), 7.65 (s, 1H), 7.58 (t, J = 8.2, 8.2 Hz, 1H), 7.32 (d, J = 8.5 Hz, 1H), 7.09 (d, 1H), 6.64 (s, 1H), 6.16 (s, 1H), 3.93 (s, 3H), 3.81 (s, 5H), 3.59 (d, J = 8.6 Hz, 1H), 3.49 (d, J = 7.8 Hz, 1H), 3.11 (s, 3H), 2.22 (s, 3H). |
| 43 | 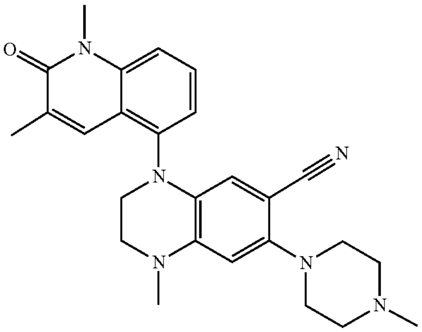 | A | LC-MS: 422.8 [M + H]+; 1H-NMR (400 MHz, Chloroform-D) δ 7.69 (t, J = 1.1, 1.1 Hz, 1H), 7.55-7.51 (m, 1H), 7.01 (dd, J = 7.8, 0.9 Hz, 2H), 6.21 (s, 1H), 6.13 (s, 1H), 3.79 (s, 3H), 3.74 (s, 2H), 3.53 (s, 2H), 3.13 (t, J = 4.8, 4.8 Hz, 4H), 2.35 (s, 3H), 2.22 (d, J = 1.3 Hz, 3H). |
| 44 | 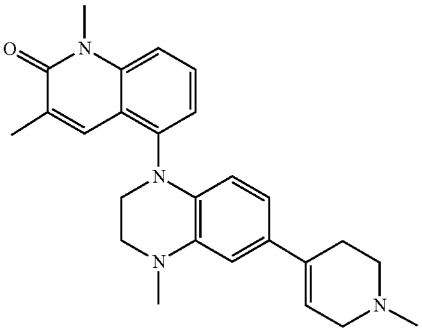 [SMILES: Cc1cc2c(N3CCN(C)c4cc(C5=CCN(C)CC5)ccc43)cccc2n(C)c1=O] | A | LC-MS: 414.9 [M + H]+; 1H-NMR (400 MHz, Chloroform-D) δ 7.68 (d, J = 1.3 Hz, 1H), 7.55 (t, J = 8.2, 8.2 Hz, 1H), 7.29 (s, 1H), 7.11 (d, J = 7.7 Hz, 1H), 6.66 (s, 1H), 6.49 (dd, J = 8.4, 2.1 Hz, 1H), 5.99 (d, J = 8.4 Hz, 1H), 5.85 (s, 1H), 3.84 (s, 1H), 3.78 (s, 3H), 3.72-3.54 (m, 5H), 3.35 (s, 3H), 3.01 (s, 3H), 2.86 (s, 3H), 2.81 (s, 2H), 2.21 (d, J = 1.2 Hz, 3H). |

-continued

| Example | Structure | Coupling Method | Analytical data |
|---|---|---|---|
| 45 | 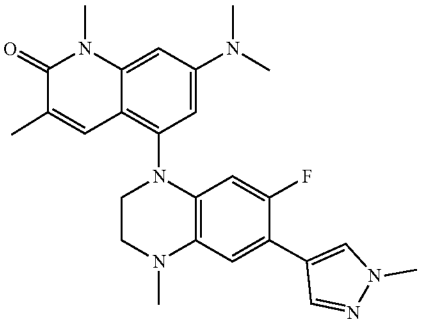 [SMILES: Cc1cc2c(N3CCN(C)c4cc(-c5cnn(C)c5)c(F)cc43)cc(N(C)C)cc2n(C)c1=O] | B | LC-MS: 461.2 [M + H]+; 1H-NMR (400 MHz, DMSO-D6) δ 7.90 (d, J = 1.8 Hz, 1H), 7.71 (s, 1H), 7.43 (s, 1H), 6.74 (d, J = 7.5 Hz, 1H), 6.66 (d, J = 2.3 Hz, 1H), 6.46 (d, J = 2.3 Hz, 1H), 5.57 (d, J = 13.2 Hz, 1H), 3.84 (d, J = 4.1 Hz, 3H), 3.65 (d, J = 4.2 Hz, 3H), 3.56 (d, J = 11.5 Hz, 2H), 3.46 (d, J = 4.4 Hz, 2H), 3.05 (d, J = 4.6 Hz, 6H), 2.94 (s, 3H), 2.01 (d, J = 4.6 Hz, 3H). |
| 46 | 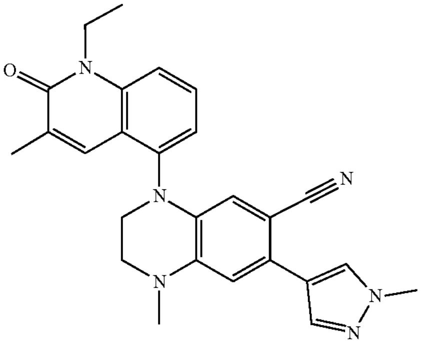 [SMILES: CCn1c(=O)c(C)cc2c(N3CCN(C)c4cc(-c5cnn(C)c5)c(C#N)cc43)cccc21] | A | LC-MS: 439.4 [M + H]+; 1H-NMR (400 MHz, DMSO-D6) δ 8.04 (s, 1H), 7.77 (s, 1H), 7.7 (s, 1H), 7.65-7.63 (m, 1H), 7.52-7.50 (m, 1H), 7.28-7.27 (m, 1H), 6.68 (s, 1H), 5.86 (s, 1H), 4.33-4.28 (m, 2H), 3.83 (s, 3H), 3.76-3.68 (m, 2H), 3.54-3.48 (m, 2H), 3.04 (s, 3H), 2.07 (s, 3H), 1.24-1.19 (m, 3H). |
| 47 | 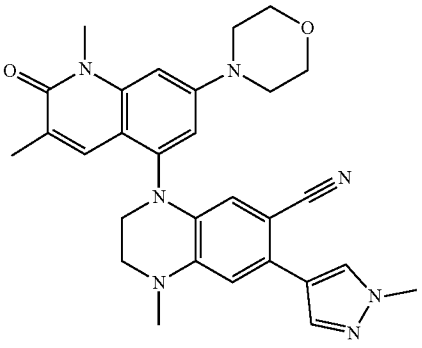 [SMILES: Cc1cc2c(N3CCN(C)c4cc(-c5cnn(C)c5)c(C#N)cc43)cc(N3CCOCC3)cc2n(C)c1=O] | B | LC-MS: 510.3 [M + H]+; 1H-NMR (400 MHz, DMSO-D6) δ 8.06 (s, 1H), 7.80 (s, 1H), 7.52 (s, 1H), 6.94 (d, J = 2.0 Hz, 1H), 6.76 (d, J = 1.8 Hz, 1H), 6.70 (s, 1H), 5.87 (s, 1H), 3.87 (s, 3H), 3.84 (s, 3H), 3.82 (s, 2H), 3.76 (t, J = 4.9, 4.9 Hz, 5H), 3.67 (s, 3H), 3.50 (d, J = 4.7 Hz, 2H), 3.07 (s, 3H), 2.03 (s, 3H). |
| 48 | 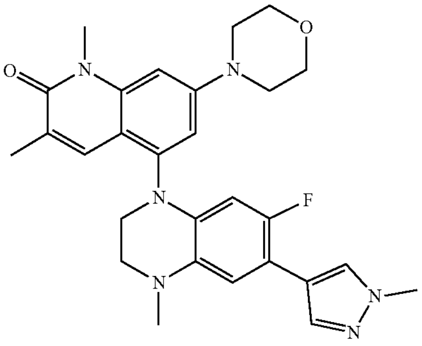 [SMILES: Cc1cc2c(N3CCN(C)c4cc(-c5cnn(C)c5)c(F)cc43)cc(N3CCOCC3)cc2n(C)c1=O] | B | LC-MS: 503.65 $[M + H]^+$; 1H-NMR (400 MHz, DMSO-D6) δ 7.87 (d, J = 1.9 Hz, 1H), 7.69 (d, J = 1.3 Hz, 1H), 7.44 (d, J = 1.4 Hz, 1H), 6.89 (d, J = 2.2 Hz, 1H), 6.74-6.70 (m, 2H), 5.55 (s, 1H), 3.83 (d, J = 3.5 Hz, 1H), 3.30-3.29 (m, 6H), 3.80 (s, 3H), 3.72 (d, J = 4.7 Hz, 3H), 3.63 (s, 3H), 3.55-3.51 (m, 1H), 3.45-3.42 (m, 1H), 2.91 (s, 3H), 1.99 (d, J = 1.2 Hz, 3H). |

-continued

| Example | Structure | Coupling Method | Analytical data |
|---|---|---|---|
| 49 | 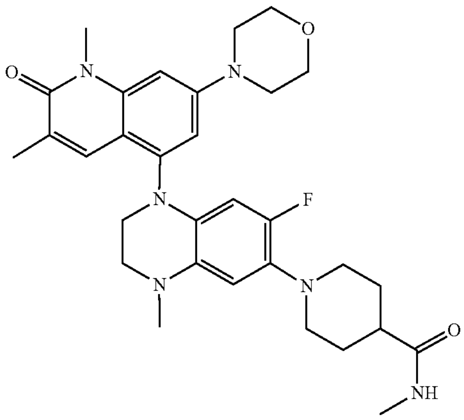 [SMILES: CNC(=O)C1CCN(c2cc3c(cc2F)N(c2cc(N4CCOCC4)cc4c2cc(C)c(=O)n4C)CCN3C)CC1] | B | LC-MS: 563.3 [M + H]+; 1H-NMR (400 MHz, Chloroform-D) δ 7.55-7.53 (m, 1H), 6.67 (s, 1H), 6.55 (s, 1H), 6.30 (s, 1H), 5.87 (s, 1H), 3.87-3.82 (m, 4H), 3.71 (s, 4H), 3.60 (s, 1H), 3.44 (d, J = 8.2 Hz, 1H), 3.30 (d, J = 23.6 Hz, 3H), 3.22 (td, J = 4.5, 4.4, 2.2 Hz, 4H), 2.93 (s, 3H), 2.81 (d, J = 4.8 Hz, 3H), 2.66 (d, J = 14.8 Hz, 2H), 2.19 (t, J = 4.2, 4.2 Hz, 1H), 2.15 (d, J = 1.2 Hz, 3H), 1.94-1.81 (m, 4H). |
| 50 | 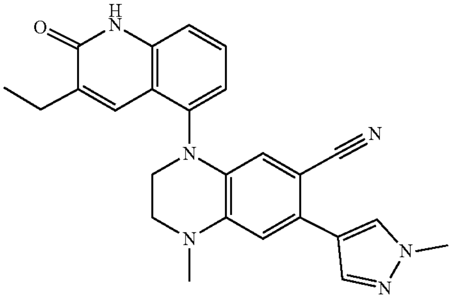 [SMILES: CCc1cc2c(N3CCN(C)c4cc(-c5cnn(C)c5)c(C#N)cc43)cccc2[nH]c1=O] | A | LC-MS: 424.95 [M + H]+; 1H-NMR (300 MHz, Chloroform-D + meod) δ 7.85 (s, 1H), 7.74 (s, 1H), 7.62 (s, 1H), 7.48 (m, 1H), 7.19 (s, 1H), 7.03 (s, 1H), 6.63 (s, 1H), 6.25 (s, 1H), 3.92 (s, 3H), 3.85-3.4 (m, 4H), 3.10 (s, 3H), 2.63-2.60 (m, 2H), 1.31 (s, 3H). |
| 51 | 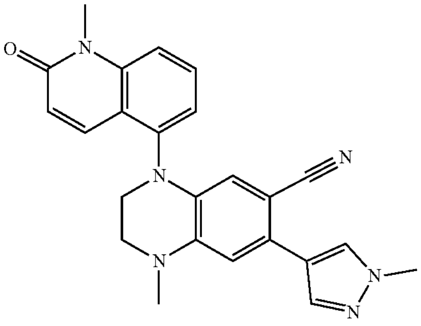 [SMILES: CN1CCN(c2cccc3c2ccc(=O)n3C)c2cc(C#N)c(-c3cnn(C)c3)cc21] | A | LC-MS: 411.3 [M + H]+; 1H-NMR (300 MHz, DMSO-d6) δ 8.07 (s, 1H), 7.81-7.72 (m, 3H), 7.54 (d, J = 8.7 Hz, 1H), 7.25 (d, J = 7.8 Hz, 1H), 6.71 (s, 1H), 6.63 (d, J = 6.3 Hz, 1H), 3.87 (s, 3H), 3.77-3.70 (m, 2H), 3.66 (s, 4H), 3.64-3.48 (m, 2H), 3.07 (s, 3H). |
| 52 | 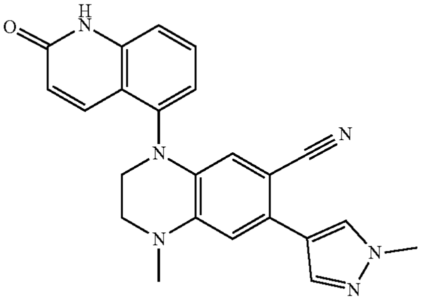 [SMILES: CN1CCN(c2cccc3[nH]c(=O)ccc23)c2cc(C#N)c(-c3cnn(C)c3)cc21] | A | LC-MS: 397.3 [M + H]+; 1H-NMR (400 MHz, Chloroform-D) δ 10.72 (s, 1H), 7.94-7.82 (m, 2H), 7.75 (d, J = 0.9 Hz, 1H), 7.57 (t, J = 8.0, 8.0 Hz, 1H), 7.24 (d, J = 8.3 Hz, 1H), 7.05 (dd, J = 7.8, 0.9 Hz, 1H), 6.75-6.55 (m, 2H), 6.25 (s, 1H), 3.94 (s, 3H), 3.88-3.28 (m, 4H), 3.11 (s, 3H). |

-continued

| Example | Structure | Coupling Method | Analytical data |
|---|---|---|---|
| 53 | 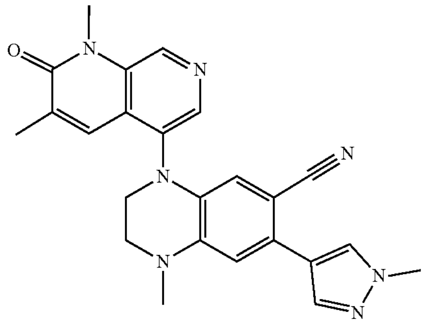 [SMILES: Cc1cc2c(N3CCN(C)c4cc(-c5cnn(C)c5)c(C#N)cc43)cncc2n(C)c1=O] | A | LC-MS: 425.8 [M + H]$^+$; 1H-NMR (400 MHz, Chloroform-D) δ 8.75 (s, 1H), 8.32 (s, 1H), 7.88 (s, 1H), 7.76 (s, 1H), 7.58-7.57 (m, 1H), 6.67 (s, 1H), 6.19 (s, 1H), 3.94 (s, 3H), 3.87 (s, 3H), 3.72 (d, J = 36.3 Hz, 4H), 3.13 (s, 3H), 2.27 (d, J = 1.3 Hz, 3H). |
| 54 | 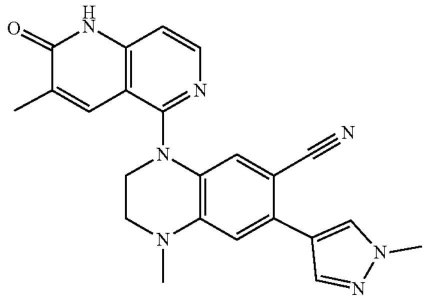 [SMILES: Cc1cc2c(N3CCN(C)c4cc(-c5cnn(C)c5)c(C#N)cc43)nccc2[nH]c1=O] | B | LC-MS: 412.3 [M + H]$^+$; 1H-NMR (400 MHz, DMSO-D6) δ 12.16 (s, 1H), 8.42-8.37 (d, 1H), 8.14 (s, 1H), 7.87 (s, J = 1.0 Hz, 1H), 7.66 (s, J = 1.3, 1.3 Hz, 1H), 6.97 (dd, J = 5.3, 1.1 Hz, 1H), 6.81 (s, J = 1.1 Hz, 1H), 6.55 (s, J = 1.1 Hz, 1H), 3.89 (d, J = 1.1 Hz, 3H), 3.73 (t, J = 4.7, 4.7 Hz, 2H), 3.53 (s, 2H), 3.09 (s, 3H), 2.06 (s, J = 1.4 Hz, 3H). |
| 55 | 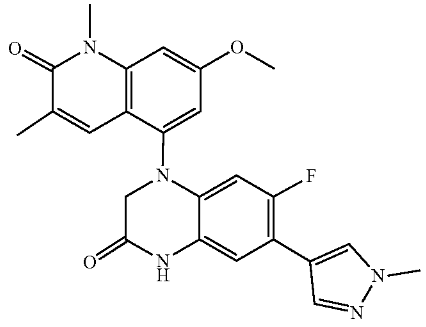 [SMILES: COc1cc(N2CC(=O)Nc3cc(-c4cnn(C)c4)c(F)cc32)c2cc(C)c(=O)n(C)c2c1] | A | LC-MS: 448.15 [M + H]$^+$; 1H-NMR (400 MHz, DMSO-D6) δ 10.73 (s, 1H), 3.98-3.95 (m, 1H), 7.89 (d, J = 2.1 Hz, 1H), 7.61 (s, 1H), 7.53 (s, 1H), 7.10 (d, J = 7.4 Hz, 1H), 7.02 (d, J = 2.3 Hz, 1H), 6.97 (d, J = 2.3 Hz, 1H), 5.73 (s, 1H), 4.50 (d, J = 15.3 Hz, 1H), 3.92 (s, 4H), 3.86 (s, 3H), 3.68 (s, 3H), 2.01 (d, J = 1.2 Hz, 3H). |
| 56 | 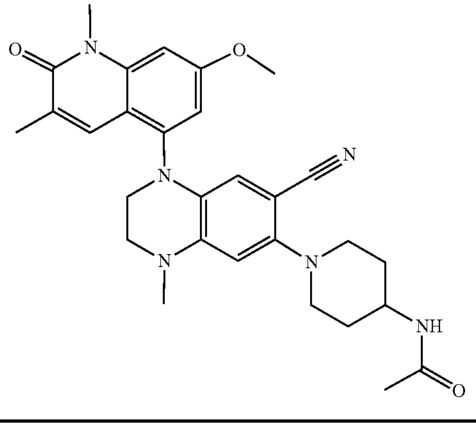 | A | LC-MS: 515.2 [M + H]$^+$; 1H-NMR (600 MHz, Chloroform-D) δ 7.58 (s, 1H), 6.70 (s, 1H), 6.59 (s, 1H), 6.18 (s, 2H), 5.37 (d, J = 7.8 Hz, 1H), 3.93-3.91 (m, 1H), 3.89 (s, 3H), 3.75 (s, 3H), 2.04-2.02 (m, 2H), 3.71 (d, J = 14.2 Hz, 2H), 3.51 (d, J = 11.0 Hz, 2H), 3.42 (d, J = 15.1 Hz, 2H), 3.07 (s, 3H), 2.81 (d, J = 9.6 Hz, 2H), 2.17 (s, 3H), 1.99 (s, 3H), 1.65-1.63 (m, 2H). |

Example-57: 1-Methyl-7-(1-methyl-1H-pyrazol-4-yl)-4-(3-methyl-2-oxo-1,2-dihydroquinolin-5-yl)-1,2,3,4-tetrahydroquinoxaline-6-carbaldehyde

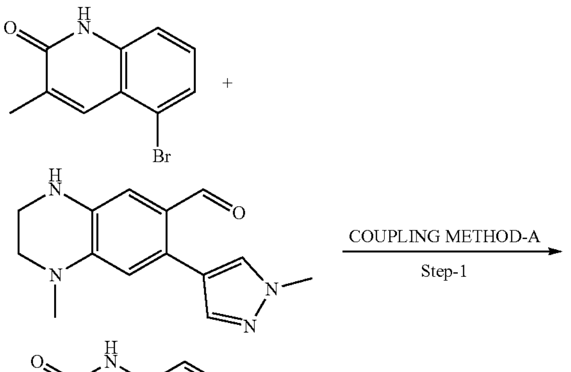

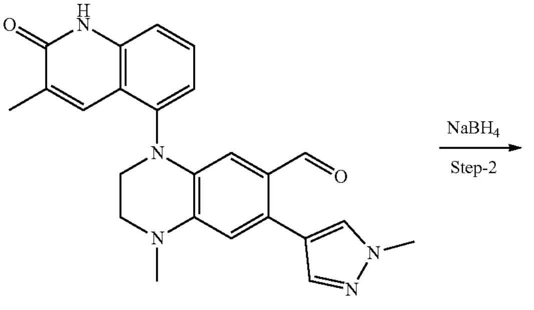

Example-57

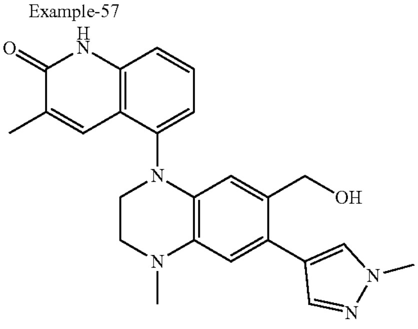

Example-58

The compound of Example 57 was prepared as per the similar procedure described in COUPLING METHOD-A by using 5-bromo-3-methylquinolin-2(1H)-one & intermediate 1-methyl-7-(1-methyl-1H-pyrazol-4-yl)-1,2,3,4-tetrahydroquinoxaline-6-carbaldehyde with appropriate variations in reactants, quantities of reagents, solvents and reaction conditions. LC-MS: 414.5 [M+H]$^+$.

Example-58: 5-(7-(Hydroxymethyl)-4-methyl-6-(1-methyl-1H-pyrazol-4-yl)-3,4-dihydroquinoxalin-1(2H)-yl)-3-methylquinolin-2(1H)-one An ice cold solution of compound of Example-57 (100 mg, 0.24 mmol) in methanol (4 mL) was added sodium borohydride (14 mg, 0.36 mmol). The reaction mixture was gradually warmed to RT and stirred for 12 h. Solvent evaporated off to get the crude compound. This crude compound was purified by preparative HPLC using column: GEMINI NX C18, (21.2 mm×150 mm); eluents A: 0.01% AMMONIA, B: (1:1) ACETONITRILE:METHANOL eluted with the flow rate of 16 mL/minute using gradient programme-25% B at 0 minute, 35% B at 2 minutes, 55% of B at 8 minutes. This afforded the 1H-NMRd compound (10 mg, 9.9%) LC-MS:416.5 [M+H]$^+$;

1H-NMR (400 MHz, DMSO-D6) δ 7.80 (s, 1H), 7.70 (s, 1H), 7.58 (s, 1H), 7.47 (t, J=8.0, 8.0 Hz, 1H), 7.20 (d, J=8.2 Hz, 1H), 7.00 (d, J=7.7 Hz, 1H), 6.60 (s, 1H), 6.08 (s, 1H), 4.10 (s, 2H), 3.84 (s, 3H), 3.60 (m, 4H), 2.92 (s, 3H), 2.06 (s, 3H).

Example-59: 1-(7-Cyano-1-(7-methoxy-1,3-dimethyl-2-oxo-1,2-dihydroquinolin-5-yl)-4-methyl-1,2,3,4-tetrahydroquinoxalin-6-yl)-N-(2-hydroxyethyl)piperidine-4-carboxamide

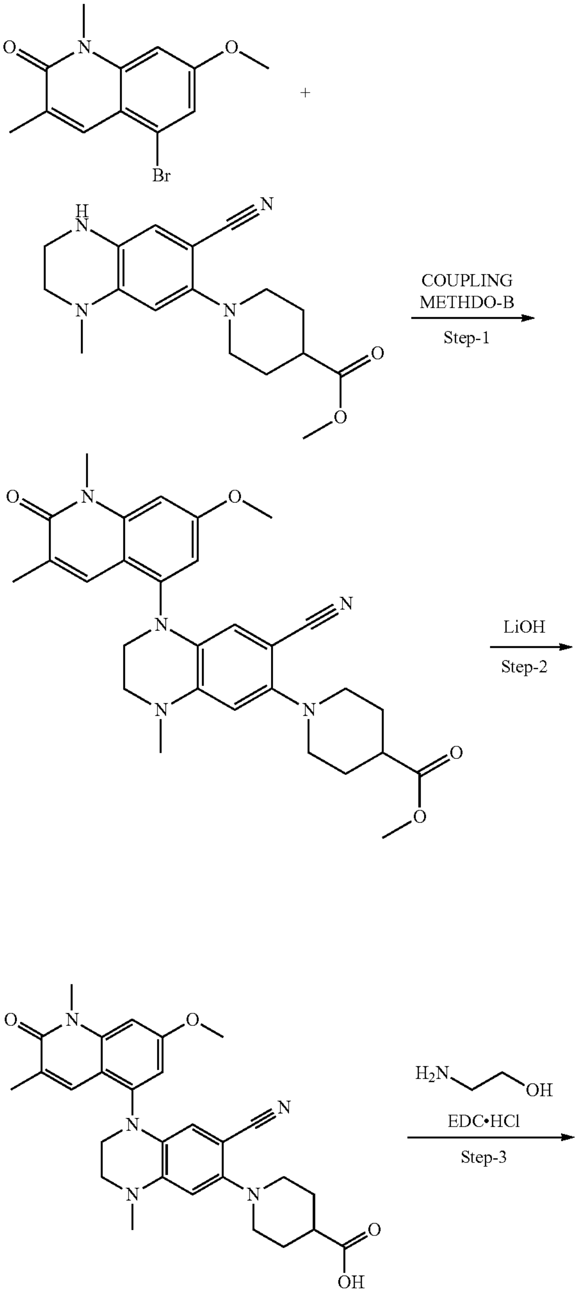

-continued

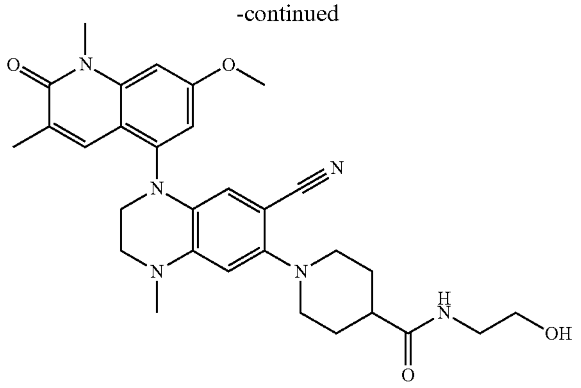

Example-59

Step-1: Synthesis of methyl 1-(7-cyano-1-(7-methoxy-1,3-dimethyl-2-oxo-1,2-dihydroquinolin-5-yl)-4-methyl-1,2,3,4-tetrahydroquinoxalin-6-yl)piperidine-4-carboxylate This compound was prepared using the similar protocol described in COUPLING METHOD-A using reactants 5-bromo-7-methoxy-1,3-dimethylquinolin-2(1H)-one & methyl 1-(7-cyano-4-methyl-1,2,3,4-tetrahydroquinoxalin-6-yl)piperidine-4-carboxylate with appropriate variations in reactants, quantities of reagents, solvents and reaction conditions. LC-MS: 516.2 $[M+H]^+$.

Step-2: Synthesis of 1-(7-cyano-1-(7-methoxy-1,3-dimethyl-2-oxo-1,2-dihydroquinolin-5-yl)-4-methyl-1,2,3,4-tetrahydroquinoxalin-6-yl)piperidine-4-carboxylic acid A solution of methyl 1-(7-cyano-1-(7-methoxy-1,3-dimethyl-2-oxo-1,2-dihydroquinolin-5-yl)-4-methyl-1,2,3,4-tetrahydroquinoxalin-6-yl)piperidine-4-carboxylate (70 mg, 0.13 mmol) in THE (2 mL) was added lithium hydroxide (10 mg, 0.4 mmol) in water (2 mL) and the mixture was stirred at RT for overnight. The reaction mixture was acidified with 1N HCl and extracted with ethyl acetate. The organic portion was washed with brine, dried over sodium sulphate and concentrated to get the crude compound (50 mg). The product used as such in the next step. LC-MS: 502.15 $[M+H]^+$.

Step-3: Synthesis of 1-(7-cyano-1-(7-methoxy-1,3-dimethyl-2-oxo-1,2-dihydroquinolin-5-yl)-4-methyl-1,2,3,4-tetrahydroquinoxalin-6-yl)-N-(2-hydroxyethyl)piperidine-4-carboxamide A cold solution of 1-(7-cyano-1-(7-methoxy-1,3-dimethyl-2-oxo-1,2-dihydroquinolin-5-yl)-4-methyl-1,2,3,4-tetrahydroquinoxalin-6-yl)piperidine-4-carboxylic acid (50 mg, 0.1 mmol) in DMF (5 mL) was added N,N-diisopropylethylamine (0.03 mL, 0.13 mmol), HATU (46 mg, 0.12 mmol) and 2-aminoethan-1-ol (10 mg, 0.15 mmol). The mixture was stirred for 2 h, water was added, extracted with ethyl acetate, and organic portion was washed with saturated aq. sodium bicarbonate, dried over sodium sulphate and concentrated to get the crude compound. The crude was purified by flash chromatography using 1-5% Methanol in DCM as eluent to give pure compound (47 mg, 86.7%) LC-MS: 544.9 $[M+H]^+$; 1H-NMR (600 MHz, DMSO-D6) δ 7.81 (d, J=5.7 Hz, 1H), 7.60 (d, J=1.4 Hz, 1H), 6.88 (d, J=1.7 Hz, 1H), 6.75 (t, J=1.7, 1.7 Hz, 1H), 5.86 (s, 1H), 4.66 (dd, J=5.5, 1.2 Hz, 1H), 3.88 (d, J=1.3 Hz, 3H), 3.73-3.70 (m, 2H), 3.67 (d, J=1.2 Hz, 3H), 3.47-3.43 (m, 2H), 3.39-3.37 (m, 2H), 3.32-3.30 (m, 2H), 3.11 (dd, J=5.9, 1.2 Hz, 2H), 3.04 (d, J=1.2 Hz, 3H), 2.67 (d, J=13.3 Hz, 2H), 2.21 (d, J=4.5 Hz, 1H), 2.04 (d, J=1.4 Hz, 3H), 1.73-1.67 (m, 4H), 6.25-6.21 (s, 1H).

Example-60: 4-(7-(2-Hydroxyethoxy)-1,3-dimethyl-2-oxo-1,2-dihydroquinolin-5-yl)-1-methyl-7-(1-methyl-1H-pyrazol-4-yl)-1,2,3,4-tetrahydroquinoxaline-6-carbonitrile

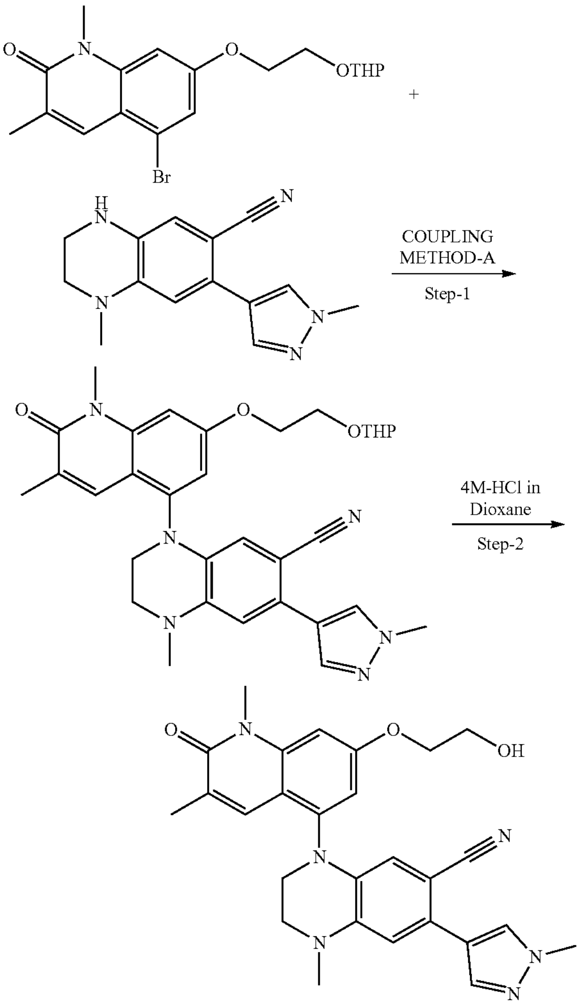

Example-60

Step-1: Synthesis of 4-(1,3-dimethyl-2-oxo-7-(2-((tetrahydro-2H-pyran-2-yl)oxy)ethoxy)-1,2-dihydroquinolin-5-yl)-1-methyl-7-(1-methyl-1H-pyrazol-4-yl)-1,2,3,4-tetrahydroquinoxaline-6-carbonitrile This compound was prepared using the similar protocol described in COUPLING METHOD-A using intermediates 5-bromo-1,3-dimethyl-7-(2-((tetrahydro-2H-pyran-2-yl)oxy)ethoxy)quinolin-2(1H)-one & 1-methyl-7-(1-methyl- 1H-pyrazol-4-yl)-1,2,3,4-tetrahydroquinoxaline-6-carbonitrile with appropriate variations in reactants, quantities of reagents, solvents and reaction conditions. LC-MS: 569.4 $[M+H]^+$.

Step-2: Synthesis of 4-(7-(2-hydroxyethoxy)-1,3-dimethyl-2-oxo-1,2-dihydroquinolin-5-yl)-1-methyl-7-(1-methyl-1H-pyrazol-4-yl)-1,2,3,4-tetrahydroquinoxaline-6-carbonitrile A suspension of 4-(1,3-dimethyl-2-oxo-7-(2-((tetrahydro-2H-pyran-2-yl)oxy)ethoxy)-1,2-dihydroquinolin-5-yl)-1-methyl-7-(1-methyl-1H-pyrazol-4-yl)-1,2,3,4-tetrahydroquinoxaline-6-carbonitrile (100 mg, 0.17 mmol) in 4M HCl in 1,4-dioxane (5 mL) was stirred for 12 h. The solvent was evaporated and the residue obtained was washed with ether to get the crude compound. This crude compound was purified by preparative HPLC using column: KINETEX (150 mm×21.2 mm); Eluents A: Water, B: ACETONITRILE. Eluted with the flow rate of 20 mL/minute using gradient programme-30% B at 0 minute, 60% B at 10 minutes, this afforded the title compound (20 mg, 43.2%) LC-MS:485.4 $[M+H]^+$; 1H-NMR (400 MHz, Chloroform-D) δ 7.88 (s, 1H), 7.76 (s, 1H), 7.55 (s, 1H), 6.79 (s, 1H), 6.70 (s, 1H), 6.64 (s, 1H), 6.22 (s, 1H), 4.20 (d, J=4.3 Hz, 2H), 4.03 (d, J=4.2 Hz, 2H), 3.93 (s, 3H), 3.76 (s, 4H), 3.58 (s, 2H), 3.47 (s, 2H), 3.11 (s, 3H), 2.18 (s, 3H).

Example-61: 4-(7-(2-(4-Acetylpiperazin-1-yl)ethoxy)-1,3-dimethyl-2-oxo-1,2-dihydroquinolin-5-yl)-1-methyl-7-(1-methyl-1H-pyrazol-4-yl)-1,2,3,4-tetrahydroquinoxaline-6-carbonitrile

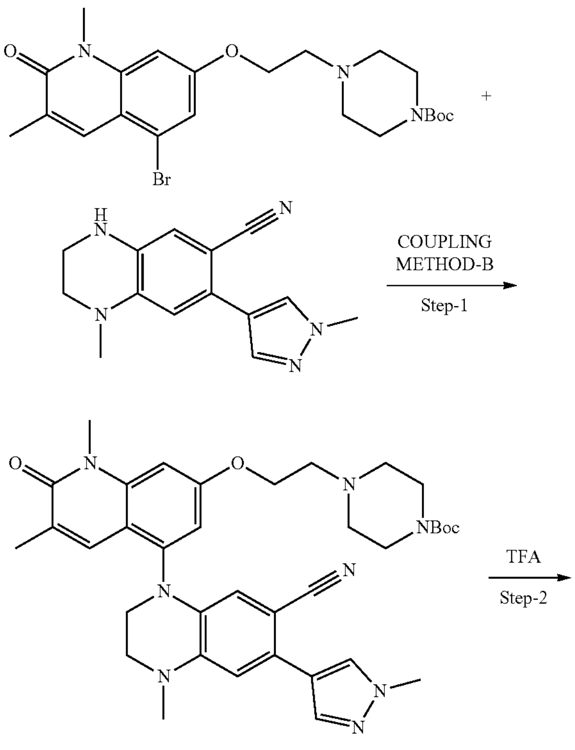

-continued

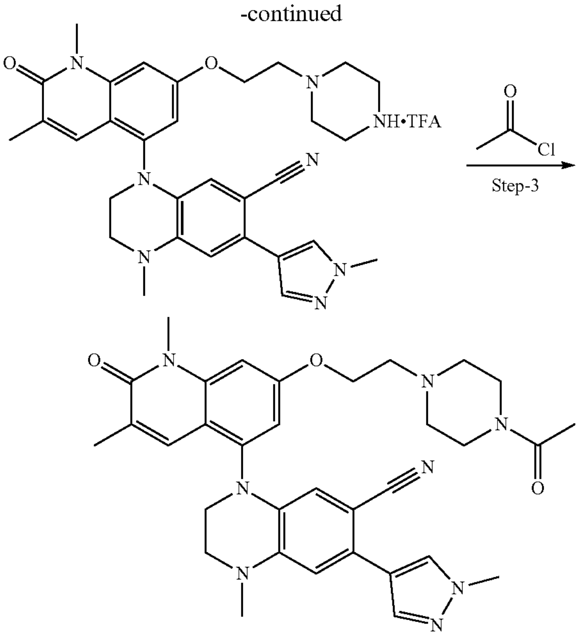

Example-61

Step-1: Synthesis of tert-butyl 4-(2-((5-(7-cyano-4-methyl-6-(1-methyl-1H-pyrazol-4-yl)-3,4-dihydroquinoxalin-1(2H)-yl)-1,3-dimethyl-2-oxo-1,2-dihydroquinolin-7-yl)oxy)ethyl)piperazine-1-carboxylate This compound was prepared using the similar protocol described in COUPLING METHOD-B using intermediates tert-butyl 4-(2-((5-bromo-1,3-dimethyl-2-oxo-1,2-dihydroquinolin-7-yl)oxy)ethyl)piperazine-1-carboxylate & 1-methyl-7-(1-methyl-1H-pyrazol-4-yl)-1,2,3,4-tetrahydroquinoxaline-6-carbonitrile with appropriate variations in reactants, quantities of reagents, solvents and reaction conditions. LC-MS: 653.0 $[M+H]^+$.

Step-2: Synthesis of 4-(1,3-dimethyl-2-oxo-7-(2-(4-(2,2,2-trifluoroacetyl)-414-piperazin-1-yl)ethoxy)-1,2-dihydroquinolin-5-yl)-1-methyl-7-(1-methyl-1H-pyrazol-4-yl)-1,2,3,4-tetrahydroquinoxaline-6-carbonitrile A suspension of tert-butyl 4-(2-((5-(7-cyano-4-methyl-6-(1-methyl-1H-pyrazol-4-yl)-3,4-dihydroquinoxalin-1(2H)-yl)-1,3-dimethyl-2-oxo-1,2-dihydroquinolin-7-yl)oxy)ethyl)piperazine-1-carboxylate (500 mg, 0.77 mmol) in TFA (3 mL) and DCM (5 mL) was stirred for 4 h. The solvent was evaporated and the residue obtained was washed with ether to get the crude compound (500 mg). This was used as such in the next step without any purification. LC-MS: 553.1 [M+H]+.

Step-3: Synthesis of 4-(7-(2-(4-acetylpiperazin-1-yl)ethoxy)-1,3-dimethyl-2-oxo-1,2-dihydroquinolin-5-yl)-1-methyl-7-(1-methyl-1H-pyrazol-4-yl)-1,2,3,4-tetrahydroquinoxaline-6-carbonitrile A solution of 4-(1,3-dimethyl-2-oxo-7-(2-(4-(2,2,2-trifluoroacetyl)-414-piperazin-1-yl)ethoxy)-1,2-dihydroquinolin-5-yl)-1-methyl-7-(1-methyl-1H-pyrazol-4-yl)-1,2,3,4-tetrahydroquinoxaline-6-carbonitrile (80 mg, 0.123 mmol)

in DCM (10 mL) was added trimethylamine (62 mg, 0.615 mmol). Acetyl chloride (14.5 mg, 0.184 mmol) was added dropwise at 0° C. and stirred for 2 h. The reaction mixture was diluted with DCM and washed with water and brine solutions, dried over sodium sulphate and concentrated to get the crude compound. This crude compound was purified by preparative HPLC using column: KINETEX $C_{18}$, (21.2 mm×150 mm); Eluted with eluents-A: 0.1% ammonia, B: ACETONITRILE. with the flow rate of 15 mL/minute using gradient programme-25% B at 0 min, 35% B at 2 min and 60% B at 8 min to give title compound (20 mg, 27.3%); LC-MS:594.71 [M+H]+; 1H-NMR (400 MHz, Chloroform-D) δ 7.86 (d, J=0.8 Hz, 1H), 7.75 (d, J=0.9 Hz, 1H), 7.55 (d, J=1.5 Hz, 1H), 6.76 (d, J=2.2 Hz, 1H), 6.68 (s, 1H), 6.64 (s, 1H), 6.21 (s, 1H), 4.19 (d, J=5.6 Hz, 2H), 3.94 (s, 3H), 3.79 (d, J=8.2 Hz, 2H), 3.76 (s, 3H), 3.66-3.64 (m, 2H), 3.58 (d, J=4.1 Hz, 1H), 3.52-3.47 (m, 3H), 3.11 (s, 3H), 2.89 (d, J=5.5 Hz, 2H), 2.60-2.54 (m, 4H), 2.18 (d, J=1.2 Hz, 3H), 2.09 (s, 3H).

Example-62 & Example-63: 4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile & 1-acetyl-4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile

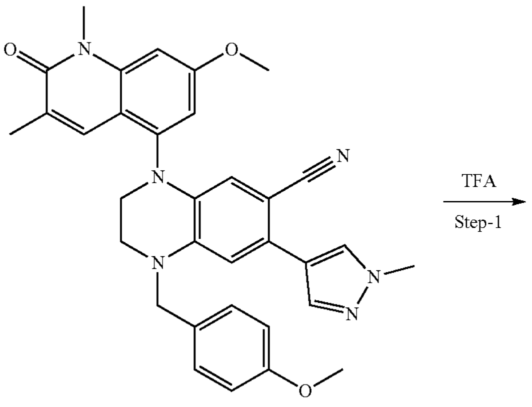

Example-8

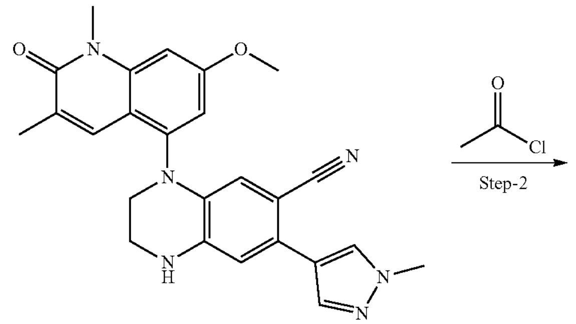

Example-62

-continued

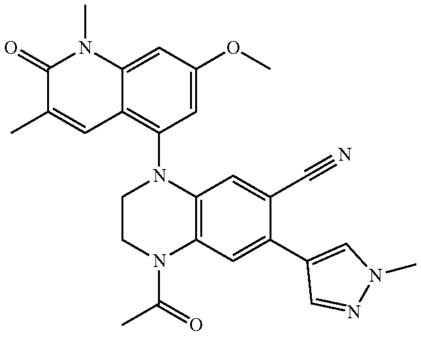

Example-63

Step-1: Synthesis of 4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile A solution of 4-(7-methoxy-1,3-dimethyl-2-oxo-1,2-dihydroquinolin-5-yl)-1-(4-methoxybenzyl)-7-(1-methyl-1H-pyrazol-4-yl)-1,2,3,4-tetrahydroquinoxaline-6-carbonitrile (Example-8) (200 mg, 0.5 mmol) in TFA was heated to 100° C. for 2 h. TFA was evaporated off and the residue was washed with ether to get the crude compound. The crude was purified by preparative HPLC to get the pure title compound (30 mg, 19%). LC-MS:441.1 [M+H]+; 1H-NMR (400 MHz, Chloroform-D) δ 7.86 (d, J=0.8 Hz, 1H), 7.70 (d, J=0.8 Hz, 1H), 7.60-7.57 (m, 1H), 6.75 (d, J=2.4 Hz, 1H), 6.69 (d, J=2.3 Hz, 1H), 6.65 (s, 1H), 6.28 (s, 1H), 4.47 (s, 1H), 3.92 (d, J=4.2 Hz, 6H), 3.77 (s, 6H), 3.62-3.55 (m, 3H), 2.19 (s, J=1.2 Hz, 3H).

Step-2: Synthesis of 1-acetyl-4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile A solution of 4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile (100 mg, 0.22 mmol) in DMF (2 mL) was added pyridine (0.09 mL, 1.13 mmol). Acetyl chloride was added to this mixture at 0° C. and gradually warmed to RT. This was stirred for 12 h and added into water to get solid. Solid filtered and dried to get crude title compound. Purification was done by preparative HPLC to give the title compound (40 mg, 36.5%) LC-MS: 483.1 $[M+H]^+$; 1H-NMR (400 MHz, Chloroform-D) δ 7.84 (d, J=0.9 Hz, 1H), 7.74 (s, 1H), 7.33-7.31 (m, 1H), 6.84 (d, J=2.2 Hz, 1H), 6.71 (d, J=2.5 Hz, 2H), 6.43 (s, 1H), 4.05-3.99 (m, 1H), 3.95 (s, 3H), 3.93 (s, 3H), 3.78 (s, 3H), 3.71 (d, J=6.7 Hz, 2H), 2.42 (s, 3H), 2.19 (d, J=1.1 Hz, 3H), 4.29-4.22 (m, 1H).

Example-64: 1-Acetyl-7-(4-acetylpiperazin-1-yl)-4-(7-methoxy-1,3-dimethyl-2-oxo-1,2-dihydroquinolin-5-yl)-1,2,3,4-tetrahydroquinoxaline-6-carbonitrile

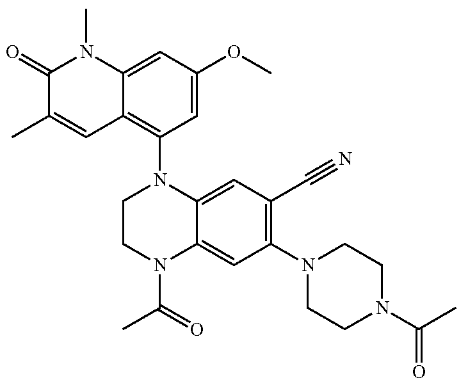 [SMILES: COc1cc(N2CCN(C(C)=O)c3cc(N4CCN(C(C)=O)CC4)c(C#N)cc32)c2cc(C)c(=O)n(C)c2c1]

Example-64 was prepared according to the procedure described in the synthesis of Example-63 with appropriate variations in reactants, quantities of reagents, solvents and reaction conditions. LC-MS: 529.2 $[M+H]^+$; 1H-NMR (400 MHz, Chloroform-D) δ 7.34 (s, 1H), 6.81 (d, J=2.3 Hz, 2H), 6.66 (d, J=2.3 Hz, 1H), 6.39 (s, 1H), 4.18 (s, 2H), 4.00 (s, 2H), 3.91 (s, 3H), 3.80 (s, 1H), 3.76 (s, 3H), 3.65 (dd, J=8.5, 4.6 Hz, 3H), 3.06 (s, 2H), 3.00 (d, J=5.1 Hz, 2H), 2.38 (s, 3H), 2.18 (d, J=1.3 Hz, 3H), 2.13 (s, 3H).

Example-65: 6-Cyano-4-(7-methoxy-1,3-dimethyl-2-oxo-1,2-dihydroquinolin-5-yl)-N-methyl-7-(1-methyl-1H-pyrazol-4-yl)-3,4-dihydroquinoxaline-1(2H)-carboxamide

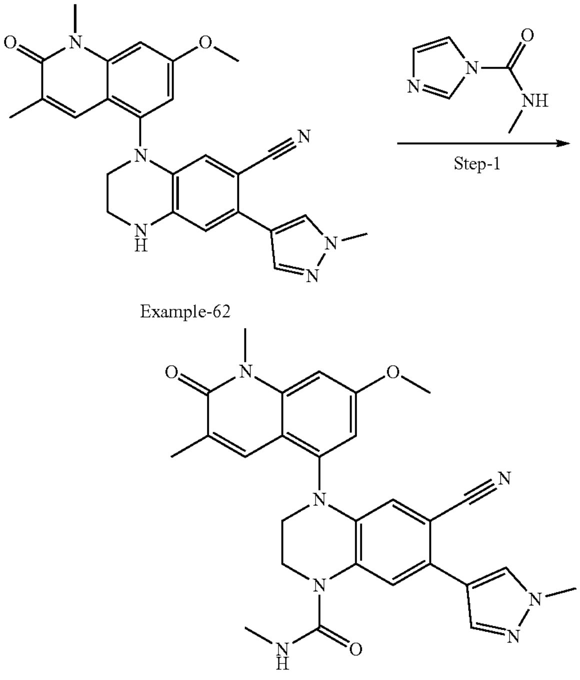

Example-65

A solution of 4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile (Ex. 62) (300 mg, 0.68 mmol) in Chloroform (15 mL) was added trimethylamine (0.48 mL, 3.4 mmol) and N-methyl-1H-imidazole-1-carboxamide (170 mg, 2.3 mmol). This resultant mixture was heated to 50° C. for 12 h, then solvent evaporated to get the crude mass. The crude compound was purified by preparative HPLC to get pure title compound (18 mg, 5.3%) LC-MS: 498.1$[M+H]^+$; 1H-NMR (600 MHz, Chloroform-D) δ 7.84 (d, J=2.5 Hz, 1H), 7.72 (d, J=2.4 Hz, 1H), 7.43 (s, 1H), 7.30 (s, 1H), 6.82 (d, J=2.6 Hz, 1H), 6.67 (d, J=2.4 Hz, 1H), 6.42 (d, J=2.7 Hz, 1H), 5.30 (d, J=5.1 Hz, 1H), 4.18 (s, 1H), 3.92 (dd, J=15.5, 2.9 Hz, 7H), 3.76 (d, J=2.8 Hz, 3H), 3.63 (q, J=4.4, 4.0, 4.0 Hz, 2H), 2.93 (d, J=4.3 Hz, 3H), 2.16 (s, 3H).

Example-66: Ethyl 2-(6-cyano-4-(7-methoxy-1,3-dimethyl-2-oxo-1,2-dihydroquinolin-5-yl)-7-(1-methyl-1H-pyrazol-4-yl)-3,4-dihydroquinoxalin-1(2H)-yl)acetate

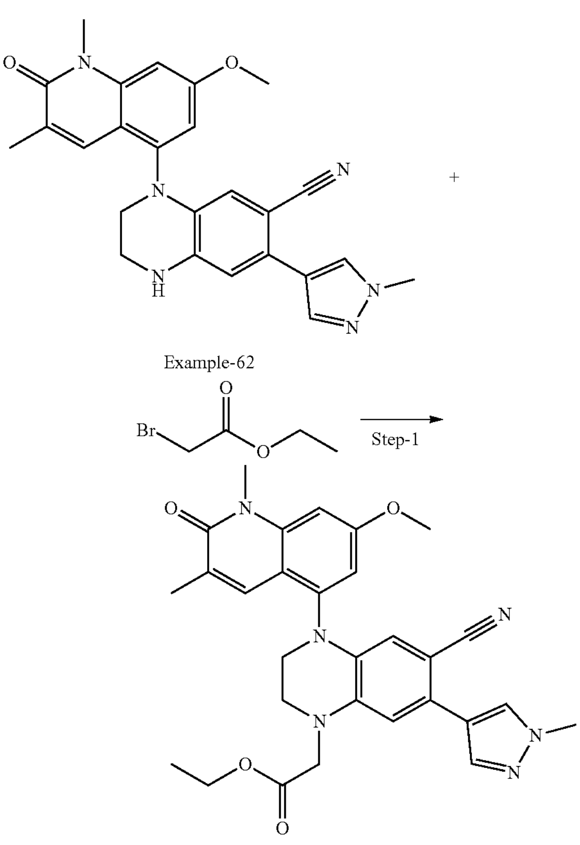

Example-66

A solution of 4-(7-methoxy-1,3-dimethyl-2-oxo-1,2-dihydroquinolin-5-yl)-7-(1-methyl-1H-pyrazol-4-yl)-1,2,3,4-tetrahydroquinoxaline-6-carbonitrile (500 mg, 1.1 mmol) and ethyl 2-bromoacetate (379 mg, 2.2 mmol) in DMF (10 mL) was added caesium carbonate (1460 mg, 0.5 mmol). The mixture was heated to 80° C. for 24 h, then cooled to room temperature and added water. This mixture was extracted with ethyl acetate and organic portion was washed with water, brine and dried over sodium sulphate and concentrated to get the residue. The residue was purified by preparative TLC using 50% ethyl acetate in hexane to give title compound (140 mg, 19.5%) LC-MS: 526.7[M+H]$^+$; 1H-NMR (400 MHz, Chloroform-D) δ 7.84 (s, 1H), 7.68 (s, 1H), 7.59 (s, 1H), 6.75 (d, J=2.3 Hz, 1H), 6.68 (d, J=2.3 Hz, 1H), 6.52 (s, 1H), 6.28 (s, 1H), 4.27 (q, J=7.1, 7.1, 7.1 Hz, 3H), 4.17 (d, J=16.2 Hz, 2H), 3.93 (s, 6H), 3.77 (s, 3H), 3.62-3.57 (m, 3H), 2.19 (d, J=1.3 Hz, 3H), 1.29 (d, J=1.8 Hz, 3H).

Example-67, 68 and 69

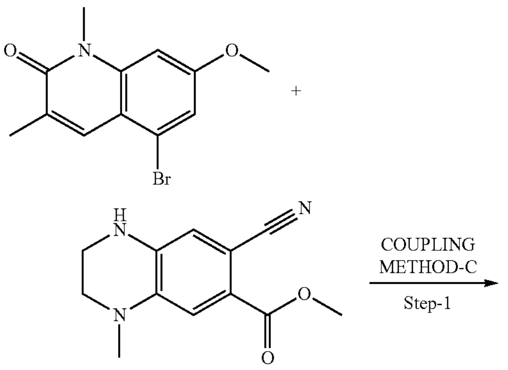

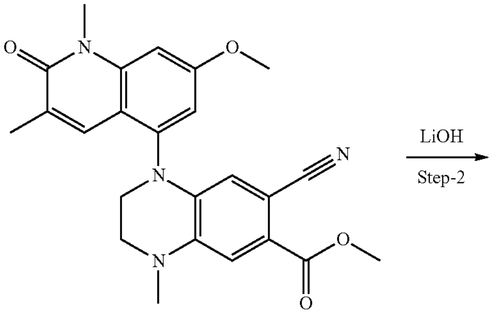

Example-67

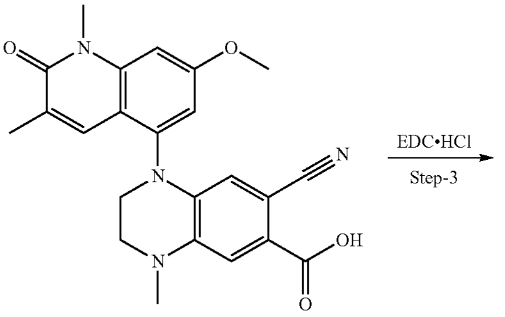

Example-68

-continued

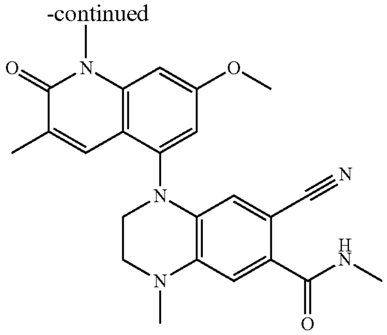

Example-69

Step-1: Synthesis of methyl 7-cyano-1-(7-methoxy-1,3-dimethyl-2-oxo-1,2-dihydroquinolin-5-yl)-4-methyl-1,2,3,4-tetrahydroquinoxaline-6-carboxylate (Example-67)

This compound was prepared using the similar protocol described in COUPLING METHOD-C using reactants 5-bromo-7-methoxy-1,3-dimethylquinolin-2(1H)-one & methyl 7-cyano-4-methyl-1,2,3,4-tetrahydroquinoxaline-6-carboxylate with appropriate variations in reactants, quantities of reagents, solvents and reaction conditions. LC-MS: 433.4 [M+H]$^+$. $^1$H-NMR (400 MHz, DMSO-D6) δ 7.51 (s, 1H), 7.14 (s, 1H), 6.98 (dd, J=16.1, 2.0 Hz, 2H), 5.97 (s, 1H), 3.91 (s, 3H), 3.89-3.86 (m, 1H), 3.82 (s, 3H), 3.74 (d, J=9.2 Hz, 1H), 3.68 (s, 3H), 3.61 (dd, J=9.4, 5.6 Hz, 1H), 3.53-3.49 (m, 1H), 3.06 (s, 3H), 2.04 (s, 3H).

Step-2: Synthesis of 7-cyano-1-(7-methoxy-1,3-dimethyl-2-oxo-1,2-dihydroquinolin-5-yl)-4-methyl-1,2,3,4-tetrahydroquinoxaline-6-carboxylic acid (Example-68)

A stirred solution of methyl 7-cyano-1-(7-methoxy-1,3-dimethyl-2-oxo-1,2-dihydroquinolin-5-yl)-4-methyl-1,2,3,4-tetrahydroquinoxaline-6-carboxylate (150 mg, 0.34 mmol) was taken in methanol (5 mL) and THE (5 mL) was added lithium hydroxide (72 mg, 1.73 mmol) in water (5 mL) at room temperature. The reaction mixture was heated to 60° C. for an hour, then cooled to room temperature and then to 0° C. Acidified with Aq. Citric acid, solid separated was filtered, washed with water, dried to get pure title compound (70 mg, 48.2%). LC-MS: 433.4 [M+H]$^+$; 1H-NMR (400 MHz, DMSO-D6) δ 7.52 (s, 1H), 7.15 (s, 1H), 6.97 (dd, J=17.3, 2.3 Hz, 2H), 5.94 (s, 1H), 3.91 (s, 3H), 3.86 (d, J=9.5 Hz, 1H), 3.78-3.72 (m, 1H), 3.68 (s, 3H), 3.59 (d, J=11.5 Hz, 1H), 3.50 (d, J=11.6 Hz, 1H), 3.05 (s, 3H), 2.04 (s, 3H).

Step-3: Synthesis of 7-cyano-1-(7-methoxy-1,3-dimethyl-2-oxo-1,2-dihydroquinolin-5-yl)-N,4-dimethyl-1,2,3,4-tetrahydroquinoxaline-6-carboxamide (Example-69)

A solution of 7-cyano-1-(7-methoxy-1,3-dimethyl-2-oxo-1,2-dihydroquinolin-5-yl)-4-methyl-1,2,3,4-tetrahydroquinoxaline-6-carboxylic acid (70 mg, 0.16 mmol) and N,N-Diisopropylethylamine (64 mg, 0.5 mmol) in DMF (5 mL) was cooled to 0° C. This mixture was added EDC.HCl (38 mg, 0.25 mmol), HOBT (33 mg, 0.25 mmol) and 1M methylamine in THE (2.5 mL) sequentially. After stirring at room temperature for 6 h, water was added to reaction mixture, precipitate formed was filtered and washed with water to get crude compound. This crude was purified by flash chromatography using 1-5% methanol in DCM as eluent to get pure title compound (35 mg, 48.5%). LC-MS: 432.2 $[114+H]^+$; 1H-NMR (400 MHz, DMSO-D6) δ 7.53-7.50 (s, 1H), 7.14 (s, 1H), 6.98 (dd, J=16.8, 2.3 Hz, 2H), 5.97 (s, 1H), 3.91 (s, 3H), 3.82 (s, 3H), 3.77-3.73 (m, 1H), 3.68 (s, 3H), 3.59 (t, J=3.6, 3.6 Hz, 2H), 3.52-3.49 (m, 2H), 3.06 (s, 3H), 2.04 (s, 3H).

Example-70: 4-(7-Methoxy-1,3-dimethyl-2-oxo-1,2-dihydroquinolin-5-yl)-1-methyl-7-(1-methylpiperidin-4-yl)-1,2,3,4-tetrahydroquinoxaline-6-carbonitrile

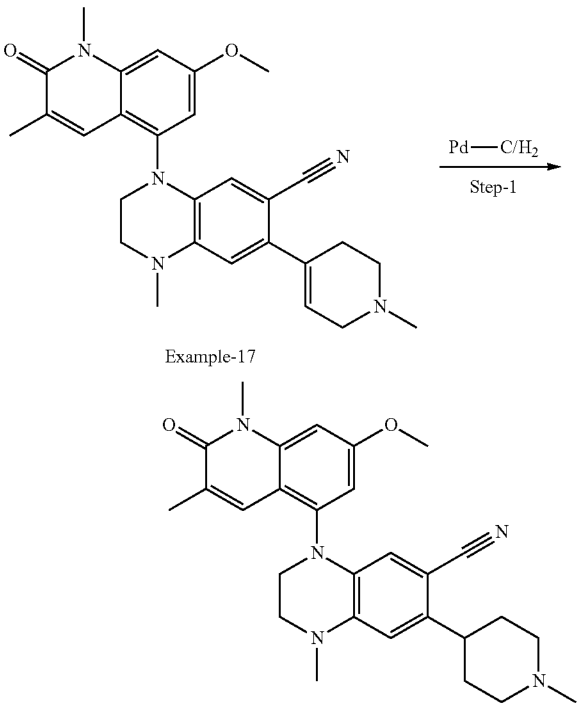

Example-17

Example-70

A solution of 4-(7-methoxy-1,3-dimethyl-2-oxo-1,2-dihydroquinolin-5-yl)-1-methyl-7-(1-methyl-1,2,3,6-tetrahydropyridin-4-yl)-1,2,3,4-tetrahydroquinoxaline-6-carbonitrile (250 mg, 0.53 mmol) in ethyl acetate (5 ml) and ethanol (5 mL) was added 10% Pd—C (25 mg, 10% W/W) and stirred under positive pressure of hydrogen using a bladder. After 12 h, Pd—C was filtered off, filtrate evaporated to get the crude mass and the crude compound was purified by flash chromatography by eluting with 5-10% Methanol in DCM to give pure title compound (30 mg, 12%) LC-MS: 471.8 $[M+H]^+$; 1H-NMR (400 MHz, Chloroform-D) δ 7.56-7.54 (m, 1H), 6.73 (d, J=2.3 Hz, 1H), 6.65 (d, J=2.2 Hz, 1H), 6.51 (s, 1H), 6.14 (s, 1H), 3.90 (s, 3H), 3.76 (s, 3H), 3.75-3.74 (m, 1H), 3.53 (t, J=6.0, 6.0 Hz, 2H), 3.47-3.41 (m, 2H), 3.03 (s, 3H), 2.98 (d, J=11.3 Hz, 2H), 2.81 (d, J=7.2 Hz, 1H), 2.34 (s, 3H), 2.17 (d, J=1.3 Hz, 3H), 2.13-2.08 (m, 2H), 1.83 (d, J=9.7 Hz, 3H).

Example-71: 2-((5-(7-Cyano-4-methyl-6-(1-methyl-1H-pyrazol-4-yl)-3,4-dihydroquinoxalin-1(2H)-yl)-1,3-dimethyl-2-oxo-1,2-dihydroquinolin-7-yl)oxy)acetic acid

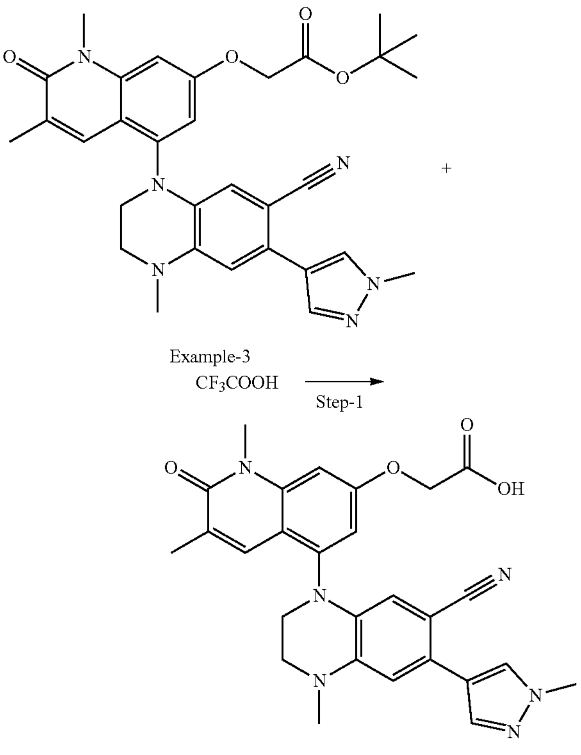

Example-71

Tert-butyl 2-((5-(7-cyano-4-methyl-6-(1-methyl-1H-pyrazol-4-yl)-3,4-dihydroquinoxalin-1(2H)-yl)-1,3-dimethyl-2-oxo-1,2-dihydroquinolin-7-yl)oxy)acetate (250 mg, 0.45 mmol) in DCM (4 mL) was added TFA (4 mL) and stirred for 2 h at room temperature. The reaction mass was then concentrated to dryness and washed with ether to get crude compound. The crude was purified by preparative HPLC to get the pure title compound (10 mg, 4.4%). LC-MS: 499.3 $[M+H]^+$ Example-72: 2-((1,3-Dimethyl-5-(4-methyl-6-(1-methyl-1H-pyrazol-4-yl)-3,4-dihydroquinoxalin-1(2H)-yl)-2-oxo-1,2-dihydroquinolin-7-yl)oxy)acetic acid Example-73: 2-((1,3-Dimethyl-5-(4-methyl-6-(1-methyl-1H-pyrazol-4-yl)-3,4-dihydroquinoxalin-1(2H)-yl)-2-oxo-1,2-dihydroquinolin-7-yl)oxy)-N-methoxyacetamide

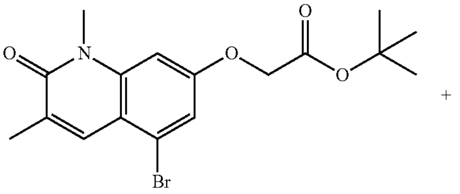

-continued

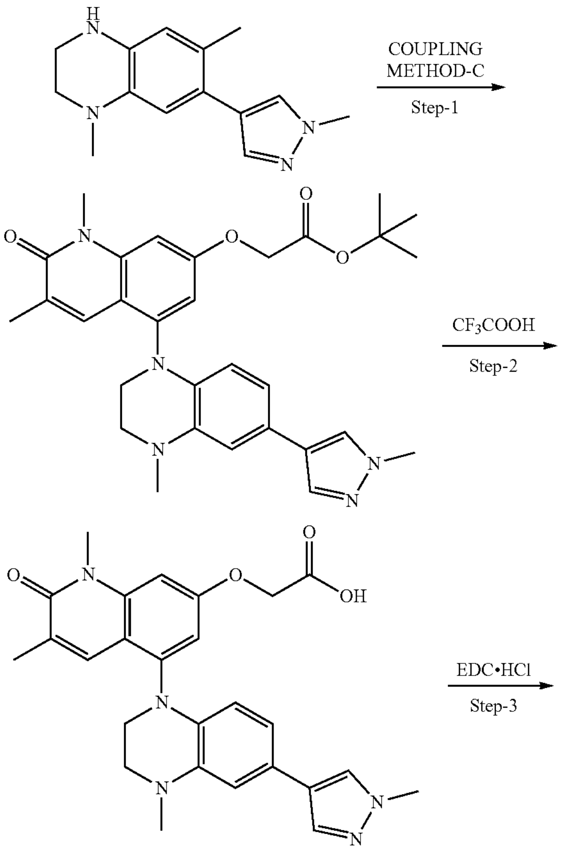

Example-72

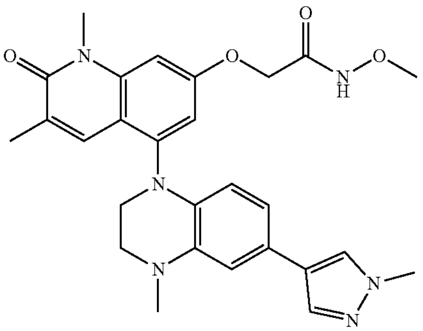

Example-73

Step-1: Synthesis of tert-butyl 2-((1,3-dimethyl-5-(4-methyl-6-(1-methyl-1H-pyrazol-4-yl)-3,4-dihydroquinoxalin-1(2H)-yl)-2-oxo-1,2-dihydroquinolin-7-yl)oxy)acetate This compound was prepared using the similar protocol described in COUPLING METHOD-C using intermediates tert-butyl 2-((5-bromo-1,3-dimethyl-2-oxo-1,2-dihydroquinolin-7-yl)oxy)acetate & 1-methyl-7-(1-methyl-1H-pyrazol-4-yl)-1,2,3,4-tetrahydroquinoxaline with appropriate variations in reactants, quantities of reagents, solvents and reaction conditions. LC-MS: 530.5 $[M+H]^+$.

Step-2: Synthesis of 2-((1,3-dimethyl-5-(4-methyl-6-(1-methyl-1H-pyrazol-4-yl)-3,4-dihydroquinoxalin-1(2H)-yl)-2-oxo-1,2-dihydroquinolin-7-yl)oxy) acetic acid (Example-72)

This compound was prepared using the similar protocol described in the synthesis of Example-69 with appropriate variations in reactants, quantities of reagents, solvents and reaction conditions. LC-MS: 474.4 $[M+H]^+$. 1H-NMR (400 MHz, DMSO-D6) δ 7.91 (s, 1H), 7.66 (s, 1H), 7.58 (d, J=1.5 Hz, 1H), 6.76 (dd, J=7.9, 2.1 Hz, 2H), 3.34-3.32 (m, 2H), 6.65 (d, J=2.2 Hz, 1H), 6.57-6.54 (m, 1H), 3.73-3.70 (m, 2H), 5.89 (d, J=8.2 Hz, 1H), 4.40 (s, 2H), 3.81 (s, 3H), 3.59 (s, 3H), 2.96 (s, 3H), 2.02 (d, J=1.2 Hz, 3H).

Step-3: Synthesis of 2-((1,3-dimethyl-5-(4-methyl-6-(1-methyl-1H-pyrazol-4-yl)-3,4-dihydroquinoxalin-1(2H)-yl)-2-oxo-1,2-dihydroquinolin-7-yl)oxy)-N-methoxyacetamide This compound was prepared using the similar protocol described in the synthesis of Example-69 with appropriate variations in reactants, quantities of reagents, solvents and reaction conditions (30 mg, 28.1%). LC-MS: 503.4 $[M+H]^+$. 1H-NMR (400 MHz, Chloroform-D) δ 9.0 (s, 1H), 7.69 (s, 1H), 7.66 (d, J=0.8 Hz, 1H), 7.50 (s, 1H), 6.77-6.76 (d, J=2 Hz, 1H), 6.68 (s, 2H), 6.60 (dd, J=2, 8 Hz, 1H), 6.16 (s, 1H), 4.62 (s, 2H), 3.92 (s, 3H), 3.83 (s, 3H), 3.73 (s, 3H), 3.7-3.3 (m, 4H), 3.03 (s, 3H), 2.18 (d, J=1.2 Hz, 3H).

Example-74: 5-(4-(Ethylsulfonyl)-6-(1-methyl-1H-pyrazol-4-yl)-3,4-dihydroquinoxalin-1(2H)-yl)-1,3-dimethylquinolin-2(1H)-one

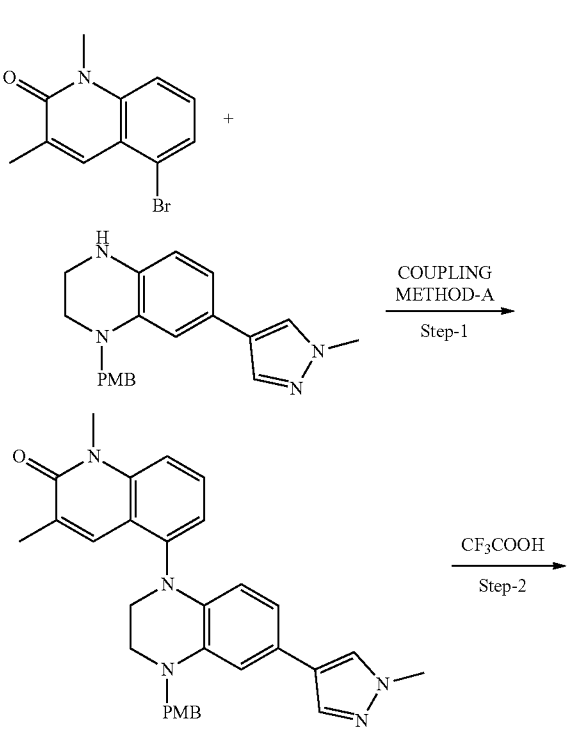

-continued

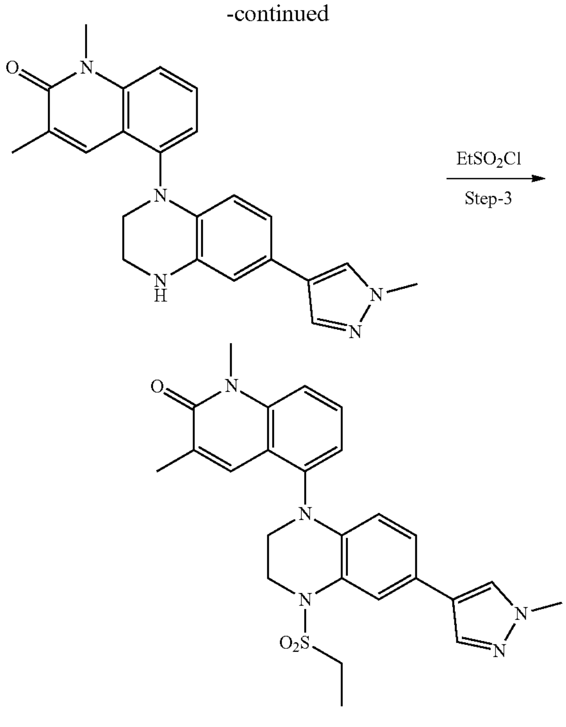

Example-74

Step-1: Synthesis of 5-(4-(4-methoxybenzyl)-6-(1-methyl-1H-pyrazol-4-yl)-3,4-dihydroquinoxalin-1(2H)-yl)-1,3-dimethylquinolin-2(1H)-one This compound was prepared using the similar protocol described in COUPLING METHOD-A using intermediates 5-bromo-1,3-dimethylquinolin-2(1H)-one & 1-(4-methoxybenzyl)-7-(1-methyl-1H-pyrazol-4-yl)-1,2,3,4-tetrahydroquinoxaline with appropriate variations in reactants, quantities of reagents, solvents and reaction conditions. LC-MS: 505.2 $[M+H]^+$.

Step-2: Synthesis of 1,3-dimethyl-5-(6-(1-methyl-1H-pyrazol-4-yl)-3,4-dihydroquinoxalin-1(2H)-yl)quinolin-2(1H)-one This compound was prepared using the similar protocol described in synthesis of Example-63 with appropriate variations in reactants, quantities of reagents, solvents and reaction conditions. LC-MS: 385.2 $[M+H]^+$.

Step-3: Synthesis of 5-(4-(ethylsulfonyl)-6-(1-methyl-1H-pyrazol-4-yl)-3,4-dihydroquinoxalin-1(2H)-yl)-1,3-dimethylquinolin-2(1H)-one A cooled solution of 1,3-dimethyl-5-(6-(1-methyl-1H-pyrazol-4-yl)-3,4-dihydroquinoxalin-1(2H)-yl)quinolin-2(1H)-one (100 mg, 0.25 mmol) and Pyridine (0.05 mL, 0.32 mmol) in Chloroform (4 mL) was added Ethane sulfonyl chloride (0.05 mL, 0.52 mmol) at 0° C. After addition, mixture was heated to reflux for 4 h. Then it was cooled to room temperature and diluted with DCM, washed water, 4N—HCl, organic layer was dried over sodium sulphate and concentrated to dryness to give crude mass. Crude compound was purified by preparative HPLC to give pure title compound (18 mg, 14.5%). LC-MS: 478.1 $[M+H]^+$. 1H-NMR (600 MHz, Chloroform-D) δ 7.65 (s, 1H), 7.62 (s, 1H), 7.59 (s, 1H), 7.55-7.54 (m, 1H), 7.50 (s, 1H), 7.33 (d, J=9 Hz, 1H), 7.24 (s, 2H), 7.091 (d, J=7.2 Hz, 1H), 6.95 (d, J=8.4 Hz, 1H), 6.18 (d, J=8.4 Hz, 1H), 4.09 (brs, 1H), 3.98 (brs, 1H), 3.89 (s, 3H), 3.78 (s, 3H), 3.70 (brs, 2H), 3.25-3.24 (m, 2H), 2.20 (s, 3H), 1.49-1.47 (m, 3H).

Example-75: 4-(1,3-Dimethyl-2-oxo-1,2-dihydroquinolin-5-yl)-N-methyl-7-(1-methyl-1H-pyrazol-4-yl)-3,4-dihydroquinoxaline-1(2H)-carboxamide

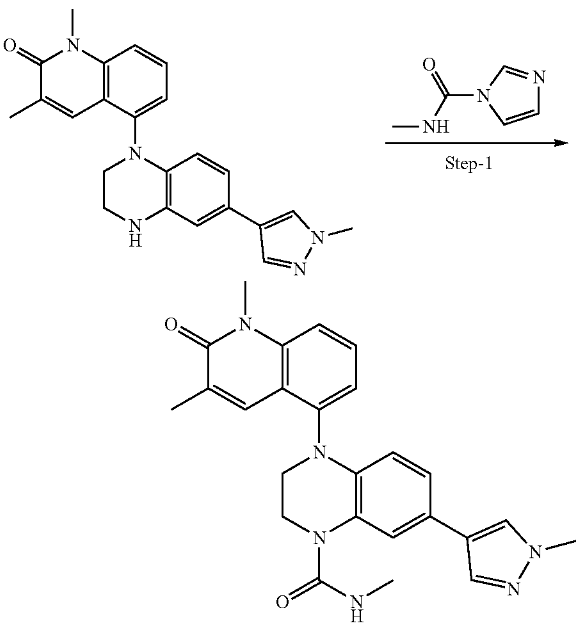

Example-75

This compound was prepared using the similar protocol described in preparation of Example-64 using intermediate 1,3-dimethyl-5-(6-(1-methyl-1H-pyrazol-4-yl)-3,4-dihydroquinoxalin-1(2H)-yl)quinolin-2(1H)-one from Step-2 of Example-74 with appropriate variations in reactants, quantities of reagents, solvents and reaction conditions (18 mg, 17.1%). LC-MS: 443.2 $[M+H]^+$. 1H-NMR (600 MHz, Chloroform-D) δ 7.62 (d, J=4.4 Hz, 1H), 7.56 (t, J=4.3, 4.3 Hz, 1H), 7.50 (s, 1H), 7.48 (s, 1H), 7.33 (t, J=4.3, 4.3 Hz, 2H), 7.14-7.10 (m, 1H), 6.93 (d, J=3.8 Hz, 1H), 6.19-6.17 (m, 1H), 5.44 (d, J=5.4 Hz, 1H), 4.16 (s, 1H), 3.96 (s, 1H), 3.91 (s, 3H), 3.78 (s, 3H), 3.62 (t, J=4.7, 4.7 Hz, 2H), 2.90 (d, J=4.4, 4.4 Hz, 3H), 2.18 (d, J=4.2 Hz, 3H).

Example-76: 1,3-Dimethyl-5-(8-methyl-2-(1-methyl-1H-pyrazol-4-yl)-7,8-dihydropteridin-5(6H)-yl)-7-morpholinoquinolin-2(1H)-one

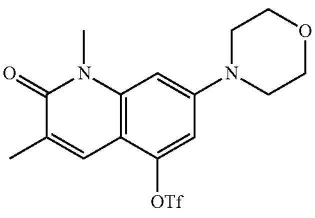

+

-continued

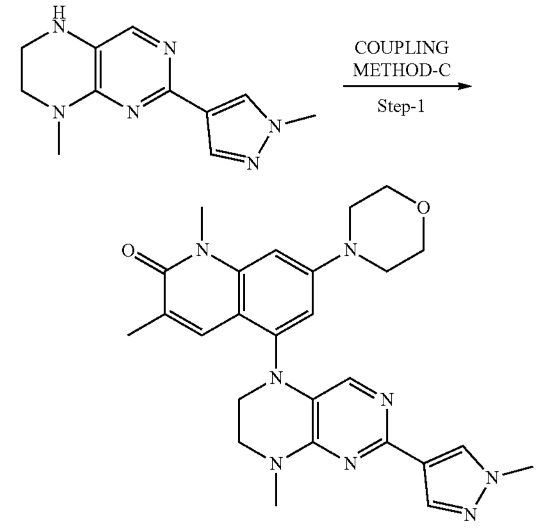

Example-76

This compound was prepared using the similar protocol described in COUPLING METHOD-C using intermediates 1,3-dimethyl-7-morpholino-2-oxo-1,2-dihydroquinolin-5-yl trifluoromethanesulfonate & 8-methyl-2-(1-methyl-1H-pyrazol-4-yl)-5,6,7,8-tetrahydropteridine with appropriate variations in reactants, quantities of reagents, solvents and reaction conditions (40 mg, 19.12%). LC-MS: 487.1 $[M+H]^+$. 1H-NMR (400 MHz, methanol-d4) δ 8.18 (s, 1H), 7.98 (s, 1H), 7.69 (s, 1H), 6.99 (d, J=1.6 Hz, 1H), 6.82 (d, J=1.2 Hz, 1H), 6.60 (s, 1H), 4.05-4.02 (m, 1H), 3.93 (s, 3H), 3.89-3.83 (m, 5H), 3.4 (s, 3H), 3.71 (s, 1H), 3.61-3.58 (s, 1H), 3.41 (s, 3H), 3.35-3.29 (m, 4H), 2.09 (s, 3H).

Example-77: 4-(3-Amino-1-methyl-2-oxo-1,2-dihydroquinolin-5-yl)-1-methyl-7-(1-methyl-1H-pyrazol-4-yl)-1,2,3,4-tetrahydroquinoxaline-6-carbonitrile

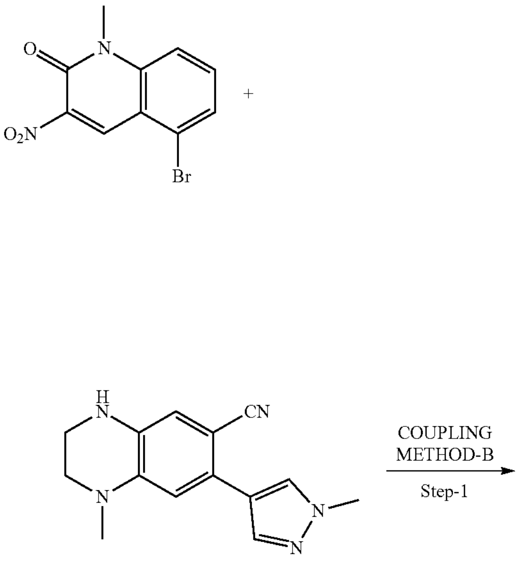

-continued

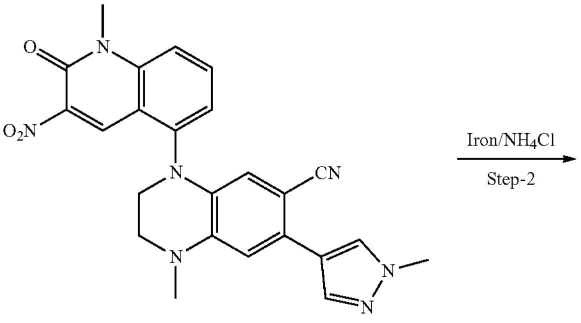

E77a

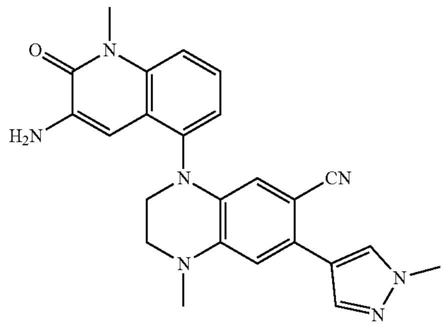

Example-77

Step-1: Synthesis of 1-methyl-7-(1-methyl-1H-pyrazol-4-yl)-4-(1-methyl-3-nitro-2-oxo-1,2-dihydroquinolin-5-yl)-1,2,3,4-tetrahydroquinoxaline-6-carbonitrile This compound was prepared using the similar protocol described in COUPLING METHOD-B using intermediates 5-bromo-1-methyl-3-nitroquinolin-2(1H)-one & 1-methyl-7-(1-methyl-1H-pyrazol-4-yl)-1,2,3,4-tetrahydroquinoxaline-6-carbonitrile with appropriate variations in reactants, quantities of reagents, solvents and reaction conditions. LC-MS: 455.95 $[M+H]^+$.

Step-2: Synthesis of 4-(3-amino-1-methyl-2-oxo-1,2-dihydroquinolin-5-yl)-1-methyl-7-(1-methyl-1H-pyrazol-4-yl)-1,2,3,4-tetrahydroquinoxaline-6-carbonitrile A solution of 1-methyl-7-(1-methyl-1H-pyrazol-4-yl)-4-(1-methyl-3-nitro-2-oxo-1,2-dihydroquinolin-5-yl)-1,2,3,4-tetrahydroquinoxaline-6-carbonitrile (200 mg, 0.43 mmol) in ethanol (6 mL) was added ammonium chloride (70 mg, 1.3 mmol) dissolved in water (2 mL). Then iron (245 mg, 4.3 mmol) was added and heated to 100° C. After heating for 5 h, the reaction mixture was cooled to room temperature extracted with DCM, organic portion was washed with saturated sodium bicarbonate, dried over sodium sulphate and concentrated to dryness to get residue. Residue was purified by flash chromatography using 30-50% ethyl acetate in hexanes as eluent to yield pure title compound (10 mg, 5.3%). LC-MS: 425.95 $[M+H]^+$. 1H-NMR (400 MHz, DMSO-D6) δ 8.06 (d, J=0.7 Hz, 1H), 7.80 (d, J=0.8 Hz, 1H), 7.46-7.32 (m, 3H), 7.17 (dd, J=7.4, 1.3 Hz, 1H), 6.71 (d, J=12.9 Hz, 2H), 5.81 (s, 1H), 5.66 (s, 2H), 3.87 (s, 3H), 3.74 (s, 3H), 3.53 (d, J=8.6 Hz, 2H), 3.16 (s, 1H), 3.07 (s, 3H)

Example-78: 1,3-Dimethyl-5-(4-(tetrahydro-2H-pyran-4-yl)-3,4-dihydroquinoxalin-1(2H)-yl)quinolin-2(1H)-one

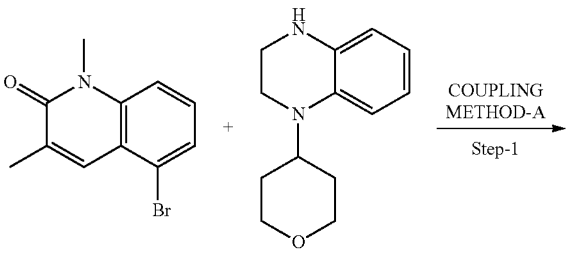

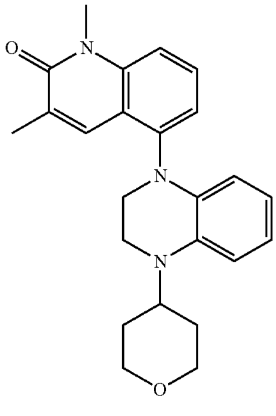

Example-78

This compound was prepared using the similar protocol described in COUPLING METHOD-A using 5-bromo-1,3-dimethylquinolin-2(1H)-one & 1-(tetrahydro-2H-pyran-4-yl)-1,2,3,4-tetrahydroquinoxaline with appropriate variations in reactants, quantities of reagents, solvents and reaction conditions (80 mg, 37.2%). LC-MS: 390 $[M+H]^+$.

Example-79: 5-(7-Acetyl-4-methyl-3,4-dihydroquinoxalin-1(2H)-yl)-7-methoxy-1,3-dimethylquinolin-2(1H)-one

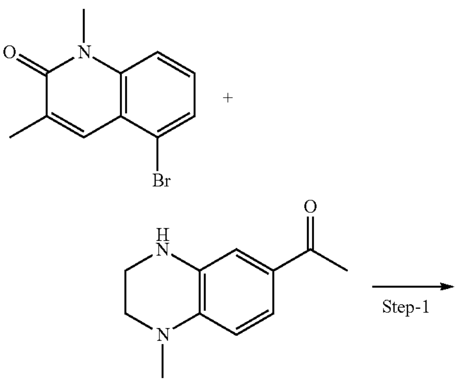

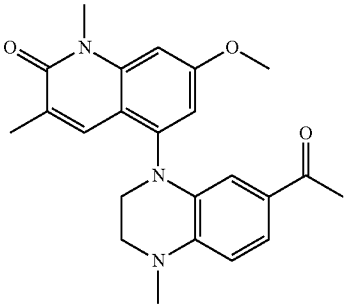

Example-79

A degassed mixture of 5-bromo-1,3-dimethylquinolin-2(1H)-one (200 mg, 0.7 mmol) and 1-(1-methyl-1,2,3,4-tetrahydroquinoxalin-6-yl)ethan-1-one (140 mg, 0.71 mmol) and sodium tert-butoxide (170 mg, 1.77 mmol) in 1,4-Dioxane (5 mL) was added Xantphos (80 mg, 0.014 mmol) and $Pd_2(dba)_3$ (70 mg, 0.07 mmol), heated to 100° C. After 12 h, reaction mass was cooled and diluted with 10% methanol in DCM, filtered through celite bed and concentrated to dryness to get the crude compound. Crude compound was purified by flash chromatography using 70% ethyl acetate in hexane and further purified by preparative HPLC to give pure title compound (200 mg, 71.96%). LC-MS: 392.15 $[M+H]^+$. 1H-NMR (400 MHz, Chloroform-D) δ 7.61 (s, 1H), 7.43-7.40 (m, 1H), 6.77 (d, J=1.6 Hz, 1H), 6.70 (d, J=2.4 Hz, 1H), 6.64 (d, J=2.4 Hz, 1H), 6.62-6.60 (m, 1H), 3.88 (d, J=3.2 Hz, 3H), 3.75 (s, 3H), 3.73 (s, 2H), 3.60 (brs, 1H), 3.49 (brs, 1H), 3.09 (s, 3H), 2.32 (s, 3H), 2.15 (d, J=1.6 Hz, 3H).

The examples 80 & 81 were prepared according to the procedures described in the synthesis of Example-79 with appropriate variations in reactants, quantities of reagents, solvents and reaction conditions and with appropriate coupling methods explained in Example-1, 2 or 3.

| Example | Structure | Coupling Method | Analytical data |
|---|---|---|---|
| 80 | 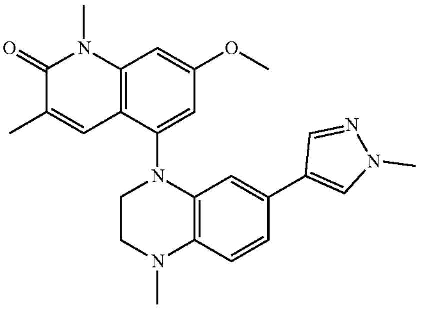 | A | LC-MS: 430.4 [M + H]$^+$; 1H-NMR (300 MHz, Chloroform-D) δ 7.68 (s, 1H), 7.42 (d, J = 0.8 Hz, 1H), 7.22 (s, 1H), 6.85 (dd, J = 8.2, 1.9 Hz, 1H), 6.75-6.70 (m, 2H), 6.68 (d, J = 8.3 Hz, 1H), 6.22 (d, J = 2.1 Hz, 1H), 3.86 (s, 3H), 3.82 (s, 3H), 3.76 (s, 3H), 3.65 (s, 1H), 3.52 (s, 1H), 3.35 (s, 2H), 2.99 (s, 3H), 2.18 (d, J = 1.2 Hz, 3H). |
| 81 | 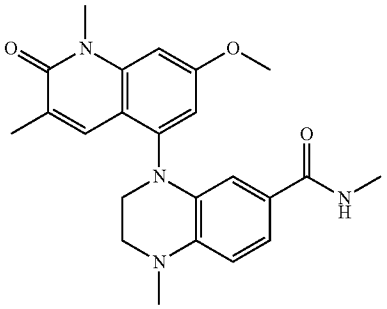 | A | LC-MS: 407.2 [M + H]$^+$; 1H-NMR (400 MHz, Chloroform-D) δ 7.61-7.58 (m, 1H), 7.15 (dd, J = 8.4, 2.1 Hz, 1H), 6.69-6.65 (m, 2H), 6.61 (d, J = 8.4 Hz, 1H), 6.55 (s, 1H), 5.76 (d, J = 5.6 Hz, 1H), 3.86 (s, 3H), 3.76 (s, 1H), 3.73 (s, 3H), 3.61 (s, 2H), 3.41 (s, 1H), 3.04 (s, 3H), 2.84 (d, J = 4.8 Hz, 3H), 2.15 (d, J = 1.2 Hz, 3H). |

Example-82: 2-((5-(7-Cyano-4-methyl-3,4-dihydroquinoxalin-1(2H)-yl)-1,3-dimethyl-2-oxo-1,2-dihydroquinolin-7-yl)oxy)acetic acid

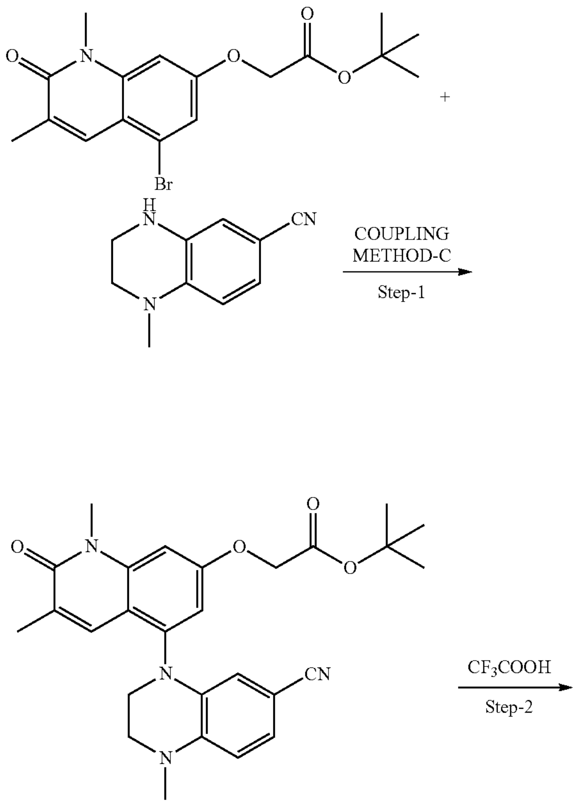

-continued

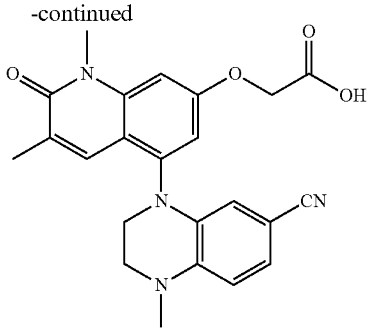

Example-82

Step-1: Synthesis of tert-butyl 2-((5-(7-cyano-4-methyl-3,4-dihydroquinoxalin-1(2H)-yl)-1,3-dimethyl-2-oxo-1,2-dihydroquinolin-7-yl)oxy)acetate This compound was prepared using the similar protocol described in COUPLING METHOD-A using intermediates tert-butyl 2-((5-bromo-1,3-dimethyl-2-oxo-1,2-dihydroquinolin-7-yl)oxy)acetate & 1-methyl-1,2,3,4-tetrahydroquinoxaline-6-carbonitrile with appropriate variations in reactants, quantities of reagents, solvents and reaction conditions. LC-MS: 475.4 [M+H]$^+$.

Step-2: Synthesis of 2-((5-(7-cyano-4-methyl-3,4-dihydroquinoxalin-1(2H)-yl)-1,3-dimethyl-2-oxo-1,2-dihydroquinolin-7-yl)oxy)acetic acid This compound was prepared using the similar protocol described in the synthesis of Example-69 with appropriate variations in reactants, quantities of reagents, solvents and reaction conditions (30 mg, 67.8%). LC-MS: 419.4 [M+H]$^+$;

1H-NMR (600 MHz, Chloroform-D) δ 13.05 (s, 1H), 7.56 (s, 1H), 7.04 (dd, J=1.8, 8.4 Hz, 1H), 6.94 (s, 1H), 6.86 (d, J=2.4 Hz, 1H), 6.65 (d, J=8.4 Hz, 1H), 5.91 (d, J=1.8 Hz, 1H), 4.85 (s, 2H), 3.78-3.70 (m, 2H), 3.64 (s, 3H), 3.51-3.45 (m, 3H), 3.01 (s, 3H), 2.03 (s, 3H).

Example-83: N-hydroxy-2-(4-(7-methoxy-1,3-dimethyl-2-oxo-1,2-dihydroquinolin-5-yl)-1-methyl-1,2,3,4-tetrahydroquinoxalin-6-yl)acetamide

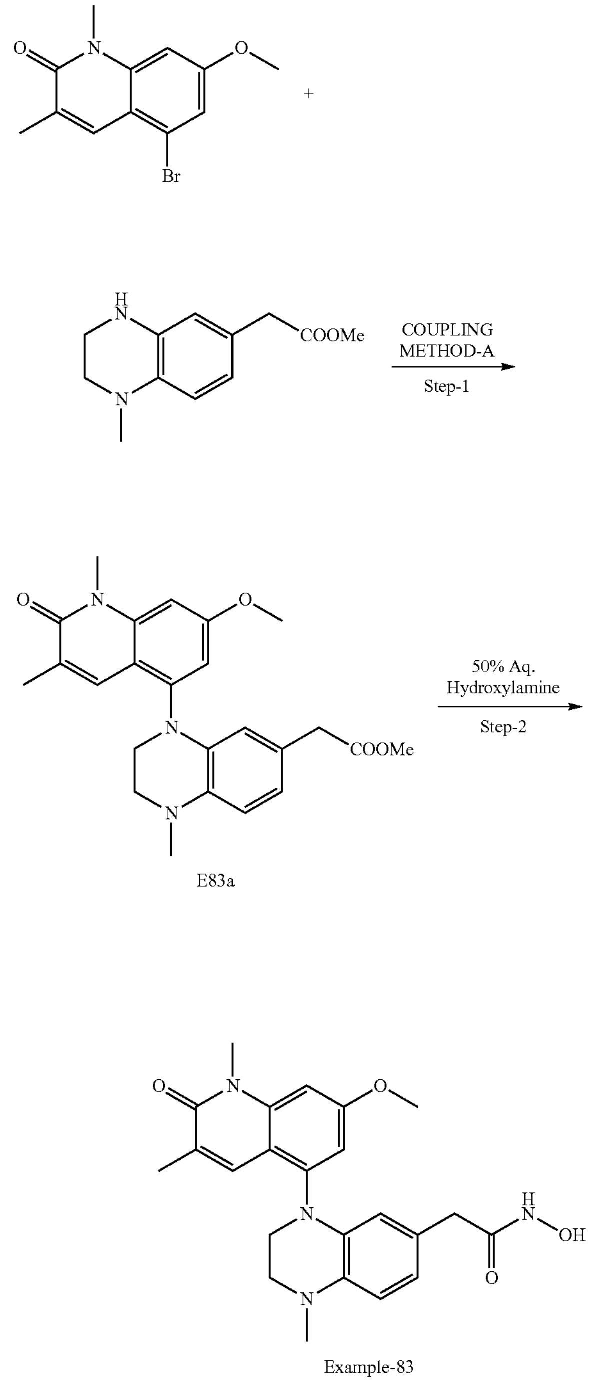

E83a

Example-83

Step-1: Synthesis of tert-butyl 2-((5-(7-cyano-4-methyl-3,4-dihydroquinoxalin-1(2H)-yl)-1,3-dimethyl-2-oxo-1,2-dihydroquinolin-7-yl)oxy)acetate This compound was prepared using the similar protocol described in COUPLING METHOD-A using intermediates 5-bromo-7-methoxy-1,3-dimethylquinolin-2(1H)-one & methyl 2-(1-methyl-1,2,3,4-tetrahydroquinoxalin-6-yl)acetate with appropriate variations in reactants, quantities of reagents, solvents and reaction conditions. LC-MS: 422.2 $[M+H]^+$.

Step-2: Synthesis of N-hydroxy-2-(4-(7-methoxy-1,3-dimethyl-2-oxo-1,2-dihydroquinolin-5-yl)-1-methyl-1,2,3,4-tetrahydroquinoxalin-6-yl)acetamide A stirred solution of E83a (200 mg, 0.47 mmol) was added sodium methoxide (130 mg, 2.3 mmol) and 50% aq. hydroxylamine (4.7 mmol) stirred at room temperature for 2 h. Then reaction mixture was acidified with 1N HCl and diluted with 10% methanol in chloroform. Organic portion was dried over sodium sulphate and concentrated to get the crude compound. This was purified by preparative HPLC to give pure title compound (170 mg, 85.6%). LC-MS: 421.2 $[M+H]^+$. 1H-NMR (400 MHz, Chloroform-D) δ 7.56 (s, 1H), 6.70-6.68 (m, 2H), 6.59-6.58 (m, 2H), 5.94 (s, 1H), 3.87 (s, 3H), 3.75 (brs, 1H), 3.73 (s, 3H), 3.65 (brs, 1H), 3.58-3.52 (m, 1H), 3.35 (brs, 1H), 3.26 (s, 2H), 2.97 (s, 3H), 2.16 (s, 3H).

Example-84: 7-Methoxy-1,3-dimethyl-5-(4-methyl-7-(2H-tetrazol-5-yl)-3,4-dihydroquinoxalin-1(2H)-yl)quinolin-2(1H)-one

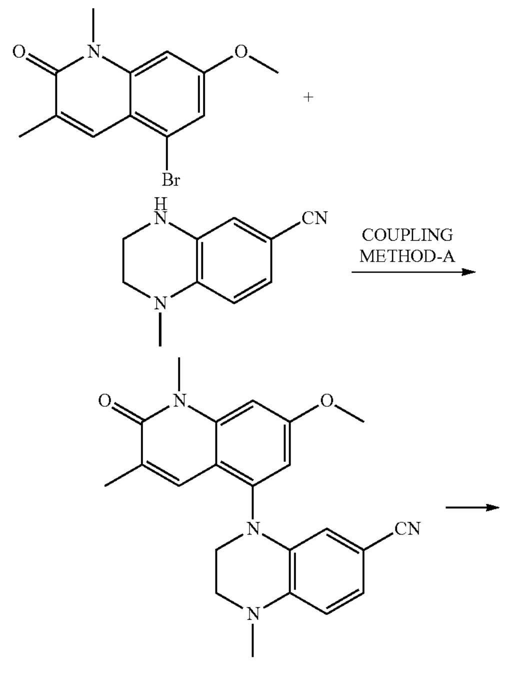

E84a

-continued

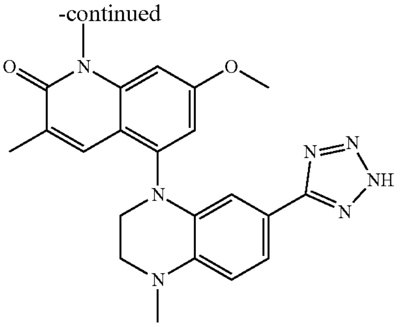

Example-84

Step-1: Synthesis of 4-(7-methoxy-1,3-dimethyl-2-oxo-1,2-dihydroquinolin-5-yl)-1-methyl-1,2,3,4-tetrahydroquinoxaline-6-carbonitrile This compound was prepared using the similar protocol described in COUPLING METHOD-A using 5-bromo-7-methoxy-1,3-dimethylquinolin-2(1H)-one & 1-methyl-1,2,3,4-tetrahydroquinoxaline-6-carbonitrile with appropriate variations in reactants, quantities of reagents, solvents and reaction conditions. LC-MS: 422.2 [M+H]+.

Step-2: Synthesis of 7-methoxy-1,3-dimethyl-5-(4-methyl-7-(2H-tetrazol-5-yl)-3,4-dihydroquinoxalin-1(2H)-yl)quinolin-2(1H)-one A solution of E84a (100 mg, 0.26 mmol) in toluene (4 mL) was added trimethylsillylazide (46 mg, 0.4 mmol) and dibutyltin oxide and heated to 120° C. for 24 h. The reaction mixture was cooled to room temperature, extracted with ethyl acetate, organic portion was dried over sodium sulphate and concentrated to get residue. The residue was purified by flash chromatography using 20-50% ethyl acetate in hexanes as eluent to give pore title compound (70 mg, 62.8%). LC-MS: 417.75 $[M+H]^+$; 1H-NMR (400 MHz, Chloroform-D) δ 7.75 (d, J=6.4 Hz, 1H), 7.68 (d, J=1.2 Hz, 1H), 7.27-7.26 (m, 1H), 6.78 (d, J=2.3 Hz, 2H), 6.63 (d, J=2.2 Hz, 1H), 3.85 (s, 3H), 3.63-3.58 (m, 3H), 3.39 (s, 4H), 3.08 (s, 3H), 1.89 (d, J=1.2 Hz, 3H).

Example-85: 4-(1,3-dimethyl-2-oxo-1,2-dihydroquinolin-5-yl)-1-methyl-1,2,3,4-tetrahydroquinoxaline-6-sulfonamide

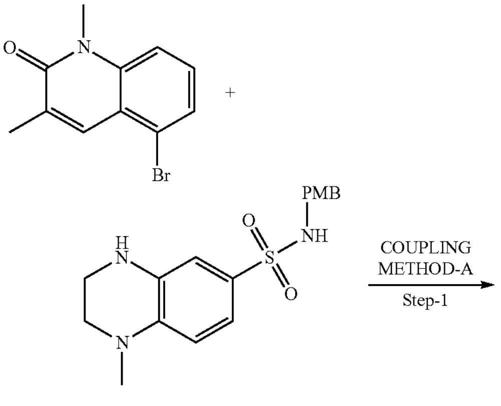

-continued

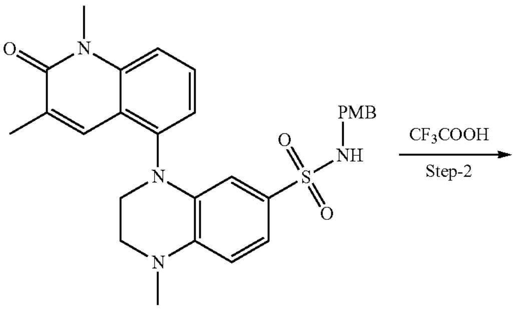

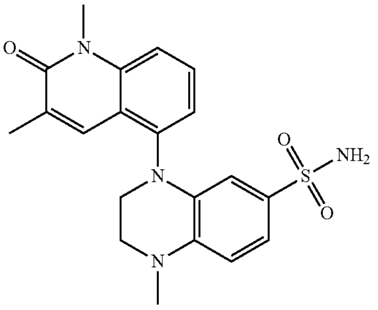

Example-85

Step-1: Synthesis of 4-(1,3-dimethyl-2-oxo-1,2-dihydroquinolin-5-yl)-N-(4-methoxybenzyl)-1-methyl-1,2,3,4-tetrahydroquinoxaline-6-sulfonamide This compound was prepared using the similar protocol described in COUPLING METHOD-A using intermediates 5-bromo-1,3-dimethylquinolin-2(1H)-one & N-(4-methoxybenzyl)-1-methyl-1,2,3,4-tetrahydroquinoxaline-6-sulfonamide with appropriate variations in reactants, quantities of reagents, solvents and reaction conditions. LC-MS: 519.6 [M+H]+.

Step-2: Synthesis of 4-(1,3-dimethyl-2-oxo-1,2-dihydroquinolin-5-yl)-1-methyl-1,2,3,4-tetrahydroquinoxaline-6-sulfonamide A solution of compound 4-(1,3-dimethyl-2-oxo-1,2-dihydroquinolin-5-yl)-N-(4-methoxybenzyl)-1-methyl-1,2,3,4-tetrahydroquinoxaline-6-sulfonamide (120 mg, 0.23 mmol) in trifluoroacetic acid (3 mL), heated to 100° C. After heating for 2 h, solvent evaporated completely to get residue and residue. The residue was purified by preparative HPLC to get pure title compound. LC-MS: 398.2 $[M+H]^+$; 1H-NMR (400 MHz, Chloroform-D) δ 7.66 (d, J=1.2 Hz, 1H), 7.57-7.53 (m, 1H), 7.30 (dd, J=8.5, 2.2 Hz, 2H), 7.10-7.07 (m, 1H), 6.63 (d, J=8.6 Hz, 1H), 6.52 (d, J=2.2 Hz, 1H), 4.44 (s, 2H), 3.78 (s, 4H), 3.72 (s, 1H), 3.63-3.59 (m, 1H), 3.47 (d, J=3.3 Hz, 1H), 3.08 (s, 3H), 2.21 (d, J=1.2 Hz, 3H).

The below examples (86-90) were prepared according to the protocols described in the synthesis of Example-85 with appropriate variations in reactants, quantities of reagents, solvents and reaction conditions with appropriate coupling methods.

| Example | Structure | Coupling Method | Analytical data |
|---|---|---|---|
| 86 | 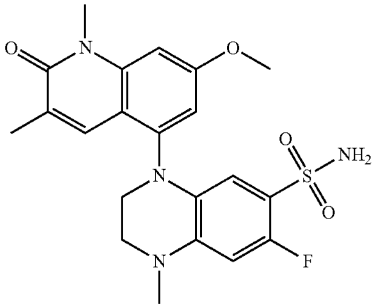 [SMILES: COc1cc(N2CCN(C)c3cc(F)c(S(N)(=O)=O)cc32)c2cc(C)c(=O)n(C)c2c1] | A | LC-MS: 446.8 [M + H]$^+$; 1H-NMR (400 MHz, Chloroform-D) δ 7.57 (t, J = 1.0, 1.0 Hz, 1H), 6.68 (s, 1H), 6.57 (d, J = 2.3 Hz, 1H), 6.52 (d, J = 7.2 Hz, 1H), 6.39 (d, J = 12.9 Hz, 1H), 3.88 (s, 3H), 3.74 (s, 3H), 3.69 (d, J = 7.1 Hz, 2H), 3.46 (s, 2H), 2.18 (d, J = 1.2 Hz, 3H), 1.58 (s, 3H). |
| 87 | 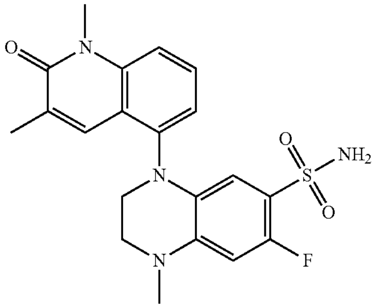 [SMILES: Cc1cc2c(N3CCN(C)c4cc(F)c(S(N)(=O)=O)cc43)cccc2n(C)c1=O] | A | LC-MS: 417.2 [M + H]$^+$; 1H-NMR (400 MHz, Chloroform-D) δ 7.68-7.68 (m, 1H), 7.52 (d, J = 0.7 Hz, 1H), 7.25 (d, J = 0.8 Hz, 1H), 7.00 (dd, J = 7.8, 0.9 Hz, 1H), 6.48 (d, J = 7.3 Hz, 1H), 6.40 (d, J = 12.9 Hz, 1H), 3.48-3.43 (m, 2H), 4.75 (d, J = 7.5 Hz, 3H), 3.78 (s, 2H), 3.71 (d, J = 8.8 Hz, 1H), 3.56 (s, 1H), 3.06 (s, 3H), 2.23 (d, J = 1.2 Hz, 3H). |
| 88 | 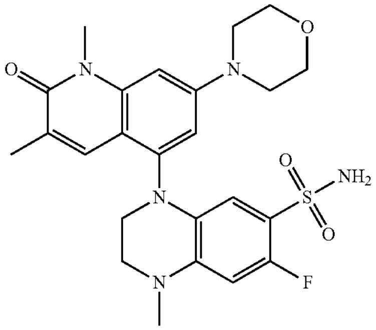 [SMILES: Cc1cc2c(N3CCN(C)c4cc(F)c(S(N)(=O)=O)cc43)cc(N3CCOCC3)cc2n(C)c1=O] | B | LC-MS: 501.8 [M + H]$^+$; 1H-NMR (400 MHz, DMSO-d6) δ 7.51 (s, 1H), 7.04 (s, 2H), 6.7 (s, 1H), 6.51 (d, J = 12.8 Hz, 1H), 6.14 (d, J = 7.6 Hz, 1H), 3.72 (brs, 5H), 3.63 (s, 3H), 3.39 (m, 1H), 3.38 (brs, 2H), 3.35 (brs, 4H), 2.97 (s, 2H), 2.00 (s, 5H). |
| 89 | 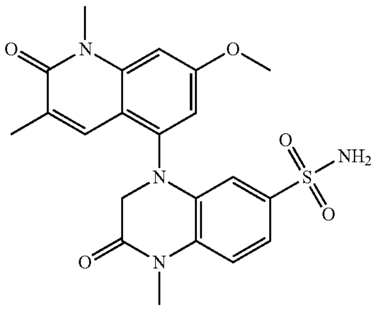 [SMILES: COc1cc(N2CC(=O)N(C)c3ccc(S(N)(=O)=O)cc32)c2cc(C)c(=O)n(C)c2c1] | C | LC-MS: 443.2 [M + H]$^+$; 1H-NMR (600 MHz, DMSO-D6) δ 7.51 (s, 1H), 7.32 (s, 2H), 7.17 (s, 2H), 7.00 (d, J = 16.0 Hz, 2H), 6.45 (s, 1H), 4.57 (d, J = 15.2 Hz, 1H), 4.07 (d, J = 15.3 Hz, 1H), 3.93 (s, 3H), 3.69 (s, 3H), 3.42 (s, 3H), 1.98 (s, 3H). |

-continued

| Example | Structure | Coupling Method | Analytical data |
|---|---|---|---|
| 90 | 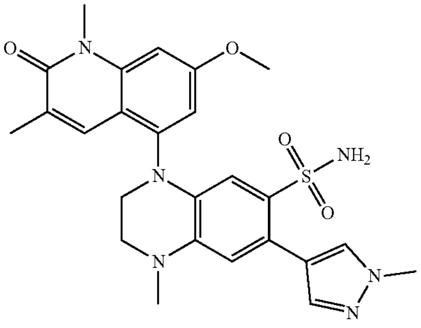 | C | LC-MS: 509.2 [M + H]$^+$; 1H-NMR (300 MHz, DMSO-D6) δ 7.84 (s, 1H), 7.65 (m, 1H), 7.60 (s, 1H), 6.9 (s, 1H), 6.79 (d, J = 1.8 Hz, 1H), 6.58 (s, 1H), 6.51 (s, 1H), 6.47 (s, 2H), 3.89 (s, 3H), 3.83 (s, 3H), 3.68 (m, 5H), 3.59-3.5 (m, 1H), 3.45 (brs, 1H), 2.99 (s, 3H), 2.07 (s, 3H). |

Example-91: 7-(4,5-Dihydroisoxazol-5-yl)-4-(7-methoxy-1,3-dimethyl-2-oxo-1,2-dihydroquinolin-5-yl)-1-methyl-1,2,3,4-tetrahydroquinoxaline-6-sulfonamide

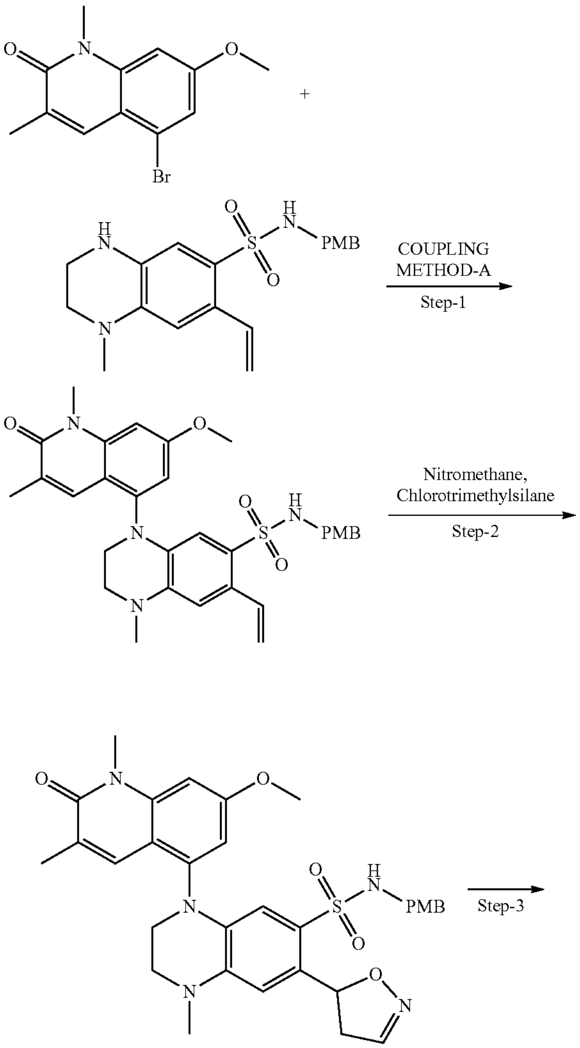

-continued

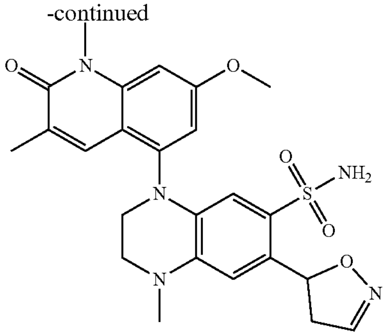

Example-91

Step-1: Synthesis of 4-(7-methoxy-1,3-dimethyl-2-oxo-1,2-dihydroquinolin-5-yl)-N-(4-methoxybenzyl)-1-methyl-7-vinyl-1,2,3,4-tetrahydroquinoxaline-6-sulfonamide This compound was prepared using the similar protocol described in COUPLING METHOD-A using intermediates 5-bromo-7-methoxy-1,3-dimethylquinolin-2(1H)-one & N-(4-methoxybenzyl)-1-methyl-7-vinyl-1,2,3,4-tetrahydroquinoxaline-6-sulfonamide with appropriate variations in reactants, quantities of reagents, solvents and reaction conditions. LC-MS: 575.6 [M+H]$^+$.

Step-2: Synthesis of 7-(4,5-dihydroisoxazol-5-yl)-4-(7-methoxy-1,3-dimethyl-2-oxo-1,2-dihydroquinolin-5-yl)-N-(4-methoxybenzyl)-1-methyl-1,2,3,4-tetrahydroquinoxaline-6-sulfonamide A mixture of compound 4-(7-methoxy-1,3-dimethyl-2-oxo-1,2-dihydroquinolin-5-yl)-N-(4-methoxybenzyl)-1-methyl-7-vinyl-1,2,3,4-tetrahydroquinoxaline-6-sulfonamide (20 mg, 0.03 mmol), nitromethane (10 mg, 0.12 mmol) and chlorotrimethylsilane in toluene and stirred at room temperature. After 48 h, solvent concentrated to get residue. The residue was purified by preparative TLC to get the pure title compound (10 mg, 53.9%).

Step-3: Synthesis of 7-(4,5-dihydroisoxazol-5-yl)-4-(7-methoxy-1,3-dimethyl-2-oxo-1,2-dihydroquinolin-5-yl)-1-methyl-1,2,3,4-tetrahydroquinoxaline-6-sulfonamide This compound was prepared using the similar protocol described in the synthesis of Example-69 with appropriate variations in reactants, quantities of reagents, solvents and reaction conditions (10 mg, 12.56%). LC-MS: 498.3 $[M+H]^+$; 1H-NMR (400 MHz, Chloroform-D) δ 7.52 (s, 1H), 7.24 (s, 1H), 6.71 (s, 2H), 6.64 (s, 1H), 4.65-4.60 (m, 2H), 3.88 (s, 3H), 3.74 (s, 4H), 3.57-3.44 (m, 4H), 3.07 (s, 3H), 2.17 (s, 3H).

Example-92: (R)-4-(7-(3-Hydroxypyrrolidin-1-yl)-1,3-dimethyl-2-oxo-1,2-dihydroquinolin-5-yl)-1-methyl-1,2,3,4-tetrahydroquinoxaline-6-sulfonamide

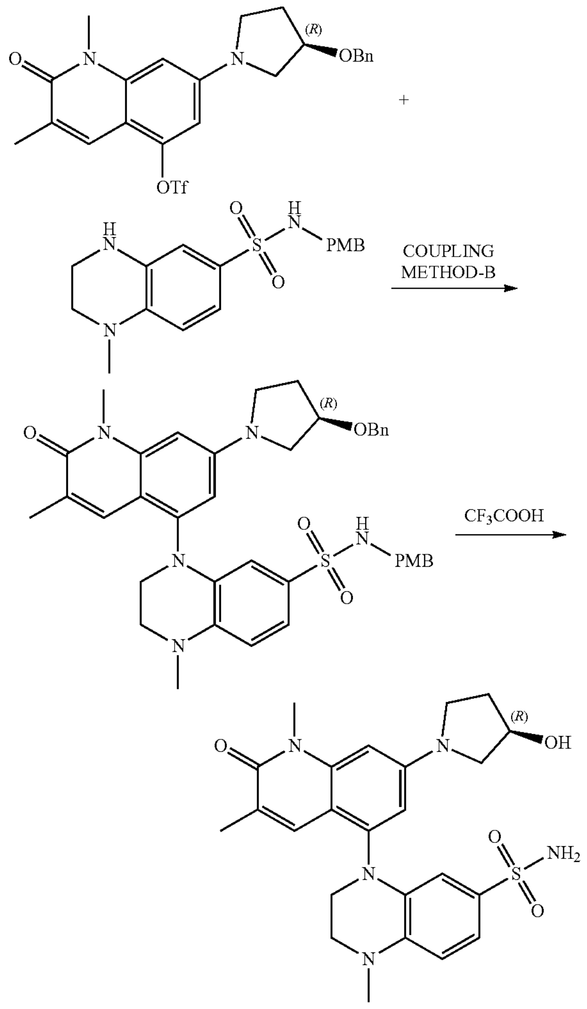

Example-92

Step-1: Synthesis of (R)-4-(7-(3-(benzyloxy)pyrrolidin-1-yl)-1,3-dimethyl-2-oxo-1,2-dihydroquinolin-5-yl)-N-(4-methoxybenzyl)-1-methyl-1,2,3,4-tetrahydroquinoxaline-6-sulfonamide This compound was prepared using the similar protocol described in COUPLING METHOD-A using (R)-7-(3-(benzyloxy)pyrrolidin-1-yl)-1,3-dimethyl-2-oxo-1,2-dihydroquinolin-5-yl trifluoromethanesulfonate & N-(4-methoxybenzyl)-1-methyl-1,2,3,4-tetrahydroquinoxaline-6-sulfonamide with appropriate variations in reactants, quantities of reagents, solvents and reaction conditions. LC-MS: 575.6 $[M+H]^+$.

Step-2: Synthesis of (R)-4-(7-(3-hydroxypyrrolidin-1-yl)-1,3-dimethyl-2-oxo-1,2-dihydroquinolin-5-yl)-1-methyl-1,2,3,4-tetrahydroquinoxaline-6-sulfonamide This compound was prepared using the similar protocol described in synthesis of Example-63 with appropriate variations in reactants, quantities of reagents, solvents and reaction conditions (30 mg, 38.77%). LC-MS: 484.2 $[M+H]^+$. 1H-NMR (400 MHz, DMSO-D6) δ 7.46 (d, J=1.4 Hz, 1H), 7.07-7.04 (m, 1H), 6.83 (s, 2H), 6.65 (d, J=8.5 Hz, 1H), 6.43 (d, J=2.1 Hz, 1H), 6.34 (d, J=5.0 Hz, 1H), 6.27 (s, 1H), 5.03 (s, 1H), 4.42 (s, 1H), 3.79 (d, J=3.4 Hz, 1H), 3.63 (s, 4H), 3.55-3.40 (m, 5H), 3.18 (d, J=8.0 Hz, 1H), 2.98 (s, 3H), 2.09-2.06 (m, 1H), 1.99 (d, J=1.2 Hz, 3H), 1.93-1.91 (m, 1H).

Example-93: 4-(7-Methoxy-1,3-dimethyl-2-oxo-1,2-dihydroquinolin-5-yl)-N,N,1-trimethyl-1,2,3,4-tetrahydroquinoxaline-6-sulfonamide

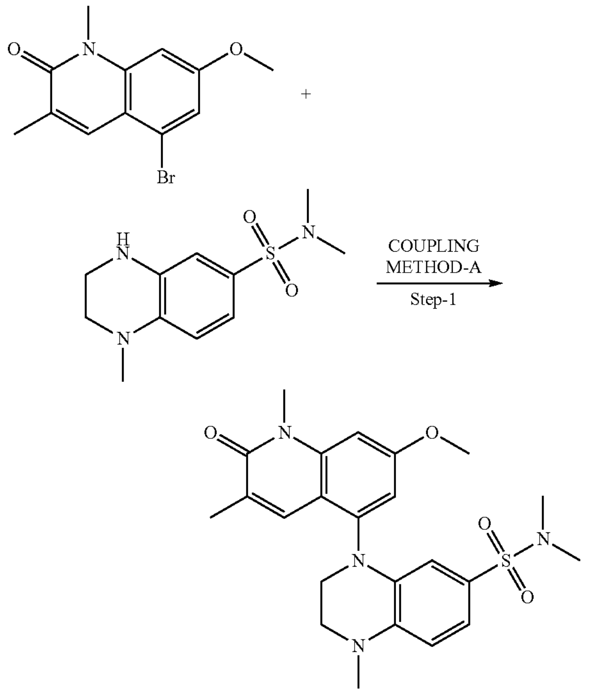

Example-93

Step-1: Synthesis of 4-(7-methoxy-1,3-dimethyl-2-oxo-1,2-dihydroquinolin-5-yl)-N,N,1-trimethyl-1,2,3,4-tetrahydroquinoxaline-6-sulfonamide A solution of N,N,1-trimethyl-1,2,3,4-tetrahydroquinoxaline-6-sulfonamide (100 mg, 0.39 mmol) and 5-bromo-7-methoxy-1,3-dimethylquinolin-2(1H)-one (140 mg, 0.47 mmol) in 1,4-Dioxane (5 mL) was added $Pd_2(dba)_3$ (35 mg, 0.039 mmol), Xantphos (22 mg, 0.039 mmol) and Sodium tert-butoxide (120 mg, 1.17 mmol). The mixture was stirred at 100° C. for overnight. The mixture was cooled to RT, added water and extracted with ethyl acetate. Organic extracts were washed with brine, dried over Sodium sulphate and concentrated to get the residue. The residue was purified by preparative HPLC to afford pure compound (7 mg, 4.3%). LC-MS: 457.3 [M+H]$^+$; 1H-NMR (400 MHz, Chloroform-D) δ 7.54 (s, 1H), 7.17-7.14 (m, 1H), 6.65 (d, J=1.9 Hz, 3H), 6.43 (d, J=2.2 Hz, 1H), 3.89 (s, 3H), 3.48-3.45 (m, 3H), 3.75 (s, 2H), 3.62 (d, J=10.3 Hz, 2H), 3.08 (s, 3H), 2.46 (s, 6H), 2.13 (s, 3H).

The examples (94-102) were prepared according to the protocols described in the synthesis of Example-93 with appropriate variations in reactants, quantities of reagents, solvents and reaction conditions with appropriate coupling methods.

| Example | Structure | Coupling Method | Analytical data |
|---|---|---|---|
| 94 | 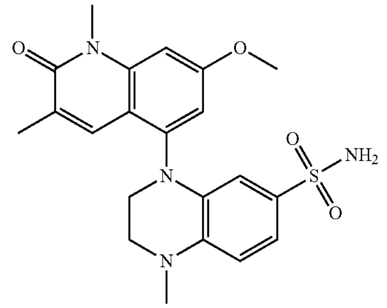 [SMILES: COc1cc(N2CCN(C)c3ccc(S(N)(=O)=O)cc32)c2cc(C)c(=O)n(C)c2c1] | A | LC-MS: 429.1 [M + H]$^+$; 1H-NMR (400 MHZ, Chloroform-D) δ 7.55 (s, 1H), 7.30 (dd, J = 8.5, 2.2 Hz, 1H), 6.72 (d, J = 2.2 Hz, 1H), 6.67 (d, J = 2.2 Hz, 1H), 6.62 (d, J = 8.6 Hz, 1H), 6.57 (s, 1H), 4.47 (s, 2H), 3.89 (s, 3H), 3.78 (s, 1H), 3.74 (s, 3H), 3.71-3.69 (m, 1H), 3.61 (t, J = 7.6, 7.6 Hz, 1H), 3.45 (d, J = 10.6 Hz, 1H), 3.07 (s, 3H), 2.16 (d, J = 1.2 Hz, 3H). |
| 95 | 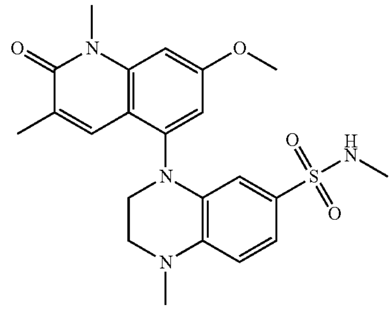 | A | LC-MS: 442.9 [M + H]$^+$; 1H-NMR (400 MHZ, DMSO-d6) δ 7.55 (s, 1H), 7.04-7.02 (m, 1H), 6.91-6.83 (m, 2H), 6.83 (d, J = 2Hz, 1H), 6.70-6.67 (m, 1H), 6.24 (d, J = 2.4 Hz, 1H), 3.88 (s, 3H), 3.85-3.75 (m, 1H), 3.67 (s, 4H), 3.58-3.56 (m, 1H), 3.48-3.47 (m, 1H), 3.00 (s, 3H), 2.15 (d, J = 5.2 Hz, 3H), 2.00 (s, 3H). |
| 96 | 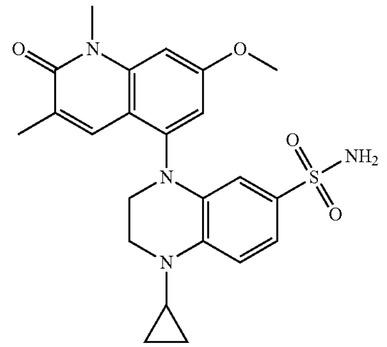 [SMILES: COc1cc(N2CCN(C3CC3)c3ccc(S(N)(=O)=O)cc32)c2cc(C)c(=O)n(C)c2c1] | A | LC-MS: 455.1 [M + H]$^+$; 1H-NMR (600 MHz, Chloroform-D) δ 7.51 (s, 1H), 7.30 (d, J = 2.2 Hz, 1H), 7.21 (d, J = 8.7 Hz, 1H), 6.73 (d, J = 2.6 Hz, 1H), 6.68 (d, J = 2.6 Hz, 1H), 6.56 (d, J = 2.5 Hz, 1H), 4.44 (s, 2H), 3.88 (d, J = 2.7 Hz, 3H), 2.51-2.49 (m, 1H), 3.75 (d, J = 2.6 Hz, 3H), 3.67 (d, J = 32.8 Hz, 2H), 3.59 (s, 1H), 3.50 (d, J = 7.8 Hz, 1H), 2.17 (s, 3H), 0.96 (s, 2H), 0.71 (d, J = 33.7 Hz, 2H). |
| 97 | 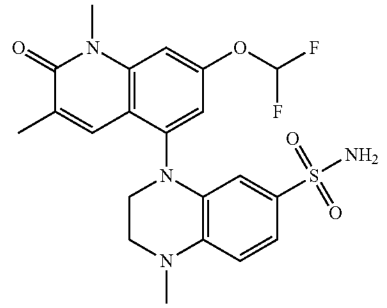 [SMILES: Cc1cc2c(N3CCN(C)c4ccc(S(N)(=O)=O)cc43)cc(OC(F)F)cc2n(C)c1=O] | A | LC-MS: 464.9 [M + H]$^+$; 1H-NMR (400 MHZ, DMSO-D6) δ 9.88 (s, 1H), 7.72 (s, 1H), 7.08 (d, J = 15.6 Hz, 1H), 6.75 (t, J = 2.7, 2.7 Hz, 1H), 6.68 (d, J = 2.3 Hz, 1H), 6.41 (d, J = 8.5 Hz, 1H), 5.96 (s, 1H), 3.58 (s, 3H), 3.45 (dt, J = 26.6, 5.2, 5.2 Hz, 2H), 3.24 (q, J = 4.1, 4.1, 3.3 Hz, 4H), 2.82 (s, 3H), 2.05-2.00 (m, 3H). |

-continued

| Example | Structure | Coupling Method | Analytical data |
|---|---|---|---|
| 98 | 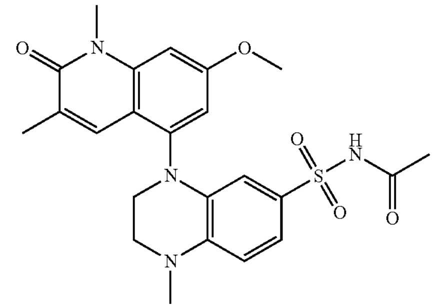 [SMILES: COc1cc(N2CCN(C)c3ccc(S(=O)(=O)NC(C)=O)cc32)c2cc(C)c(=O)n(C)c2c1] | A | LC-MS: 471.1 [M + H]$^+$; 1H-NMR (400 MHZ, Chloroform-D) δ 8.10 (s, 1H), 7.52 (s, 1H), 7.44 (d, J = 2.3 Hz, 1H), 6.71-6.55 (m, 4H), 3.90 (s, 3H), 3.78 (dd, J = 8.1, 4.4 Hz, 2H), 3.69 (s, 3H), 3.62-3.59 (m, 1H), 3.48 (s, 1H), 3.09 (s, 3H), 2.13 (d, J = 1.3 Hz, 3H), 1.94 (s, 3H). |
| 99 | 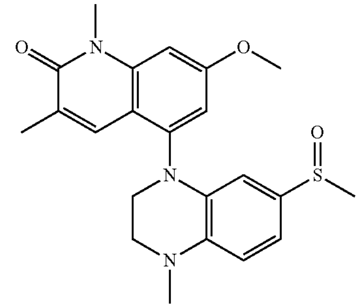 | B | LC-MS: 412.2 [M + H]$^+$; 1H-NMR (400 MHZ, Chloroform-D) δ 7.54 (s, 1H), 7.09-6.9 (m, 1H), 6.71-6.67 (m, 2H), 6.33 (s, 1H), 6.25 (s, 1H), 3.88 (s, 3H), 3.75 (brs, 1H), 3.74 (s, 3H), 3.70-3.59 (m, 2H), 3.45 (brs, 1H), 3.04 (s, 3H), 2.50-2.46 (m, 3H), 2.14 (s, 3H). |
| 100 | 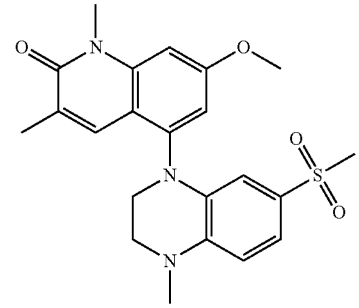 | A | LC-MS: 427.8 [M + H]$^+$; 1H-NMR (400 MHZ, Chloroform-D) δ 7.52 (s, 1H), 7.31-7.29 (m, 1H), 6.72 (d, J = 2Hz, 1H), 6.66-6.64 (m, 2H), 6.55 (d, J = 2.4 Hz, 1H), 3.89 (s, 3H), 3.77-3.75 (m, 4H), 3.24-3.20 (m, 1H), 3.49-3.47 (m, 1H), 3.09 (s, 1H), 3.81 (s, 3H), 2.81 (s, 3H), 2.15 (s, 3H). |
| 101 | 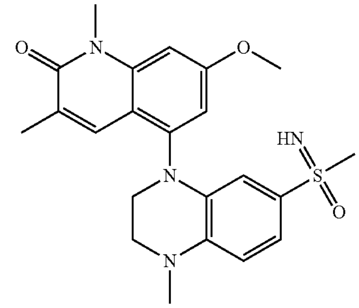 | A | LC-MS: 427 [M + H]$^+$; 1H-NMR (400 MHz, DMSO-D6) δ 8.18 (d, J = 1.4 Hz, 1H), 6.95 (d, J = 2.3 Hz, 1H), 6.84 (s, 1H), 6.50 (d, J = 8.5 Hz, 1H), 6.37 (d, J = 2.1 Hz, 1H), 6.26 (d, J = 2.2 Hz, 1H), 6.02 (s, 1H), 3.70 (s, 3H), 3.56 (s, 3H), 3.33 (s, 3H), 3.25 (tt, J = 4.8, 4.8, 2.4, 2.4 Hz, 4H), 2.84 (s, 3H), 2.12 (d, J = 1.2 Hz, 3H). |
| 102 | 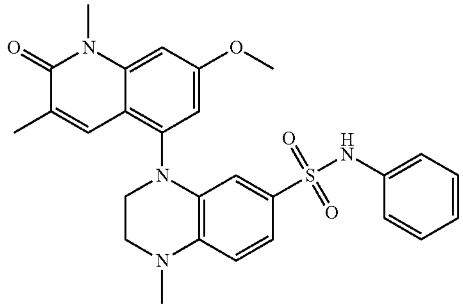 [SMILES: COc1cc(N2CCN(C)c3ccc(S(=O)(=O)Nc4ccccc4)cc32)c2cc(C)c(=O)n(C)c2c1] | B | LC-MS: 505.3 [M + H]$^+$; 1H-NMR (400 MHZ, Chloroform-D) δ 7.447 (s, 1H), 7.16-7.0 (m, 3H), 6.89 (s, 1H), 6.89-6.87 (m, 2H), 6.7 (d, J = 2 Hz, 1H), 6.57 (d, J = 2 Hz, 1H), 6.51-6.49 (m, 1H), 6.42-6.37 (m, 2H), 3.87 (s, 3H), 3.74 (s, 3H), 3.70 (s, 2H), 3.58 (s, 1H), 3.48 (s, 1H), 3.02 (s, 3H), 2.11 (s, 3H). |

Example-103: N-((4-(1,3-dimethyl-2-oxo-1,2-dihydroquinolin-5-yl)-1-methyl-1,2,3,4-tetrahydroquinoxalin-6-yl)sulfonyl)acetamide

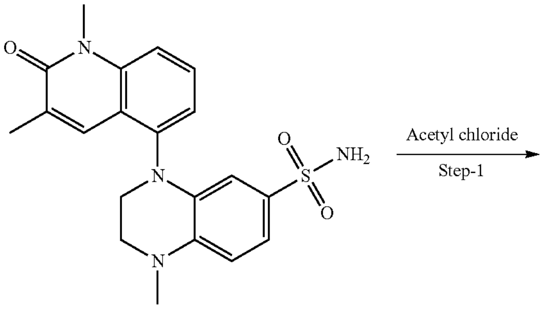

Example-86

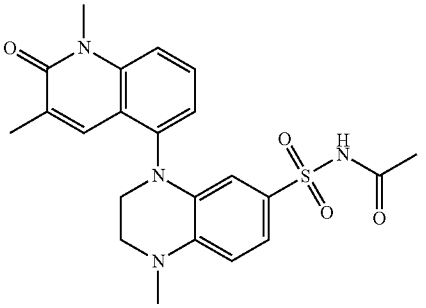

Example-103

A solution of 4-(1,3-dimethyl-2-oxo-1,2-dihydroquinolin-5-yl)-1-methyl-1,2,3,4-tetrahydroquinoxaline-6-sulfonamide (80 mg, 0.2 mmol) in DCM (5 mL) was cooled to 0° C. and added trimethylamine (60 mg, 0.6 mmol), 4-dimethylaminopyridine (5 mg, 0.04 mmol) followed by dropwise addition of acetyl chloride (50 mg, 0.6 mmol). The reaction mixture was gradually warmed to room temperature, stirred for 4 h. Then quenched with water, extracted into DCM, organic portion was dried over sodium sulphate and concentrated to get the crude compound. The crude compound was purified by preparative HPLC to get pure title compound (30 mg, 34.05%) LC-MS: 441.2 $[M+H]^+$; 1H-NMR (400 MHz, Chloroform-D) δ 7.90 (s, 1H), 7.63 (s, 1H), 7.58-7.54 (m, 1H), 7.45-7.42 (m, 1H), 7.29-7.27 (m, 1H), 7.08-7.06 (m, 1H), 6.64-6.61 (m, 1H), 6.53 (d, J=2 Hz, 1H), 3.79-3.77 (m, 2H), 3.74 (s, 3H), 3.62-3.58 (m, 1H), 3.49-3.45 (m, 1H), 3.09 (s, 3H), 2.19 (d, J=1.6 Hz, 3H), 1.94 (s, 3H).

The Examples 104-113 were prepared according to the protocols described in the synthesis of Example-103 with appropriate variations in reactants, quantities of reagents, solvents and reaction conditions.

| Example | Structure | Analytical data |
|---|---|---|
| 104 | 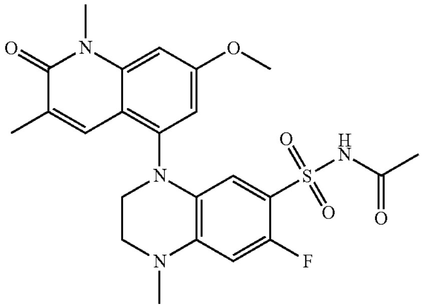 [SMILES: COc1cc(N2CCN(C)c3cc(F)c(S(=O)(=O)NC(C)=O)cc32)c2cc(C)c(=O)n(C)c2c1] | LC-MS: 489.2 $[M + H]^+$; 1H-NMR (300 MHZ, DMSO-D6) δ 11.88 (s, 1H), 7.60 (s, 1H), 6.8 (d, J = 1.8 Hz, 1H), 6.78 (d, J = 2.7 Hz, 1H), 6.56-6.52 (m, 1H), 6.28-6.25 (m, 1H), 3.89 (s, 3H), 3.7 (s, 2H), 3.67 (s, 3H), 3.48 (s, 2H), 3.03 (s, 3H), 2.04 (s, 3H), 1.80 (s, 3H). |
| 105 | 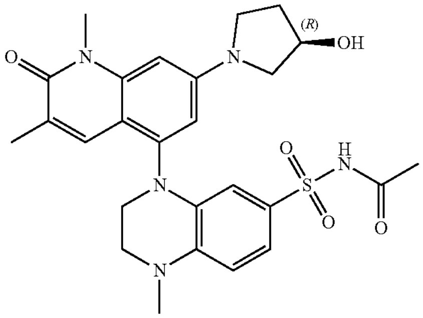 | LC-MS: 526.2 $[M + H]^+$; 1H-NMR (400 MHZ, DMSO-D6) δ 7.42 (s, 1H), 7.15 (d, J = 6.3 Hz, 1H), 6.64 (s, 1H), 6.46 (d, J = 2.0 Hz, 1H), 6.33 (d, J = 2.2 Hz, 1H), 6.27 (d, J = 1.7 Hz, 1H), 5.04 (s, 1H), 4.43 (s, 1H), 3.82 (dd, J = 7.8, 3.5 Hz, 1H), 3.71 (s, 1H), 3.63 (s, 3H), 3.51-3.42 (m, 5H), 3.21 (s, 1H), 3.02 (s, 3H), 2.08 (s, 1H), 1.97 (s, 4H), 1.71 (s, 3H), 11.51-11.46 (m, 1H). |

-continued

| Example | Structure | Analytical data |
| --- | --- | --- |
| 106 | 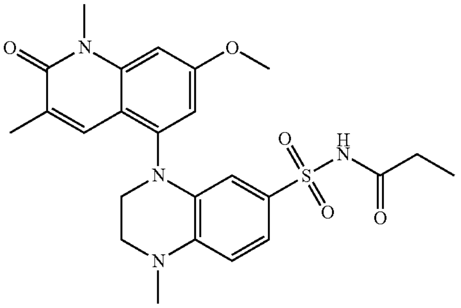 [SMILES: CCC(=O)NS(=O)(=O)c1ccc2c(c1)N(c1cc(OC)cc3c1cc(C)c(=O)n3C)CCN2C] | LC-MS: 485.2 [M + H]$^+$; 1H-NMR (400 MHZ, DMSO-D6) δ 11.41 (s, 1H), 7.55 (s, 1H), 7.19-7.16 (m, 1H), 6.9 (s, 1H), 6.8 (s, 1H), 6.67-6.65 (d, J = 8.4 Hz, 1H), 6.310-6.305 (d, J = 1.5 Hz, 1H), 3.89 (s, 3H), 3.80-3.75 (m, 2H), 3.67 (s, 3H), 3.59-3.49 (m, 3H), 3.026 (s, 3H), 2.015 (s, 3H), 1.99 (d, J = 6.8 Hz, 1H), 2.007 (s, 3H). |
| 107 | 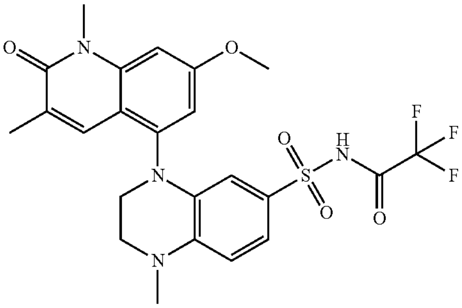 [SMILES: COc1cc(N2CCN(C)c3ccc(S(=O)(=O)NC(=O)C(F)(F)F)cc32)c2cc(C)c(=O)n(C)c2c1] | LC-MS: 525.2 [M + H]$^+$; 1H-NMR (300 MHZ, DMSO-D6) δ 7.56 (s, 1H), 7.18 (d, J = 8.4 Hz, 1H), 6.9 (s, 1H), 6.8 (s, 1H), 6.66-6.64 (m, 1H), 6.33 (d, J = 1.2 Hz, 1H), 3.9 (s, 1H), 3.8 (s, 3H), 3.67 (s, 3H), 3.61-3.49 (m, 3H), 3.01 (s, 3H), 2.007 (s, 3H). |
| 108 | 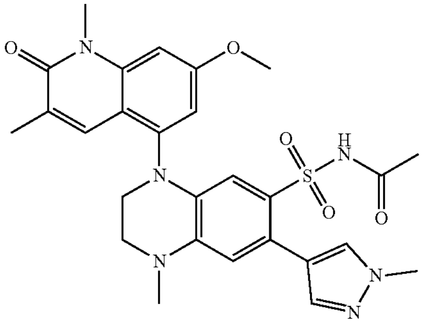 [SMILES: COc1cc(N2CCN(C)c3cc(-c4cnn(C)c4)c(S(=O)(=O)NC(C)=O)cc32)c2cc(C)c(=O)n(C)c2c1] | LC-MS: 551.2 [M + H]$^+$; 1H-NMR (600 MHZ, DMSO-D6) δ 11.15 (s, 1H), 7.74 (s, 1H), 7.63 (s, 1H), 7.49 (s, 1H), 6.92 (d, J = 1.8 Hz, 1H), 6.82 (d, J = 1.8 Hz, 1H), 6.55 (s, 1H), 6.44 (s, 1H), 3.89 (s, 3H), 3.84 (s, 3H), 3.79-3.69 (m, 2H), 3.67 (s, 3H), 3.56-3.43 (m, 2H), 3.0 (s, 3H), 2.05 (s, 3H), 1.57 (s, 3H). |
| 109 | 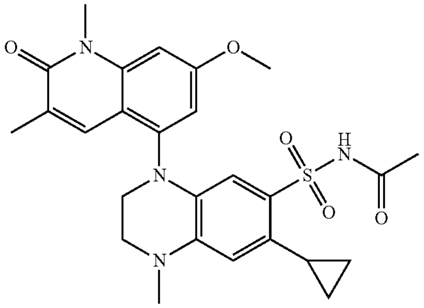 [SMILES: COc1cc(N2CCN(C)c3cc(C4CC4)c(S(=O)(=O)NC(C)=O)cc32)c2cc(C)c(=O)n(C)c2c1] | LC-MS: 511.4 [M + H]$^+$; 1H-NMR (400 MHZ, Chloroform-D) δ 7.94 (s, 1H), 7.57 (s, 1H), 6.86 (s, 1H), 6.69 (s, 1H), 6.62 (s, 1H), 6.27 (s, 1H), 3.87 (s, 3H), 3.74 (s, 3H), 3.69 (s, 1H), 3.58 (d, J = 8.4 Hz, 1H), 3.4 (s, 1H), 3.06 (s, 3H), 2.46 (t, J = 10.8, 5.6 Hz, 1H), 2.16 (s, 3H), 1.92 (s, 3H), 1.0-0.9 (m, 2H), 0.75 (s, 2H). |
| 110 | 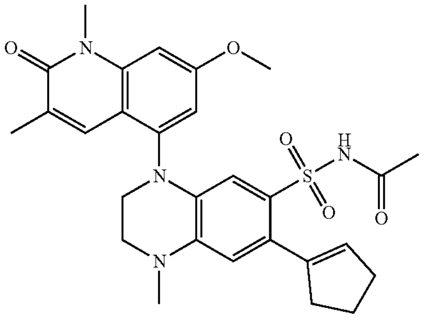 [SMILES: COc1cc(N2CCN(C)c3cc(C4=CCCC4)c(S(=O)(=O)NC(C)=O)cc32)c2cc(C)c(=O)n(C)c2c1] | LC-MS: 537.6 [M + H]$^+$; 1H-NMR (400 MHZ, Chloroform-D) δ 7.57 (s, 2H), 6.80 (s, 1H), 6.71 (d, J = 2 Hz, 1H), 6.66 (d, J = 2.4 Hz, 1H), 6.38 (s, 1H), 5.74 (s, 1H), 3.88 (s, 3H), 3.74 (s, 3H), 3.72-3.58 (m, 2H), 3.47 (s, 1H), 3.06 (s, 3H), 2.7-2.5 (m, 4H), 2.16 (d, J = 0.8 Hz, 3H), 2.03-2.01 (m, 2H), 1.91 (s, 3H). |

-continued
| Example | Structure | Analytical data |
|---|---|---|
| 111 | 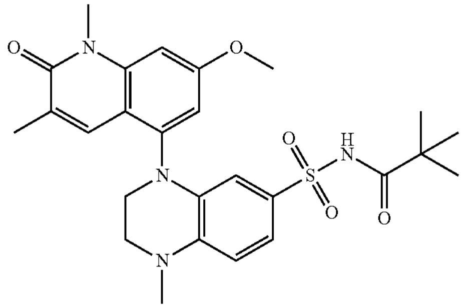 [SMILES: COc1cc(N2CCN(C)c3ccc(S(=O)(=O)NC(=O)C(C)(C)C)cc32)c2cc(C)c(=O)n(C)c2c1] | LC-MS: 513.2 [M + H]$^+$; 1H-NMR (600 MHZ, Chloroform-D) δ 7.81 (s, 1H), 7.52-7.45 (m, 2H), 6.71 (d, J = 1.8 Hz, 1H), 6.63-6.548 (m, 2H), 6.544 (s, 1H), 3.87 (s, 3H), 3.73 (s, 5H), 3.57-3.43 (m, 2H), 3.07 (s, 3H), 2.1 (s, 3H), 1.9 (d, J = 1.2 Hz, 3H), 1.48 (s, 4H), 1.02-0.99 (m, 3H). |
| 112 | 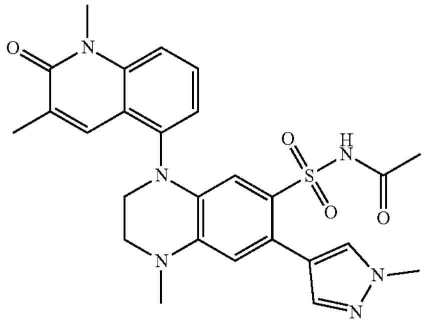 [SMILES: CC(=O)NS(=O)(=O)c1cc2c(cc1-c1cnn(C)c1)N(C)CCN2c1cccc2c1cc(C)c(=O)n2C] | LC-MS: 521.2 [M + H]$^+$; 1H-NMR (400 MHZ, Chloroform-D) δ 11.12 (s, 1H), 7.74 (s, 2H), 7.70-7.60 (m, 1H), 7.48-7.46 (m, 2H), 7.19-7.17 (m, 1H), 6.51 (s, 1H), 6.45 (s, 1H), 3.84 (s, 3H), 3.78-3.74 (m, 2H), 3.69 (s, 3H), 3.60-3.53 (m, 1H), 3.47-3.43 (m, 1H), 3.01 (s, 3H), 2.11 (s, 3H), 1.56 (s, 3H). |
| 113 | 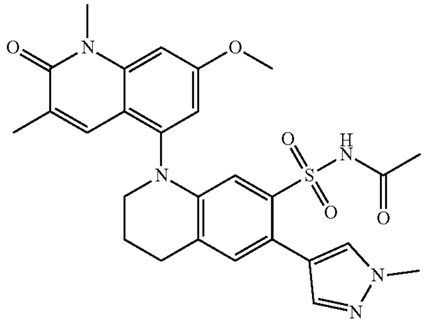 [SMILES: COc1cc(N2CCCc3cc(-c4cnn(C)c4)c(S(=O)(=O)NC(C)=O)cc32)c2cc(C)c(=O)n(C)c2c1] | LC-MS: 536.1 [M + H]$^+$; 1H-NMR (400 MHZ, DMSO-D6) 8 7.96 (s, 1H), 7.61 (s, 2H), 7.02 (s,1H), 6.91 (s, 1H), 6.77 (s, 1H), 6.68 (s, 1H), 3.89 (s, 3H), 3.80 (s, 3H), 3.66 (s, 3H), 3.50 (brs, 2H), 2.88 (brs, 2H), 2.07 (s, 3H), 1.90 (s, 2H), 1.40 (s, 3H). |

Example-114: 1-(7-Methoxy-1,3-dimethyl-2-oxo-1,2-dihydroquinolin-5-yl)-4-methyl-1,2,3,4-tetrahydroquinoxaline-6-sulfonamide

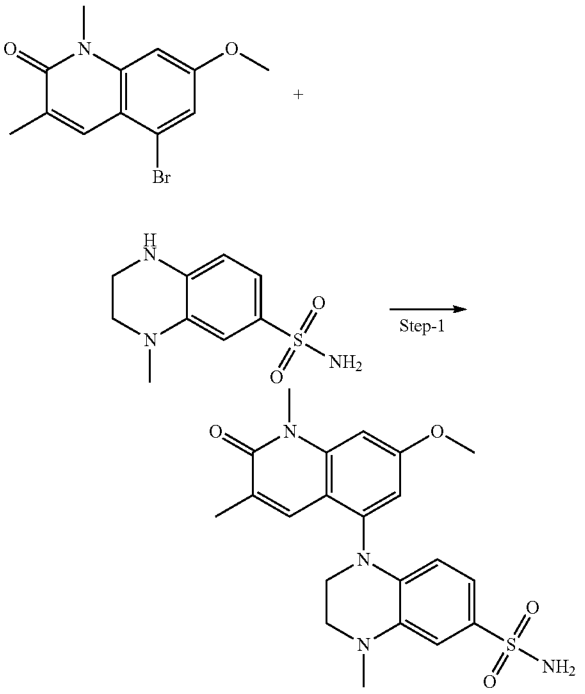

Example-114

This compound was prepared using the similar protocol described in COUPLING METHOD-A using 5-bromo-7-methoxy-1,3-dimethylquinolin-2(1H)-one & 4-methyl-1,2,3,4-tetrahydroquinoxaline-6-sulfonamide with appropriate variations in reactants, quantities of reagents, solvents and reaction conditions. LC-MS: 428.5 $[M+H]^+$; 1H-NMR (400 MHz, DMSO-D6) δ 7.655 (s, 1H), 6.78-6.73 (m, 2H), 6.66 (d, J=2.4 Hz, 1H), 6.49 (d, J=2 Hz, 1H), 6.40 (d, J=8.4 Hz, 1H), 3.756 (s, 3H), 3.56 (s, 3H), 3.20 (s, 3H), 2.78 (s, 3H), 1.98 (s, 3H), 1.9 (d, J=1.2 Hz, 3H).

Example-115: 1-Methyl-4-(3-methyl-2-oxo-1,2-dihydroquinolin-5-yl)-1,2,3,4-tetrahydroquinoxaline-6-carbonitrile

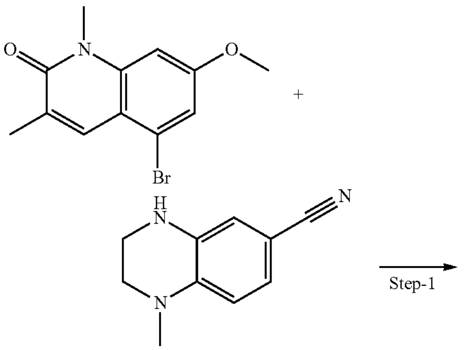

-continued

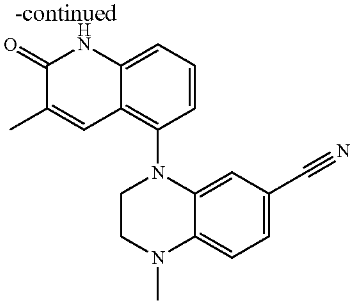

Example-115

This compound was prepared using the similar protocol described in COUPLING METHOD-B using intermediates 5-bromo-7-methoxy-1,3-dimethylquinolin-2(1H)-one & 1-methyl-1,2,3,4-tetrahydroquinoxaline-6-carbonitrile with appropriate variations in reactants, quantities of reagents, solvents and reaction conditions (80 mg, 28%). LC-MS: 331 $[M+H]^+$. 1H-NMR (400 MHz, DMSO-D6) δ 11.93 (s, 1H), 7.63 (s, 1H), 7.53 (t, J=8.0, 8.0 Hz, 1H), 7.26 (d, J=8.3 Hz, 1H), 7.04 (dd, J=12.4, 4.7 Hz, 2H), 6.66 (d, J=8.4 Hz, 1H), 5.94 (s, J=2.0 Hz, 1H), 3.74 (s, 2H), 3.56 (s, 3H), 3.02 (s, 3H), 2.05 (s, 2H).

Example-116: 7-Methoxy-1,3-dimethyl-5-(1-methyl-7-(1-methyl-1H-pyrazol-4-yl)-2,3-dihydropyrido[3,4-b]pyrazin-4(1H)-yl)quinolin-2(1H)-one

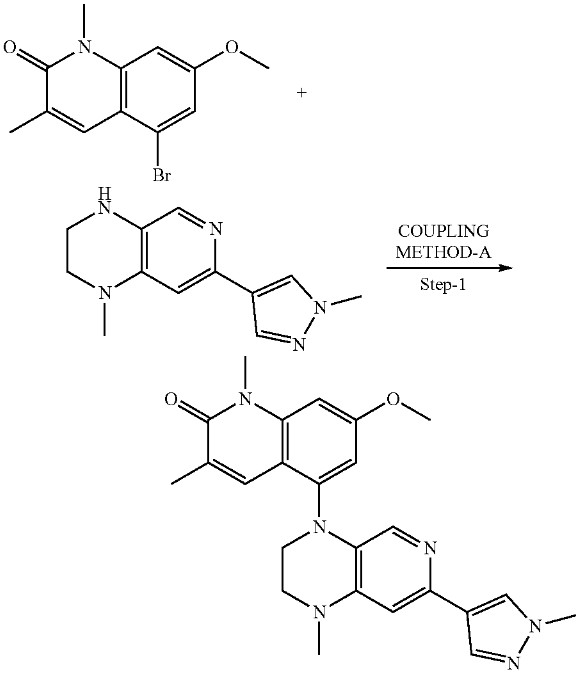

Example-116

A solution of 5-bromo-7-methoxy-1,3-dimethylquinolin-2(1H)-one (100 mg, 0.43 mmol) and 1-methyl-7-(1-methyl-1H-pyrazol-4-yl)-1,2,3,4-tetrahydropyrido[3,4-b]pyrazine (197 mg, 0.52 mmol) in 1,4-dioxane (4 mL) was added $Pd_2(dba)_3$ (39 mg, 0.043 mmol), Xantphos (24 mg, 0.043 mmol) and sodium tert-butoxide (123 mg, 1.29 mmol). The mixture was stirred at 100° C. for overnight. The mixture was cooled to RT, added water, extracted with 10% methanol in DCM. Organic extracts were washed with brine, dried over Sodium sulphate and concentrated to get the residue. The residue was purified by preparative HPLC purification chromatography to get the pure compound (100 mg, 65.5%). LC-MS: 430 $[M+H]^+$; 1H-NMR (600 MHz, Chloroform-D) δ 7.80 (d, J=21.4 Hz, 2H), 7.67 (s, 1H), 7.24 (s, 1H), 6.68-6.64 (m, 3H), 3.91 (s, 3H), 3.87 (s, 3H), 3.74 (s, 5H), 3.57 (d, J=10.6 Hz, 1H), 3.45 (s, 1H), 3.10 (s, 3H), 2.17 (s, 3H).

The Examples-117-144 were prepared according to the protocols described in the synthesis of Example-116 with appropriate variations in reactants, quantities of reagents, solvents and reaction conditions with appropriate coupling methods.

| Example | Structure | Coupling Method | Analytical data |
|---|---|---|---|
| 117 | 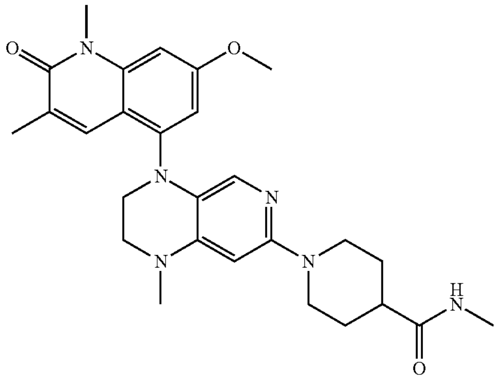 | A | LC-MS: 491.1 $[M + H]^+$; 1H-NMR (600 MHZ, Chloroform-D) δ 7.75 (s, 1H), 7.02 (s, 1H), 6.60 (d, J = 2.5 Hz, 1H), 6.52 (s, 1H), 5.89 (s, 1H), 5.53-5.51 (m, 1H), 4.13 (d, J = 9.9 Hz, 2H), 3.84 (d, J = 2.4 Hz, 3H), 3.72 (s, 3H), 3.57 (d, J = 32.1 Hz, 3H), 3.03 (d, J = 2.6 Hz, 3H), 2.82 (d, J = 4.7 Hz, 3H), 2.75 (t, J = 11.8, 11.8 Hz, 2H), 2.26 (m, 1H), 2.19 (s, 3H), 1.92 (d, J = 12.0 Hz, 2H), 1.79-1.76 (m, 2H). |
| 118 | 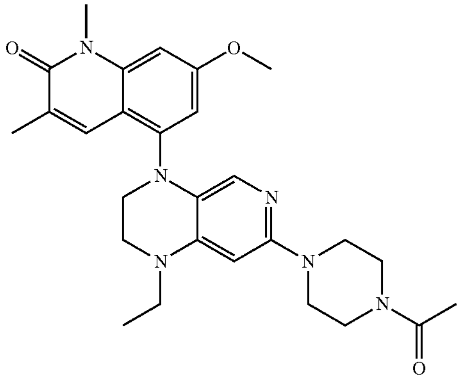 [SMILES: CCN1CCN(c2cc(OC)cc3c2cc(C)c(=O)n3C)c2cnc(N3CCN(C(C)=O)CC3)cc21] | A | LC-MS: 491.4 $[M + H]^+$; 1H-NMR (600 MHZ, Chloroform-D) δ 3.57 (s, 4H), 3.45 (d, J = 7.4 Hz, 5H), 3.31 (s, 2H), 2.19 (s, 3H), 2.12 (s, 3H), 1.26 (s, 3H), 3.74-3.73 (m, 6H), 7.04 (s, 1H), 7.76-7.75 (m, 1H), 6.60 (s, 1H), 6.50 (s, 1H), 5.90 (s, 1H), 3.85 (s, 3H). |
| 119 | 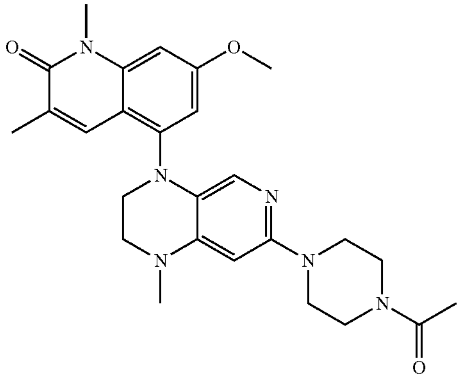 [SMILES: COc1cc(N2CCN(C)c3cc(N4CCN(C(C)=O)CC4)ncc32)c2cc(C)c(=O)n(C)c2c1] | A | LC-MS: 477.3 $[M + H]^+$; 1H-NMR (600 MHZ, Chloroform-D) δ 7.71 (s, 1H), 6.98 (s, 1H), 6.62 (d, J = 2.3 Hz, 1H), 6.53 (d, J = 2.1 Hz, 1H), 5.85 (s, 1H), 3.86 (s, 3H), 3.73 (d, J = 5.5 Hz, 6H), 3.56 (t, J = 5.2, 5.2 Hz, 3H), 3.46 (s, 3H), 3.32 (t, J = 5.3, 5.3 Hz, 3H), 3.06 (s, 3H), 2.18 (s, 3H), 2.12 (s, 3H). |

-continued

| Example | Structure | Coupling Method | Analytical data |
|---|---|---|---|
| 120 | 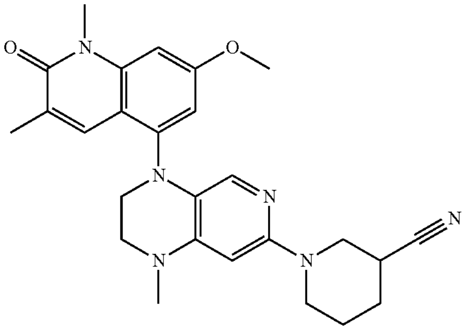 [SMILES: COc1cc(N2CCN(C)c3cc(N4CCCC(C#N)C4)ncc32)c2cc(C)c(=O)n(C)c2c1] | A | LC-MS: 459.3 [M + H]+; 1H-NMR (400 MHZ, Chloroform-D) δ 7.73 (s, 1H), 2.05-2.02 (m, 2H), 6.61 (s, 1H), 1.65-1.64 (m, 2H), 6.54 (s, 1H), 1.83-1.81 (m, 2H), 3.73-3.72 (m, 3H), 3.62 (s, 3H), 5.89-5.89 (m, 1H), 3.31 (s, 1H), 3.12 (s, 1H), 3.04 (s, 3H), 7.01-7.00 (m, 1H), 2.81 (s, 1H), 3.98-3.97 (m, 1H), 3.85-3.85 (m, 3H), 2.19 (d, J = 1.2 Hz, 3H). |
| 121 | 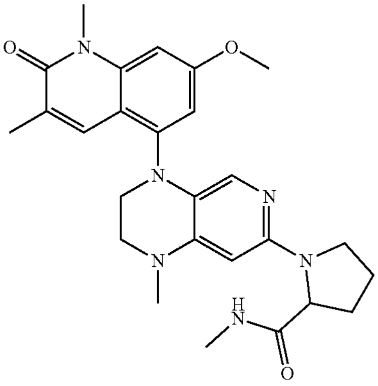 [SMILES: CNC(=O)C1CCCN1c1cc2c(cn1)N(c1cc(OC)cc3c1cc(C)c(=O)n3C)CCN2C] | A | LC-MS: 477.4 [M + H]+; 1H-NMR (400 MHZ, Chloroform-D) δ 3.49 (s, 2H), 3.39 (s, 1H), 3.09 (s, 3H), 2.73 (d, J = 4.7 Hz, 3H), 2.19 (d, J =1.2 Hz, 6H), 2.01 (s, 1H), 3.66-3.61 (m, 1H), 7.63 (s, 1H), 6.66 (d, J = 2.3 Hz, 2H), 6.56 (d, J = 2.2 Hz, 1H), 5.54 (s, 1H), 4.54 (s, 1H), 3.88 (s, 3H), 3.73 (s, 5H). |
| 122 | 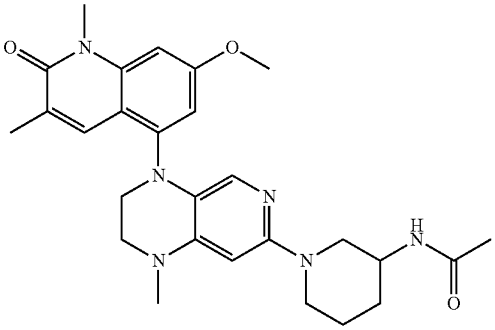 [SMILES: COc1cc(N2CCN(C)c3cc(N4CCCC(NC(C)=O)C4)ncc32)c2cc(C)c(=O)n(C)c2c1] | A | LC-MS: 491 [M + H]+; 1H-NMR (600 MHZ, Chloroform-D) δ 7.54 (s, 1H), 6.71 (s, 1H), 6.58 (s, 2H), 5.93-5.90 (m, 1H), 4.09 (brs, 1H), 3.89 (s, 4H), 3.74 (s, 3H), 3.71-3.65 (m, 1H), 3.53-3.48 (m, 3H), 3.338 (s, 2H), 3.20 (s, 3H), 2.18 (s, 3H), 1.99 (s, 4H), 1.88 (brs, 2H), 1.78-1.73 (m, 3H). |
| 123 | 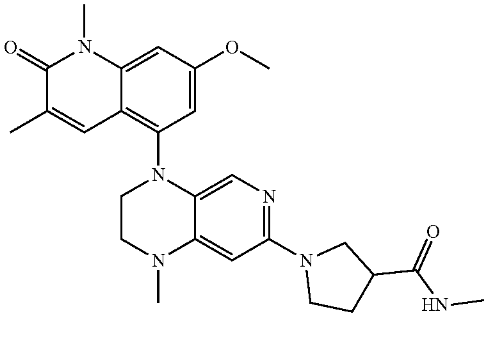 | A | LC-MS: 477.3 [M + H]+; 1H-NMR (400 MHZ, Chloroform-D) δ 7.79-7.77 (s, 1H), 7.04 (s, 1H), 6.57 (d, J = 2 Hz, 1H), 6.48 (d, J = 2.4 Hz, 1H), 5.75 (s, 1H), 5.58 (s, 1H), 3.84 (s, 3H), 3.72 (s, 3H), 3.63-3.59 (m, 3H), 3.55 (s, 2H), 3.43-3.39 (m, 3H), 3.02 (s, 3H), 2.98 (s, 1H), 2.82 (d, J = 4.7 Hz, 3H), 2.24 (t, J = 6.2, 6.2 Hz, 2H), 2.20 (s, 3H). |

-continued

| Example | Structure | Coupling Method | Analytical data |
|---|---|---|---|
| 124 | 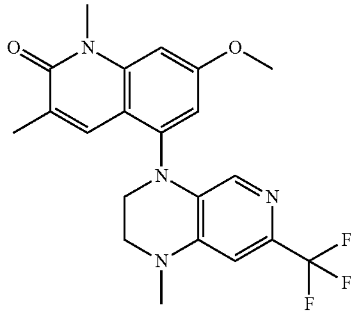 [SMILES: COc1cc(N2CCN(C)c3cc(C(F)(F)F)ncc32)c2cc(C)c(=O)n(C)c2c1] | A | LC-MS: 419.4 [M + H]+; 1H-NMR (400 MHZ, Chloroform-D) δ 7.54 (s, 1H), 7.26 (s, 1H), 6.80 (s, 1H), 6.74 (d, J = 2.4 Hz, 1H), 6.66 (d, J = 2 Hz, 1H), 3.88 (s, 3H), 3.79-3.76 (m, 2H), 3.74 (s, 3H), 3.62-3.57 (m, 1H), 3.50-3.45 (m, 1H), 3.10 (s, J = 1.6 Hz, 3H), 2.17 (d, J = 1.2 Hz, 3H). |
| 125 | 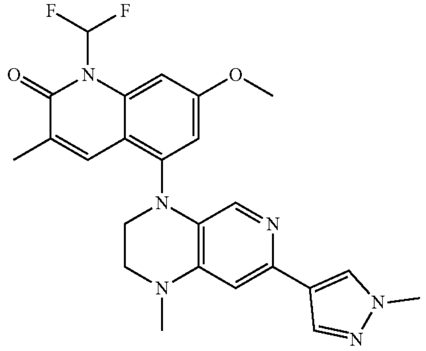 | A | LC-MS: 467.3 [M + H]+; 1H-NMR (400 MHZ, Chloroform-D) δ 7.98-7.96 (m, 1H), 7.81 (d, J = 0.7 Hz, 1H), 7.70 (s, 1H), 7.13 (s, 1H), 7.09 (d, J = 2.4 Hz, 1H), 6.88 (d, J = 2.5 Hz, 1H), 6.65 (s, 1H), 3.91 (s, 3H), 3.90 (s, 3H), 3.73 (d, J = 2.3 Hz, 4H), 3.48 (s, 1H), 3.12 (s, 3H), 2.30 (d, J = 1.0 Hz, 3H). |
| 126 | 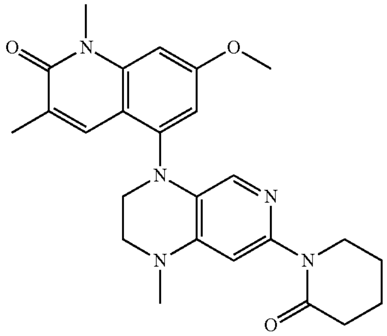 [SMILES: COc1cc(N2CCN(C)c3cc(N4CCCCC4=O)ncc32)c2cc(C)c(=O)n(C)c2c1] | A | LC-MS: 448.4 [M + H]+; 1H-NMR (600 MHZ, Chloroform-D) δ 7.65 (s, 1H), 7.04 (s, 1H), 6.75 (s, 1H), 6.68-6.66 (m, 2H), 3.87 (d, J = 7.2 Hz, 3H), 3.74-3.73 (m, 7H), 3.52 (brs, 1H), 3.42 (brs, 1H), 3.04 (s, 3H), 2.55-2.53 (m, 2H), 2.18 (d, J = 6 Hz, 3H), 1.89 (t, J = 6, 3 Hz, 4H). |
| 127 | 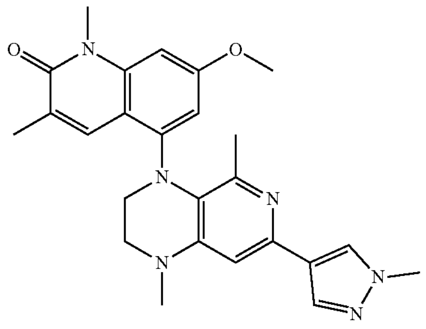 | A | LC-MS: 445.3 [M + H]+; 1H-NMR (400 MHZ, Chloroform-D) δ 8.12 (s, 1H), 7.86 (s, 1H), 7.21 (s, 1H), 6.71 (s, 1H), 6.51 (s, 1H), 6.03 (s, 1H), 3.93 (s, 3H), 3.76 (s, 3H), 3.73 (s, 3H), 3.58-3.53 (m, 2H), 3.42-3.38 (m, 1H), 3.12 (s, 3H), 3.14 (s, 1H), 2.30 (s, 3H), 2.04 (s, 3H). |

-continued

| Example | Structure | Coupling Method | Analytical data |
|---|---|---|---|
| 128 | 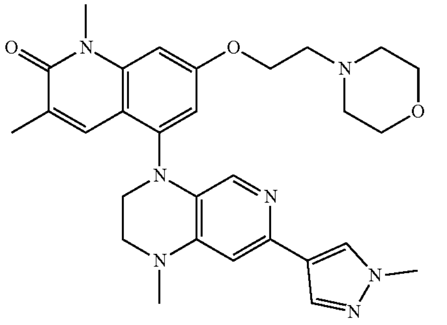 [SMILES: Cc1cc2c(N3CCN(C)c4cc(-c5cnn(C)c5)ncc43)cc(OCCN3CCOCC3)cc2n(C)c1=O] | A | LC-MS: 530.6 [M + H]+; 1H-NMR (600 MHZ, Chloroform-D) δ 8.47 (s, 1H), 7.84 (s, 1H), 7.52 (s, 1H), 7.0 (s, 1H), 6.73 (s, 1H), 6.66 (d, J = 1.8 Hz, 1H ), 6.64 (s, 1H), 4.18-4.15 (m, 3H), 3.90 (s, 3H), 3.89-3.87 (m, 2H), 3.73 (d, J = 4.8 Hz, 5H), 3.71 (s, 3H), 3.55 (d, J = 4.2 Hz, 3H), 3.21 (s, 3H), 2.83-2.81 (m, 3H), 2.15 (s, 3H). |
| 129 | 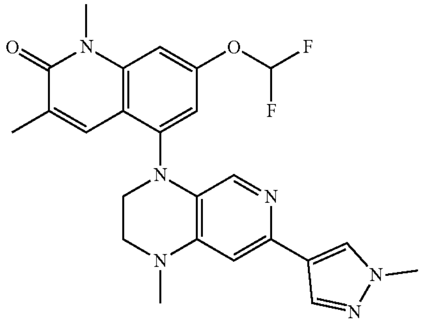 | A | LC-MS: 467.1 [M + H]+; 1H-NMR (600 MHZ, Chloroform-D) δ 7.95 (s, 1H), 7.83 (s, 1H), 7.68 (s, 1H), 7.21 (s, 1H), 6.98 (s, 1H), 6.81 (s, 1H), 6.67 (s, 1H), 3.18-3.16 (m, 3H), 3.92 (s, 3H), 3.74 (s, 3H), 3.60 (s, 1H), 3.48 (d, J = 7.4 Hz, 2H), 2.20 (s, 3H), 1.46 (s, 1H), 1.21 (d, J = 7.1 Hz, 2H), 0.83 (s, 1H), 7.27-7.26 (m, 1H). |
| 130 | 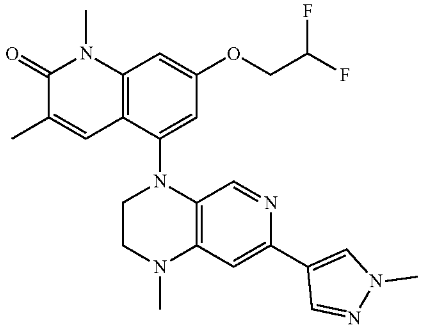 | A | LC-MS: 481.2 [M + H]+; 1H-NMR (400 MHZ, Chloroform-D) δ 7.82 (d, J = 0.8 Hz, 1H), 7.78 (s, 1H), 7.70-7.69 (m, 1H), 6.70-6.64 (m, 3H), 6.09 (t, J = 4.0, 4.0 Hz, 1H), 4.27-4.20 (m, 2H), 3.91 (s, 3H), 3.73 (s, 3H), 3.66-3.44 (m, 4H), 3.10 (s, 3H), 2.19 (d, J = 1.2 Hz, 4H). |
| 131 | 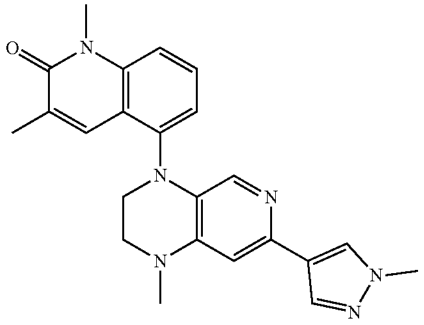 | A | LC-MS: 401.4 [M + H]+; 1H-NMR (400 MHZ, Chloroform-D) δ 7.81 (s, 1H), 7.77 (s, 2H), 7.53-7.49 (m, 1H), 7.25 (s, 1H), 7.24-7.17 (m, 1H), 7.05-7.03 (m, 1H), 6.56 (d, J = 2 Hz, 1H), 3.90 (s, 3H), 3.774 (s, 3H), 3.75-3.42 (m, 4H), 3.10 (m, 3H), 2.21 (s, 3H). |

-continued

| Example | Structure | Coupling Method | Analytical data |
|---|---|---|---|
| 132 | 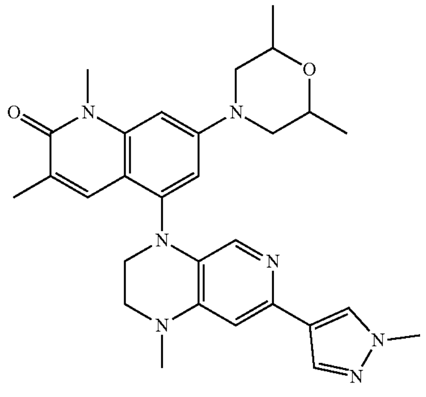 | C | LC-MS: 514.6 [M + H]+; 1H-NMR (400 MHZ, Chloroform-D) δ 7.82 (s, 1H), 7.77 (s, 1H), 7.60 (s, 1H), 7.22 (s, 1H), 6.68 (s, 1H), 6.65 (s, 1H), 6.55 (s, 1H), 3.90 (s, 3H), 3.77-3.74 (m, 7H), 3.58-3.45 (m, 4H), 3.10 (s, 3H), 3.52-3.47 (m, 2H), 2.16 (s, 3H), 1.27 (s, 3H), 1.26 (s, 3H). |
| 133 | 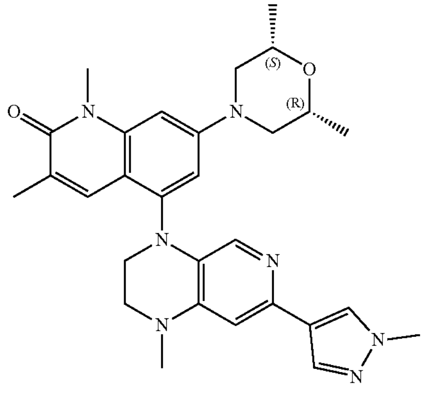 | B | LC-MS: 514.3 [M + H]+; 1H-NMR (400 MHZ, Methanol-d) δ 7.96 (s, 1H), 7.85 (s, 1H), 7.67 (s, 1H), 6.91 (s, 1H), 6.85 (s, 1H), 6.80 (s, 1H), 6.77 (s, 1H), 3.89 (s, 3H), 3.83-3.79 (m, 2H), 3.75 (s, 3H), 3.58-3.54 (m, 3H), 3.14 (s, 3H), 2.47-2.45 (brs, 2H), 2.08 (s, 3H), 1.92 (brs, 3H), 1.24-1.23 (m, 6H). |
| 134 | 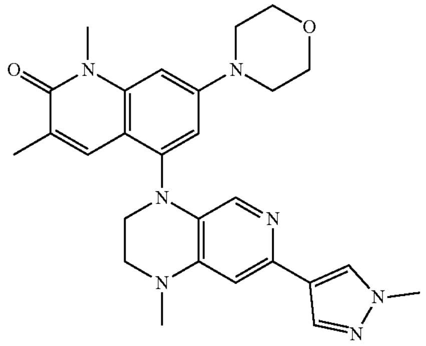 | B | LC-MS: 485.9 [M + H]+; 1H-NMR (600 MHZ, Chloroform-D) δ 7.77 (s, 1H), 7.63 (s, 1H), 6.67 (s, 1H), 3.45-3.42 (m, 1H), 6.65 (s, 2H), 3.91 (s, 3H), 3.86 (d, J = 4.9 Hz, 5H), 3.73 (s, 4H), 3.59 (s, 1H), 3.24-3.22 (m, 4H), 3.10 (s, 3H), 2.17 (d, J = 1.4 Hz, 3H), 6.57-6.56 (m, 2H). |
| 135 | 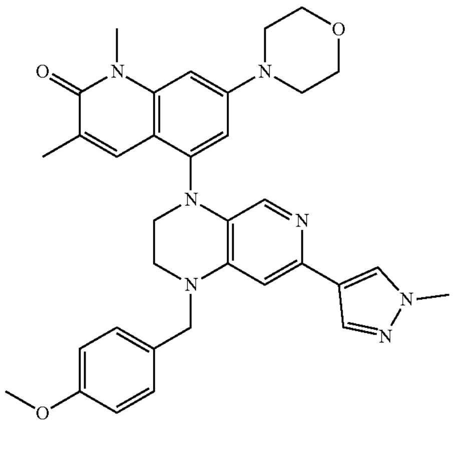 | C | LC-MS: 592.2 [M + H]+; 1H-NMR (400 MHZ, Chloroform-D) δ 7.70 (s, 1H), 7.65 (s, 1H), 7.30 (s, 1H), 7.27 (t, J = 8, 4.8 Hz, 3H), 6.92-6.90 (m, 2H), 6.74 (s, 1H ), 6.65 (d, J = 2.4 Hz, 1H), 6.45 (s, 1H), 4.52-4.66 (m, 3H), 3.88 (s, 3H), 3.87-3.84 (m, 4H), 3.81 (s, 3H), 3.73 (s, 3H), 3.69-3.50 (m, 3H), 3.24 (d, J = 4 Hz, 4H), 2.18 (d, J = 1.2 Hz, 3H). |

-continued

| Example | Structure | Coupling Method | Analytical data |
|---|---|---|---|
| 136 | 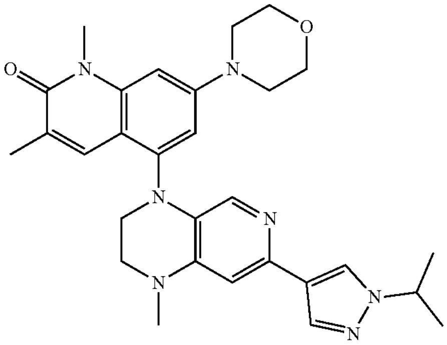 [SMILES: Cc1cc2c(N3CCN(C)c4cc(-c5cnn(C(C)C)c5)ncc43)cc(N3CCOCC3)cc2n(C)c1=O] | C | LC-MS: 514.1 [M + H]+; 1H-NMR (400 MHZ, Chloroform-D) δ 7.85 (s, 1H), 7.82 (s, 1H), 7.62 (s, 1H), 7.27 (s, 1H), 6.66 (d, J = 3.6 Hz, 2H), 6.56 (d, J = 2 Hz, 1H), 4.54-4.45 (m, 1H), 3.86-3.84 (m, 4H), 3.73 (s, 3H), 3.71-3.49 (m, 4H), 3.24-3.22 (m, 4H), 3.10 (m, 3H), 2.16 (m, 3H), 1.52-1.50 (m, 6H). |
| 137 | 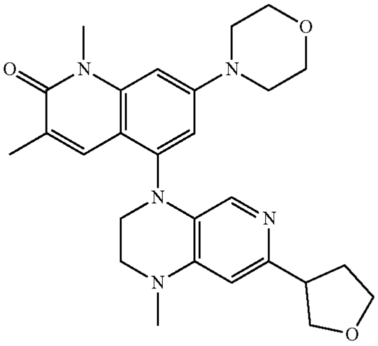 [SMILES: Cc1cc2c(N3CCN(C)c4cc(C5CCOC5)ncc43)cc(N3CCOCC3)cc2n(C)c1=O] | C | LC-MS: 476.5 [M + H]+; 1H-NMR (600 MHz, Chloroform-D) δ 7.36-7.35 (s, 1H), 6.86-6.84 (s, 1H), 6.64 (s, 1H), 6.62 (d, J = 2.4 Hz, 1H), 6.50 (d, J = 2.4 Hz, 1H), 4.09-4.04 (m, 1H), 4.0-3.91 (m, 3H), 3.88-3.87 (m, 5H), 3.84-3.73 (m, 4H), 3.29-3.27 (m, 3H), 3.23 (s, 3H), 2.53 (d, J = 5.4 Hz, 1H), 2.19 (s, 3H), 2.02-1.96 (m, 2H), 0.88-0.82 (m, 3H). |
| 138 | 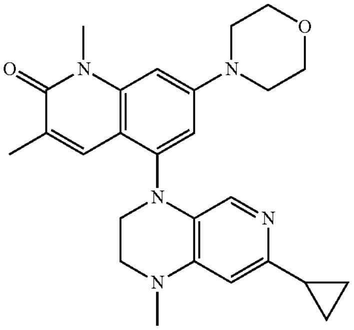 [SMILES: Cc1cc2c(N3CCN(C)c4cc(C5CC5)ncc43)cc(N3CCOCC3)cc2n(C)c1=O] | C | LC-MS: 446.2 [M + H]+; 1H-NMR (400 MHZ, DMSO-D6) δ 7.57 (s, 1H), 6.78 (s, 1H), 6.74 (s, 1H), 6.68 (s, 1H), 6.42 (s, 1H), 3.74-3.72 (m, 4H ), 3.64 (s, 3H), 3.33 (s, 7H), 3.28 (d, J = 4.4 Hz, 4H), 2.98 (s, 3H), 2.015 (s, 3H), 1.89-1.77 (m, 2H). |
| 139 | 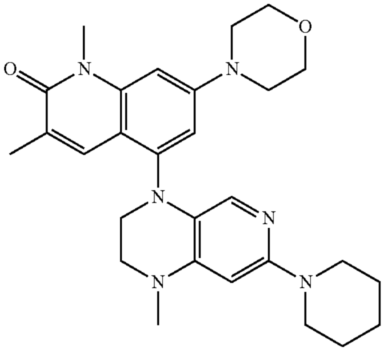 [SMILES: Cc1cc2c(N3CCN(C)c4cc(N5CCCCC5)ncc43)cc(N3CCOCC3)cc2n(C)c1=O] | C | LC-MS: 489.5 [M + H]+; 1H-NMR (600 MHz, Chloroform-D) δ 7.70 (s, 1H), 7.05 (s, 1H), 6.55 (d, J = 1.8 Hz, 1H), 6.47 (s, 1H), 5.89 (s, 1H), 3.84-3.83 (m, 4H), 3.70 (s, 3H), 3.61-3.48 (m, 3H), 3.34-3.32 (m, 4H), 3.75 (brs, 2H), 3.19 (s, 4H), 3.01 (s, 3H), 2.17 (s, 3H), 1.64-1.59 (m, 2H), 1.57 (s, 3H). |

-continued

| Example | Structure | Coupling Method | Analytical data |
| --- | --- | --- | --- |
| 140 | 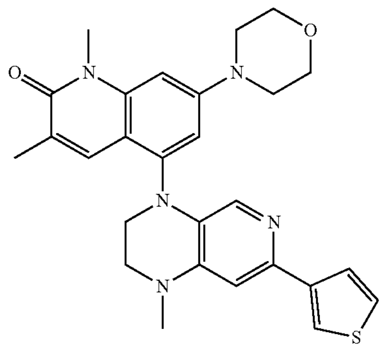 [SMILES: Cc1cc2c(N3CCN(C)c4cc(-c5ccsc5)ncc43)cc(N3CCOCC3)cc2n(C)c1=O] | C | LC-MS: 488.3 [M + H]$^+$; 1H-NMR (400 MHZ, Chloroform-D) δ 7.54 (s, 2H), 7.28 (s, 1H), 7.23 (s, 1H), 7.09 (s, 1H), 6.80 (s, 1H), 6.68 (d, J = 1.6 Hz, 1H), 6.60 (s, 1H), 3.87-3.85 (m, 3H), 3.75 (brs, 2H), 3.73 (s, 3H), 3.60 (brs, 2H), 3.50 (brs, 2H), 3.26-3.24 (m, 3H), 3.16 (s, 3H), 2.17 (s, 3H). |
| 141 | 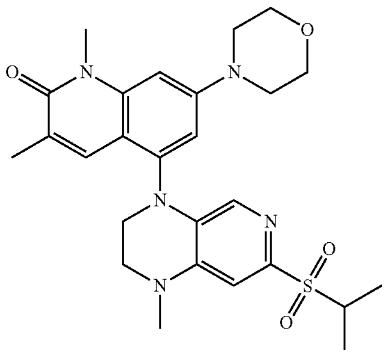 [SMILES: Cc1cc2c(N3CCN(C)c4cc(S(=O)(=O)C(C)C)ncc43)cc(N3CCOCC3)cc2n(C)c1=O] | C | LC-MS: 512.3 [M + H]$^+$; 1H-NMR (400 MHZ, Chloroform-D) δ 7.44 (s, 1H), 7.28 (s, 1H), 7.21 (s, 1H), 6.69 (d, J = 2.4 Hz, 1H), 6.62 (d, J =1.6 Hz, 1H), 3.88-3.86 (m, 4H), 3.79 (s, 2H), 3.73 (s, 3H), 3.68-3.62 (m, 2H), 3.48-3.45 (m, 1H), 3.27-3.25 (m, 4H), 3.11 (s, 3H), 2.17 (s, 3H), 1.32-1.26 (m, 6H). |
| 142 | 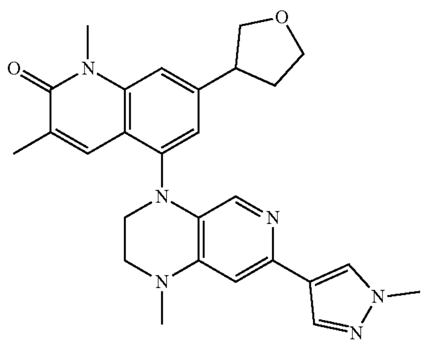 | C | LC-MS: 471.4 [M + H]$^+$; 1H-NMR (600 MHZ, Chloroform-D) δ 7.81 (s, 1H), 7.77 (s, 1H), 7.70 (s, 1H), 7.14 (s, 1H), 7.10 (s, 1H), 6.97 (s, 1H), 6.65 (s, 1H), 4.14-4.087 (m, 1H), 4.080 (brs, 1H), 3.90 (s, 3H), 3.81-3.77 (m, 2H), 3.79 (s, 3H), 3.75-3.73 (m, 1H), 3.57 (brs, 1H), 3.48-3.44 (m, 2H), 3.10 (s, 3H), 2.43-2.40 (m, 2H), 2.19 (s, 3H), 2.02-1.99 (m, 1H). |
| 143 | 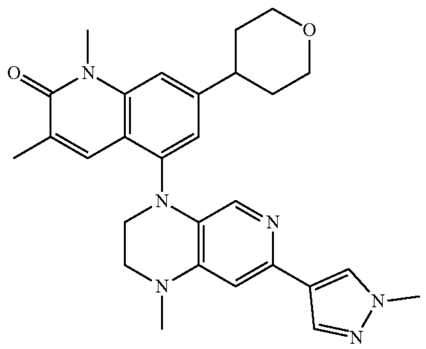 | C | LC-MS: 485.4 [M + H]$^+$; 1H-NMR (600 MHZ, Chloroform-D) δ 7.82 (s, 1H), 7.77 (s, 1H), 7.72 (s, 1H), 7.17 (s, 1H), 7.06 (s, 1H), 6.949 (d, J = 1.2 Hz, 1H ), 6.66 (s, 1H), 4.09-4.07 (m, 2H), 3.90 (s, 3H), 3.77 (s, 3H), 3.76-3.72 (m, 2H), 3.58-3.43 (m, 4H), 3.11 (s, 3H), 2.86-2.82 (m, 1H), 2.20 (d, J = 1.2 Hz, 3H), 1.85-1.78 (m, 4H). |

-continued

| Example | Structure | Coupling Method | Analytical data |
|---|---|---|---|
| 144 | 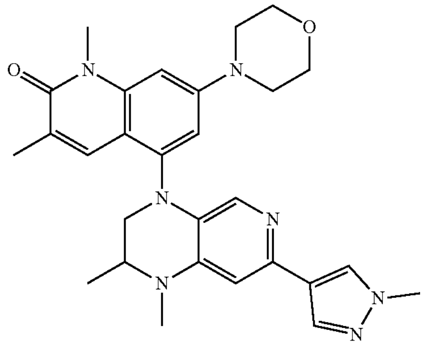 | C | LC-MS: 500.4 [M + H]$^+$; 1H-NMR (400 MHZ, Chloroform-D) δ 7.95 (s, 1H), 7.75 (s, 1H), 7.55 (s, 1H), 6.85-6.82 (m, 2H), 6.71 (s, 2H), 3.82 (s, 3H), 3.81 (s, 1H), 3.77-3.75 (m, 5H), 3.66 (s, 3H), 3.31 (brs, 6 Hz ), 3.04 (s, 3H), 2.02 (s, 3H), 3.69-3.50 (m, 3H), 3.24 (d, J = 4 Hz, 4H), 2.18 (d, J = 1.2 Hz, 3H). |

Example-145: 7-Hydroxy-1,3-dimethyl-5-(1-methyl-7-(1-methyl-1H-pyrazol-4-yl)-2,3-dihydropyrido[3,4-b]pyrazin-4(1H)-yl)quinolin-2(1H)-one

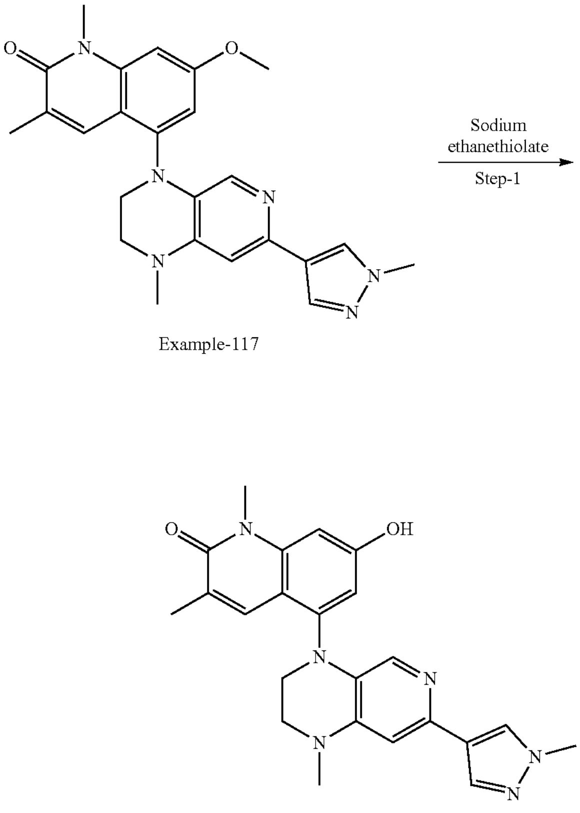

Example-117

Example-145

A solution of 7-methoxy-1,3-dimethyl-5-(1-methyl-7-(1-methyl-1H-pyrazol-4-yl)-2,3-dihydropyrido[3,4-b]pyrazin-4(1H)-yl)quinolin-2(1H)-one (500 mg, 1.16 mmol) in DMF (25 mL) was added Sodium ethanethiolate (980 mg, 11.6 mmol). The mixture was stirred at 110° C. for 12 h. The reaction mixture was then cooled to room temperature and quenched with saturated ammonium chloride solution, washed with brine, dried over sodium sulphate, concentrated to get crude residue. Residue was purified by preparative TLC using 10% methanol in DCM as eluent (10 mg). LC-MS: 549.4 [M+H]$^+$; 1H-NMR (300 MHz, DMSO-D6) δ 8.05 (s, 1H), 7.81 (s, 1H), 7.65 (s, 1H), 7.0 (s, 1H), 6.81 (s, 1H), 6.75 (s, 1H), 6.50 (s, 1H), 3.82 (s, 3H), 3.69-3.45 (m, 8H), 3.03 (s, 3H), 2.02 (s, 3H).

Example-146: 7-((1S,4S)-2-oxa-5-azabicyclo[2.2.1]heptan-5-yl)-1,3-dimethyl-5-(1-methyl-7-(1-methyl-1H-pyrazol-4-yl)-2,3-dihydropyrido[3,4-b]pyrazin-4(1H)-yl)quinolin-2(1H)-one

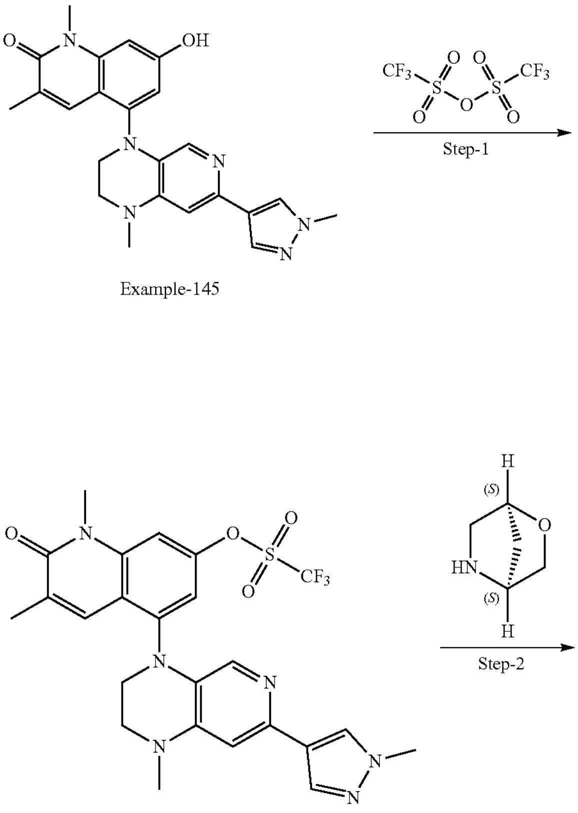

Example-145

-continued

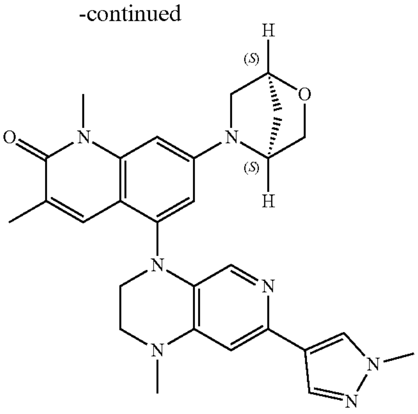

Example-146

Step-1: Synthesis of 1,3-dimethyl-5-(1-methyl-7-(1-methyl-1H-pyrazol-4-yl)-2,3-dihydropyrido[3,4-b]pyrazin-4(1H)-yl)-2-oxo-1,2-dihydroquinolin-7-yl trifluoromethanesulfonate A solution of 7-hydroxy-1,3-dimethyl-5-(1-methyl-7-(1-methyl-1H-pyrazol-4-yl)-2,3-dihydropyrido[3,4-b]pyrazin-4(1H)-yl)quinolin-2(1H)-one (450 mg, 1.08 mmol) in DCM (10 mL) was cooled to 0° C. and added pyridine (210 mg, 2.7 mmol) followed by dropwise addition of trifluoromethanesulfonic anhydride (460 mg, 1.62 mmol). The reaction mixture was added water after 3 h, organic portion was washed with saturated sodium bicarbonate solution and brine solution, dried over sodium sulphate and concentrated to dryness to get residue. The residue was purified by silica gel (60-120 mesh) column chromatography using 70-80% ethyl acetate in hexane as eluent. This afforded title compound (400 mg, 67.52%). LC-MS: 549.4 $[M+H]^+$.

Step-2: Synthesis of 7-((1S,4S)-2-oxa-5-azabicyclo[2.2.1]heptan-5-yl)-1,3-dimethyl-5-(1-methyl-7-(1-methyl-1H-pyrazol-4-yl)-2,3-dihydropyrido[3,4-b]pyrazin-4(1H)-yl)quinolin-2(1H)-one This compound was prepared using the similar protocol described in COUPLING METHOD-C using 1,3-dimethyl-5-(1-methyl-7-(1-methyl-1H-pyrazol-4-yl)-2,3-dihydropyrido[3,4-b]pyrazin-4(1H)-yl)-2-oxo-1,2-dihydroquinolin-7-yl trifluoromethanesulfonate & (1S,4S)-2-oxa-5-azabicyclo[2.2.1]hepta with appropriate variations in reactants, quantities of reagents, solvents and reaction conditions (40 mg, 29.77%). LC-MS: 498.6 $[M+H]^+$; 1H-NMR (400 MHz, Chloroform-D) δ 7.83 (s, 1H), 7.79 (s, 1H), 7.6 (s, 1H), 7.9-3 (s, 1H), 7.20 (s, 1H), 7.65 (s, 1H), 7.48 (s, 1H), 4.70 (s, 1H), 4.5-4.42 (m, 1H), 3.92 (s, 3H), 3.89 (s, 1H), 3.80-3.70 (m, 4H), 3.62-3.52 (s, 2H), 3.39-3.48 (m, 2H), 3.25-3.21 (m, 2H), 3.1 (s, 3H), 2.15 (s, 3H), 2.04-1.97 (brs, 2H).

The below examples (147-150) were prepared according to the protocols described in the synthesis of Example-147 with appropriate variations in reactants, quantities of reagents, solvents and reaction conditions with appropriate coupling methods.

| Example | Structure | Coupling Method | Analytical data |
|---|---|---|---|
| 147 | 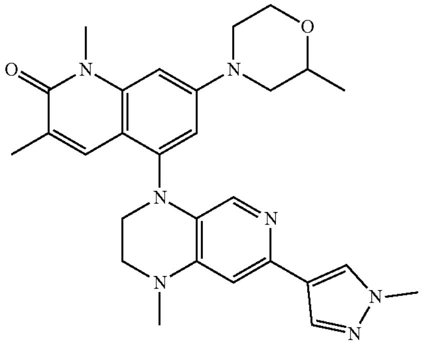 | — | LC-MS: 500.4 $[M + H]^+$; 1H-NMR (600 MHZ, Chloroform-D) δ 7.81 (s, 1H), 7.50 (s, 1H), 7.10 (s, 1H), 6.66-6.64 (m, 2H), 6.59 (s, 1H), 4.03 (d, J = 2.4 Hz, 1H ), 4.01 (d, J = 2.4 Hz, 1H), 3.91 (s, 3H), 3.85 (brs, 1H), 3.79-3.76 (m, 3H), 3.74 (s, 3H), 3.59-3.45 (m, 3H), 3.19 (s, 3H), 2.96-2.92 (m, 1H), 2.62-2.58 (m, 1H), 2.21-2.19 (m, 1H), 2.16 (s, 3H), 1.25 (s, 3H). |
| 148 | 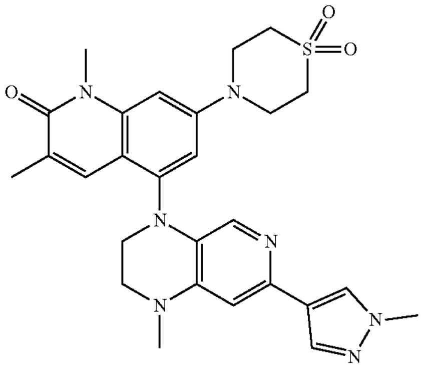 | C | LC-MS: 534.5 $[M + H]^+$; 1H-NMR (400 MHz, Chloroform-D) δ 7.81-7.79 (m, 2H), 7.63 (s, 1H), 7.26-7.25 (s, 1H), 6.66-6.59 (4H), 3.91-3.87 (m, 7H), 3.72-3.71 (m, 5H), 3.59 (brs, 1H), 3.44 (brs, 1H), 3.13-3.10 (7H), 2.18 (s, 3H). |

-continued

| Example | Structure | Coupling Method | Analytical data |
|---|---|---|---|
| 149 | 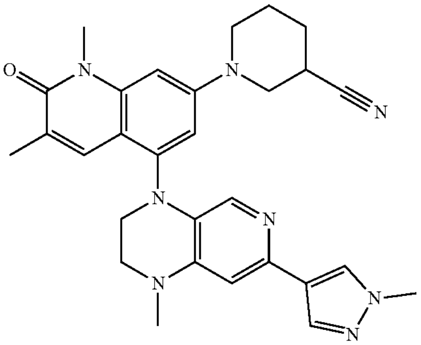 | C | LC-MS: 509.3 [M + H]$^+$; 1H-NMR (400 MHZ, Chloroform-D) δ 7.82 (s, 1H), 7.81 (s, 1H), 7.78 (s, 1H), 7.61 (s, 1H), 7.23 (s, 1H), 6.67 (d, J = 1.6 Hz, 1H), 6.65 (s, 1H), 6.59 (d, J = 2 Hz, 1H), 3.90 (s, 3H), 3.73 (s, 3H), 3.62-3.53 (m, 3H), 3.49-3.27 (m, 3H), 3.25-3.15 (m, 2H), 3.11 (s, 3H), 2.90 (brs, 2H), 2.17 (s, 3H), 2.09-1.90 (m, 2H). |
| 150 | 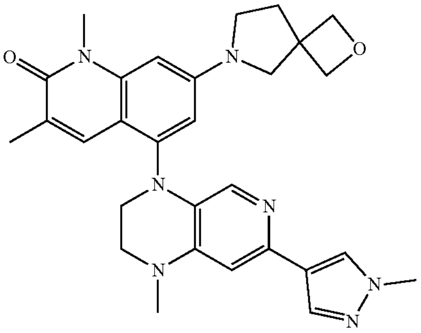 | C | LC-MS: 512.2 [M + H]$^+$; 1H-NMR (600 MHZ, Chloroform-D) δ 7.81 (s, 1H), 7.77 (s, 1H), 7.6 (s, 1H), 7.24 (s, 1H), 6.64 (s, 1H), 6.32 (s, 1H), 6.16 (s, 1H), 4.72 (d, J = 6 Hz, 2H), 4.66 (d, J = 6 Hz, 2H), 3.9 (s, 3H), 3.76-3.74 (m, 2H), 3.72 (s, 3H), 3.60 (s, 2H), 3.42-3.32 (m, 4H), 3.10 (s, 3H), 2.34-2.32 (m, 2H), 2.15 (s, 3H). |

Example-151: 7-Isopropyl-1,3-dimethyl-5-(1-methyl-7-(1-methyl-1H-pyrazol-4-yl)-2,3-dihydropyrido[3,4-b]pyrazin-4(1H)-yl)quinolin-2(1H)-one

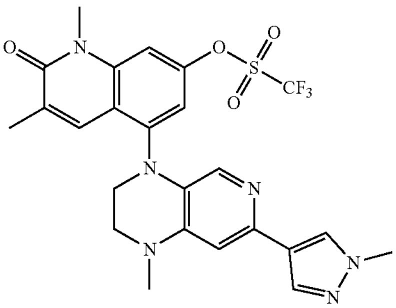

E147a

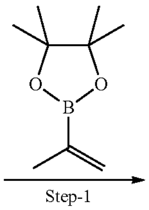

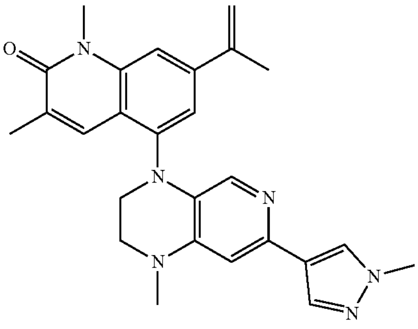

E151a

Step-2

-continued

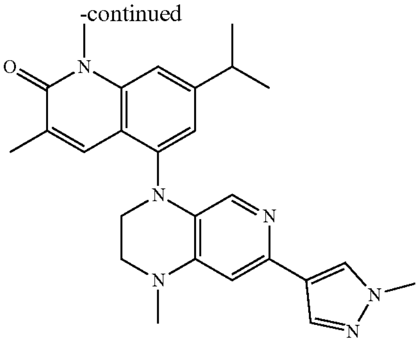

Example-151

Step-1: Synthesis of 1,3-dimethyl-5-(1-methyl-7-(1-methyl-1H-pyrazol-4-yl)-2,3-dihydropyrido[3,4-b]pyrazin-4(1H)-yl)-7-(prop-1-en-2-yl)quinolin-2(1H)-one A degassed solution of 1,3-dimethyl-5-(1-methyl-7-(1-methyl-1H-pyrazol-4-yl)-2,3-dihydropyrido[3,4-b]pyrazin-4(1H)-yl)-2-oxo-1,2-dihydroquinolin-7-yl trifluoromethanesulfonate (150 mg, 0.27 mmol), 4,4,5,5-tetramethyl-2-(prop-1-en-2-yl)-1,3,2-dioxaborolane (230 mg, 1.35 mmol) in DMF (8 mL) was added potassium carbonate (110 mg, 0.81 mmol) and Pd(DPPF)$Cl_2$ (20 mg, 0.03 mmol) and heated to 100° C. for 12 h. The reaction mixture was passed through celite pad, washed with 10% methanol in DCM, filtrate concentrated to get crude title compound (100 mg). LC-MS: 441.5 [M+H]$^+$.

Step-2: Synthesis of 7-isopropyl-1,3-dimethyl-5-(1-methyl-7-(1-methyl-1H-pyrazol-4-yl)-2,3-dihydropyrido[3,4-b]pyrazin-4(1H)-yl)quinolin-2(1H)-one A solution of 1,3-dimethyl-5-(1-methyl-7-(1-methyl-1H-pyrazol-4-yl)-2,3-dihydropyrido[3,4-b]pyrazin-4(1H)-yl)-7-(prop-1-en-2-yl)quinolin-2(1H)-one (100 mg, 0.23 mmol) in ethanol (10 mL) was added 10% Pd—C (120 mg) and stirred under the positive pressure of hydrogen using a bladder and stirred for 1 h. The reaction mixture was then filtered through celite and washed with 10% methanol in DCM. The filtrate was concentrated to get crude compound. The crude compound was purified by preparative HPLC to get pure title compound (7 mg, 6.8%) LC-MS: 443.7 $[M+H]^+$; 1H-NMR (400 MHz, Chloroform-D) δ 7.81 (s, 1H), 7.78 (s, 1H), 7.69 (s, 1H), 7.13 (s, 1H), 7.073 (s, 1H), 6.95 (d, J=0.8 Hz, 1H), 6.64 (s, 1H), 3.89 (s, 3H), 3.77 (s, 3H), 3.74 (brs, 2H), 3.57 (brs, 1H), 3.46 (brs, 1H), 3.10 (s, 3H), 2.99-2.96 (m, 1H), 2.18 (d, J=1.2 Hz, 3H), 1.28 (d, J=7.2 Hz, 3H), 1.245 (s, 3H).

The examples (152-154) were prepared according to the protocols described in the synthesis of Example-151 with appropriate variations in reactants, quantities of reagents, solvents and reaction conditions with appropriate coupling methods.

| Example | Structure | Spectral data |
|---|---|---|
| 152 | 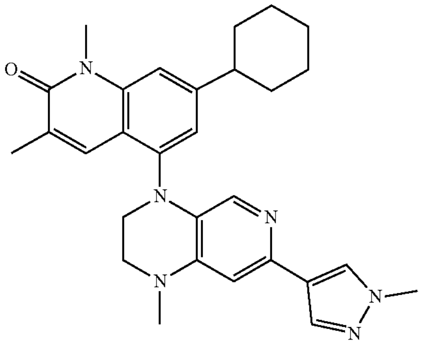 [SMILES: Cc1cc2c(N3CCN(C)c4cc(-c5cnn(C)c5)ncc43)cc(C3CCCCC3)cc2n(C)c1=O] | LC-MS: 483.2 $[M + H]^+$; 1H-NMR (400 MHz, Chloroform-D) δ 7.81 (s, 1H), 7.78 (s, 1H), 7.69 (s, 1H), 7.16 (s, 1H), 7.05 (s, 1H), 6.94 (s, 1H), 6.64 (s, 1H), 3.90 (s, 3H), 3.77 (s, 3H), 3.74-3.72 (m, 2H), 3.57-3.55 (m, 1H), 3.47-3.43 (m, 1H), 3.10 (s, 3H), 2.59-2.55 (m, 1H), 2.18 (s, 3H), 1.90-1.83 (s, 4H), 1.46-1.35 (m, 4H), 1.28-1.23 (m, 2H). |
| 153 | 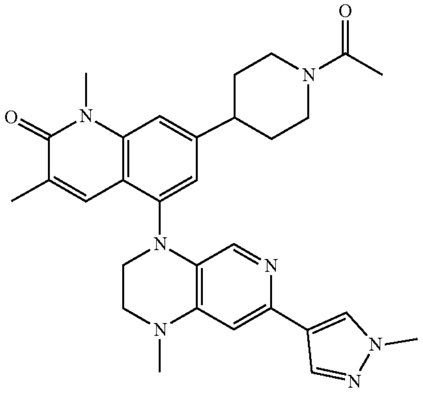 [SMILES: CC(=O)N1CCC(c2cc(N3CCN(C)c4cc(-c5cnn(C)c5)ncc43)c3cc(C)c(=O)n(C)c3c2)CC1] | LC-MS: 526.4 $[M + H]^+$; 1H-NMR (400 MHz, Chloroform-D) δ 7.82 (s, 1H), 7.70 (s, 1H), 7.23 (s, 1H), 7.16 (s, 1H), 7.03 (d, J = 5.2 Hz, 1H), 6.90 (s, 1H), 6.65 (s, 1H), 4.81-4.79 (m, 1H), 3.92 (brs, 1H), 3.90 (s, 3H), 3.76 (s, 3H), 3.74 (s, 2H), 3.57 (brs, 1H), 3.18-3.14 (m, 1H), 3.11 (s, 3H), 2.82 (brs, 2H), 2.63-2.59 (m, 1H), 2.20 (s, 3H), 2.12 (s, 3H), 1.90 (brs, 2H), 1.68 (s, 2H). |
| 154 | 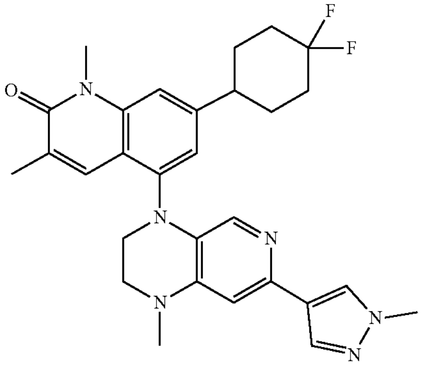 [SMILES: Cc1cc2c(N3CCN(C)c4cc(-c5cnn(C)c5)ncc43)cc(C3CCC(F)(F)CC3)cc2n(C)c1=O] | LC-MS: 519.2 $[M + H]^+$; 1H-NMR (400 MHz, Chloroform-D) δ 7.81-7.79 (m, 2H), 7.69 (s, 1H), 7.14 (s, 1H), 7.04 (s, 1H), 6.92 (s, 1H), 6.64 (s, 1H), 3.89 (s, 3H), 3.76 (s, 5H), 3.57-3.45 (m, 2H), 3.10 (s, 3H), 2.67 (brs, 2H), 2.18 (brs, 5H), 1.93-1.79 (m, 5H). |

Example-155: 7-(3-Hydroxyprop-1-yn-1-yl)-1,3-dimethyl-5-(1-methyl-7-(1-methyl-1H-pyrazol-4-yl)-2,3-dihydropyrido[3,4-b]pyrazin-4(1H)-yl)quinolin-2(1H)-one

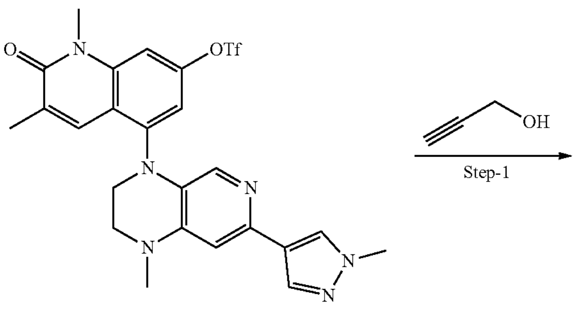

E147a

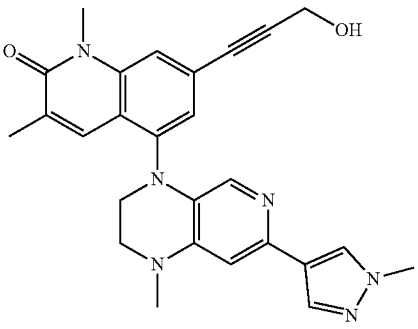

Example-155

A degassed solution of 1,3-dimethyl-5-(1-methyl-7-(1-methyl-1H-pyrazol-4-yl)-2,3-dihydropyrido[3,4-b]pyrazin-4(1H)-yl)-2-oxo-1,2-dihydroquinolin-7-yl trifluoromethanesulfonate (40 mg, 0.07 mmol) and prop-2-yn-1-ol (10 mg, 110 mmol) in DMF was added CuI (10 mg, 0.04 mmol), trimethylamine (20 mg, 0.21 mmol) and $Pd(PPh_3)_2C_{12}$ (10 mg, 10 mmol). The mixture was heated to 100° C. for 12 h and cooled to room temperature, extracted with ethyl acetate, washed with ice cold water and brine solution, dried over sodium sulphate and concentrated to get the crude compound. The crude was purified by preparative HPLC to give pure title compound (20 mg, 62.8%) LC-MS: 455.3 $[M+H]^+$; 1H-NMR (600 MHz, Chloroform-D) δ 7.93 (s, 1H), 7.82 (s, 1H), 7.69 (s, 1H), 7.2 (s, 2H), 7.05 (s, 1H), 6.65 (s, 1H), 4.45 (s, 2H), 3.9 (s, 3H), 3.72 (s, 5H), 3.56 (s, 1H), 3.46 (s, 1H), 3.13 (s, 3H), 2.21 (s, 3H).

Example-156: 7-Isopropoxy-1,3-dimethyl-5-(1-methyl-7-(1-methyl-1H-pyrazol-4-yl)-2,3-dihydropyrido[3,4-b]pyrazin-4(1H)-yl)quinolin-2(1H)-one

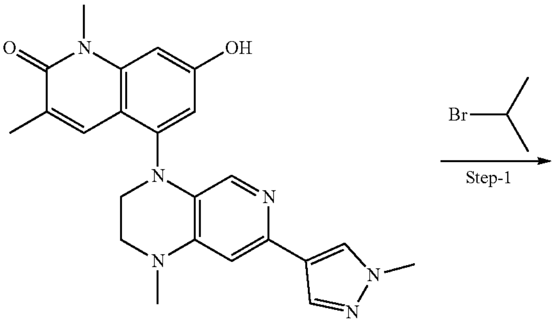

Example-146

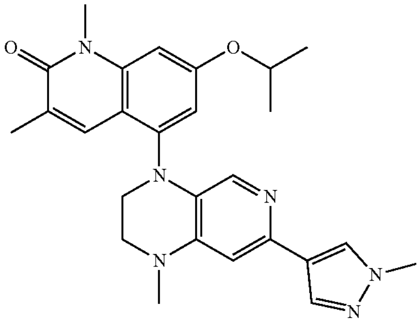

Example-156

A solution of 7-hydroxy-1,3-dimethyl-5-(1-methyl-7-(1-methyl-1H-pyrazol-4-yl)-2,3-dihydropyrido[3,4-b]pyrazin-4(1H)-yl)quinolin-2(1H)-one (300 mg, 0.72 mmol), 2-bromopropane (130 mg, 1.08 mmol) in DMF (3 mL) was added $Cs_2CO_3$ (700 mg, 2.16 mmol). The reaction mixture was stirred at 80° C. for 12 h. Then the reaction mixture was extracted with 10% methanol in DCM, organic portion was washed with brine solution, dried over $Na_2SO_4$ and concentrated to get the residue. The residue was purified by preparative HPLC to give title compound (5 mg, 1.51%)). LC-MS: 459.5 $[M+H]^+$; 1H-NMR (400 MHz, Chloroform-D) 7.81-7.79 (m, 2H), 7.65 (s, 1H), 7.26-7.23 (m, 1H), 6.68 (d, J=2.4 Hz, 1H), 6.64 (s, 1H), 6.61 (d, J=1.6 Hz, 1H), 4.62-4.59 (m, 1H), 3.90 (s, 3H), 3.71 (s, 3H), 3.70 (s, 2H), 3.59 (brs, 1H), 3.48 (brs, 1H), 3.09 (s, 3H), 2.16 (d, J=0.8 Hz, 3H), 1.36-1.34 (m, 6H).

The examples (157 & 159) were prepared according to the protocols described in the synthesis of Example-156 with appropriate variations in reactants, quantities of reagents, solvents and reaction conditions with appropriate coupling methods.

| Example | Structure | Spectral data |
|---|---|---|
| 157 | 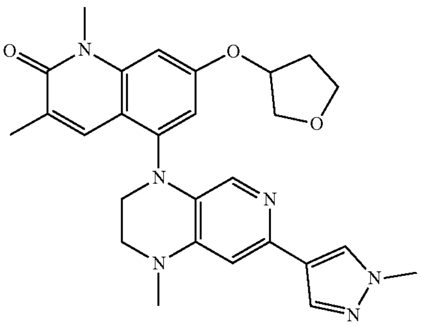 [SMILES: Cc1cc2c(N3CCN(C)c4cc(-c5cnn(C)c5)ncc43)cc(OC3CCOC3)cc2n(C)c1=O] | LC-MS: 487.3 [M + H]$^+$; 1H-NMR (300 MHz, Chloroform-D) δ 7.82 (s, 1H), 7.77 (s, 1H), 7.67 (s, 1H), 7.27 (s, 1H), 6.65 (s, 2H), 6.59 (s, 1H), 5.0 (brs, 1H), 3.99-3.91 (m, 4H), 3.91 (s, 3H), 3.71 (s, 3H), 3.70-3.62 (m, 2H), 3.49 (s, 1H), 3.1 (s, 3H), 2.45 (s, 1H), 2.18 (m, 1H), 2.17 (s, 3H), 2.16-2.05 (m, 1H). |
| 158 | 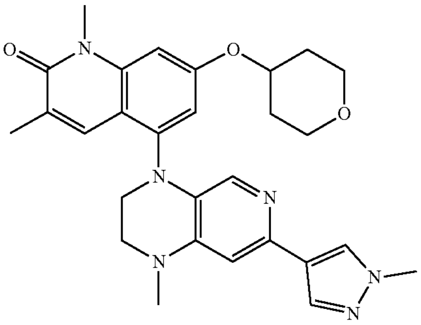 [SMILES: Cc1cc2c(N3CCN(C)c4cc(-c5cnn(C)c5)ncc43)cc(OC3CCOCC3)cc2n(C)c1=O] | LC-MS: 501.4 [M + H]$^+$; 1H-NMR (400 MHz, Chloroform-D) δ 7.82 (s, 1H), 7.77 (s, 1H), 7.66 (s, 1H), 7.24 (s, 1H), 6.71 (d, J = 1.6 Hz, 1H), 6.65 (t, J = 4.4, 2 Hz, 2H), 4.56 (m, 1H), 3.92-4.01 (m, 2H), 3.91 (s, 3H), 3.75 (brs, 2H), 3.72 (s, 3H), 3.59 (s, 3H), 3.45 (brs, 2H), 3.10 (s, 3H), 2.17 (s, 3H), 2.04 (brs, 1H), 1.8 (brs, 1H). |
| 159 | 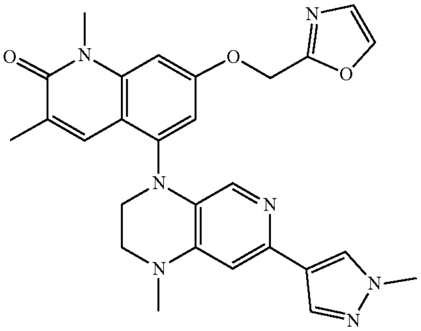 [SMILES: Cc1cc2c(N3CCN(C)c4cc(-c5cnn(C)c5)ncc43)cc(OCc3ncco3)cc2n(C)c1=O] | LC-MS [M + H]$^+$; 1H-NMR (400 MHz, Chloroform-D) δ 7.82-7.79 (m, 2H), 7.69-7.67 (m, 2H), 7.25-7.15 (m, 1H), 6.85 (d, J = 2 Hz, 1H), 6.72 (d, J = 4 Hz, 1H), 6.65 (s, 1H), 5.21 (s, 2H), 3.90 (s, 3H), 3.71 (s, 3H), 3.70-3.45 (m, 5H), 3.09 (s, 3H), 2.17 (s, 3H). |

Example-160: 4-(1,3-Dimethyl-7-morpholino-2-oxo-1,2-dihydroquinolin-5-yl)-1-methyl-7-(1-methyl-1H-pyrazol-4-yl)-1,2,3,4-tetrahydropyrido[3,4-b]pyrazine 6-oxide

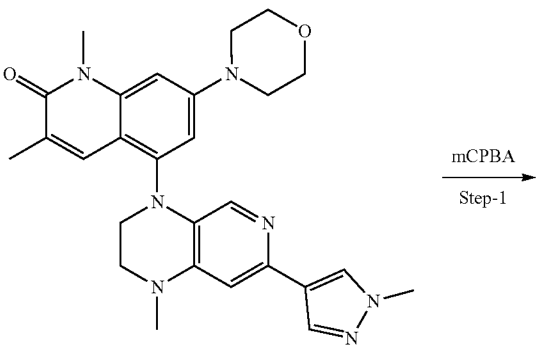

Example-135

-continued

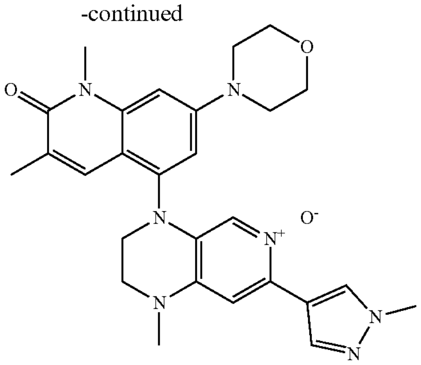

Example-160

A solution of 1,3-dimethyl-5-(1-methyl-7-(1-methyl-1H-pyrazol-4-yl)-2,3-dihydropyrido[3,4-b]pyrazin-4(1H)-yl)-7-morpholinoquinolin-2(1H)-one (200 mg, 0.41 mmol) in ethanol (5 mL) and Chloroform (5 mL) was cooled to 0° C. and the reaction mixture was stirred at 50° C. for 24 h. After which the mixture was basified with saturated sodium bicarbonate solution and extracted with ethyl acetate, organic portion was dried over sodium sulphate and concentrated to get the crude compound. The crude was purified by preparative HPLC to give the title compound (20 mg, 9.7%) LC-MS: [M+H]+; 1H-NMR (400 MHz, DMSO-d6) δ 8.22 (s, 1H), 8.05 (s, 1H), 8.00 (s, 1H), 7.82 (d, J=0.8 Hz, 2H), 6.98 (s, 1H), 6.85 (s, 1H), 4.43-4.40 (m, 2H), 4.31-4.20 (m, 3H), 3.82 (s, 3H), 3.80-3.78 (m, 2H), 3.73 (s, 3H), 3.63-3.60 (m, 3H), 3.07 (s, 3H), 2.88-2.86 (m, 2H), 2.12 (s, 3H).

Example-161: 1,3-Dimethyl-5-(7-(1-methyl-1H-pyrazol-4-yl)-2,3-dihydropyrido[3,4-b]pyrazin-4(1H)-yl)-7-morpholinoquinolin-2(1H)-one Example-162: 5-(1-Acetyl-7-(1-methyl-1H-pyrazol-4-yl)-2,3-dihydropyrido[3,4-b]pyrazin-4(1H)-yl)-1,3-dimethyl-7-morpholinoquinolin-2(1H)-one

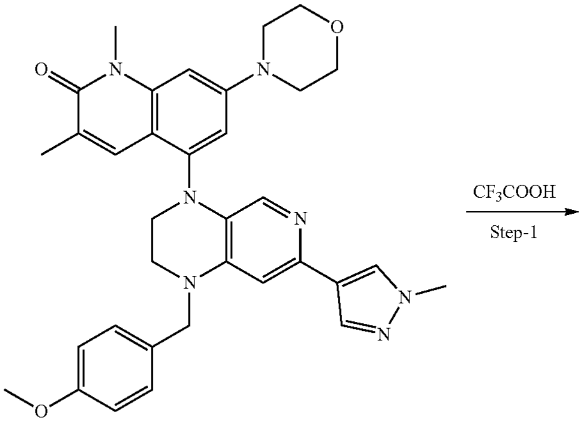

Example-136

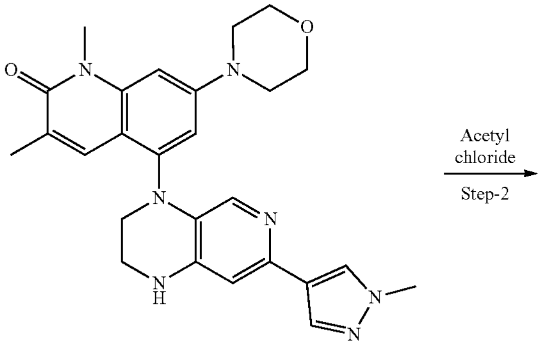

Example-161

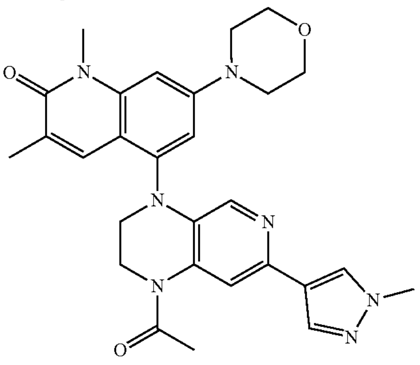
Example-162

Step-1: Synthesis of 1,3-dimethyl-5-(7-(1-methyl-1H-pyrazol-4-yl)-2,3-dihydropyrido[3,4-b]pyrazin-4(1H)-yl)-7-morpholinoquinolin-2(1H)-one A solution of 5-(1-(4-methoxybenzyl)-7-(1-methyl-1H-pyrazol-4-yl)-2,3-dihydropyrido[3,4-b]pyrazin-4(1H)-yl)-1,3-dimethyl-7-morpholinoquinolin-2(1H)-one (600 mg, 1.01 mmol) in TFA was heated to 100° C. for 2 h. TFA evaporated off, the residue was washed with ether to get the crude compound. The crude was purified by preparative HPLC to get the pure title compound (30 mg, 19%). LC-MS:472 [M+H]+; 1H-NMR (600 MHz, chloroform-D) δ 8.57 (s, 1H), 7.89 (s, 1H), 7.76 (s, 1H), 7.63 (s, 1H), 6.70-6.68 (m, 1H), 6.58 (d, J=1.2 Hz, 1H), 4.95 (brs, 1H), 3.90 (s, 3H), 3.87-3.86 (m, 4H), 3.74 (s, 3H), 3.72-3.70 (m, 4H), 3.57 (t, J=8.4, 4.8 Hz, 2H), 3.26 (d, J=3.6 Hz, 3H), 2.18 (s, 3H).

Step-2: Synthesis of 5-(1-acetyl-7-(1-methyl-1H-pyrazol-4-yl)-2,3-dihydropyrido[3,4-b]pyrazin-4(1H)-yl)-1,3-dimethyl-7-morpholinoquinolin-2(1H)-one This compound was prepared using the similar protocol described in Step-3 of Example-61 with appropriate variations in reactants, quantities of reagents, solvents and reaction conditions (20 mg, 35.4%). LC-MS: 514 $[M+H]^+$; 1H-NMR (400 MHz, Chloroform-D) δ 7.81 (s, 1H), 7.75 (s, 1H), 7.56 (s, 1H), 7.41 (s, 1H), 7.22 (s, 1H), 6.73 (d, J=2.4 Hz, 1H), 6.65 (d, J=1.6 Hz, 1H), 4.26 (brs, 2H), 4.0 (brs, 1H), 3.92 (s, 3H), 3.87-3.85 (m, 4H), 3.74 (s, 3H), 3.69 (brs, 2H), 3.26 (d, J=2.4 Hz, 3H), 2.45 (s, 3H), 2.17 (s, 3H).

Example-163: 5-(1-(Difluoromethyl)-7-(1-methyl-1H-pyrazol-4-yl)-2,3-dihydropyrido[3,4-b]pyrazin-4(1H)-yl)-1,3-dimethyl-7-morpholinoquinolin-2(1H)-one

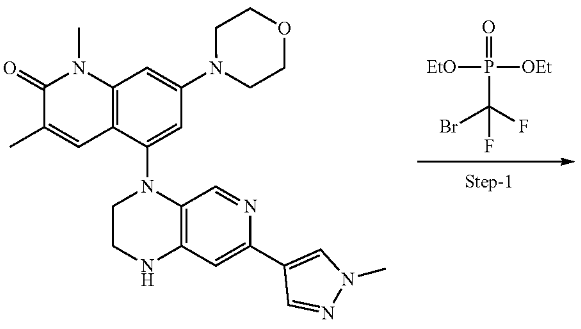

Example-161

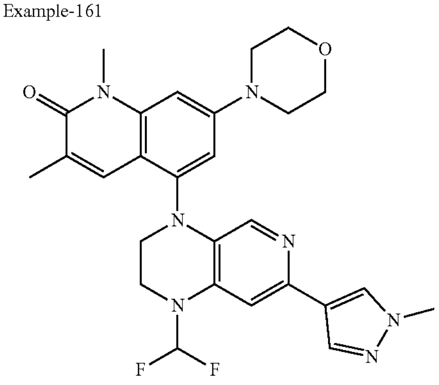
Example-163

A solution of 1,3-dimethyl-5-(7-(1-methyl-1H-pyrazol-4-yl)-2,3-dihydropyrido[3,4-b]pyrazin-4(1H)-yl)-7-morpholinoquinolin-2(1H)-one (20 mg, 0.04 mmol) in DCM (1 mL) was added CsF (10 mg, 0.04 mmol) followed by diethyl (bromodifluoromethyl)phosphonate (10 mg, 0.04 mmol) and stirred at room temperature for 12 h. water was added in reaction mixture and extracted with ethyl acetate, organic portion was washed with brine solution and dried over sodium sulphate and concentrated to get the crude. The crude was purified by preparative HPLC to get the pure title compound (5 mg, 24%). LC-MS: 522.2 $[M+H]^+$; 1H-NMR (400 MHz, Chloroform-D) δ 8.82 (s, 1H), 7.98 (s, 1H), 7.56 (s, 2H), 7.40 (s, 1H), 7.09 (s, 1H), 6.71-6.66 (m, 2H), 4.0 (s, 3H), 3.98 (s, 1H), 3.92-3.90 (m, 3H), 3.75 (s, 3H), 3.73 (s, 2H), 3.61-3.59 (m, 2H), 3.32-3.10 (m, 4H), 2.19 (s, 3H).

Example-164: 2-(4-(1,3-Dimethyl-7-morpholino-2-oxo-1,2-dihydroquinolin-5-yl)-7-(1-methyl-1H-pyrazol-4-yl)-3,4-dihydropyrido[3,4-b]pyrazin-1(2H)-yl) acetic acid

Example-165: 2-(4-(1,3-Dimethyl-7-morpholino-2-oxo-1,2-dihydroquinolin-5-yl)-7-(1-methyl-1H-pyrazol-4-yl)-3,4-dihydropyrido[3,4-b]pyrazin-1(2H)-yl)-N-methylacetamide

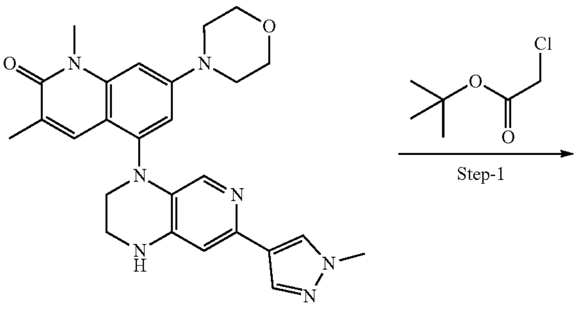

Example-161

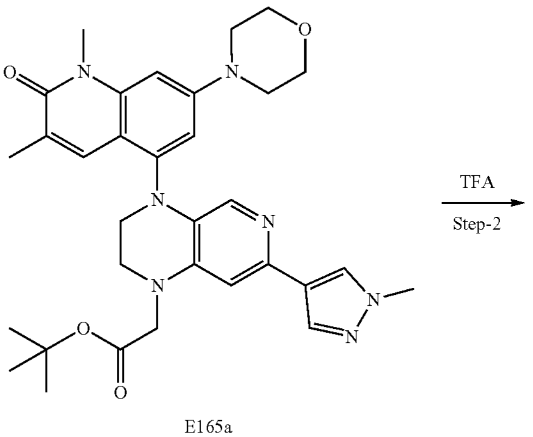

E165a

-continued

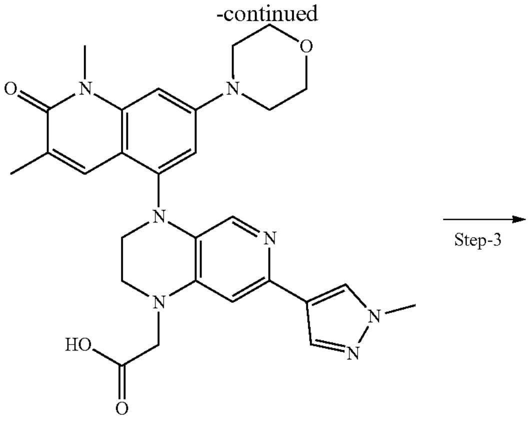

Example-164

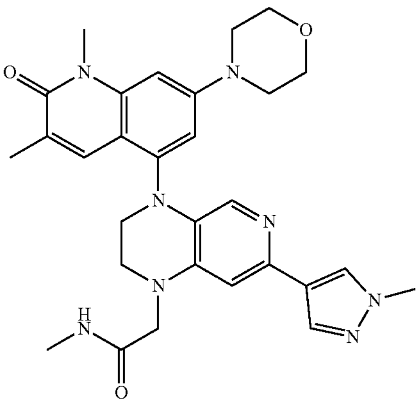

Example-165

Step-1: Synthesis of tert-butyl 2-(4-(1,3-dimethyl-7-morpholino-2-oxo-1,2-dihydroquinolin-5-yl)-7-(1-methyl-1H-pyrazol-4-yl)-3,4-dihydropyrido[3,4-b]pyrazin-1(2H)-yl)acetate A solution of 1,3-dimethyl-5-(7-(1-methyl-1H-pyrazol-4-yl)-2,3-dihydropyrido[3,4-b]pyrazin-4(1H)-yl)-7-morpholinoquinolin-2(1H)-one (500 mg, 1.06 mmol) in DMF (15 mL) was added $Cs_2CO_3$ (1040 mg, 3.18 mmol) followed by tert-butyl chloroacetate (210 mg, 1.38 mmol), the mixture was heated to 50° C. for 12 h. Then water was added to the reaction mixture and extracted with ethyl acetate, organic portion was washed with brine solution and dried over sodium sulphate and concentrated to get the crude. The crude compound was purified by Flash chromatography using 10% Methanol in DCM to get pure title compound (400 mg, 64.4%) LC-MS: 586.3 $[M+H]^+$.

Step-2: Synthesis of 2-(4-(1,3-dimethyl-7-morpholino-2-oxo-1,2-dihydroquinolin-5-yl)-7-(1-methyl-1H-pyrazol-4-yl)-3,4-dihydropyrido[3,4-b]pyrazin-1(2H)-yl)acetic acid A solution of tert-butyl 2-(4-(1,3-dimethyl-7-morpholino-2-oxo-1,2-dihydroquinolin-5-yl)-7-(1-methyl-1H-pyrazol-4-yl)-3,4-dihydropyrido[3,4-b]pyrazin-1(2H)-yl)acetate (200 mg, 0.34 mmol) in TFA (10 mL) was stirred at room temperature for 1 h. Solvent completely evaporated off to get residue. The residue was purified by preparative HPLC to get the pure title compound (100 mg, 55.54%) LC-MS:

530.6 [M+H]$^+$; 1H-NMR (400 MHz, DMSO-D6) δ 8.02 (s, 1H), 7.78 (s, 1H), 7.64 (s, 1H), 6.98 (s, 1H), 6.81 (s, 1H), 6.78 (d, J=1.6 Hz, 1H), 6.69 (s, 1H), 4.30 (s, 2H), 3.82 (s, 3H), 3.72-3.3.69 (m, 4H), 3.65 (s, 3H), 3.55-3.46 (m, 3H), 3.33 (s, 3H), 3.28-3.27 (m, 3H), 2.03 (s, 3H).

Step-3: Synthesis of 2-(4-(1,3-dimethyl-7-morpholino-2-oxo-1,2-dihydroquinolin-5-yl)-7-(1-methyl-1H-pyrazol-4-yl)-3,4-dihydropyrido[3,4-b]pyrazin-1(2H)-yl)-N-methylacetamide This compound was prepared using the similar protocol described in Example-69 (Step-3) with appropriate variations in reactants, quantities of reagents, solvents and reaction conditions (20 mg, 19.4%). LC-MS: 543.3 [M+H]$^+$; 1H-NMR (400 MHz, Chloroform-D) δ 7.77-7.72 (m, 2H), 7.61 (s, 1H), 7.34 (s, 1H), 6.67 (s, 1H), 6.58 (s, 1H), 6.52 (s, 1H), 6.40 (s, 1H), 4.03 (d, J=3.6 Hz, 2H), 3.89 (s, 3H), 3.86-3.80 (m, 6H), 3.73 (s, 3H), 3.66 (brs, 1H), 3.53 (brs, 1H), 3.23 (d, J=3.2 Hz, 4H), 2.90 (d, J=5.2 Hz, 3H), 2.17 (s, 3H).

Example-166: 5-(6-(4-Acetylpiperazin-1-yl)-3,4-dihydro-1,7-naphthyridin-1(2H)-yl)-7-methoxy-1,3-dimethylquinolin-2(1H)-one

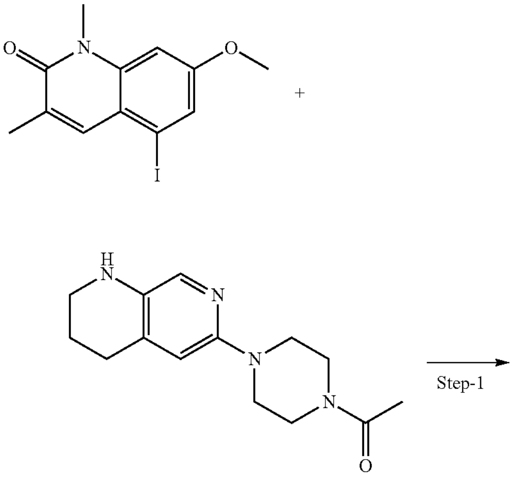

-continued

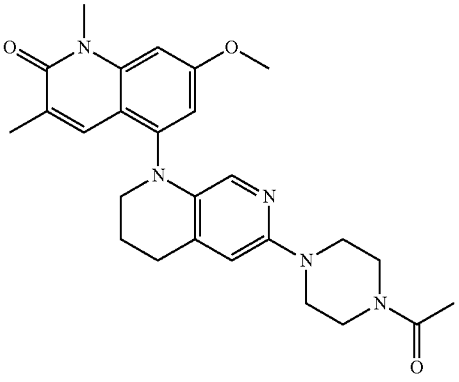

Example-166

A degassed solution of 5-iodo-7-methoxy-1,3-dimethylquinolin-2(1H)-one (380 mg, 1.15 mmol) & 1-(4-(1,2,3,4-tetrahydro-1,7-naphthyridin-6-yl)piperazin-1-yl)ethan-1-one (100 mg, 0.38 mmol) in 1,4-dioxane was added $NaOBu^t$ (110 mg, 1.15 mmol) followed by Pd2(dba)3 (36 mg, 0.038 mmol), Xantphos (23 mg, 0.038 mmol). The resultant mixture was stirred at 100° C. for 12 h, cooled to room temperature, water was added, extracted with ethyl acetate and organic portion was washed with brine solution and dried over sodium sulphate and concentrated to get the crude. The crude compound was purified by preparative HPLC to get the pure title compound (60 mg, 49.4%). LC-MS: 462 [M+H]$^+$; 1H-NMR (300 MHz, Chloroform-D) δ 7.66-7.65 (m, 1H), 7.20 (s, 1H), 6.66 (d, J=5.9 Hz, 2H), 6.46 (s, 1H), 3.85 (s, 3H), 3.73 (s, 5H), 3.54 (t, J=2.7, 2.7 Hz, 4H), 3.40 (d, J=2.8 Hz, 2H), 3.29 (d, J=2.3 Hz, 2H), 2.91 (s, 2H), 2.18 (s, 3H), 2.12 (s, 5H).

The below examples (167-171) were prepared according to the protocols described in the synthesis of Example-166 with appropriate variations in reactants, quantities of reagents, solvents and reaction conditions with appropriate coupling methods.

| Example | Structure | Coupling Method | Spectral data |
|---|---|---|---|
| 167 | 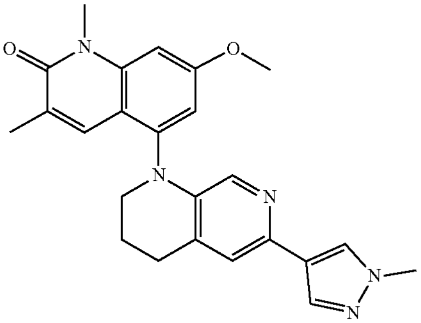 [SMILES: COc1cc(N2CCCc3cc(-c4cnn(C)c4)ncc32)c2cc(C)c(=O)n(C)c2c1] | — | LC-MS: 416.3 [M + H]$^+$; 1H-NMR (400 MHz, Chloroform-D) δ 7.81 (s, 1H), 7.75 (s, 1H), 7.57 (s, 1H), 7.42 (s, 1H), 7.17 (s, 1H), 6.75-6.71 (m, 2H), 3.91 (s, 3H), 3.87 (s, 3H), 3.75 (s, 3H), 3.59 (d, J = 4.3 Hz, 2H), 2.97 (d, J = 10.1 Hz, 2H), 2.18 (d, J = 1.2 Hz, 5H). |

-continued

| Example | Structure | Coupling Method | Spectral data |
|---|---|---|---|
| 168 | 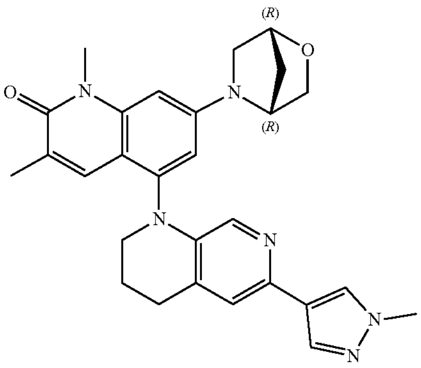 | A | LC-MS: 483.4 [M + H]$^+$; 1H-NMR (400 MHz, Chloroform-D) δ 8.36 (d, J = 2.4 Hz, 1H), 7.85-7.84 (d, J = 1.6 Hz, 1H), 7.50 (s, 1H), 7.23-7.19 (m, 1H), 7.07 (s, 1H), 6.40-6.34 (m, 2H), 4.73 (s, 1H), 4.55-4.51 (m, 1H), 3.95 (d, J = 2.4 Hz, 3H), 3.93-3.91 (m, 1H), 3.74 (d, J = 3.2 Hz, 3H), 3.71-3.68 (m, 2H), 3.62-3.58 (m, 1H), 3.31-3.25 (m, 1H), 3.18-3.15 (m, 2H), 2.28 (d, J = 4 Hz, 3H), 2.15 (s, 3H), 2.08-2.00 (m, 2H). |
| 169 | 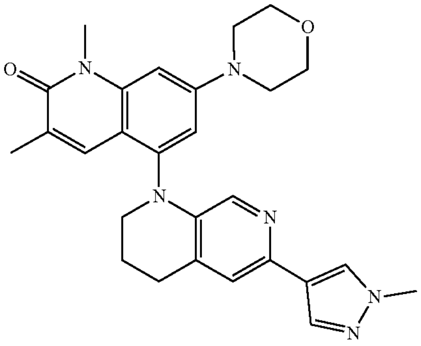 [SMILES: Cc1cc2c(N3CCCc4cc(-c5cnn(C)c5)ncc43)cc(N3CCOCC3)cc2n(C)c1=O] | C | LC-MS: 471 [M + H]$^+$; 1H-NMR (400 MHz, Chloroform-D) δ 7.80 (s, 2H), 7.51 (s, 1H), 7.41 (s, 1H), 7.18 (s, 1H), 6.72 (d, J = 1.8 Hz, 1H), 6.62 (s, 1H), 4.75 (brs, 1H), 3.91 (s, 3H), 3.88-3.84 (s, 4H), 3.74 (s, 3H), 3.60-3.56 (m, 3H), 3.27-3.24 (m, 4H), 2.98-2.26 (m, 1H), 2.36-2.20 (m, 1H), 2.17 (s, 3H). |
| 170 | 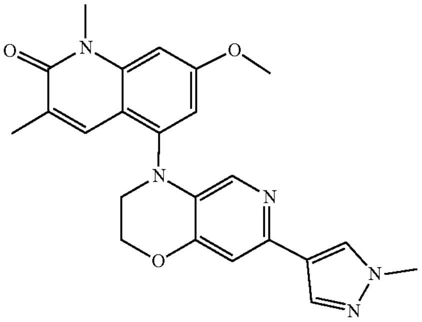 [SMILES: COc1cc(N2CCOc3cc(-c4cnn(C)c4)ncc32)c2cc(C)c(=O)n(C)c2c1] | A | LC-MS: 418 [M + H]$^+$; 1H-NMR (300 MHz, DMSO-D6) δ 8.14 (s, 1H), 7.89 (s, 1H), 7.79 (s, 1H), 7.26 (s, 2H), 6.932 (d, J = 7.5 Hz, 2H), 4.61 (s, 1H), 4.50 (s, 1H), 3.88 (s, 3H), 3.84 (s, 3H), 3.68 (s, 3H), 3.64 (s, 2H), 2.07 (s, 3H). |
| 171 | 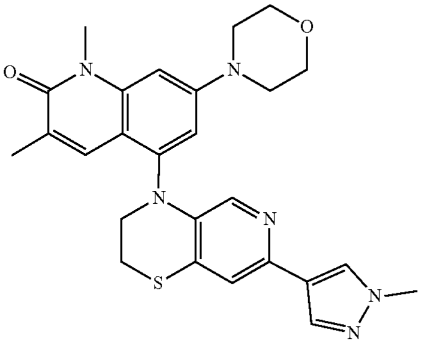 [SMILES: Cc1cc2c(N3CCSc4cc(-c5cnn(C)c5)ncc43)cc(N3CCOCC3)cc2n(C)c1=O] | C | LC-MS: 489 [M + H]$^+$; 1H-NMR (400 MHz, Chloroform-D) δ 7.80 (s, 1H), 7.79 (s, 1H), 7.54 (s, 1H), 7.41 (s, 1H), 7.25 (s, 1H), 6.63-6.59 (m, 2H), 3.9 (s, 3H), 3.87-3.84 (m, 4H), 3.73 (s, 3H), 3.65-3.29 (m, 4H), 3.24 (d, J = 2 Hz, 4H), 2.18 (s, 3H). |

Example-172: 1,3-Dimethyl-5-(7-(1-methyl-1H-pyrazol-4-yl)-1-oxido-2,3-dihydro-4H-pyrido[4,3-b][1,4]thiazin-4-yl)-7-morpholinoquinolin-2(1H)-one

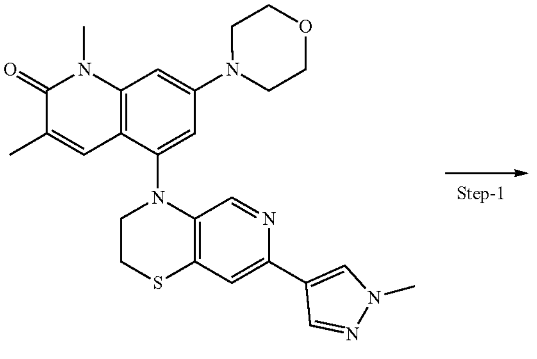

Example-171

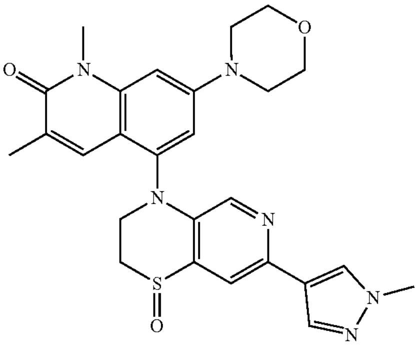

Example-172

A solution of 1,3-dimethyl-5-(7-(1-methyl-1H-pyrazol-4-yl)-2,3-dihydro-4H-pyrido[4,3-b][1,4]thiazin-4-yl)-7-morpholinoquinolin-2(1H)-one (150 mg, 0.31 mmol) in DCM (15 mL) was cooled to 0° C. and added mCPBA (160 mg, 0.93 mmol). The reaction mixture was stirred for 24 h at room temperature, basified with $NaHCO_3$, extracted with 10% methanol in DCM, dried over sodium sulphate and concentrated to get the mixture of 1,3-dimethyl-5-(7-(1-methyl-1H-pyrazol-4-yl)-1-oxido-2,3-dihydro-4H-pyrido[4,3-b][1,4]thiazin-4-yl)-7-morpholinoquinolin-2(1H)-one and 1,3-dimethyl-5-(7-(1-methyl-1H-pyrazol-4-yl)-1,1-dioxido-2,3-dihydro-4H-pyrido[4,3-b][1,4]thiazin-4-yl)-7-morpholinoquinolin-2(1H)-one. Further this mixture was purified by preparative HPLC to get the pure title compound (20 mg, 33.03%) LC-MS: 504.6 $[M+H]^+$; 1H-NMR (600 MHz, Chloroform-D) δ 7.85 (s, 1H), 7.75 (d, J=5.4 Hz, 2H), 7.66 (d, J=6.6 Hz, 1H), 7.46-7.40 (m, 1H), 6.78 (s, 1H), 6.72-6.68 (m, 1H), 4.42-4.36 (m, 1H), 3.93 (s, 3H), 3.87-3.86 (m, 4H), 3.76 (s, 3H), 3.70-3.67 (m, 1H), 3.38-3.31 (m, 1H), 3.28 (d, J=4.2 Hz, 4H), 3.13-3.09 (m, 1H), 2.18 (s, 3H).

Example-173: 4-(1,3-Dimethyl-7-morpholino-2-oxo-1,2-dihydroquinolin-5-yl)-7-(1-methyl-1H-pyrazol-4-yl)-3,4-dihydro-2H-pyrido[4,3-b][1,4]thiazine 6-oxide 1,1-dioxide

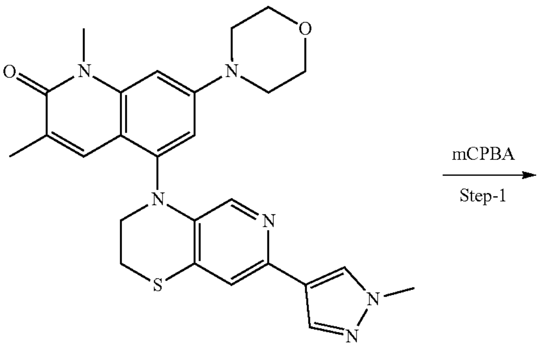

Example-171

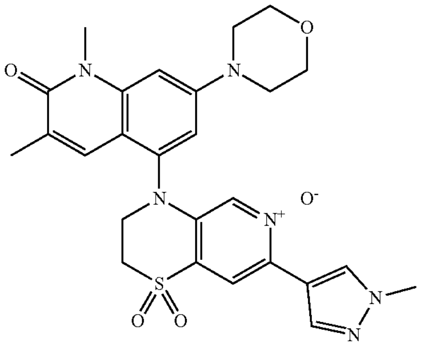

Example-173

A solution of 1,3-dimethyl-5-(7-(1-methyl-1H-pyrazol-4-yl)-2,3-dihydro-4H-pyrido[4,3-b][1,4]thiazin-4-yl)-7-morpholinoquinolin-2(1H)-one (100 mg, 0.31 mmol) in DCM (10 mL) was cooled to 0° C. and added mCPBA (70 mg, 0.4 mmol). The reaction mixture was stirred for 42 h at room temperature, basified with $NaHCO_3$, extracted with 10% methanol in DCM, dried over sodium sulphate and concentrated to get crude compound. The crude compound was purified by preparative HPLC to get the pure title compound (20 mg, 18.6%). LC-MS: 536.6 $[M+H]^+$; 1H-NMR (600 MHz, Chloroform-D) δ 8.60 (s, 1H), 7.88 (s, 1H), 7.81 (s, 1H), 7.77 (s, 1H), 7.57-7.55 (m, 3H), 4.75-4.71 (m, 2H), 4.35-4.32 (m, 1H), 4.21-4.18 (m, 1H), 4.0-3.95 (m, 3H), 3.93 (s, 3H), 3.91 (s, 1H), 3.86 (s, 3H), 3.68-3.59 (m, 2H), 3.17-3.14 (m, 2H), 2.26 (s, 3H).

Example-174: 6-(4-Acetylpiperazin-1-yl)-7-(difluoromethyl)-1',3'-dimethyl-7'-morpholino-3,4-dihydro-2H-[1,5'-biquinolin]-2'(1'H)-one

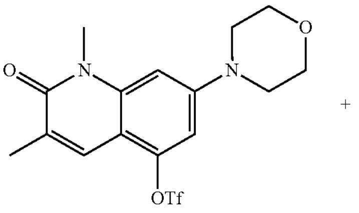

-continued

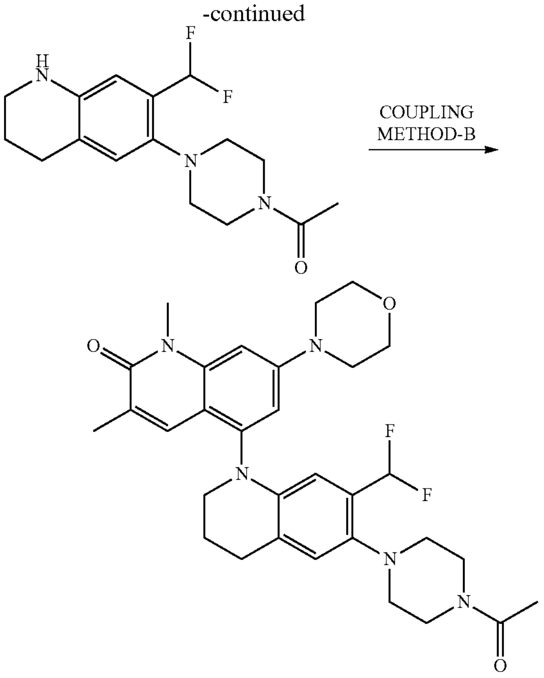

Example-174

A degassed solution of 1,3-dimethyl-7-morpholino-2-oxo-1,2-dihydroquinolin-5-yl trifluoromethanesulfonate (70 mg, 0.16 mmol) & 1-(4-(7-(difluoromethyl)-1,2,3,4-tetrahydroquinolin-6-yl)piperazin-1-yl)ethan-1-one (50 mg, 0.16 mmol) in 1,4-Dioxane (3 mL) was added $Pd_2(dba)_3$ (20 mg, 0.002 mmol), Xantphos (10 mg, 0.02 mmol) and Caesium carbonate (160 mg, 0.49 mmol). The mixture was stirred at 100° C. for 12 h. Then the mixture was filtered through celite, and concentrated to get the residue. The residue was purified by preparative HPLC to afford pure compound (16 mg, 17.6%). LC-MS: 566.3$[M+H]^+$; 1H-NMR (400 MHz, Chloroform-D) δ 7.91 (s, 1H), 7.38 (d, J=1.2 Hz, 1H), 6.84 (s, 1H), 6.15 (s, 1H), 4.39 (s, 3H), 3.83-3.77 (m, 6H), 3.67 (s, 3H), 3.56 (d, J=4.6 Hz, 4H), 3.03 (d, J=6.6 Hz, 2H), 2.18-2.14 (m, 2H), 2.10 (d, J=1.2 Hz, 3H).

The below examples (175-191) were prepared according to the protocols described in the synthesis of Example-174 with appropriate variations in reactants, quantities of reagents, solvents and reaction conditions with appropriate coupling methods.

| Example | Structure | Coupling Method | Spectral data |
|---|---|---|---|
| 175 | 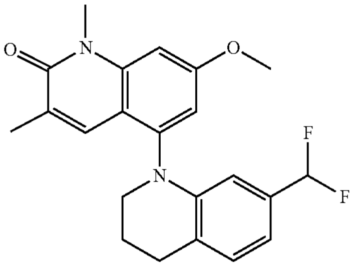 [SMILES: COc1cc(N2CCCc3ccc(C(F)F)cc32)c2cc(C)c(=O)n(C)c2c1] | A | LC-MS: 385.1 $[M + H]^+$; 1H-NMR (300 MHz, Chloroform-D) δ 7.54 (d, J = 1.1 Hz, 1H), 7.13 (d, J = 6.6 Hz, 1H), 6.79 (d, J = 1.3 Hz, 1H), 6.76 (d, J = 0.7 Hz, 1H), 6.71 (s, 1H), 6.19 (d, J = 1.2 Hz, 1H), 3.88 (s, 3H), 3.75 (s, 3H), 3.56 (d, J = 5.2 Hz, 2H), 2.99 (s, 2H), 2.17 (d, J = 1.2 Hz, 3H), 2.13 (d, J = 4.9 Hz, 2H), 6.33-6.31 (m, 1H). |
| 176 | 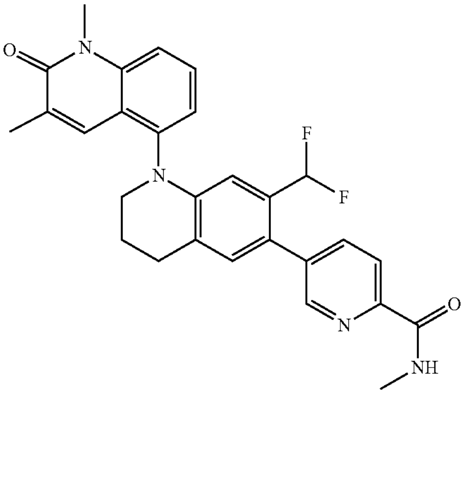 [SMILES: CNC(=O)c1ccc(-c2cc3c(cc2C(F)F)N(c2cccc4c2cc(C)c(=O)n4C)CCC3)cn1] | A | LC-MS: 489.4 $[M + H]^+$; 1H-NMR (400 MHz, Chloroform-D) δ 8.51 (d, J = 2.1 Hz, 1H), 8.22 (dd, J = 8.0, 0.8 Hz, 1H), 8.01 (d, J = 5.4 Hz, 1H), 7.80 (dd, J = 8.0, 2.2 Hz, 1H), 7.66 (s, J = 1.3 Hz, 1H), 7.58 (t, J = 8.0 Hz, 1H), 7.35 (d, J = 8.6 Hz, 1H), 7.15 (d, J = 0.9 Hz, 1H), 7.05 (s, 1H), 6.41 (s, 1H), 3.81 (s, 3H), 3.63 (m, J = 10.1, 4.8, 4.8 Hz, 2H), 3.08-3.02 (m, 4H), 2.26-2.23 (m, 3H). |

-continued

| Example | Structure | Coupling Method | Spectral data |
|---|---|---|---|
| 177 | 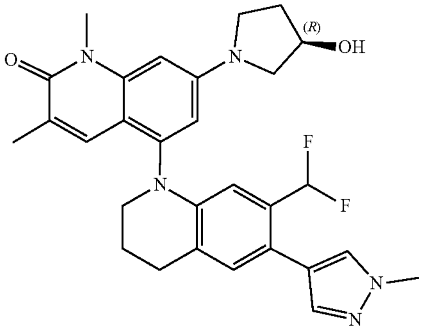 | — | LC-MS: 520.1 [M + H]+; 1H-NMR (400 MHz, Chloroform-D) δ 3.72-3.71 (m, 3H), 7.49 (s, 1H), 6.42 (s, 1H), 6.23 (s, 1H), 4.66 (s, 1H), 3.02-2.99 (m, 2H), 3.94 (s, 3H), 7.53-7.52 (m, 1H), 6.49-6.47 (m, 1H), 3.57 (s, 4H), 3.43-3.36 (m, 2H), 2.22 (d, J = 4.8 Hz, 3H), 2.15 (s, 4H), 1.87 (s, 1H), 7.08-7.07 (m, 1H), 7.40-7.39 (m, 1H). |
| 178 | 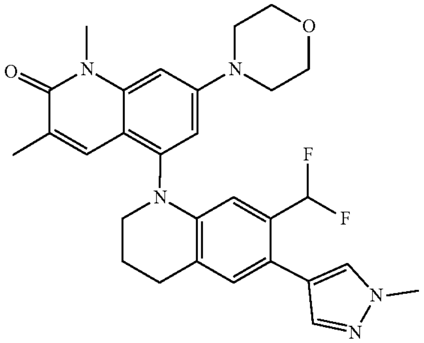 [SMILES: Cc1cc2c(N3CCCc4cc(-c5cnn(C)c5)c(C(F)F)cc43)cc(N3CCOCC3)cc2n(C)c1=O] | B | LC-MS: 520.65 [M + H]+; 1H-NMR (400 MHz, DMSO-D6) δ 7.68 (s, 1H), 7.48 (s, 1H), 7.44 (s, 1H), 7.08 (s, 1H), 6.89 (s, 1H), 6.74 (d, J = 2.1 Hz, 1H), 6.13 (s, 1H), 3.82 (s, 3H), 3.72 (d, J = 4.9 Hz, 3H), 3.64 (s, 3H), 3.58 (d, J = 9.8 Hz, 1H), 3.46 (s, 2H), 3.26 (t, J = 4.7, 4.7 Hz, 4H), 2.91 (s, 2H), 2.06 (s, 3H), 2.00 (s, 3H). |
| 179 | 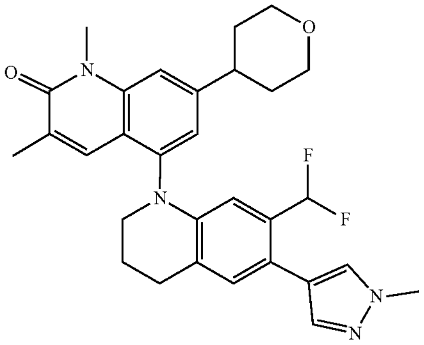 [SMILES: Cc1cc2c(N3CCCc4cc(-c5cnn(C)c5)c(C(F)F)cc43)cc(C3CCOCC3)cc2n(C)c1=O] | B | LC-MS: 519.4 [M + H]+; 1H-NMR (400 MHz, Chloroform-D) δ 7.63 (s, 1H), 7.53 (s, 1H), 7.39 (s, 1H), 7.13 (s, 1H), 7.08 (s, 1H), 7.03 (d, J = 1.2 Hz, 1H), 6.55-6.27 (m, 1H), 4.10-4.07 (m, 2H), 3.94 (s, 3H), 3.80 (s, 3H), 3.59-3.50 (m, 4H), 2.99-2.98 (m, 2H), 2.90-2.87 (m, 1H), 2.21 (d, J = 12. Hz, 3H), 2.17-2.15 (m, 2H), 1.87-1.81 (m, 4H). |
| 180 | 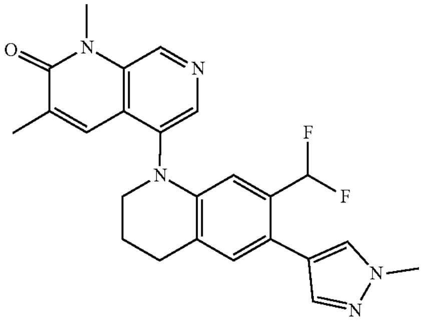 [SMILES: Cc1cc2c(N3CCCc4cc(-c5cnn(C)c5)c(C(F)F)cc43)cncc2n(C)c1=O] | C | LC-MS: 436.2 [M + H]+; 1H-NMR (400 MHz, Chloroform-D) δ 8.74 (s, 1H), 8.37 (d, J = 1.2 Hz, 1H), 7.60 (s, 1H), 7.54 (d, J = 0.8 Hz, 1H), 7.41 (s, 1H), 7.11 (d, J = 1.4 Hz, 1H), 6.41 (d, J = 5.6 Hz, 2H), 3.94 (d, J = 1.2 Hz, 3H), 3.86 (d, J = 1.2 Hz, 3H), 3.63 (s, 2H), 3.02 (s, 2H), 2.27 (d, J = 1.3 Hz, 3H), 2.24-2.18 (m, 2H). |

-continued

| Example | Structure | Coupling Method | Spectral data |
|---|---|---|---|
| 181 | 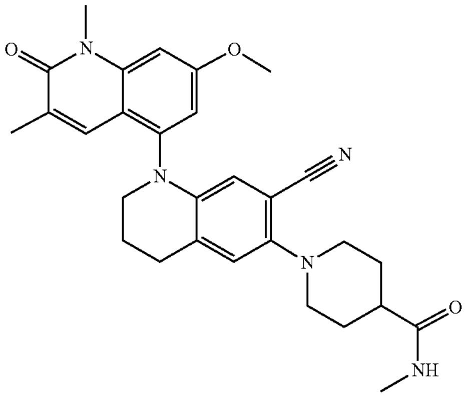 [SMILES: CNC(=O)C1CCN(c2cc3c(cc2C#N)N(c2cc(OC)cc4c2cc(C)c(=O)n4C)CCC3)CC1] | A | LC-MS: 500.4 [M + H]$^+$; 1H-NMR (600 MHz, Chloroform-D) δ 7.49 (s, 1H), 6.76-6.73 (m, 2H), 6.63 (d, J = 2.5 Hz, 1H), 6.24 (d, J = 2.7 Hz, 1H), 5.55 (s, 1H), 3.88 (d, J = 2.6 Hz, 3H), 3.74 (d, J = 2.8 Hz, 3H), 3.51 (d, J = 15.2 Hz, 2H), 3.38 (s, 2H), 2.99-2.91 (m, 2H), 2.81 (d, J = 4.5 Hz, 3H), 2.70 (dd, J = 11.8, 2.7 Hz, 2H), 2.22 (d, J = 4.1 Hz, 1H), 2.16 (s, 3H), 2.11 (s, 1H), 2.00-1.96 (m, 2H), 1.91-1.87 (m, 2H). |
| 182 | 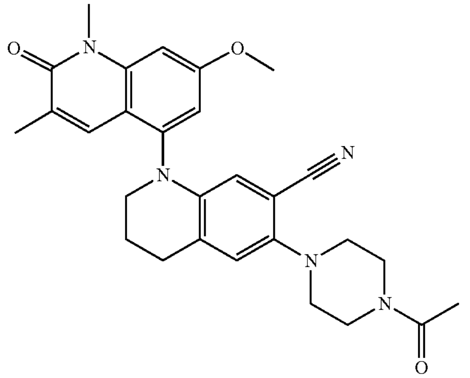 [SMILES: COc1cc(N2CCCc3cc(N4CCN(C(C)=O)CC4)c(C#N)cc32)c2cc(C)c(=O)n(C)c2c1] | A | LC-MS: 486 [M + H]$^+$; 1H-NMR (400 MHz, DMSO-D6) δ 7.56-7.55 (m, 1H), 6.98 (s, 1H), 6.95 (d, J = 2.3 Hz, 1H), 6.82 (s, 1H), 6.05 (s, 1H), 3.89 (s, 3H), 3.68 (s, 3H), 3.58-3.53 (m, 5H), 3.45 (d, J = 5.1 Hz, 1H), 2.94 (d, J = 5.1 Hz, 4H), 2.88 (d, J = 5.0 Hz, 2H), 2.12 (s, 2H), 2.06 (d, J = 1.2 Hz, 3H), 2.03 (s, 3H). |
| 183 | 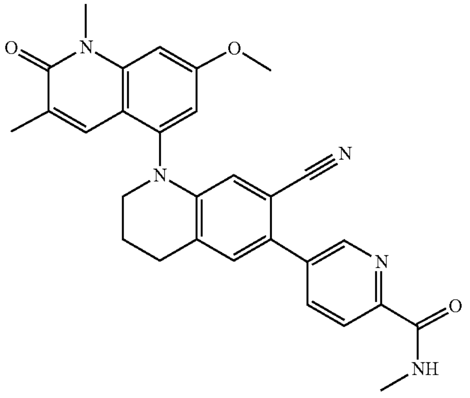 [SMILES: CNC(=O)c1ccc(-c2cc3c(cc2C#N)N(c2cc(OC)cc4c2cc(C)c(=O)n4C)CCC3)cn1] | A | LC-MS: 493.9 [M + H]$^+$; 1H-NMR (400 MHz, Chloroform-D) δ 8.67 (s, 1H), 8.24 (s, 1H), 7.98-7.94 (m, 1H), 7.44 (s, 1H), 7.20 (s, 1H), 6.83 (d, J = 2.3 Hz, 1H), 6.71 (s, 1H), 6.39 (s, 1H), 3.94 (s, 3H), 3.79 (s, 3H), 3.66-3.62 (m, 2H), 3.06 (d, J = 4.7 Hz, 5H), 2.21 (d, J = 1.3 Hz, 5H). |
| 184 | 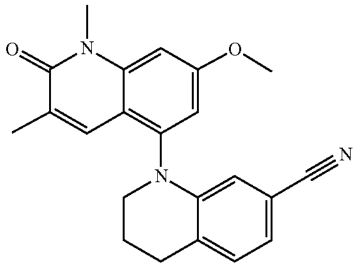 [SMILES: COc1cc(N2CCCc3ccc(C#N)cc32)c2cc(C)c(=O)n(C)c2c1] | A | LC-MS: 360.1 [M + H]$^+$; 1H-NMR (400 MHz, Chloroform-D) δ 7.45-7.43 (m, 1H), 7.09 (s, 1H), 6.90 (dd, J = 7.7, 1.6 Hz, 1H), 6.79 (d, J = 2.3 Hz, 1H), 6.68 (s, 1H), 6.25 (d, J = 1.6 Hz, 1H), 3.91 (s, 3H), 3.77 (s, 3H), 3.61-3.56 (m, 2H), 2.99 (d, J = 5.9 Hz, 2H), 2.18-2.13 (m, 5H). |

-continued

| Example | Structure | Coupling Method | Spectral data |
|---|---|---|---|
| 185 | 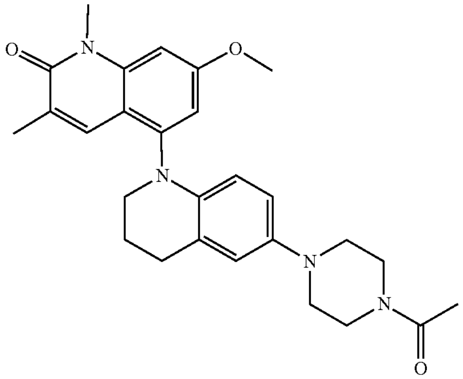 [SMILES: COc1cc(N2CCCc3cc(N4CCN(C(C)=O)CC4)ccc32)c2cc(C)c(=O)n(C)c2c1] | A | LC-MS: 461.1 [M + H]$^+$; 1H-NMR (600 MHz, Chloroform-D) δ 7.64 (s, 1H), 6.68 (d, J = 18.8 Hz, 3H), 6.52-6.49 (m, 1H), 6.12 (d, J = 8.9 Hz, 1H), 3.84 (s, 3H), 3.73 (s, 3H), 3.58-3.49 (m, 6H), 2.98 (dd, J = 13.1, 7.89 Hz, 8H), 2.16 (s, 3H), 2.11 (d, J = 2.8 Hz, 3H). |
| 186 | 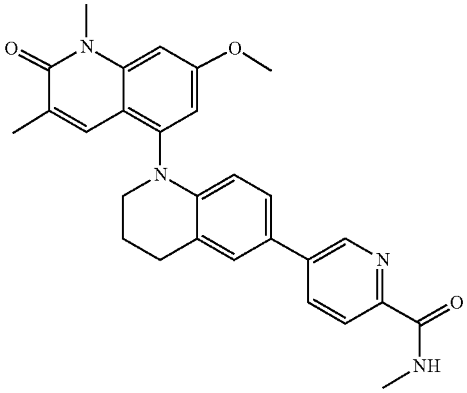 [SMILES: CNC(=O)c1ccc(-c2ccc3c(c2)CCCN3c2cc(OC)cc3c2cc(C)c(=O)n3C)cn1] | A | LC-MS: 469.3 [M + H]$^+$; 1H-NMR (600 MHz, Chloroform-D) δ 8.67 (d, J = 2.5 Hz, 1H), 8.16 (d, J = 5.8 Hz, 1H), 7.91 (dd, J = 8.2, 2.4 Hz, 2H), 7.55 (s, 1H), 7.34 (d, J = 2.4 Hz, 1H), 7.14-7.12 (m, 1H), 6.76 (d, J = 2.4 Hz, 1H), 6.18 (d, J = 8.7 Hz, 1H), 3.88 (s, 3H), 3.75 (s, 3H), 3.64-3.57 (m, 2H), 3.06-3.01 (m, 5H), 2.17 (s, 5H). |
| 187 | 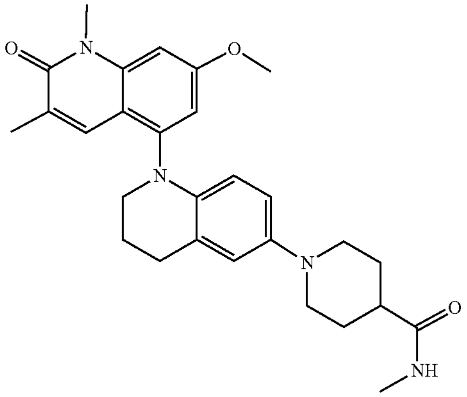 [SMILES: CNC(=O)C1CCN(c2ccc3c(c2)CCCN3c2cc(OC)cc3c2cc(C)c(=O)n3C)CC1] | A | LC-MS: 475.2 [M + H]$^+$; 1H-NMR (600 MHz, Chloroform-D) δ 7.66 (s, 1H), 6.65 (s, 2H), 6.53 (s, 1H), 6.12 (s, 1H), 5.50 (s, 1H), 3.83 (s, 3H), 3.72 (s, 3H), 3.53-3.43 (m, 4H), 2.91 (s, 1H), 2.82 (d, J = 4.4 Hz, 3H), 2.59 (s, 3H), 2.16 (s, 3H), 2.09 (s, 3H), 1.88 (d, J = 44.8 Hz, 4H). |
| 188 | 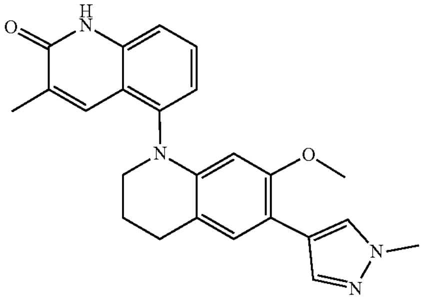 [SMILES: COc1cc2c(cc1-c1cnn(C)c1)CCCN2c1cccc2[nH]c(=O)c(C)cc12] | A | LC-MS: 401 [M + H]$^+$; 1H-NMR (400 MHz, DMSO-D6) δ 11.83 (s, 1H), 8.68 (s, 1H), 7.59 (s, 1H), 7.46 (t, J = 7.9, 7.9 Hz, 1H), 7.31 (d, J = 8.3 Hz, 1H), 7.19 (s, 1H), 7.06 (d, J = 7.5 Hz, 1H), 6.20 (s, 1H), 5.94 (s, 1H), 3.50 (s, 2H), 3.01-2.96 (t, 2H), 2.65 (s, 3H), 2.22-2.20 (m, 3H), 1.92 (s, 3H), 1.69-1.62 (m, 2H). |

-continued
| Example | Structure | Coupling Method | Spectral data |
|---|---|---|---|
| 189 | 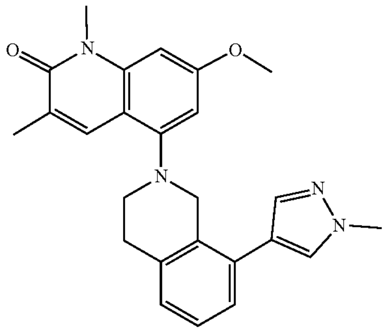 [SMILES: COc1cc(N2CCc3cccc(-c4cnn(C)c4)c3C2)c2cc(C)c(=O)n(C)c2c1] | A | LC-MS: 415.3 $[M + H]^+$; 1H-NMR (600 MHz, Chloroform-D) δ 7.82 (s, 1H), 7.53 (s, 1H), 7.37 (s, 1H), 7.24 (s, 1H), 7.18 (d, J = 7.6 Hz, 2H), 6.55-6.48 (m, 2H), 4.18 (s, 2H), 3.90 (dd, J = 18.1, 1.1 Hz, 6H), 3.72 (d, J = 1.1 Hz, 3H), 3.35 (s, 2H), 3.16 (s, 2H), 2.18 (s, 3H). |
| 190 | 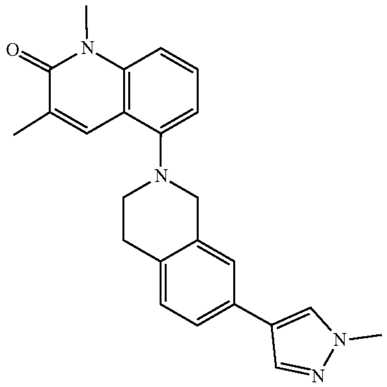 [SMILES: Cc1cc2c(N3CCc4ccc(-c5cnn(C)c5)cc4C3)cccc2n(C)c1=O] | A | LC-MS: 385 $[M + H]^+$; 1H-NMR (400 MHz, DMSO-D6) δ 3.28-3.26 (s, 1H), 4.20 (s, 2H), 3.85 (s, 3H), 3.05-3.02 (s, 2H), 3.65 (s, 3H), 2.15 (d, J = 1.2 Hz, 3H), 5.76-5.75 (s, 1H), 8.09 (s, 1H), 7.95 (s, 1H), 7.82 (d, J = 0.8 Hz, 1H), 7.53 (t, J = 8.2 Hz, 1H), 7.40-7.37 (m, 2H), 7.24 (m, 2H), 7.06 (dd, J = 7.9, 0.8 Hz, 1H). |
| 191 | 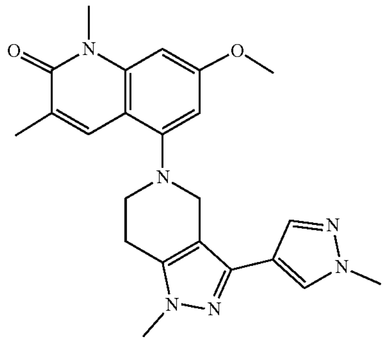 [SMILES: COc1cc(N2CCc3c(c(-c4cnn(C)c4)nn3C)C2)c2cc(C)c(=O)n(C)c2c1] | A | LC-MS: 419.4 $[M + H]^+$; 1H-NMR (400 MHz, DMSO-D6) δ 7.94 (s, 1H), 7.81 (d, J = 1.4 Hz, 1H), 7.66 (s, 1H), 6.76 (s, 1H), 6.69 (d, J = 2.1 Hz, 1H), 4.06 (s, 2H), 3.88 (d, J = 1.7 Hz, 3H), 3.84 (d, J = 1.8 Hz, 3H), 3.73 (s, 3H), 3.64 (d, J = 4.0 Hz, 3H), 3.29 (s, 2H), 2.91 (s, 2H), 2.10 (d, J = 1.1 Hz, 3H). |

Example-192: 5-(7-(Difluoromethyl)-7'-methoxy-1',3'-dimethyl-2'-oxo-1',2',3,4-tetrahydro-2H-[1,5'-biquinolin]-6-yl)-N-methylpicolinamide

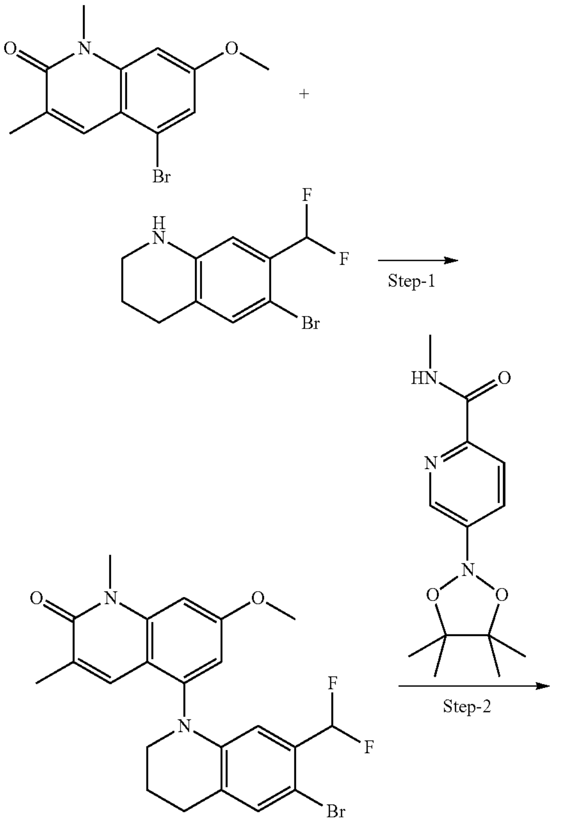

192Ea

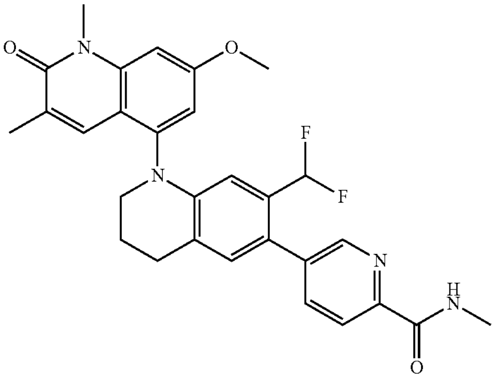

Example-192

Step-1: Synthesis of 6-bromo-7-(difluoromethyl)-7'-methoxy-1',3'-dimethyl-3,4-dihydro-2H-[1,5'-biquinolin]-2'(1'H)-one This compound was prepared using the similar protocol described in COUPLING METHOD-A using intermediates 5-bromo-7-methoxy-1,3-dimethylquinolin-2(1H)-one & 6-bromo-7-(difluoromethyl)-1,2,3,4-tetrahydroquinoline with appropriate variations in reactants, quantities of reagents, solvents and reaction conditions. LC-MS: 465.0 $[M+2H]^+$.

Step-2: Synthesis of 5-(7-(difluoromethyl)-7'-methoxy-1',3'-dimethyl-2'-oxo-1',2',3,4-tetrahydro-2H-[1,5'-biquinolin]-6-yl)-N-methylpicolinamide A degassed solution of 6-bromo-7-(difluoromethyl)-7'-methoxy-1',3'-dimethyl-3,4-dihydro-2H-[1,5'-biquinolin]-2'(1'H)-one (60 mg, 0.12 mmol) and N-methyl-5-(4,4,5,5-tetramethyl-1,3,2-dioxazolidin-2-yl)picolinamide (37 mg, 0.14 mmol) in 1,4-Dioxane (3 mL) and water (1 mL) was added Pd(Amphos)$Cl_2$ (10 mg, 0.02 mmol) and potassium carbonate carbonate (35 mg, 0.25 mmol). The mixture was stirred at 100° C. for 4 h. The reaction mixture was then cooled to room temperature, water was added and the mixture was extracted with ethyl acetate. Organic extracts were washed with water and brine, dried over sodium sulphate and concentrated to get the crude compound. The crude compound was purified by preparative HPLC to get the pure title compound (20 mg, 29.8%). LC-MS: 519 $[M+2H]^+$. 1H-NMR (400 MHz, chloroform-D) δ 3.90 (s, 3H), 3.82-3.80 (m, 2H), 3.68 (s, 3H), 3.06 (s, 3H), 2.93 (t, J=6.4 Hz, 2H), 2.26 (s, 3H), 2.16-2.14 (m, 3H), 6.64-6.63 (m, 1H), 8.53-8.52 (m, 1H), 8.26-8.24 (m, 1H), 7.08-7.07 (m, 1H), 8.03-8.02 (m, 1H), 7.83-7.81 (m, 1H), 7.35 (s, 1H), 7.95-7.94 (m, 1H).

Example-193: 7-(Difluoromethyl)-7'-((R)-3-hydroxypyrrolidin-1-yl)-1',3'-dimethyl-6-(1-methyl-1H-pyrazol-4-yl)-3,3',4,4'-tetrahydro-2H-[1,5'-biquinolin]-2'(1'H)-one

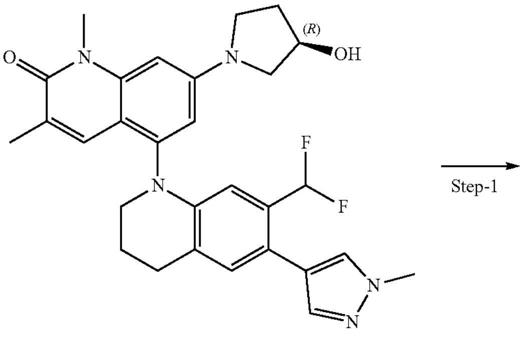

Example-177

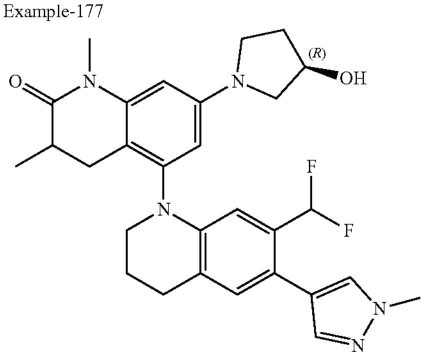

Example-193

This compound was prepared using the similar protocol described in Example-70 with appropriate variations in reactants, quantities of reagents, solvents and reaction conditions (20 mg, 29.49%). LC-MS: 522.3 $[M+2H]^+$. 1H-NMR (600 MHz, Chloroform-D) δ 7.52 (d, J=2.5 Hz, 1H), 7.39 (d, J=2.7 Hz, 1H), 7.03 (s, 1H), 6.58-6.44 (m, 2H), 6.15 (d, J=5.1 Hz, 2H), 4.62 (s, 1H), 3.93 (d, J=2.2 Hz, 3H), 3.61-3.49 (m, 5H), 3.40 (s, 3H), 3.33-3.27 (m, 2H), 2.96-2.90 (m, 2H), 2.72 (q, J=5.4, 4.8, 4.8 Hz, 1H), 2.53 (d, J=8.6 Hz, 1H), 2.37-2.34 (m, 1H), 2.20-2.10 (m, 5H), 1.18-1.14 (m, 4H).

Example-194: 7-Hydroxy-1',3'-dimethyl-6-(1-methyl-1H-pyrazol-4-yl)-7'-(tetrahydro-2H-pyran-4-yl)-3,4-dihydro-2H-[1,5'-biquinolin]-2'(1'H-one

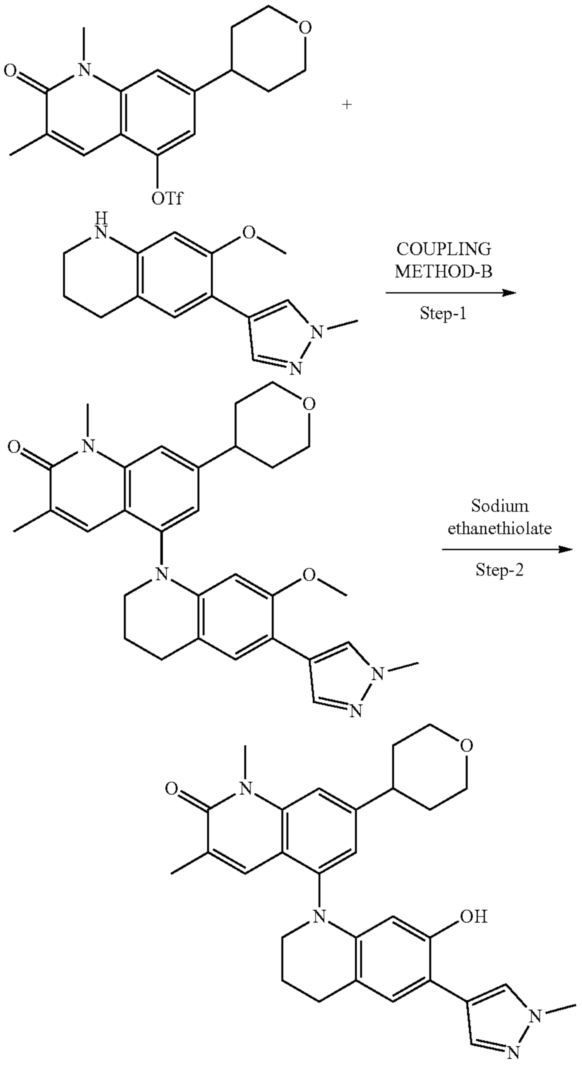

Example-194

Step-1: Synthesis of 7-methoxy-1',3'-dimethyl-6-(1-methyl-1H-pyrazol-4-yl)-7-(tetrahydro-2H-pyran-4-yl)-3,4-dihydro-2H-[1,5'-biquinolin]-2'(1'H)-one This compound was prepared using the similar protocol described in COUPLING METHOD-B using intermediates 1,3-dimethyl-2-oxo-7-(tetrahydro-2H-pyran-4-yl)-1,2-dihydroquinolin-5-yl trifluoromethanesulfonate & 7-methoxy-6-(1-methyl-1H-pyrazol-4-yl)-1,2,3,4-tetrahydroquinoline with appropriate variations in reactants, quantities of reagents, solvents and reaction conditions. LC-MS: 499.4 $[M+1H]^+$.

Step-2: Synthesis of 7-hydroxy-1',3'-dimethyl-6-(1-methyl-1H-pyrazol-4-yl)-7-(tetrahydro-2H-pyran-4-yl)-3,4-dihydro-2H-[1,5'-biquinolin]-2'(1'H)-one This compound was prepared using the similar protocol described in Example-145 with appropriate variations in reactants, quantities of reagents, solvents and reaction conditions (30 mg, 28.5%). LC-MS: 485.4 $[M+H]^+$; 1H-NMR (400 MHz, Chloroform-D) δ 7.67 (s, 1H), 7.65 (s, 1H), 7.61 (s, 1H), 7.08 (s, 1H), 7.07 (s, 1H), 7.04 (s, 1H), 5.63 (s, 1H), 4.10-4.07 (m, 2H), 3.90 (s, 3H), 3.70 (s, 3H), 3.61-3.51 (m, 4H), 2.96-2.84 (m, 3H), 2.18-2.17 (m, 2H), 2.15 (s, 3H), 1.87-1.80 (m, 4H).

Example-195: 5-(6-(Difluoromethyl)-5-(1-methyl-1H-pyrazol-4-yl)indolin-1-yl)-7-methoxy-1,3-dimethylquinolin-2(1H)-one

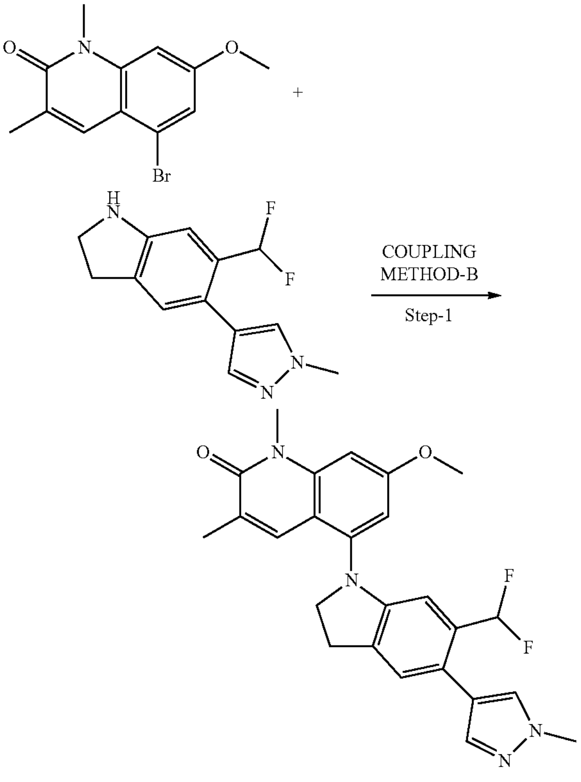

Example-195

This compound was prepared using the similar protocol described in COUPLING METHOD-A with appropriate variations in reactants, quantities of reagents, solvents and reaction conditions (20 mg, 10%). LC-MS: 451.3 $[M+1H]^+$; 1H-NMR (600 MHz, chloroform-D) δ 7.72 (s, 1H), 7.55 (s, 1H), 7.42 (s, 1H), 7.20 (s, 1H), 6.76 (s, 1H), 6.70 (d, J=2.2 Hz, 1H), 6.62 (s, 1H), 3.89-3.87 (m, 4H), 6.50 (s, 1H), 3.99 (s, 1H), 3.96 (s, 3H), 3.76 (s, 3H), 3.23 (m, 2H), 2.20 (s, 3H).

Example-196: N-(7'-methoxy-1',3'-dimethyl-2'-oxo-1',2',3,4-tetrahydro-2H-[1,5'-biquinolin]-7-yl)acetamide

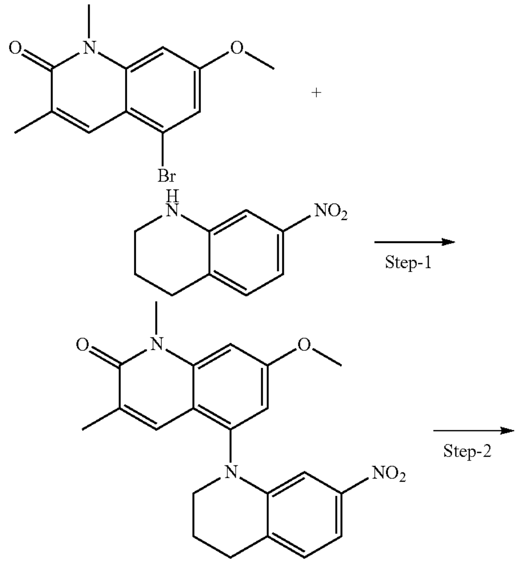

E196a

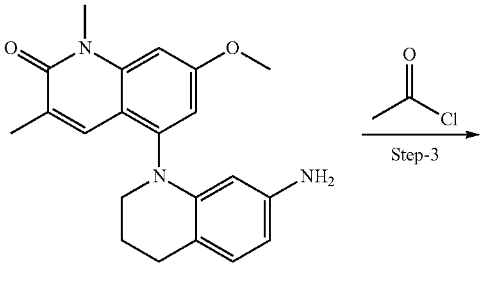

E196b

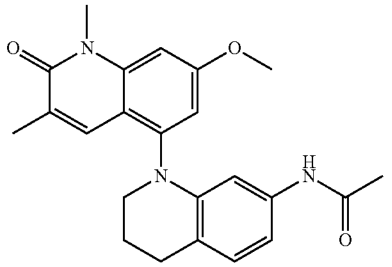

Example-196

Step-1: Synthesis of 7'-methoxy-1',3'-dimethyl-7-nitro-3,4-dihydro-2H-[1,5'-biquinolin]-2'(1'H)-one A degassed solution of 5-bromo-7-methoxy-1,3-dimethylquinolin-2(1H)-one (100 mg, 0.35 mmol) and 7-nitro-1,2,3,4-tetrahydroquinoline (80 mg, 0.43 mmol) in toluene (5 mL) was added $Pd(OAc)_2$ (20 mg, 0.07 mmol), rac-BINAP (40 mg, 0.07 mmol) and $Cs_2CO_3$ (350 mg, 1.06 mmol). The mixture was stirred at 100° C. for overnight. The mixture was cooled to room temperature, added water, extracted with ethyl acetate. Organic extracts were washed with brine, dried over sodium sulphate and concentrated to get the residue. The residue was purified by silica gel column chromatography using 10% methanol in DCM as eluent to afford pure compound (80 mg, 60.2%). LC-MS: 380.25 $[M+H]^+$.

Step-2: Synthesis of 7-amino-7'-methoxy-1',3'-dimethyl-3,4-dihydro-2H-[1,5'-biquinolin]-2'(1'H)-one This compound was prepared using the similar protocol described in example-77 with appropriate variations in reactants, quantities of reagents, solvents and reaction conditions. LC-MS: 349.9 $[M+1H]^+$;

Step-3: Synthesis of N-(7'-methoxy-1',3'-dimethyl-2'-oxo-1',2',3,4-tetrahydro-2H-[1,5'-biquinolin]-7-yl)acetamide This compound was prepared using the similar protocol described in Example-63 with appropriate variations in reactants, quantities of reagents, solvents and reaction conditions. LC-MS: 392.15 $[M+1H]^+$; 1H-NMR (400 MHz, DMSO-D6) δ 9.40 (s, 1H), 7.55 (s, 1H), 7.02 (s, J=8.4 Hz, 1H), 6.90-6.86 (m, 2H), 6.76 (s, 1H), 6.03 (s, 1H), 3.86 (s, 3H), 3.65 (s, 3H), 3.51 (s, 1H), 3.40 (d, J=4 Hz, 1H), 2.83-2.79 (m, 2H), 2.05-2.0 (s, 4H), 1.81 (s, 3H).

Example-197: N-(7'-methoxy-1',3'-dimethyl-2'-oxo-1',2',3,4-tetrahydro-2H-[1,5'-biquinolin]-7-yl)methanesulfonamide

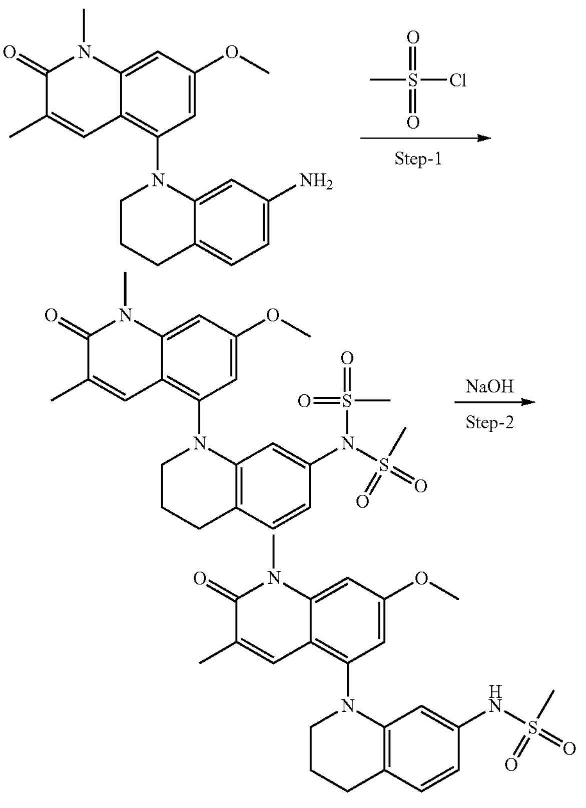

Step-1: Synthesis of N-(7'-methoxy-1',3'-dimethyl-2'-oxo-1',2',3,4-tetrahydro-2H-[1,5'-biquinolin]-7-yl)-N-(methylsulfonyl)methanesulfonamide An ice cold solution of 7-amino-7'-methoxy-1',3'-dimethyl-3,4-dihydro-2H-[1,5'-biquinolin]-2'(1'H)-one (150 mg, 0.43 mmol) in DCM (5 mL) and trimethylamine (130 mg, 1.29 mmol) was added methanesulfonyl chloride (50 mg, 0.43 mmol) dropwise. After stirring at room temperature for 3 h, reaction mixture was extracted with DCM, organic portion was washed with saturated $NaHCO_3$ solution, brine solution and dried over $Na_2SO_4$ and concentrated to get crude compound (150 mg). LC-MS: 506.15 $[M+1H]^+$.

Step-2: Synthesis of N-(7'-methoxy-1',3'-dimethyl-2'-oxo-1',2',3,4-tetrahydro-2H-[1,5'-biquinolin]-7-yl) methanesulfonamide Sodium hydroxide (20 mg, 0.59 mmol) in water (3 mL) was added to a stirred solution of N-(7'-methoxy-1',3'-dimethyl-2'-oxo-1',2',3,4-tetrahydro-2H-[1,5'-biquinolin]-7-yl)-N-(methylsulfonyl)methanesulfonamide (150 mg, 0.3 mmol) THE at room temperature for 13 h. The mixture was cooled to room temperature, diluted with water and ethyl acetate, organic portion was washed with water, dried over $Na_2SO_4$ and concentrated. The crude compound was washed with 30% ethyl acetate in hexane to get pure title compound (28 mg, 21.8%). LC-MS: 42815 $[M+1H]^+$; 1H-NMR (300 MHz, DMSO-D6) δ 9.1 (s, 1H), 7.54 (s, 1H), 6.97-6.92 (m, 2H), 6.23 (s, 1H), 6.509 (d, J=8.4 Hz, 1H), 3.88 (s, 3H), 3.68 (s, 3H), 3.60 (s, 1H), 3.41 (s, 1H), 2.83 (s, 2H), 2.74 (s, 4H), 2.1 (s, 2H), 2.04 (s, 3H).

Example-198: 7'-Methoxy-1',3'-dimethyl-7-(1H-pyrazol-4-yl)-3,4-dihydro-2H-[1,5'-biquinolin]-2'(1'H)-one

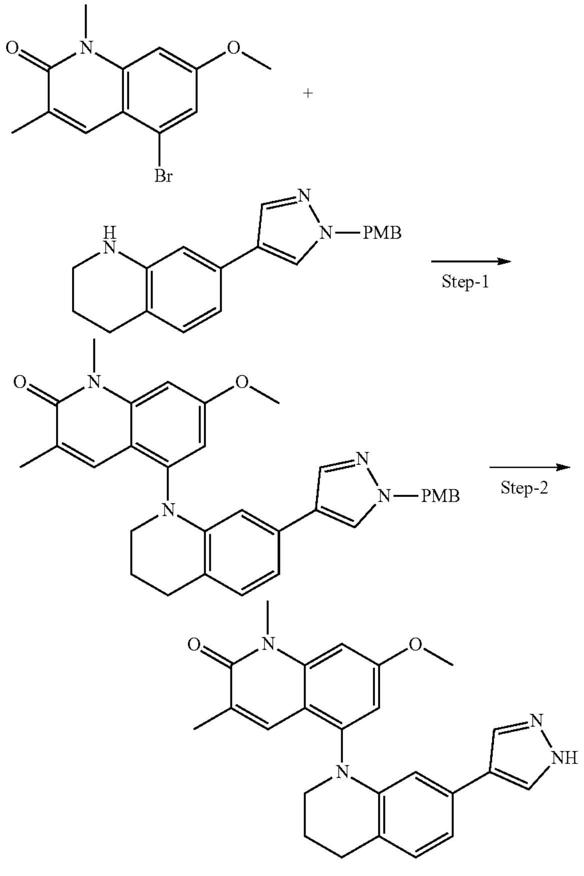

Example-198

Step-1: Synthesis of 7'-methoxy-7-(1-(4-methoxybenzyl)-1H-pyrazol-4-yl)-1',3'-dimethyl-3,4-dihydro-2H-[1,5'-biquinolin]-2'(1'H)-one This compound was prepared using the similar protocol described in COUPLING METHOD-A using intermediates 5-bromo-7-methoxy-1,3-dimethylquinolin-2(1H)-one & 7-(1-(4-methoxybenzyl)-1H-pyrazol-4-yl)-1,2,3,4-tetrahydroquinoline with appropriate variations in reactants, quantities of reagents, solvents and reaction conditions. LC-MS: 491.1 [M+1H Step-2: Synthesis of 7'-methoxy-1',3'-dimethyl-7-(1H-pyrazol-4-yl)-3,4-dihydro-2H-[1,5'-biquinolin]-2'(1'H)-one This compound was prepared using the similar protocol described in step-1 of example-62 with appropriate variations in reactants, quantities of reagents, solvents and reaction conditions (30 mg, 29.96%). LC-MS: 401.1 $[M+1H]^+$; 1H-NMR (400 MHz, chloroform-D) δ 7.65-7.64 (m, 1H), 7.55 (s, 2H), 7.10-7.06 (m, 1H), 6.83 (dd, J=7.7, 1.7 Hz, 1H), 6.76-6.74 (m, 2H), 6.24 (d, J=1.7 Hz, 1H), 3.87 (s, 3H), 3.76 (s, 3H), 3.55 (s, 2H), 2.99-2.94 (m, 2H), 2.18 (d, J=1.3 Hz, 5H).

Example-199: N-((7'-methoxy-1',3'-dimethyl-2'-oxo-1',2',3,4-tetrahydro-2H-[1,5'-biquinolin]-7 yl)sulfonyl)acetamide

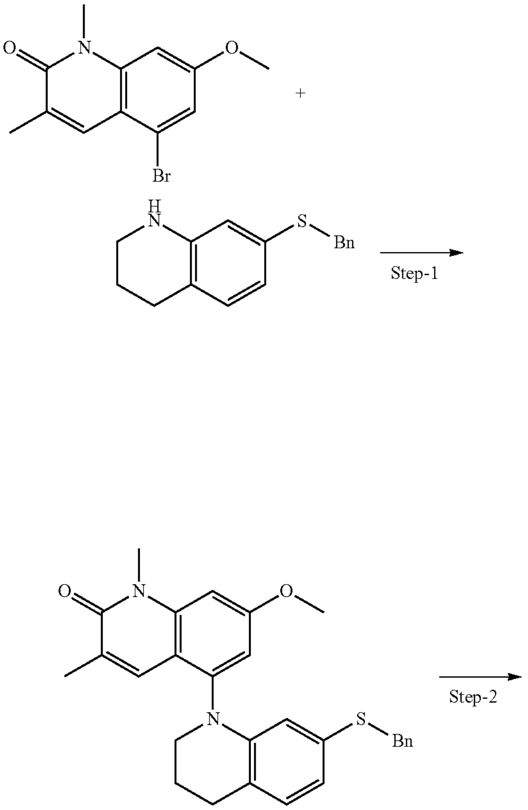

-continued

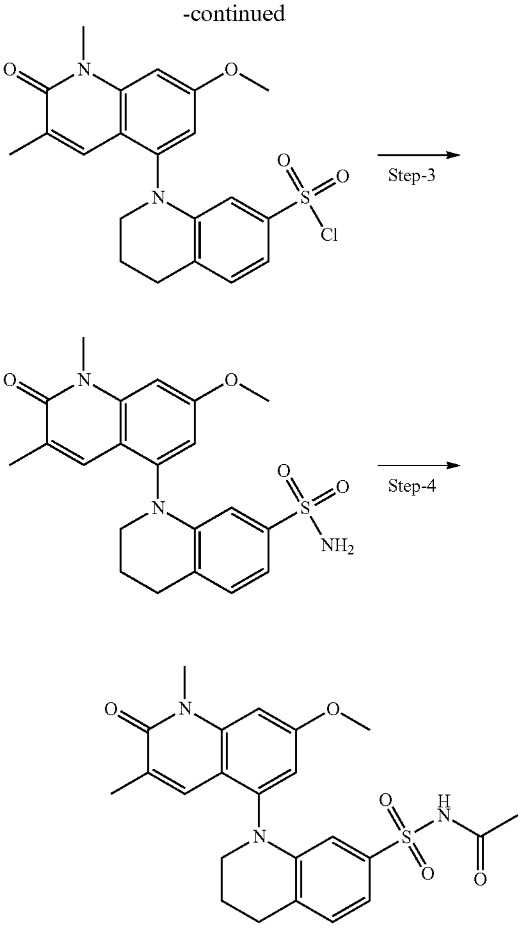

Example-199

Step-1: Synthesis of 7-(benzylthio)-7'-methoxy-1',3'-dimethyl-3,4-dihydro-2H-[1,5'-biquinolin]-2'(1'H)-one This compound was prepared using the similar protocol described in COUPLING METHOD-A using intermediates 5-bromo-7-methoxy-1,3-dimethylquinolin-2(1H)-one & 7-(benzylthio)-1,2,3,4-tetrahydroquinoline with appropriate variations in reactants, quantities of reagents, solvents and reaction conditions.

Step-2: Synthesis of 7'-methoxy-1',3'-dimethyl-2'-oxo-1',2',3,4-tetrahydro-2H-[1,5'-biquinoline]-7-sulfonyl chloride To an ice-cooled solution of 7-(benzylthio)-7'-methoxy-1',3'-dimethyl-3,4-dihydro-2H-[1,5'-biquinolin]-2'(1'H)-one (150 mg, 0.33 mmol) in acetonitrile (3.0 mL) was added acetic acid (3.0 mL) and water (1.0 mL), then pinch wise addition of N-chlorosuccinimide (0.18 g, 1.32 mmol) over a period of 5 min. The reaction mixture was stirred for 2 hr at room temperature, after completion of reaction, reaction mixture was diluted with water, extracted with EtOAc, organic layer was washed with aqueous $NaHCO_3$ solution (50 mL) and brine (50 mL). The organic layers dried over sodium sulphate and concentrated under reduced pressure. The crude product was directly used for the next step without further purification. LC-MS: 433 $[M+H]^+$.

Step-3: Synthesis of T-methoxy-1',3'-dimethyl-2'-oxo-1',2',3,4-tetrahydro-2H-[1,5'-biquinoline]-7-sulfonamide To an ice-cooled solution of 7'-methoxy-1',3'-dimethyl-2'-oxo-1',2',3,4-tetrahydro-2H-[1,5'-biquinoline]-7-sulfonyl chloride (150 mg, 0.32 mmol) in THF (2 mL) was added ammonia in THF (20 mL, 0.5M in THF). The reaction mixture was stirred at room temperature for 2 h, after completion of reaction; reaction mixture was concentrated and purified by combi flash using EtOAc/pet ether as eluents to give the title compound as off-white solid (80 mg, 56%). LC-MS: 414.2 $[M+H]^+$.

Step-4: Synthesis of N-((7'-methoxy-1',3'-dimethyl-2'-oxo-1',2',3,4-tetrahydro-2H-[1,5'-biquinolin]-7-yl)sulfonyl)acetamide To an ice-cooled solution of 7'-methoxy-1',3'-dimethyl-2'-oxo-1',2',3,4-tetrahydro-2H-[1,5'-biquinoline]-7-sulfonamide (80 mg, 0.19 mmol) in DCM (2.5 mL) was added triethylamine (0.058 g, 0.58 mmol), DMAP (0.002 g, 0.019 mmol) and acetic anhydride (0.039 g, 0.38 mmol). The reaction mixture was stirred for 16 h at room temperature, after completion of reaction, reaction mixture was concentrated and residue was diluted with EtOAc and was washed with water (50 mL) and brine (50 mL), dried over sodium sulphate and concentrated under reduced pressure. The crude product was purified by preparative HPLC to afford title compound as white solid (40 mg, 55.5%). LC-MS: 356.2 $[M+H]^+$; 1H NMR (400 MHz, DMSO-D6) δ 11.72 (s, 1H), 7.52 (s, 1H), 7.18-7.24 (m, 1H), 7.06-7.08 (m, 1H), 6.97 (d, J=1.6 Hz, 1H), 6.86 (d, J=2.4 Hz, 1H), 6.39 (d, J=1.6 Hz, 1H), 3.89 (s, 3H), 3.69 (s, 3H), 3.60-3.65 (m, 1H), 3.48-3.52 (m, 1H), 2.96-2.94 (m, 2H), 2.54 (s, 3H), 2.10-2.03 (m, 2H), 2.04 (s, 3H).

Example-200: 7-(4-Acetylpiperazin-1-yl)-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one

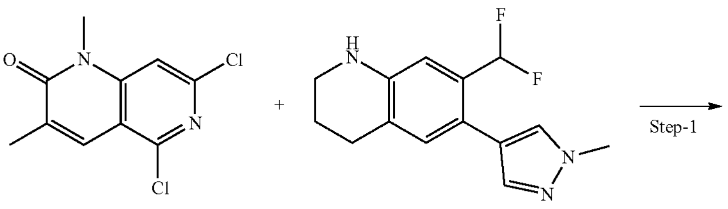

-continued

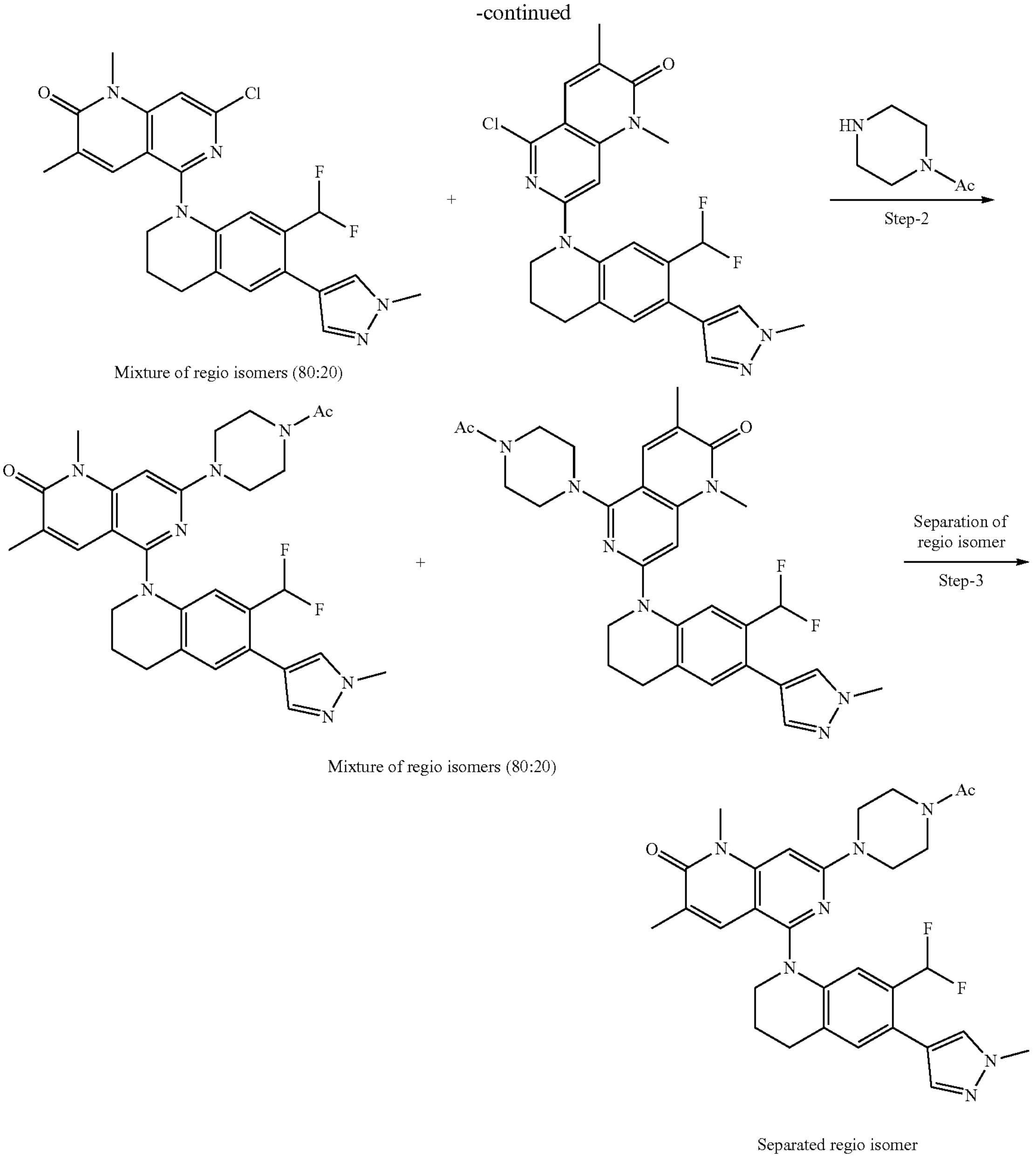

Step-1: Synthesis of 7-(4-acetylpiperazin-1-yl)-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one A degassed solution of 5,7-dichloro-1,3-dimethyl-1,6-naphthyridin-2(1H)-one (800 mg, 3.29 mmol) and 7-(difluoromethyl)-6-(1-methyl-1H-pyrazol-4-yl)-1,2,3,4-tetrahydroquinoline (950 mg, 3.62 mmol) in 1,4-dioxane (20 mL) was added potassium carbonate (1360 mg, 9.87 mmol), rac-BINAP (410 mg, 0.66 mmol), $Pd_2(dba)_3$ (150 mg, 0.17 mmol). The reaction mixture was heated to 100° C. for 16 h. This was cooled and filtered through Celite bed and concentrated to get the residue. The residue was purified by silica gel (100-200 mesh) column chromatography using 40% ethyl acetate in hexane. This afforded the mixture of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one and 5-chloro-7-(7-(difluoromethyl)-6-(1-methyl-1H-pyrazol-4-yl)-3,4-dihydroquinolin-1(2H)-yl)-1,3-dimethyl-1,6-naphthyridin-2(1H)-one in ~80:20 ratio. LC-MS: 470.2 $[M+H]^+$.

Step-2: Synthesis of 7-(4-acetylpiperazin-1-yl)-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one A degassed solution of an approximate 80:20 mixture of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one and 5-chloro-7-(7-(difluoromethyl)-6-(1-methyl-1H-pyrazol-4-yl)-3,4-dihydroquinolin-1(2H)-yl)-1,3-dimethyl-1,6-naphthyridin-2(1H)-one (200 mg, 0.43 mmol) and N-Acetyl piperazine (80 mg, 0.64 mmol) was added Potassium carbonate (180 mg 1.28 mmol), BINAP (50 mg, 0.09 mmol), $Pd_2(dba)_3$ (20 mg, 0.02 mmol). This resultant mixture was heated in a screw cap sealed tube for 16 h. The reaction mixture was passed through Celite bed and concentrated to get residue. LC-MS: 562.4 $[M+H]^+$.

Step-3: Synthesis of 7-(4-acetylpiperazin-1-yl)-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one The residue was purified in preparative HPLC using 0.01% ammonia in water and acetonitrile was mobile phase using column GEMINI-NX (150 mm×21.2 mm; 5.0 μl with the flow rate of 20 mL per minute. This afforded pure 7-(4-acetylpiperazin-1-yl)-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one (10 mg, 4.14%). LC-MS: 562.4 $[M+H]^+$; 1H-NMR (600 MHz, Chloroform-D) δ 7.55 (s, 1H), 7.42 (s, 2H), 7.12 (s, 1H), 6.80 (s, 1H), 6.46 (s, 1H), 6.13 (s, 1H), 3.96 (s, 3H), 3.76 (s, 4H), 3.675 (m, 5H), 3.581-3.566 (t, J=5.4, 3.6 Hz, 4H), 2.987-2.967 (t, J=6 Hz, 2H), 2.144-2.116 (d, J=16.8 Hz, 8H).

Example-201: 1-(5-(7-(Difluoromethyl)-6-(1-methyl-1H-pyrazol-4-yl)-3,4-dihydroquinolin-1(2H)-yl)-1,3-dimethyl-2-oxo-1,2-dihydro-1,6-naphthyridin-7-yl)-N-methylpyrrolidine-3-carboxamide

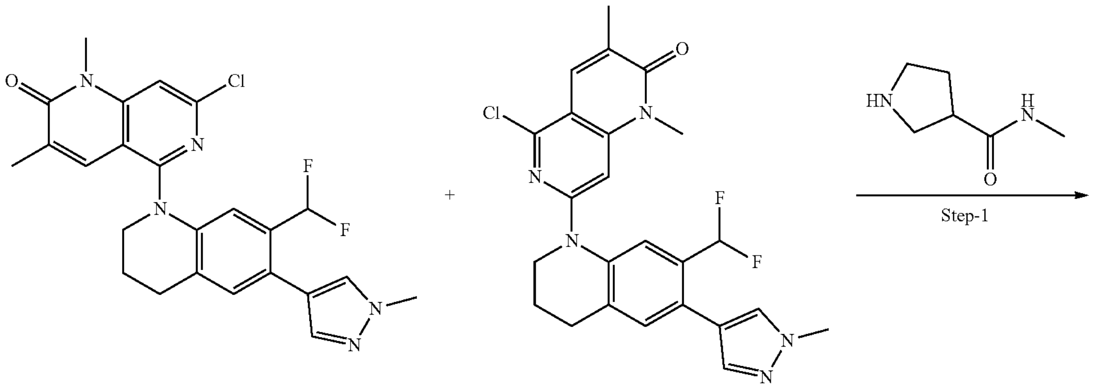

Mixture of regio isomers (80:20)

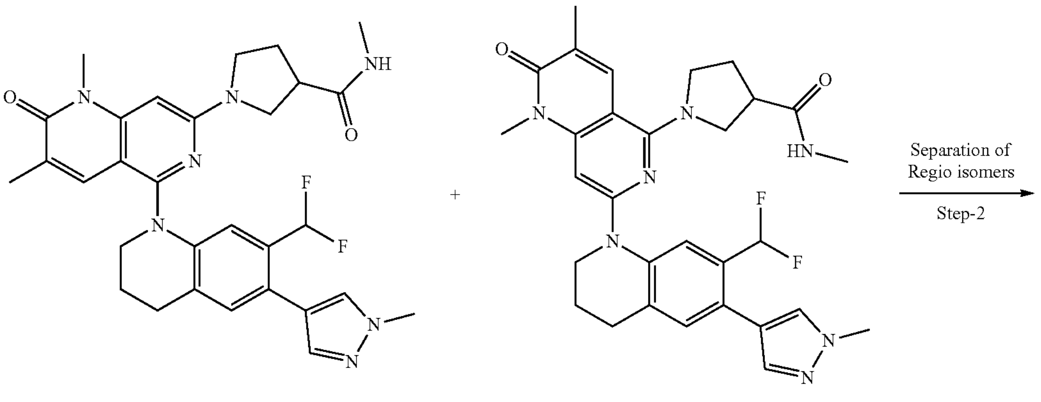

Mixture of regio Isomers (80:20)

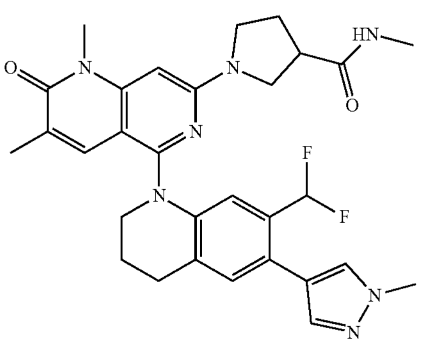

Example 201

Step-1: Synthesis of 1-(5-(7-(difluoromethyl)-6-(1-methyl-1H-pyrazol-4-yl)-3,4-dihydroquinolin-1(2H)-yl)-1,3-dimethyl-2-oxo-1,2-dihydro-1,6-naphthyridin-7-yl)-N-methylpyrrolidine-3-carboxamide Coupling method-D: A solution of an approximate 80:20 mixture of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one and 5-chloro-7-(7-(difluoromethyl)-6-(1-methyl-1H-pyrazol-4-yl)-3,4-dihydroquinolin-1(2H)-yl)-1,3-dimethyl-1,6-naphthyridin-2(1H)-one (200 mg, 0.43 mmol) and N-methylpyrrolidine-3-carboxamide (270 mg, 2.13 mmol) in DMF (4 mL) was added potassium carbonate (350 mg, 2.56 mmol) and heated to 100° C. for overnight. After cooling the reaction mixture to room temperature, ice was added, solid separated. Solid filtered and washed with water and dried. LC-MS: 562.2 $[M+H]^+$.

Step-2: Synthesis of 1-(5-(7-(difluoromethyl)-6-(1-methyl-1H-pyrazol-4-yl)-3,4-dihydroquinolin-1(2H)-yl)-1,3-dimethyl-2-oxo-1,2-dihydro-1,6-naphthyridin-7-yl)-N-methylpyrrolidine-3-carboxamide The crude solid obtained in Step-1 was purified by Silica gel column chromatography. And further purified in preparative HPLC using mobile phase 0.02% ammonia in water and acetonitrile using column YMC (150 mm×21.2 mm); 5.0μ with the flow rate of 20 mL per minute. This afforded pure 1-(5-(7-(difluoromethyl)-6-(1-methyl-1H-pyrazol-4-yl)-3,4-dihydroquinolin-1(2H)-yl)-1,3-dimethyl-2-oxo-1,2-dihydro-1,6-naphthyridin-7-yl)-N-methylpyrrolidine-3-carboxamide (90 mg, 37.2%). LC-MS: 562.3 $[M+H]^+$; 1H-NMR (400 MHz, Chloroform-D) δ 7.55 (d, J=0.7 Hz, 1H), 7.41-7.40 (m, 1H), 7.10 (s, 1H), 6.75-6.75 (m, 1H), 6.45 (s, 1H), 5.84 (s, 1H), 5.61 (s, 1H), 3.95 (s, 3H), 3.73 (td, J=13.8, 12.8, 7.9 Hz, 5H), 3.64 (s, 3H), 3.50-3.45 (m, 2H), 3.00-2.96 (m, 3H), 2.33-2.24 (m, 4H), 2.13 (dd, J=6.5, 5.0 Hz, 3H), 2.09 (d, J=1.1 Hz, 3H).

Example-202: 7-((1S,4S)-2-oxa-5-azabicyclo[2.2.1]heptan-5-yl)-1,3-dimethyl-5-(1-methyl-7-(1-methyl-1H-pyrazol-4-yl)-2,3-dihydropyrido[3,4-b]pyrazin-4(1H)-yl)-1,6-naphthyridin-2(1H)-one

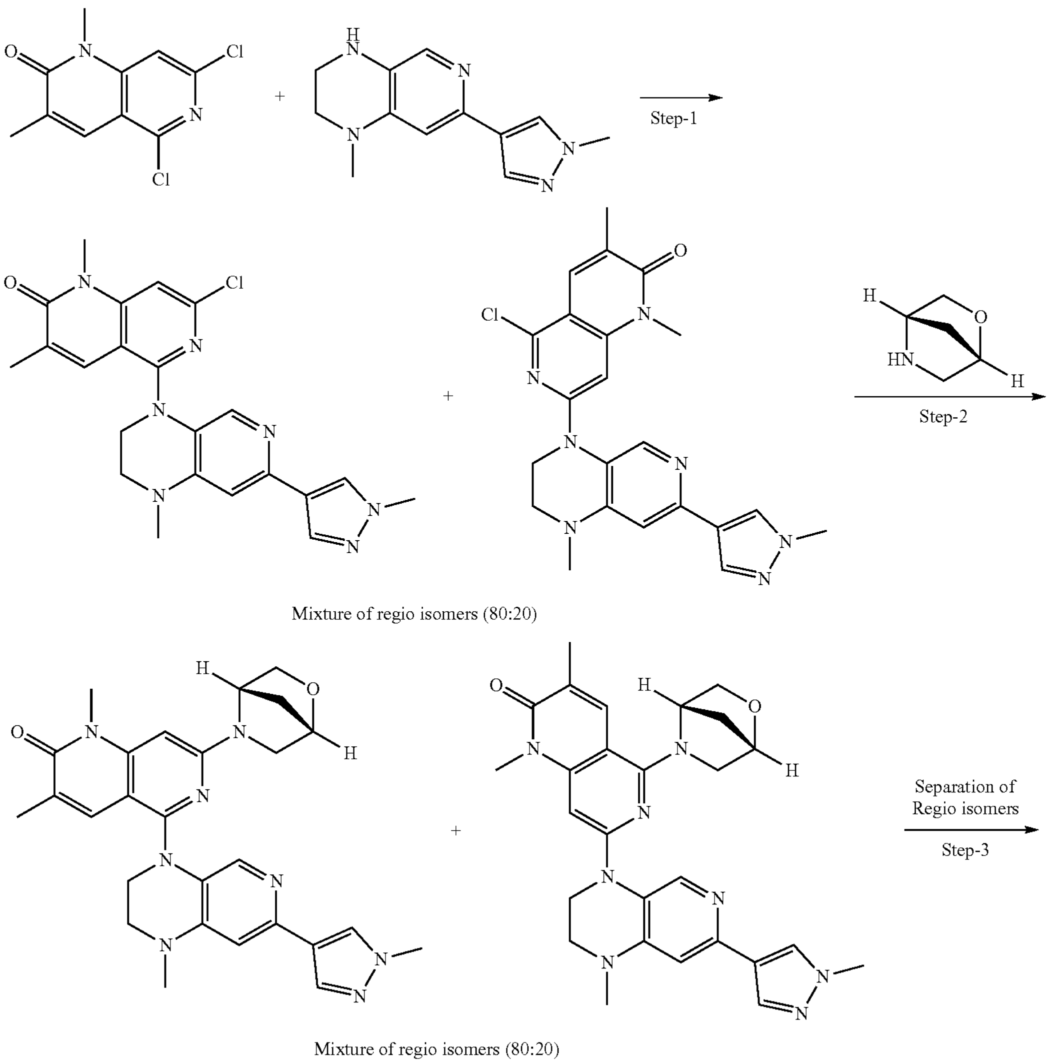

-continued

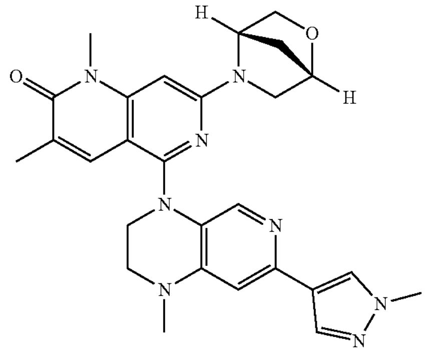

Example-202

Step-1: Synthesis of 7-chloro-1,3-dimethyl-5-(1-methyl-7-(1-methyl-1H-pyrazol-4-yl)-2,3-dihydro-pyrido[3,4-b]pyrazin-4(1H)-yl)-1,6-naphthyridin-2(1H)-one & 5-chloro-1,3-dimethyl-7-(1-methyl-7-(1-methyl-1H-pyrazol-4-yl)-2,3-dihydropyrido[3,4-b]pyrazin-4(1H)-yl)-1,6-naphthyridin-2(1H)-one This compound was prepared using the similar protocol described in step-1 of example-200 using intermediates 5,7-dichloro-1,3-dimethyl-1,6-naphthyridin-2(1H)-one & 1-methyl-7-(1-methyl-1H-pyrazol-4-yl)-1,2,3,4-tetrahydro-pyrido[3,4-b]pyrazine with appropriate variations in reactants, quantities of reagents, solvents and reaction conditions. LC-MS: 436.5 $[M+H]^+$.

Step-2: Synthesis of 7-((1S,4S)-2-oxa-5-azabicyclo[2.2.1]heptan-5-yl)-1,3-dimethyl-5-(1-methyl-7-(1-methyl-1H-pyrazol-4-yl)-2,3-dihydropyrido[3,4-b]pyrazin-4(1H)-yl)-1,6-naphthyridin-2(1H)-one & 5-((1S,4S)-2-oxa-5-azabicyclo[2.2.1]heptan-5-yl)-1,3-dimethyl-7-(1-methyl-7-(1-methyl-1H-pyrazol-4-yl)-2,3-dihydropyrido[3,4-b]pyrazin-4(1H)-yl)-1,6-naphthyridin-2(1H)-one Coupling method-E: A solution of an approximate 80:20 mixture of 7-chloro-1,3-dimethyl-5-(1-methyl-7-(1-methyl-1H-pyrazol-4-yl)-2,3-dihydropyrido[3,4-b]pyrazin-4(1H)-yl)-1,6-naphthyridin-2(1H)-one & 5-chloro-1,3-dimethyl-7-(1-methyl-7-(1-methyl-1H-pyrazol-4-yl)-2,3-dihydropyrido[3,4-b]pyrazin-4(1H)-yl)-1,6-naphthyridin-2(1H)-one (50 mg, 0.11 mmol) and (1S,4S)-2-oxa-5-azabicyclo[2.2.1]heptane (60 mg, 0.44 mmol) in DMSO (2 mL) was added potassium carbonate (90 mg, 0.66 mmol) and copper iodide (10 mg, 0.06 mmol) and heated to 125° C. for 48 h. After cooling the reaction mixture to room temperature, reaction mixture was diluted with 10% methanol in chloroform and water. Organic portion was washed with water and dried over sodium sulphate and concentrated to get crude compound. Crude compound was purified by flash chromatography using mobile phase 10% methanol in chloroform to get title mixture. LC-MS: 499.5 $[M+H]^+$.

Step-3: Purification of mixture 7-((1S,4S)-2-oxa-5-azabicyclo[2.2.1]heptan-5-yl)-1,3-dimethyl-5-(1-methyl-7-(1-methyl-1H-pyrazol-4-yl)-2,3-dihydro-pyrido[3,4-b]pyrazin-4(1H)-yl)-1,6-naphthyridin-2(1H)-one & 5-((1S,4S)-2-oxa-5-azabicyclo[2.2.1]heptan-5-yl)-1,3-dimethyl-7-(1-methyl-7-(1-methyl-1H-pyrazol-4-yl)-2,3-dihydropyrido[3,4-b]pyrazin-4(1H)-yl)-1,6-naphthyridin-2(1H)-one The crude compound obtained in step-1 was purified in Combiflash® chromatography using 10% methanol in chloroform as eluent. This was further purified in preparative HPLC using mobile phase 0.02% TFA in water and (1:1) acetonitrile methanol. (1:1) acetonitrile methanol was in gradient of 20% at 0 min, 30% at 2 minute and 40% at $9^{th}$ minute using column KINETEX EVO C18 (150 mm×21.2 mm); 5.0µ with the flow rate of 20 mL per minute. This afforded pure 7-((1S,4S)-2-oxa-5-azabicyclo[2.2.1]heptan-5-yl)-1,3-dimethyl-5-(1-methyl-7-(1-methyl-1H-pyrazol-4-yl)-2,3-dihydropyrido[3,4-b]pyrazin-4(1H)-yl)-1,6-naphthyridin-2(1H)-one (15 mg, 30.09%). LC-MS: 499.1 $[M+H]^+$; 1H-NMR (400 MHz, Chloroform-D) δ 7.82 (s, 2H), 7.46 (s, 1H), 7.41 (s, 1H), 6.64 (s, 1H), 5.75 (s, 1H), 4.98 (s, 1H), 4.72 (s, 1H), 3.91 (s, 3H), 3.86 (s, 2H), 3.80-3.78 (m, 2H), 3.63-3.61 (m, 5H), 3.53-3.51 (m, 1H), 3.40-3.37 (m, 1H), 3.11 (s, 3H), 2.06 (s, 3H), 1.95 (s, 2H).

The below examples (203-232) were prepared according to the protocols described in the synthesis of Example-201, Example-202 and Example-203 with appropriate variations in reactants, quantities of reagents, solvents and reaction conditions with appropriate coupling methods.

| Example | Structure | Coupling Method | Spectral data |
|---|---|---|---|
| 203 | 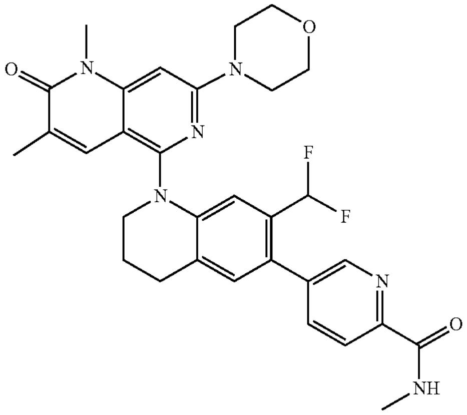 [SMILES: CNC(=O)c1ccc(-c2cc3c(cc2C(F)F)N(c2nc(N4CCOCC4)cc4c2cc(C)c(=O)n4C)CCC3)cn1] | D | LC-MS: 575.2 [M + H]$^+$; 1H-NMR (400 MHz, Chloroform-D) δ 8.57 (d, J = 2.1 Hz, 1H), 8.28 (d, J = 8.0 Hz, 1H), 8.02 (s, 2H), 7.88-7.86 (m, 1H), 7.13 (s, 1H), 6.64 (s, 1H), 4.00 (t, J = 6.1, 6.1 Hz, 2H), 3.91 (t, J = 4.6, 4.6 Hz, 4H), 3.58 (s, 3H), 3.31 (s, 4H), 3.08 (d, J = 5.0 Hz, 3H), 2.89 (t, J = 6.5, 6.5 Hz, 2H), 2.23 (d, J = 1.2 Hz, 3H), 2.11-2.08 (m, 2H), 7.63-7.62 (m, 1H). |
| 204 | 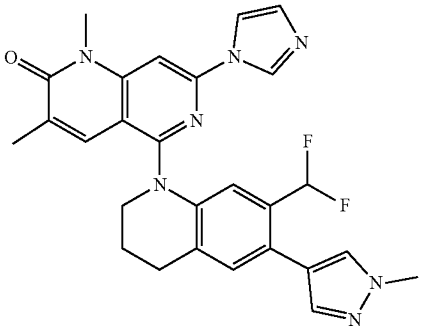 [SMILES: Cc1cc2c(N3CCCc4cc(-c5cnn(C)c5)c(C(F)F)cc43)nc(-n3ccnc3)cc2n(C)c1=O] | E | LC-MS: 502.2 [M + H]$^+$; 1H-NMR (400 MHz, Chloroform-D) δ 8.35 (s, 1H), 7.62 (s, 2H), 7.47-7.44 (m, 2H), 7.20 (d, J = 12.8 Hz, 2H), 6.95 (s, 1H), 6.80 (s, 1H), 6.60-6.32 (m, 1H), 3.96 (s, 3H), 3.90-3.88 (m, 2H), 3.78 (s, 3H), 3.30 (brs, 2H), 2.19-2.14 (m, 5H). |
| 205 | 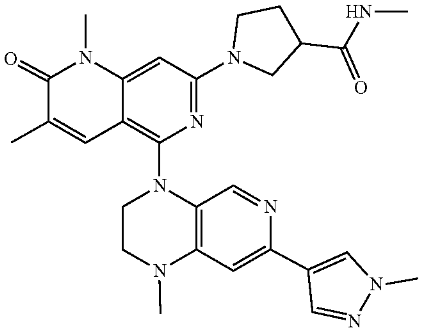 [SMILES: CNC(=O)C1CCN(c2cc3c(cc(C)c(=O)n3C)c(N3CCN(C)c4cc(-c5cnn(C)c5)ncc43)n2)C1] | D | LC-MS: 528.1 [M + H]$^+$; 1H-NMR (600 MHz, Chloroform-D) δ 7.83 (s, 1H), 7.80 (s, 1H), 7.46 (s, 1H), 7.42 (s, 1H), 6.64 (s, 1H), 5.76 (s, 1H), 3.91 (s, 3H), 3.81-3.79 (m, 3H), 3.67-3.63 (m, 3H), 3.61 (s, 4H), 3.48 (d, J = 9.1 Hz, 1H), 3.11 (s, 3H), 2.99 (s, 1H), 2.84 (s, 3H), 2.30-2.25 (m, 2H), 2.06 (s, 3H). |
| 206 | 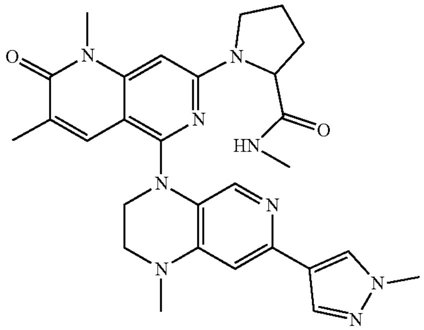 [SMILES: CNC(=O)C1CCCN1c1cc2c(cc(C)c(=O)n2C)c(N2CCN(C)c3cc(-c4cnn(C)c4)ncc32)n1] | D | LC-MS: 528.2 [M + H]$^+$; 1H-NMR (400 MHz, Chloroform-D) δ 8.41 (s, 1H), 7.89 (s, 1H), 7.41 (d, J = 1.2 Hz, 1H), 6.68 (s, 1H), 5.99 (s, 1H), 4.36 (s, 1H), 3.97 (s, 3H), 3.84 (s, 1H), 3.73 (d, J = 13.0 Hz, 4H), 3.62 (s, 3H), 3.42 (q, J = 8.9, 8.6, 8.6 Hz, 2H), 7.12-7.03 (m, 1H), 3.30 (s, 3H), 2.65 (d, J = 4.7 Hz, 3H), 2.32-2.20 (m, 3H), 2.15 (d, J = 1.2 Hz, 3H), 2.04 (s, 3H), 7.72-7.64 (m, 1H). |

-continued

| Example | Structure | Coupling Method | Spectral data |
| --- | --- | --- | --- |
| 207 | 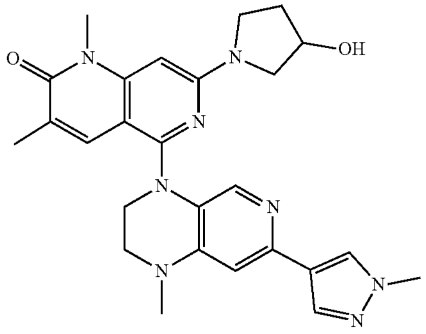 [SMILES: Cc1cc2c(N3CCN(C)c4cc(-c5cnn(C)c5)ncc43)nc(N3CCC(O)C3)cc2n(C)c1=O] | D | LC-MS: 487.2 $[M + H]^+$; 1H-NMR (400 MHz, Chloroform-D) δ 7.93 (s, 1H), 7.83 (s, 1H), 7.46 (d, J = 5.7 Hz, 2H), 6.64 (s, 1H), 5.77 (s, 1H), 4.57 (s, 1H), 3.13-3.12 (m, 3H), 3.91 (s, 3H), 3.80 (s, 2H), 3.61 (s, 7H), 2.14 (dd, J = 8.4, 4.1 Hz, 5H), 2.07 (s, 3H). |
| 208 | 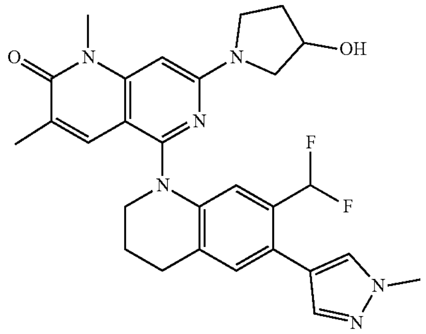 [SMILES: Cc1cc2c(N3CCCc4cc(-c5cnn(C)c5)c(C(F)F)cc43)nc(N3CCC(O)C3)cc2n(C)c1=O] | D | LC-MS: 521.15 $[M + H]^+$; 1H-NMR (600 MHz, Chloroform-D) δ 6.75 (s, 1H), 5.85 (s, 1H), 4.61-4.59 (m, 1H), 7.55 (s, 1H), 7.42 (s, 2H), 3.95 (s, 3H), 3.76 (d, J = 4.8 Hz, 2H), 3.65 (s, 8H), 2.97 (s, 2H), 2.18 (dd, J = 8.9, 4.8 Hz, 4H), 2.09 (d, J = 1.2 Hz, 4H), 7.11-7.10 (m, 1H). |
| 209 | 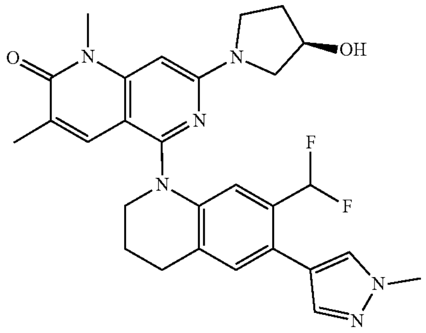 [SMILES: Cc1cc2c(N3CCCc4cc(-c5cnn(C)c5)c(C(F)F)cc43)nc(N3CC[C@@H](O)C3)cc2n(C)c1=O] | D | LC-MS: 521.2 $[M + H]^+$; 1H-NMR (400 MHz, Chloroform-D) δ 7.55 (s, 1H), 7.40 (t, J = 1.0, 1.0 Hz, 2H), 7.10 (s, 1H), 6.75 (s, 1H), 6.45 (s, 1H), 5.84 (s, 1H), 4.61 (s, 1H), 3.95 (s, 3H), 3.76 (d, J = 4.7 Hz, 2H), 3.63 (d, J = 8.1 Hz, 7H), 2.97 (s, 2H), 2.15 (d, J = 5.5 Hz, 4H), 2.09 (s, 3H), 1.71 (s, 1H). |
| 210 | 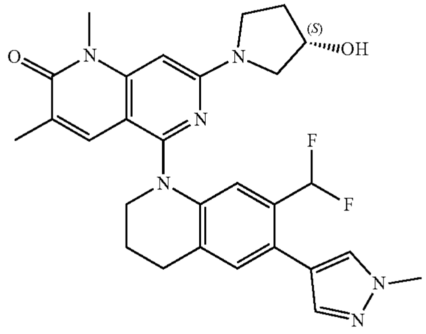 | D | LC-MS: 521.3 $[M + H]^+$; 1H-NMR (400 MHz, Chloroform-D) δ 7.55 (d, J = 0.7 Hz, 1H), 7.42-7.39 (m, 2H), 7.10 (d, J = 1.1 Hz, 1H), 6.75 (s, 1H), 6.45 (s, 1H), 5.84 (s, 1H), 4.62-4.60 (m, 1H), 3.94 (s, 3H), 3.75 (td, J = 4.0, 3.8, 2.4 Hz, 2H), 3.63 (d, J = 7.0 Hz, 7H), 2.96 (d, J = 6.6 Hz, 2H), 2.17-2.10 (m, 4H), 2.09 (d, J = 1.2 Hz, 3H). |

-continued

| Example | Structure | Coupling Method | Spectral data |
|---|---|---|---|
| 211 | 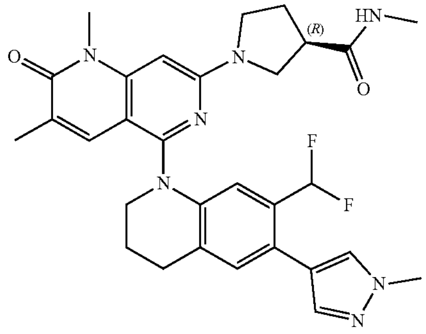 | D | LC-MS: 562.1 [M + H]+; 1H-NMR (600 MHz, Chloroform-D) δ 7.55 (s, 1H), ,7.40 (s, 2H), 7.10 (s, 1H), 6.45 (s, 1H), 5.63 (s, 1H), 3.95 (s, 3H), 3.76-3.70 (m, 6H), 3.64 (s, 3H), 3.48-3.46 (m, 1H), 3.00 (d, J = 7.8 Hz, 2H), 5.84-5.83 (m, 1H), 2.84 (s, 3H), 2.32 (d, J = 4.1 Hz, 1H), 2.24 (q, J = 3.7, 3.7, 3.3 Hz, 1H), 2.13 (s, 2H), 2.09 (s, 3H), 6.75-6.74 (m, 1H). |
| 212 | 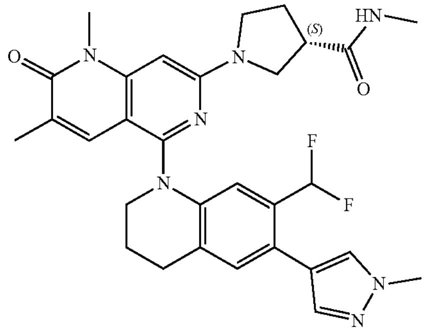 | D | LC-MS: 562.1 [M + H]+; 1H-NMR (600 MHz, Chloroform-D) δ 7.55 (s, 1H), 7.41 (d, J = 7.1 Hz, 2H), 6.75 (s, 1H), 6.45 (s, 1H), 5.85 (s, 1H), 5.60-5.58 (m, 1H), 3.95 (s, 3H), 3.81-3.69 (m, 5H), 3.64 (s, 3H), 3.48-3.47 (m, 1H), 2.97 (d, J = 6.4 Hz, 3H), 2.85 (d, J = 4.9 Hz, 3H), 2.33-2.25 (m, 2H), 2.14-2.07 (m, 5H), 7.10-7.07 (m, 1H). |
| 213 | 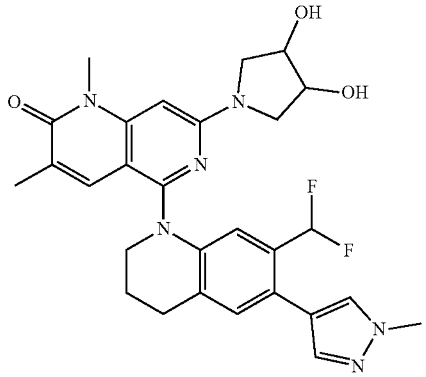 [SMILES: Cc1cc2c(N3CCCc4cc(-c5cnn(C)c5)c(C(F)F)cc43)nc(N3CC(O)C(O)C3)cc2n(C)c1=O] | D | LC-MS: 537.2 [M + H]+; 1H-NMR (400 MHz, DMSO-D6) δ 7.76 (s, 1H), 7.51 (s, 1H), 7.43 (s, 1H), 7.16 (s, 1H), 6.72 (s, 1H), 6.48 (s, 1H), 6.02 (s, 1H), 4.95 (d, J = 4.6 Hz, 2H), 4.16-4.13 (m, 2H), 3.86 (s, 3H), 3.65 (d, J = 5.6 Hz, 2H), 3.57 (s, 5H), 3.30 (d, J = 4.5 Hz, 2H), 2.92 (s, 2H), 2.09-2.05 (m, 2H), 1.97 (d, J = 1.2 Hz, 3H). |
| 214 | 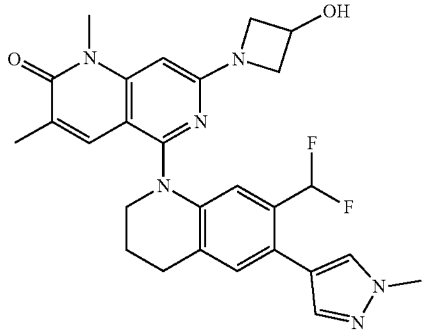 | D | LC-MS: 501.1 [M + H]+; 1H-NMR (400 MHz, Chloroform-D) δ 7.54 (d, J = 0.7 Hz, 1H), 7.41 (d, J = 5.9 Hz, 2H), 7.10 (s, 1H), 6.70 (s, 1H), 6.45 (s, 1H), 5.78 (s, 1H), 4.79 (s, 2H), 4.32 (dd, J = 9.8, 6.3 Hz, 2H), 3.95 (s, 3H), 3.89 (dd, J = 9.7, 4.3 Hz, 2H), 3.73 (d, J = 5.7 Hz, 2H), 3.62 (s, 3H), 2.97 (d, J = 6.5 Hz, 2H), 2.13 (s, 2H), 2.09 (s, 3H). |

-continued

| Example | Structure | Coupling Method | Spectral data |
|---|---|---|---|
| 215 | 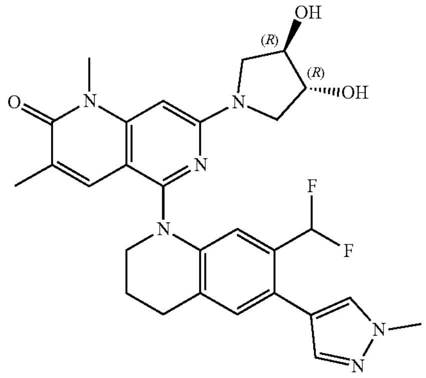 | D | LC-MS: 537.3 $[M + H]^+$; 1H-NMR (400 MHz, DMSO-D6) δ 7.76 (s, 1H), 7.51 (s, 1H), 7.43 (s, 1H), 7.17 (s, 1H), 6.72 (s, 1H), 6.48 (s, 1H), 6.04 (s, 1H), 5.16 (s, 2H), 4.04 (s, 2H), 3.86 (s, 3H), 3.64 (d, J = 5.6 Hz, 2H), 3.58 (s, 5H), 2.92 (d, J = 6.7 Hz, 2H), 2.08 (d, J = 5.4 Hz, 2H), 1.97 (d, J = 1.2 Hz, 3H). |
| 216 | 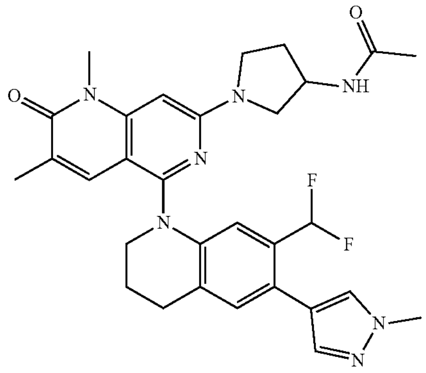 [SMILES: CC(=O)NC1CCN(c2cc3c(cc(C)c(=O)n3C)c(N3CCCc4cc(-c5cnn(C)c5)c(C(F)F)cc43)n2)C1] | D | LC-MS: 562.3 $[M + H]^+$; 1H-NMR (600 MHz, Chloroform-D) δ 7.55 (s, 1H), 7.42 (s, 2H), 7.10 (s, 1H), 6.75 (s, 1H), 6.46 (s, 1H), 5.81 (s, 1H), 4.61 (s, 1H), 3.95 (s, 3H), 3.76 (d, J = 5.2 Hz, 3H), 3.58-3.50 (m, 6H), 2.97 (s, 2H), 2.30 (d, J = 7.1 Hz, 1H), 2.15 (d, J = 6.0 Hz, 2H), 2.09 (s, 3H), 2.00 (d, J = 2.6 Hz, 4H). |
| 217 | 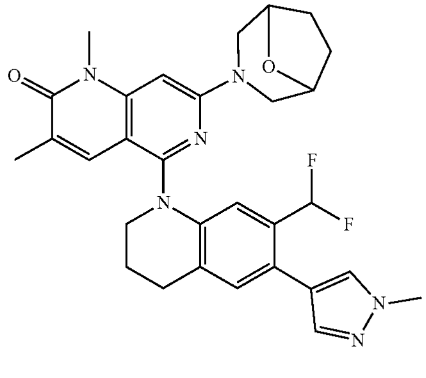 | D | LC-MS: 574.4 $[M + H]^+$; 1H-NMR (400 MHz, Chloroform-D) δ 3.74 (s, 2H), 3.65 (s, 3H), 3.13 (d, J = 2.1 Hz, 2H), 2.97 (s, 2H), 2.13-2.10 (m, 5H), 1.96 (s, 2H), 1.85 (s, 2H), 1.54 (s, 2H), 3.87-3.84 (m, 2H), 7.55 (d, J = 0.8 Hz, 1H), 7.11 (s, 1H), 6.46 (s, 1H), 6.01 (s, 1H), 7.42-7.41 (m, 2H), 4.48 (s, 2H), 6.82-6.81 (m, 1H), 3.95 (s, 3H). |
| 218 | 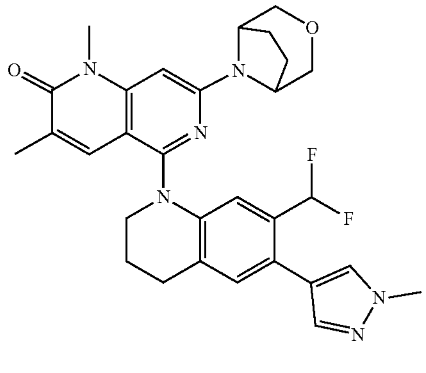 [SMILES: Cc1cc2c(N3CCCc4cc(-c5cnn(C)c5)c(C(F)F)cc43)nc(N3C4CCC3COC4)cc2n(C)c1=O] | D | LC-MS: 547.4 $[M + H]^+$; 1H-NMR (400 MHz, Chloroform-D) δ 3.82 (s, 2H), 3.73 (d, J = 5.6 Hz, 3H), 3.59 (dd, J = 10.8, 1.7 Hz, 5H), 2.96 (s, 2H), 2.12-2.10 (m, 7H), 1.99 (t, J = 3.7, 3.7 Hz, 2H), 3.95-3.93 (m, 2H), 7.55 (s, 1H), 7.42 (s, 2H), 7.10 (s, 1H), 6.80 (s, 1H), 6.46 (s, 1H), 6.08 (s, 1H), 4.44 (d, J = 3.8 Hz, 2H). |

-continued

| Example | Structure | Coupling Method | Spectral data |
|---|---|---|---|
| 219 | 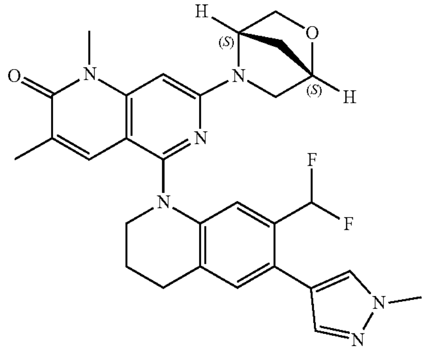 | D | LC-MS: 533.2 [M + H]+; 1H-NMR (600 MHz, Chloroform-D) δ 6.45 (s, 1H), 5.82 (s, 1H), 4.74-4.72 (m, 1H), 7.55 (s, 1H), 7.42 (d, J = 2.4 Hz, 2H), 3.95 (s, 3H), 3.84 (s, 2H), 5.00-4.98 (m, 1H), 3.74 (d, J = 5.8 Hz, 2H), 3.64 (s, 3H), 3.54 (d, J = 1.6 Hz, 1H), 3.39 (s, 1H), 2.96 (d, J = 6.6 Hz, 2H), 6.79-6.78 (m, 1H), 2.14 (d, J = 5.9 Hz, 2H), 7.10-7.09 (m, 1H), 2.10-2.08 (m, 3H), 1.94 (s, 2H). |
| 220 | 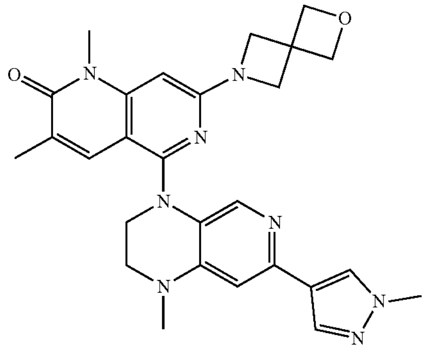 [SMILES: Cc1cc2c(N3CCN(C)c4cc(-c5cnn(C)c5)ncc43)nc(N3CC4(COC4)C3)cc2n(C)c1=O] | D | LC-MS: 499.2 [M + H]+; 1H-NMR (400 MHz, Chloroform-D) δ 7.82 (s, 1H), 7.78 (s, 1H), 7.45 (s, 1H), 7.36 (s, 1H), 6.64 (s, 1H), 5.70 (s, 1H), 4.85 (s, 3H), 4.20 (s, 3H), 3.86 (s, 2H), 3.90 (s, 3H), 3.79 (brs, 2H), 3.62 (brs, 2H), 3.60 (s, 3H), 3.10 (s, 3H), 2.04 (s, 3H). |
| 221 | 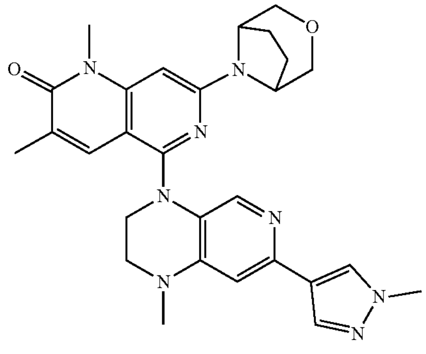 [SMILES: Cc1cc2c(N3CCN(C)c4cc(-c5cnn(C)c5)ncc43)nc(N3C4CCC3COC4)cc2n(C)c1=O] | D | LC-MS: 513.5 [M + H]+; 1H-NMR (400 MHz, Chloroform-D) δ 7.82 (s, 1H), 7.78 (s, 1H), 7.47 (s, 1H), 7.41 (s, 1H), 6.64 (s, 1H), 6.01 (s, 1H), 4.45 (s, 2H), 3.90 (s, 3H), 3.85-3.82 (m, 2H), 3.78 (s, 2H), 3.61 (s, 3H), 3.58-3.45 (m, 3H), 3.10 (s, 3H), 2.10-2.02 (m, 6H), 1.63 (brs, 2H). |
| 222 | 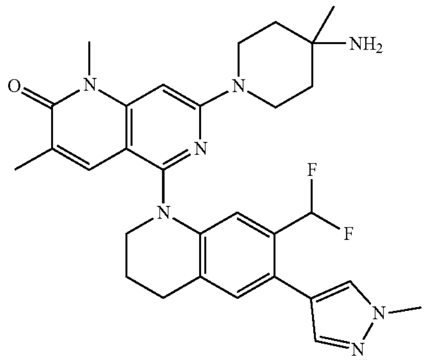 [SMILES: Cc1cc2c(N3CCCc4cc(-c5cnn(C)c5)c(C(F)F)cc43)nc(N3CCC(C)(N)CC3)cc2n(C)c1=O] | D | LC-MS: 448.3 [M + H]+; 1H-NMR (300 MHz, Chloroform-D) δ 7.64 (s, 1H), 7.51 (s, 1H), 7.48 (s, 1H), 7.15 (s, 1H), 6.69-6.61 (m, 1H), 6.5-6.3 (m, 2H), 3.9 (s, 3H), 3.77-3.73 (m, 4H), 3.66-3.61 (m, 6H), 2.96 (d, J = 6.3 Hz, 2H), 2.14-2.11 (m, 2H), 2.02 (s, 3H), 1.6 (d, J = 3.9 Hz, 4H), 1.2 (s, 3H). |

-continued
| Example | Structure | Coupling Method | Spectral data |
|---|---|---|---|
| 223 | 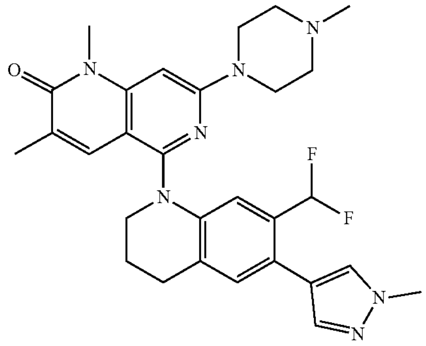 [SMILES: Cc1cc2c(N3CCCc4cc(-c5cnn(C)c5)c(C(F)F)cc43)nc(N3CCN(C)CC3)cc2n(C)c1=O] | D | LC-MS: 434.4 [M + H]+; 1H-NMR (400 MHz, Chloroform-D) δ 7.54 (s, 1H), 7.41 (s, 1H), 7.39 (s, 1H), 7.10 (s, 1H), 6.77 (s, 1H), 6.58-6.30 (3m, 1H), 6.06 (s, 1H), s 3.94 (s, 3H), 3.77-3.74 (m, 2H), 3.65 (s, 3H), 3.62-3.60 (m, 4H), 2.96 (brs, 2H), 2.52-2.49 (m, 4H), 2.34 (s, 3H), 2.13-2.09 (m, 5H). |
| 224 | 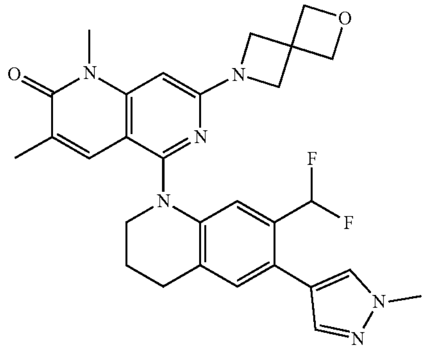 [SMILES: Cc1cc2c(N3CCCc4cc(-c5cnn(C)c5)c(C(F)F)cc43)nc(N3CC4(COC4)C3)cc2n(C)c1=O] | D | LC-MS: 533.5 [M + H]+; 1H-NMR (400 MHz, Chloroform-D) δ 7.56 (s, 1H), 7.43-7.41 (m, 2H), 7.11 (s, 1H), 6.71 (s, 1H), 6.60-6.33 (m, 1H), 5.75 (s, 1H), 4.86 (s, 4H), 4.22 (s, 4H), 3.96 (s, 3H), 3.76-3.73 (m, 2H), 3.65 (s, 3H), 2.98 (brs, 2H), 2.17-2.14 (m, 2H), 2.10 (s, 3H). |
| 225 | 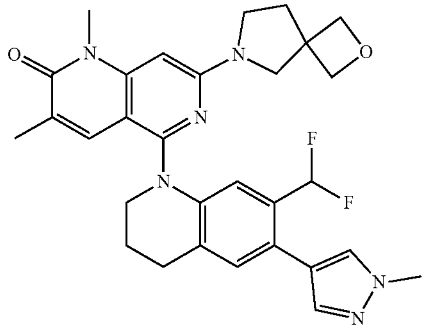 [SMILES: Cc1cc2c(N3CCCc4cc(-c5cnn(C)c5)c(C(F)F)cc43)nc(N3CCC4(COC4)C3)cc2n(C)c1=O] | D | LC-MS: 547.5 [M + H]+; 1H-NMR (600 MHz Chloroform-D) δ 7.54 (s, 1H), 7.41-7.39 (m, 2H), 7.10 (s, 1H), 6.74 (s, 1H), 6.54-6.35 (m, 1H), 5.81 (s, 1H), 4.71 (d, J = 6 Hz, 2H), 4.64 (d, J = 5.4 Hz, 2H), 3.94 (s, 2H), 3.75 (d, J = 5.4 Hz, 3H), 3.64 (s, 3H), 3.51-3.49 (m, 2H), 2.97-2.95 (m, 1H), 2.33-2.30 (m, 2H), 2.16-2.12 (m, 2H), 2.08 (s, 3H), 1.61 (s, 3H). |
| 226 | 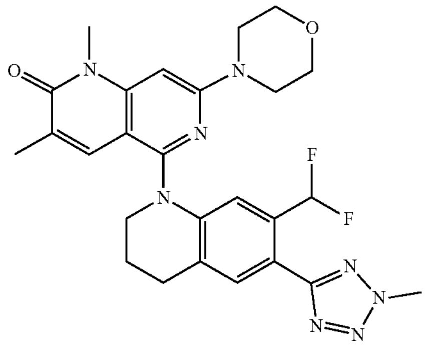 [SMILES: Cc1cc2c(N3CCCc4cc(-c5nnn(C)n5)c(C(F)F)cc43)nc(N3CCOCC3)cc2n(C)c1=O] | D | LC-MS: 523.3 [M + H]+; 1H-NMR (400 MHz, Chloroform-D) δ 7.90 (s, 1H), 7.61-7.34 (m, 2H), 6.84 (s, 1H), 6.15 (s, 1H), 4.39 (s, 3H), 3.83-3.80 (m, 6H), 3.66 (s, 3H), 3.57-3.55 (m, 4H), 3.02 (brs, 2H), 2.20-2.10 (m, 5H). |

-continued

| Example | Structure | Coupling Method | Spectral data |
|---|---|---|---|
| 227 | 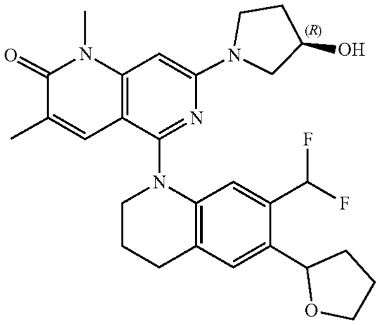 | D | LC-MS: 511.4 [M + H]$^+$; 1H-NMR (600 MHz, Chloroform-D) δ 7.35 (s, 1H), 7.25-7.23 (m, 1H), 6.70-6.61 (m, 1H), 6.53 (d, J = 7.2 Hz, 1H), 5.81 (s, 1H), 5.0-4.98 (m, 1H), 4.59 (brs, 1H), 4.13-4.10 (m, 1H), 3.91-3.88 (m, 1H), 3.74-3.68 (m, 2H), 3.62 (d, J = 7.8 Hz, 3H), 3.60-3.54 (m, 4H), 2.93 (brs, 2H), 2.29-2.17 (m, 1H), 2.17-2.08 (m, 4H), 2.06 (s, 3H), 2.04-1.99 (m, 2H), 1.76-1.72 (m, 2H). |
| 228 | 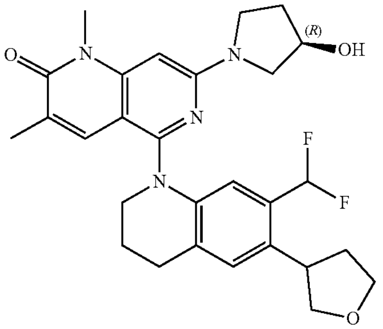 | D | LC-MS: 511.4 [M + H]$^+$; 1H-NMR (400 MHz, Chloroform-D) δ 7.37 (s, 1H), 7.12 (s, 1H), 6.47-6.44 (m, 1H), 5.82 (s, 1H), 4.61 (brs, 1H), 4.1-4.05 (m, 2H), 3.9-3.8 (m, 1H), 3.76-3.742 (m, 3H), 3.64 (s, 3H), 3.62-3.58 (m, 3H), 2.93 (brs, 2H), 2.45-2.43 (m, 1H), 2.16-2.13 (m, 3H), 2.07 (s, 3H), 2.05-2.0 (m, 1H), 1.57 (s, 4H). |
| 229 | 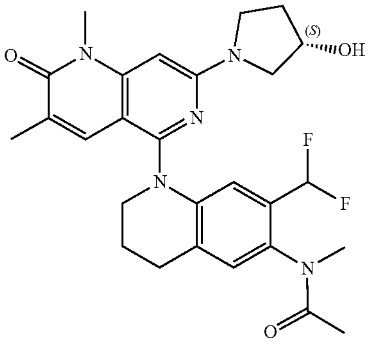 | D | LC-MS: 512.2 [M + H]$^+$; 1H-NMR (600 MHz, Chloroform-D) δ 7.96 (s, 1H), 7.80 (s, 1H), 6.95 (s, 1H), 6.56 (s, 1H), 6.32 (s, 1H), 4.55 (s, 1H), 3.99 (d, J = 6.2 Hz, 1H), 3.88 (dt, J = 12.8, 5.1, 5.1 Hz, 2H), 3.69 (dt, J = 3.7, 1.8, 1.8 Hz, 1H), 3.64 (d, J = 4.0 Hz, 1H), 3.56 (d, J = 1.1 Hz, 3H), 3.22 (d, J = 1.2 Hz, 3H), 2.82 (s, 2H), 2.20 (d, J = 1.1 Hz, 3H), 2.10-2.03 (m, 5H), 1.85 (d, J = 5.2 Hz, 3H). |
| 230 | 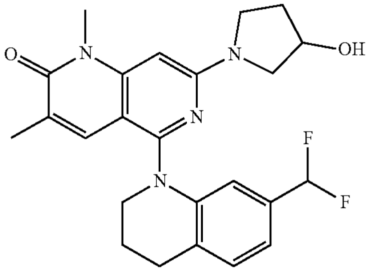 [SMILES: Cc1cc2c(N3CCCc4ccc(C(F)F)cc43)nc(N3CCC(O)C3)cc2n(C)c1=O] | D | LC-MS: 441.15 [M + H]$^+$; 1H-NMR (400 MHz, Chloroform-D) δ 7.36 (s, 1H), 7.15 (d, 7.6 Hz, 1H), 6.78-6.76 (m, 1H), 6.47 (s, 1H), 6.46-6.22 (m, 1H), 5.83 (s, 1H), 4.61 (brs, 1H), 3.73 (brs, 2H), 3.64-3.58 (m, 6H), 2.96 (brs, 2H), 2.13-2.12 (m, 3H), 2.06 (s, 3H), 1.56 (brs, 3H). |
| 231 | 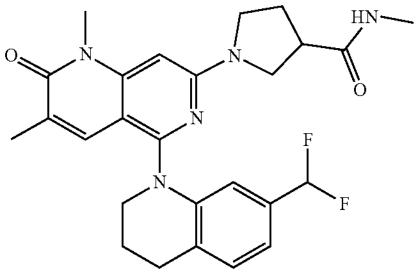 [SMILES: CNC(=O)C1CCN(c2cc3c(cc(C)c(=O)n3C)c(N3CCCc4ccc(C(F)F)cc43)n2)C1] | D | LC-MS: 482.1 [M + H]$^+$; 1H-NMR (600 MHz, Chloroform-D) δ 7.36 (d, J = 3.6 Hz, 1H), 7.14 (d, J = 7.3 Hz, 1H), 6.86 (d, J = 7.7 Hz, 1H), 6.35 (d, J = 3.7 Hz, 1H), 5.84 (s, 1H), 5.59 (s, 1H), 3.76-3.70 (m, 4H), 3.63 (d, J = 3.7 Hz, 3H), 3.47 (d, J = 8.8 Hz, 1H), 2.97 (dd, J = 25.2, 6.8 Hz, 3H), 2.85 (d, J = 4.4 Hz, 3H), 2.31-2.25 (m, 2H), 2.12 (d, J = 5.9 Hz, 2H), 2.07 (d, J = 3.7 Hz, 3H), 6.49-6.48 (m, 1H). |

-continued
| Example | Structure | Coupling Method | Spectral data |
|---|---|---|---|
| 232 | 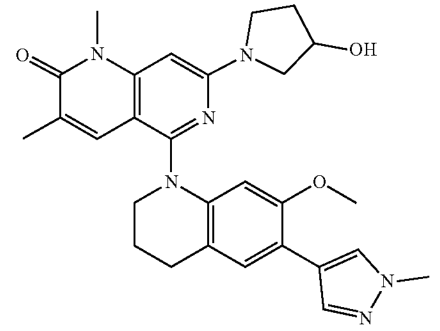 [SMILES: COc1cc2c(cc1-c1cnn(C)c1)CCCN2c1nc(N2CCC(O)C2)cc2c1cc(C)c(=O)n2C] | D | LC-MS: 501.15 [M + H]$^+$; 1H-NMR (600 MHz, Chloroform-D) δ 7.77 (s, 1H), 7.71 (s, 1H), 7.44 (s, 1H), 7.20 (s, 1H), 6.03 (s, 1H), 5.79 (s, 1H), 4.62 (s, 1H), 3.90 (s, 3H), 3.79-3.75 (m, 2H), 3.64 (d, J = 5.5 Hz, 5H), 3.48 (s, 3H), 2.89 (d, J = 6.6 Hz, 2H), 2.18-2.11 (m, 6H), 2.06 (s, 3H). |
Example-233: 5-(7-(Difluoromethyl)-6-(1-methyl-1H-pyrazol-4-yl)-3,4-dihydroquinolin-1(2H)-yl)-7-methoxy-1,3-dimethyl-1,6-naphthyridin-2(1H)-one
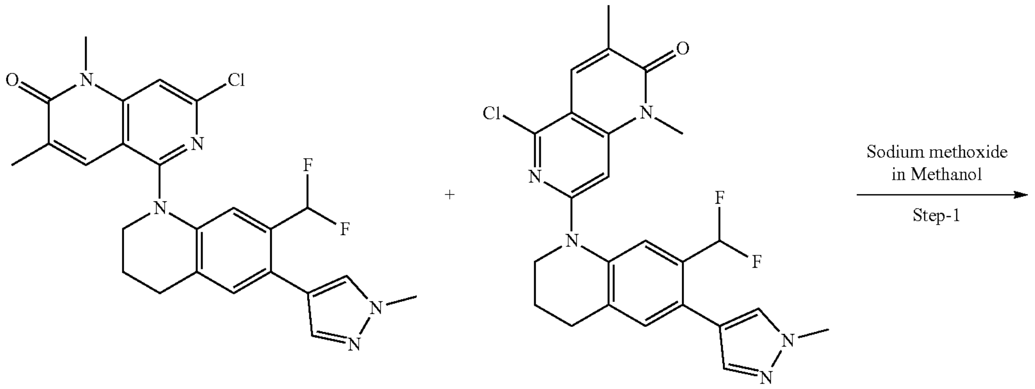
Mixture of regio isomers (80:20)
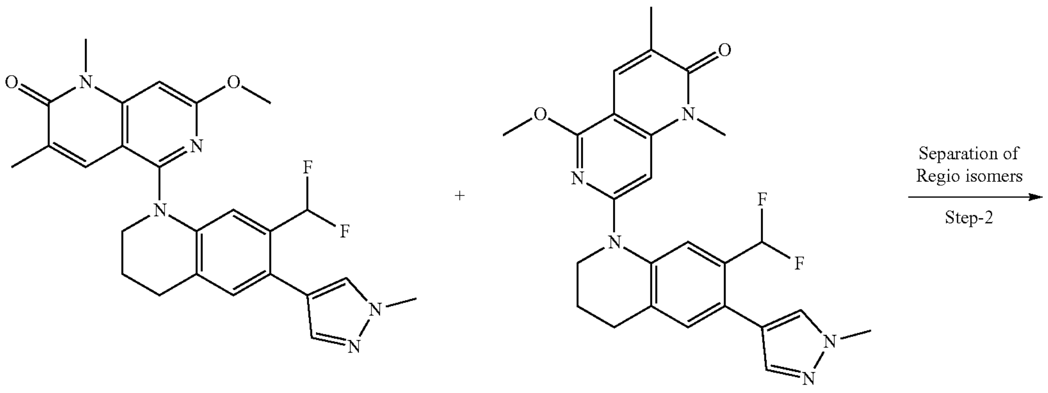
Mixture of regio isomers (80:20)

-continued

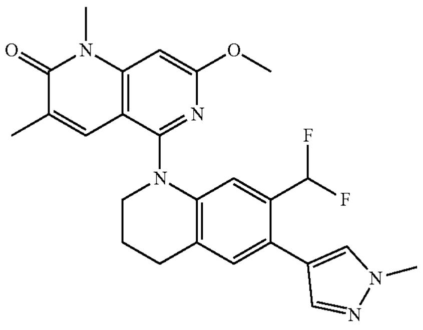

Example-233

Step-1: Synthesis of 5-(7-(difluoromethyl)-6-(1-methyl-1H-pyrazol-4-yl)-3,4-dihydroquinolin-1(2H)-yl)-7-methoxy-1,3-dimethyl-1,6-naphthyridin-2(1H)-one The mixture of E00a and E200b (150 mg, 0.32 mmol) in methanol (10 mL) was added sodium methoxide (20 mg 46.5 mmol) at room temperature. Then the mixture was heated to 70° C. for 48 h. The reaction mixture was then cooled to RT, added water, extracted with ethyl acetate, extracts were dried over sodium sulphate and concentrated to residue. LC-MS: 501.15 $[M+H]^+$;

Step-2: Separation of 5-(7-(difluoromethyl)-6-(1-methyl-1H-pyrazol-4-yl)-3,4-dihydroquinolin-1(2H)-yl)-7-methoxy-1,3-dimethyl-1,6-naphthyridin-2(1H)-one & 7-(7 (difluoromethyl)-6-(1-methyl-1H-pyrazol-4-yl)-3,4-dihydroquinolin-1(2H)-yl)-5-methoxy-1,3-dimethyl-1,6-naphthyridin-2(1H)-one The residue from Step-1 was purified by prep HPLC using mobile phase 0.02% ammonium hydroxide in water and Acetonitrile in column: KINETEX EVO $C_{18}$ (21.2 mm×150 mm) with flow rate of 20 mL/minute. This afforded 5-(7-(difluoromethyl)-6-(1-methyl-1H-pyrazol-4-yl)-3,4-dihydroquinolin-1(2H)-yl)-7-methoxy-1,3-dimethyl-1,6-naphthyridin-2(1H)-one (30 mg, 20.1%) LC-MS: 466.3 $[M+H]^+$. 1H-NMR (400 MHz, Chloroform-D) δ 7.57 (t, J=1.0, 1.0 Hz, 1H), 7.47-7.43 (m, 2H), 7.14 (d, J=1.5 Hz, 1H), 6.75 (s, 1H), 6.48-6.43 (m, 1H), 6.33 (d, J=1.2 Hz, 1H), 3.98-3.96 (m, 3H), 3.93-3.92 (m, 3H), 3.81 (t, J=5.4, 5.4 Hz, 2H), 3.68-3.67 (m, 3H), 2.99 (d, J=6.5 Hz, 2H), 2.18 (d, J=6.3 Hz, 2H), 2.13 (t, J=1.2, 1.2 Hz, 3H).

Example-234: 5-(7-(Difluoromethyl)-6-(1-methyl-1H-pyrazol-4-yl)-3,4-dihydroquinolin-1(2H)-yl)-1,3-dimethyl-7-morpholino-1,6-naphthyridin-2(1H)-one

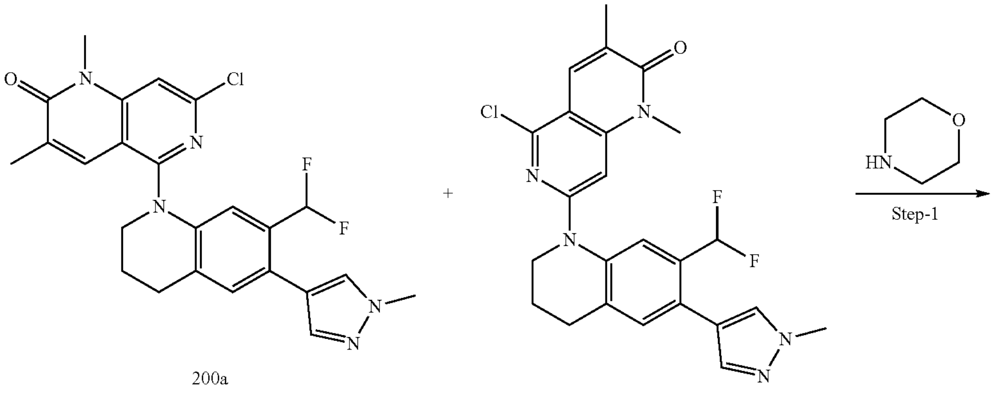

200a

200b

Mixture of regio isomers (80:20)

-continued

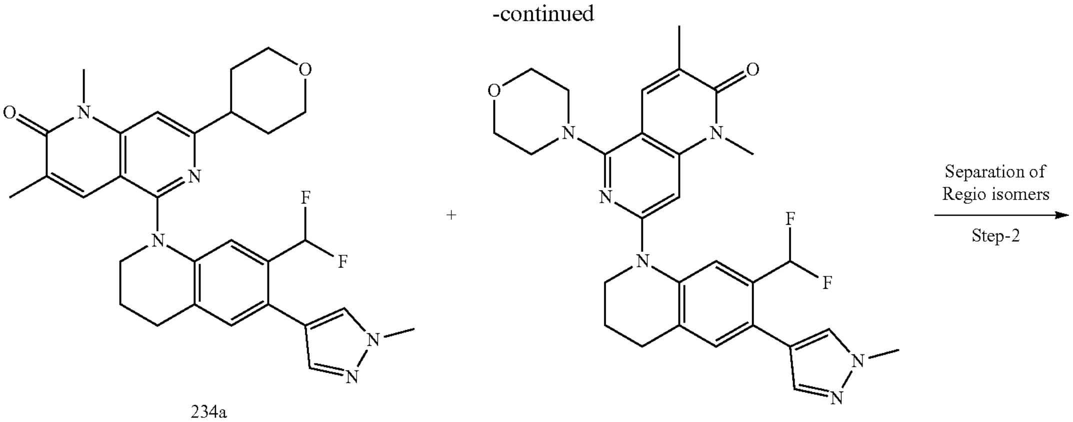

234a

234b

Mixture of regio isomers (80:20)

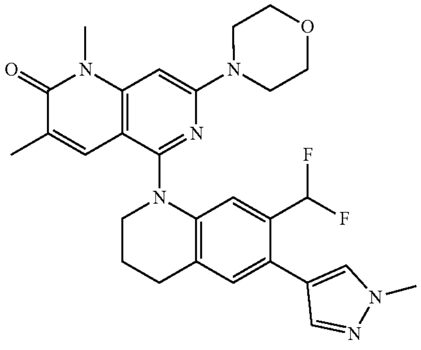

Example-234

Step-1: Synthesis of 5-(7-(difluoromethyl)-6-(1-methyl-1H-pyrazol-4-yl)-3,4-dihydroquinolin-1(2H)-yl)-1,3-dimethyl-7-morpholino-1,6-naphthyridin-2(1H)-one & 7-(7-(difluoromethyl)-6-(1-methyl-1H-pyrazol-4-yl)-3,4-dihydroquinolin-1(2H)-yl)-1,3-dimethyl-5-morpholino-1,6-naphthyridin-2(1H)-one A solution of an approximate 80:20 mixture of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one and 5-chloro-7-(7-(difluoromethyl)-6-(1-methyl-1H-pyrazol-4-yl)-3,4-dihydroquinolin-1(2H)-yl)-1,3-dimethyl-1,6-naphthyridin-2(1H)-one (200 mg 0.43 mmol) in DMF (8 mL) was added Morpholine (110 mg, 1.28 mmol) and heated to 110° C. for overnight. After cooling the reaction mixture to room temperature, water was added. Solid separated was filtered and dried. LC-MS: 520.8 $[M+H]^+$;

Step-2: Purification of 5-(7-(difluoromethyl)-6-(1-methyl-1H-pyrazol-4-yl)-3,4-dihydroquinolin-1(2H)-yl)-1,3-dimethyl-7-morpholino-1,6-naphthyridin-2(1H)-one & 7-(7-(difluoromethyl)-6-(1-methyl-1H-pyrazol-4-yl)-3,4-dihydroquinolin-1(2H)-yl)-1,3-dimethyl-5-morpholino-1,6-naphthyridin-2(1H)-one The crude solid obtained in step-1 was purified by preparative HPLC using mobile phase 0.01% TFA in acetonitrile in water using column ZZORBAX ECLIPSE C18 (150 mm×20 mm); 5.0μ with the flow rate of 20 mL per minute. This afforded pure 5-(7-(difluoromethyl)-6-(1-methyl-1H-pyrazol-4-yl)-3,4-dihydroquinolin-1(2H)-yl)-1,3-dimethyl-7-morpholino-1,6-naphthyridin-2(1H)-one (30 mg, 13.4%). LC-MS: 520.8 $[M+H]^+$; 1H-NMR (300 MHz, chloroform-D) δ 7.55 (d, J=0.7 Hz, 1H), 7.41 (d, J=3.0 Hz, 2H), 7.11 (s, 1H), 6.78 (s, 1H), 6.12 (s, 1H), 3.95 (s, 3H), 3.82 (dd, J=5.8, 3.8 Hz, 4H), 3.77 (d, J=5.7 Hz, 2H), 3.66 (s, 3H), 3.56 (dd, J=5.6, 4.1 Hz, 4H), 2.98 (d, J=6.5 Hz, 2H), 2.15 (d, J=5.9 Hz, 2H), 2.10 (d, J=1.2 Hz, 4H).

Example-235: 5-(7-(Difluoromethyl)-6-(1-methyl-2-oxo-1,2-dihydropyridin-3-yl)-3,4-dihydroquinolin-1(2H)-yl)-1,3-dimethyl-7-(tetrahydro-2H-pyran-4-yl)-1,6-naphthyridin-2(1H)-one

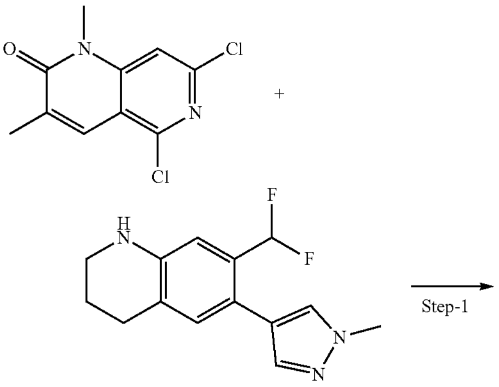

-continued

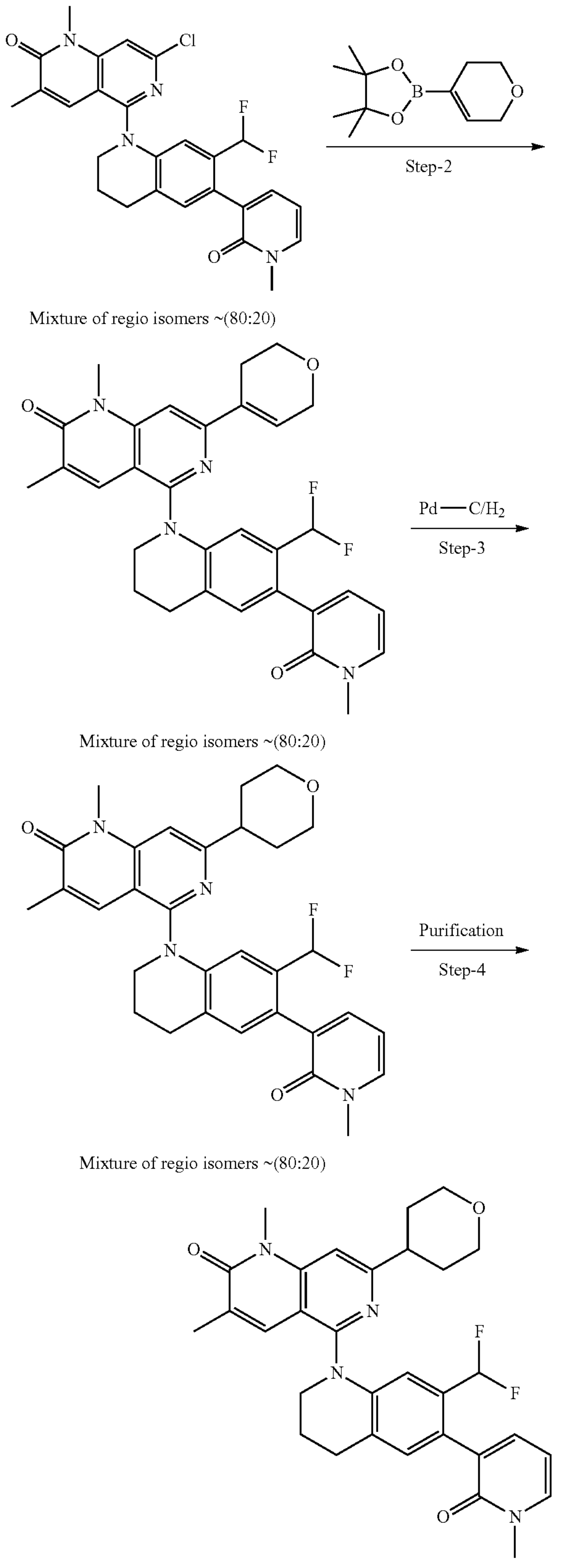

Example-235
Separated single
regioisomer

Step-1: Synthesis of 7-chloro-5-(7-(difluoromethyl)-6-(1-methyl-2-oxo-1,2-dihydropyridin-3-yl)-3,4-dihydroquinolin-1(2H)-yl)-1,3-dimethyl-1,6-naphthyridin-2(1H)-one A solution of an approximate 80:20 mixture of 7-chloro-5-(7-(difluoromethyl)-6-(1-methyl-2-oxo-1,2-dihydropyridin-3-yl)-3,4-dihydroquinolin-1(2H)-yl)-1,3-dimethyl-1,6-naphthyridin-2(1H)-one and 5-chloro-7-(7-(difluoromethyl)-6-(1-methyl-2-oxo-1,2-dihydropyridin-3-yl)-3,4-dihydroquinolin-1(2H)-yl)-1,3-dimethyl-1,6-naphthyridin-2(1H)-one (300 mg 1.03 mmol) in 1,4-dioxane (8 mL) was added potassium carbonate (430 mg, 3.09 mmol), Rac-BINAP (130 mg, 0.21 mmol), $Pd_2(dba)_3$ (90 mg, 0.1 mmol). The reaction mixture was heated to 100° C. for overnight. After cooling the reaction mixture to room temperature extracted with 10% methanol in DCM, organic portion was dried over sodium sulphate and concentrated to get crude mixture of regioisomers (80:20) 7-chloro-5-(7-(difluoromethyl)-6-(1-methyl-2-oxo-1,2-dihydropyridin-3-yl)-3,4-dihydroquinolin-1(2H)-yl)-1,3-dimethyl-1,6-naphthyridin-2(1H)-one & 5-chloro-7-(7-(difluoromethyl)-6-(1-methyl-2-oxo-1,2-dihydropyridin-3-yl)-3,4-dihydroquinolin-1(2H)-yl)-1,3-dimethyl-1,6-naphthyridin-2(1H)-one. LC-MS: 497.2[M+H]$^+$;

Step-2: Synthesis of 5-(7-(Difluoromethyl)-6-(1-methyl-2-oxo-1,2-dihydropyridin-3-yl)-3,4-dihydroquinolin-1(2H)-yl)-7-(3,6-dihydro-2H-pyran-4-yl)-1,3-dimethyl-1,6-naphthyridin-2(1H)-one A degassed solution of 7-chloro-5-(7-(difluoromethyl)-6-(1-methyl-2-oxo-1,2-dihydropyridin-3-yl)-3,4-dihydroquinolin-1(2H)-yl)-1,3-dimethyl-1,6-naphthyridin-2(1H)-one (80 mg, 0.16 mmol) and 2-(3,6-dihydro-2H-pyran-4-yl)-4,4,5,5-tetramethyl-1,3,2-dioxaborolane (50 mg, 0.24 mmol) in 1,2-dimethoxy ethane (2 mL) and water (0.5 mL). $Pd(Amphos)Cl_2$ (10 mg, 0.02 mmol) and potassium carbonate carbonate (70 mg, 0.48 mmol) was then added in the mixture. The mixture was stirred at 100° C. for 4 h. The reaction mixture was then cooled to room temperature, added water and extracted with ethyl acetate. Organic extracts were washed with water, brine dried over Sodium sulphate and concentrated to get the crude compound. The crude compound was passed through flash column using Combiflash® chromatography using 90% ethyl acetate in hexane as eluent to give mixture of regioisomers (~80:20) 5-(7-(difluoromethyl)-6-(1-methyl-2-oxo-1,2-dihydropyridin-3-yl)-3,4-dihydroquinolin-1(2H)-yl)-7-(3,6-dihydro-2H-pyran-4-yl)-1,3-dimethyl-1,6-naphthyridin-2(1H)-one & 7-(7-(difluoromethyl)-6-(1-methyl-2-oxo-1,2-dihydropyridin-3-yl)-3,4-dihydroquinolin-1(2H)-yl)-5-(3,6-dihydro-2H-pyran-4-yl)-1,3-dimethyl-1,6-naphthyridin-2(1H)-one (150 mg). LC-MS: 545.0 [M+H]$^+$;

Step-3: 5-(7-(difluoromethyl)-6-(1-methyl-2-oxo-1,2-dihydropyridin-3-yl)-3,4-dihydroquinolin-1(2H)-yl)-1,3-dimethyl-7-(tetrahydro-2H-pyran-4-yl)-1,6-naphthyridin-2(1H)-one A solution of mixture E235b (150 mg, 0.28 mmol) was added 10% Pd—C (0.3 g, 300% W/W) in 1:1 ethyl acetate and ethanol (10 mL). The reaction mixture was stirred under positive pressure of hydrogen in bladder for 24 h. Pd—C filtered off, filtrate concentrated to get the crude compound. This was purified by preparative TLC by eluting with 10% methanol in DCM to get the mixture of regioisomers 5-(7-

(difluoromethyl)-6-(1-methyl-2-oxo-1,2-dihydropyridin-3-yl)-3,4-dihydroquinolin-1(2H)-yl)-1,3-dimethyl-7-(tetrahydro-2H-pyran-4-yl)-1,6-naphthyridin-2(1H)-one & 7-(7-(difluoromethyl)-6-(1-methyl-2-oxo-1,2-dihydropyridin-3-yl)-3,4-dihydroquinolin-1(2H)-yl)-1,3-dimethyl-5-(tetrahydro-2H-pyran-4-yl)-1,6-naphthyridin-2(1H)-one (24 mg).

Step-4: Purification of 5-(7-(difluoromethyl)-6-(1-methyl-2-oxo-1,2-dihydropyridin-3-yl)-3,4-dihydroquinolin-1(2H)-yl)-1,3-dimethyl-7-(tetrahydro-2H-pyran-4-yl)-1,6-naphthyridin-2(1H)-one The regioisomers obtained in the Step-3 were separated by preparative HPLC using Column: ZORBAX (21.2 mm×150 mm) and eluents A=0.1% TFA IN water; B=CAN in the gradient programme of 40% of B at 0 minute, 50% at 2nd minute and 60% at 10th minute. This yielded (20 mg, 13.075). LC-MS: 547.3 $[M+H]^+$; 1H-NMR (400 MHz, Chloroform-D) δ 7.81 (s, 1H), 7.75 (s, 1H), 7.57 (s, 1H), 7.42 (s, 1H), 7.17 (s, 1H), 6.75-6.71 (m, 2H), 3.91 (s, 3H), 3.87 (s, 3H), 3.75 (s, 3H), 3.59 (d, J=4.3 Hz, 2H), 2.97 (d, J=10.1 Hz, 2H), 2.18 (d, J=1.2 Hz, 5H).

The below examples (236-240) were prepared according to the protocols described in the synthesis of Example-235 with appropriate variations in reactants, quantities of reagents, solvents and reaction conditions with appropriate coupling methods.

| Example | Structure | Spectral data |
|---|---|---|
| 236 | 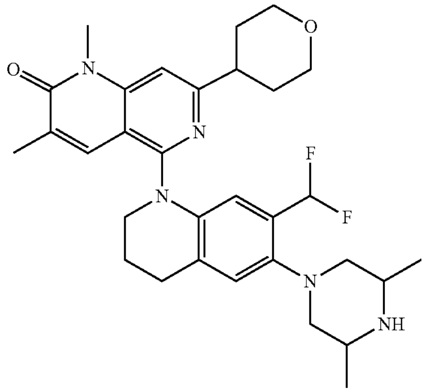 [SMILES: Cc1cc2c(N3CCCc4cc(N5CC(C)NC(C)C5)c(C(F)F)cc43)nc(C3CCOCC3)cc2n(C)c1=O] | LC-MS: 552.4 $[M + H]^+$; 1H-NMR (400 MHz, Chloroform-D) δ 7.51 (s, 1H), 7.12 (s, 1H), 6.94-6.85 (m, 1H), 6.57 (s, 1H), 4.09-4.06 (m, 2H), 3.75-3.74 (m, 2H), 3.72 (s, 3H), 3.56-3.50 (m, 3H), 3.06-3.02 (m, 2H), 2.95-2.92 (m, 3H), 2.87-2.84 (m, 2H), 2.40-2.35 (m, 2H), 2.14 (s, 3H), 2.12-2.10 (m, 3H), 1.93-1.87 (m, 4H), 1.10-1.08 (m, 6H). |
| 237 | 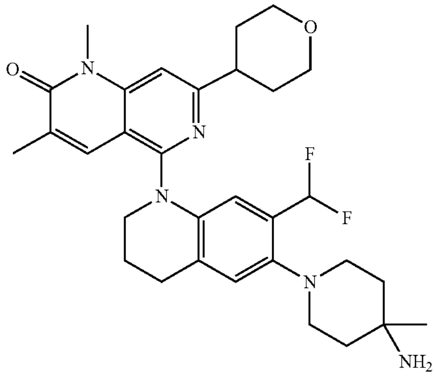 [SMILES: Cc1cc2c(N3CCCc4cc(N5CCC(C)(N)CC5)c(C(F)F)cc43)nc(C3CCOCC3)cc2n(C)c1=O] | LC-MS: 552.4 $[M + H]^+$; 1H-NMR (400 MHz, Chloroform-D) δ 7.50 (s, 1H), 7.02 (s, 1H), 7.00 (s, 1H), 6.88 (s, 1H), 6.83 (s, 1H), 6.74 (s, 1H), 6.57 (s, 1H), 4.07 (s, 1H), 4.05 (s, 1H), 3.74-3.73 (m, 2H), 3.71 (s, 3H), 3.54-3.49 (m, 2H), 2.94-2.91 (m, 5H), 2.80-2.77 (m, 2H), 2.13 (s, 3H), 2.09 (s, 2H), 1.92-1.87 (m, 4H), 1.71-1.66 (m, 3H), 1.56 (brs, 1H), 1.19 (s, 3H). |
| 238 | 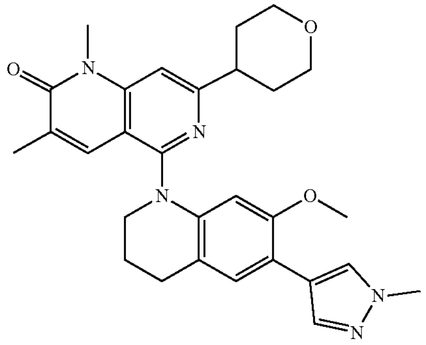 [SMILES: COc1cc2c(cc1-c1cnn(C)c1)CCCN2c1nc(C2CCOCC2)cc2c1cc(C)c(=O)n2C] | LC-MS: 500.3 $[M + H]^+$; 1H-NMR (400 MHz, Chloroform-D) δ 7.78 (s, 1H), 7.71 (s, 1H), 7.58 (s, 1H), 7.22 (s, 1H), 6.84 (s, 1H), 5.93 (s, 1H), 4.11-4.08 (m, 2H), 3.90 (s, 3H), 3.880-3.77 (m, 2H), 3.73 (s, 3H), 3.55-3.54 (m, 2H), 3.46 (s, 3H), 3.05-2.95 (m, 1H), 2.93-2.90 (m, 2H), 2.14 (s, 3H), 2.12 (s, 2H), 1.93-1.89 (m, 4H). |

-continued

| Example | Structure | Spectral data |
|---|---|---|
| 239 | 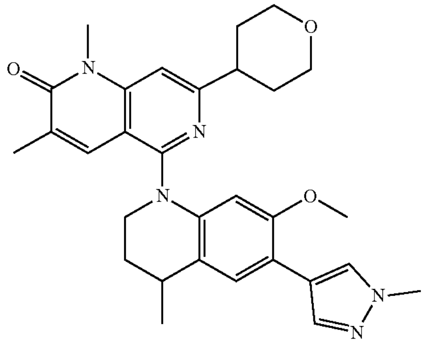 [SMILES: COc1cc2c(cc1-c1cnn(C)c1)C(C)CCN2c1nc(C2CCOCC2)cc2c1cc(C)c(=O)n2C] | LC-MS: 514.3 [M + H]$^+$; 1H-NMR (400 MHz, Chloroform-D) δ 7.79 (s, 1H), 7.71 (s, 1H), 7.55 (s, 1H), 7.30 (s, 1H), 6.84 (s, 1H), 5.9 (s, 1H), 4.11 (s, 1H), 4.08 (s, 1H), 3.91 (s, 3H), 3.85 (s, 1H), 3.73 (s, 3H), 3.58-3.52 (m, 3H), 3.45 (s, 3H), 3.07-3.05 (m, 2H), 2.14 (brs, 2H), 2.13 (s, 3H), 1.96-1.91 (m, 4H), 1.43-1.41 (m, 3H). |
| 240 | 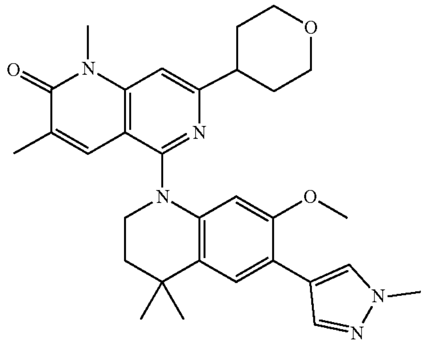 [SMILES: COc1cc2c(cc1-c1cnn(C)c1)C(C)(C)CCN2c1nc(C2CCOCC2)cc2c1cc(C)c(=O)n2C] | LC-MS: 528.4 [M + H]$^+$; 1H-NMR (400 MHz, Chloroform-D) δ 7.78 (s, 1H), 7.70 (s, 1H), 7.55 (s, 1H), 7.40 (s, 1H), 6.83 (s, 1H), 5.90 (s, 1H), 4.11 (s, 1H), 4.08 (s, 1H), 3.91 (s, 3H), 3.81 (brs, 2H), 3.73 (s, 3H), 3.58-3.52 (m, 2H), 3.43 (s, 3H), 2.98-2.97 (m, 1H), 2.13 (s, 3H), 1.97-1.91 (m, 6H), 1.43-(s, 6H). |

Example-241: 5-(7-(Difluoromethyl)-6-(1-methyl-1H-pyrazol-4-yl)-3,4-dihydroquinolin-1(2H)-yl)-7-(3,6-dihydro-2H-pyran-4-yl)-1,3-dimethyl-1,6-naphthyridin-2(1H)-one

Example-242: 5-(7-(Difluoromethyl)-6-(1-methyl-1H-pyrazol-4-yl)-3,4-dihydroquinolin-1(2H)-yl)-1,3-dimethyl-7-(tetrahydro-2H-pyran-4-yl)-1,6-naphthyridin-2(1H)-one

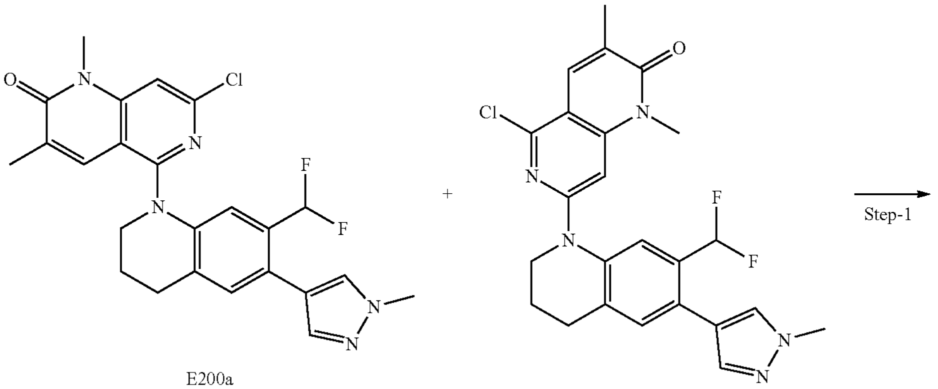

E200a

+

E200b

Mixture of regio isomers (80:20)

-continued

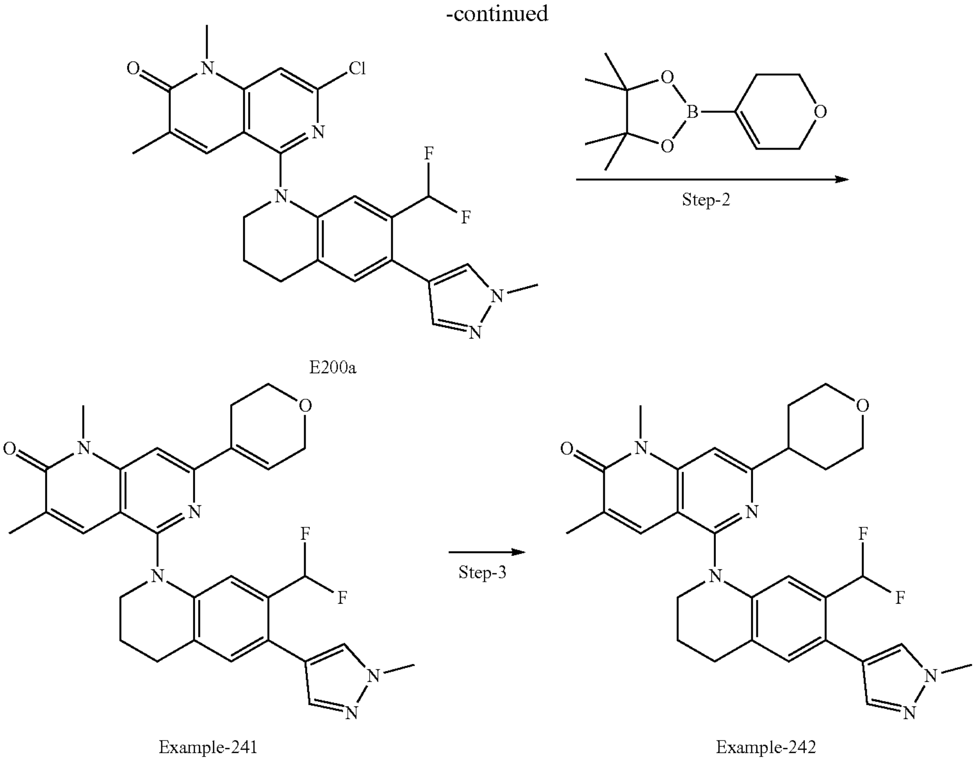

E200a

Example-241

Example-242

Step-1: Synthesis of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one A (80:20) regioisomeric mixture of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one and 5-chloro-7-(7-(difluoromethyl)-6-(1-methyl-1H-pyrazol-4-yl)-3,4-dihydroquinolin-1(2H)-yl)-1,3-dimethyl-1,6-naphthyridin-2(1H)-one (1000 mg, 3.7 mmol) was dissolved in ethyl acetate (4 mL, ~4 WT/VOL), after scratching with spatula, compound 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one started separating as solid precipitate. This was stand for 48 h, precipitate was filtered and washed with cold ethyl acetate and dried to get a single isomer (750 mg, 42.02%) LC-MS: 470.4 $[M+H]^+$;

Step-2: Synthesis of 5-(7-(difluoromethyl)-6-(1-methyl-1H-pyrazol-4-yl)-3,4-dihydroquinolin-1(2H)-yl)-7-(3,6-dihydro-2H-pyran-4-yl)-1,3-dimethyl-1,6-naphthyridin-2(1H)-one A degassed solution of 7-chloro-5-(7-(difluoromethyl)-6-(1-methyl-1H-pyrazol-4-yl)-3,4-dihydroquinolin-1(2H)-yl)-1,3-dimethyl-1,6-naphthyridin-2(1H)-one (750 mg 0.1.03 mmol) and 2-(3,6-dihydro-2H-pyran-4-yl)-4,4,5,5-tetramethyl-1,3,2-dioxaborolane (402 mg, 1.2 mmol) in dioxane (16 mL) and water (4 mL). The mixture was then added Pd(Amphos)$Cl_2$ (560 mg, 0.08 mmol) and potassium carbonate carbonate (660 mg, 4.7 mmol). The mixture was stirred at 100° C. for 4 h. The reaction mixture was then cooled to room temperature, water was added and the mixture was extracted with ethyl acetate. Organic extracts were washed with water, brine dried over sodium sulphate and concentrated to get the crude compound. The crude compound was recrystallized with ethyl acetate and washed with diethyl ether to get the pure title compound (600 mg, 72.6%). LC-MS: 518.3 $[M+H]^+$; 1H-NMR (400 MHz, Chloroform-D) δ 7.55 (d, J=0.4 Hz, 1H), 7.51 (s, 1H), 7.41 (s, 1H), 7.12 (s, 1H), 7.02 (s, 1H), 6.85 (s, 1H), 6.68 (s, 1H), 6.58-6.25 (m, 1H), 4.39 (d, J=3.2 Hz, 2H), 3.97-3.95 (m, 2H), 3.94 (d, J=2.4 Hz, 3H), 3.85-3.82 (m, 2H), 3.76 (s, 3H), 2.99 (brs, 2H), 2.64 (d, J=1.6 Hz, 2H), 2.18-2.17 (m, 2H), 2.15 (d, J=1.6 Hz, 3H).

Step-3: Synthesis of 5-(7-(difluoromethyl)-6-(1-methyl-1H-pyrazol-4-yl)-3,4-dihydroquinolin-1(2H)-yl)-1,3-dimethyl-7-(tetrahydro-2H-pyran-4-yl)-1,6-naphthyridin-2(1H)-one A solution of 5-(7-(difluoromethyl)-6-(1-methyl-1H-pyrazol-4-yl)-3,4-dihydroquinolin-1(2H)-yl)-7-(3,6-dihydro-2H-pyran-4-yl)-1,3-dimethyl-1,6-naphthyridin-2(1H)-one (2300 mg, 4.4 mmol) was added 10% Pd—C (1.655 g, 1.55 mmol) in ethyl acetate (100 mL) and THE (30 mL). The mixture was stirred under positive pressure of hydrogen in bladder for 12 h. Pd—C filtered off, filtrate concentrated to get the crude compound. This was purified by flash chromatography using 40-60% ethyl acetate in hexanes as eluent. This was further recrystallized in ethyl acetate to get 5-(7-(difluoromethyl)-6-(1-methyl-1H-pyrazol-4-yl)-3,4-dihydroquinolin-1(2H)-yl)-1,3-dimethyl-7-(tetrahydro-2H-pyran-4-yl)-1,6-naphthyridin-2(1H)-one (1200 mg, 51.9%). LC-MS: 520.5 $[M+H]^+$; 1H-NMR (400 MHz, Chloroform-D) δ 7.54 (s, 1H), 7.42 (s, 1H), 7.12 (s, 1H), 6.89 (s, 1H), 6.65 (s, 1H), 6.58-6.43 (m, 1H), 4.13-4.08 (m, 2H), 3.95 (s, 3H), 3.76-3.82 (m, 2H), 3.72 (s, 3H), 3.58-3.50 (m, 3H), 2.93-3.02 (m, 3H), 2.20-2.12 (m, 5H), 1.99-1.84 (m, 4H).

Example-243: 5-(7-(Difluoromethyl)-6-(1-methyl-1H-pyrazol-4-yl)-3,4-dihydroquinolin-1(2H)-yl)-7-((R)-3-hydroxypyrrolidin-1-yl)-1,3-dimethyl-3,4-dihydro-1,6-naphthyridin-2(1H)-one

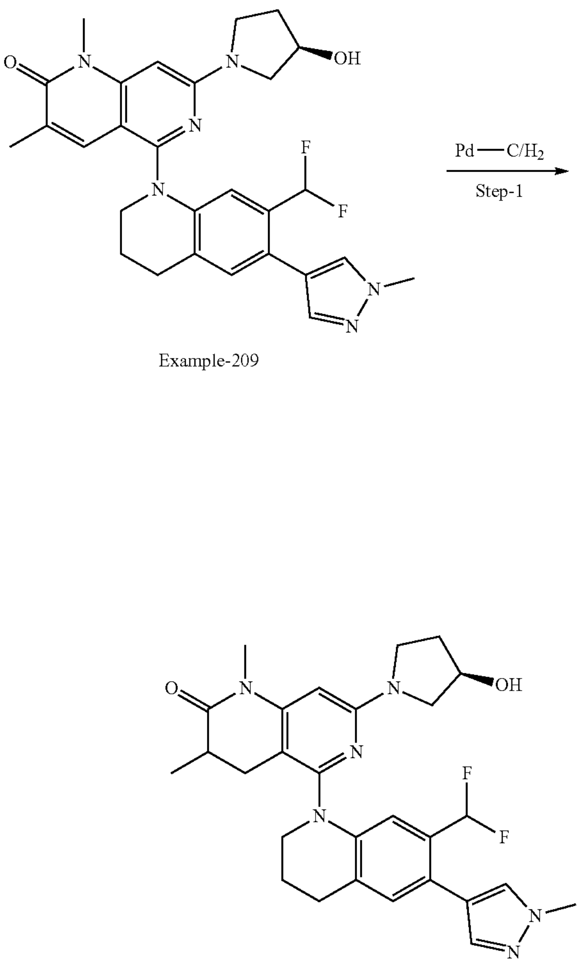

Example-209

Example-243

A solution of (R)-5-(7-(difluoromethyl)-6-(1-methyl-1H-pyrazol-4-yl)-3,4-dihydroquinolin-1(2H)-yl)-7-(3-hydroxy-pyrrolidin-1-yl)-1,3-dimethyl-1,6-naphthyridin-2(1H)-one (19 mg, 0.039 mmol) in ethanol (10 mL) was hydrogenated in a Parr reactor using 10% Palladium on carbon (19 mg) at 70 PSI for 4 days. The mixture was then filtered through celite and the filtrate was concentrated to get reside. The residue was purified by preparative HPLC to get pure title compound (20 mg, 95.68%). LC-MS: 523.2 $[M+H]^+$; 1H-NMR (400 MHz, chloroform-D) δ 3.60 (s, 4H), 3.37-3.36 (m, 3H), 1.16 (s, 3H), 2.91-2.90 (m, 2H), 2.59 (s, 2H), 1.73-1.73 (m, 1H), 2.26-2.25 (m, 1H), 2.13 (dd, J=6.4, 2.2 Hz, 4H), 3.73-3.72 (m, 2H), 7.52-7.50 (m, 1H), 7.40-7.40 (m, 1H), 3.93 (s, 3H), 7.06-7.05 (m, 1H), 5.83-5.82 (m, 1H), 6.63 (s, 1H), 4.58 (s, 1H).

Example-244: 5-(7-Hydroxy-6-(1-methyl-1H-pyrazol-4-yl)-3,4-dihydroquinolin-1(2H)-yl)-1,3-dimethyl-7-(tetrahydro-2H-pyran-4-yl)-1,6-naphthyridin-2(1H)-one

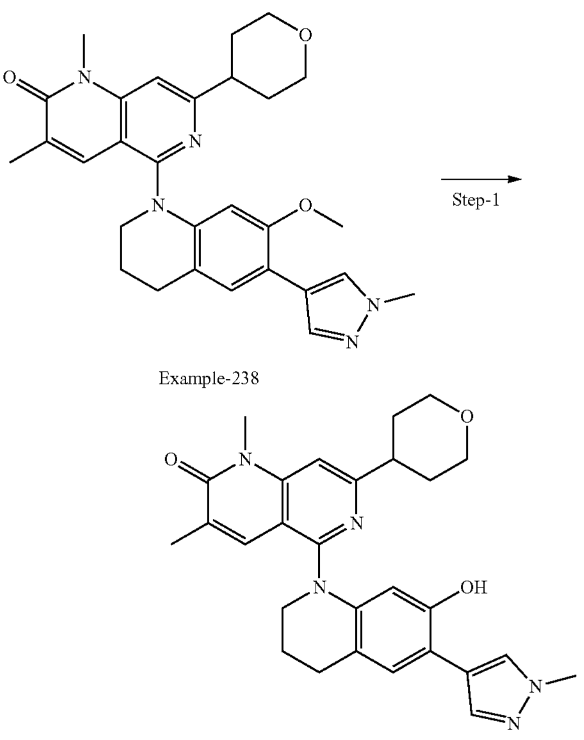

Example-238

Example-244

This compound was prepared using the similar protocol described in Example-194 with appropriate variations in reactants, quantities of reagents, solvents and reaction conditions (10 mg, 20.5%). LC-MS: 486.3 $[114+H]^+$; 1H-NMR (400 MHz, Chloroform-D) δ 7.68 (s, 1H), 7.63 (s, 1H), 7.59 (s, 1H), 7.08 (s, 1H), 6.82 (s, 1H), 5.79 (s, 1H), 5.65 (s, 1H), 4.12 (s, 1H), 4.09 (s, 1H), 3.91 (s, 3H), 3.75 (brs, 2H), 3.66 (s, 3H), 3.56-3.52 (m, 2H), 3.02-2.89 (m, 3H), 2.15 (s, 2H), 2.12 (d, J=0.8 Hz, 3H), 1.94-1.88 (m, 4H).

Example-245:5-(7-Hydroxy-6-(1-methyl-1H-pyrazol-4-yl)-3,4-dihydroquinolin-1(2H)-yl)-7-(3-hydroxypyrrolidin-1-yl)-1,3-dimethyl-1,6-naphthyridin-2(1H)-one

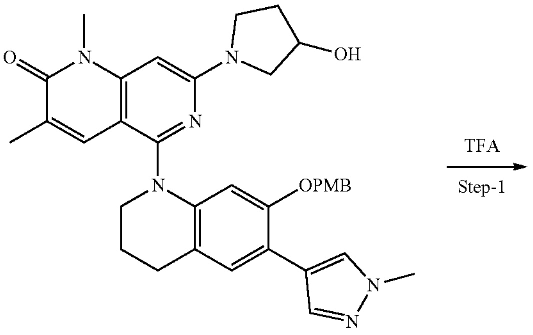

-continued

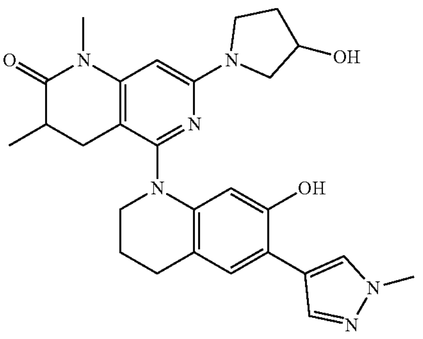

Example-245

-continued

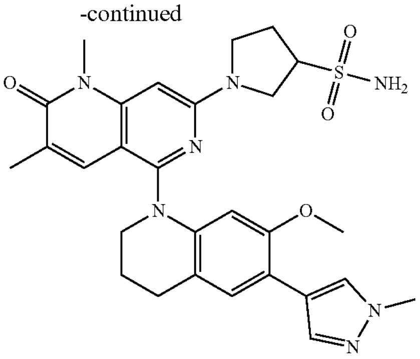

Example-246

This compound was prepared using the similar protocol described in Example-161 with appropriate variations in reactants, quantities of reagents, solvents and reaction conditions (20 mg, 13.7%). LC-MS: 487.1 [114+H]$^+$; 1H-NMR (300 MHz, Chloroform-D) δ 7.70-7.69 (m, 2H), 7.42 (s, 2H), 7.07 (s, 2H), 5.92 (s, 2H), 3.91 (s, 1H), 3.8 (s, 3H), 3.69 (s, 2H), 3.61-3.55 (m, 2H), 3.5 (s, 3H), 2.86-2.82 (m, 3H), 2.13-2.10 (m, 4H), 2.0 (s, 3H).

Example-246: 1-(5-(7-Methoxy-6-(1-methyl-1H-pyrazol-4-yl)-3,4-dihydroquinolin-1(2H)-yl)-1,3-dimethyl-2-oxo-1,2-dihydro-1,6-naphthyridin-7-yl) pyrrolidine-3-sulfonamide

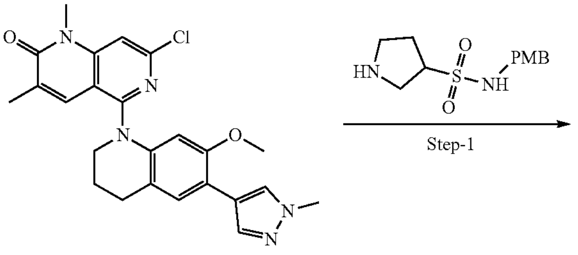

Step-1: Synthesis of 1-(5-(7-methoxy-6-(1-methyl-1H-pyrazol-4-yl)-3,4-dihydroquinolin-1(2H)-yl)-1,3-dimethyl-2-oxo-1,2-dihydro-1,6-naphthyridin-7-yl)-N-(4-methoxybenzyl)pyrrolidine-3-sulfonamide This compound was prepared using the similar protocol described in Example-202 using intermediates 7-chloro-5-(7-methoxy-6-(1-methyl-1H-pyrazol-4-yl)-3,4-dihydroquinolin-1(2H)-yl)-1,3-dimethyl-1,6-naphthyridin-2(1H)-one & N-(4-methoxybenzyl)pyrrolidine-3-sulfonamide with appropriate variations in reactants, quantities of reagents, solvents and reaction conditions. LC-MS: 564.1 [M+H]$^+$;

Step-2: Synthesis of 1-(5-(7-methoxy-6-(1-methyl-1H-pyrazol-4-yl)-3,4-dihydroquinolin-1(2H)-yl)-1,3-dimethyl-2-oxo-1,2-dihydro-1,6-naphthyridin-7-yl) pyrrolidine-3-sulfonamide This compound was prepared using the similar protocol described in example-62 with appropriate variations in reactants, quantities of reagents, solvents and reaction conditions (10 mg, 35.48%). LC-MS: 487.1 [M+H]$^+$; 1H-NMR (600 MHz, chloroform-D) δ 7.76 (s, 1H), 7.70 (s, 1H), 7.43-7.41 (m, 1H), 7.2 (s, 1H), 6.0 (s, 1H), 5.8 (s, 1H), 4.75-4.71 (m, 2H), 4.0-3.9 (m, 2H), 3.94-3.90 (m, 1H), 3.89 (s, 3H), 3.79-3.72 (m, 3H), 3.63 (s, 3H), 3.61-3.58 (m, 1H), 3.48 (d, J=6 Hz, 3H), 2.58-2.49 (m, 2H), 2.17-2.09 (m, 2H), 2.05 (s, 3H).

Example-247 & Example-248: 4-(1,3-Dimethyl-7-((1-methylpiperidin-3-yl)methoxy)-2-oxo-1,2-dihydroquinolin-5-yl)-1-methyl-7-(1-methyl-1H-pyrazol-4-yl)-1,2,3,4-tetrahydroquinoxaline-6-carbonitrile

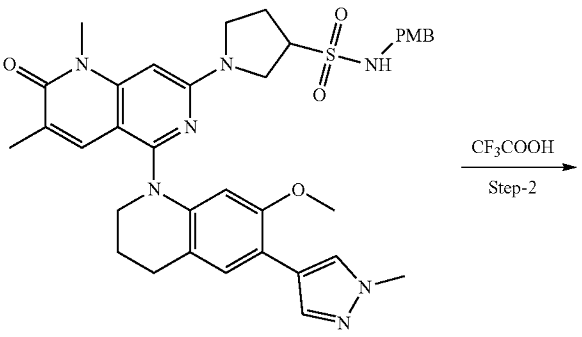

E246a

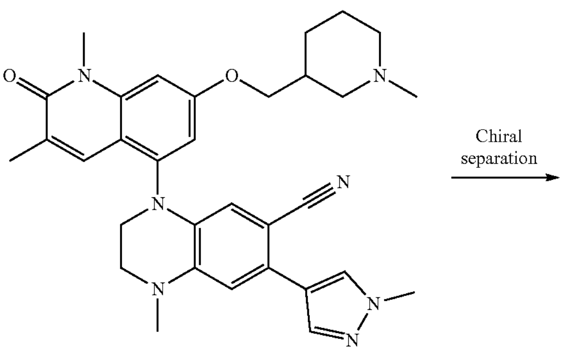

Example-35

-continued

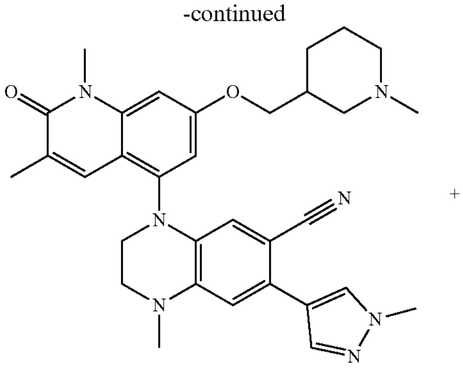

Isomer-1
Example-247

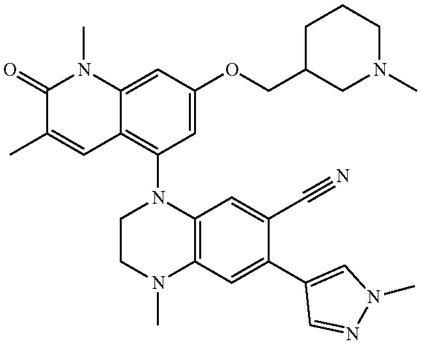

Isomer-2
Example-248

Enantiomers of racemic compound 4-(1,3-dimethyl-7-((1-methylpiperidin-3-yl)methoxy)-2-oxo-1,2-dihydroquinolin-5-yl)-1-methyl-7-(1-methyl-1H-pyrazol-4-yl)-1,2,3,4-tetrahydroquinoxaline-6-carbonitrile were separated by chiral preparative HPLC to give two separated enantiomers (isomer-1, example-247 & isomer-2, example-248).

Characterization data of isomer-1 (Example-247): LC-MS: 552.4 $[M+H]^+$; 1H-NMR (600 MHz, DMSO-D6) δ 8.08 (s, 1H), 7.82 (d, J=1.2 Hz, 1H), 7.60 (s, 1H), 6.94 (d, J=1.9 Hz, 1H), 6.88 (t, J=1.9, 1.9 Hz, 1H), 6.71 (d, J=1.5 Hz, 1H), 5.91 (d, J=1.3 Hz, 1H), 4.02 (m, 3H), 3.88 (d, J=1.5 Hz, 3H), 3.79 (m, 2H), 3.68 (d, J=1.5 Hz, 3H), 3.53-3.48 (m, 2H), 3.08 (s, 3H), 2.83 (d, J=10.7 Hz, 1H), 2.64-2.61 (m, 1H), 2.40-2.37 (m, 1H), 2.16 (s, 4H), 2.05 (s, 4H), 1.90 (d, J=7.6 Hz, 1H), 1.67 (s, 1H), 1.52-1.48 (m, 1H).

Characterization data of Isomer-2 (Example-248): LC-MS: 552.4 $[M+H]^+$; 1H-NMR (600 MHz, DMSO-D6) δ 8.08 (s, 1H), 7.82 (d, J=1.2 Hz, 1H), 7.60 (s, 1H), 6.94 (s, 1H), 6.88 (s, 1H), 6.71 (d, J=1.5 Hz, 1H), 5.91 (s, 1H), 4.02 (t, J=11.7, 5.2, 5.2 Hz, 2H), 3.88 (d, J=1.5 Hz, 3H), 3.82-3.75 (m, 2H), 3.68 (s, 3H), 3.54-3.48 (m, 2H), 3.08 (s, 3H), 2.84 (s, 1H), 2.61 (t, 1H), 2.16 (s, 3H), 2.05 (s, 4H), 1.91 (s, 1H), 1.83 (s, 1H), 1.76-1.62 (m, 3H), 1.50 (m, 1H).

The below isomer compounds (249-252) were separated by the procedure similar to the one described in Example-247 and Example-248 with appropriate change in separation methods as shown in the table.

| Example | Structure | Separation method | Spectral data |
|---|---|---|---|
| 249 | Isomer-1 of Example-99 | Column: Chiralpak IH (250 mm x 20 mm); Mobile Phase: Hexane (A); 50% Ethanol in Methanol (B); Flow: 15 ml; Isocratic: 60:40 (A: B). | LC-MS: $[M + H]^+$; 412.3; 1 H-NMR (400 MHZ, Chloroform-D) δ 7.58 (s, 1 H), 7.09-6.9 (m, 1 H), 6.75-6.62 (m, 3 H), 6.65-6.49 (m, 1 H), 3.88 (s, 3 H), 3.75 (brs, 1 H), 3.74 (s, 3 H), 3.70-3.61 (m, 2 H), 3.39-3.48 (brs, 1 H), 3.04 (s, 3 H), 2.55-2.46 (m, 3 H), 2.14 (s, 3 H). |
| 250 | Isomer-2 of Example-99 | Column: Chiralpak IH (250mm x 20 mm); Mobile Phase: Hexane (A); 50% Ethanol in Methanol (B); Flow: 15 ml; Isocratic: 60:40 (A: B). | LC-MS: $[M + H]^+$; 412.3; 1 H-NMR (400 MHZ, Chloroform-D) δ 7.58 (s, 1 H), 7.09-6.9 (m, 1 H), 6.75-6.62 (m, 3 H), 6.65-6.49 (m, 1 H), 3.88 (s, 3 H), 3.75 (brs, 1 H), 3.74 (s, 3 H), 3.70-3.61 (m, 2 H), 3.39-3.48 (brs, 1 H), 3.04 (s, 3 H), 2.55-2.46 (m, 3 H), 2.14 (s, 3 H). |
| 251 | Isomer-1 of Example-227 | Column: Regis (s, s) whelk-01, (250 mm x 21.2 mm); Mobile phase: Hexane (A); 0.1% Diethylamine in 50% Ethanol in Methanol (B); Flow: 15 ml Isocratic: 50:50 (A: B) | LC-MS: $[M + H]^+$; 510.6; LC-MS: $[M + H]^+$; 510.6; 1 H-NMR (400 MHz, Chloroform-D) δ 7.35 (s, 1 H), 7.23 (s, 1 H), 6.61(t, 1 H), 6.53 (s, 1 H), 5.8 (s, 1 H), 5.02-4.89 (m, 1 H), 4.6 (brs, 1 H), 4.23-4.18 (m, 1 H), 3.86-3.78 (m, 1 H), 3.73-3.70 (m, 2 H), 3.62-3.57 (m, 7 H), 2.93 (brs, 2 H), 2.61-2.57 (m, 1 H), 2.11-2.05 (m, 9 H), 1.6-1.42 (m, 2 H). |

-continued

| Example | Structure | Separation method | Spectral data |
|---|---|---|---|
| 252 | Isomer-2 of Example-227 | Column: Regis (s, s) whelk-01,(250 mm × 21.2 mm); Mobile phase: Hexane (A); 0.1% Diethylamine in 50% Ethanol in Methanol (B); Flow: 15 ml) Isocratic: 50:50 (A: B) | LC-MS: $[M + H]^+$; 510.6; 1 H-NMR (400 MHZ, Chloroform-D) δ 7.35 (s, 1 H), 7.23 (s, 1 H), 6.61 (t, 1 H), 6.53 (s, 1 H), 5.8(s, 1 H), 5.02-4.89 (m, 1 H), 4.6 (brs, 1 H), 4.23-4.18(m, 1 H), 3.86-3.78 (m, 1 H), 3.73-3.70 (m, 2 H), 3.62-3.57 (m, 7 H), 2.93 (brs, 2 H), 2.61-2.57 (m, 1 H), 2.11-2.05 (m, 9 H), 1.6-1.42 (m, 2 H). |

Example-P1: CBP TR-FRET Assay

The potency of compounds to inhibit CREBBP enzyme was tested in a TR-FRET displacement assay using recombinant CREBBP bromodomain obtained from BPS Bioscience, USA. The assay buffer was 50 mM HEPES (pH 7.5), 50 mM NaCl, 0.008% Brij 35, 0.01% BSA, 1 mM TCEP. 50 nM of CREBBP & 500 nM of Biotinylated ligand was incubated at room temperature for 30 minutes, the reaction was initiated by adding pre-incubated enzyme ligand mixture to the test compounds. After 60 min incubation, the reaction was stopped by the addition of stop mix containing 1 nM of LANCE Europium-anti-6×His antibody (Perkin Elmer, USA) and 40 nM of Sure Light Allophycocyanin-Streptavidin (Perkin Elmer, USA). Fluorescence emission of the samples at 665 and 615 nm were measured at an excitation of 340 nm and their ratio was plotted against the compound concentrations to generate dose-response curve. The percent inhibition of the test compounds is calculated using the ratio of enzyme activity controls. The results are given below.

| Example | % Inhibition (10 μM) | Example | % Inhibition (10 μM) |
|---|---|---|---|
| 1 | 99 | 52 | 83 |
| 5 | 38 | 54 | 91 |
| 6 | 100 | 58 | 91 |
| 7 | 90 | 78 | 25 |
| 35 | 96 | 101 | 27 |
| 36 | 100 | 126 | 46 |
| 37 | 100 | 188 | 25 |
| 38 | 98 | 190 | 52 |
| 42 | 96 | 192 | 47 |
| 46 | 98 | 247 | 95 |
| 50 | 90 | 248 | 100 |
| 51 | 99 | | |

elected compounds of the present invention were screened in the above-mentioned assay procedures and $IC_{50}$ values were determined by fitting the dose-response data to sigmoidal curve fitting equation using Graph pad prism software V7. The results are summarized into groups A, B and C in the table given below. Herein the group "A" refers to $IC_{50}$ values lower than 0.05 μM, the group "B" refers to $IC_{50}$ values between 0.051-0.1 μM (both inclusive) and the group "C" refers to $IC_{50}$ values higher than 0.01 μM.

| Group | Example |
|---|---|
| A | 1, 2, 7, 9-23, 25, 26, 28-32, 34-43, 45, 47-49, 53, 56, 59-61, 65-69, 71-73, 76, 84, 86, 88, 90, 91, 94-95, 98, 104, 105, 108-110, 112, 115, 127, 132, 134, 136, 140, 142, 146, 150, 153, 158, 162, 165, 167-171, 176, 178, 179, 181-183, 195, 200, 201, 208-219, 222-225, 228, 234-238, 242, 244, 245, 247, 248 and 251. |
| B | 27, 33, 55, 58, 63, 70, 79, 82, 85, 87, 93, 96, 99, 100, 106, 107, 116, 124, 128, 130,133, 135, 141, 143-145, 147, 134, 151, 152, 154, 155-157, 159, 164, 166, 174, 177, 180, 186, 205, 226, 227, 232, 233, 239, 241 and 246. |
| C | 3, 6, 8, 24, 44, 46, 50-52, 54, 57, 62, 74, 75, 77, 80, 81, 83, 89, 97, 102, 103, 111, 114, 117-123, 129, 131, 137-139, 148, 160, 161, 163, 175, 184, 185, 187, 189, 191, 193, 196-199, 203-207, 220, 221, 230, 243, 250 and 252. |

Example-P2: P300 TR-FRET Assay

The potency of compounds to inhibit P300 enzyme was tested in a TR-FRET displacement assay using recombinant P300 bromodomain obtained from BPS Bioscience, USA. The assay buffer was 50 mM HEPES (pH 7.5), 50 mM NaCl, 0.008% Brij 35, 0.01% BSA, 1 mM TCEP. 50 nM of P300 & 500 nM of Biotinylated ligand was incubated at room temperature for 30 minutes, the reaction was initiated by adding the pre-incubated enzyme ligand mixture to the test compounds. After 60 min incubation, the reaction was stopped by the addition of stop mix containing 1 nM of LANCE Europium-anti-6×His antibody (Perkin Elmer, USA) and 40 nM of Sure Light Allophycocyanin-Streptavidin (Perkin Elmer, USA). Fluorescence emission of the samples at 665 and 615 nm were measured at an excitation of 340 nm and their ratio was plotted against the compound concentrations to generate dose-response curve.

Selected compounds of the present invention were screened in the above-mentioned assay procedures and $IC_{50}$ values were determined by fitting the dose-response data to sigmoidal curve fitting equation using Graph pad prism software V7. The results are summarized into groups A, B and C in the table given below. Herein the group "A" refers to $IC_{50}$ values lower than 25 nM, the group "B" refers to $IC_{50}$ values between 25.01 nM-50 nM (both inclusive) and the group "C" refers to $IC_{50}$ values higher than 50 μM.

| Group | Example |
|---|---|
| A | 1, 2, 9, 11-14, 16, 23, 35-37, 39, 48, 60, 69, 71, 72, 94, 108, 176, 178, 180, 201, 209, 211, 212, 215, 234, 242, 247 and 248. |
| B | 10, 15, 18-20, 25, 40, 42, 62, 67, 68, 86, 195, 210 and 225. |
| C | 3, 6-8, 17, 38, 54, 57, 77, 80, 134, 146 and 224. |

Example-P3: BRD4 FL TR-FRET Assay

The potency of compounds to inhibit BRD4 FL enzyme was tested in a TR-FRET displacement assay using recombinant BRD4 FL bromodomain obtained In-house. The assay buffer was 50 mM HEPES (pH 7.5), 50 mM NaCl, 500 μM CHAPS. 10 nM of BRD4 FL & 300 nM of Biotinylated Acetyl histone H4 (Lys 5, 8, 12, 16) (Millipore, USA) was incubated at room temperature for 30 minutes, the reaction was initiated by adding the pre-incubated enzyme ligand mixture to the test compounds. After 30 min incubation, the reaction was stopped by the addition of stop mix containing 1 nM of Europium Streptavidin cryptate (Cisbio, USA) and 5 nM of Mab ANTI 6HIS-XL665 (Cisbio, USA) dilutes in assay buffer containing 2.4M Potassium Fluoride. Fluorescence emission of the samples at 665 and 615 nm were measured at an excitation of 340 nm and their ratio was plotted against the compound concentrations to generate dose-response curve. The percent inhibition of the test compounds is calculated using the ratio of enzyme activity controls. The results are given below.

| Example | % Inhibition (10 μM) | Example | % Inhibition (10 μM) |
|---|---|---|---|
| 7 | 77 | 137 | 26 |
| 26 | 24 | 139 | 43 |
| 42 | 81 | 147 | 66 |
| 52 | 35 | 148 | 55 |
| 5 | 48 | 151 | 49 |
| 69 | 39 | 152 | 48 |
| 79 | 56 | 153 | 45 |
| 98 | 56 | 156 | 47 |
| 103 | 36 | 157 | 41 |
| 104 | 48 | 161 | 16 |
| 106 | 16 | 163 | 16 |
| 107 | 15 | 164 | 38 |
| 112 | 44 | 165 | 51 |
| 116 | 50 | 199 | 45 |
| 120 | 34 | 204 | 12 |
| 122 | 33 | 205 | 43 |
| 127 | 32 | 217 | 46 |
| 130 | 48 | 230 | 21 |
| 131 | 52 | 241 | 22 |

Selected compounds of the present invention were screened in the above-mentioned assay procedures and $IC_{50}$ values were determined by fitting the dose-response data to sigmoidal curve fitting equation using Graph pad prism software V7. The results are summarized into groups A, B and C in the table given below. Herein the group "A" refers to $IC_{50}$ value lower than 2 μM, the group "B" refers to $IC_{50}$ value between 2.01-5 μM (both inclusive) and the group "C" refers to $IC_{51}$) value higher than 5 μM.

| Group | Example |
|---|---|
| A | 1-3, 7-20, 22-25, 28-30, 32, 34-43, 45, 47, 48, 50, 53, 56, 58, 60-63, 67, 71, 76, 80, 81, 90, 93, 99, 115, 124, 140, 141, 155, 158, 168, 169, 171, 174, 177, 178, 197, 201, 209, 210-213, 215, 216, 222-225, 228, 232, 234-239, 242, 244, 246-248 and 251. |
| B | 6, 27, 29, 31, 33, 46, 51, 65, 66, 68, 70, 73, 77, 82, 83, 85-88, 91, 92, 94-96, 100, 102, 119, 129, 132, 133, 135, 136, 138, 149, 150, 154, 159, 162, 166, 167, 170, 179, 180-183, 193, 196, 198, 200, 203, 208, 214, 218-220, 226, 233, 243, 245, 249 and 250. |
| C | 59, 72, 74-75, 108-110, 117, 118, 128, 134, 142-145, 184-187, 202, 206, 207, 221 and 229. |

INCORPORATION BY REFERENCE

All publications and patents mentioned herein are hereby incorporated by reference in their entirety as if each individual publication or patent were specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of formula (I):

(I)

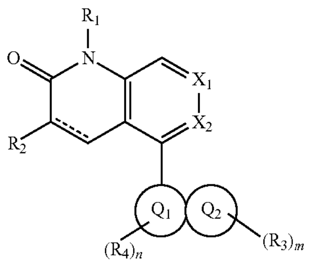

or a pharmaceutically acceptable salt, a stereoisomer, a tautomer, an N-oxide or an ester thereof, wherein ------ is a double bond;

—$X_1$—$X_2$— is —$CR_{X1}$—$CR_{X2}$—, —N—$CR_{X2}$— or —$CR_{X1}$—N—;

each $R_{X1}$ and $R_{X2}$ independently are hydrogen, —$OR_a$, alkyl, alkynyl-OH, —N(alkyl)$_2$, cycloalkyl, heterocycloalkyl or heteroaryl; wherein the cycloalkyl, heterocycloalkyl and heteroaryl are optionally substituted with 1 to 3 substituent(s) selected from alkyl, acyl, halogen, —CN, oxo, —$NH_2$, —OH, —NHCO-alkyl, —$SO_2NH_2$ and —CONH-alkyl;

$R_a$ is hydrogen, alkyl, haloalkyl, (heterocycloalkyl) alkyl-, heterocycloalkyl, heteroaryl or (heteroaryl) alkyl-; wherein alkyl, at each occurrence, is optionally substituted with 1 to 3 substituent(s) independently selected from —OH, —COOH, —COO-alkyl, alkoxy, —N(alkyl)$_2$, and —CONH—O-alkyl; and wherein heterocycloalkyl and/or heteroaryl are each optionally substituted with 1 to 3 substituent(s) independently selected from alkyl, oxo and acyl;

$Q_1$ is 5- to 7-membered heterocycloalkyl ring;

$Q_2$ is fused 5- to 6-membered heteroaryl ring or fused benzo ring;

$R_1$ is hydrogen, alkyl or haloalkyl;

$R_2$ is hydrogen, alkyl or —$NH_2$;

$R_3$, at each occurrence, independently, is hydrogen, halogen, —CN, alkyl, alkoxy, haloalkyl, —CHO, acyl, —CONH-alkyl, —COO-alkyl, —COOH, —OH, —$SO_2NH_2$, —$SO_2$NH-alkyl, —$SO_2$N(alkyl)$_2$, —$SO_2$NH-aryl, —SO-alkyl, —$SO_2$-alkyl, —$SO_2$NHCO-alkyl, —$SO_2$NHCO-haloalkyl, —S(O)

(NH)-alkyl, —$NHSO_2$-alkyl, —NHCO-alkyl, —N(alkyl)CO-alkyl, heteroaryl, heterocycloalkyl, carbocyclyl or cycloalkyl; wherein alkyl, at each occurrence, is independently optionally substituted with 1 to 3 occurrence(s) of $R_{3A}$; heteroaryl is optionally substituted with 1 to 3 occurrence(s) of $R_{3B}$; and heterocycloalkyl is optionally substituted with 1 to 3 occurrence(s) of $R_{3C}$;

$R_{3A}$, at each occurrence, independently, is alkoxy, —OH, —CONHOH or —NHCO-alkyl;

$R_{3B}$, at each occurrence, independently, is alkyl, alkoxy, —OH, —COOH, oxo, —COO-alkyl, —CONH-alkyl or —CONH—OH;

$R_{3C}$, at each occurrence, independently, is alkyl, —CN, —OH, —$NH_2$, —N(alkyl)$_2$, acyl, oxo, —CONH-alkyl, —NHCO-alkyl or —CONH-alkyl-OH;

$R_4$, at each occurrence, independently, is hydrogen, alkyl, haloalkyl, acyl, —CONH-alkyl, oxo, —$SO_2$-alkyl, aralkyl, heteroaryl, heterocycloalkyl or cycloalkyl; wherein alkyl, aryl, aralkyl, heteroaryl and/or heterocycloalkyl are each optionally substituted with 1 to 3 occurrence(s) of $R_{4A}$;

$R_{4A}$, at each occurrence, independently, is alkoxy, —$COOCH_2CH_3$, —COOH or —CONH-alkyl;

m is 1, 2, 3 or 4; and n is 1, 2, 3 or 4.

2. The compound of claim 1, wherein —$X_1$—$X_2$— is —$CR_{X1}$—$CR_{X2}$— or —$CR_{X1}$—N—.

3. The compound of claim 1, wherein $R_1$ is alkyl or haloalkyl; and $R_2$ represents alkyl or amino.

4. The compound of claim 1, wherein $R_{X1}$ is hydrogen, —$OR_a$, —$CH_3$, —C≡$CCH_2OH$, —N$(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl, wherein each cyclic group is optionally substituted with 1 to 2 substituent(s) independently selected from —$CH_3$, —$COCH_3$, —F, —CN, oxo, —$NH_2$, —OH, —$NHCOCH_3$, —$SO_2NH_2$ and —$CONHCH_3$; and $R_{X2}$ is hydrogen or alkyl.

5. The compound of claim 4, wherein $R_a$ is —$CH_3$, —CH$(CH_3)_2$, —$CH_2$—COOC$(CH_3)_3$, —$CH_2$-piperidinyl($CH_3$), —$CH_2$—$CH_2$-morpholine, —$CH_2$—$CH_2$—$OCH_3$, —$CH_2$—$CH_2$—N$(CH_3)_2$, azetidinyl, —$CH_2$-oxazole, —$CH_2$—$CH_2$—OH, —$CH_2$—$CH_2$-piperizinyl($COCH_3$), —$CH_2$—COOH, —$CH_2$—CONH($OCH_3$), —$CHF_2$ or —$CH_2$—$CHF_2$.

6. The compound of claim 1, wherein $Q_1$ is 5- to 6-membered heterocycloalkyl ring.

7. The compound of claim 1, wherein $Q_2$ is fused benzo ring.

8. The compound of claim 1, wherein

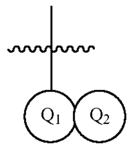

is

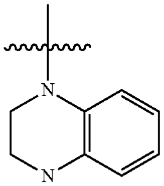, 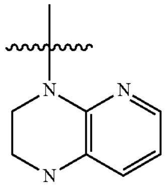, 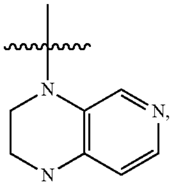 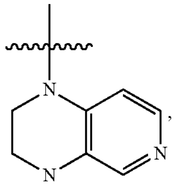, 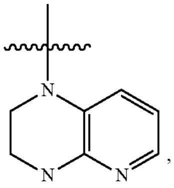, 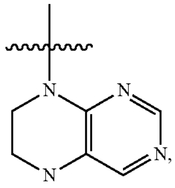 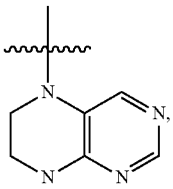, 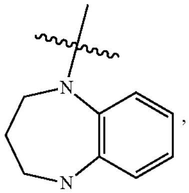, 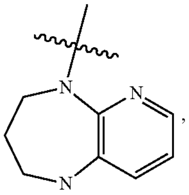, 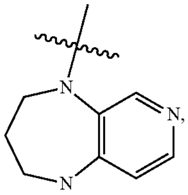, 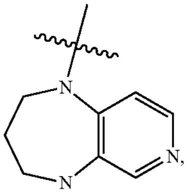 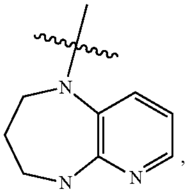, 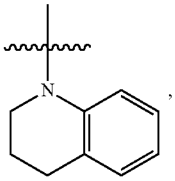 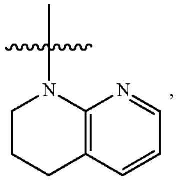, 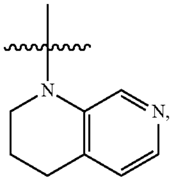, 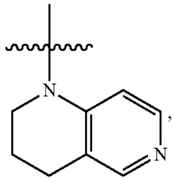, 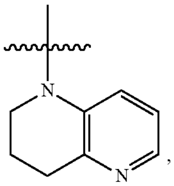 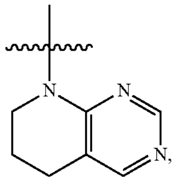

-continued

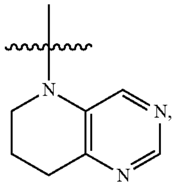

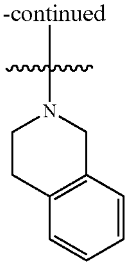
,
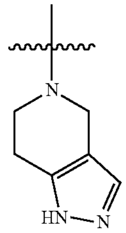
,

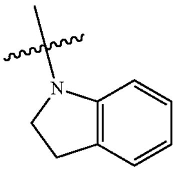
,
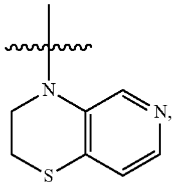

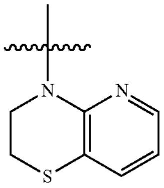
,
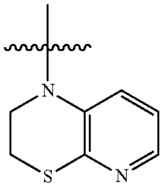
,

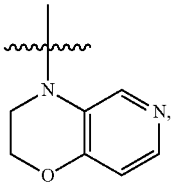

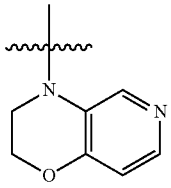
or

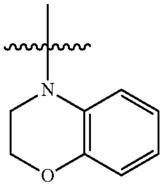
.

9. The compound of claim 1, wherein $R_3$, at each occurrence, independently, is hydrogen, halogen, —CN, alkyl, alkoxy, haloalkyl, acyl, —CONH-alkyl, —COO-alkyl, —$NHSO_2$-alkyl, —NHCO-alkyl, —N(alkyl)CO-alkyl, heteroaryl, heterocycloalkyl, or cycloalkyl; wherein alkyl, at each occurrence, is independently optionally substituted with 1 to 3 occurrence(s) of $R_{3A}$; heteroaryl is optionally substituted with 1 to 3 occurrence(s) of $R_{3B}$; and heterocycloalkyl is optionally substituted with 1 to 3 occurrence(s) of $R_{3C}$.

10. The compound of claim 1, is represented by a compound of formula (IA):

(IA)

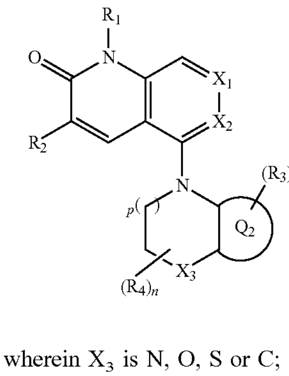

wherein $X_3$ is N, O, S or C; and p is 0, 1 or 2.

11. The compound of claim 10, wherein each $R_1$ and $R_2$ independently is hydrogen or —$CH_3$;

—$X_1$—$X_2$— is —$CR_{X1}$—$CR_{X2}$—, —N—$CR_{X2}$— or —$CR_{X1}$—N—;

$R_{X1}$ is hydrogen, —$OR_a$, —$CH_3$, —C≡$CCH_2OH$, —$N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro[3.3]heptanyl, 3-oxa-8-azabicyclo[3.2.1]octanyl, 2-oxa-6-azaspiro[3.4]octanyl, 2-oxa-5-azabicyclo[2.2.1]heptanyl, cyclohexanyl, imidazolyl or isooxazolyl; wherein each cyclic group is optionally substituted with 1 to 2 substituent(s) independently selected from —$CH_3$, —$COCH_3$, —F, —CN, oxo, —$NH_2$, —OH, —$NHCOCH_3$, —$SO_2NH_2$ and —$CONHCH_3$;

$R_{X2}$ is hydrogen or alkyl;

$R_a$ is hydrogen, alkyl, haloalkyl, (heterocycloalkyl) alkyl-, heterocycloalkyl, heteroaryl or (heteroaryl) alkyl-; wherein alkyl, at each occurrence, is optionally substituted by 1 to 3 substituent(s) independently selected from heterocycloalkyl, —COOH, alkoxy, —N(alkyl)$_2$ and —CONH—O-alkyl; and wherein heterocycloalkyl and heteroaryl are optionally substituted by 1 to 3 substituent(s) independently selected from alkyl and acyl;

the formula

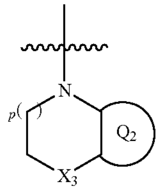

is

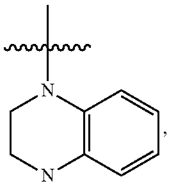
,
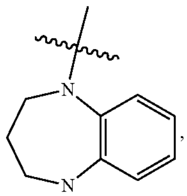
,

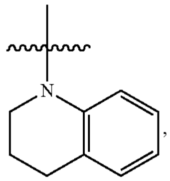
,
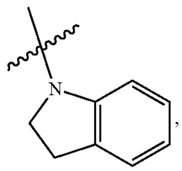
,

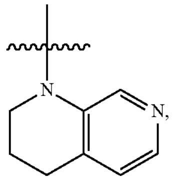

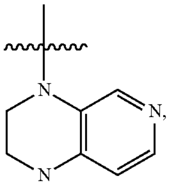

-continued

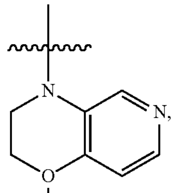

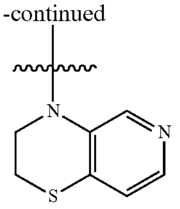

or

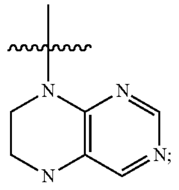

$R_3$, at each occurrence, independently, is $-CH_3$, $-CH_2OH$, $-CH_2CONHOH$, —F, —CN, $-OCH_3$, $-CHF_2$, $-CF_3$, —CHO, acyl, $-CONHCH_3$, $-COOCH_3$, —COOH, —OH, $-SO_2NH_2$, $-SO_2NHCH_3$, $-SO_2N(CH_3)_2$, $-SO_2NH$(phenyl), $-SOCH_3$, $-SO_2CH_3$, $-SO_2CH(CH_3)_2$, $-SO_2NHCOCH_3$, $-SO_2NHCOCF3$, —S(O) (NH) $CH_3$, $-NHSO_2CH_3$, $-NHSO_2CH_2CH_3$, $-NHSO_2CH(CH_3)_3$, $-NHCOCH_3$, $-N(CH_3)COCH_3$, pyrazolyl, pyridyl, tetrazolyl, thienyl, 2H-pyridyl, dihydropyridyl, dihydrooxazolyl, tetrahydrofuranyl, morpholinyl, piperazinyl, pyrrolidinyl, piperidinyl or azetidinyl; wherein the pyrazolyl, pyridyl, tetrazolyl and thienyl are optionally substituted with 1 to 3 substituent(s) independently selected from alkyl, alkoxy, —OH, —COOH, oxo, —COO-alkyl, —CONH-alkyl and —CONH—OH; and the 2H-pyridyl, dihydropyridyl, dihydrooxazolyl, tetrahydrofuranyl, morpholinyl, piperazinyl, pyrrolidinyl, piperidinyl and azetidinyl are optionally substituted with 1 to 3 substituent(s) independently selected from $-CH_3$, —CN, —OH, $-NH_2$, $-N(CH_3)_2$, $-COCH_3$, oxo, $-CONHCH_3$, $-NHCOCH_3$ and $-CONHCH_2CH_2OH$;

$R_4$, at each occurrence, independently, is hydrogen, $-CH_3$, $-CH_2CH_3$, $-CH_2COOH$, $-CH_2$(p-($OCH_3$) phenyl), $-CHF_2$, $-COCH_3$, $-CH_2COOCH_2CH_3$, $-CH_2CONHCH_3$, $-CONHCH_3$, oxo, $-SO_2CH_2CH_3$, morpholinyl, pyranyl or cyclopropyl; and n is 1, 2 or 3.

12. The compound of claim 1, represented by compound of formula (IB):

(IB)

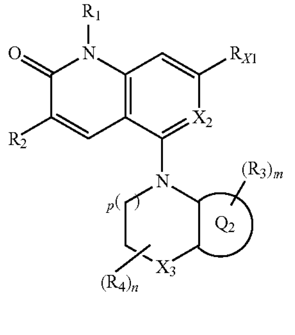

wherein $X_3$ is N, O, S or C; and p is 0, 1 or 2.

13. The compound of claim 12, wherein $X_2$ is CH or N;

$R_{X1}$ is hydrogen, $-OR_a$, $-CH_3$, $-C{\equiv}CCH_2OH$, $-N(CH_3)_2$, azetidinyl, furanyl, pyrrolidinyl, piperazinyl, piperidinyl, morpholinyl, thiomorpholinyl, pyranyl, dihydropyranyl, 8-oxa-3-azabicyclo[3.2.1]octanyl, 3-oxa-6-azabicyclo[3.1.1]heptanyl, 2-oxa-6-azaspiro [3.3]heptanyl, 3-oxa-8-azabicyclo[3.2.1]octanyl, 2-oxa-6-azaspiro[3.4]octanyl, 2-oxa-5-azabicyclo [2.2.1]heptanyl, cyclohexanyl, imidazolyl or isooxazolyl; wherein each cyclic group is optionally substituted with 1 to 2 substituent(s) independently selected from $-CH_3$, $-COCH_3$, —F, —CN, oxo, $-NH_2$, —OH, $-NHCOCH_3$, $-SO_2NH_2$ and $-CONHCH_3$;

$R_a$ is $-CH_3$, $-CH(CH_3)_2$, $-CH_2-COOC(CH_3)_3$, $-CH_2$-piperidinyl ($CH_3$), $-CH_2-CH_2$-morpholine, $-CH_2-CH_2-OCH_3$, $-CH_2-CH_2-N(CH_3)_2$, azetidinyl, $-CH_2$-oxazole, $-CH_2-CH_2-OH$, $-CH_2-CH_2$-piperizinyl ($COCH_3$), $-CH_2-COOH$, $-CH_2-CONH(OCH_3)$, $-CHF_2$ or $-CH_2-CHF_2$;

$Q_2$ is

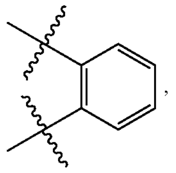

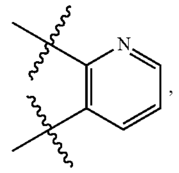

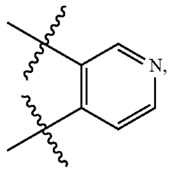

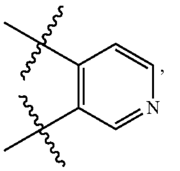

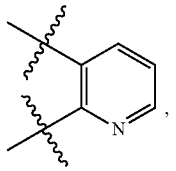

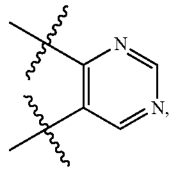

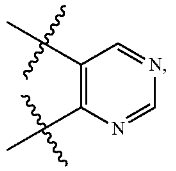

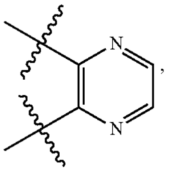

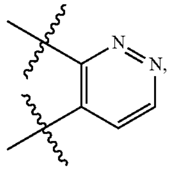

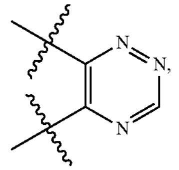

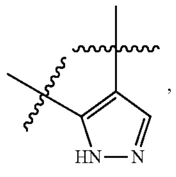

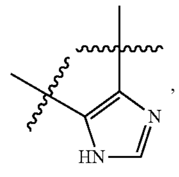

-continued

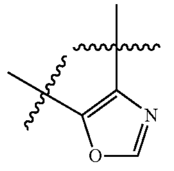 or 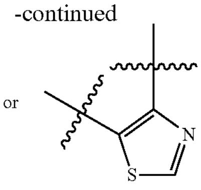 ;

$R_3$, at each occurrence, independently, is hydrogen, $—CH_3$, $—CH_2OH$, $—CH_2CONHOH$, —F, —CN, $—OCH_3$, $—CHF_2$, $—CF_3$, —CHO, acyl, $—CONHCH_3$, $—COOCH_3$, —COOH, —OH, $—SO_2NH_2$, $—SO_2NHCH_3$, $—SO_2N(CH_3)_2$, $—SO_2NH$ (phenyl), $—SOCH_3$, $—SO_2CH_3$, $—SO_2CH(CH_3)_2$, $—SO_2NHCOCH_3$, $—SO_2NHCOCF3$, —S(O)(NH) $CH_3$, $—NHSO_2CH_3$, $—NHSO_2CH_2CH_3$, $—NHSO_2CH(CH_3)_3$, $—NHCOCH_3$, $—N(CH_3)COCH_3$, pyrazolyl, pyridyl, tetrazolyl or thienyl; wherein the pyrazolyl, pyridyl, tetrazolyl and thienyl are optionally substituted with 1 to 3 substituent(s) independently selected from alkyl, alkoxy, —OH, —COOH, oxo, —COO-alkyl, —CONH-alkyl and —CONH—OH;

$R_4$, at each occurrence, independently, is hydrogen, $—CH_3$, $—CH_2CH_3$, $—CH_2COOH$, $—CH_2$(p-($OCH_3$)phenyl), $—CHF_2$, $—COCH_3$, $—CH_2COOCH_2CH_3$, $—CH_2CONHCH_3$, $—CONHCH_3$, oxo, $—SO_2CH_2CH_3$, morpholinyl, pyranyl or cyclopropyl; wherein morpholinyl, pyranyl and cyclopropyl are optionally substituted with 1 to 3 substituent(s) independently selected from $—OCH_3$, $—COOCH_2CH_3$, —COOH and $—CONHCH_3$;

$X_3$ is N, O, S or C;

p is 0, 1 or 2; and n is 1, 2 or 3.

14. The compound of claim 1, represented by compound of formulae (IC), (IE), (IF) or (IG):

(IC)

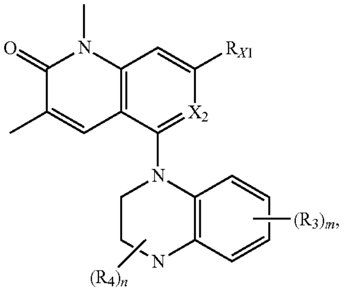

(IE)

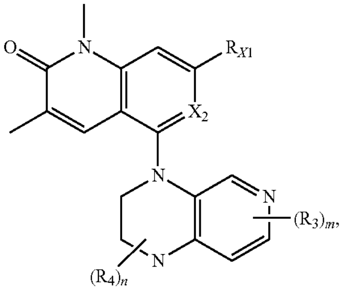

-continued (IF)

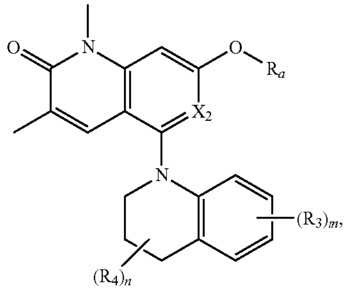 or (IG)

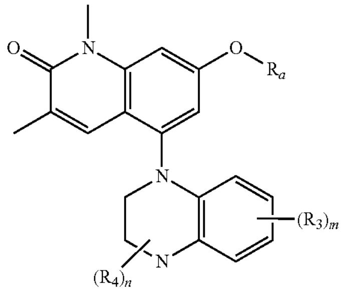

15. The compound of claim 1, is represented by a compound of formula (ID), (ID)

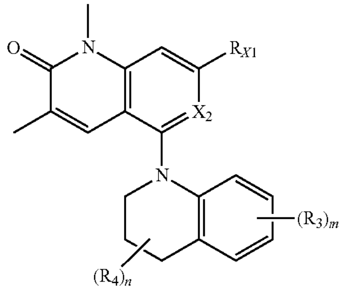

16. The compound of claim 1, is selected from:

| Example | Structure |
| --- | --- |
| 1 | 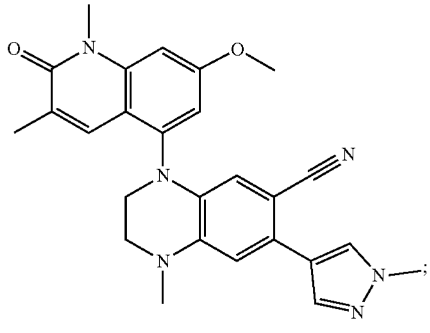 [SMILES: COc1cc(N2CCN(C)c3cc(-c4cnn(C)c4)c(C#N)cc32)c2cc(C)c(=O)n(C)c2c1] |

-continued
| Example | Structure |
|---|---|
| 2 | 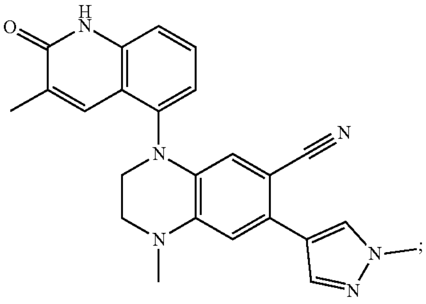 [SMILES: Cc1cc2c(N3CCN(C)c4cc(-c5cnn(C)c5)c(C#N)cc43)cccc2[nH]c1=O] |
| 3 | 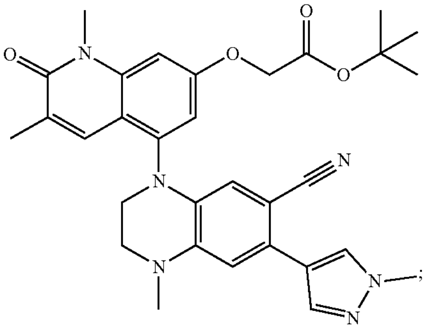 [SMILES: Cc1cc2c(N3CCN(C)c4cc(-c5cnn(C)c5)c(C#N)cc43)cc(OCC(=O)OC(C)(C)C)cc2n(C)c1=O] |
| 4 | 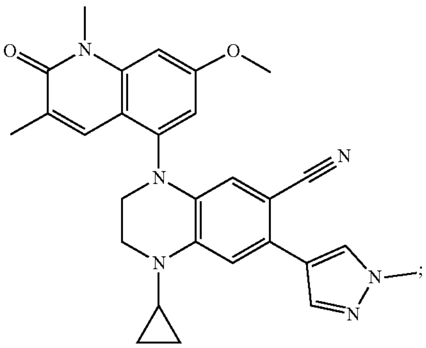 [SMILES: COc1cc(N2CCN(C3CC3)c3cc(-c4cnn(C)c4)c(C#N)cc32)c2cc(C)c(=O)n(C)c2c1] |
| 5 | 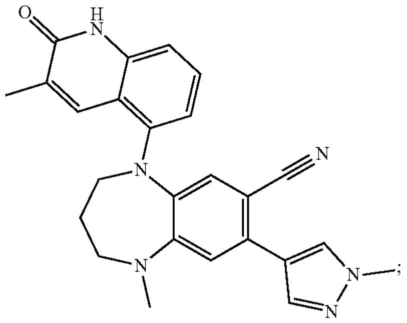 |
-continued
| Example | Structure |
|---|---|
| 6 | 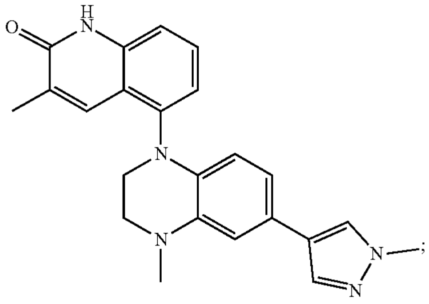 [SMILES: Cc1cc2c(N3CCN(C)c4cc(-c5cnn(C)c5)ccc43)cccc2[nH]c1=O] |
| 7 | 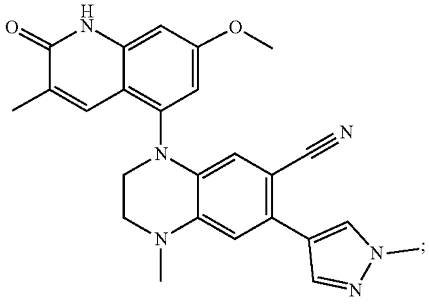 [SMILES: COc1cc(N2CCN(C)c3cc(-c4cnn(C)c4)c(C#N)cc32)c2cc(C)c(=O)[nH]c2c1] |
| 8 | 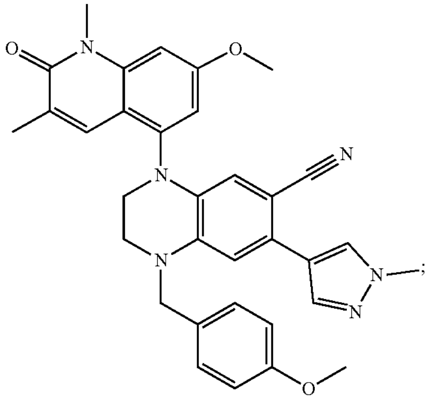 [SMILES: COc1ccc(CN2CCN(c3cc(OC)cc4c3cc(C)c(=O)n4C)c3cc(C#N)c(-c4cnn(C)c4)cc32)cc1] |
| 9 | 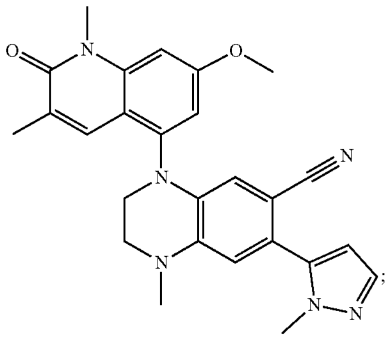 [SMILES: COc1cc(N2CCN(C)c3cc(-c4ccnn4C)c(C#N)cc32)c2cc(C)c(=O)n(C)c2c1] |

-continued
| Example | Structure |
|---|---|
| 10 | 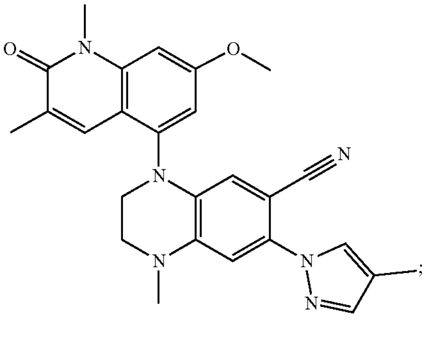 [SMILES: COc1cc(N2CCN(C)c3cc(-n4cc(C)cn4)c(C#N)cc32)c2cc(C)c(=O)n(C)c2c1] |
| 11 | 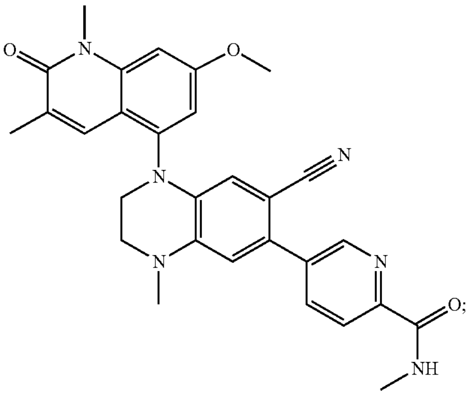 [SMILES: CNC(=O)c1ccc(-c2cc3c(cc2C#N)N(c2cc(OC)cc4c2cc(C)c(=O)n4C)CCN3C)cn1] |
| 12 | 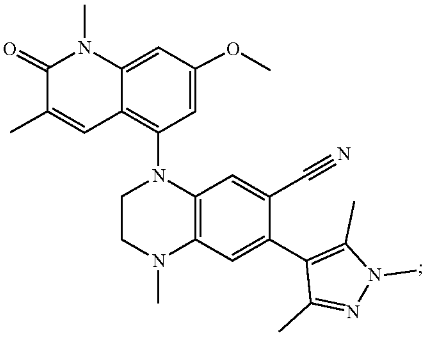 [SMILES: COc1cc(N2CCN(C)c3cc(-c4c(C)nn(C)c4C)c(C#N)cc32)c2cc(C)c(=O)n(C)c2c1] |
| 13 | 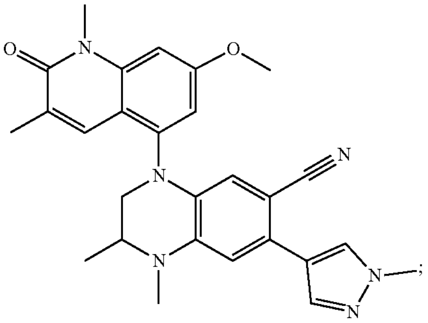 [SMILES: COc1cc(N2CC(C)N(C)c3cc(-c4cnn(C)c4)c(C#N)cc32)c2cc(C)c(=O)n(C)c2c1] |
-continued
| Example | Structure |
|---|---|
| 14 | 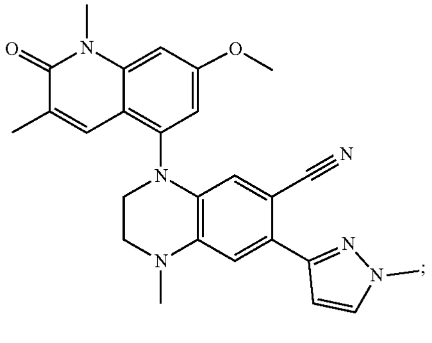 [SMILES: COc1cc(N2CCN(C)c3cc(-c4ccn(C)n4)c(C#N)cc32)c2cc(C)c(=O)n(C)c2c1] |
| 15 | 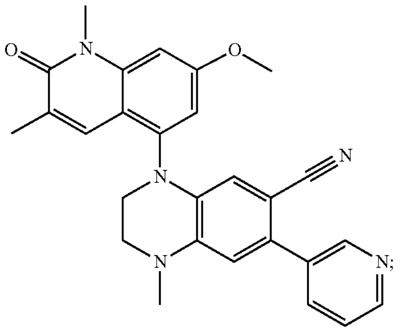 [SMILES: COc1cc(N2CCN(C)c3cc(-c4cccnc4)c(C#N)cc32)c2cc(C)c(=O)n(C)c2c1] |
| 16 | 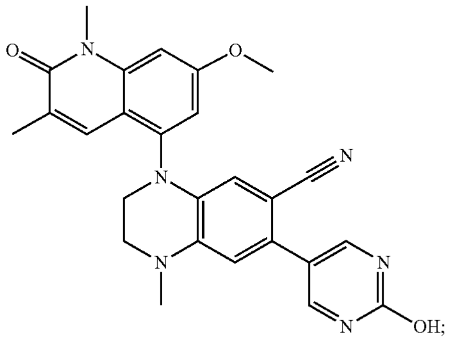 [SMILES: COc1cc(N2CCN(C)c3cc(-c4cnc(O)nc4)c(C#N)cc32)c2cc(C)c(=O)n(C)c2c1] |
| 17 | 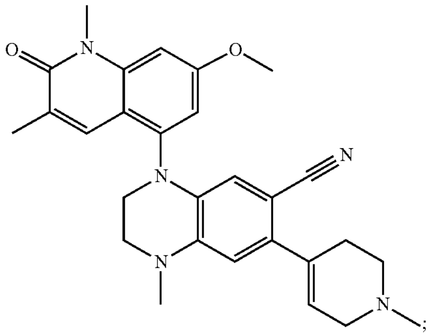 [SMILES: COc1cc(N2CCN(C)c3cc(C4=CCN(C)CC4)c(C#N)cc32)c2cc(C)c(=O)n(C)c2c1] |

-continued
| Example | Structure |
|---|---|
| 18 | 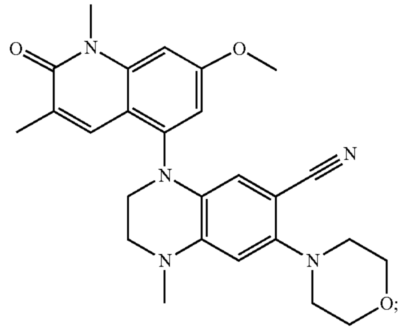 [SMILES: COc1cc(N2CCN(C)c3cc(N4CCOCC4)c(C#N)cc32)c2cc(C)c(=O)n(C)c2c1] |
| 19 | 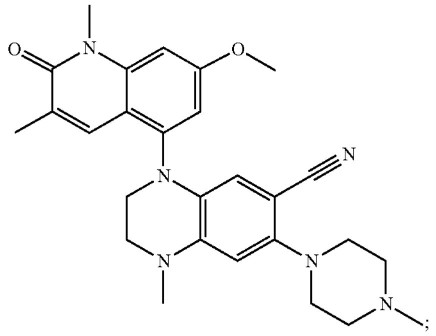 [SMILES: COc1cc(N2CCN(C)c3cc(N4CCN(C)CC4)c(C#N)cc32)c2cc(C)c(=O)n(C)c2c1] |
| 20 | 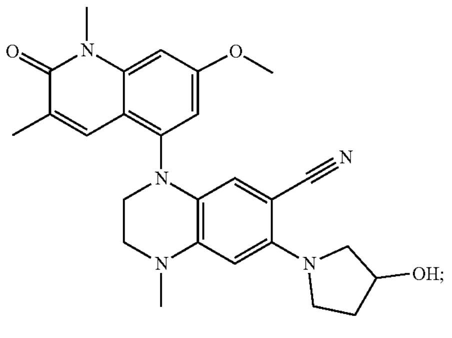 [SMILES: COc1cc(N2CCN(C)c3cc(N4CCC(O)C4)c(C#N)cc32)c2cc(C)c(=O)n(C)c2c1] |
| 21 | 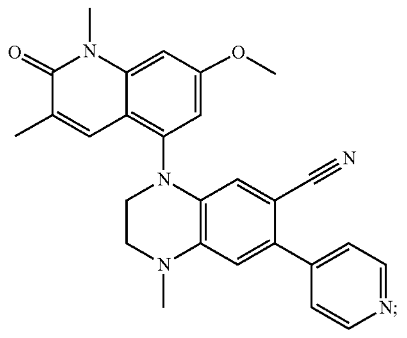 [SMILES: COc1cc(N2CCN(C)c3cc(-c4ccncc4)c(C#N)cc32)c2cc(C)c(=O)n(C)c2c1] |
-continued
| Example | Structure |
|---|---|
| 22 | 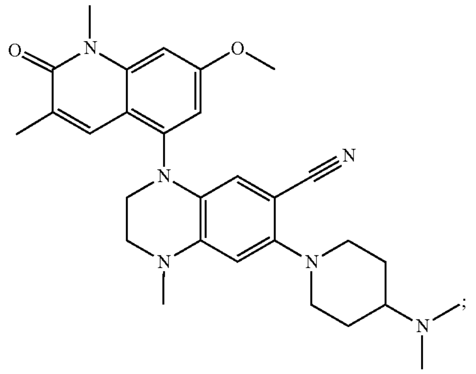 [SMILES: COc1cc(N2CCN(C)c3cc(N4CCC(N(C)C)CC4)c(C#N)cc32)c2cc(C)c(=O)n(C)c2c1] |
| 23 | 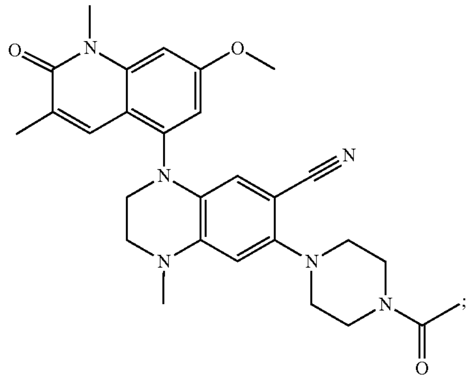 [SMILES: COc1cc(N2CCN(C)c3cc(N4CCN(C(C)=O)CC4)c(C#N)cc32)c2cc(C)c(=O)n(C)c2c1] |
| 24 | 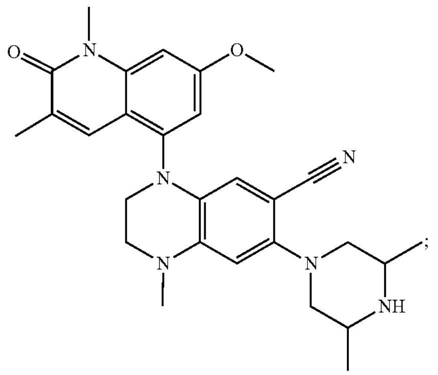 [SMILES: COc1cc(N2CCN(C)c3cc(N4CC(C)NC(C)C4)c(C#N)cc32)c2cc(C)c(=O)n(C)c2c1] |
| 25 | 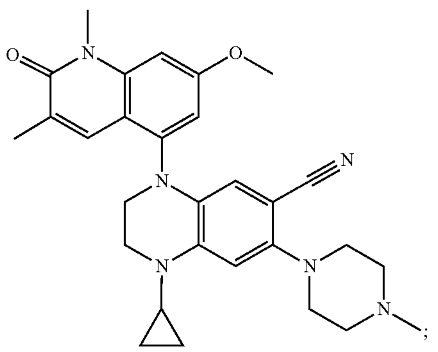 [SMILES: COc1cc(N2CCN(C3CC3)c3cc(N4CCN(C)CC4)c(C#N)cc32)c2cc(C)c(=O)n(C)c2c1] |

-continued
| Example | Structure |
| --- | --- |
| 26 | 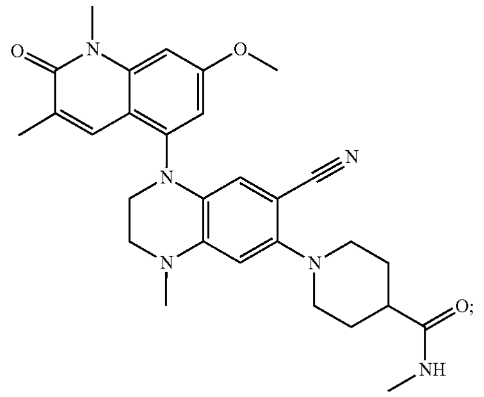 [SMILES: CNC(=O)C1CCN(c2cc3c(cc2C#N)N(c2cc(OC)cc4c2cc(C)c(=O)n4C)CCN3C)CC1] |
| 27 | 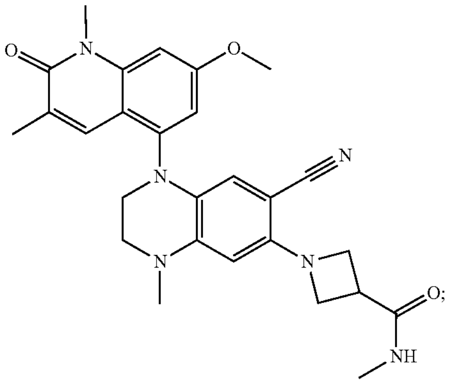 [SMILES: CNC(=O)C1CN(c2cc3c(cc2C#N)N(c2cc(OC)cc4c2cc(C)c(=O)n4C)CCN3C)C1] |
| 28 | 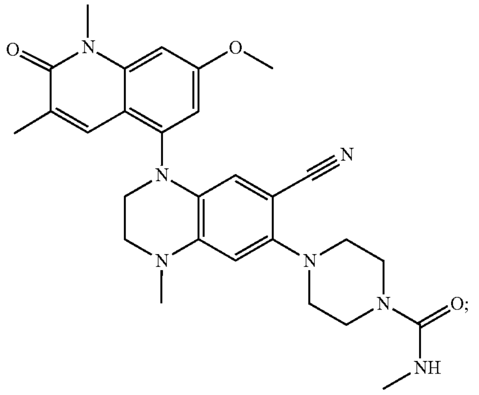 [SMILES: CNC(=O)N1CCN(c2cc3c(cc2C#N)N(c2cc(OC)cc4c2cc(C)c(=O)n4C)CCN3C)CC1] |
| 29 | 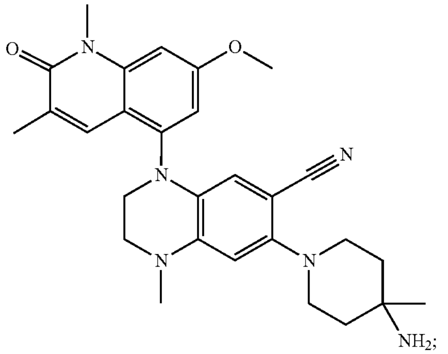 [SMILES: COc1cc(N2CCN(C)c3cc(N4CCC(C)(N)CC4)c(C#N)cc32)c2cc(C)c(=O)n(C)c2c1] |
| 30 | 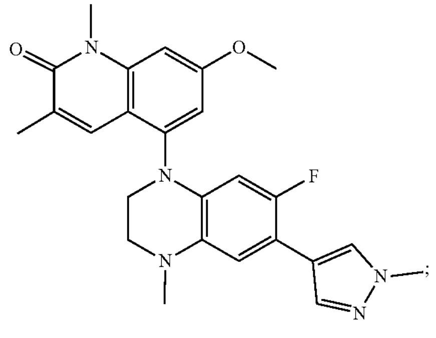 [SMILES: COc1cc(N2CCN(C)c3cc(-c4cnn(C)c4)c(F)cc32)c2cc(C)c(=O)n(C)c2c1] |
| 31 | 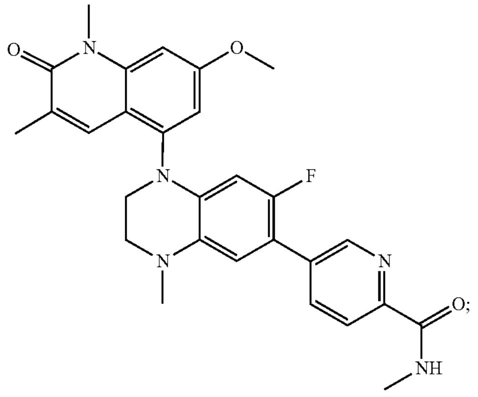 [SMILES: CNC(=O)c1ccc(-c2cc3c(cc2F)N(c2cc(OC)cc4c2cc(C)c(=O)n4C)CCN3C)cn1] |
| 32 | 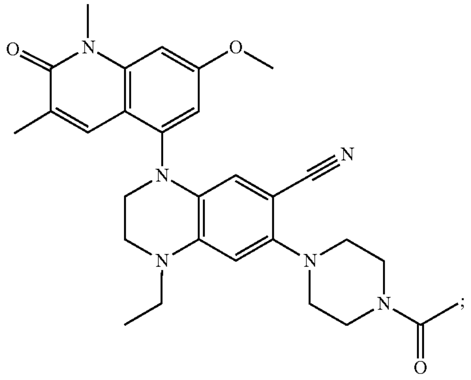 [SMILES: CCN1CCN(c2cc(OC)cc3c2cc(C)c(=O)n3C)c2cc(C#N)c(N3CCN(C(C)=O)CC3)cc21] |
| 33 | 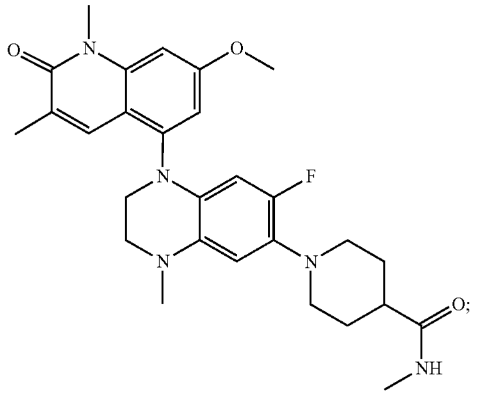 [SMILES: CNC(=O)C1CCN(c2cc3c(cc2F)N(c2cc(OC)cc4c2cc(C)c(=O)n4C)CCN3C)CC1] |

-continued
| Example | Structure |
|---|---|
| 34 | 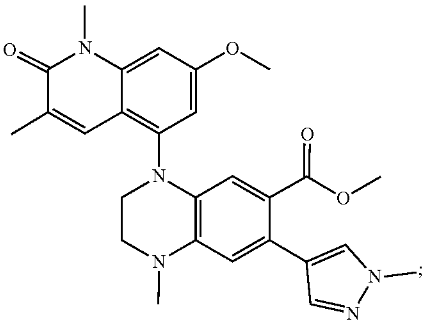 [SMILES: COC(=O)c1cc2c(cc1-c1cnn(C)c1)N(C)CCN2c1cc(OC)cc2c1cc(C)c(=O)n2C] |
| 35 | 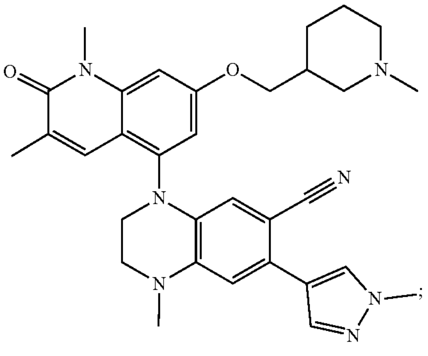 [SMILES: Cc1cc2c(N3CCN(C)c4cc(-c5cnn(C)c5)c(C#N)cc43)cc(OCC3CCCN(C)C3)cc2n(C)c1=O] |
| 36 | 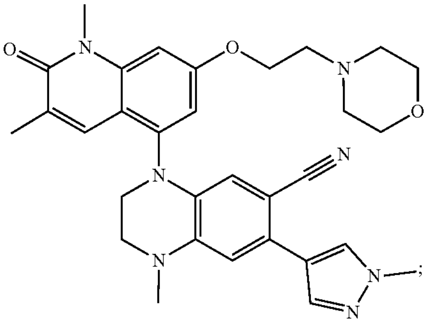 [SMILES: Cc1cc2c(N3CCN(C)c4cc(-c5cnn(C)c5)c(C#N)cc43)cc(OCCN3CCOCC3)cc2n(C)c1=O] |
| 37 | 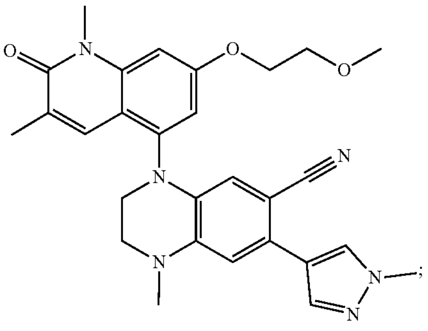 [SMILES: COCCOc1cc(N2CCN(C)c3cc(-c4cnn(C)c4)c(C#N)cc32)c2cc(C)c(=O)n(C)c2c1] |
| 38 | 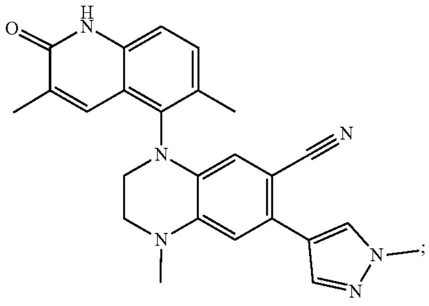 [SMILES: Cc1ccc2[nH]c(=O)c(C)cc2c1N1CCN(C)c2cc(-c3cnn(C)c3)c(C#N)cc21] |
| 39 | 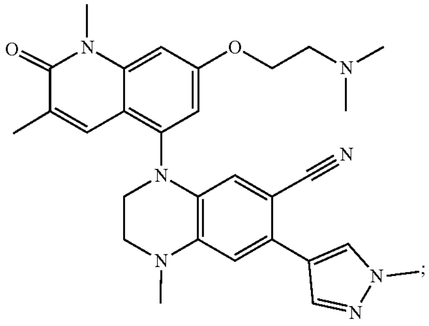 [SMILES: Cc1cc2c(N3CCN(C)c4cc(-c5cnn(C)c5)c(C#N)cc43)cc(OCCN(C)C)cc2n(C)c1=O] |
| 40 | 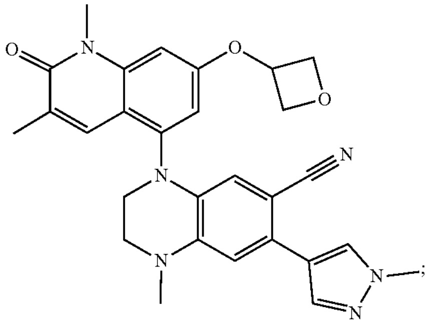 [SMILES: Cc1cc2c(N3CCN(C)c4cc(-c5cnn(C)c5)c(C#N)cc43)cc(OC3COC3)cc2n(C)c1=O] |
| 41 | 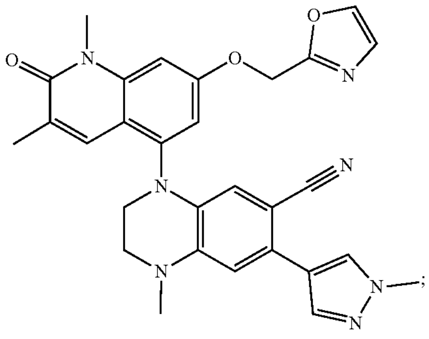 [SMILES: Cc1cc2c(N3CCN(C)c4cc(-c5cnn(C)c5)c(C#N)cc43)cc(OCc3ncco3)cc2n(C)c1=O] |

-continued
| Example | Structure |
|---|---|
| 42 | 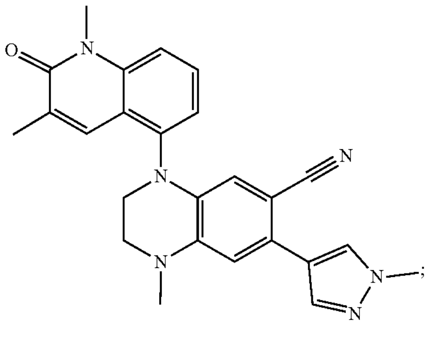 [SMILES: Cc1cc2c(N3CCN(C)c4cc(-c5cnn(C)c5)c(C#N)cc43)cccc2n(C)c1=O] |
| 43 | 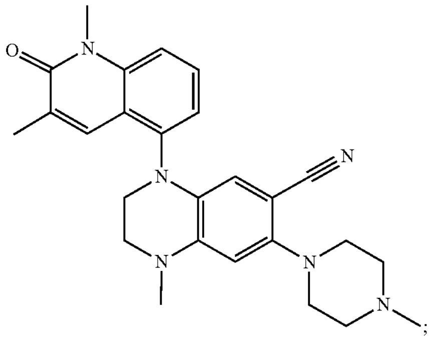 [SMILES: Cc1cc2c(N3CCN(C)c4cc(N5CCN(C)CC5)c(C#N)cc43)cccc2n(C)c1=O] |
| 44 | 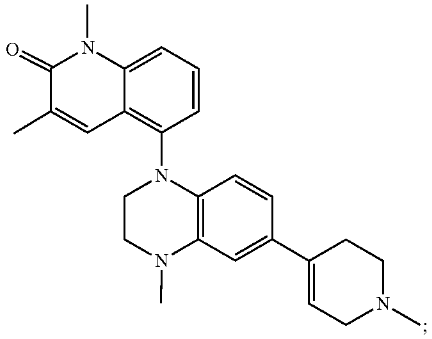 [SMILES: Cc1cc2c(N3CCN(C)c4cc(C5=CCN(C)CC5)ccc43)cccc2n(C)c1=O] |
| 45 | 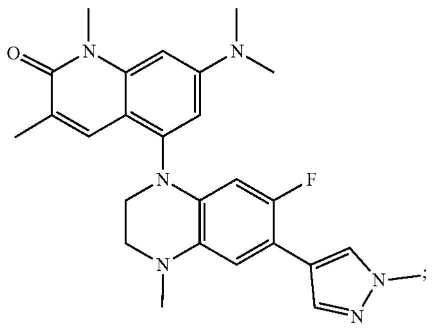 [SMILES: Cc1cc2c(N3CCN(C)c4cc(-c5cnn(C)c5)c(F)cc43)cc(N(C)C)cc2n(C)c1=O] |
-continued
| Example | Structure |
|---|---|
| 46 | 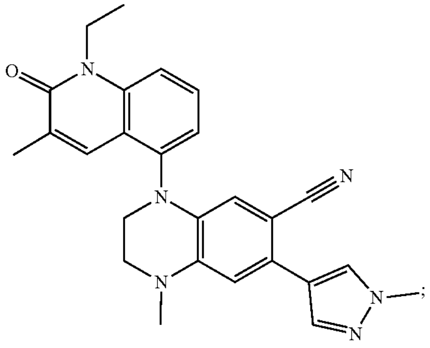 [SMILES: CCn1c(=O)c(C)cc2c(N3CCN(C)c4cc(-c5cnn(C)c5)c(C#N)cc43)cccc21] |
| 47 | 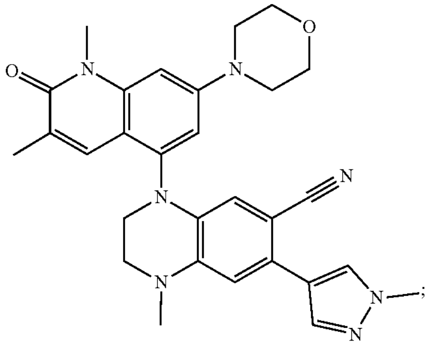 [SMILES: Cc1cc2c(N3CCN(C)c4cc(-c5cnn(C)c5)c(C#N)cc43)cc(N3CCOCC3)cc2n(C)c1=O] |
| 48 | 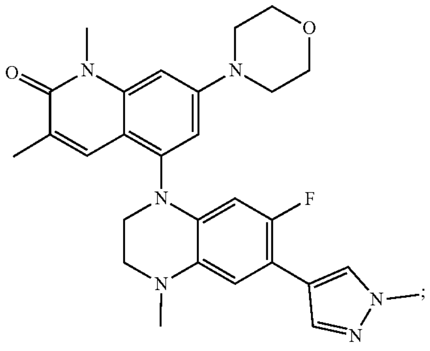 [SMILES: Cc1cc2c(N3CCN(C)c4cc(-c5cnn(C)c5)c(F)cc43)cc(N3CCOCC3)cc2n(C)c1=O] |
| 49 | 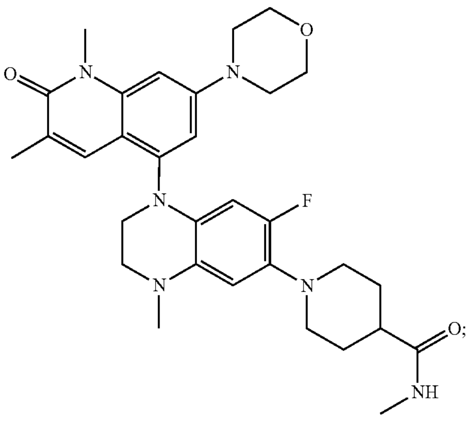 [SMILES: CNC(=O)C1CCN(c2cc3c(cc2F)N(c2cc(N4CCOCC4)cc4c2cc(C)c(=O)n4C)CCN3C)CC1] |

| Example | Structure |
|---|---|
| 50 | 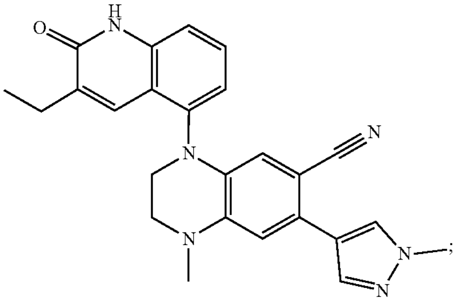 [SMILES: CCc1cc2c(N3CCN(C)c4cc(-c5cnn(C)c5)c(C#N)cc43)cccc2[nH]c1=O] |
| 51 | 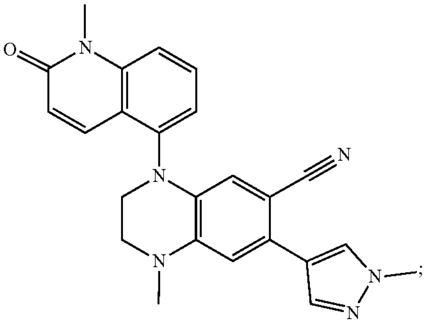 [SMILES: CN1CCN(c2cccc3c2ccc(=O)n3C)c2cc(C#N)c(-c3cnn(C)c3)cc21] |
| 52 | 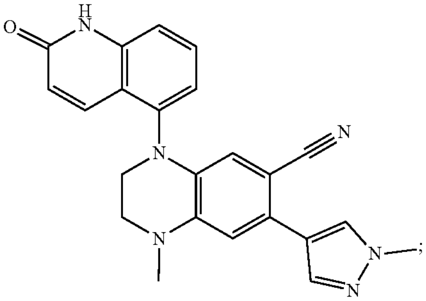 [SMILES: CN1CCN(c2cccc3[nH]c(=O)ccc23)c2cc(C#N)c(-c3cnn(C)c3)cc21] |
| 53 | 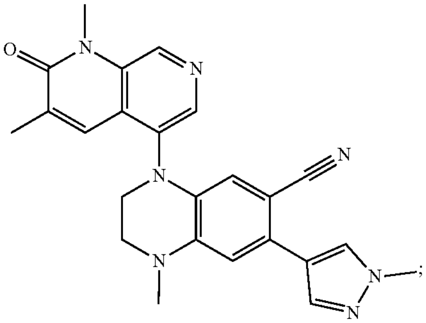 [SMILES: Cc1cc2c(N3CCN(C)c4cc(-c5cnn(C)c5)c(C#N)cc43)cncc2n(C)c1=O] |
| Example | Structure |
|---|---|
| 54 | 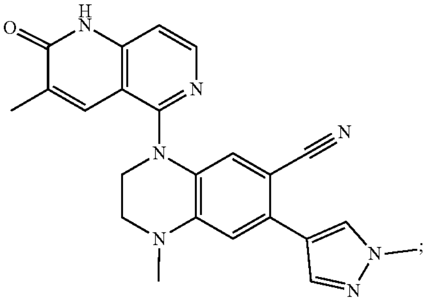 |
| 55 | 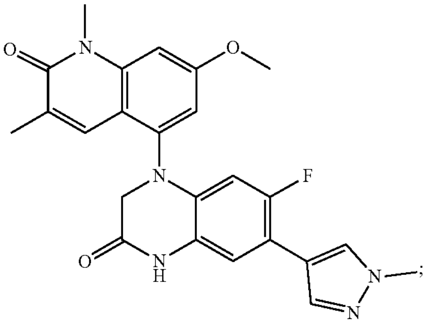 [SMILES: COc1cc(N2CC(=O)Nc3cc(-c4cnn(C)c4)c(F)cc32)c2cc(C)c(=O)n(C)c2c1] |
| 56 | 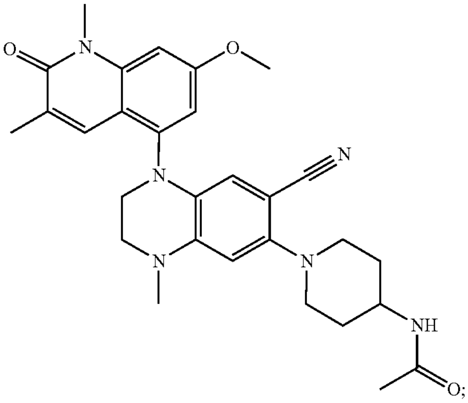 [SMILES: COc1cc(N2CCN(C)c3cc(N4CCC(NC(C)=O)CC4)c(C#N)cc32)c2cc(C)c(=O)n(C)c2c1] |
| 57 | 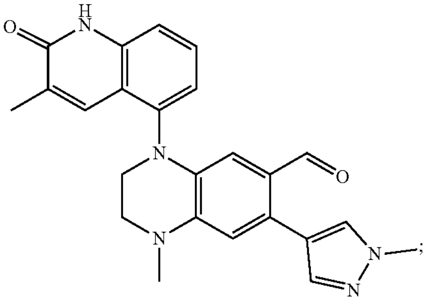 [SMILES: Cc1cc2c(N3CCN(C)c4cc(-c5cnn(C)c5)c(C=O)cc43)cccc2[nH]c1=O] |

-continued
| Example | Structure |
| --- | --- |
| 58 | 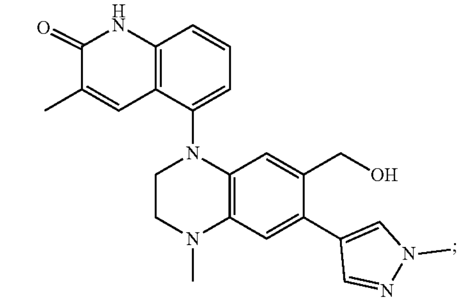 [SMILES: Cc1cc2c(N3CCN(C)c4cc(-c5cnn(C)c5)c(CO)cc43)cccc2[nH]c1=O] |
| 59 | 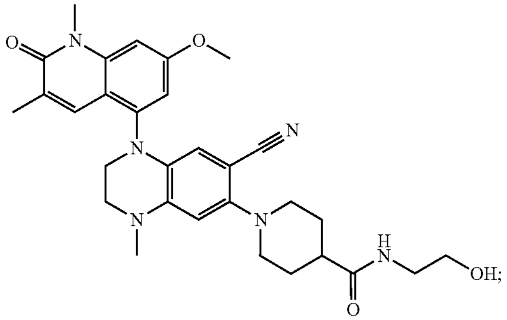 [SMILES: COc1cc(N2CCN(C)c3cc(N4CCC(C(=O)NCCO)CC4)c(C#N)cc32)c2cc(C)c(=O)n(C)c2c1] |
| 60 | 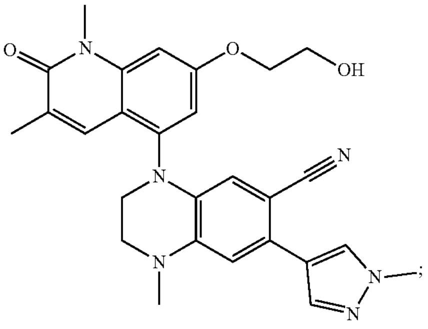 [SMILES: Cc1cc2c(N3CCN(C)c4cc(-c5cnn(C)c5)c(C#N)cc43)cc(OCCO)cc2n(C)c1=O] |
| 61 | 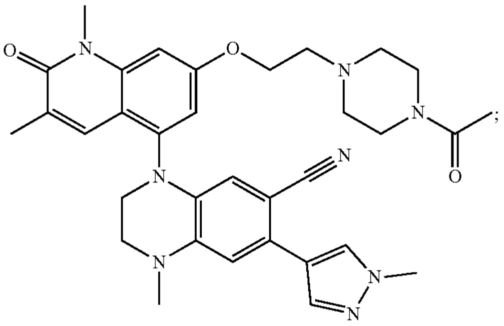 [SMILES: CC(=O)N1CCN(CCOc2cc(N3CCN(C)c4cc(-c5cnn(C)c5)c(C#N)cc43)c3cc(C)c(=O)n(C)c3c2)CC1] |
| 62 | 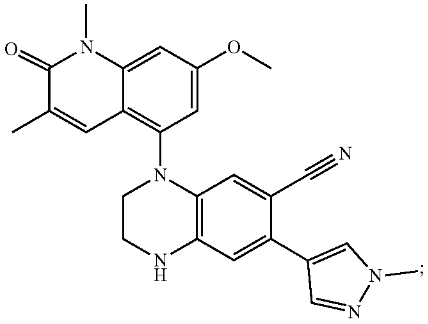 [SMILES: COc1cc(N2CCNc3cc(-c4cnn(C)c4)c(C#N)cc32)c2cc(C)c(=O)n(C)c2c1] |
| 63 | 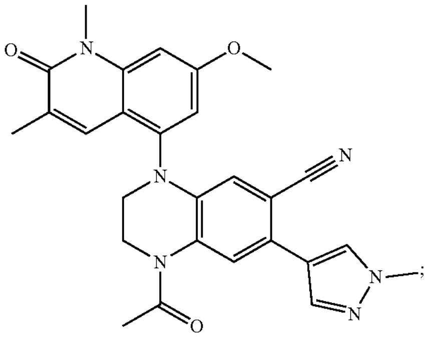 [SMILES: COc1cc(N2CCN(C(C)=O)c3cc(-c4cnn(C)c4)c(C#N)cc32)c2cc(C)c(=O)n(C)c2c1] |
| 64 | 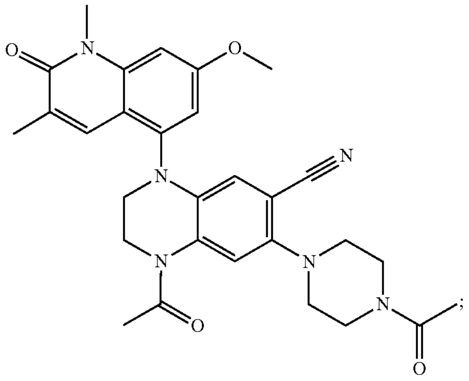 [SMILES: COc1cc(N2CCN(C(C)=O)c3cc(N4CCN(C(C)=O)CC4)c(C#N)cc32)c2cc(C)c(=O)n(C)c2c1] |
| 65 | 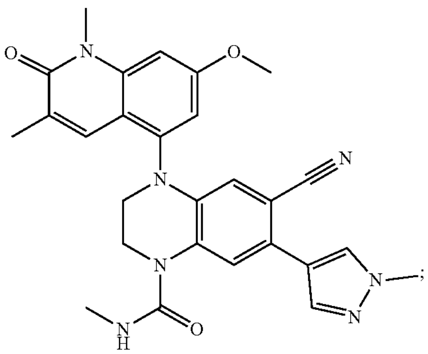 [SMILES: CNC(=O)N1CCN(c2cc(OC)cc3c2cc(C)c(=O)n3C)c2cc(C#N)c(-c3cnn(C)c3)cc21] |

| Example | Structure |
| --- | --- |
| 66 | 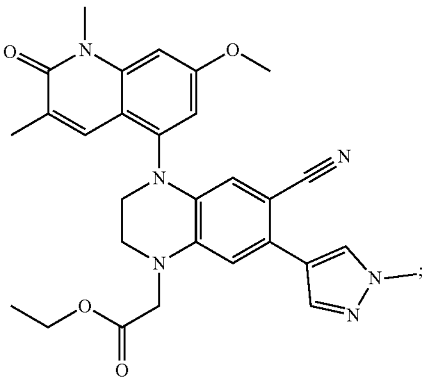 [SMILES: CCOC(=O)CN1CCN(c2cc(OC)cc3c2cc(C)c(=O)n3C)c2cc(C#N)c(-c3cnn(C)c3)cc21] |
| 67 | 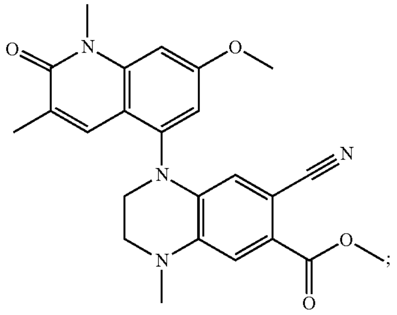 [SMILES: COC(=O)c1cc2c(cc1C#N)N(c1cc(OC)cc3c1cc(C)c(=O)n3C)CCN2C] |
| 68 | 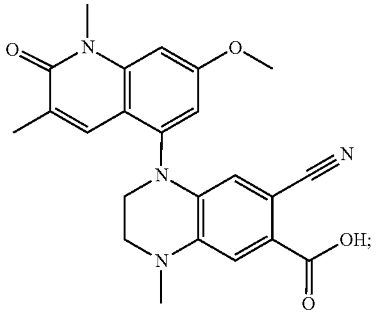 [SMILES: COc1cc(N2CCN(C)c3cc(C(=O)O)c(C#N)cc32)c2cc(C)c(=O)n(C)c2c1] |
| 69 | 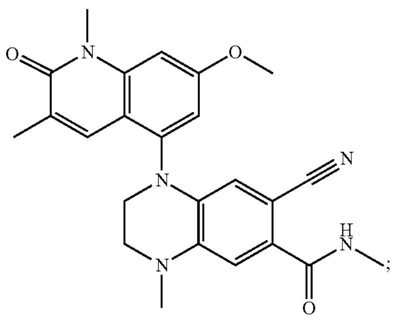 [SMILES: CNC(=O)c1cc2c(cc1C#N)N(c1cc(OC)cc3c1cc(C)c(=O)n3C)CCN2C] |
| Example | Structure |
| --- | --- |
| 70 | 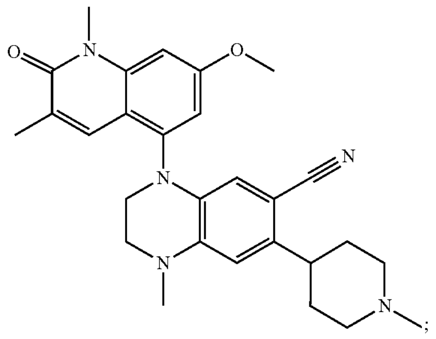 |
| 71 | 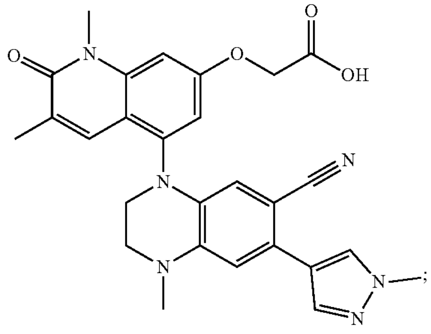 [SMILES: Cc1cc2c(N3CCN(C)c4cc(-c5cnn(C)c5)c(C#N)cc43)cc(OCC(=O)O)cc2n(C)c1=O] |
| 72 | 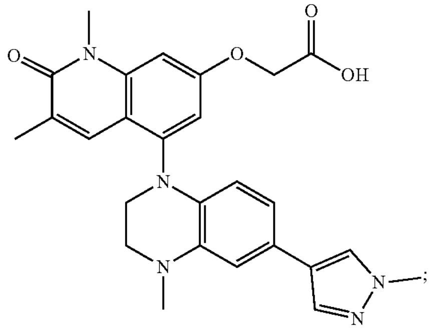 [SMILES: Cc1cc2c(N3CCN(C)c4cc(-c5cnn(C)c5)ccc43)cc(OCC(=O)O)cc2n(C)c1=O] |
| 73 | 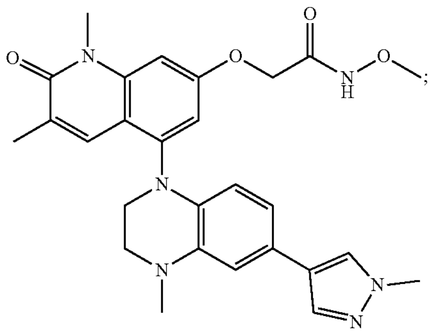 [SMILES: CONC(=O)COc1cc(N2CCN(C)c3cc(-c4cnn(C)c4)ccc32)c2cc(C)c(=O)n(C)c2c1] |

-continued
| Example | Structure |
| --- | --- |
| 74 | 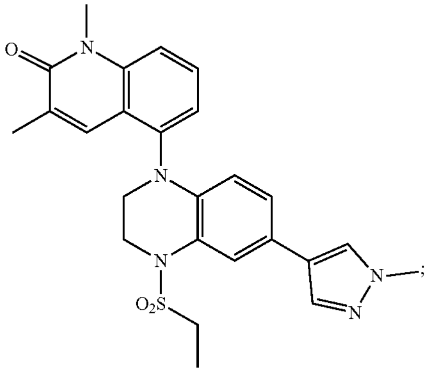 [SMILES: CCS(=O)(=O)N1CCN(c2cccc3c2cc(C)c(=O)n3C)c2ccc(-c3cnn(C)c3)cc21] |
| 75 | 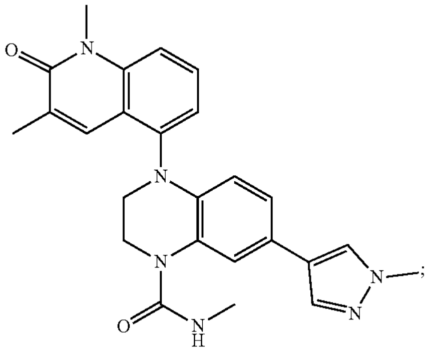 [SMILES: CNC(=O)N1CCN(c2cccc3c2cc(C)c(=O)n3C)c2ccc(-c3cnn(C)c3)cc21] |
| 76 | 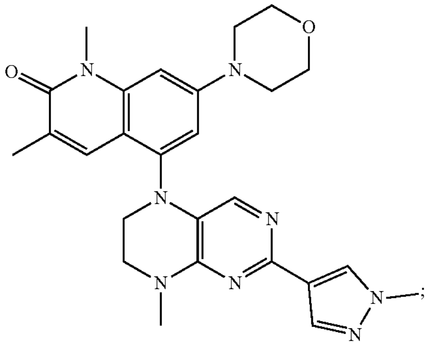 [SMILES: Cc1cc2c(N3CCN(C)c4nc(-c5cnn(C)c5)ncc43)cc(N3CCOCC3)cc2n(C)c1=O] |
| 77 | 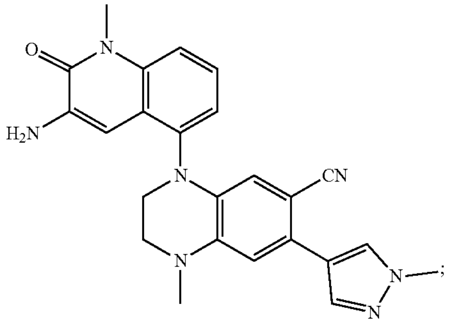 [SMILES: CN1CCN(c2cccc3c2cc(N)c(=O)n3C)c2cc(C#N)c(-c3cnn(C)c3)cc21] |
-continued
| Example | Structure |
| --- | --- |
| 78 | 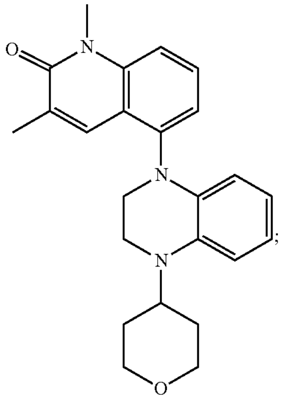 [SMILES: Cc1cc2c(N3CCN(C4CCOCC4)c4ccccc43)cccc2n(C)c1=O] |
| 79 | 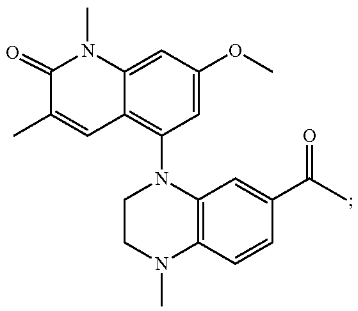 [SMILES: COc1cc(N2CCN(C)c3ccc(C(C)=O)cc32)c2cc(C)c(=O)n(C)c2c1] |
| 80 | 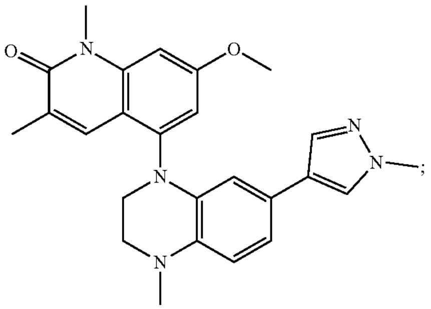 [SMILES: COc1cc(N2CCN(C)c3ccc(-c4cnn(C)c4)cc32)c2cc(C)c(=O)n(C)c2c1] |
| 81 | 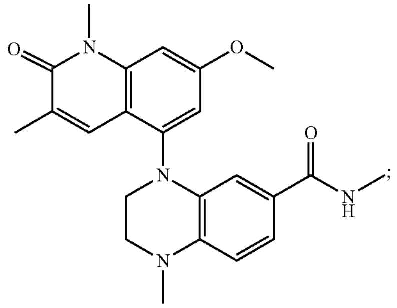 [SMILES: CNC(=O)c1ccc2c(c1)N(c1cc(OC)cc3c1cc(C)c(=O)n3C)CCN2C] |

-continued
| Example | Structure |
|---|---|
| 82 | 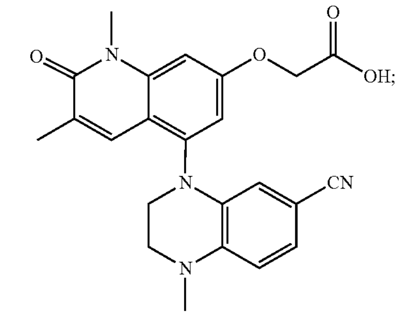 [SMILES: Cc1cc2c(N3CCN(C)c4ccc(C#N)cc43)cc(OCC(=O)O)cc2n(C)c1=O] |
| 83 | 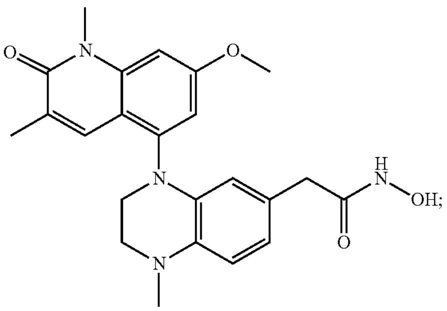 [SMILES: COc1cc(N2CCN(C)c3ccc(CC(=O)NO)cc32)c2cc(C)c(=O)n(C)c2c1] |
| 84 | 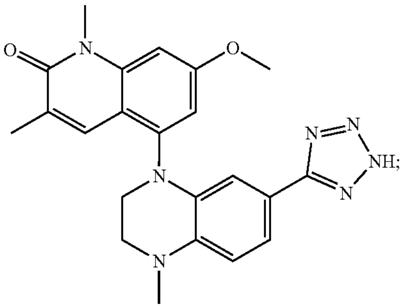 [SMILES: COc1cc(N2CCN(C)c3ccc(-c4nn[nH]n4)cc32)c2cc(C)c(=O)n(C)c2c1] |
| 85 | 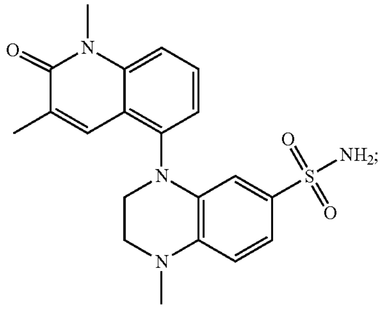 [SMILES: Cc1cc2c(N3CCN(C)c4ccc(S(N)(=O)=O)cc43)cccc2n(C)c1=O] |
-continued
| Example | Structure |
|---|---|
| 86 | 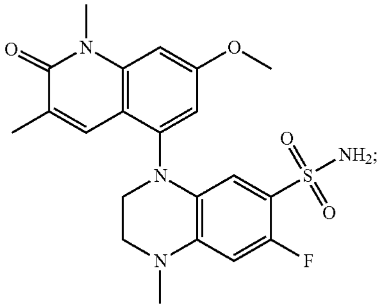 [SMILES: COc1cc(N2CCN(C)c3cc(F)c(S(N)(=O)=O)cc32)c2cc(C)c(=O)n(C)c2c1] |
| 87 | 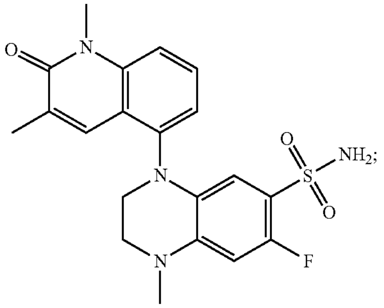 [SMILES: Cc1cc2c(N3CCN(C)c4cc(F)c(S(N)(=O)=O)cc43)cccc2n(C)c1=O] |
| 88 | 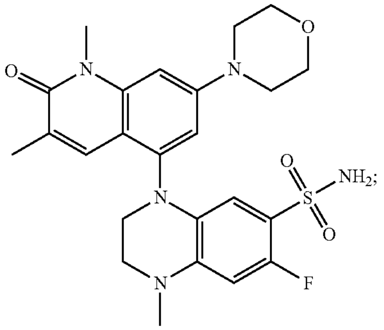 [SMILES: Cc1cc2c(N3CCN(C)c4cc(F)c(S(N)(=O)=O)cc43)cc(N3CCOCC3)cc2n(C)c1=O] |
| 89 | 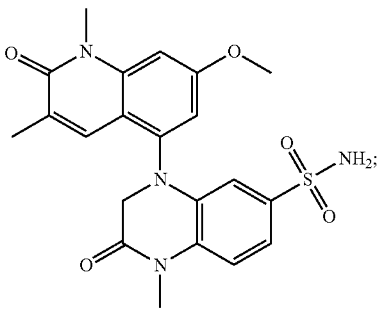 [SMILES: COc1cc(N2CC(=O)N(C)c3ccc(S(N)(=O)=O)cc32)c2cc(C)c(=O)n(C)c2c1] |

-continued
| Example | Structure |
|---|---|
| 90 | 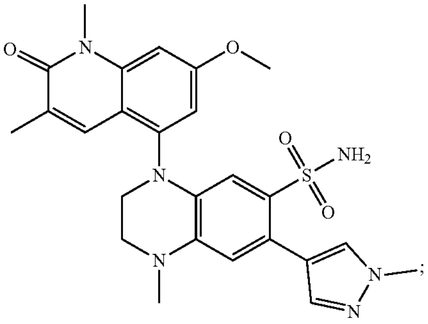 [SMILES: COc1cc(N2CCN(C)c3cc(-c4cnn(C)c4)c(S(N)(=O)=O)cc32)c2cc(C)c(=O)n(C)c2c1] |
| 91 | 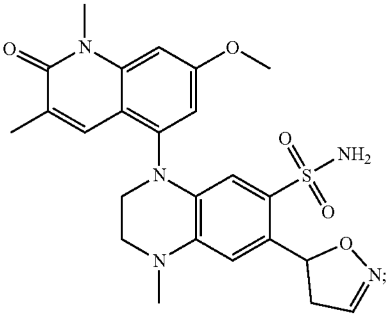 [SMILES: COc1cc(N2CCN(C)c3cc(C4CC=NO4)c(S(N)(=O)=O)cc32)c2cc(C)c(=O)n(C)c2c1] |
| 92 | 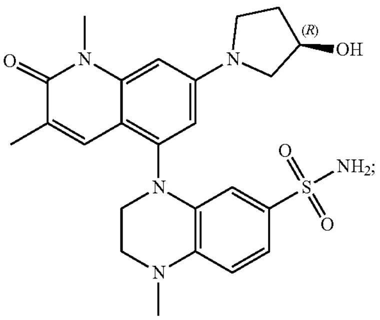 |
| 93 | 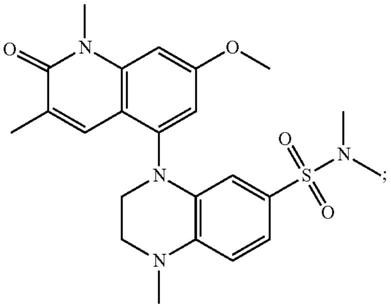 [SMILES: COc1cc(N2CCN(C)c3ccc(S(=O)(=O)N(C)C)cc32)c2cc(C)c(=O)n(C)c2c1] |
| 94 | 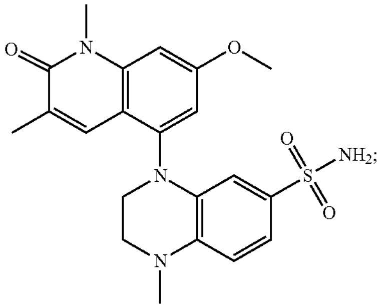 [SMILES: COc1cc(N2CCN(C)c3ccc(S(N)(=O)=O)cc32)c2cc(C)c(=O)n(C)c2c1] |
| 95 | 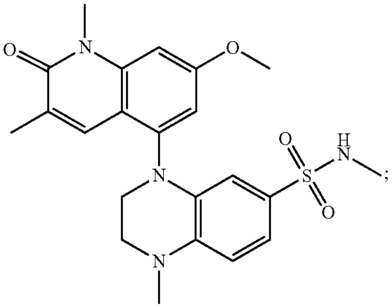 [SMILES: CNS(=O)(=O)c1ccc2c(c1)N(c1cc(OC)cc3c1cc(C)c(=O)n3C)CCN2C] |
| 96 | 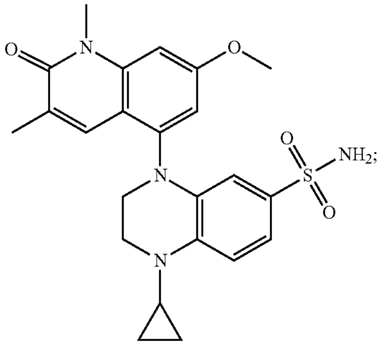 [SMILES: COc1cc(N2CCN(C3CC3)c3ccc(S(N)(=O)=O)cc32)c2cc(C)c(=O)n(C)c2c1] |
| 97 | 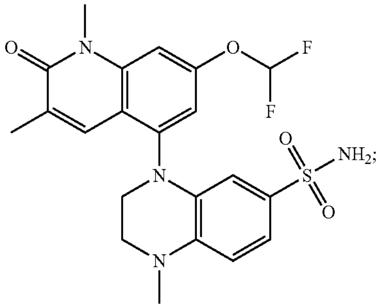 [SMILES: Cc1cc2c(N3CCN(C)c4ccc(S(N)(=O)=O)cc43)cc(OC(F)F)cc2n(C)c1=O] |

-continued
| Example | Structure |
|---|---|
| 98 | 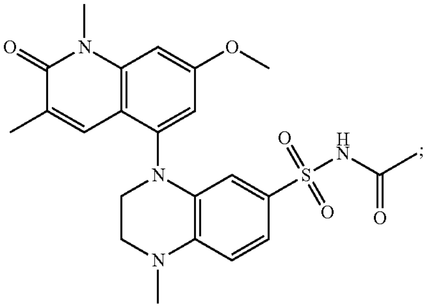 [SMILES: COc1cc(N2CCN(C)c3ccc(S(=O)(=O)NC(C)=O)cc32)c2cc(C)c(=O)n(C)c2c1] |
| 99 | 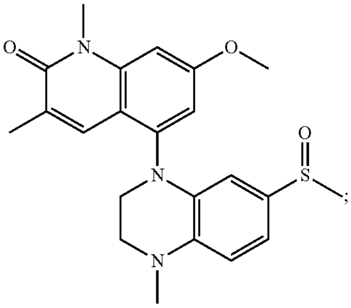 [SMILES: COc1cc(N2CCN(C)c3ccc(S(C)=O)cc32)c2cc(C)c(=O)n(C)c2c1] |
| 100 | 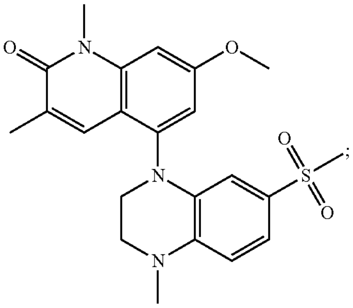 [SMILES: COc1cc(N2CCN(C)c3ccc(S(C)(=O)=O)cc32)c2cc(C)c(=O)n(C)c2c1] |
| 101 | 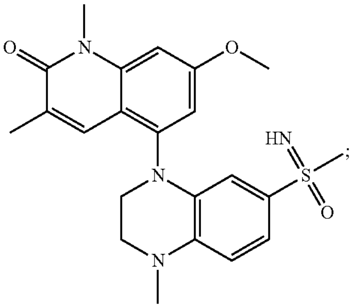 [SMILES: COc1cc(N2CCN(C)c3ccc(S(C)(=N)=O)cc32)c2cc(C)c(=O)n(C)c2c1] |
| 102 | 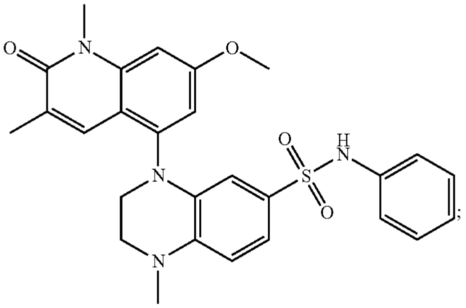 [SMILES: COc1cc(N2CCN(C)c3ccc(S(=O)(=O)Nc4ccccc4)cc32)c2cc(C)c(=O)n(C)c2c1] |
-continued
| Example | Structure |
|---|---|
| 103 | 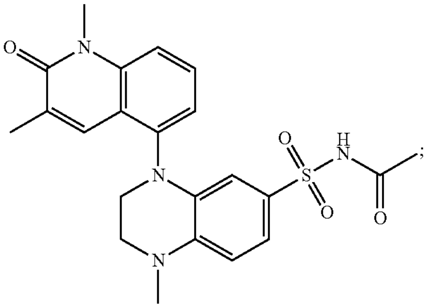 [SMILES: CC(=O)NS(=O)(=O)c1ccc2c(c1)N(c1cccc3c1cc(C)c(=O)n3C)CCN2C] |
| 104 | 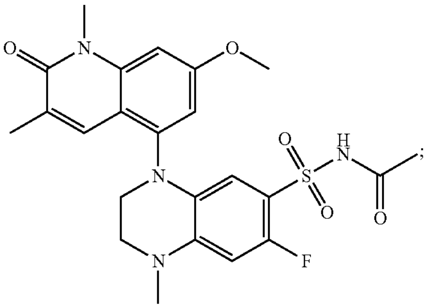 [SMILES: COc1cc(N2CCN(C)c3cc(F)c(S(=O)(=O)NC(C)=O)cc32)c2cc(C)c(=O)n(C)c2c1] |
| 105 | 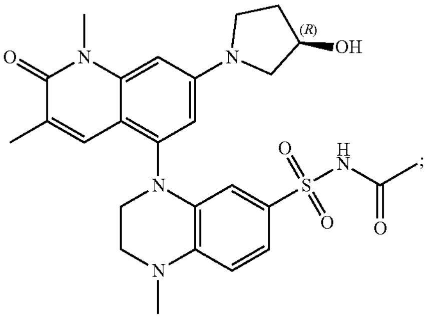 |
| 106 | 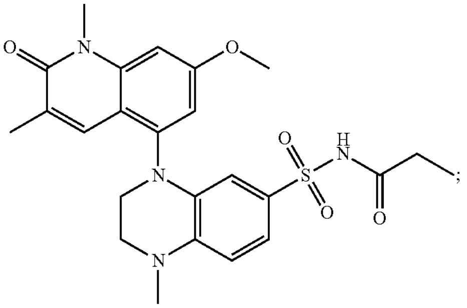 [SMILES: CCC(=O)NS(=O)(=O)c1ccc2c(c1)N(c1cc(OC)cc3c1cc(C)c(=O)n3C)CCN2C] |

-continued
| Example | Structure |
|---|---|
| 107 | 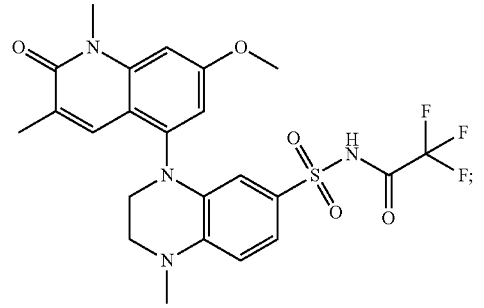 [SMILES: COc1cc(N2CCN(C)c3ccc(S(=O)(=O)NC(=O)C(F)(F)F)cc32)c2cc(C)c(=O)n(C)c2c1] |
| 108 | 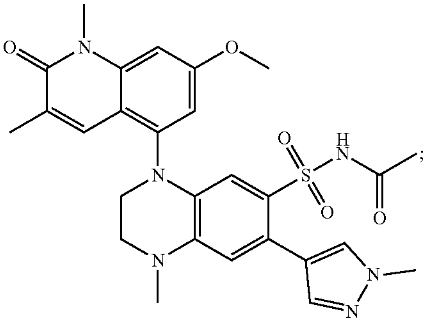 [SMILES: COc1cc(N2CCN(C)c3cc(-c4cnn(C)c4)c(S(=O)(=O)NC(C)=O)cc32)c2cc(C)c(=O)n(C)c2c1] |
| 109 | 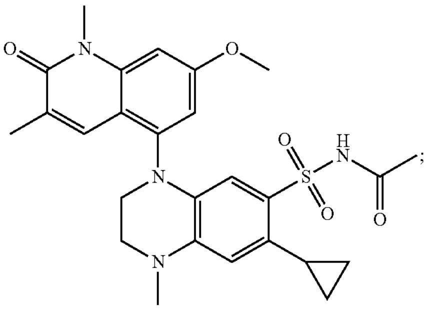 [SMILES: COc1cc(N2CCN(C)c3cc(C4CC4)c(S(=O)(=O)NC(C)=O)cc32)c2cc(C)c(=O)n(C)c2c1] |
| 110 | 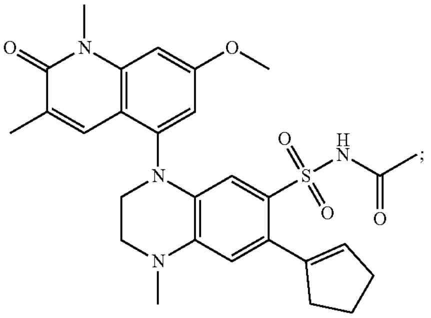 [SMILES: COc1cc(N2CCN(C)c3cc(C4=CCCC4)c(S(=O)(=O)NC(C)=O)cc32)c2cc(C)c(=O)n(C)c2c1] |
-continued
| Example | Structure |
|---|---|
| 111 | 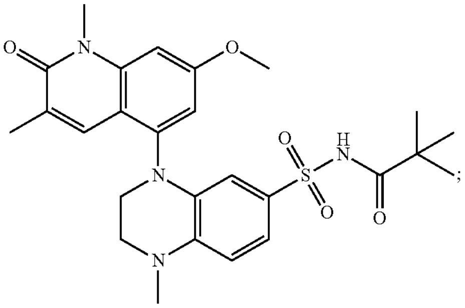 [SMILES: COc1cc(N2CCN(C)c3ccc(S(=O)(=O)NC(=O)C(C)(C)C)cc32)c2cc(C)c(=O)n(C)c2c1] |
| 112 | 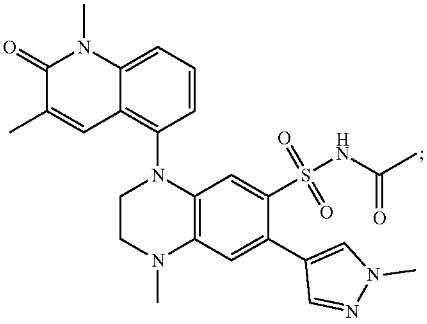 [SMILES: CC(=O)NS(=O)(=O)c1cc2c(cc1-c1cnn(C)c1)N(C)CCN2c1cccc2c1cc(C)c(=O)n2C] |
| 113 | 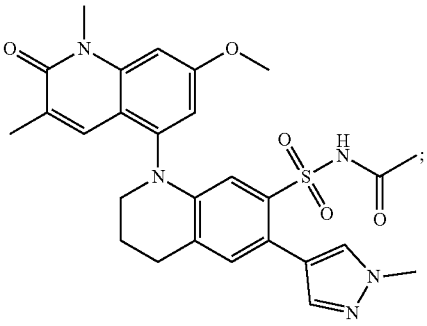 [SMILES: COc1cc(N2CCCc3cc(-c4cnn(C)c4)c(S(=O)(=O)NC(C)=O)cc32)c2cc(C)c(=O)n(C)c2c1] |
| 114 | 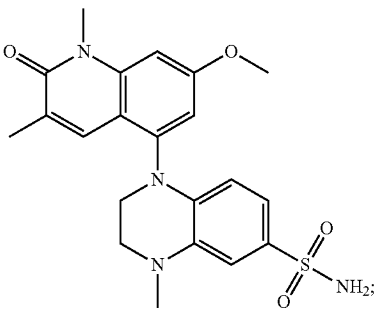 [SMILES: COc1cc(N2CCN(C)c3cc(S(N)(=O)=O)ccc32)c2cc(C)c(=O)n(C)c2c1] |

| Example | Structure |
|---|---|
| 115 | 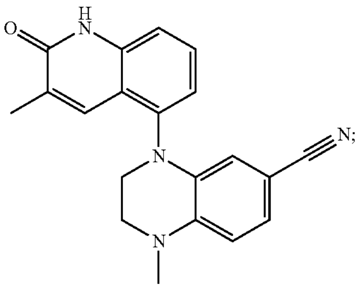 [SMILES: Cc1cc2c(N3CCN(C)c4ccc(C#N)cc43)cccc2[nH]c1=O] |
| 116 | 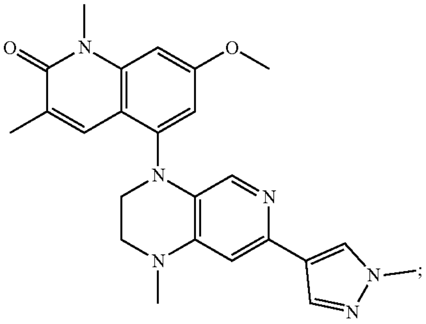 |
| 117 | 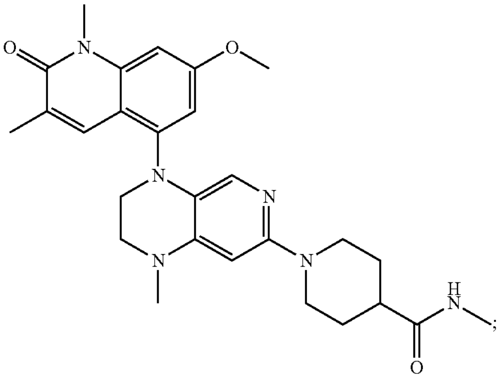 [SMILES: CNC(=O)C1CCN(c2cc3c(cn2)N(c2cc(OC)cc4c2cc(C)c(=O)n4C)CCN3C)CC1] |
| 118 | 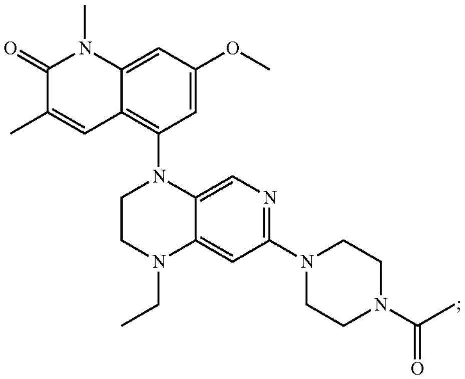 [SMILES: CCN1CCN(c2cc(OC)cc3c2cc(C)c(=O)n3C)c2cnc(N3CCN(C(C)=O)CC3)cc21] |
| Example | Structure |
|---|---|
| 119 | 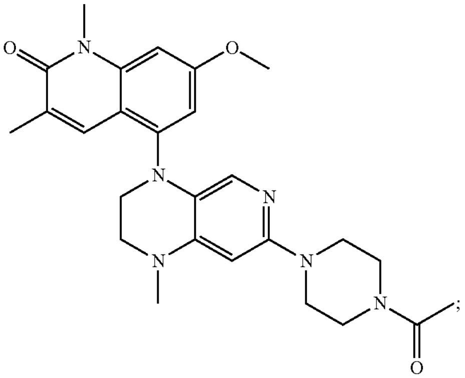 [SMILES: COc1cc(N2CCN(C)c3cc(N4CCN(C(C)=O)CC4)ncc32)c2cc(C)c(=O)n(C)c2c1] |
| 120 | 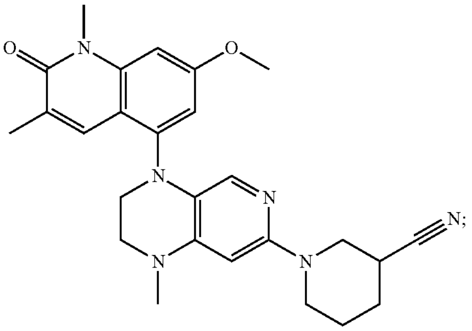 [SMILES: COc1cc(N2CCN(C)c3cc(N4CCCC(C#N)C4)ncc32)c2cc(C)c(=O)n(C)c2c1] |
| 121 | 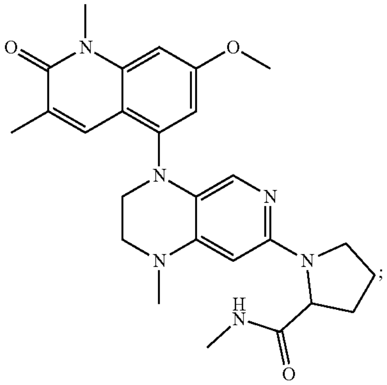 [SMILES: CNC(=O)C1CCCN1c1cc2c(cn1)N(c1cc(OC)cc3c1cc(C)c(=O)n3C)CCN2C] |
| 122 | 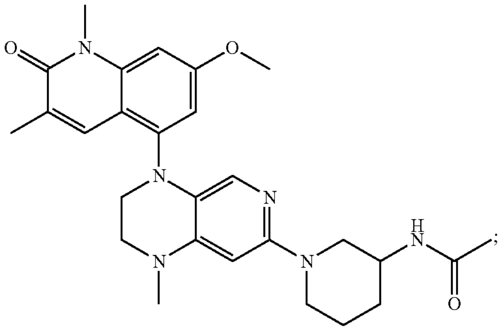 [SMILES: COc1cc(N2CCN(C)c3cc(N4CCCC(NC(C)=O)C4)ncc32)c2cc(C)c(=O)n(C)c2c1] |

-continued
| Example | Structure |
|---|---|
| 123 | 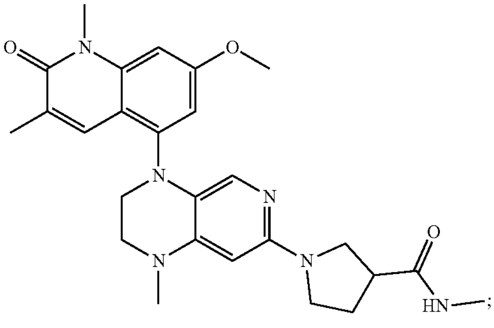 [SMILES: CNC(=O)C1CCN(c2cc3c(cn2)N(c2cc(OC)cc4c2cc(C)c(=O)n4C)CCN3C)C1] |
| 124 | 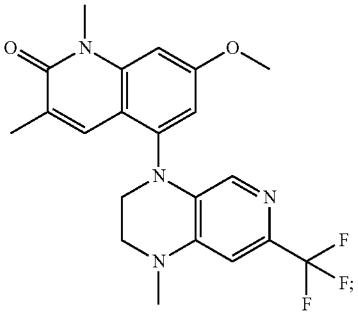 [SMILES: COc1cc(N2CCN(C)c3cc(C(F)(F)F)ncc32)c2cc(C)c(=O)n(C)c2c1] |
| 125 | 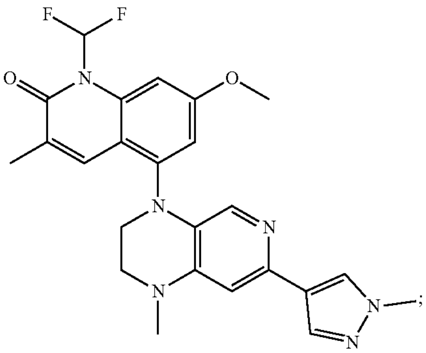 [SMILES: COc1cc(N2CCN(C)c3cc(-c4cnn(C)c4)ncc32)c2cc(C)c(=O)n(C(F)F)c2c1] |
| 126 | 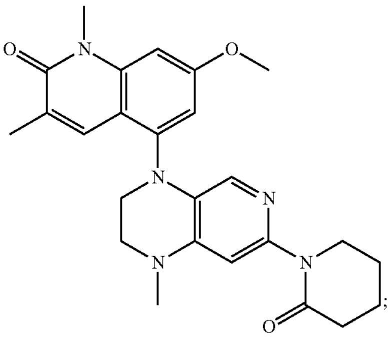 [SMILES: COc1cc(N2CCN(C)c3cc(N4CCCCC4=O)ncc32)c2cc(C)c(=O)n(C)c2c1] |
| 127 | 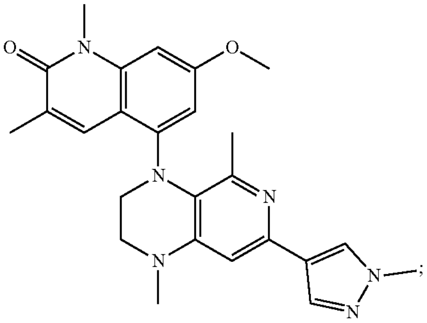 [SMILES: COc1cc(N2CCN(C)c3cc(-c4cnn(C)c4)nc(C)c32)c2cc(C)c(=O)n(C)c2c1] |
| 128 | 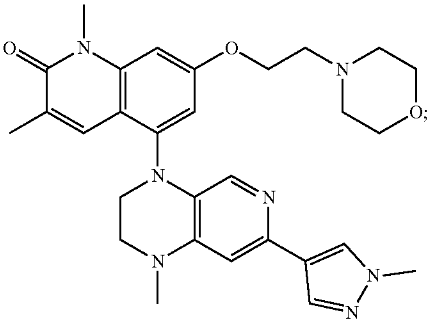 [SMILES: Cc1cc2c(N3CCN(C)c4cc(-c5cnn(C)c5)ncc43)cc(OCCN3CCOCC3)cc2n(C)c1=O] |
| 129 | 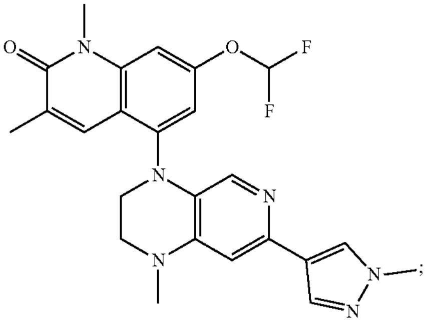 [SMILES: Cc1cc2c(N3CCN(C)c4cc(-c5cnn(C)c5)ncc43)cc(OC(F)F)cc2n(C)c1=O] |
| 130 | 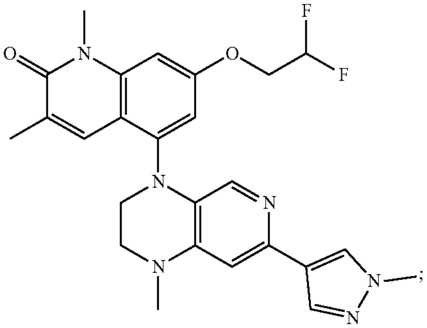 [SMILES: Cc1cc2c(N3CCN(C)c4cc(-c5cnn(C)c5)ncc43)cc(OCC(F)F)cc2n(C)c1=O] |

| Example | Structure |
|---|---|
| 131 | 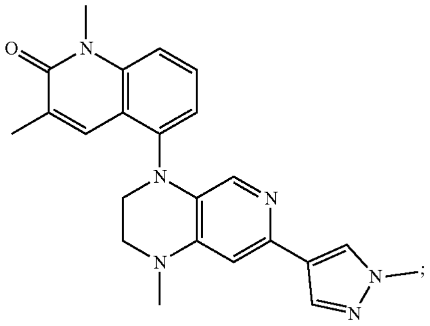 [SMILES: Cc1cc2c(N3CCN(C)c4cc(-c5cnn(C)c5)ncc43)cccc2n(C)c1=O] |
| 132 | 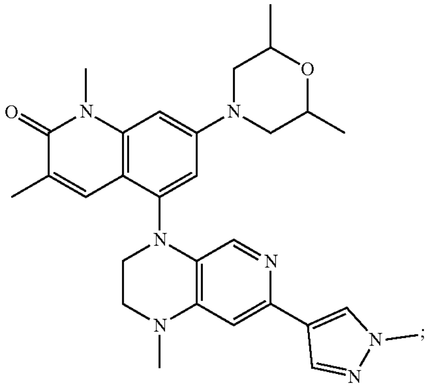 [SMILES: Cc1cc2c(N3CCN(C)c4cc(-c5cnn(C)c5)ncc43)cc(N3CC(C)OC(C)C3)cc2n(C)c1=O] |
| 133 | 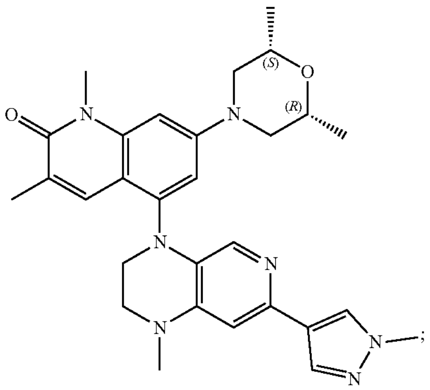 |
| 134 | 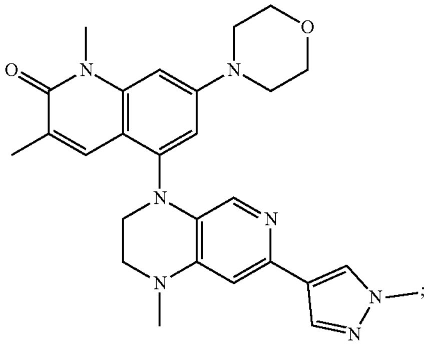 [SMILES: Cc1cc2c(N3CCN(C)c4cc(-c5cnn(C)c5)ncc43)cc(N3CCOCC3)cc2n(C)c1=O] |
| Example | Structure |
|---|---|
| 135 | 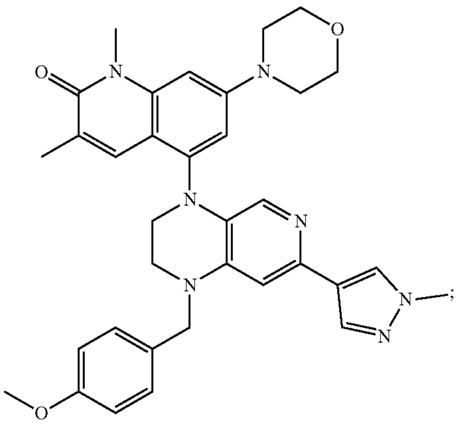 |
| 136 | 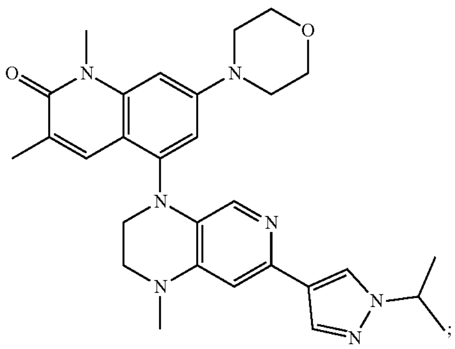 [SMILES: Cc1cc2c(N3CCN(C)c4cc(-c5cnn(C(C)C)c5)ncc43)cc(N3CCOCC3)cc2n(C)c1=O] |
| 137 | 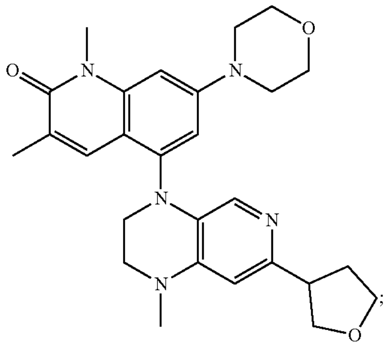 [SMILES: Cc1cc2c(N3CCN(C)c4cc(C5CCOC5)ncc43)cc(N3CCOCC3)cc2n(C)c1=O] |
| 138 | 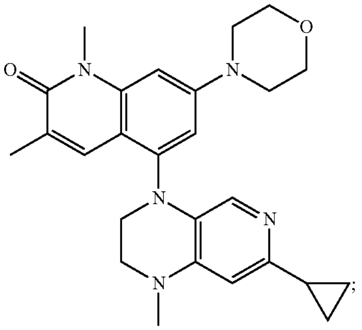 [SMILES: Cc1cc2c(N3CCN(C)c4cc(C5CC5)ncc43)cc(N3CCOCC3)cc2n(C)c1=O] |

-continued
| Example | Structure |
|---|---|
| 139 | 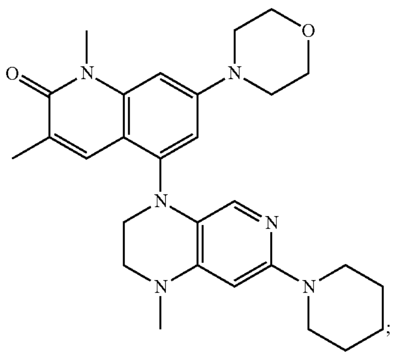 [SMILES: Cc1cc2c(N3CCN(C)c4cc(N5CCCCC5)ncc43)cc(N3CCOCC3)cc2n(C)c1=O] |
| 140 | 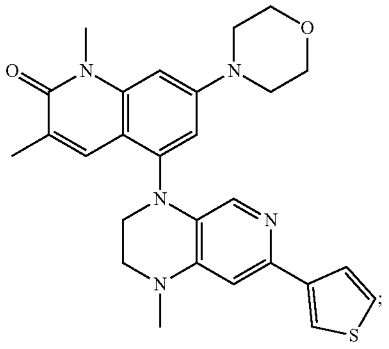 [SMILES: Cc1cc2c(N3CCN(C)c4cc(-c5ccsc5)ncc43)cc(N3CCOCC3)cc2n(C)c1=O] |
| 141 | 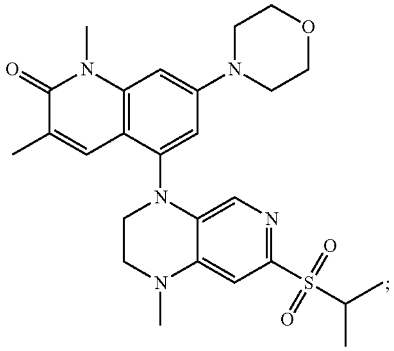 [SMILES: Cc1cc2c(N3CCN(C)c4cc(S(=O)(=O)C(C)C)ncc43)cc(N3CCOCC3)cc2n(C)c1=O] |
| 142 | 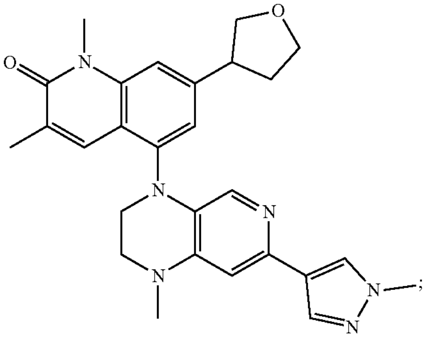 [SMILES: Cc1cc2c(N3CCN(C)c4cc(-c5cnn(C)c5)ncc43)cc(C3CCOC3)cc2n(C)c1=O] |
-continued
| Example | Structure |
|---|---|
| 143 | 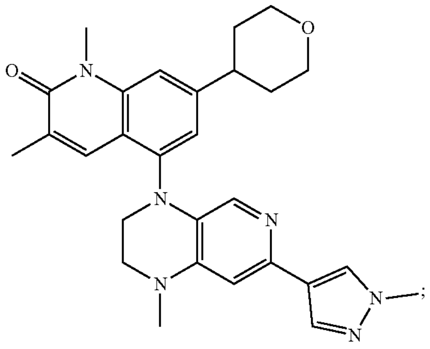 [SMILES: Cc1cc2c(N3CCN(C)c4cc(-c5cnn(C)c5)ncc43)cc(C3CCOCC3)cc2n(C)c1=O] |
| 144 | 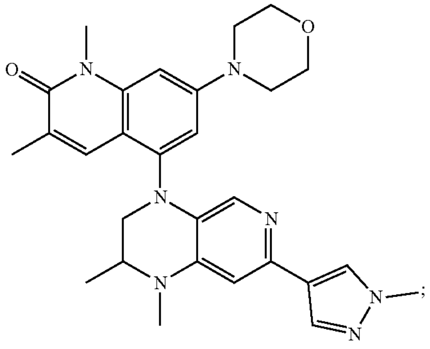 [SMILES: Cc1cc2c(N3CC(C)N(C)c4cc(-c5cnn(C)c5)ncc43)cc(N3CCOCC3)cc2n(C)c1=O] |
| 145 | 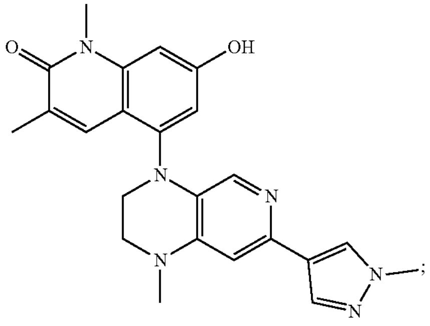 [SMILES: Cc1cc2c(N3CCN(C)c4cc(-c5cnn(C)c5)ncc43)cc(O)cc2n(C)c1=O] |
| 146 | 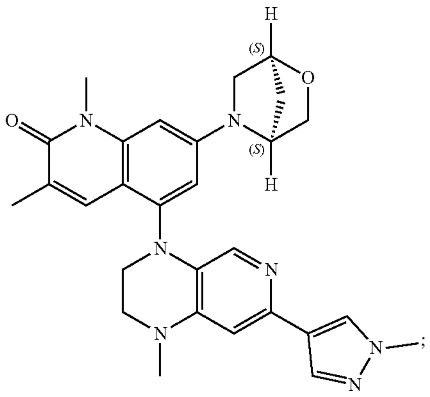 |

-continued
| Ex-am-ple | Structure |
|---|---|
| 147 | 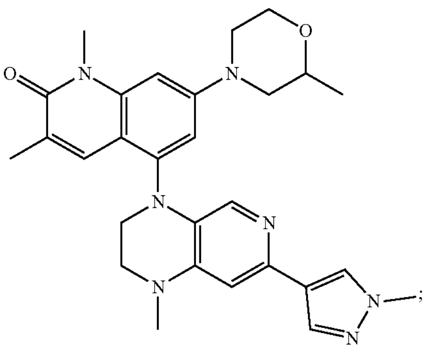 [SMILES: Cc1cc2c(N3CCN(C)c4cc(-c5cnn(C)c5)ncc43)cc(N3CCOC(C)C3)cc2n(C)c1=O] |
| 148 | 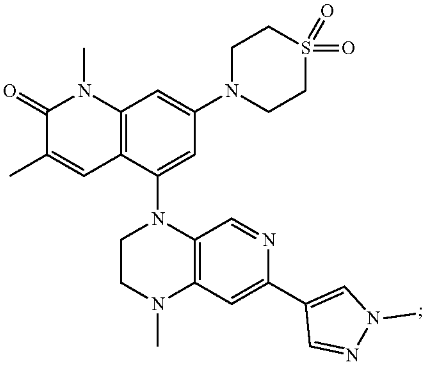 [SMILES: Cc1cc2c(N3CCN(C)c4cc(-c5cnn(C)c5)ncc43)cc(N3CCS(=O)(=O)CC3)cc2n(C)c1=O] |
| 149 | 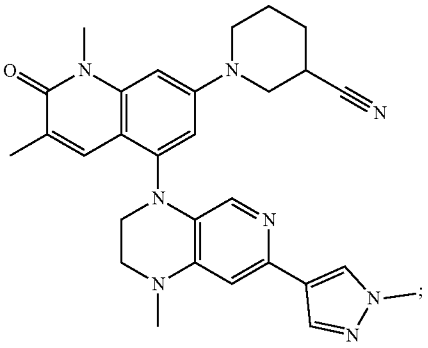 [SMILES: Cc1cc2c(N3CCN(C)c4cc(-c5cnn(C)c5)ncc43)cc(N3CCCC(C#N)C3)cc2n(C)c1=O] |
| 150 | 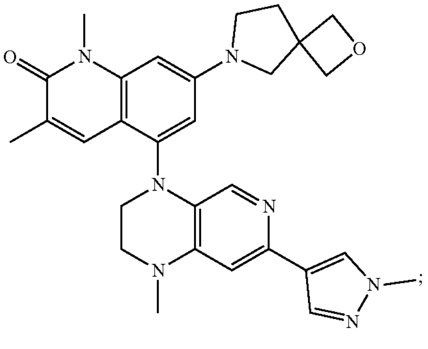 [SMILES: Cc1cc2c(N3CCN(C)c4cc(-c5cnn(C)c5)ncc43)cc(N3CCC4(COC4)C3)cc2n(C)c1=O] |
-continued
| Ex-am-ple | Structure |
|---|---|
| 151 | 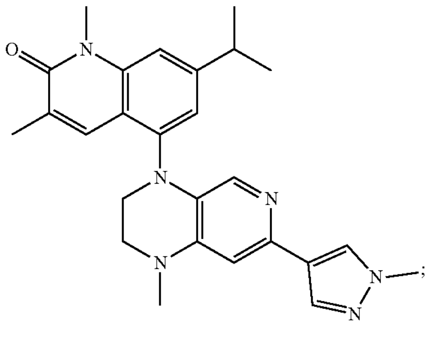 [SMILES: Cc1cc2c(N3CCN(C)c4cc(-c5cnn(C)c5)ncc43)cc(C(C)C)cc2n(C)c1=O] |
| 152 | 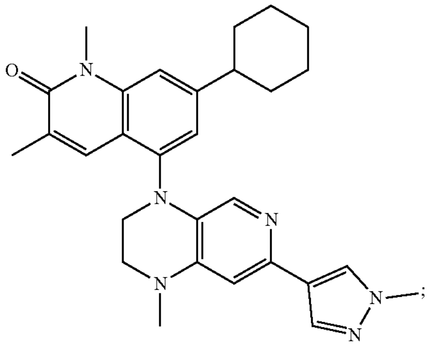 [SMILES: Cc1cc2c(N3CCN(C)c4cc(-c5cnn(C)c5)ncc43)cc(C3CCCCC3)cc2n(C)c1=O] |
| 153 | 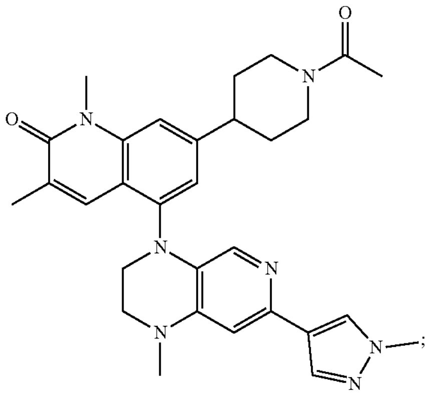 [SMILES: CC(=O)N1CCC(c2cc(N3CCN(C)c4cc(-c5cnn(C)c5)ncc43)c3cc(C)c(=O)n(C)c3c2)CC1] |
| 154 | 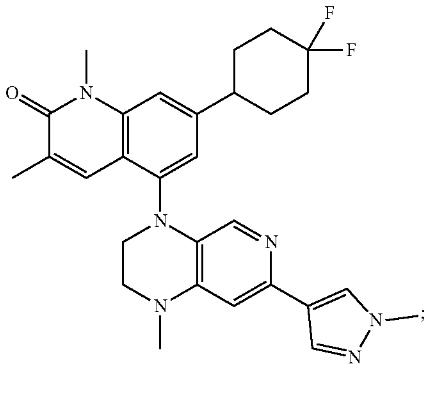 [SMILES: Cc1cc2c(N3CCN(C)c4cc(-c5cnn(C)c5)ncc43)cc(C3CCC(F)(F)CC3)cc2n(C)c1=O] |

-continued
| Example | Structure |
|---|---|
| 155 | 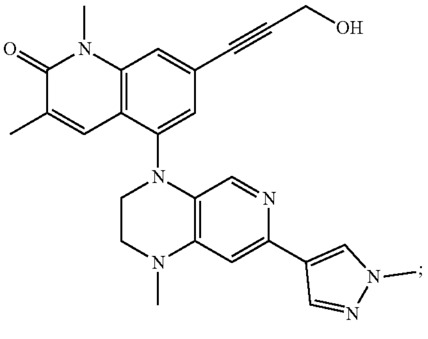 [SMILES: Cc1cc2c(N3CCN(C)c4cc(-c5cnn(C)c5)ncc43)cc(C#CCO)cc2n(C)c1=O] |
| 156 | 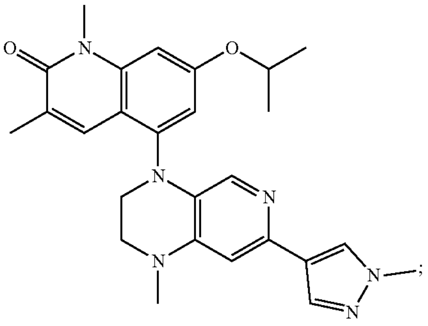 [SMILES: Cc1cc2c(N3CCN(C)c4cc(-c5cnn(C)c5)ncc43)cc(OC(C)C)cc2n(C)c1=O] |
| 157 | 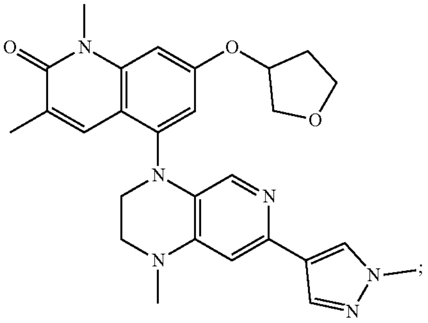 [SMILES: Cc1cc2c(N3CCN(C)c4cc(-c5cnn(C)c5)ncc43)cc(OC3CCOC3)cc2n(C)c1=O] |
| 158 | 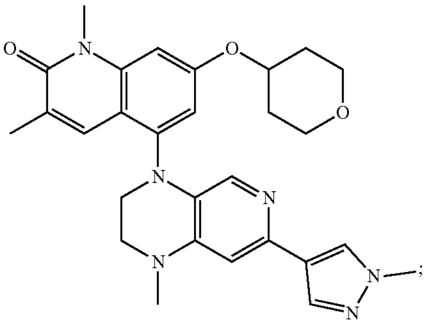 [SMILES: Cc1cc2c(N3CCN(C)c4cc(-c5cnn(C)c5)ncc43)cc(OC3CCOCC3)cc2n(C)c1=O] |
-continued
| Example | Structure |
|---|---|
| 159 | 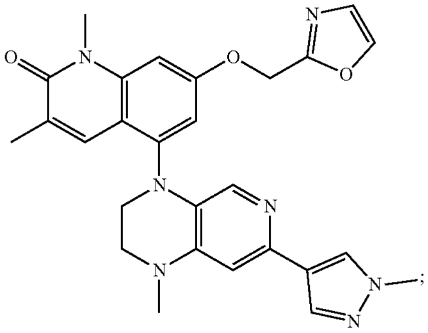 [SMILES: Cc1cc2c(N3CCN(C)c4cc(-c5cnn(C)c5)ncc43)cc(OCc3ncco3)cc2n(C)c1=O] |
| 160 | 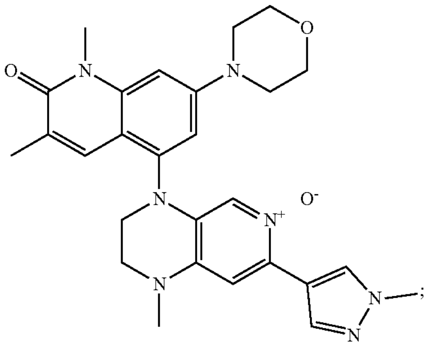 |
| 161 | 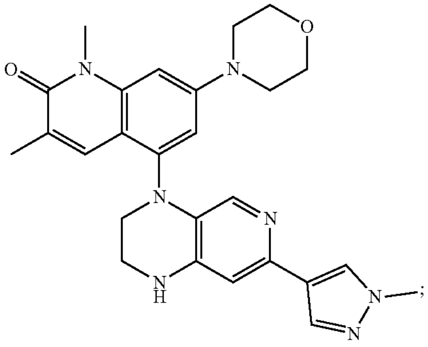 [SMILES: Cc1cc2c(N3CCNc4cc(-c5cnn(C)c5)ncc43)cc(N3CCOCC3)cc2n(C)c1=O] |
| 162 | 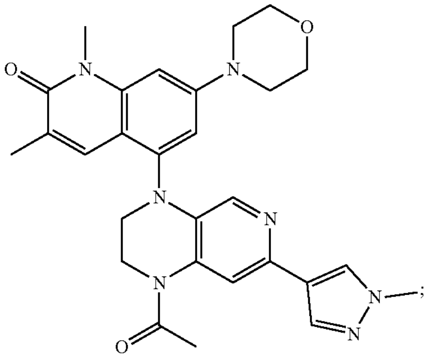 [SMILES: CC(=O)N1CCN(c2cc(N3CCOCC3)cc3c2cc(C)c(=O)n3C)c2cnc(-c3cnn(C)c3)cc21] |

-continued
| Example | Structure |
|---|---|
| 163 | 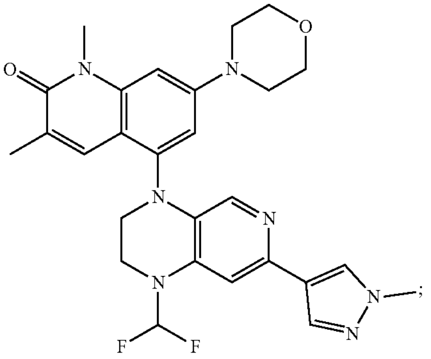 [SMILES: Cc1cc2c(N3CCN(C(F)F)c4cc(-c5cnn(C)c5)ncc43)cc(N3CCOCC3)cc2n(C)c1=O] |
| 164 | 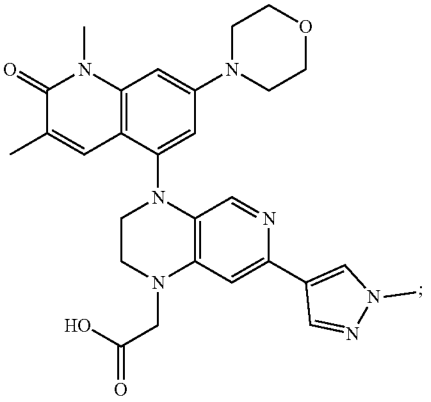 [SMILES: Cc1cc2c(N3CCN(CC(=O)O)c4cc(-c5cnn(C)c5)ncc43)cc(N3CCOCC3)cc2n(C)c1=O] |
| 165 | 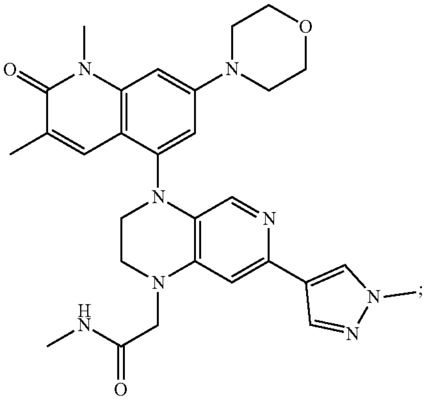 [SMILES: CNC(=O)CN1CCN(c2cc(N3CCOCC3)cc3c2cc(C)c(=O)n3C)c2cnc(-c3cnn(C)c3)cc21] |
| 166 | 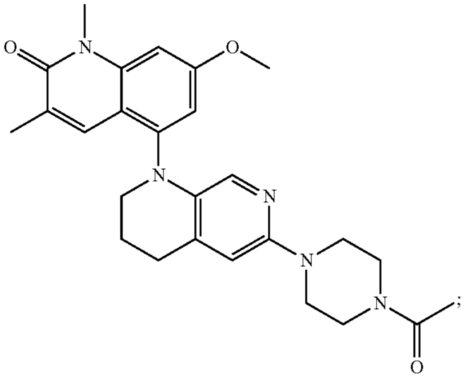 [SMILES: COc1cc(N2CCCc3cc(N4CCN(C(C)=O)CC4)ncc32)c2cc(C)c(=O)n(C)c2c1] |
-continued
| Example | Structure |
|---|---|
| 167 | 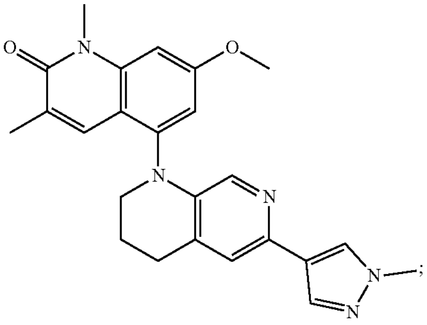 [SMILES: COc1cc(N2CCCc3cc(-c4cnn(C)c4)ncc32)c2cc(C)c(=O)n(C)c2c1] |
| 168 | 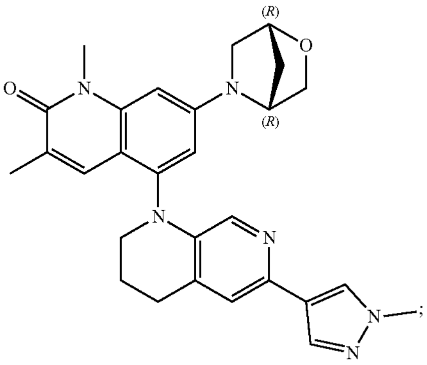 |
| 169 | 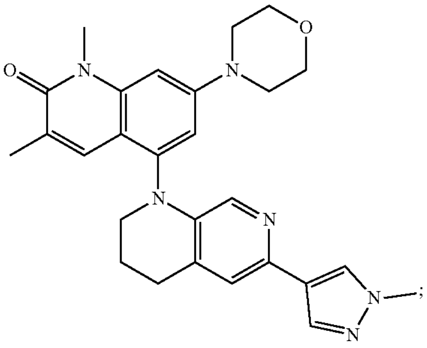 [SMILES: Cc1cc2c(N3CCCc4cc(-c5cnn(C)c5)ncc43)cc(N3CCOCC3)cc2n(C)c1=O] |
| 170 | 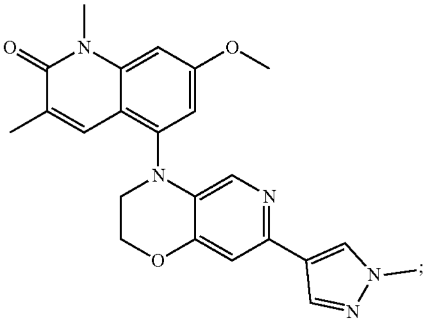 [SMILES: COc1cc(N2CCOc3cc(-c4cnn(C)c4)ncc32)c2cc(C)c(=O)n(C)c2c1] |

-continued
| Example | Structure |
|---|---|
| 171 | 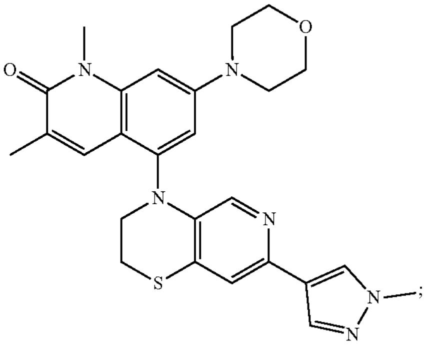 [SMILES: Cc1cc2c(N3CCSc4cc(-c5cnn(C)c5)ncc43)cc(N3CCOCC3)cc2n(C)c1=O] |
| 172 | 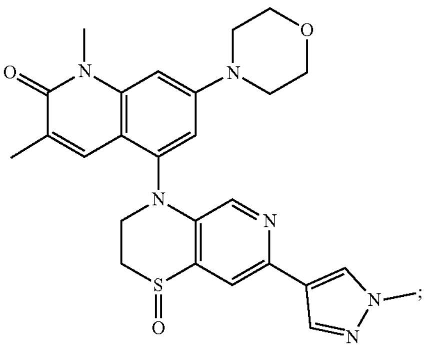 [SMILES: Cc1cc2c(N3CCS(=O)c4cc(-c5cnn(C)c5)ncc43)cc(N3CCOCC3)cc2n(C)c1=O] |
| 173 | 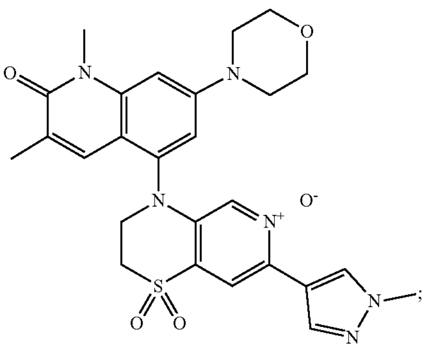 |
| 174 | 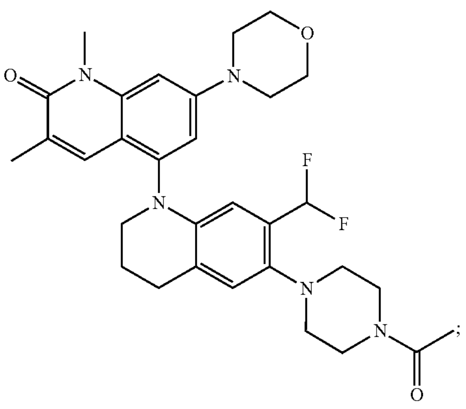 [SMILES: CC(=O)N1CCN(c2cc3c(cc2C(F)F)N(c2cc(N4CCOCC4)cc4c2cc(C)c(=O)n4C)CCC3)CC1] |
-continued
| Example | Structure |
|---|---|
| 175 | 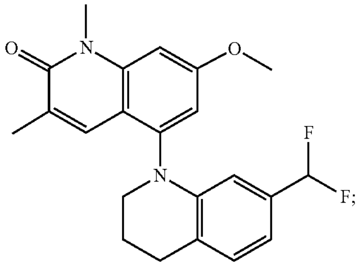 [SMILES: COc1cc(N2CCCc3ccc(C(F)F)cc32)c2cc(C)c(=O)n(C)c2c1] |
| 176 | 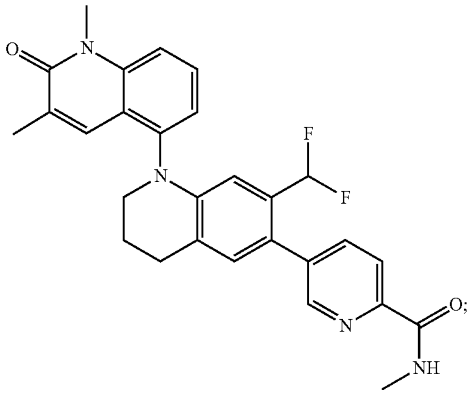 [SMILES: CNC(=O)c1ccc(-c2cc3c(cc2C(F)F)N(c2cccc4c2cc(C)c(=O)n4C)CCC3)cn1] |
| 177 | 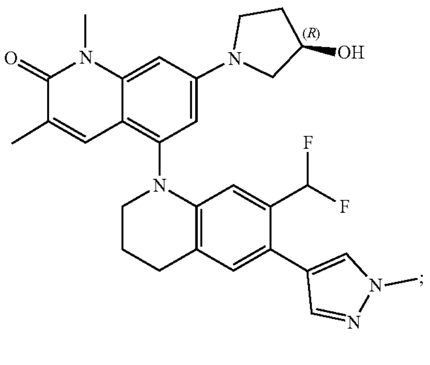 |
| 178 | 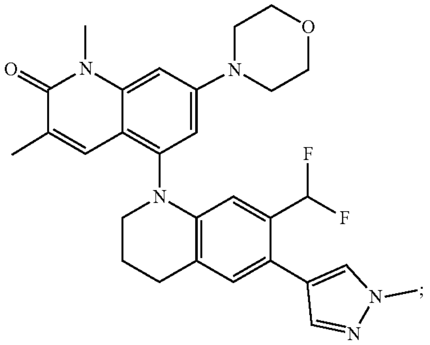 [SMILES: Cc1cc2c(N3CCCc4cc(-c5cnn(C)c5)c(C(F)F)cc43)cc(N3CCOCC3)cc2n(C)c1=O] |

-continued
| Example | Structure |
|---|---|
| 179 | 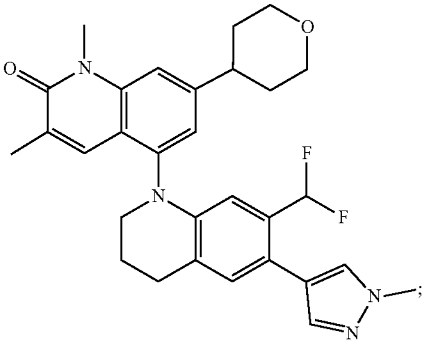 [SMILES: Cc1cc2c(N3CCCc4cc(-c5cnn(C)c5)c(C(F)F)cc43)cc(C3CCOCC3)cc2n(C)c1=O] |
| 180 | 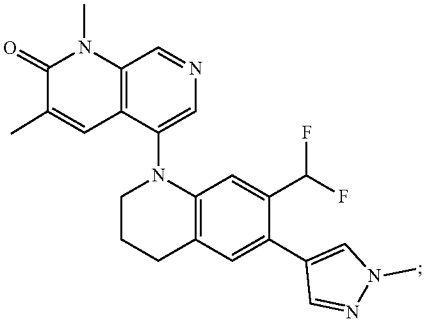 [SMILES: Cc1cc2c(N3CCCc4cc(-c5cnn(C)c5)c(C(F)F)cc43)cncc2n(C)c1=O] |
| 181 | 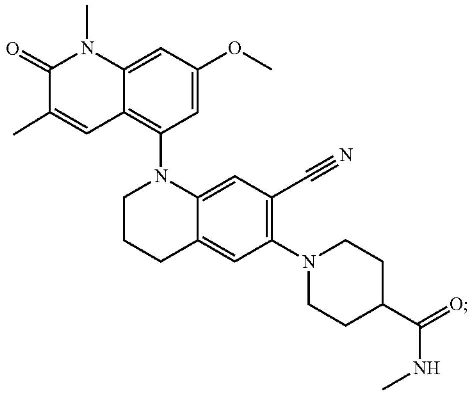 [SMILES: CNC(=O)C1CCN(c2cc3c(cc2C#N)N(c2cc(OC)cc4c2cc(C)c(=O)n4C)CCC3)CC1] |
| 182 | 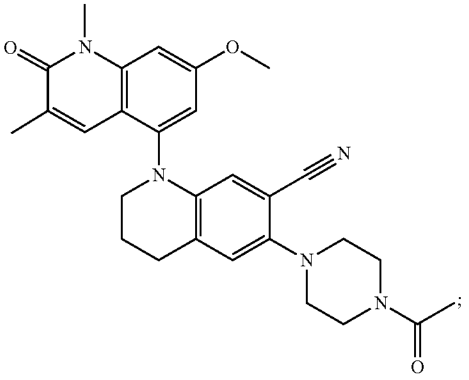 [SMILES: COc1cc(N2CCCc3cc(N4CCN(C(C)=O)CC4)c(C#N)cc32)c2cc(C)c(=O)n(C)c2c1] |
-continued
| Example | Structure |
|---|---|
| 183 | 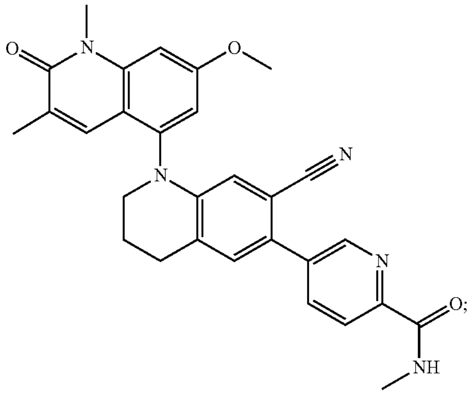 [SMILES: CNC(=O)c1ccc(-c2cc3c(cc2C#N)N(c2cc(OC)cc4c2cc(C)c(=O)n4C)CCC3)cn1] |
| 184 | 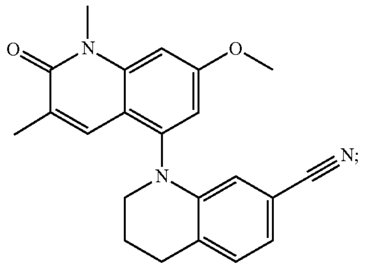 [SMILES: COc1cc(N2CCCc3ccc(C#N)cc32)c2cc(C)c(=O)n(C)c2c1] |
| 185 | 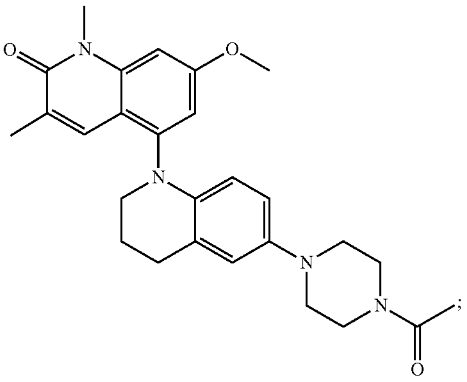 [SMILES: COc1cc(N2CCCc3cc(N4CCN(C(C)=O)CC4)ccc32)c2cc(C)c(=O)n(C)c2c1] |
| 186 | 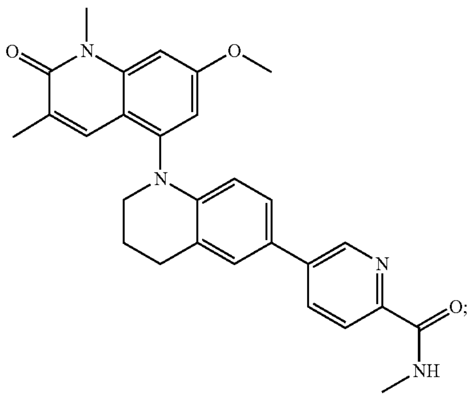 [SMILES: CNC(=O)c1ccc(-c2ccc3c(c2)CCCN3c2cc(OC)cc3c2cc(C)c(=O)n3C)cn1] |

-continued
| Example | Structure |
| --- | --- |
| 187 | 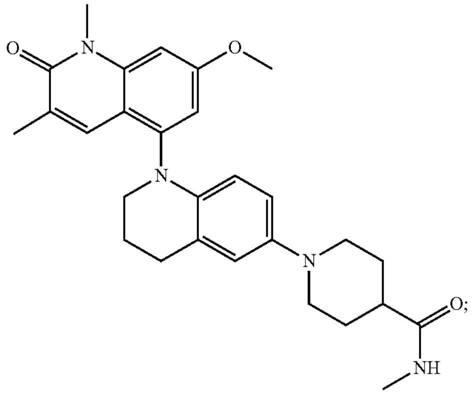 [SMILES: CNC(=O)C1CCN(c2ccc3c(c2)CCCN3c2cc(OC)cc3c2cc(C)c(=O)n3C)CC1] |
| 188 | 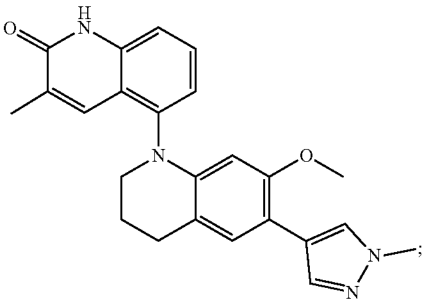 [SMILES: COc1cc2c(cc1-c1cnn(C)c1)CCCN2c1cccc2[nH]c(=O)c(C)cc12] |
| 189 | 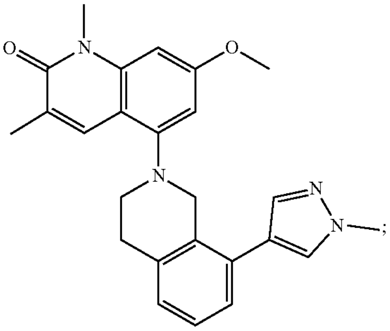 [SMILES: COc1cc(N2CCc3cccc(-c4cnn(C)c4)c3C2)c2cc(C)c(=O)n(C)c2c1] |
| 190 | 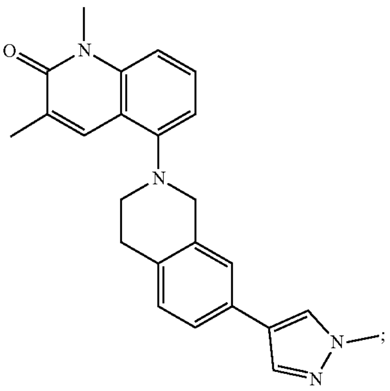 [SMILES: Cc1cc2c(N3CCc4ccc(-c5cnn(C)c5)cc4C3)cccc2n(C)c1=O] |
| 191 | 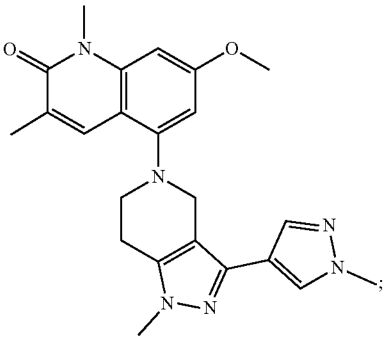 [SMILES: COc1cc(N2CCc3c(c(-c4cnn(C)c4)nn3C)C2)c2cc(C)c(=O)n(C)c2c1] |
| 192 | 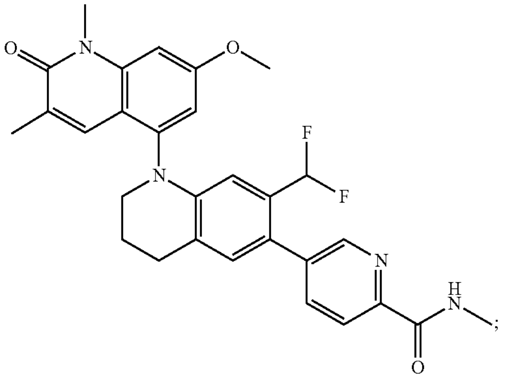 [SMILES: CNC(=O)c1ccc(-c2cc3c(cc2C(F)F)N(c2cc(OC)cc4c2cc(C)c(=O)n4C)CCC3)cn1] |
| 194 | 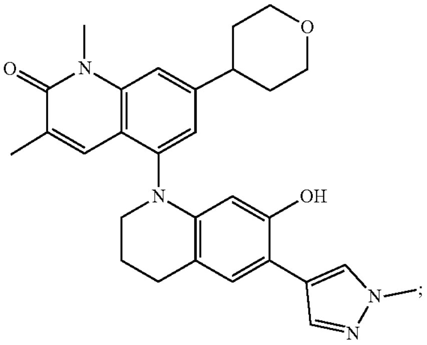 [SMILES: Cc1cc2c(N3CCCc4cc(-c5cnn(C)c5)c(O)cc43)cc(C3CCOCC3)cc2n(C)c1=O] |
| 195 | 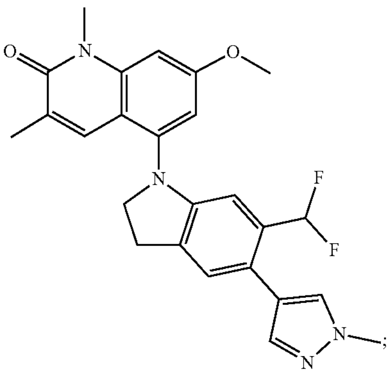 [SMILES: COc1cc(N2CCc3cc(-c4cnn(C)c4)c(C(F)F)cc32)c2cc(C)c(=O)n(C)c2c1] |

-continued
| Example | Structure |
|---|---|
| 196 | 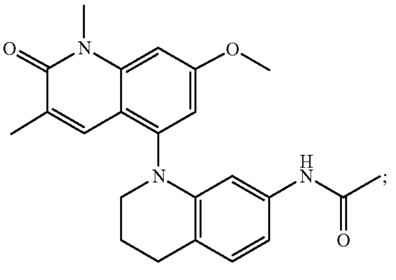 [SMILES: COc1cc(N2CCCc3ccc(NC(C)=O)cc32)c2cc(C)c(=O)n(C)c2c1] |
| 197 | 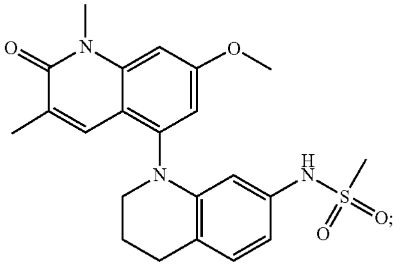 [SMILES: COc1cc(N2CCCc3ccc(NS(C)(=O)=O)cc32)c2cc(C)c(=O)n(C)c2c1] |
| 198 | 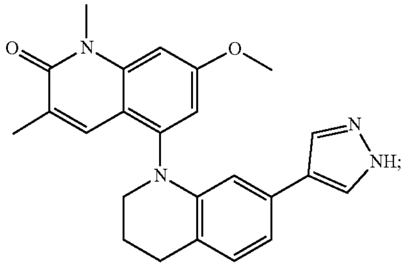 [SMILES: COc1cc(N2CCCc3ccc(-c4cn[nH]c4)cc32)c2cc(C)c(=O)n(C)c2c1] |
| 199 | 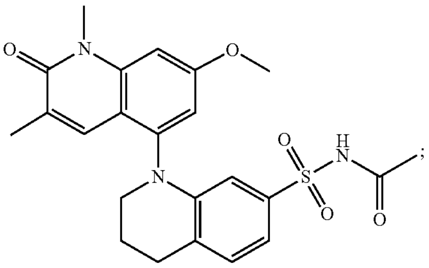 [SMILES: COc1cc(N2CCCc3ccc(S(=O)(=O)NC(C)=O)cc32)c2cc(C)c(=O)n(C)c2c1] |
| 200 | 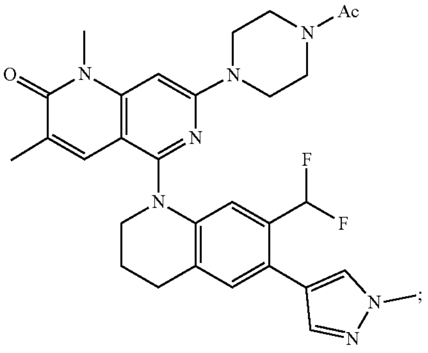 [SMILES: CC(=O)N1CCN(c2cc3c(cc(C)c(=O)n3C)c(N3CCCc4cc(-c5cnn(C)c5)c(C(F)F)cc43)n2)CC1] |
-continued
| Example | Structure |
|---|---|
| 201 | 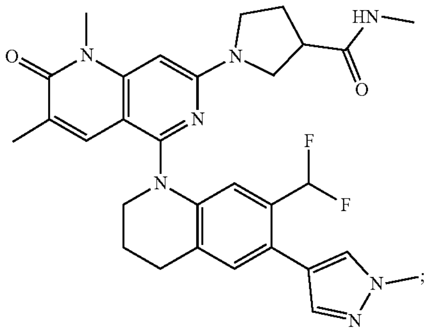 [SMILES: CNC(=O)C1CCN(c2cc3c(cc(C)c(=O)n3C)c(N3CCCc4cc(-c5cnn(C)c5)c(C(F)F)cc43)n2)C1] |
| 202 | 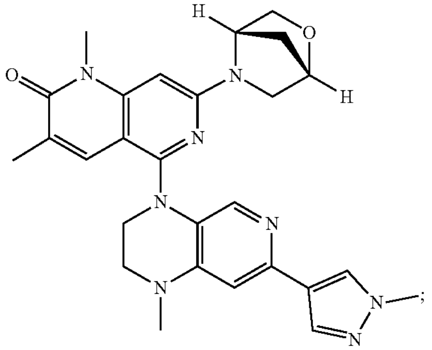 [SMILES: Cc1cc2c(N3CCN(C)c4cc(-c5cnn(C)c5)ncc43)nc(N3C[C@@H]4C[C@H]3CO4)cc2n(C)c1=O] |
| 203 | 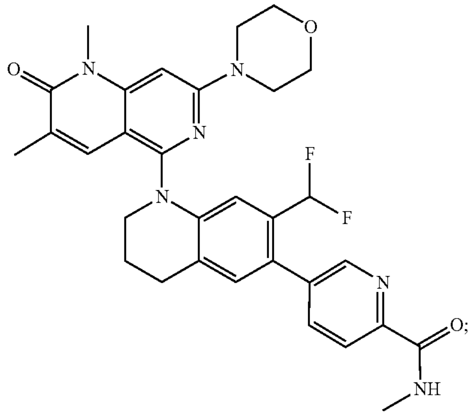 [SMILES: CNC(=O)c1ccc(-c2cc3c(cc2C(F)F)N(c2nc(N4CCOCC4)cc4c2cc(C)c(=O)n4C)CCC3)cn1] |
| 204 | 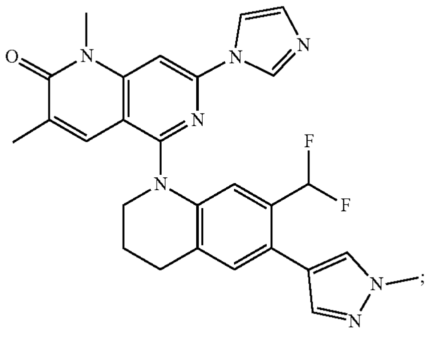 [SMILES: Cc1cc2c(N3CCCc4cc(-c5cnn(C)c5)c(C(F)F)cc43)nc(-n3ccnc3)cc2n(C)c1=O] |

-continued
| Example | Structure |
| --- | --- |
| 205 | 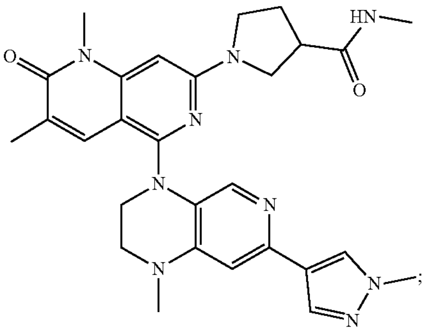 [SMILES: CNC(=O)C1CCN(c2cc3c(cc(C)c(=O)n3C)c(N3CCN(C)c4cc(-c5cnn(C)c5)ncc43)n2)C1] |
| 206 | 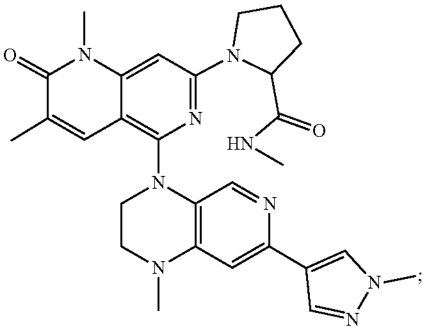 [SMILES: CNC(=O)C1CCCN1c1cc2c(cc(C)c(=O)n2C)c(N2CCN(C)c3cc(-c4cnn(C)c4)ncc32)n1] |
| 207 | 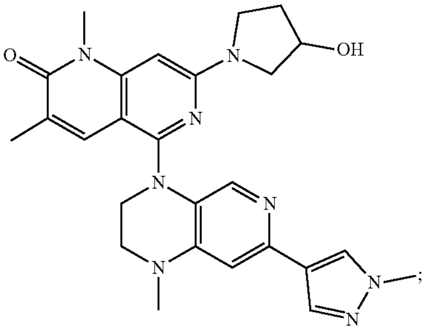 [SMILES: Cc1cc2c(N3CCN(C)c4cc(-c5cnn(C)c5)ncc43)nc(N3CCC(O)C3)cc2n(C)c1=O] |
| 208 | 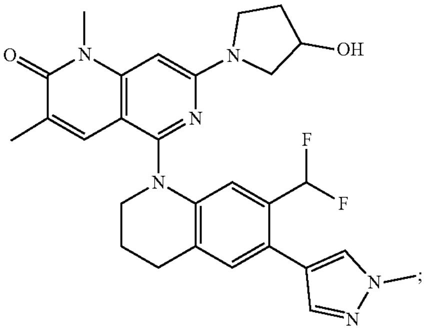 [SMILES: Cc1cc2c(N3CCCc4cc(-c5cnn(C)c5)c(C(F)F)cc43)nc(N3CCC(O)C3)cc2n(C)c1=O] |
| 209 | 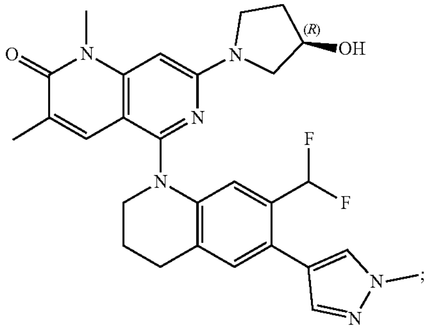 |
| 210 | 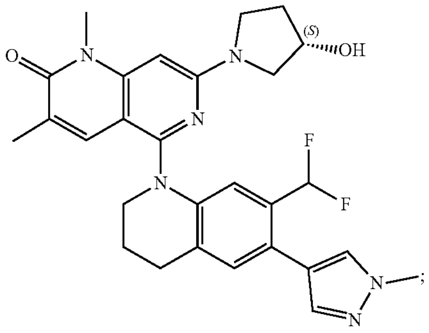 |
| 211 | 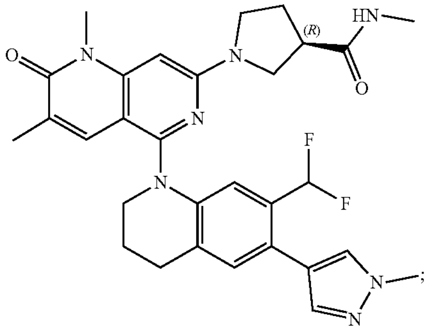 |
| 212 | 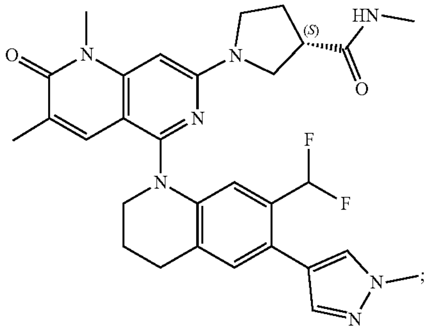 |

-continued
| Example | Structure |
| --- | --- |
| 213 | 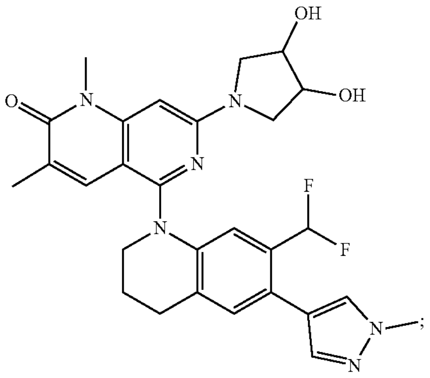 [SMILES: Cc1cc2c(N3CCCc4cc(-c5cnn(C)c5)c(C(F)F)cc43)nc(N3CC(O)C(O)C3)cc2n(C)c1=O] |
| 214 | 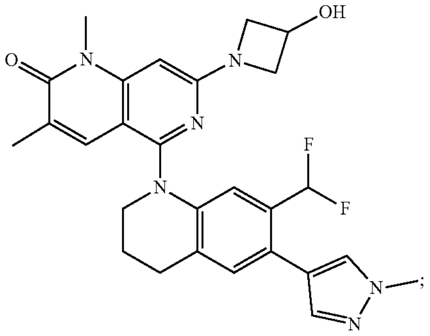 [SMILES: Cc1cc2c(N3CCCc4cc(-c5cnn(C)c5)c(C(F)F)cc43)nc(N3CC(O)C3)cc2n(C)c1=O] |
| 215 | 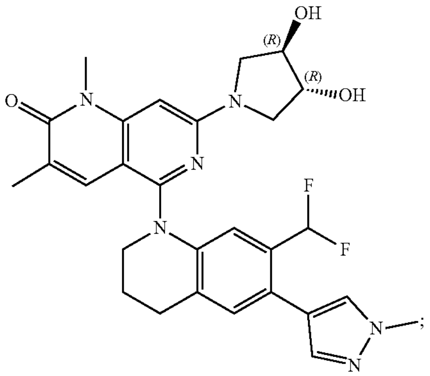 |
| 216 | 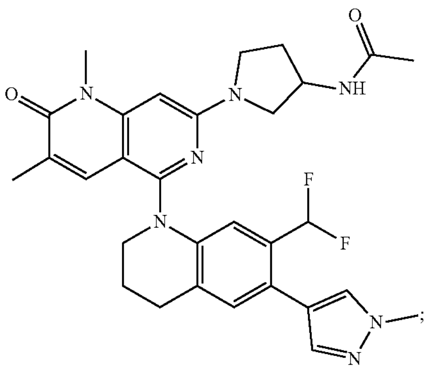 [SMILES: CC(=O)NC1CCN(c2cc3c(cc(C)c(=O)n3C)c(N3CCCc4cc(-c5cnn(C)c5)c(C(F)F)cc43)n2)C1] |
-continued
| Example | Structure |
| --- | --- |
| 217 | 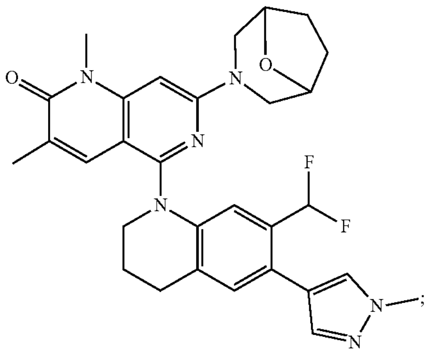 [SMILES: Cc1cc2c(N3CCCc4cc(-c5cnn(C)c5)c(C(F)F)cc43)nc(N3CC4CCC(C3)O4)cc2n(C)c1=O] |
| 218 | 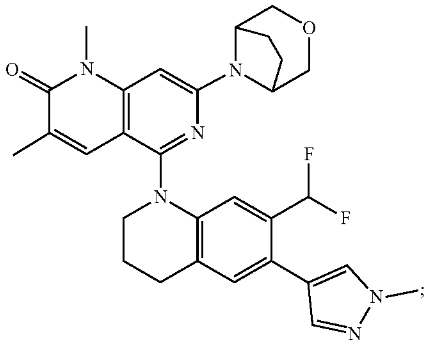 [SMILES: Cc1cc2c(N3CCCc4cc(-c5cnn(C)c5)c(C(F)F)cc43)nc(N3C4CCC3COC4)cc2n(C)c1=O] |
| 219 | 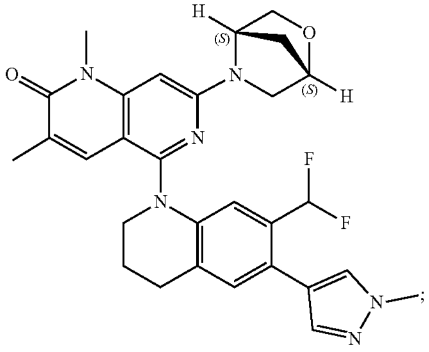 |
| 220 | 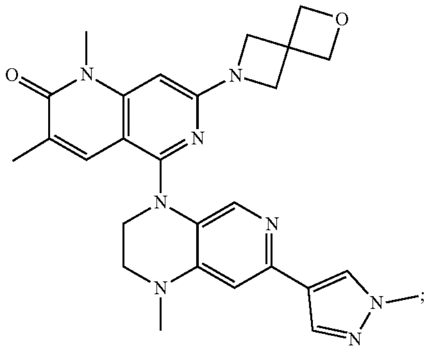 [SMILES: Cc1cc2c(N3CCN(C)c4cc(-c5cnn(C)c5)ncc43)nc(N3CC4(COC4)C3)cc2n(C)c1=O] |

-continued
| Example | Structure |
|---|---|
| 221 | 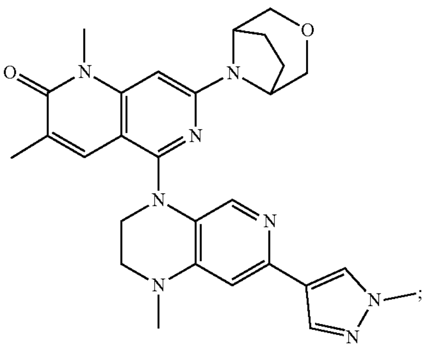 [SMILES: Cc1cc2c(N3CCN(C)c4cc(-c5cnn(C)c5)ncc43)nc(N3C4CCC3COC4)cc2n(C)c1=O] |
| 222 | 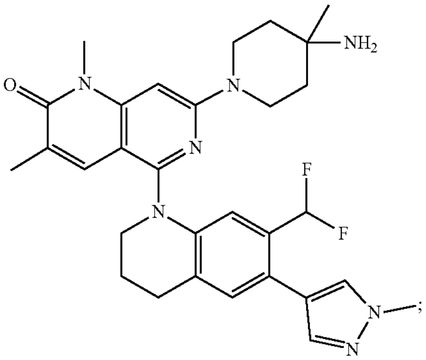 [SMILES: Cc1cc2c(N3CCCc4cc(-c5cnn(C)c5)c(C(F)F)cc43)nc(N3CCC(C)(N)CC3)cc2n(C)c1=O] |
| 223 | 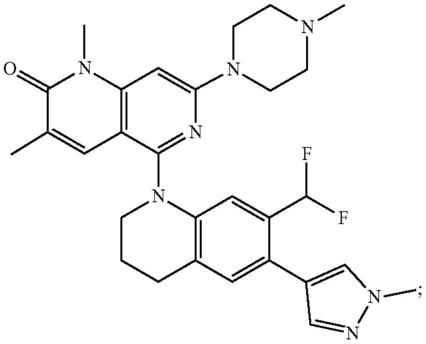 [SMILES: Cc1cc2c(N3CCCc4cc(-c5cnn(C)c5)c(C(F)F)cc43)nc(N3CCN(C)CC3)cc2n(C)c1=O] |
| 224 | 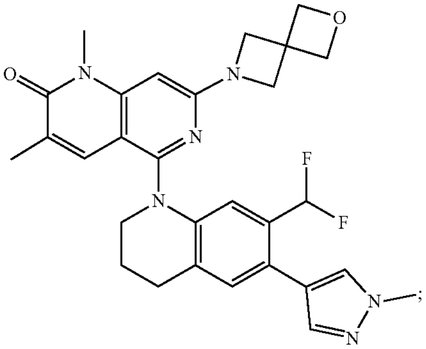 [SMILES: Cc1cc2c(N3CCCc4cc(-c5cnn(C)c5)c(C(F)F)cc43)nc(N3CC4(COC4)C3)cc2n(C)c1=O] |
-continued
| Example | Structure |
|---|---|
| 225 | 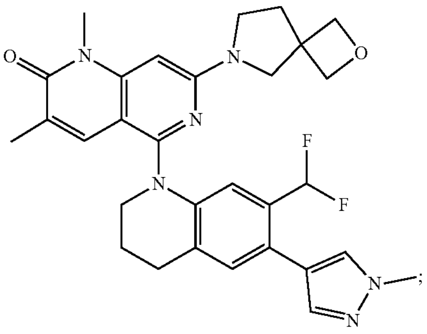 [SMILES: Cc1cc2c(N3CCCc4cc(-c5cnn(C)c5)c(C(F)F)cc43)nc(N3CCC4(COC4)C3)cc2n(C)c1=O] |
| 226 | 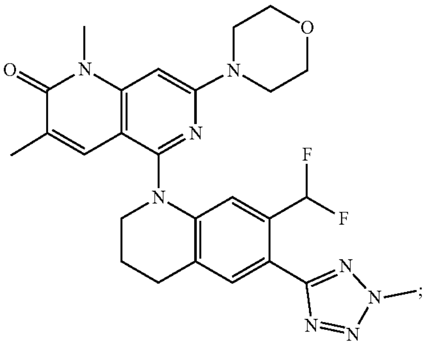 [SMILES: Cc1cc2c(N3CCCc4cc(-c5nnn(C)n5)c(C(F)F)cc43)nc(N3CCOCC3)cc2n(C)c1=O] |
| 227 | 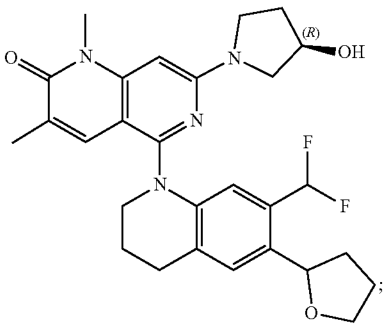 |
| 228 | 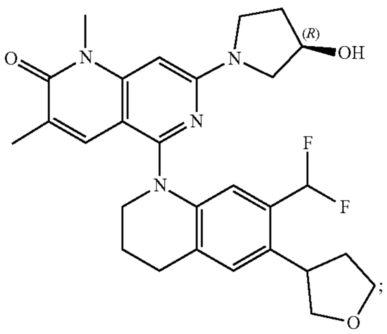 |

-continued
| Example | Structure |
|---|---|
| 229 | 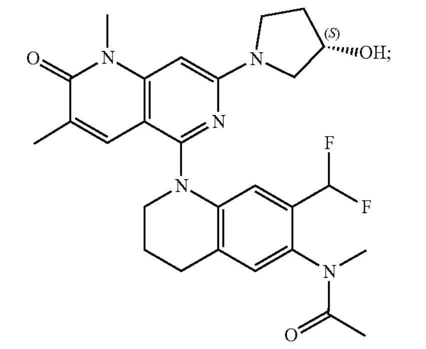 |
| 230 | 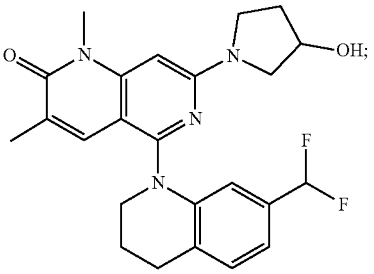 [SMILES: Cc1cc2c(N3CCCc4ccc(C(F)F)cc43)nc(N3CCC(O)C3)cc2n(C)c1=O] |
| 231 | 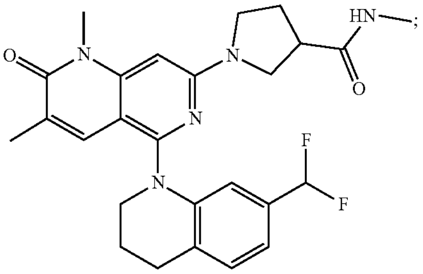 [SMILES: CNC(=O)C1CCN(c2cc3c(cc(C)c(=O)n3C)c(N3CCCc4ccc(C(F)F)cc43)n2)C1] |
| 232 | 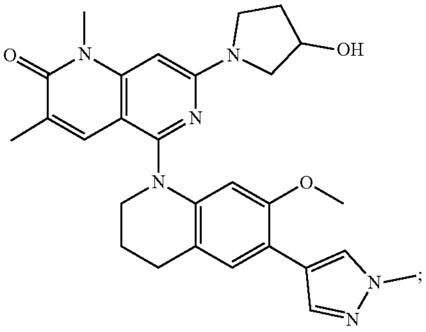 [SMILES: COc1cc2c(cc1-c1cnn(C)c1)CCCN2c1nc(N2CCC(O)C2)cc2c1cc(C)c(=O)n2C] |
| 233 | 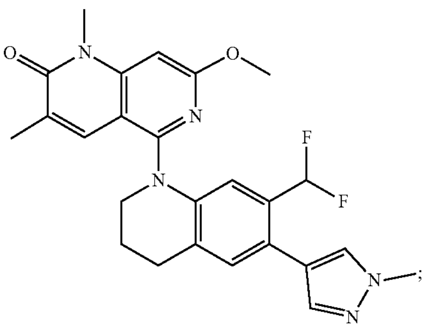 [SMILES: COc1cc2c(cc(C)c(=O)n2C)c(N2CCCc3cc(-c4cnn(C)c4)c(C(F)F)cc32)n1] |
-continued
| Example | Structure |
|---|---|
| 234 | 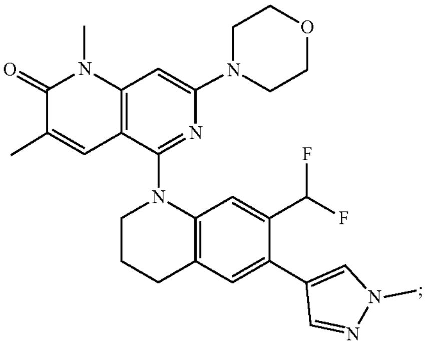 [SMILES: Cc1cc2c(N3CCCc4cc(-c5cnn(C)c5)c(C(F)F)cc43)nc(N3CCOCC3)cc2n(C)c1=O] |
| 235 | 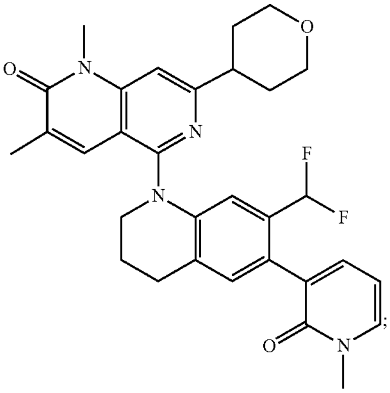 [SMILES: Cc1cc2c(N3CCCc4cc(-c5cccn(C)c5=O)c(C(F)F)cc43)nc(C3CCOCC3)cc2n(C)c1=O] |
| 236 | 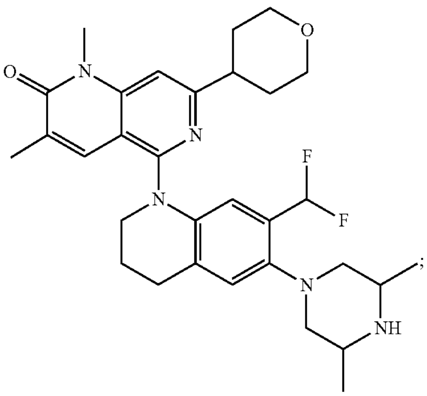 [SMILES: Cc1cc2c(N3CCCc4cc(N5CC(C)NC(C)C5)c(C(F)F)cc43)nc(C3CCOCC3)cc2n(C)c1=O] |
| 237 | 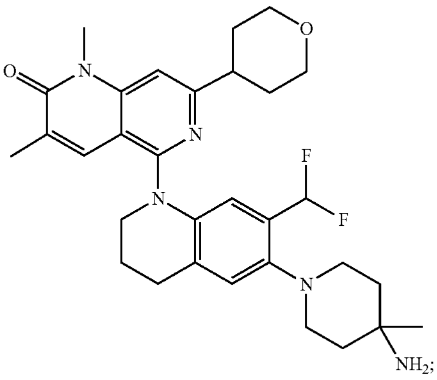 [SMILES: Cc1cc2c(N3CCCc4cc(N5CCC(C)(N)CC5)c(C(F)F)cc43)nc(C3CCOCC3)cc2n(C)c1=O] |

-continued
| Example | Structure |
| --- | --- |
| 238 | 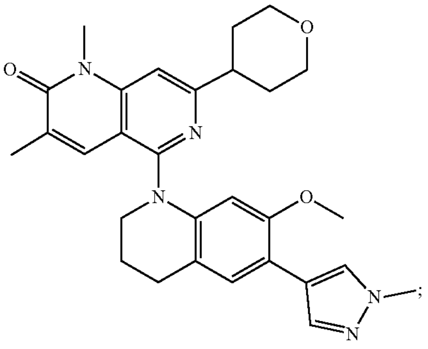 [SMILES: COc1cc2c(cc1-c1cnn(C)c1)CCCN2c1nc(C2CCOCC2)cc2c1cc(C)c(=O)n2C] |
| 239 | 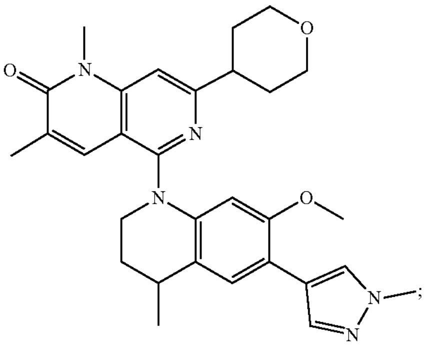 [SMILES: COc1cc2c(cc1-c1cnn(C)c1)C(C)CCN2c1nc(C2CCOCC2)cc2c1cc(C)c(=O)n2C] |
| 240 | 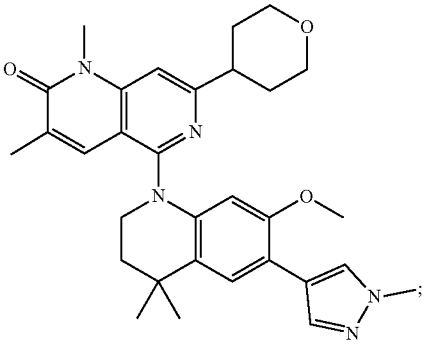 [SMILES: COc1cc2c(cc1-c1cnn(C)c1)C(C)(C)CCN2c1nc(C2CCOCC2)cc2c1cc(C)c(=O)n2C] |
| 241 | 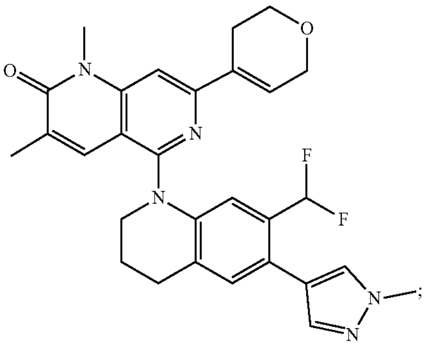 [SMILES: Cc1cc2c(N3CCCc4cc(-c5cnn(C)c5)c(C(F)F)cc43)nc(C3=CCOCC3)cc2n(C)c1=O] |
-continued
| Example | Structure |
| --- | --- |
| 242 | 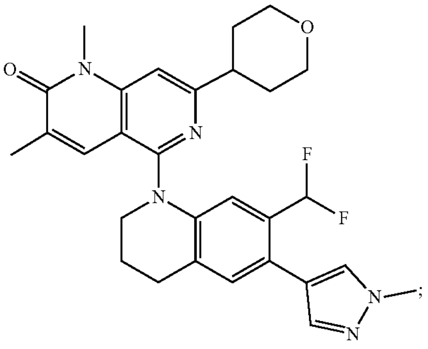 [SMILES: Cc1cc2c(N3CCCc4cc(-c5cnn(C)c5)c(C(F)F)cc43)nc(C3CCOCC3)cc2n(C)c1=O] |
| 244 | 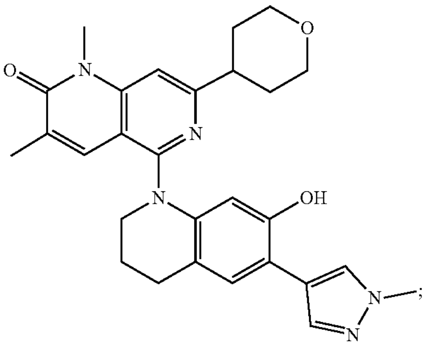 [SMILES: Cc1cc2c(N3CCCc4cc(-c5cnn(C)c5)c(O)cc43)nc(C3CCOCC3)cc2n(C)c1=O] |
| 245 | 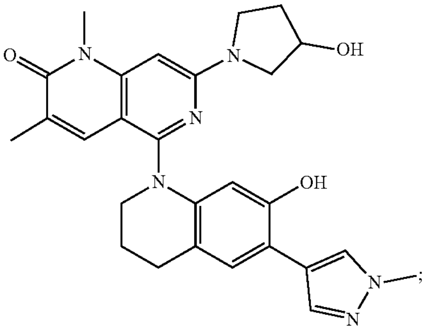 [SMILES: Cc1cc2c(N3CCCc4cc(-c5cnn(C)c5)c(O)cc43)nc(N3CCC(O)C3)cc2n(C)c1=O] |
| 246 | 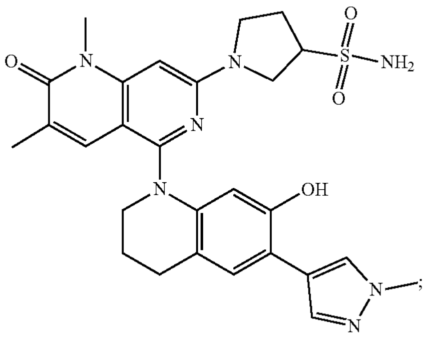 [SMILES: Cc1cc2c(N3CCCc4cc(-c5cnn(C)c5)c(O)cc43)nc(N3CCC(S(N)(=O)=O)C3)cc2n(C)c1=O] |

-continued

| Example | Structure |
| --- | --- |
| 247 | 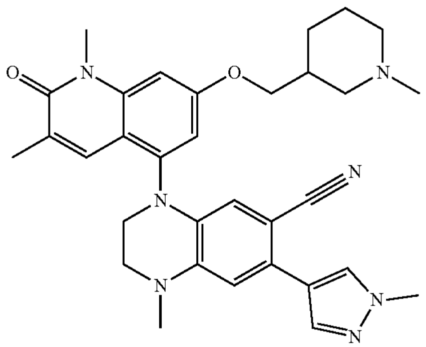 Isomer-1 of Example 35; |
| 248 | 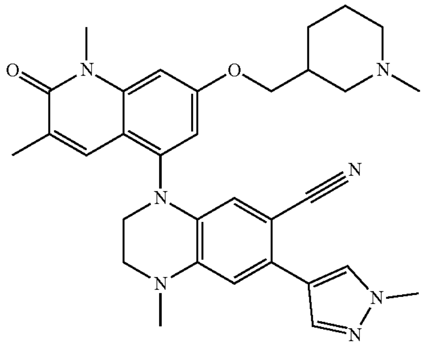 Isomer-2 of Example 35; |
| 249 | 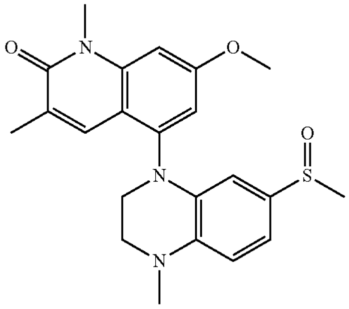 Isomer-1 of Example 99; |
| 250 | 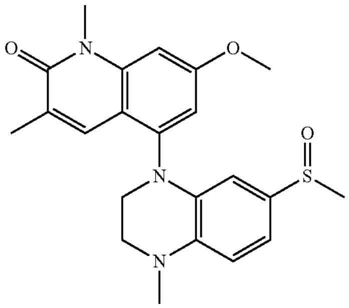 Isomer-2 of Example 99; |
| 251 | 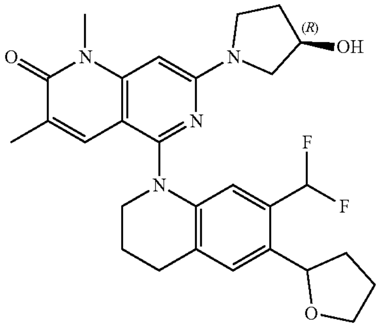 Isomer-1 of Example 227; and |
| 252 | 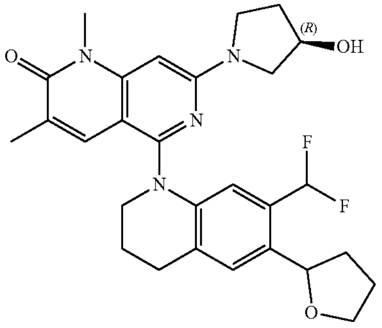 Isomer-2 of Example 227; |

or a pharmaceutically acceptable salt, a stereoisomer, a tautomer, an N-oxide or an ester thereof.

17. A pharmaceutical composition comprising the compound of claim 1 or a pharmaceutically acceptable salt or stereoisomer thereof, and a pharmaceutically acceptable carrier or excipient.

18. A method of inhibiting CBP, EP300 and/or BRD4 FL enzyme in a subject suffering from CBP, EP300 and/or BRD4 FL enzymes mediated disease or disorder, the method comprising administering to the subject in need thereof a therapeutically effective amount of compound of formula (I), or a pharmaceutically acceptable salt, a stereoisomer, a tautomer, an N-oxide or an ester thereof, according to claim 1.

19. The method of claim 18, wherein the CBP, EP300 and/or BRD4 FL enzyme mediated disease or disorder is a) a fibrotic lung disease selected from idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD) and pulmonary arterial hypertension; or b) a cancer selected from acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cancer of male and female reproductive system, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastro-intestinal tumors, germ cell testicular cancer, glioma, glioblastoma, gliosarcoma, head and neck squamous cell carcinoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, Hodgkin's lymphoma, non-Hodgkin's lymphoma, malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor; or c) an inflammatory disease, an inflammatory condition, and an autoimmune disease, selected from Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's arteritis, toxic shock, thyroiditis, type I diabetes, ulcerative colitis, uveitis, vitiligo, vasculitis and Wegener's granulomatosis.

* * * * *